US012600947B2

(12) United States Patent
Pereira et al.

(10) Patent No.: US 12,600,947 B2
(45) Date of Patent: Apr. 14, 2026

(54) COMPOSITION FOR REPROGRAMMING CELLS INTO PLASMACYTOID DENDRITIC CELLS OR INTERFERON TYPE I-PRODUCING CELLS, METHODS AND USES THEREOF

(71) Applicant: Asgard Therapeutics AB, Lund (SE)

(72) Inventors: Carlos Filipe Ribeiro Lemos Pereira, Caminha (PT); Cristiana Ferreira Pires, Palhaça (PT); Fábio Fiúza Rosa, Leiria (PT); Abigail Altman, Malmö (SE)

(73) Assignee: ASGARD THERAPEUTICS AB, Lund (SE)

( * ) Notice: Subject to any disclaimer, the term of this patent is extended or adjusted under 35 U.S.C. 154(b) by 908 days.

(21) Appl. No.: 17/766,369

(22) PCT Filed: Oct. 9, 2020

(86) PCT No.: PCT/EP2020/078429
§ 371 (c)(1),
(2) Date: Apr. 4, 2022

(87) PCT Pub. No.: WO2021/069672
PCT Pub. Date: Apr. 15, 2021

(65) Prior Publication Data
US 2024/0052312 A1    Feb. 15, 2024

(30) Foreign Application Priority Data

Oct. 10, 2019    (PT) .......................................... 115833
Jan. 10, 2020    (EP) .................................... 20151310

(51) Int. Cl.
| | |
|---|---|
| *C12N 15/63* | (2006.01) |
| *A61K 40/19* | (2025.01) |
| *A61K 40/22* | (2025.01) |
| *A61K 40/24* | (2025.01) |
| *A61K 40/41* | (2025.01) |
| *A61K 40/42* | (2025.01) |
| *A61K 40/46* | (2025.01) |
| *C12N 5/0784* | (2010.01) |
| *C12N 15/86* | (2006.01) |

(52) U.S. Cl.
CPC ............ *C12N 5/0639* (2013.01); *A61K 40/19* (2025.01); *A61K 40/22* (2025.01); *A61K 40/24* (2025.01); *A61K 40/416* (2025.01); *A61K 40/42* (2025.01); *A61K 40/46* (2025.01); *C12N 15/86* (2013.01); *C12N 2501/60* (2013.01); *C12N 2506/00* (2013.01)

(58) Field of Classification Search
CPC .. C12N 5/0639; C12N 2501/60; C12N 15/63; A61K 40/19
See application file for complete search history.

(56) References Cited

U.S. PATENT DOCUMENTS

| | | | |
|---|---|---|---|
| 11,345,891 B2 * | 5/2022 | Ribeiro Lemos Pereira et al. ...... | C12N 5/0639 |
| 2012/0046346 A1 | 2/2012 | Rossi et al. | |
| 2012/0208861 A1 * | 8/2012 | Kaisho et al. ....... | A61K 31/713 514/44 A |
| 2012/0251618 A1 | 10/2012 | Schrum et al. | |
| 2012/0295954 A1 * | 11/2012 | Collard et al. ....... | A61K 31/713 514/44 A |

FOREIGN PATENT DOCUMENTS

| | | | | |
|---|---|---|---|---|
| EP | 3385373 A1 | 10/2018 | | |
| WO | 2012/019168 A2 | 2/2012 | | |
| WO | WO2018136551 A1 * | 7/2018 | ............. | A61K 35/15 |
| WO | WO2018185709 A1 * | 10/2018 | ........... | C12N 5/0784 |

OTHER PUBLICATIONS

Swiecki et al. (2015) "The multifaceted biology of plasmacytoid dendritic cells" Nature Reviews Immunology, 15(8), 471-485. (Year: 2015).*
UniProtKB/Swiss-Prot: Q0255, "RecName: Full=Interferon regulatory factor 8; Short=IRF-8; AltName: Full=Interferon consensus sequence-binding protein; Short=H-ICSBP; Short=ICSBP", entry dated: Feb. 5, 2025, available from: National Library of Medicine (US), National Center for Biotechnology Information. (Year: 2025).*
NCBI Reference Sequence: NM_002163.4, "*Homo sapiens* interferon regulatory factor 8 (IRF8), transcript variant 2, mRNA", entry dated: Mar. 17, 2024, available from: National Library of Medicine (US), National Center for Biotechnology Information. (Year: 2024).*
Sasaki et al. (2012) "Spi-B is critical for plasmacytoid dendritic cell function and development" Blood, The Journal of the American Society of Hematology, 120(24), 4733-4743. (Year: 2012).*
Nagasawa et al. (2008) "Development of human plasmacytoid dendritic cells depends on the combined action of the basic helix-loop-helix factor E2-2 and the Ets factor Spi-B" European journal of immunology, 38(9), 2389-2400. (Year: 2008).*
Rosa et al. (Dec. 7, 2018) "Direct reprogramming of fibroblasts into antigen-presenting dendritic cells" Science immunology, 3(30), eaau4292. (Year: 2018).*
Escalante et al. (2002) "Crystal structure of PU. 1/IRF-4/DNA ternary complex" Molecular cell, 10(5), 1097-1105. (Year: 2002).*
(Continued)

*Primary Examiner* — James Joseph Graber
(74) *Attorney, Agent, or Firm* — DINSMORE & SHOHL LLP

(57) ABSTRACT

The present disclosure relates to compositions, constructs and vectors for reprogramming cells into plasmacytoid dendritic cells or interferon type I-producing cells, methods and uses thereof. The present disclosure relates to the development of methods for making plasmacytoid dendritic cells or interferon type I-producing cells that promote anti-viral and anti-tumoral immune responses from differentiated, multipotent or pluripotent stem cells by introducing and expressing isolated/synthetic transcription factors. More particularly, the disclosure provides methods for obtain plasmacytoid dendritic cells or interferon type I-producing cells by direct cellular reprogramming with the surprisingly use of combinations of specific transcription factors.

6 Claims, 22 Drawing Sheets

Specification includes a Sequence Listing.

(56) References Cited

OTHER PUBLICATIONS

Gurtu et al. (1996) "IRES bicistronic expression vectors for efficient creation of stable mammalian cell lines" Biochemical and biophysical research communications, 229:295-298. (Year: 1996).*

Felipe et al. (2000) "Tricistronic and tetracistronic retroviral vectors for gene transfer" Human gene therapy 11:1921-1931. (Year: 2000).*

Movassagh et al. (2004) "Proteins of the Ikaros family control dendritic cell maturation required to induce optimal Th1 T cell differentiation" International immunology, 16(6), 867-875. (Year: 2004).*

Altman et al. (2024) "3010-Transcription Factor Blueprints Underlying Dendritic Cell Diversity" Experimental Hematology, 137:104298, abstract. (Year: 2024).*

Sakaguchi, et al., Naturally arising CD4+ regulatory T cells for immunologic self-tolerance and negative control of Immune responses. Annu Rev Immunol., 22:531-62, 2004.

Sasaki, et al., Spi-B is critical for plasmacytoid dendritic cell function and development. Blood, Dec. 6, 2012;120(24):4733-43.

Scarpa, et al., Characterization of Recombinant Helper Retroviruses from Moloney-Based Vectors in Ecotropic and Amphotropic Packaging Cell Lines. Virology, 180,849-852, 1991.

Schraml, et al., Defining dendritic cells. Current Opinion in Immunology, 2015, 32:13-20.

Schraml, et al., Genetic Tracing via DNGR-1 Expression History Defines Dendritic Cells as a Hematopoietic Lineage. Cell, 154, 843-858, Aug. 15, 2013.

Seth, et al., Mechanism of Enhancement of DNA Expression Consequent to Cointernalization of a Replication Deficient Adenovirus and Unmodified Plasmid DNA. Journal of Virology, Feb. 1994, p. 933-940.

Sichien, et al., Development of conventional dendritic cells: from common bone marrow progenitors to multiple subsets in peripheral tissues. Mucosal Immunology, 10: 831-844, 2017.

Song, et al., Direct Reprogramming of Hepatic Myofibroblasts into Hepatocytes In Vivo Attenuates Liver Fibrosis. Cell Stem Cell, 18, 797-808, 2016.

Sontag, et al., Modelling IRF8 Deficient Human Hematopoiesis and Dendritic Cell Development with Engineered iPS Cells. Stem Cells, 35:898-908, 2017.

Subklewe, et al., New generation dendritic cell vaccine for immunotherapy of acute myeloid leukemia. Cancer Immunol Immunother, 63:1093-1103, 2014.

Swiecki, et al., The multifaceted biology of plasmacytoid dendritic cells. Nat Rev Immunol., Aug. 2015 ; 15(8): 471-485.

Takahashi, et al., Induction of Pluripotent Stem Cells from Adult Human Fibroblasts by Defined Factors. Cell, Nov. 30, 2007;131(5):861-72.

Takahashi, et al., Induction of Pluripotent Stem Cells from Mouse Embryonic and Adult Fibroblast Cultures by Defined Factors. Cell, 126: 663-676, Aug. 25, 2006.

Tel, et al., Natural Human Plasmacytoid Dendritic Cells Induce Antigen-Specific T-Cell Responses in Melanoma Patients. Cancer Res, 73(3) Feb. 1, 2013.

Torper, et al., Generation of induced neurons via direct conversion in vivo. Proc Natl Acad Sci USA, Apr. 23, 2013;110(17):7038-43.

Vierbuchen, et al., Direct conversion of fibroblasts to functional neurons by defined factors, Nature, 463:1035-1041, 2010.

Weaver, et al., Th17: An Effector CD4 T Cell Lineage with Regulatory T Cell Ties. Immunity, 24, 677-688, Jun. 2006.

Xie, et al., Stepwise Reprogramming of B Cells into Macrophages. Cell, 117: 663-676, May 28, 2004.

Xu, et al., Direct Lineage Reprogramming: Strategies, Mechanisms, and Applications. Cell Stem Cell, Feb. 5, 2015;16(2):119-34.

Yao, et al., Restoration of vision after de novo genesis of rod photoreceptors in mammalian retinas. Nature, Aug. 2018; 560(7719): 484-488.

Zeng, et al., Generation and transcriptional programming of intestinal dendritic cells: essential role of retinoic acid. Mucosal Immunology, 9: 183-193, 2016.

Zhou, et al., In vivo reprogramming of adult pancreatic exocrine cells to B-cells, Nature, 455(7213): 627-632, Oct. 2, 2008.

Zhu, et al., CD4 T cells: fates, functions, and faults. Blood, 112(5): 1557-1569, 2008.

Aoi, et al., Generation of Pluripotent Stem Cells from Adult Mouse Liver and Stomach Cells. Science, 321 (5889), 699-702 (2008).

Aricó, et al., Type I Interferons and Cancer: An Evolving Story Demanding Novel Clinical Applications. Cancers, 2019, 11, 1943; doi: 10.3390/cancers11121943 (2019).

Barr, et al., Efficient catheter-mediated gene transfer into the heart using replication-defective adenovirus. Gene Therapy ,1, 51-58. (1994).

Berkner, et al., Development of adenovirus vectors for the expression of heterologous genes. Biotechniques, vol. 6, No. 7. 616-629 (1988).

Bett, et al., Packaging Capacity and Stability of Human Adenovirus Type 5 Vectors. Journal of Virology, Oct. 1993, p. 5911-5921. vol. 67, No. 10 (1993).

Boostels, et al., Transcriptional regulation of DC fate specification. Molecular Immunology, 121, 38-46 (2020).

Boris-Lawrie, et al., Recent advances in retrovirus vector technology. Current Opinion in Genetics and Development, 3:102-109. (1993).

Brown, et al., Transcriptional Basis of Mouse and Human Dendritic Cell Heterogeneity. Cell, 179, 846-863.(2019).

Burns, et al., Vesicular stomatitis virus G glycoprotein pseudotyped retroviral vectors: Concentration to very high titer and efficient gene transfer into mammalian and nonmammalian cells. Proc. Natl. Acad. Sci. USA, 90, pp. 8033-8037. (1993).

Caldarale, et al., Plasmacytoid Dendritic Cells Depletion and Elevation of IFNg Dependent Chemokines CXCL9 and CXCL 10 in Children With Multisystem Inflammatory Syndrome, Front. Immunol., 12: 654587, Mar. 26, 2021.

Cervantes-Barragan, et al., Plasmacytoid dendritic cells control T-cell response to chronic viral infection. Proc Natl Acad Sci U S A, Feb. 21, 2012;109(8):3012-7. doi: 10.1073/pnas.1117359109. Epub Feb. 6, 2012. (2012).

Cheng, et al., Conversion of hepatoma cells to hepatocyte-like cells by defined hepatocyte nuclear factors. Cell Research, vol. 29, pp. 124-135 (2019).

Ciancanelli, et al., Life-threatening influenza and impaired interferon amplification in human IRF7 deficiency. Science, Apr. 24, 2015; 348(6233): 448-453. doi:10.1126/science.aaa1578. (2015).

Collin, et al., Human dendritic cell subsets: an update. Immunology, 154, 3-20 (2018).

Datta, et al., Optimizing Dendritic Cell-Based Approaches for Cancer Immunotherapy. Yale Journal of Biology and Medicine, 87: 491-518, 2014.

Debs, et al., Regulation of gene expression in vivo by liposome-mediated delivery of a purified transcription factor. The Journal of Biological Chemistry, 265(18): 10189-10192, Jun. 25, 1990.

Gabriele, et al., The role of the interferon regulatory factor (IRF) family in dendritic cell development and function. Cytokine & Growth Factor Reviews, 18, 503-510 (2007).

Haj-Ahmad, et al., Development of a Helper-Independent Human Adenovirus Vector and Its Use in the Transfer of the Herpes Simplex Virus Thymidine Kinase Gene. Journal of Virology, Jan. 1986, vol. 57, No. 1, p. 267-274 (1986).

Hanna, et al., Direct Reprogramming of Terminally Differentiated Mature B Lymphocytes to Pluripotency. Cell, 133, 250-264, Apr. 18, 2008.

Jayawardena, et al., MicroRNA-mediated in vitro and in vivo Direct Reprogramming of Cardiac Fibroblasts to Cardiomyocytes. Circ Res., May 25, 2012; 110(11): 1465-1473.

Kopf, et al., Disruption of the murine IL-4 gene blocks Th2 cytokine responses. Nature, Mar. 18, 1993;362(6417):245-8.

Kurita, et al., In vivo reprogramming of wound-resident cells generates skin epithelial tissue. Nature, 561: 243-247, (2018).

Laoui, et al., The tumour microenvironment harbours ontogenically distinct dendritic cell populations with opposing effects on tumour immunity. Nat Commun, Dec. 23, 2016;7:13720. doi: 10.1038/ncomms13720. (2016).

(56) References Cited

OTHER PUBLICATIONS

Levin, et al., Interferon deficiency syndrome. Clin. exp. Immunol., 60: 267-273, 1985.

Liu, et al., Plasmacytoid dendritic cells induce NK cell-dependent, tumor antigen-specific T cell cross-priming and tumor regression in mice. J. Clin. Invest., 118:1165-1175 (2008).

Lou, et al., Plasmacytoid dendritic cells synergize with myeloid dendritic cells in the induction of antigen-specific antitumor immune responses. J Immunol, Feb. 1, 2007;178(3):1534-41.

Marro, et al., Direct Lineage Conversion of Terminally Differentiated Hepatocytes to Functional Neurons. Cell Stem Cell, Oct. 4, 2011; 9(4): 374-382.

Matsuda, et al., Pioneer Factor NeuroD1 Rearranges Transcriptional and Epigenetic Profiles to Execute Microglia-Neuron Conversion, Neuron, Feb. 6, 2019;101(3):472-485.e7.

Merad, et al., The Dendritic Cell Lineage: Ontogeny and Function of Dendritic Cells and Their Subsets in the Steady State and the Inflamed Setting. Annu Rev Immunol., 2013;31:563-604, 2013.

Miller, et al., Improved Retroviral Vectors for Gene Transfer and Expression. Biotechniques, Oct. 1989; 7(9):980-990.

Miller, et al., Retrovirus Packaging Cells. Human Gene Therapy, 1:5-14 (1990).

Mittereder, et al., Evaluation of the efficacy and safety of in vitro, adenovirus-mediated transfer of the human cystic fibrosis transmembrane conductance regulator cDNA. Hum Gene Ther., Jun. 1994;5(6):717-29.

Moreno, et al., In Situ Gene Therapy via AAV-CRISPR-Cas9-Mediated Targeted Gene Regulation. Mol Ther., Jul. 5, 2018;26(7):1818-1827.

Mosmann, et al., TH1 and TH2 Cells: Different Patterns of Lymphokine Secretion Lead to Different Functional Properties. Ann. Rev. Immunol., 1989; 7:145-73.

Niu, et al., In vivo reprogramming of astrocytes to neuroblasts in the adult brain, Nat Cell Biol., Oct. 2013; 15(10).

Pang, et al., Induction of human neuronal cells by defined transcription factors. Nature, May 26, 2011;476(7359):220-3.

Pawlowski, et al., Inducible and Deterministic Forward Programming of Human Pluripotent Stem Cells into Neurons, Skeletal Myocytes, and Oligodendrocytes. Stem Cell Reports J, 8:803-812, Apr. 11, 2017.

Pereira, et al., Direct Reprogramming of Resident NG2 Glia into Neurons with Properties of Fast-Spiking Parvalbumin-Containing Interneurons. Stem Cell Reports, vol. 9, 742-751, Sep. 12, 2017.

Pereira, et al., Hematopoietic Reprogramming in vitro Informs in vivo Identification of Hemogenic Precursors to Definitive Hematopoietic Stem Cells. Dev Cell, Mar. 7, 2016; 36(5): 525-539.

Pereira, et al., Induction of a Hemogenic Program in Mouse Fibroblasts. Cell Stem Cell, Aug. 1, 2013; 13(2): 205-218.

Pereira, et al., Reprogramming cell fates: insights from combinatorial approaches. Ann. N.Y. Acad. Sci., 1266: 7-17, 2012.

Pires, et al., Understanding and Modulating Immunity With Cell Reprogramming. Front. Immunol. 10:2809, 2019.

Plantinga, et al., Conventional and Monocyte-Derived CD11b+ Dendritic Cells Initiate and Maintain T Helper 2 Cell-Mediated Immunity to House Dust Mite Allergen. Immunity 38, 322-335, Feb. 21, 2013.

Qian, et al., In vivo reprogramming of murine cardiac fibroblasts into induced cardiomyocytes. Nature, May 31, 2012;485(7400):593-8.

Reizis, et al., Plasmacytoid Dendritic Cells: Development, Regulation, and Function. Immunity. Jan. 15, 2019;50(1):37-50.

Remer, et al. ,Vaccination with plasmacytoid dendritic cells induces protection against infection with Leishmania major in mice. Eur. J. Immunol., 37: 2463-2473, 2007.

Rich, et al., Development and analysis of recombinant adenoviruses for gene therapy of cystic fibrosis. Hum Gene Ther., Aug. 1993;4(4):461-76.

Rosa, et al., Direct reprogramming of fibroblasts into antigen-presenting dendritic cells. Sci Immunol. Dec. 7, 2018;3(30):eaau4292.

Rosa, et al., Direct Reprogramming of Mouse Embryonic Fibroblasts to Conventional Type 1 Dendritic Cells by Enforced Expression of Transcription Factors. Bio-protocol 10(10): e3619, (2020.

Saichi, et al, Single-cell RNA sequencing of blood antigen-presenting cells in severe COVID-19 reveals multi-process defects in antiviral immunity. Cell Biol 23, 538-551, 2021.

* cited by examiner

A

B

A

B

A

B

C

COMPOSITION FOR REPROGRAMMING CELLS INTO PLASMACYTOID DENDRITIC CELLS OR INTERFERON TYPE I-PRODUCING CELLS, METHODS AND USES THEREOF

CROSS REFERENCE TO RELATED APPLICATIONS

This application is a U.S. National Stage under 35 U.S.C. § 371 of PCT/EP2020/078429 filed Oct. 9, 2020, which depends from and claims priority to European patent application number 20151310.8 filed Jan. 10, 2020 and Portugal patent application number 115833 filed Oct. 10, 2019, the entire contents of each of which are incorporated herein by reference.

TECHNICAL FIELD

The present disclosure relates to compositions for reprogramming cells into plasmacytoid dendritic cells or interferon type I-producing cells, methods and uses thereof.

The present disclosure relates to the development of methods for making plasmacytoid dendritic cells or interferon type I-producing cells that promote immune antiviral and anti-tumoral responses from differentiated, multipotent or pluripotent stem cells by introducing and expressing isolated/synthetic transcription factors. More particularly, the disclosure provides methods for obtain plasmacytoid dendritic cells or interferon type I-producing cells by direct cellular reprogramming with the surprisingly beneficial use of combinations of specific transcription factors.

BACKGROUND

Cellular reprogramming relies on rewiring the epigenetic and transcriptional network of one cell state to that of a different cell type. Transcription factor (TF)-transduction experiments have highlighted the plasticity of adult somatic or differentiated cells, providing new technologies to generate any desired cell type. Through forced expression of TFs, it is possible to reprogram somatic or differentiated cells into induced pluripotent stem cells (iPSCs) that are remarkably similar to embryonic stem cells (Takahashi et al., 2006; Takahashi et al., 2007). Alternatively, a somatic cell can also be converted into another specialized cell type (Pereira et al., 2012). Direct lineage conversion has proven successful to reprogram mouse and human fibroblasts into several cell types, such as neurons, cardiomyocytes and hepatocytes, using TFs specifying the target-cell identity (Xu et al., 2015). Lineage conversions were also demonstrated in the hematopoietic system, where forced expression of TFs induced a macrophage fate in B cells and fibroblasts (Xie et al., 2004) and the direct reprogramming of mouse fibroblasts into clonogenic hematopoietic progenitors was achieved with the transcription factors Gata2, Gfi1b, cFos and Etv6 (Pereira et al., 2013). These four TFs induce a dynamic, multi-stage hemogenic process that progresses through an endothelial-like intermediate, recapitulating developmental hematopoiesis in vitro (Pereira et al., 2016).

Reprogrammed cells are very promising therapeutic tools for regenerative medicine, and cells obtained by differentiation of iPSCs are already being tested in clinical studies.

Cellular reprogramming strategies have highlighted the flexibility of cell fates with the possibility to use cell type-specific TFs to convert somatic cells into pluripotency.

Direct lineage conversion of one differentiated cell type into another has also been demonstrated and explored to elucidate cell biology mechanisms and for regenerative medicine purposes. Recently, we have demonstrated that antigen presenting dendritic cells (DCs) can be reprogrammed from unrelated cell types by a small combination of TFs (Rosa et al., 2018). Classically, it is thought that a myeloid DC-committed progenitor gives rise to functionally different DC subsets: conventional DCs (cDCs) and plasmacytoid DCs (pDCs). cDCs are professional antigen presenting cells (APC) driving antigen-specific immune responses, while pDCs are professional producers of type I interferon during viral infection. They exhibit both innate and adaptive immune functions and can act as APCs impacting T cell responses directly. The timing and exact mechanisms regulating the divergence of the different subsets during DC development is still to be established.

Document EP 3 385 373 relates to compositions, nucleic acid constructs, methods and kits thereof for cell induction or reprogramming cells to conventional dendritic cell state or antigen presenting cell state, based, in part, on the surprising effect described in this document in of novel use of combinations of transcription factors that permit induction or reprogramming of differentiated or undifferentiated cells into DCs or APCs.

The combination of transcription factors described in document EP 3 385 373 induces DCs with surface phenotype, transcriptional signature and functional properties characteristic of the cDC1 subset of DCs. The ability to secrete interferon type I, e.g. interferon alpha (IFN-α) and beta (IFN-β) was not previously described.

The induced pDCs or interferon type I-producing cells described herein recapitulate typical pDC functional property of detecting nucleic acids and responding by secreting type I interferons (Reizis 2019).

These facts are disclosed in order to illustrate the technical problem addressed by the present disclosure.

SUMMARY

The present subject matter identifies several isolated transcription factors that surprisingly reprogram or induce differentiated cells, multipotent or pluripotent stem cells into pDCs or interferon type I-producing cells, in vitro, ex vivo or in vivo.

Surprisingly, the induced pDCs or interferon type I-producing cells generated by reprograming as described in the present disclosure, are intrinsically able to secrete type I interferon required to induce an antiviral or anti-tumoral responses.

Surprisingly, the induced pDCs or interferon type I-producing cells generated by reprograming as described in the present disclosure, are intrinsically able to respond to toll-like receptor 7 (TLR7) and TLR9 ligands by secreting increased amounts of type I interferon, e.g. interferon alpha (IFN-α) and beta (IFN-β) required to induce an antiviral response.

DCs are professional APCs located throughout the body functioning at the interface of the innate and adaptive immune system. DCs are able to provide a crucial link between the external environment and the adaptive immune system through their ability to capture, process and present antigens loaded on major histocompatibility complex (MHC) class I and MHC class II molecules to T cells, targeting them to different types of immune responses. Firstly, DCs have to capture antigens and process them through major histocompatibility complex (MHC) class I and MHC class II. Following their activation, DCs are able to migrate towards the local draining lymph nodes priming multiple B cell and T cell responses, a key feature of adaptive immunity. The early protective efficacy is primarily conferred by the induction of antigen-specific antibodies produced by B lymphocytes. The long-term protection against specific antigens requires the persistence of specific antibodies and the generation of immunological memory that could provide a rapid and efficient response after subsequent antigen exposure. DCs, as professional APCs, have the ability to cross-present antigens, meaning that, in addition to its classical ability to present exogenous antigens on MHC class II and endogenous antigens on MHC class I, they are also able to present exogenous antigens on MHC class I, a critical step for the generation of cytotoxic T lymphocyte responses (CTL).

The ontogeny and/or microenvironment in which DCs are positioned may result in the expression of distinct combinations of surface receptors by DCs. For example, phenotypic criteria allow the classification of mouse DCs into different subpopulations. Of these, cDCs in lymphoid tissues are traditionally sub-divided into cDC1 and cDC2 subpopulations. It has been argued that different DC subsets may be involved in specific recognition of certain pathogens and/or regulate different immune responses, e.g. Th1 or Th2 (immunity) or regulatory T cells (tolerance). However, the phenotype and functional behavior of DCs is also significantly conditioned by external activating stimuli, denoting significant plasticity. cDC1 and cDC2 subsets differentially prime Th1 and Th2 responses in vivo. Immune therapy for cancer relies on using DCs to prime Th1 or cytotoxic T lymphocyte responses to promote tumor clearance. Alongside cDCs, pDCs emerged as a unique subset of DCs specialized in the production of type I interferons (IFNs) following viral infection or recognition of self nucleic acids through TLR7 and TLR9. In addition to contributing to antiviral immunity, pDCs can participate in the priming of both immunogenic and tolerogenic adaptive immune responses, being implicated in the pathology of autoimmune diseases and cancer.

pDCs have the unique feature of producing more type I interferons than any other cell type in response to viruses and/or virus derived nucleic acids. TLR7 and 9 are highly expressed in pDCs, in intracellular endosomal compartments. TLR7 recognizes viral single stranded RNA and TLR9 detects viral double stranded DNA rich in unmethylated CpG oligonucleotides. Upon activation with viral nucleic acids, they induce stimulation and recruitment of the adaptor protein MyD88 and two major TLR7/9 intracellular signalling pathways. The first pathway leads to type I interferon production, which requires the translocation of IRF7 to the nucleus promoting IFN-α and IFN-β transcription and secretion. Type I interferons, secreted by pDCs upon activation with nucleic acids, are able to bridge innate and adaptive immune systems, promoting long-term T-cell survival and memory, Th1 polarization, CD8 T-cell cytolytic activity, NK cell-mediated cytotoxicity and B-cell growth and differentiation. Alternatively, activation of the second pathway leads to NF-kb-dependent induction of expression of the pro-inflammatory cytokines, TNF-α and IL-6, as well as chemokines, for example CXCL9 (MIG), CXCL10 (IP-10), CCL3 (MIP-1a), CCL4 (MIP-1b) and CCL5 (RANTES). These are in turn able to attract activated CD4 and CD8 T cells to the sites of inflammation.

Currently, DC-based immunotherapies rely on autologous DC precursors: either monocytes, which are associated with the production of less-efficient DCs, or hematopoietic progenitors, which are isolated in very low numbers. In addition, these precursor cells are commonly compromised in cancer-bearing patients, resulting in the generation of a mixture of dysfunctional and heterogeneous DCs. In contrast, non-hematopoietic cell-types such as fibroblasts are usually not affected. Human dermal fibroblasts (HDFs) also exhibit other competitive advantages; they are easily obtained from a small skin punch biopsy, easily expanded in vitro for several passages (15-20 million cells after 4 weeks) and can be conserved frozen and used on-demand. Given the fundamental role of DCs functioning at the interface of the innate and adaptive immune system, there remains a clinical need to find alternative strategies to generate homogeneous populations of functional pDCs to prime antigen-specific responses.

In recent years, pDCs have gained a special interest, due to their ability to produce large amounts of IFN and to prime T cells. pDC-deficient mice were shown to be unable to efficiently clear the lymphocytic choriomeningitis virus due to impaired CD4+ and CD8+ T cell responses (Cervantes-Barragan et al., 2012). Similarly, a null mutation in IRF7 in a patient was reported to negatively affect the production of type I and III IFN by pDCs which led to severe influenza infection (Ciancanelli et al., 2015). These findings indicate that pDCs are important to fight viral infections, especially in the early stages (Swiecki and Colonna, 2015), where IFN production can limit viral replication. Moreover, several clinical trials have explored the potential of pDCs to induce anti-tumor immune responses (Tel et al., 2013). However, the therapeutic use of pDCs seems to be limited by the low number of these cells circulating in the blood. Thus, alternative sources of DCs, particularly pDCs are needed to fulfill the therapeutic needs.

In some embodiments, polypeptide variants or family members having the same or a similar activity as the reference polypeptide having the polypeptide sequences (SEQ. ID. 49-SEQ. ID. 96) or a polypeptide being encoded by the sequences SEQ. ID. 1-SEQ. ID. 48, can be used in the compositions, methods, and kits described herein. Generally, variants of a particular polypeptide encoding a pDC-inducing factor for use in the compositions, vectors, constructs, methods, and kits described herein will have at least about 90%, at least about 91%, at least about 92%, at least about 93%, at least about 94%, at least about 95%, at least about 96%, at least about 97%, at least about 98%, at least about 99% or more sequence identity to that particular reference polynucleotide or polypeptide as determined by sequence alignment programs and parameters described herein and known to those skilled in the art.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (over the whole the sequence) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimize alignment between conserved motifs, as would be apparent to a person skilled in the art. The sequence identity values, which are indicated in the present subject-matter as a percentage were determined over the entire amino acid or nucleotide sequence, using BLAST with default parameters.

In an embodiment for better results, the transcription factors may be encoded by a polynucleotide selected from the group consisting of: IRF8 (SEQ. ID. 1, SEQ. ID. 2), SPIB (SEQ. ID. 3, SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), HDAC5 (SEQ. ID. 15, SEQ. ID. 16), HHEX (SEQ. ID. 17, SEQ. ID. 18), HOXA5 (SEQ. ID. 19, SEQ. ID. 20), ID3 (SEQ. ID. 21, SEQ. ID. 22), IKZF1 (SEQ. ID. 23, SEQ. ID. 24), IKZF2 (SEQ. ID. 25, SEQ. ID. 26), IKZF3 (SEQ. ID. 27, SEQ. ID. 28), IKZF5 (SEQ. ID. 29, SEQ. ID. 30), IRF7 (SEQ. ID. 31, SEQ. ID. 32), MEF2C (SEQ. ID. 33, SEQ. ID. 34), MYB (SEQ. ID. 35, SEQ. ID. 36), RUNX2 (SEQ. ID. 37, SEQ. ID. 38), STAT3 (SEQ. ID. 39, SEQ. ID. 40), TCF4 (SEQ. ID. 41, SEQ. ID. 42), TCF12 (SEQ. ID. 43, SEQ. ID. 44), STAT1 (SEQ. ID. 45, SEQ. ID. 46), and TSC22D1 (SEQ. ID. 47, SEQ. ID. 48).

In an embodiment of the present disclosure, the transcription factor may be selected from the group consisting of: IRF8 (SEQ. ID. 49, SEQ. ID. 50), SPIB (SEQ. ID. 51, SEQ. ID. 52), ARID5A (SEQ. ID. 53, SEQ. ID. 54), BCL11A (SEQ. ID. 55, SEQ. ID. 56), CBFA2T3 (SEQ. ID. 57, SEQ. ID. 58), CREB3L2 (SEQ. ID. 59, SEQ. ID. 60), ETS1 (SEQ. ID. 61, SEQ. ID. 62), HDAC5 (SEQ. ID. 63, SEQ. ID. 64), HHEX (SEQ. ID. 65, SEQ. ID. 66), HOXA5 (SEQ. ID. 67, SEQ. ID. 68), ID3 (SEQ. ID. 69, SEQ. ID. 70), IKZF1 (SEQ. ID. 71, SEQ. ID. 72), IKZF2 (SEQ. ID. 73, SEQ. ID. 74), IKZF3 (SEQ. ID. 75, SEQ. ID. 76), IKZF5 (SEQ. ID. 77, SEQ. ID. 78), IRF7 (SEQ. ID. 79, SEQ. ID. 80), MEF2C (SEQ. ID. 81, SEQ. ID. 82), MYB (SEQ. ID. 83, SEQ. ID. 84), RUNX2 (SEQ. ID. 85, SEQ. ID. 86), STAT3 (SEQ. ID. 87, SEQ. ID. 88), TCF4 (SEQ. ID. 89, SEQ. ID. 90), TCF12 (SEQ. ID. 91, SEQ. ID. 92), STAT1 (SEQ. ID. 93, SEQ. ID. 94), and TSC22D1 (SEQ. ID. 95, SEQ. ID. 96).

In an embodiment, the transcription factors of the present disclosure may be used in veterinary or human medicine, in particular in infectious disease, or viral disease, or viral induced disease, or in cancer, or autoimmune disease or neurodegenerative disease.

In an embodiment for better results the cell may be selected from the group consisting of: a pluripotent stem cell, a multipotent stem cell, a hematopoietic stem cell, a differentiated cell, a tumor cell, a cancer cell, a cell line, in particular a mesoderm-derived cell line, such as a monocyte cell line, and mixtures thereof. In particular a mammalian cell, more in particular a mouse or a human cell.

In an embodiment for better results, the transcription factor of the present disclosure may be used as a reprogramming or inducing factor of a cell selected from the group consisting of: pluripotent stem cells, or multipotent stem cells, or differentiated cells, and mixtures thereof into a dendritic cell or interferon type I producing cell or antigen presenting cell, preferably a dendritic cell or interferon type I-producing cell.

In an embodiment for better results, the transcription factors of the present disclosure may be used as a reprogramming or inducing factor of a cell selected from the group consisting of: pluripotent stem cells, multipotent stem cells or differentiated cells, and mixtures thereof, into a dendritic cell or interferon type I-producing cell.

In an embodiment for better results, the transcription factor of the present disclosure may be used as a reprogramming or inducing factor of a cell selected from the group consisting of: a tumor cell, a cancer cell, and mixtures thereof, into antigen presenting cell.

In an embodiment, the results of the present disclosure shows that in Clec9a reporter mouse, pDCs are labeled with tdTomato fluorescent protein making this model suitable for screening pDC-inducing factor. IRF8 has been described to play a key role on cDC1 and pDC specification and is highly expressed on both DC subsets. Therefore, the present invention combined IRF8 with each of the individual 24 candidates and performed a progressive additive screen in Clec9a reporter mouse embryonic fibroblasts (MEFs).

In an embodiment, surprisingly, IRF8 combined with SPIB is sufficient to induce reporter activation. Moreover, the efficiency of reporter activation is surprisingly increased when IRF8 and SPIB are combined with BCL11A, CBFA2T3, CREB3L2, ETS1, STAT1, TCF4, TCF12 or TSC22D1. Expression of major histocompatibility complex (MHC) class II molecules, important for DC functionality, is also induced by the IRF8– and IRF8+SPIB-based combinations of pDC-inducing TFs.

In an embodiment, expression of IRF8 and SPIB is sufficient to induce surface expression of hematopoietic marker CD45. Remarkably, the surface expression of CD45 is surprisingly increased when IRF8 and SPIB are combined with IKZF1 or IKZF2.

In an embodiment, IRF8 and SPIB are able to induce the ability to secrete Interferon type I, namely IFN-α and IFN-β, and not anti-inflammatory IL-10, after stimulation with TLR7 and TLR9 ligands, a phenotypic property characteristic of pDCs. Interferon secretion is further increased when IRF8 and SPIB are combined with BCL1A, CBFA2T3, CREB3L2, ETS1, STAT1, TCF4, TCF12 or TSC22D1. Induced DCs generated with PU.1, IRF8 and BATF3 TFs do not show ability to secrete type I interferons.

In an embodiment, IRF8 and SPIB are able to induce the ability to secrete pro-inflammatory cytokines, in particular IL-6 and TNF-α, after stimulation with TLR7 and TLR9 ligands, a phenotypic property characteristic of pDCs. Cytokine secretion is further increased when IRF8 and SPIB are combined with ETS1, STAT1, TCF12 or TSC22D1.

In an embodiment, IRF8 and SPIB are able to induce the ability to secrete chemokines, namely CCL5 and CXCL10, after stimulation with TLR7 and TLR9 ligands, a phenotypic property characteristic of pDCs. Chemokine secretion is further increased when IRF8 and SPIB are combined with HOXA5, STAT1, TCF12 or TSC22D1.

An aspect of the present subject matter relates to a composition comprising a combination of at least two transcription factors encoded by an isolated or synthetic sequence at least 90% identical to a sequence from a list consisting of transcription factors selected from a list consisting of: IRF8 (SEQ. ID. 1, SEQ. ID. 2), SPIB (SEQ. ID. 3, SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), IKZF1 (SEQ. ID. 23, SEQ. ID. 24), STAT1 (SEQ. ID. 45, SEQ. ID. 46), TCF4 (SEQ. ID. 41, SEQ. ID. 42), TCF12 (SEQ. ID. 43, SEQ. ID. 44), TSC22D1 (SEQ. ID. 47, SEQ. ID. 48), and mixtures thereof;

for use in reprogramming a stem cell or a differentiated cell, or mixtures thereof, into a plasmacytoid dendritic cell or interferon producing cell or antigen-presenting cell, preferably into a plasmacytoid dendritic cell or an interferon type I-producing cell in a subject.

An aspect of the present subject-matter relates to a composition comprising at least the two transcription factors IRF8 and SPIB, for use in reprogramming a stem cell or a differentiated cell, or mixtures thereof, into a plasmacytoid dendritic cell or an interferon type I-producing cell in a subject.

In an embodiment, the composition of the present disclosure comprises at least two transcription factors as herein described with the proviso that the combination of at least two transcription factors which may be isolated or synthetic transcription factors, is not TCF4 (SEQ. ID. 41, SEQ. ID. 42) and IRF8 (SEQ. ID. 1, SEQ. ID. 2).

In an embodiment, the composition of the present disclosure further comprises one or more transcription factors selected from the group consisting of: ARID5A, BCL1A, CBFA2T3, CREB3L2, ETS1, IKZF1, STAT1, TCF4, TCF12 and TSC22D1, preferably BCL1A, CBFA2T3, CREB3L2, ETS1, IKZF1, TCF4, TCF12 and TSC22D1.

In an embodiment, the composition of the present disclosure may comprise a combination of at least two transcription factors encoded by an isolated or synthetic sequence at least 95% identical to a sequence from the group consisting of selected TFs from the group consisting of: IRF8 (SEQ. ID. 1, SEQ. ID. 2), SPIB (SEQ. ID. 3, SEQ. ID. 4), ARID5A (SEQ. ID. 5, SEQ. ID. 6), BCL1A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), IKZF1 (SEQ. ID. 23, SEQ. ID. 24), STAT1 (SEQ. ID. 45, SEQ. ID. 46), TCF4 (SEQ. ID. 41, SEQ. ID. 42), TCF12 (SEQ. ID. 43, SEQ. ID. 44), TSC22D1 (SEQ. ID. 47, SEQ. ID. 48), and mixtures thereof, preferably 96%, 97%, 98%; 99% or identical.

In an embodiment of the present disclosure the transcription factors are at least 90% identical to the sequence selected from the group consisting of: IRF8 (SEQ. ID. 1, SEQ. ID. 2), SPIB (SEQ. ID. 3, SEQ. ID. 4), ARID5A (SEQ. ID. 5, SEQ. ID. 6), BCL1A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), IKZF1 (SEQ. ID. 23, SEQ. ID. 24), STAT1 (SEQ. ID. 45, SEQ. ID. 46), TCF4 (SEQ. ID. 41, SEQ. ID. 42), TCF12 (SEQ. ID. X, SEQ. ID. X), TSC22D1 (SEQ. ID. 47, SEQ. ID. 48), and mixtures thereof, preferably 91%, 92%, 93%, 94%, 95%, 96%, 97%, 98%, 99% or identical.

In an embodiment, the composition of the present disclosure may comprise a combination of transcription factors selected from the following combinations:

IRF8 (SEQ. ID. 1, SEQ. ID. 2) and SPIB (SEQ. ID. 3, SEQ. ID. 4);

IRF8 (SEQ. ID. 1, SEQ. ID. 2), SPIB (SEQ. ID. 3, SEQ. ID. 4) and ARID5A (SEQ. ID. 5, SEQ. ID. 6);

IRF8 (SEQ. ID. 1, SEQ. ID. 2), SPIB (SEQ. ID. 5, SEQ. ID. 6) and BCL11A (SEQ. ID. 7, SEQ. ID. 8);

IRF8 (SEQ. ID. 1, SEQ. ID. 2), SPIB (SEQ. ID. 3, SEQ. ID. 4) and CBFA2T3 (SEQ. ID. 9, SEQ. ID. 10);

IRF8 (SEQ. ID. 1, SEQ. ID. 2), SPIB (SEQ. ID. 3, SEQ. ID. 4) and CREB3L2 (SEQ. ID. 11, SEQ. ID. 12);

IRF8 (SEQ. ID. 1, SEQ. ID. 2), SPIB (SEQ. ID. 3, SEQ. ID. 4) and ETS1 (SEQ. ID. 13, SEQ. ID. 14);

IRF8 (SEQ. ID. 1, SEQ. ID. 2), SPIB (SEQ. ID. 3, SEQ. ID. 4) and IKZF1 (SEQ. ID. 23, SEQ. ID. 24);

IRF8 (SEQ. ID. 1, SEQ. ID. 2), SPIB (SEQ. ID. 3, SEQ. ID. 4) and STAT1 (SEQ. ID. 45, SEQ. ID. 46);

IRF8 (SEQ. ID. 1, SEQ. ID. 2), SPIB (SEQ. ID. 3, SEQ. ID. 4) and TCF4 (SEQ. ID. 41, SEQ. ID. 42);

IRF8 (SEQ. ID. 1, SEQ. ID. 2), SPIB (SEQ. ID. 3, SEQ. ID. 4) and TCF12 (SEQ. ID. 43, SEQ. ID. 44);

IRF8 (SEQ. ID. 1, SEQ. ID. 2), SPIB (SEQ. ID. 3, SEQ. ID. 4) and TSC22D1 (SEQ. ID. 47, SEQ. ID. 48), and mixtures thereof.

In an embodiment, the composition of the present disclosure may comprise a combination of transcription factors selected from the following combinations:

IRF8 and SPIB;

IRF8, SPIB and ARID5A;

IRF8, SPIB and BCL1A;

IRF8, SPIB and CBFA2T3;

IRF8, SPIB and CREB3L2;

IRF8, SPIB and ETS1;

IRF8, SPIB and IKZF1;

IRF8, SPIB and STAT1;

IRF8, SPIB and TCF4;

IRF8, SPIB and TCF12;

IRF8, SPIB and TSC22D1; and mixtures thereof.

In an embodiment, the composition of the present disclosure may comprise the combination of transcription factors where the combination is IRF8 (SEQ. ID. 1, SEQ. ID. 2) and SPIB (SEQ. ID. 3, SEQ. ID. 4) or IRF8 (SEQ. ID. 1, SEQ. ID. 2), SPIB (SEQ. ID. 3, SEQ. ID. 4) and TCF12 (SEQ. ID. 43, SEQ. ID. 44).

In an embodiment, the composition of the present disclosure may comprise the combination of transcription factors where the combination is IRF8, SPIB and TCF12.

In an embodiment, the composition of the present disclosure may comprise the combination of transcription factors where the combination is IRF8, SPIB and TSC22D1.

In an embodiment, the composition of the present disclosure may comprise a pluripotent stem cell, or a multipotent stem cell, a differentiated cell, and mixtures thereof.

In an embodiment, the composition of the present disclosure may be used as a reprogramming or inducing factor of a cell selected from the group consisting of: a tumor cell, a cancer cell, and mixtures thereof, into an interferon type I-producing cell.

In an embodiment, the composition of the present disclosure may be used as reprogramming or inducing factors of pDCs, wherein the antigen is: a cancer antigen, a self-antigen, an allergen, an antigen from a pathogenic and/or infectious organism.

In an embodiment, the cells obtained by the use of the combination of transcriptions factors of the present disclosure have the ability to respond to TLR7 and TLR9 stimulation and/or the cells have the ability to secrete interferon type I cytokines, namely IFN-α and IFN-β.

Another aspect of the present disclosure relates to the use of the composition of the present disclosure in veterinary or human medicine, in particular in immunotherapy, or in neurodegenerative or ageing diseases, or in cancer or in infectious diseases, or as a drug screening.

Another aspect of the present disclosure relates to the use of the composition of the present disclosure in the diagnostic, therapy or treatment of cancer, antiviral immune responses and immune pathology, particularly in autoimmune diseases and immunodeficiency conditions.

In an embodiment, the pluripotent stem cell, multipotent stem cell or differentiated cell is a mammalian pluripotent stem cell, multipotent stem cell or differentiated cell, in particular a mouse or a human cell.

In an embodiment, the composition of the present disclosure may be used in the treatment, therapy or diagnosis of an infectious disease, a viral disease, or a viral-induced disease.

In an embodiment, the composition of the present disclosure may be used as an antiviral agent or as an immunogenic composition.

Another aspect of the present disclosure relates to a construct or a vector encoding at least the combination of two isolated transcription factors described in the present disclosure, preferably the encoded combination of three transcription factors, more preferably four transcription factors.

In an embodiment, the combination of at least two isolated transcription factors is in the following sequential order from 5' to 3':

SPIB (SEQ. ID. 3, SEQ. ID. 4) and IRF8 (SEQ. ID. 1, SEQ. ID. 2);

IRF8 (SEQ. ID. 1, SEQ. ID. 2) and SPIB (SEQ. ID. 3, SEQ. ID. 4);

SPIB (SEQ. ID. 3, SEQ. ID. 4), IRF8 (SEQ. ID. 1, SEQ. ID. 2) and ARID5A (SEQ. ID. 5, SEQ. ID. 6);

SPIB (SEQ. ID. 5, SEQ. ID. 6), IRF8 (SEQ. ID. 1, SEQ. ID. 2) and BCL11A (SEQ. ID. 7, SEQ. ID. 8);

SPIB (SEQ. ID. 3, SEQ. ID. 4), IRF8 (SEQ. ID. 1, SEQ. ID. 2) and CBFA2T3 (SEQ. ID. 9, SEQ. ID. 10);

SPIB (SEQ. ID. 3, SEQ. ID. 4), IRF8 (SEQ. ID. 1, SEQ. ID. 2) and CREB3L2 (SEQ. ID. 11, SEQ. ID. 12);

SPIB (SEQ. ID. 3, SEQ. ID. 4), IRF8 (SEQ. ID. 1, SEQ. ID. 2) and ETS1 (SEQ. ID. 13, SEQ. ID. 14);

SPIB (SEQ. ID. 3, SEQ. ID. 4), IRF8 (SEQ. ID. 1, SEQ. ID. 2) and IKZF1 (SEQ. ID. 23, SEQ. ID. 24);

SPIB (SEQ. ID. 3, SEQ. ID. 4), IRF8 (SEQ. ID. 1, SEQ. ID. 2) and STAT1 (SEQ. ID. 45, SEQ. ID. 46);

SPIB (SEQ. ID. 3, SEQ. ID. 4), IRF8 (SEQ. ID. 1, SEQ. ID. 2) and TCF4 (SEQ. ID. 41, SEQ. ID. 42);

SPIB (SEQ. ID. 3, SEQ. ID. 4), IRF8 (SEQ. ID. 1, SEQ. ID. 2) and TCF12 (SEQ. ID. 43, SEQ. ID. 44);

SPIB (SEQ. ID. 3, SEQ. ID. 4), IRF8 (SEQ. ID. 1, SEQ. ID. 2) and TSC22D1 (SEQ. ID. 47, SEQ. ID. 48).

Another aspect of the present disclosure relates to a construct or vector encoding at least the combination of two isolated transcription factors described in the present disclosure, preferably the encoded combination of three transcription factors, wherein the combination of at least two isolated transcription factors is in the following sequential order from 5' to 3':

SPIB (SEQ. ID. 3, SEQ. ID. 4) and IRF8 (SEQ. ID. 1, SEQ. ID. 2);

IRF8 (SEQ. ID. 1, SEQ. ID. 2) and SPIB (SEQ. ID. 3, SEQ. ID. 4);

SPIB (SEQ. ID. 3, SEQ. ID. 4), IRF8 (SEQ. ID. 1, SEQ. ID. 2) and ARID5A (SEQ. ID. 5, SEQ. ID. 6);

SPIB (SEQ. ID. 5, SEQ. ID. 6), IRF8 (SEQ. ID. 1, SEQ. ID. 2) and BCL11A (SEQ. ID. 7, SEQ. ID. 8);

SPIB (SEQ. ID. 3, SEQ. ID. 4), IRF8 (SEQ. ID. 1, SEQ. ID. 2) and CBFA2T3 (SEQ. ID. 9, SEQ. ID. 10);

SPIB (SEQ. ID. 3, SEQ. ID. 4), IRF8 (SEQ. ID. 1, SEQ. ID. 2) and CREB3L2 (SEQ. ID. 11, SEQ. ID. 12);

SPIB (SEQ. ID. 3, SEQ. ID. 4), IRF8 (SEQ. ID. 1, SEQ. ID. 2) and ETS1 (SEQ. ID. 13, SEQ. ID. 14);

SPIB (SEQ. ID. 3, SEQ. ID. 4), IRF8 (SEQ. ID. 1, SEQ. ID. 2) and IKZF1 (SED. ID. 23, SEQ. ID. 24);

SPIB (SEQ. ID. 3, SEQ. ID. 4), IRF8 (SEQ. ID. 1, SEQ. ID. 2) and STAT1 (SEQ. ID. 45, SEQ. ID. 46);

SPIB (SEQ. ID. 3, SEQ. ID. 4), IRF8 (SEQ. ID. 1, SEQ. ID. 2) and TCF4 (SEQ. ID. 41, SEQ. ID. 42);

SPIB (SEQ. ID. 3, SEQ. ID. 4), IRF8 (SEQ. ID. 1, SEQ. ID. 2) and TCF12 (SEQ. ID. 43, SEQ. ID. 44);

SPIB (SEQ. ID. 3, SEQ. ID. 4), IRF8 (SEQ. ID. 1, SEQ. ID. 2) and TSC22D1 (SEQ. ID. 47, SEQ. ID. 48).

In an embodiment, the vector is a viral vector; in particular a retroviral, an adenoviral, a lentiviral, a herpes viral, a pox viral, paramyxoviridae, rabdoviral, alphaviral, flaviral or adeno-associated viral vector.

In an embodiment, the vector or construct is synthetic mRNA, naked alphavirus RNA replicons or naked flavivirus RNA replicons.

In an aspect of the present disclosure, one or more vectors comprises at least two polynucleotide sequences encoding at least the two transcription factors IRF and SPIB, for use in reprogramming a stem cell or a differentiated cell, or mixtures thereof, into a plasmacytoid dendritic cells or an interferon type I-producing cell in a subject.

In an embodiment of the present disclosure, the one or more vectors further code for one or more transcription factors selected from the group consisting of: ARID5A, BCL1A, CBFA2T3, CREB3L2, ETS1, IKZF1, STAT1, TCF4, TCF12 and TSC22D1, preferably BCL1A, CBFA2T3, CREB3L2, ETS1, IKZF1, TCF4, TCF12 and TSC22D1.

In an embodiment of the present disclosure, the transcription factors of the one or more vectors are individually at least 90% identical to the sequences selected from the group consisting of: IRF8 (SEQ. ID. 49, SEQ. ID. 50), SPIB (SEQ. ID. 51, SEQ. ID. 52), ARID5A (SEQ. ID. 53, SEQ. ID. 54), BCL11A (SEQ. ID. 55, SEQ. ID. 56), CBFA2T3 (SEQ. ID. 57, SEQ. ID. 58), CREB3L2 (SEQ. ID. 59, SEQ. ID. 60), ETS1 (SEQ. ID. 61, SEQ. ID. 62), IKZF1 (SEQ. ID. 71, SEQ. ID. 72), TCF4 (SEQ. ID. 89, SEQ. ID. 90), TCF12 (SEQ. ID. 91, SEQ. ID. 92), STAT1 (SEQ. ID. 93, SEQ. ID. 94), and TSC22D1 (SEQ. ID. 95, SEQ. ID. 96).

In an embodiment of the present disclosure, the combination of transcription factors of the one or more vectors is selected from the following combinations:

IRF8 and SPIB;

IRF8, SPIB and ARID5A;

IRF8, SPIB and BCL1A;

IRF8, SPIB and CBFA2T3;

IRF8, SPIB and CREB3L2;

IRF8, SPIB and ETS1;

IRF8, SPIB and IKZF1;

IRF8, SPIB and STAT1;

IRF8, SPIB and TCF4;

IRF8, SPIB and TCF12; and

IRF8, SPIB and TSC22D1.

In an embodiment of the present disclosure, the combination of transcription factors of the one or more vectors is the combination of IRF8, SPIB and TCF12.

In an embodiment of the present disclosure, the combination of transcription factors of the one or more vectors is the combination of IRF8, SPIB and TSC22D1.

In an embodiment of the present disclosure, the cell used for reprogramming using the one or more vectors is selected from the group consisting of: pluripotent stem cell, multipotent stem cell, differentiated cell, tumor cell, cancer cell and mixtures thereof.

In an embodiment of the present disclosure, the one or more vectors are for use in veterinary or human medicine, in particular in the diagnosis, therapy or treatment of antiviral immune responses and immune pathology, particularly in autoimmune diseases and immunodeficiency conditions, neoplasia in particular cancer, namely solid or hematological tumors, of benign tumor, malignant tumor, early cancer, basal cell carcinoma, cervical dysplasia, soft tissue sarcoma, germ cell tumor, retinoblastoma, age-related macular degeneration, Hodgkin's lymphoma, blood cancer, prostate cancer, ovarian cancer, cervix cancer, uterus cancer, vaginal cancer, breast cancer, naso-pharynx cancer, trachea cancer, larynx cancer, bronchi cancer, bronchioles cancer, lung cancer, hollow organs cancer, esophagus cancer, stomach cancer, bile duct cancer, intestine cancer, colon cancer, colorectum cancer, rectum cancer, bladder cancer, ureter cancer, kidney cancer, liver cancer, gall bladder cancer, spleen cancer, brain cancer, lymphatic system cancer, bone cancer, pancreatic cancer, leukemia, skin cancer, or myeloma, infectious disease, viral disease or viral induced disease, central and peripheral nervous system disorder, fungal, viral, chlamydial, bacterial, nanobacterial or parasitic infectious disease, or viral disease, or viral induced disease, as an antiviral agent or as an immunogenic composition, immunotherapy, or in the treatment or therapy of neurodegenerative diseases, in the treatment or therapy of cancer or in the treatment or therapy of an infectious diseases, intradermal and transdermal therapies, HIV, infection with SARS coronavirus, Asian flu virus, herpes simplex, influenza virus, herpes zoster, hepatitis, human papillomavirus, Epstein-Barr virus, human T-lymphotropic virus or viral hepatitis, an amyloid disease in particular Amyloid A amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy—Creutzfeldt Jakob disease or for drug screening.

Another aspect of the present disclosure relates to a method for reprogramming or inducing a cell into a plasmacytoid dendritic cell or interferon type I-producing cell, comprising the following steps:

transducing a cell selected from the group consisting of: a stem cell or a differentiated cell, and mixtures thereof, with one or more vectors comprising at least two nucleic acid sequences encoding a sequence at least 90% identical, preferably at least 95% identical, to a sequence selected from the group consisting of IRF8 (SEQ. ID. 1, SEQ. ID. 2), SPIB (SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), IKZF1 (SEQ. ID. 23, SEQ. ID. 24), TCF4 (SEQ. ID. 41, SEQ. ID. 42), TCF12 (SEQ. ID. 43, SEQ. ID. 44), STAT1 (SEQ. ID. 45, SEQ. ID. 46), TSC22D1 (SEQ. ID. 47, SEQ. ID. 48) and mixtures thereof;

culturing the transduced cell in a cell media that supports growth of plasmacytoid dendritic cells or interferon type I-producing cell.

Another aspect of the present disclosure relates to an in vitro method for reprogramming or inducing a cell into a plasmacytoid dendritic cell or interferon type I-producing cell, comprising the following steps:

transducing a cell selected from the group consisting of: a stem cell or a differentiated cell, and mixtures thereof, with one or more vectors comprising at least the two transcription factors IRF8 and SPIB, culturing the transduced cell in a cell media that supports growth of plasmacytoid dendritic cells or interferon type I-producing cell.

In an embodiment, the sequence is selected from the group of combinations consisting of IRF8 (SEQ. ID. 1, SEQ. ID. 2) and SPIB (SEQ. ID. 3, SEQ. ID. 4);

IRF8 (SEQ. ID. 1, SEQ. ID. 2), SPIB (SEQ. ID. 3, SEQ. ID. 4) and ARID5A (SEQ. ID. 5, SEQ. ID. 6);

IRF8 (SEQ. ID. 1, SEQ. ID. 2), SPIB (SEQ. ID. 5, SEQ. ID. 6) and BCL11A (SEQ. ID. 7, SEQ. ID. 8);

IRF8 (SEQ. ID. 1, SEQ. ID. 2), SPIB (SEQ. ID. 3, SEQ. ID. 4) and CBFA2T3 (SEQ. ID. 9, SEQ. ID. 10);

IRF8 (SEQ. ID. 1, SEQ. ID. 2), SPIB (SEQ. ID. 3, SEQ. ID. 4) and CREB3L2 (SEQ. ID. 11, SEQ. ID. 12);

IRF8 (SEQ. ID. 1, SEQ. ID. 2), SPIB (SEQ. ID. 3, SEQ. ID. 4) and ETS1 (SEQ. ID. 13, SEQ. ID. 14);

IRF8 (SEQ. ID. 1, SEQ. ID. 2, SPIB (SEQ. ID. 3, SEQ. ID. 4) and IKZF1 (SEQ. ID. 23, SEQ. ID. 24);

IRF8 (SEQ. ID. 1, SEQ. ID. 2, SPIB (SEQ. ID. 3, SEQ. ID. 4) and STAT1 (SEQ. ID. 45, SEQ. ID. 46);

IRF8 (SEQ. ID. 1, SEQ. ID. 2), SPIB (SEQ. ID. 3, SEQ. ID. 4) and TCF4 (SEQ. ID. 41, SEQ. ID. 42);

IRF8 (SEQ. ID. 1, SEQ. ID. 2), SPIB (SEQ. ID. 3, SEQ. ID. 4) and TCF12 (SEQ. ID. 43, SEQ. ID. 44);

IRF8 (SEQ. ID. 1, SEQ. ID. 2), SPIB (SEQ. ID. 3, SEQ. ID. 4) and TSC22D1 (SEQ. ID. 47, SEQ. ID. 48) and mixtures thereof.

In an embodiment, the sequence is selected from the group of combinations consisting of:

IRF8 and SPIB;

IRF8, SPIB and ARID5A;

IRF8, SPIB and BCL1A;

IRF8, SPIB and CBFA2T3;

IRF8, SPIB and CREB3L2;

IRF8, SPIB and ETS1;

IRF8, SPIB and IKZF1;

IRF8, SPIB and STAT1;

IRF8, SPIB and TCF4;

IRF8, SPIB and TCF12;

IRF8, SPIB and TSC22D1, and mixtures thereof.

In an embodiment, the method may comprise the step of culturing the transduced cell during at least 2 days, preferably at least 5 days, more preferably at least 8 days, even more preferably at least 9 days.

In an embodiment, the transducing step further comprises at least one vector selected from the group consisting of: a nucleic acid sequence encoding IL-12; nucleic acid sequence encoding IL-4; a nucleic acid sequence encoding IFN-α; a nucleic acid sequence encoding IFN-β; a nucleic acid sequence encoding IFN-γ; a nucleic acid sequence encoding TNF; nucleic acid sequence encoding GM-CSF; nucleic acid sequence encoding siRNAs targeting IL-10 RNA, and mixtures thereof.

In an embodiment, the transducing step further comprises at least one vector comprising nucleic acids encoding immunostimulatory cytokines.

In an embodiment, the cell is selected from the group consisting of: a pluripotent stem cell, a multipotent stem cell, or a differentiated cell, and mixtures thereof; in particular a mammalian cell.

In an embodiment, the pluripotent stem cell, multipotent stem cell, or differentiated cell, is selected from the group consisting of: an endoderm-derived cell, a mesoderm-derived cell, an ectoderm-derived cell, a multipotent stem cell including a mesenchymal stem cell, a hematopoietic stem cell, an intestinal stem cell, a pluripotent stem cell and a cell line.

In an embodiment, the cell is human or non-human. In another embodiment, the cell is a mouse cell.

Another aspect of the present disclosure relates to an induced plasmacytoid dendritic cell or interferon type I-producing cell or an antigen presenting cell obtained by the in vitro method described in the present disclosure, preferably an induced plasmacytoid dendritic cell or interferon type I-producing cell.

Another aspect of the present disclosure relates to a composition comprising a plasmacytoid dendritic cell, or an interferon type I-producing cell, or an antigen presenting cell described in the present disclosure, preferably an induced plasmacytoid dendritic cell or interferon type I-producing cell, in a therapeutically effective amount and a pharmaceutically acceptable excipient.

In an embodiment, the composition may be used in veterinary or human medicine.

In an embodiment, the composition may be used in immunotherapy, or in the treatment or therapy of neurodegenerative diseases, or in the treatment or therapy of cancer or in the treatment or therapy of infectious diseases.

In an embodiment, the composition may further comprise an analgesic, an anti-inflammatory agent, a chemotherapy agent, a radiotherapy agent, an antibiotic, a diuretic, or mixtures thereof.

In an embodiment, the composition may further comprise a filler, a binder, a disintegrant, or a lubricant, or mixtures thereof.

In an embodiment, the composition may be used in intradermal and transdermal therapies.

In an embodiment, the composition may be in an injectable formulation, preferably an in-situ injection.

In an embodiment, the composition may be used in veterinary or human medicine, or in a drug screening.

In an embodiment, the composition may be used in the treatment, therapy or diagnosis of a central and peripheral nervous system disorder.

In an embodiment, the composition may be used in the treatment, therapy or diagnosis of neoplasia, in particular cancer, such as solid or hematological tumours.

In an embodiment, the composition, vectors or constructs may be used in the treatment, diagnostic or therapy of benign tumors, malignant tumors, early cancer, basal cell carcinoma, cervical dysplasia, soft tissue sarcoma, germ cell tumors, retinoblastoma, age-related macular degeneration, Hodgkin's lymphoma, blood cancer, prostate cancer, ovarian cancer, cervix cancer, uterus cancer, vaginal cancer, breast cancer, naso-pharynx cancer, trachea cancer, larynx cancer, bronchi cancer, bronchioles cancer, lung cancer, hollow organs cancer, esophagus cancer, stomach cancer, bile duct cancer, intestine cancer, colon cancer, colorectum cancer, rectum cancer, bladder cancer, ureter cancer, kidney cancer, liver cancer, gall bladder cancer, spleen cancer, brain cancer, lymphatic system cancer, bone cancer, pancreatic cancer, leukemia, skin cancer, or myeloma.

In an embodiment, the composition, vectors, or constructs may be used in the treatment, therapy or diagnosis of a fungal, viral, chlamydial, bacterial, nanobacterial or parasitic infectious disease, or a viral disease, or a viral-induced disease.

In an embodiment, the composition, vectors, or constructs may be used in the treatment, therapy or diagnosis of HIV, infection with a SARS coronavirus, Asian flu virus, herpes simplex, influenza virus, herpes zoster, hepatitis, human papillomavirus, Epstein-Barr virus, human T-lymphotropic virus or viral hepatitis.

In an embodiment, the composition, vectors, or constructs may be used in the treatment, therapy or diagnosis of an amyloid disease in particular Amyloid A amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy, such as Creutzfeldt Jakob disease.

Another aspect of the present disclosure relates to a vaccine or an injectable formulation comprising the composition, vectors, or constructs described in the present disclosure, and/or an induced plasmacytoid dendritic cell or interferon type I-producing cell as described or antigen presenting cell described in the present disclosure or mixtures thereof.

Another aspect of the present disclosure relates to a kit comprising at least one of the following components:
  the induced plasmacytoid dendritic cell or interferon type I-producing cell or antigen presenting cell of the present disclosure;
  the composition as described in the present disclosure;
  the one or more vector or construct as described in the present disclosure; or mixtures thereof.

Another aspect of the present disclosure relates to a kit comprising at least one of the following components:
  the induced plasmacytoid dendritic cell or interferon type I-producing cell of the present disclosure;
  the composition as described in the present disclosure;
  the one or more vectors or construct as described in the present disclosure; or mixtures thereof.

In an embodiment, the present disclosure provides evidence that IRF8, when combined with SPIB, kick-start a pDC program in fibroblasts. These findings provide valuable insights into pDC specification. In the future, the generation of pDCs by direct reprogramming opens avenues for inducing anti-viral immune responses with autologous-engineered cells.

DESCRIPTION OF DRAWINGS

The following figures provide preferred embodiments for illustrating the disclosure and should not be seen as limiting the scope of invention.

(CpG ODN 1668) and IFN-α (A), IFN-β (B) and IL-10 (C) cytokine secretion was quantified on supernatants using a cytometry bead array.

Figure 14:
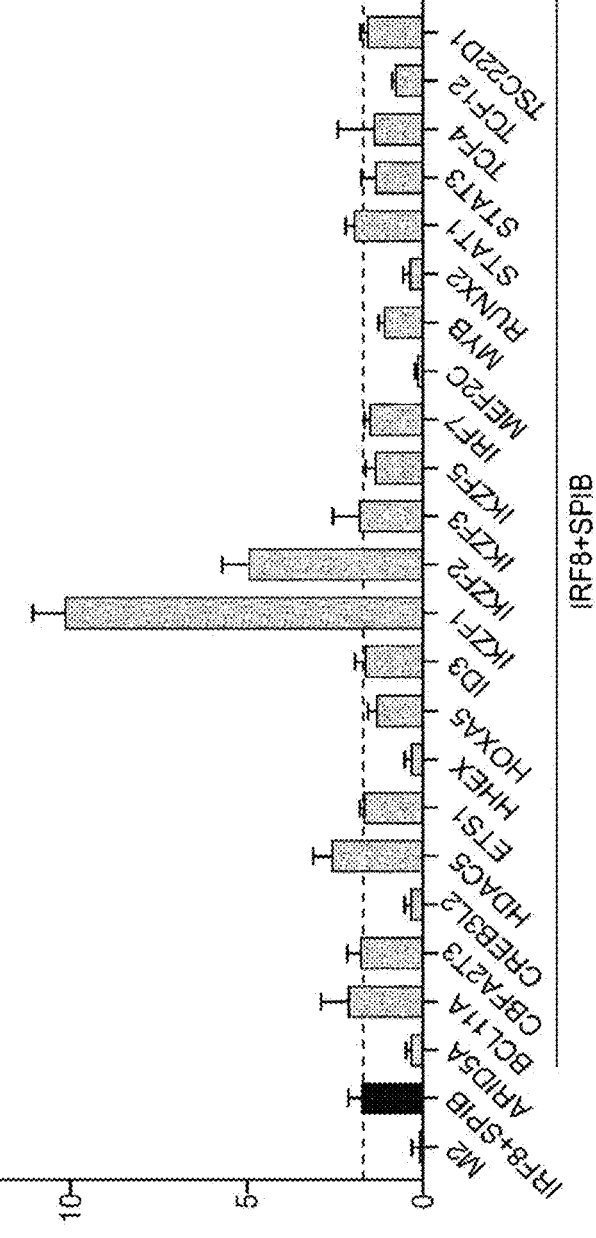
Figure 15A:
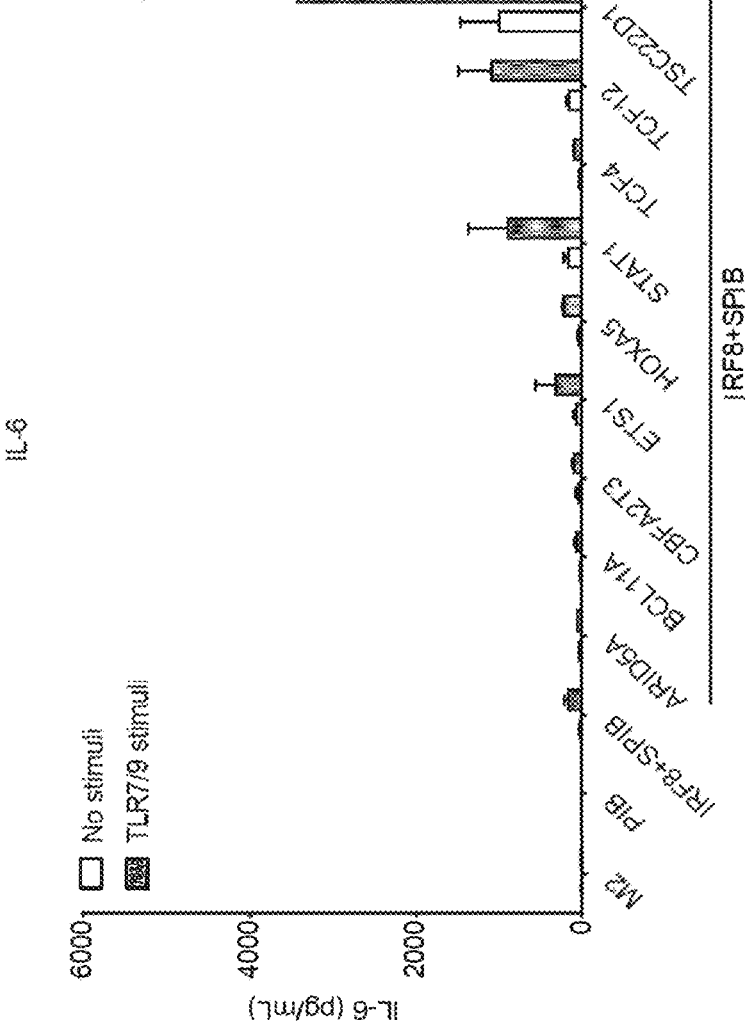
Figure 15B:
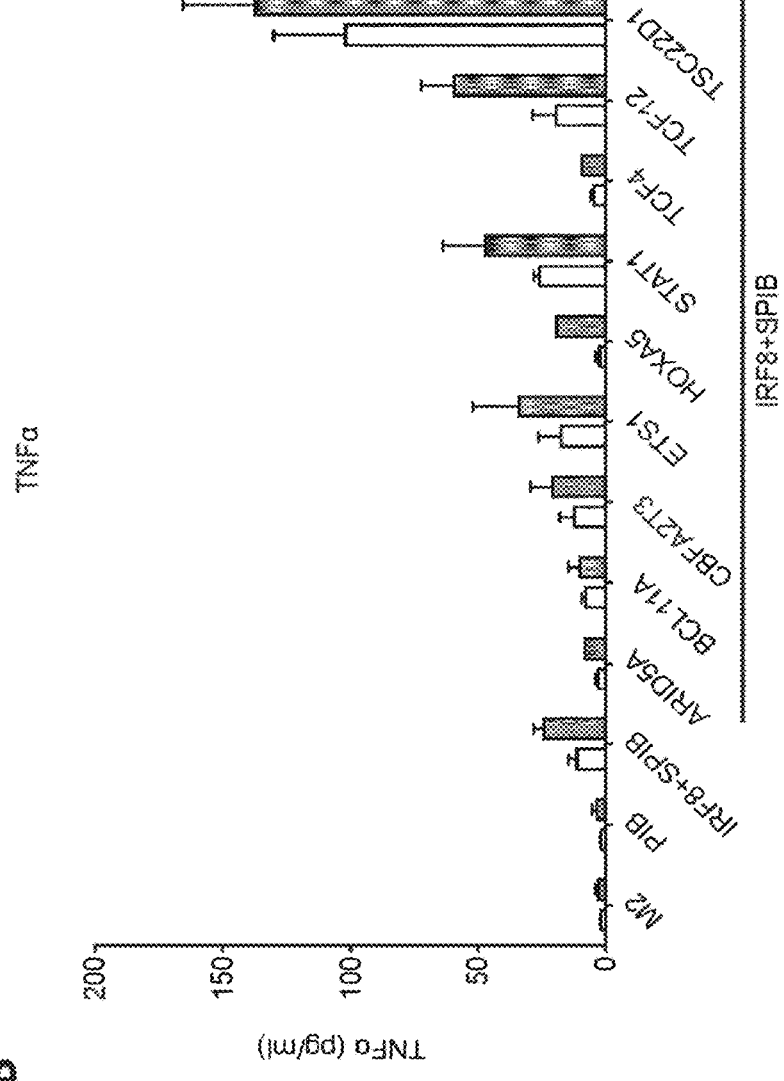
Figure 15C:
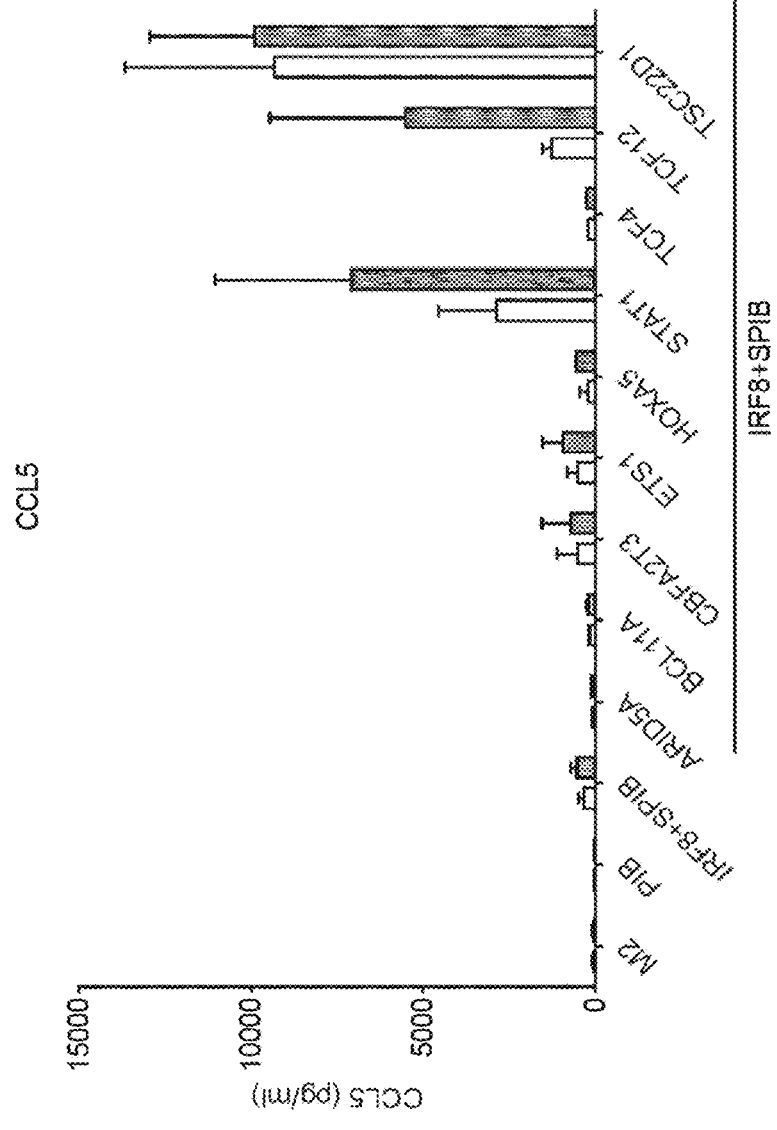
Figure 15D:
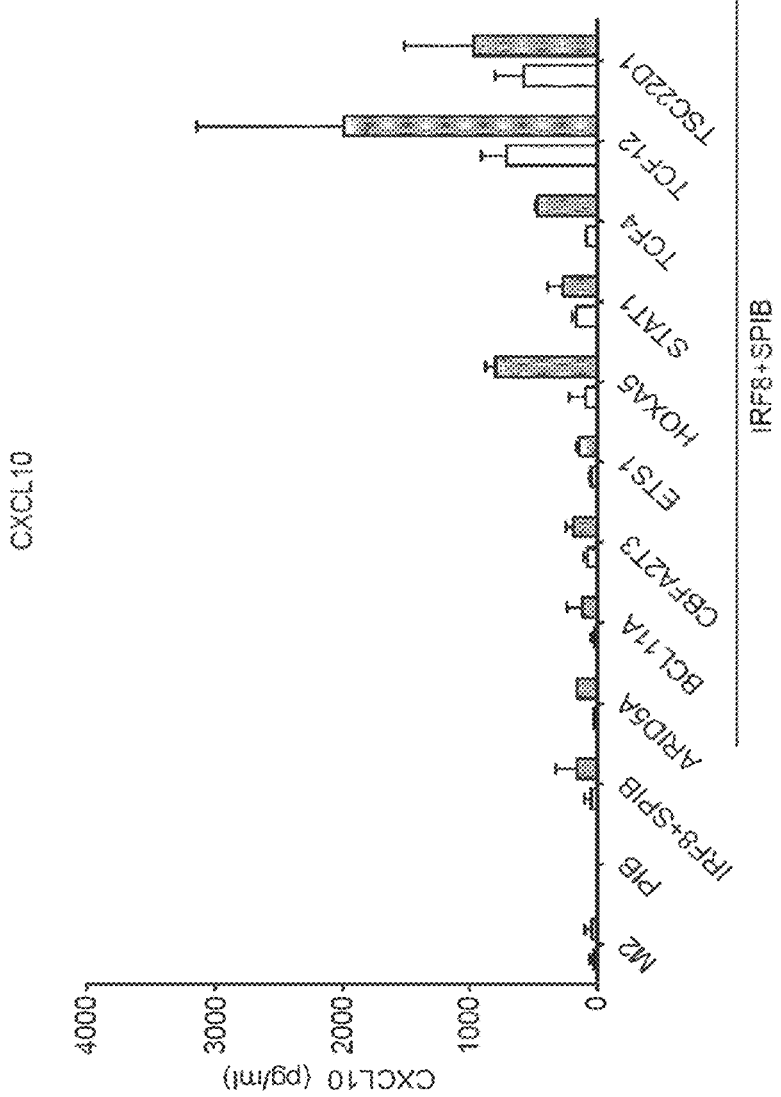

FIG. 14. Induced pDCs express CD45 at cell surface. Flow cytometry analysis of CD45 expression of MEFs transduced with M2rtTA, PIB (PU.1, IRF8 and BATF3), IRF8+SPIB alone or combined with individual pDC-inducing TFs, at day 5. M2rtTa (M2)-transduced cells were included as control.

FIG. 15. Induced pDCs secrete pro-inflammatory cytokines and chemokines upon TLR7 and TLR9 stimulation. MEFs were transduced with M2rtTA, IRF8 and SPIB alone or combined with ARID4A, BCL11A, CBFA2T3, ETS1, HOXA5, STAT1, TCF4, TCF12 and TSC22D1 and tdTomato+ cells were sorted at day 9 after addition of doxycycline. Purified tdTomato+ cells were incubated overnight with TLR7 (R848) and TLR9 (CpG ODN 1668) and IL-6 (A), TNF-α (B), CCL5 (C) and CXCL10 (D) cytokine secretion was quantified on supernatants using a cytometry bead array.

DETAILED DESCRIPTION

The present disclosure relates to compositions, nucleic acid constructs, vectors, methods and kits thereof for reprogramming cells into pDCs or interferon type I-producing cells. The aim is to produce pDCs and interferon type I-producing cells with the ability to induce antiviral and anti-tumoral responses from differentiated, multipotent or pluripotent stem cells by introducing and expressing isolated/synthetic transcription factors. More particularly, the disclosure provides methods for obtaining pDCs or interferon type I-producing cells by direct cellular reprogramming with the surprising use of combinations of specific transcription factors.

Figure 1:
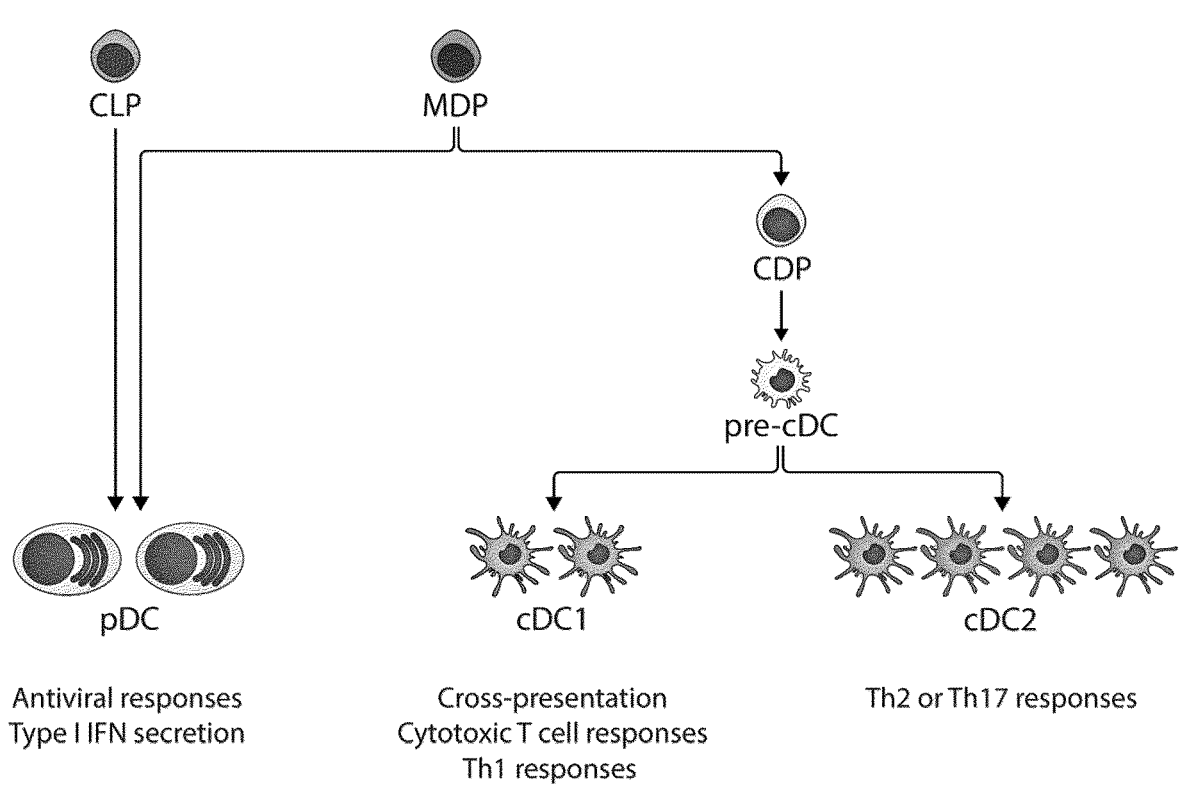
FIG. 1. Ontogeny of the main subsets of dendritic cells. While conventional dendritic cells type 1 (cDC1) and type 2 (cDC2) emerge from a pre-DC population derived from common dendritic cell Progenitors (CDP), plasmacytoid dendritic cells (pDCs) can derive either from common lymphocyte progenitors (CLP) or CDPs. pDCs emerge as a unique subset of DCs specialized in the production of type I Interferons (IFNs) following viral infection. cDC1 s excel on the ability to perform cross-presentation, inducing cytotoxic T cell responses, and polarize preferentially T helper 1 responses. cDC2s excel on presenting antigens to T helper cells polarizing T helper 2 or 17 responses.

Natural DCs are bone marrow-derived cells that are seeded in all tissues. DCs are poised to sample the environment and to transmit the gathered information to cells of the adaptive immune system (T cells and B cells). Upon antigen engulfment, DCs initiate an immune response by presenting the processed antigen, which is in the form of peptide-major histocompatibility complex (MHC) molecule complexes, to naive (that is, antigen inexperienced) T cells in lymphoid tissues. DCs can be divided in 2 main subsets: plasmacytoid DCs (pDCs), and conventional or classical DCs (cDCs) that can be further sub-divided in cDCs type 1 (cDC1s) and type 2 (cDC2s) (FIG. 1). pDCs are typically characterized by a round morphology and by the expression of low levels of MHC-1l that are up-regulated after activation. After activation, pDCs typically overexpress co-stimulatory and MHC molecules in addition to secrete various cytokines and chemokines responsible for initiating and/or enhancing many T and B lymphocyte responses, i.e. tumor necrosis factor (TNF)-α, IFN-α, IFN-β, IL-12, IL-6 and chemokines such as CCL5 and CXCL10. pDCs express high levels of the nucleic-acid sensing toll-like receptors (TLRs) TLR7 and TLR9. TLR7 or TLR9 stimulation allows the detection of pathogen-derived nucleic acids by pDCs and the production of large amounts of type I interferon i.e. IFN-α and IFN-β. Although activated pDCs can actively produce cytokines and perform both antigen presentation and cross-presentation, it is still unclear whether these functional features are performed by the same cells or by distinct functionally specialized pDC subsets. cDCs are generally identified by their high expression of major histocompatibility complex class II molecules (MHC-II), co-stimulatory molecules, such as CD80/86 and CD40, and integrin CD11c, as well as their superior capacity to migrate from non-lymphoid to lymphoid organs and stimulate naïve T cells. DNGR-1, also known as CLEC9A, is a receptor for necrotic cells that favors cross-priming of cytotoxic T lymphocyte responses (CTL) to dead cell-associated antigens in mice. DNGR-1 is selectively expressed at high levels by mouse cDC1, cDC2 and pDCs, being responsible for recognizing an intracellular ligand exposed after cell death. Recently, expression of Clec9a was shown to allow the identification of DC precursors (CDPs) committed to the conventional or plasmacytoid DC lineages and their progeny in lymphoid tissues (Schraml et al., 2015).

The successful identification of pDC-inducing factors capable of reprogramming differentiated cells to induced pDCs, as described herein, can advance our basic understanding of pDC biology in a number of ways. This work will provide thorough insight into pDC minimal transcriptional networks. In addition, the identification of pDC-inducing factors offer unprecedented opportunities to understand how pDC state is established and how key regulatory machinery is put into place.

Transcription factors (TFs) play a critical role in the specification of all cell types during development. The success of direct reprogramming strategies using TF-mediated reprogramming indicates that it is equally plausible to direct the differentiation of pluripotent ES/iPS cells or multipotent stem cells to specific fates using such factors. Accordingly, using the pDC-inducing factors identified herein, directed differentiation of ES/iPS cells to a definitive DC fate by expression of the DC-enriched TFs can be achieved. Additionally, using the pDC-inducing factors identified herein, directed differentiation of multipotent hematopoietic stem and progenitor cells to a definitive DC fate by expression of the DC-enriched TFs can be achieved.

Figure 2:
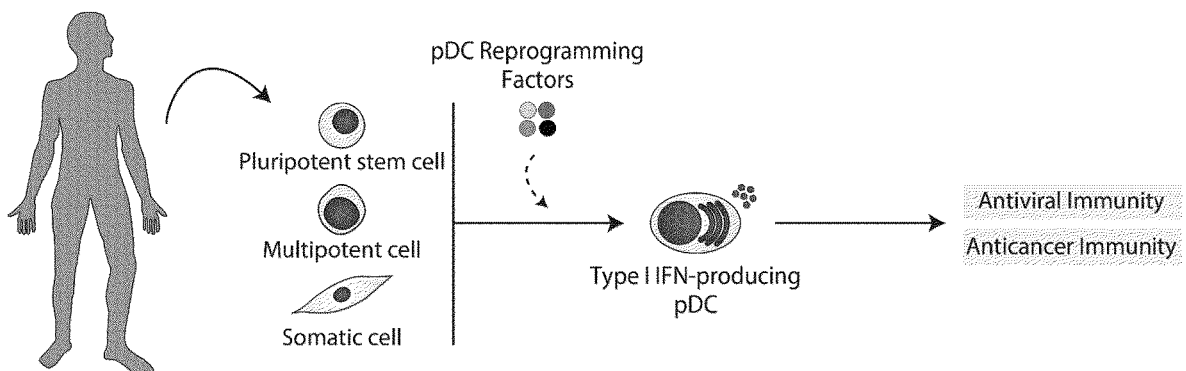
FIG. 2. Generating pDC or interferon (IFN) type I-producing cells by direct cellular reprogramming. Observation of the effect of the transcription factor (TF) combination disclosure in the present subject-matter for the induction of pDCs from pluripotent stem cells, multipotent stem cells and somatic cells, such as fibroblasts. pDCs are specialized in producing type I IFNs, and so will be applied in the context of personalized immunotherapy. Induced pDCs or pDC-inducing TF combinations will be used to induce immunity in distinct diseased context including viral infection and cancer.

Typically, nucleic acids encoding the pDC-inducing factors, e.g., DNA or RNA, or constructs thereof, are introduced into a cell, using viral vectors or without viral vectors, via one or repeated transductions or transfections, and the expression of the gene products and/or translation of the RNA molecules result in cells that are morphologically, biochemically, and functionally similar to pDCs, as described herein. These induced pDCs after priming with the adequate antigens have the ability to capture, process and present them to effectors cells of the immune system (macrophages, T-cells, B-cells, NK cells) and secrete type I IFNs, eliciting antigen-specific immune responses against viral infections and cancer (FIG. 2).

An aspect of the present disclosure is the use of TFs or the use of a combination of TFs in cancer cells (in situ or ex vivo) to force them to secrete type I IFN, present their own antigens to immune cells and secrete other pro-inflammatory cytokines and chemoattractants within the tumor microenvironment. This method represents a feasible strategy to increase the clinical outcome of anticancer immunotherapies as it bypasses cancer evasion mechanisms and increases tumor immunogenicity.

Figure 3:
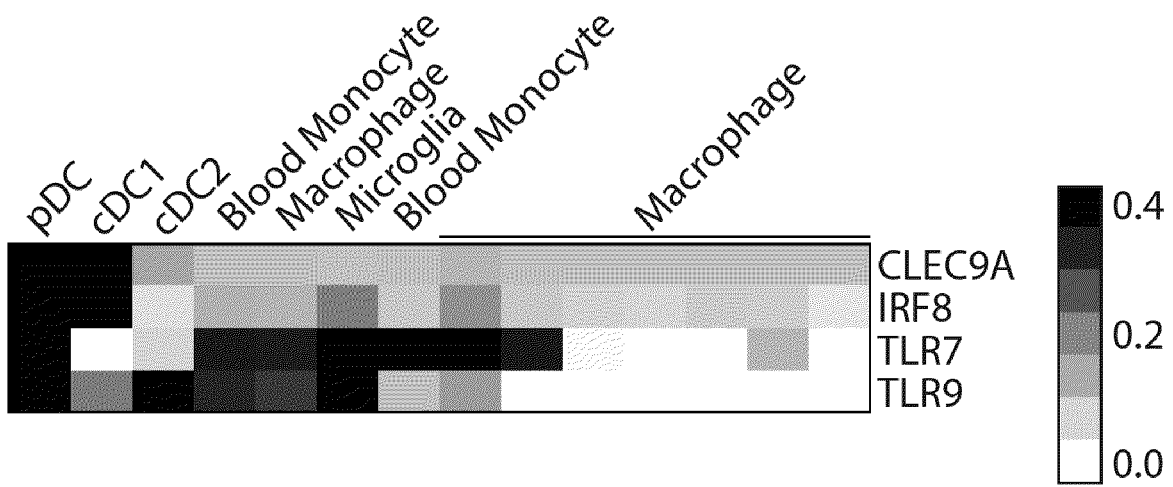
FIG. 3. Expression of Clec9a, Irf8, Tlr7 and Tlr9 is restricted to pDC. Heat map showing expression levels of Clec9a, Irf8, Tlr7 and Tlr9 in pDCs and other immune cells close in ontogeny, in particular cDC1 and cDC2, macrophages and monocytes. Expression profiles were obtained from data available in Immunological Genome Project (www.immaen.com).

Plasmacytoid DCs specifically express Tlr7 and Tlr9 when compared to cDC1 s and cDC2 and other related mononuclear cells (FIG. 3). TLR7 and TRL9 receptors allow pDCs to sense viral DNA and respond by secreting type I IFNs. Plasmacytoid DCs, as well as cDC1 s, express Clec9a and Irf8.

In an embodiment, 22 candidate TFs were selected due to their specific enriched gene expression in plasmacytoid DCs when compared to cDC1s and cDC2s (FIG. 4). 22 candidate TFs were cloned individually in a reprogramming proven Doxycycline (Dox)-inducible lentiviral vector.

Figure 4:
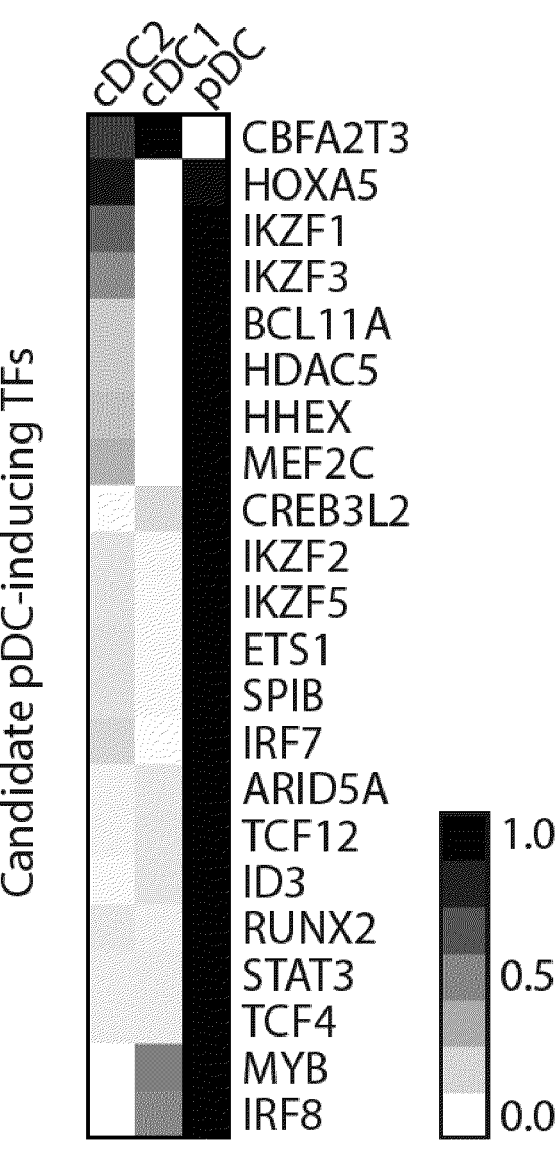
FIG. 4. TF candidates to induce pDCs. Twenty-two candidate TFs are highly enriched in pDCs, when compared with cDC1 and cDC2. Heat map showing gene expression profiles extracted from data available in Immunological Genome Project.
Figure 5:
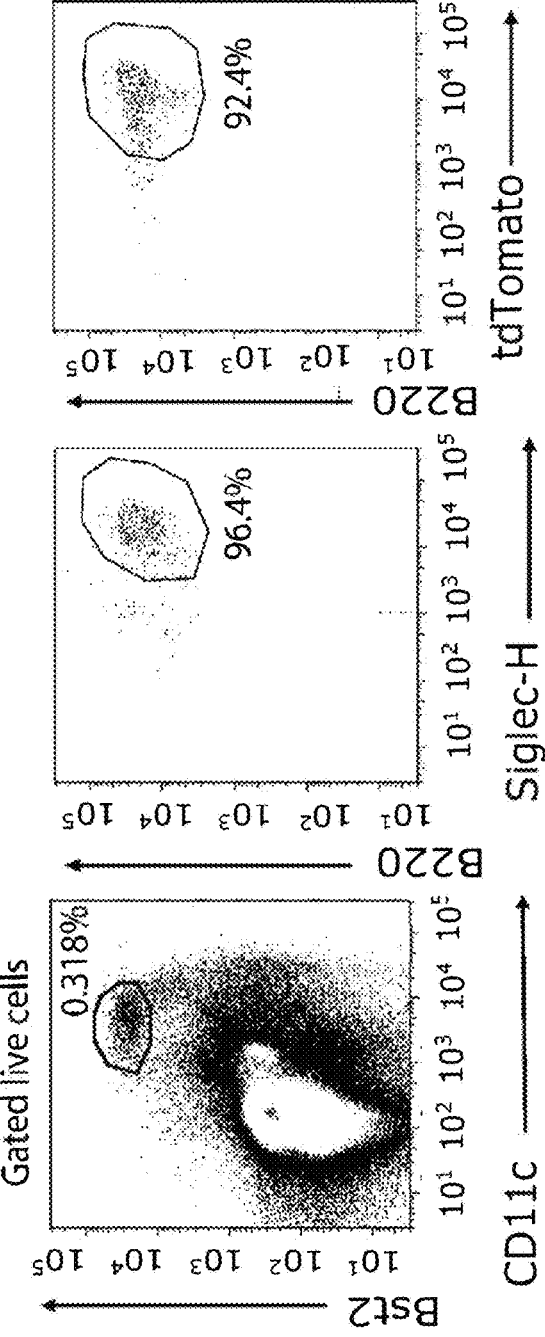
FIG. 5. Clec9a is expressed in pDCs. Expression of tdTomato on 92% of pDCs (gated as CD11c$^{low}$ BST2$^+$ B220$^+$ Siglec-H$^+$ cells) isolated from spleens of double transgenic Clec9a-Cre×Rosa26-STOP-tdTomato.

In an embodiment, in order to screen the effect of the pDC-inducing TFs and pDC-inducing TF combinations by cellular reprogramming, mouse embryonic fibroblasts (MEFs) harboring a DC-specific reporter (Clec9a-Cre×R26-stop-tdTomato) were used to screen pDC-inducing TFs ability to activate the DC-specific Clec9a-tomato reporter (FIG. 4). In Clec9a-tomato reporter mouse, the tdTomato fluorescent protein is expressed exclusively by CDPs, pre-DCs, cDCs and pDCs (Schraml et al., 2015). Macrophages, other immune lineages or monocyte-derived DCs in culture do not express Clec9a and therefore don't activate the reporter or expression of the tdTomato protein (FIG. 3). Spleen cells isolated from Clec9a reporter mice were analyzed, confirming that 92.4% of pDC cells (gated in CD11c$^{low}$ BST2$^+$ B220$^+$ SiglecH$^+$ cells) express the tdTomato fluorescent protein (FIG. 5).

Double transgenic Clec9a-tdTomato reporter MEFs were isolated from E13.5 embryos and excluded from any contaminating tdTomato+ or CD45+ cell that could be already committed to the hematopoietic lineage by fluorescent-activated cell sorting (FACS).

In an embodiment, SPIB and IRF8 are sufficient for Clec9a activation.

Figure 6:
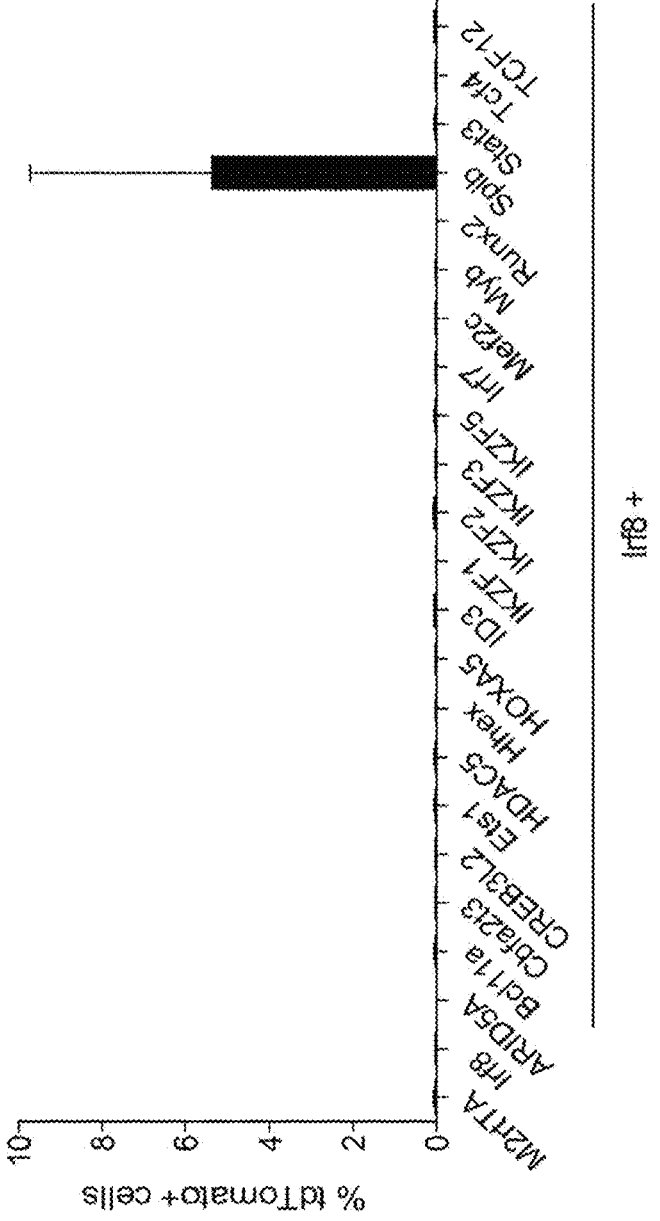
FIG. 6. IRF8 combined with SPIB induces Clec9a reporter activation. Mouse embryonic fibroblasts (MEFs) isolated from double transgenic Clec9a-tdTomato mice were transduced with pools of inducible lentiviral vectors encoding IRF8 alone or combined with additional pDC-inducing TFs and analyzed by flow cytometry 5 days after addition of Dox. Quantification of tdTomato+ cells after transduction with IRF8 alone or combined with individual pDC-inducing candidate TFs. M2rtTA-transduced cells were included as control.

In an embodiment, Clec9a reporter MEFs were transduced with IRF8 alone or combinations of 2 with IRF8 plus one of the other 21 candidate TFs and evaluated for tdTomato expression. After transduction with the 21 combinations of 2 candidate TFs or IRF8 alone, it was observed the emergence of tdTomato+ cells 5 days after adding Dox (FIG. 6). The combination of IRF8 and SPIB generated 5% of tdTomato+ cells, suggesting that IRF8 and SPIB are a minimal combination of factors required to induce reporter activation. TdTomato+ cells were not detected after transduction with control M2rtTA vector neither with IRF8 alone.

Figure 7:
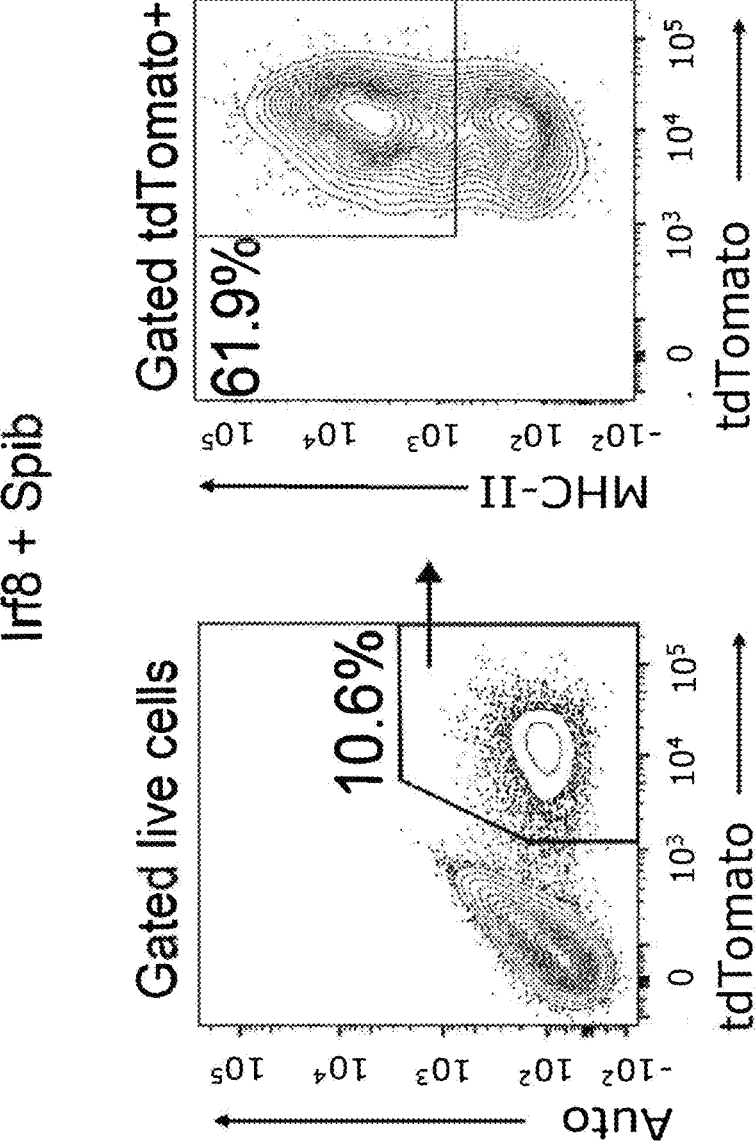
FIG. 7. Induced pDCs express antigen presenting molecules at cell surface. Flow cytometry analysis of major histocompatibility complex class II (MHC-II) expression of tdTomato+ cells generated after overexpression of IRF8 and SPIB at day 8.

In an embodiment, the antigen presenting cell marker MHC-II is expressed in approximately 60% of MEFs transduced with IRF8 and SPIB (FIG. 7).

Figure 8:
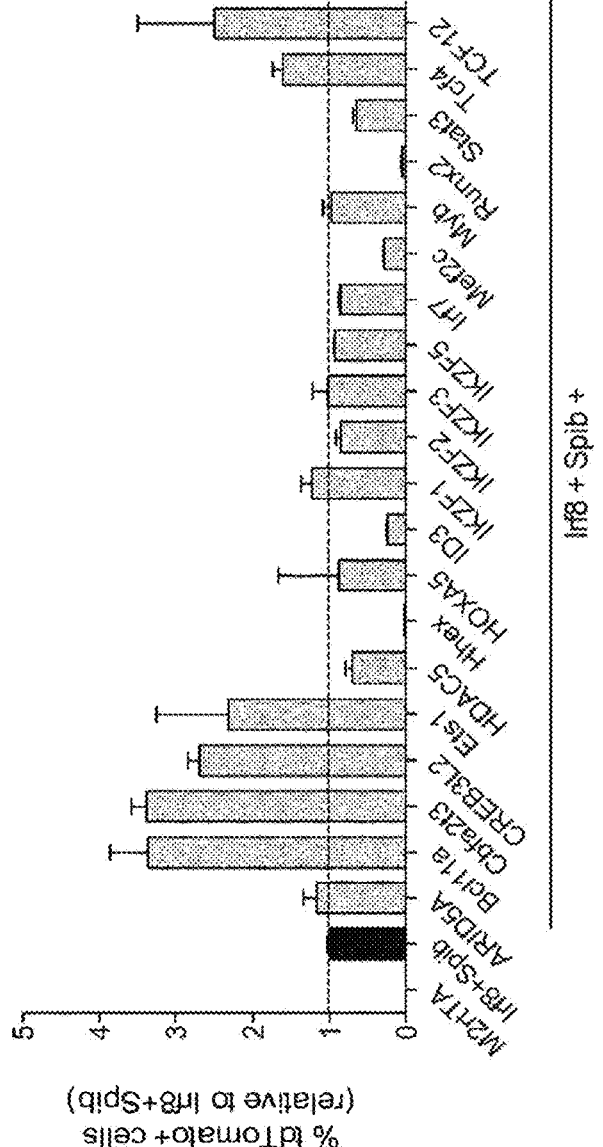
FIG. 8. Combination of additional pDC-inducing TFs with IRF8 and SPIB increases the efficiency of Clec9a reporter activation. Quantification of tdTomato+ cells after transduction of double transgenic Clec9a-tdTomato MEFs with IRF8 and SPIB alone or combined with individual pDC-inducing factors. Flow cytometry analysis was performed at day 8. M2rtTa-transduced cells were included as control.

In an embodiment the impact of expressing the remaining 20 candidates TFs together with IRF8 and SPIB was evaluated (FIG. 8). From the 20 TFs tested it was observed that HHEX, ID3, MEF2C and RUNX2 negatively impact the numbers of tdTomato+ cells generated. The addition of ARID5A, HDAC5, HOXA5, IKZF1, IKZF2, IKZF3, IKZF5, IRF7, MYB and STAT3 didn't impact the numbers of tdTomato+ cells generated. The addition of BCL11A, CBFA2T3, CREB3L2, ETS1, TCF12 and TCF4 positively impact the numbers of tdTomato+ cells generated, increasing the efficiency of reporter activation.

Figure 9:
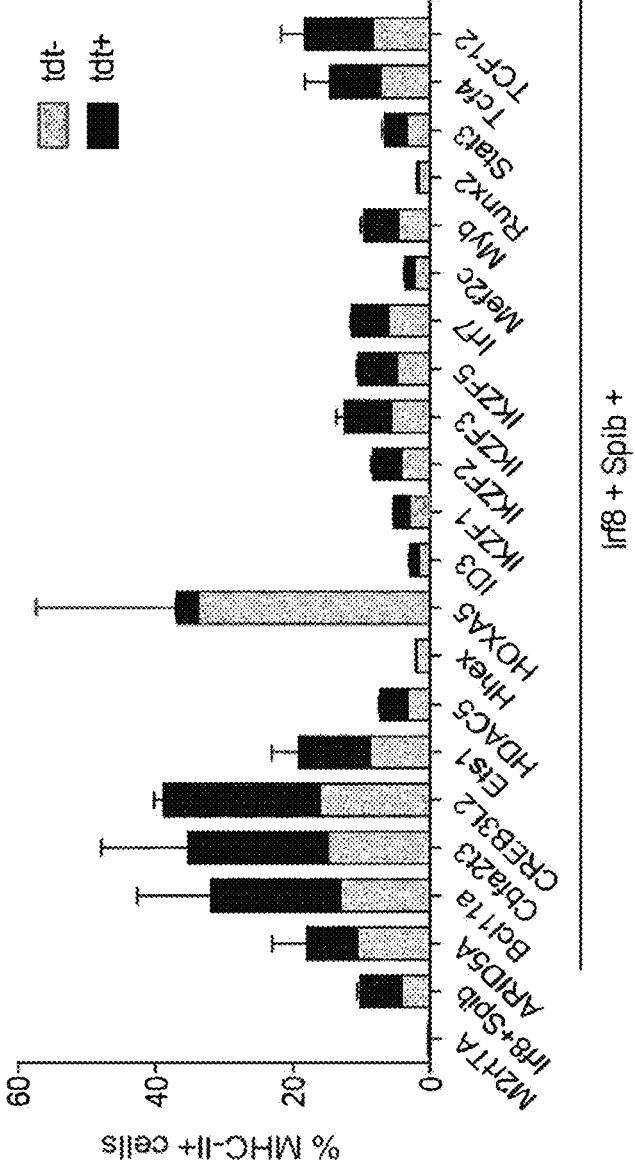
FIG. 9. Combination of additional pDC-inducing TFs with IRF8 and SPIB increases expression of MHC-II at cell surface. Flow cytometry analysis of MHC-II expression of MEFs transduced with M2rtTA, IRF8+SPIB alone or combined with individual pDC-inducing TFs, at day 8. Quantification of MHC-II levels is shown for tdTomato negative (tdT−) and positive (tdT+) populations.

In an embodiment it was evaluated if the activation of the Clec9a-tdTomato reporter was reflected in the surface expression of MHC-II, a key component of the antigen presentation machinery. Remarkably, it was observed that tdTomato+ cells at day 8 expressed MHC-II at the surface (FIG. 9).

Figure 10A:
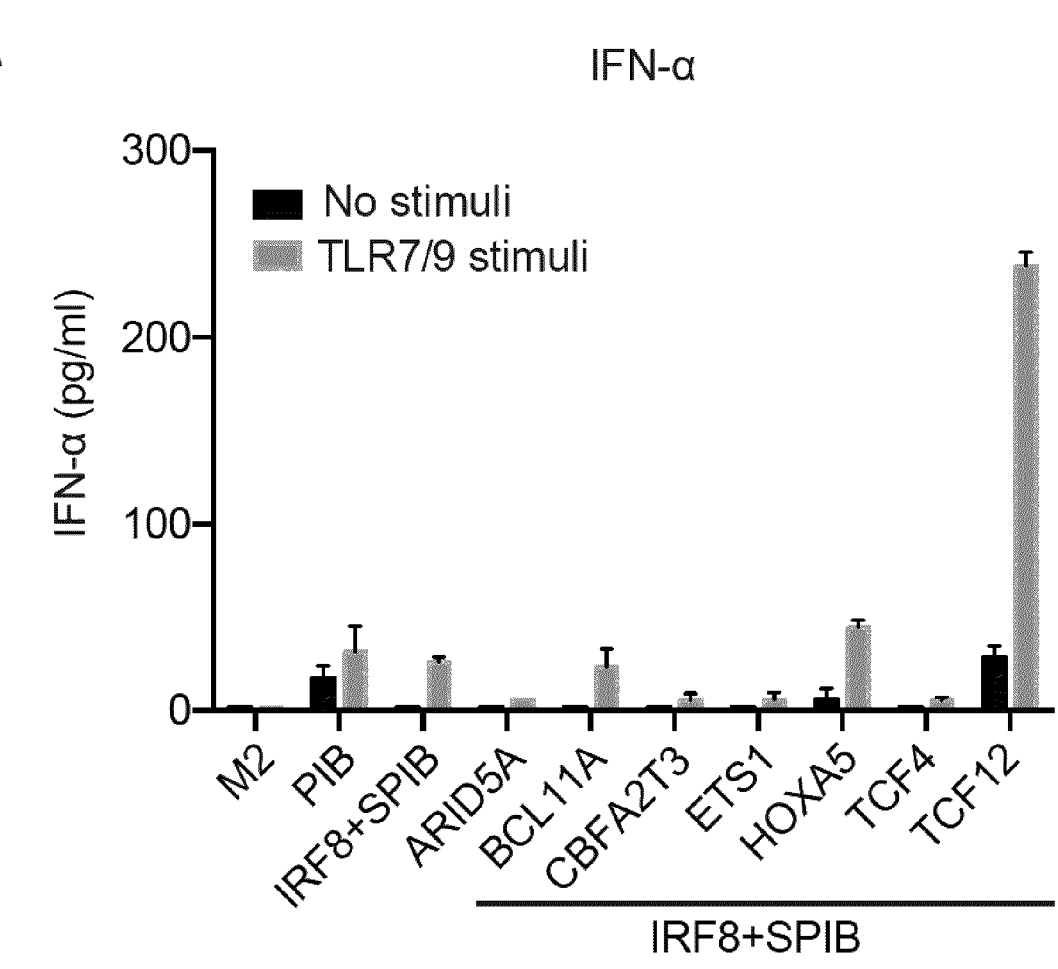
FIG. 10. Induced pDCs secrete type I Interferon upon TLR7 and TLR9 stimulation. MEFs were transduced with M2rtTA, PIB (PU.1, IRF8 and BATF3), IRF8 and SPIB alone or combined with ARID5A, BCL11A, CBFA2T3, ETS1, HOXA5, TCF4 and TCF12 and tdTomato+ cells were sorted at day 9 after addition of doxycycline. Purified tdTomato+ cells were incubated overnight with TLR7 (R848) and TLR9 (CpG ODN 1668) and IFN-α (A), IFN-β (B) and IL-10 (C) cytokine secretion was quantified on supernatants using a cytometry bead array.
Figure 10B:
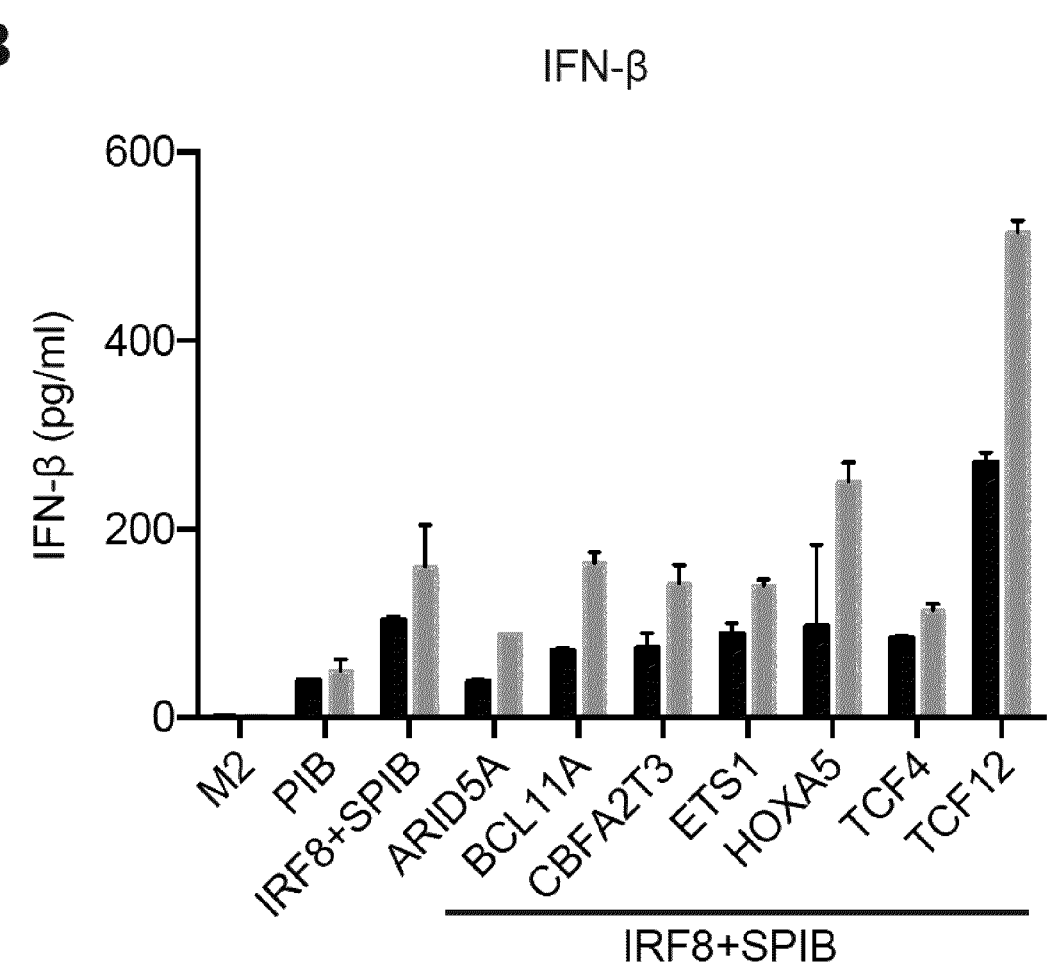
Figure 10C:
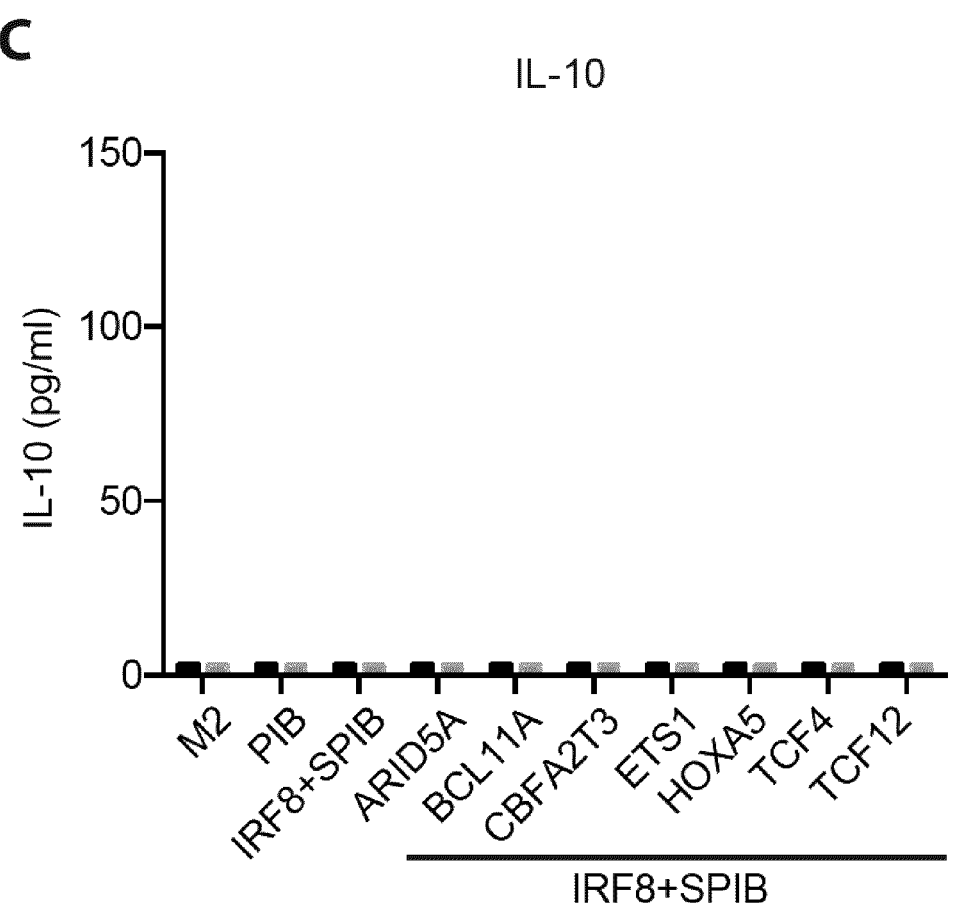

In an embodiment, in addition to MHC-II surface molecule, pDCs secrete cytokines with a pro-inflammatory function that are important for the development of T-cell responses. These responses can be initiated by the triggering of at least 11 different Toll-like receptors (TLRs), allowing the specific recognition of distinct conserved microbial or viral structures. Within the DC compartment, pDCs specifically respond to TLR7 and TLR9 triggering (FIG. 3). It was studied whether induced pDCs secrete cytokines to the media when challenged with TLR7 (using Resiquimod or R848) and TLR9 (using ODN 1668) stimulation (FIG. 10). Upon TLR challenge of induced pDCs it was observed an increase in the secretion of IFN-α by tdTomato+ cells reprogrammed with IRF8 and SPIB (16.6 fold); IRF8, SPIB and ARID5A (3.9 fold); IRF8, SPIB and BCL11A (14.8 fold); IRF8, SPIB and CBFA2T3 (3.5 fold); IRF8, SPIB and ETS1 (3.7 fold); IRF8, SPIB and TCF4 (3.6 fold); IRF8, SPIB and TCF12 (8.3 fold); and IRF8, SPIB and HOXA5 (7.7 fold), when comparing stimulated with non-stimulated cells generated by each TF combination. TLR challenge of induced pDCs also increased the secretion of IFN-β by tdTomato+ cells reprogrammed with IRF8 and SPIB (1.5 fold); IRF8, SPIB and ARID5A (2.3 fold); IRF8, SPIB and BCL11A (2.3 fold); IRF8, SPIB and CBFA2T3 (1.9 fold); IRF8, SPIB and ETS1 (1.6 fold); IRF8, SPIB and TCF4 (1.3 fold); IRF8, SPIB and TCF12 (1.9 fold); and IRF8, SPIB and HOXA5 (2.6 fold). Upon TLR stimulation of induced pDCs no increase in the secretion of the anti-inflammatory cytokine IL-10 was observed. Importantly, tdTomato+ cells obtained upon transduction with PU.1, IRF8 and BATF3 (PIB) combination of TFs did not respond to TLR7 and TLR9 and did not secrete IFN-α and IFN-β. Taken together, these data suggests that by combining Clec9a reporter activation with interferon secretion ability, we successfully identified combinations of TFs able to induce pDCs or interferon type I-secreting cells by direct cell reprogramming.

Figure 11:
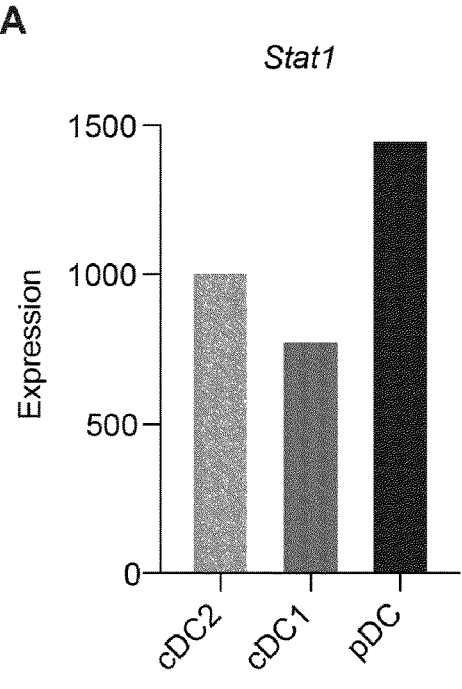
FIG. 11. Additional TF candidates to induce pDCs. Stat1 (A) and Tsc22d1 (B) are enriched in pDCs, when compared with cDC1 and cDC2. Gene expression profiles extracted from data available in Immunological Genome Project.
Figure 11:
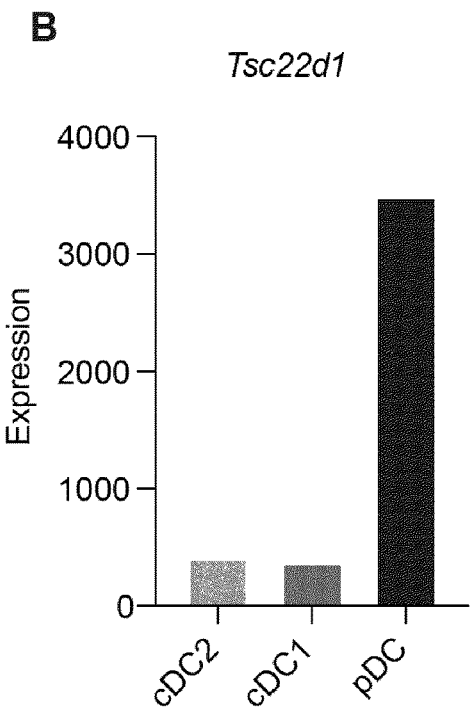
Figure 12:
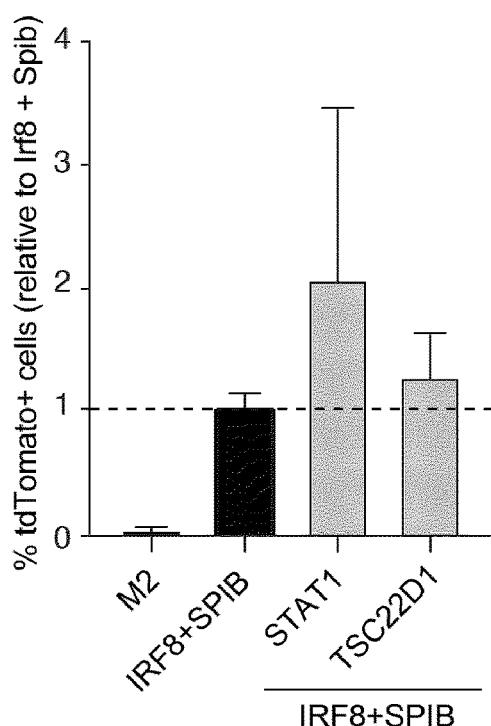
FIG. 12. Combination of additional pDC-inducing TFs with IRF8 and SPIB increases the efficiency of Clec9a reporter activation and MHC-1l surface expression. Flow cytometry analysis of (A) Clec9a reporter activation and (B) MHC-1l expression of MEFs transduced with M2rtTA (M2), IRF8+SPIB alone or combined with STAT1 or with TSC22D1. Flow cytometry analysis was performed at day 5. M2rtTa-transduced cells were included as control.
Figure 12:
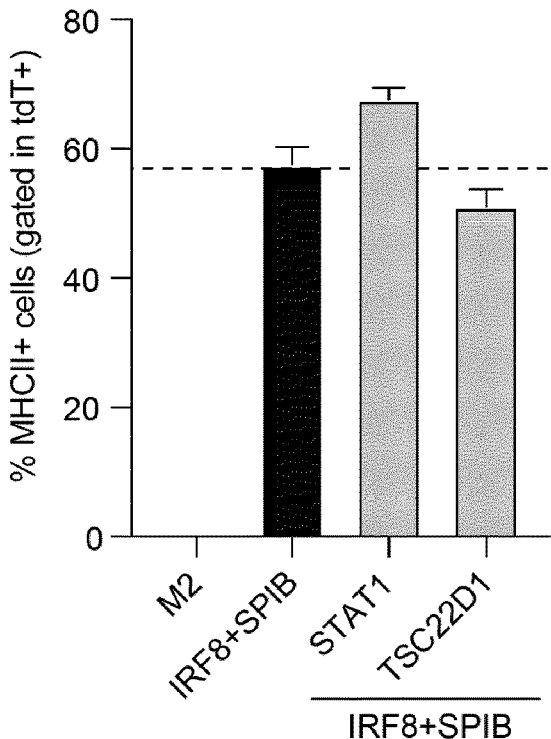

In an embodiment, two additional candidate TFs were selected due to their specific enriched gene expression in plasmacytoid DCs when compared to cDC1 s and cDC2s: STAT1 and TSC22D1 (FIG. 11). These two TFs were cloned individually in the same reprogramming proven Doxycycline (Dox)-inducible lentiviral vector and tested in combination with IRF8 and SPIB to access their ability to induce Clec9a-tdTomato reporter activation (FIG. 12). Interestingly, the addition of STAT1 or TSC22D1 to the IRF8 and SPIB combination increased Clec9a reporter activation when compared with IRF8 and SPIB alone (FIG. 12A). Induced pDCs generated by IRF8, SPIB and STAT1, and IRF8, SPIB and TSC22D1 also express MHC-II molecules at the cell surface (FIG. 12B), supporting the acquisition of pDC fate.

Figure 13A:
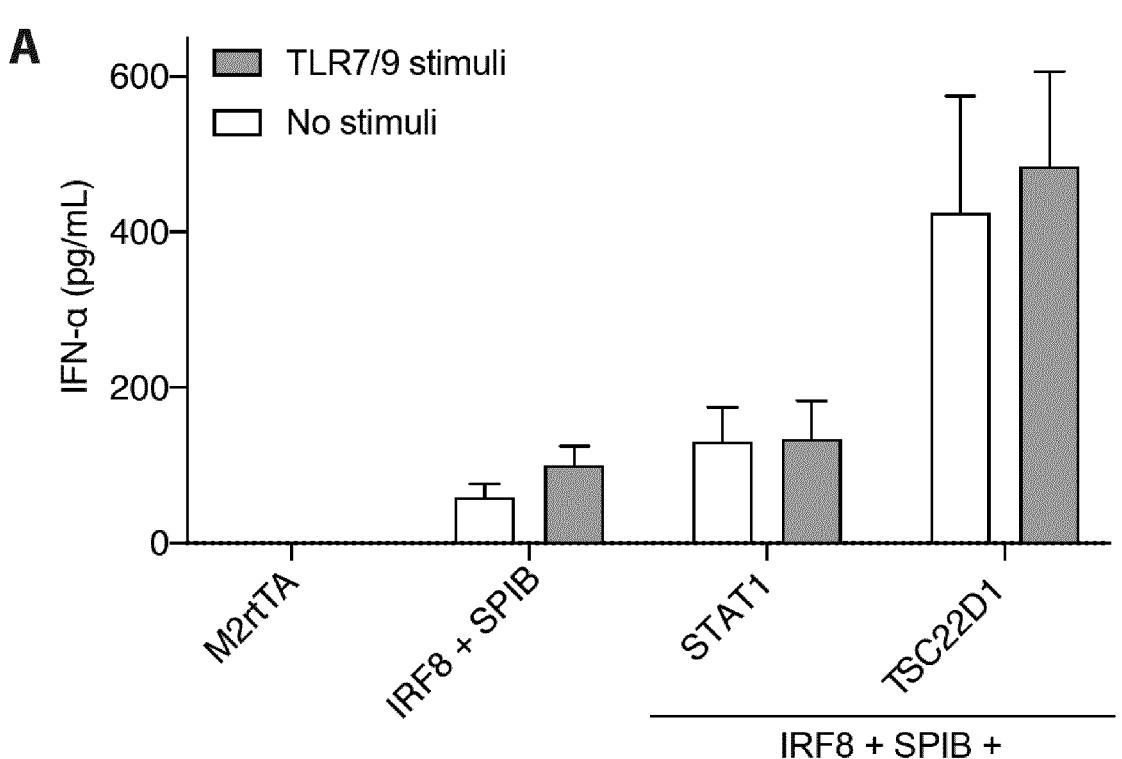
FIG. 13. Induced pDCs secrete type I Interferons upon TLR7 and TLR9 stimulation. MEFs were transduced with M2rtTA, IRF8 and SPIB alone or combined with STAT1 and TSC22D1 and tdTomato+ cells were sorted at day 9 after addition of doxycycline. Purified tdTomato+ cells were incubated overnight with triggers of TLR7 (R848) and TLR9
Figure 13B:
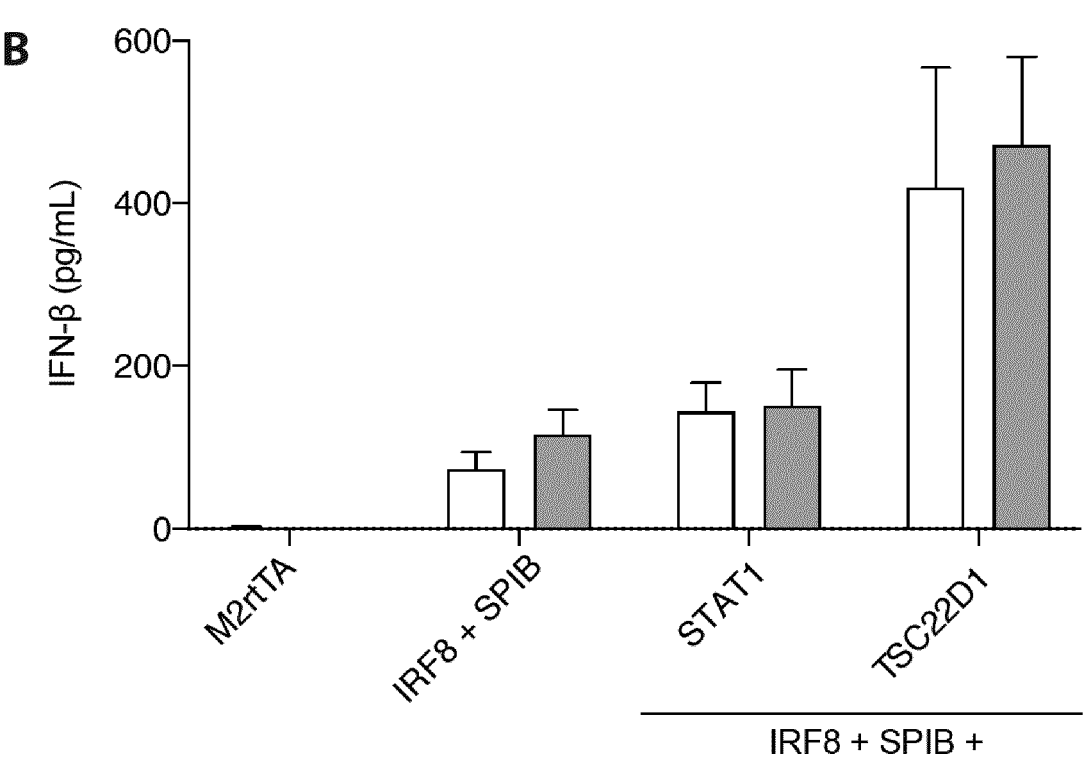
Figure 13C:
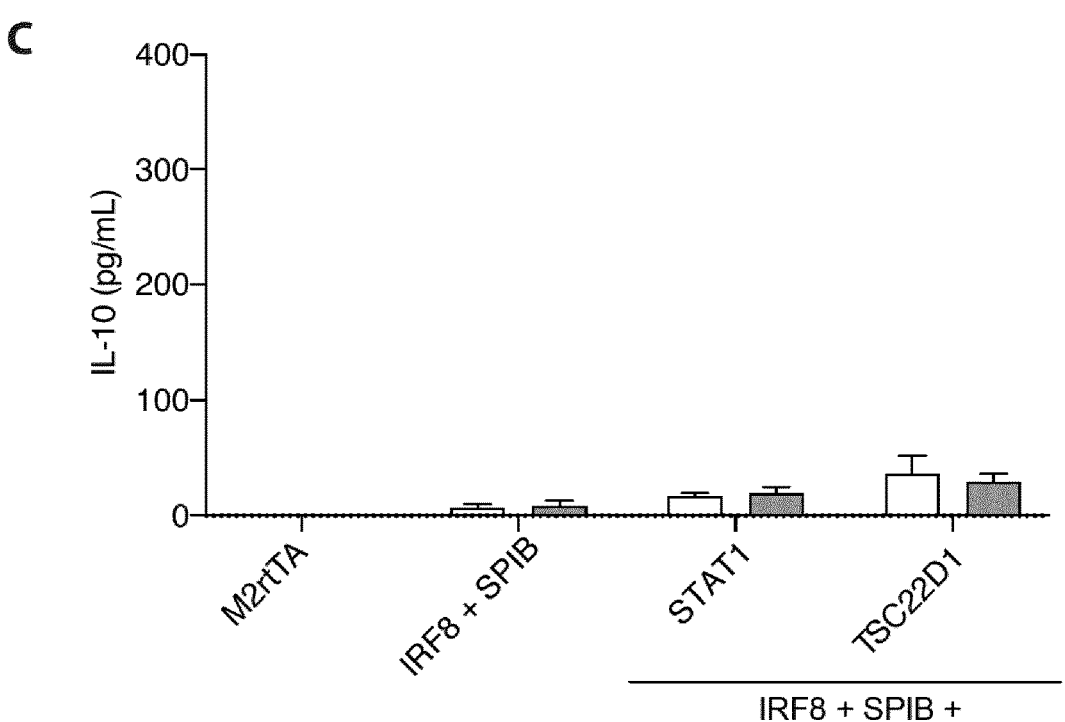

In an embodiment, induced pDCs were challenged with TLR7/9, at which an increased secretion of IFN-α by tdTomato+ cells reprogrammed with IRF8, SPIB and STAT1 (1.3 fold) and IRF8, SPIB and TSC22D1 (4.8 fold), when comparing with induced pDCs generated by IRF8 and SPIB (FIG. 13A), was observed. Addition of STAT1 or TSC22D1 also increased the secretion of IFN-β by tdTomato+ cells reprogrammed with IRF8, SPIB and STAT1 (1.3 fold) and IRF8, SPIB and TSC22D1 (4.1 fold) (FIG. 13B) in comparison with IRF8 and SPIB-induced cells. Induced pDCs generated by IRF8, SPIB and STAT1, and IRF8, SPIB and TSC22D1 were not able to secrete anti-inflammatory cytokine IL-10. These data support that IRF8, SPIB and STAT1, and IRF8, SPIB and TSC22D1 are able to induce reprogramming towards an induced pDC fate and ability to secrete type I-interferons.

In an embodiment, surface expression of hematopoietic marker CD45 is also a distinctive feature of pDCs. It was investigated whether combinations of pDC-inducing factors are able to induce surface expression of CD45. CD45 is expressed in 1.79±0.33% of induced pDCs generated with IRF8 and SPIB. Surprisingly, if IKZF1 is combined with IRF8 and SPIB, the population of CD45+ increases up to 10.16±0.91% (5.6 fold increase).

In an embodiment, the recognition of viruses or self nucleic acids by TLR7 and TLR9 in pDCs induces two alternative pathways dependent on the type of compartment in which TLR7 and TLR9 encounter their ligands. The MYD88-IRF7 pathway results in type I interferon secretion, whilst the MYD88-NF-κB pathway leads to production of pro-inflammatory cytokines and chemokines, It was then investigated if upon TLR7/9 stimulation, induced pDCs secrete additional cytokines (FIG. 15). Indeed, purified tdTomato+ cells generated by overexpression of IRF8 and SPIB secrete pro-inflammatory cytokines IL-6 and TNF-α and chemokines CCL5 and CXCL10. Importantly, the addition of STAT1, TCF12 or TSC22D1 to IRF8 and SPIB combination increases the secretion of IL-6, TNF-α, CCL5 and CXCL10, in a TLR-dependent manner. TLR challenge of induced pDCs increased the secretion of IL-6 by tdTomato+ cells reprogrammed with IRF8, SPIB and STAT1 (5.6 fold), IRF8, SPIB and TCF12 (7.5 fold) and IRF8, SPIB and TSC22D1 (3.5 fold), whilst similar increase was observed for TNF-α (1.8, 3.1, 1.3 fold, respectively). Secretion of the chemokine CCL5 by tdTomato+ cells reprogrammed with IRF8, SPIB and STAT1 (2.5 fold), IRF8, SPIB and TCF12 (3.1 fold) and IRF8, SPIB and TSC22D1 (2.4 fold) increased upon TLR challenge. As far as CXCL10, induced pDCs generated by overexpression of IRF8, SPIB and TCF12, and IRF8, SPIB and TSC22D1, also increased their secretion upon TLR stimulation, 2.8 and 1.7 fold, respectively. Taken together, this data support that we successfully identified combinations of TFs sufficient to induce pDCs in unrelated cell types with ability to respond to TLR7 and 9 stimulation through two intra-cellular pathways, leading to type-I interferon secretion and pro-inflammatory cytokines and chemokines.

In an embodiment, coding regions of each candidate TF were individually cloned into an inducible lentiviral pFUW-TetO vector in which the expression of the TFs is under the control of the tetracycline operator and a minimal CMV promoter. A previously described lentiviral vector containing the reverse tetracycline transactivator M2rtTA under the control of a constitutively active human ubiquitin C promoter (FUW-M2rtTA) was used in combination. Human embryonic kidney (HEK) 293T cells were transfected with a mixture of TF-encoding plasmids, packaging constructs and the VSV-G envelope protein. Viral supernatants were harvested after 36, 48 and 60 hours, filtered (0.45 μm, Corning) and used fresh or concentrated 40-fold with Amicon ultra centrifugal filters (Millipore).

In some embodiments, polypeptide variants or family members having the same or a similar activity as the reference polypeptide encoded by the sequences provided in the sequence list can be used in the compositions, methods, and kits described herein. Generally, variants of a particular polypeptide encoding a pDC-inducing factor for use in the compositions, methods, and kits described herein will have at least about 95%, at least about 96%, at least about 97%, at least about 98%, at least about 99% or more sequence identity to that particular reference polynucleotide or polypeptide as determined by sequence alignment programs and parameters described herein and known to those skilled in the art.

In an embodiment, *Homo sapiens* Interferon Regulatory Factor 8 (IRF8), mRNA (SEQ. ID. 1) and a codon optimized, or different codons encoding the same amino acids, are naturally also contemplated to be covered by the reference to the nucleic acid as set forth herein.

In an embodiment, *Homo sapiens* Spi-B (SPIB), mRNA (SEQ. ID. 3) and a codon optimized, or different codons encoding the same amino acids, are naturally also contemplated to be covered by the reference to the nucleic acid as set forth herein.

In an embodiment, *Homo sapiens* AT-Rich Interaction Domain 5A (ARID5A), mRNA (SEQ. ID. 5) and a codon optimized, or different codons encoding the same amino acids, are naturally also contemplated to be covered by the reference to the nucleic acid as set forth herein.

In an embodiment, *Homo sapiens* BAF Chromatin Remodeling Complex Subunit (BCL11A), mRNA (SEQ. ID. 7) and a codon optimized, or different codons encoding the same amino acids, are naturally also contemplated to be covered by the reference to the nucleic acid as set forth herein.

In an embodiment, *Homo sapiens* CBFA2/RUNX1 Partner Transcriptional Co-Repressor 3 (CBFA2T3), mRNA (SEQ. ID. 9) and a codon optimized, or different codons encoding the same amino acids, are naturally also contemplated to be covered by the reference to the nucleic acid as set forth herein.

In an embodiment, *Homo sapiens* CAMP Responsive Element Binding Protein 3 Like 2 (CREB3L2), mRNA (SEQ. ID. 11) and a codon optimized, or different codons encoding the same amino acids, are naturally also contemplated to be covered by the reference to the nucleic acid as set forth herein.

In an embodiment, *Homo sapiens* ETS Proto-Oncogene 1 (ETS1), mRNA (SEQ. ID. 13) and a codon optimized, or different codons encoding the same amino acids, are naturally also contemplated to be covered by the reference to the nucleic acid as set forth herein.

In an embodiment, *Homo sapiens* Homeobox A5 (HOXA5), mRNA (SEQ. ID. 19) and a codon optimized, or different codons encoding the same amino acids, are naturally also contemplated to be covered by the reference to the nucleic acid as set forth herein.

In an embodiment, *Homo sapiens* IKAROS Family Zinc Finger 1 (IKZF1) mRNA (SEQ. ID. 23) and a codon-optimized, or different codons encoding the same amino acids, are naturally contemplated to be covered by the reference to the nucleic acid as set forth herein.

In an embodiment, *Homo sapiens* Signal Transducer And Activator Of Transcription 1 (STAT1), mRNA (SEQ. ID. 45) and a codon-optimized, or different codons encoding the same amino acids, are naturally contemplated to be covered by the reference to the nucleic acid as set forth herein.

In an embodiment, *Homo sapiens* Transcription Factor 4 (TCF4), mRNA (SEQ. ID. 41) and a codon optimized, or different codons encoding the same amino acids, are naturally also contemplated to be covered by the reference to the nucleic acid as set forth herein.

In an embodiment, *Homo sapiens* Transcription Factor 12 (TCF12), mRNA (SEQ. ID. 43) and a codon optimized, or different codons encoding the same amino acids, are naturally also contemplated to be covered by the reference to the nucleic acid as set forth herein.

In an embodiment, *Homo sapiens* TSC22 domain family protein 1 (TSC22D1), mRNA (SEQ. ID. 47) and a codon-optimized, or different codons encoding the same amino acids, are naturally contemplated to be covered by the reference to the nucleic acid as set forth herein.

In some embodiments of the compositions, vectors, constructs, methods, and kids provided herein, the number of pDC-inducing factors used or selected to generate pDCs from a starting somatic cell, such as a fibroblast cell or hematopoietic lineage cell, a multipotent stem cell, an induced pluripotent stem cell, a cancer or tumor cell is at least two. In some embodiments, the number of pDC-inducing factors used or selected is at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least thirty, at least thirty three, at least thirty five, at least forty, or more.

In some embodiments of the compositions, vectors, constructs, methods, and kits described herein, the nucleic acid sequence or construct encoding the pDC-inducing factor(s), such as IRF8, SPIB, ARID5A, BCL1A, CBFA2T3, CREB3L2, ETS1, HOXA5, IZKF1, TCF4, TCF12 and TSC22D1 and, is inserted or operably linked into a suitable expression vector for transfection of cells using standard molecular biology techniques. As used herein, a "vector" refers to a nucleic acid molecule, such as a dsDNA molecule that provides a useful biological or biochemical property to an inserted nucleotide sequence, such as the nucleic acid constructs or replacement cassettes described herein. Examples include plasmids, phages, autonomously replicating sequences (ARS), centromeres, and other sequences that are able to replicate or be replicated in vitro or in a host cell, or to convey a desired nucleic acid segment to a desired location within a host cell. A vector can have one or more restriction endonuclease recognition sites (whether type I, II, IIs, III and IV) at which the sequences can be cut in a determinable fashion without loss of an essential biological function of the vector, and into which a nucleic acid fragment can be spliced or inserted in order to bring about its replication and cloning. Vectors can also comprise one or more recombination sites that permit exchange of nucleic acid sequences between two nucleic acid molecules. Vectors can further provide primer sites, e.g., for PCR, transcriptional and/or translational initiation and/or regulation sites, recombination signals, replicons, additional selectable markers, etc. A vector can further comprise one or more selectable markers suitable for use in the identification of cells transformed with the vector.

In some embodiments of the compositions, vectors, constructs, methods, and kits described herein, the expression vector is a viral vector. Some viral-mediated expression methods employ retrovirus, adenovirus, lentivirus, paramyxoviridae, rabdoviral, alphaviral, flaviral, herpes virus, pox virus, and adeno-associated virus (AAV) vectors, and such expression methods have been used in gene delivery and are well known in the art.

In some embodiments of the compositions, vectors, constructs, methods, and kits described herein, the viral vector is a retrovirus. Retroviruses provide a convenient platform for gene delivery. A selected gene can be inserted into a vector and packaged in retroviral particles using techniques known in the art. The recombinant virus can then be isolated and delivered to target cells of the subject either in vivo or ex vivo. A number of retroviral systems have been described. See, e.g., U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Burns et al. (1993) Proc. Natl. Acad. Sci. USA 90:8033-37; Boris-Lawrie and Temin (1993) Curr. Opin. Genet. Develop. 3:102-09. In some embodiments of the compositions, vectors, methods, and kits described herein, the retrovirus is replication deficient. Retroviral vector systems exploit the fact that a minimal vector containing the 5' and 3' LTRs and the packaging signal are sufficient to allow vector packaging, infection and integration into target cells, provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

In some embodiments of the compositions, vectors, constructs, methods, and kits described herein, the viral vector is an adenovirus-based expression vector. Unlike retroviruses, which integrate into the host genome, adenoviruses persist extra-chromosomally, thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) Bio-Techniques 6:616-29; and Rich et al. (1993) Human Gene Therapy 4:461-76). Adenoviral vectors infect a wide variety of cells, have a broad host-range, exhibit high efficiencies of infectivity, direct expression of heterologous genes at high levels, and achieve long-term expression of those genes in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. Adenoviral vectors for use in the compositions, vectors, methods, and kits described herein can be derived from any of the various adenoviral serotypes, including, without limitation, any of the over 40 serotype strains of adenovirus, such as serotypes 2, 5, 12, 40, and 41. The adenoviral vectors used herein are preferably replication-deficient and contain the pDC-inducing factor of interest operably linked to a suitable promoter.

In some embodiments of the compositions, vectors, constructs, methods, and kits described herein, the nucleic acid sequences encoding the pDC-inducing factor(s), such as IRF8, SPIB, ARID5A, BCL1A, CBFA2T3, ETS1, HOXA5, IKZF1, STAT1, TCF4, TCF12 and TSC22D1 are introduced or delivered using one or more inducible lentiviral vectors. Control of expression of pDC-inducing factors delivered using one or more inducible lentiviral vectors can be achieved, in some embodiments, by contacting a cell having at least one pDC-inducing factor in an expression vector under the control of or operably linked to an inducible promoter, with a regulatory agent (e.g., doxycycline) or other inducing agent. When using some types of inducible lentiviral vectors, contacting such a cell with an inducing agent induces expression of the pDC-inducing factors, while withdrawal of the regulatory agent inhibits expression. When using other types of inducible lentiviral vectors, the presence of the regulatory agent inhibits expression, while removal of the regulatory agent permits expression. As used herein, the term "induction of expression" refers to the expression of a gene, such as a pDC-inducing factor encoded by an inducible viral vector, in the presence of an inducing agent, for example, or in the presence of one or more agents or factors that cause endogenous expression of the gene in a cell.

In some embodiments of the aspects described herein, a doxycycline (Dox) inducible lentiviral system is used. Unlike retroviruses, lentiviruses are able to transduce quiescent cells making them amenable for transducing a wider variety of hematopoietic cell types. For example, the pFUW-tetO lentivirus system has been shown to transduce primary hematopoietic progenitor cells with high efficiency.

In some embodiments of the methods described herein, the nucleic acid sequences encoding the pDC-inducing factor(s), such as IRF8 (SEQ. ID. 1, SEQ. ID. 2), SPIB (SEQ. ID. 3, SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), HDAC5 (SEQ. ID. 15, SEQ. ID. 16), HHEX (SEQ. ID. 17, SEQ. ID. 18), HOXA5 (SEQ. ID. 19, SEQ. ID. 20), ID3 (SEQ. ID. 21, SEQ. ID. 22), IKZF1 (SEQ. ID. 23, SEQ. ID. 24), IKZF2 (SEQ. ID. 25, SEQ. ID. 26), IKZF3 (SEQ. ID. 27, SEQ. ID. 28), IKZF5 (SEQ. ID. 29, SEQ. ID. 30), IRF7 (SEQ. ID. 31, SEQ. ID. 32), MEF2C (SEQ. ID. 33, SEQ. ID. 34), MYB (SEQ. ID. 35, SEQ. ID. 36), RUNX2 (SEQ. ID. 37, SEQ. ID. 38), STAT3 (SEQ. ID. 39, SEQ. ID. 40), TCF4 (SEQ. ID. 41, SEQ. ID. 42), TCF12 (SEQ. ID. 43, SEQ. ID. 44), STAT1 (SEQ. ID. 45, SEQ. ID. 46) and TSC22D1 (SEQ. ID. 47, SEQ. ID. 48) are introduced or delivered using a non-integrating vector (e.g., adenovirus). While integrating vectors, such as retroviral vectors, incorporate into the host cell genome and can potentially disrupt normal gene function, non-integrating vectors control expression of a gene product by extra-chromosomal transcription. Since non-integrating vectors do not become part of the host genome, non-integrating vectors tend to express a nucleic acid transiently in a cell population. This is due in part to the fact that the non-integrating vectors are often rendered replication deficient. Thus, non-integrating vectors have several advantages over retroviral vectors including, but not limited to: (1) no disruption of the host genome, and (2) transient expression, and (3) no remaining viral integration products. Some non-limiting examples of non-integrating vectors for use with the methods described herein include adenovirus, baculovirus, alphavirus, picornavirus, and vaccinia virus. In some embodiments of the methods described herein, the non-integrating viral vector is an adenovirus. Other advantages of non-integrating viral vectors include the ability to produce them in high titers, their stability in vivo, and their efficient infection of host cells.

Nucleic acid constructs and vectors for use in generating induced pDCs in the compositions, vectors, constructs, methods, and kits described herein can further comprise, in some embodiments, one or more sequences encoding selection markers for positive and negative selection of cells. Such selection marker sequences can typically provide properties of resistance or sensitivity to antibiotics that are not normally found in the cells in the absence of introduction of the nucleic acid construct. A selectable marker can be used in conjunction with a selection agent, such as an antibiotic, to select in culture for cells expressing the inserted nucleic acid construct. Sequences encoding positive selection markers typically provide antibiotic resistance, i.e., when the positive selection marker sequence is present in the genome of a cell, the cell is sensitive to the antibiotic or agent. Sequences encoding negative selection markers typically provide sensitivity to an antibiotic or agent, i.e., when the negative selection marker is present in the genome of a cell, the cell is sensitive to the antibiotic or agent.

Nucleic acid constructs and vectors for use in making induced pDCs in the compositions, vectors, constructs, methods, and kits thereof described herein can further comprise, in some embodiments, other nucleic acid elements for the regulation, expression, stabilization of the construct or of other vector genetic elements, for example, promoters, enhancers, TATA-box, ribosome binding sites, IRES, 2A-like self-cleaving sequences as known to one of ordinary skill in the art.

Nucleic acid constructs and vectors for use in making induced pDCs in the compositions, vectors, constructs, methods, and kits described herein can further comprise a 2A-like self-cleaving sequences. Self-cleaving 18-22 amino acids long 2A peptides mediate 'ribosomal skipping' between the proline and glycine residues and inhibit peptide bond formation without affecting downstream translation. These peptides allow multiple proteins to be encoded as polyproteins, which dissociate into component proteins upon translation. Examples of 2A-like self cleaving sequences that can be used according to the invention include without limitation, those from Picomaviridae virus family, including aphthoviruses such as foot-and-mouth disease virus (FMDV), equine rhinitis A virus (ERAV), Thosea asigna virus (TaV) and porcine teschovirus-1 (PTV-1) and cardioviruses such as Theilovirus (e.g., Theiler's murine encephalomyelitis) and encephalomyocarditis viruses.

In some embodiments of the compositions, vectors, constructs, methods, and kits described herein, the pDC-inducing factor(s), such as IRF8 (SEQ. ID. 1, SEQ. ID. 2), SPIB (SEQ. ID. 3, SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), HOXA5 (SEQ. ID. 19, SEQ. ID. 20), IKZF1 (SEQ. ID. 23, SEQ. ID. 24), TCF4 (SEQ. ID. 41, SEQ. ID. 42), TCF12 (SEQ. ID. 43, SEQ. ID. 44), STAT1 (SEQ. ID. 45, SEQ. ID. 46), and TSC22D1 (SEQ. ID. 47, SEQ. ID. 48) and, are provided as synthetic, modified RNAs, or introduced or delivered into a cell as a synthetic, modified RNA, as described in US Patent Publication 2012-0046346-A1, the contents of which are herein incorporated by reference in their entireties. In those embodiments where synthetic, modified RNAs are used to reprogram cells to induced pDCs according to the methods described herein, the methods can involve repeated contacting of the cells or involve repeated transfections of the synthetic, modified RNAs encoding pDC-inducing factors, such as for example, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, or more transfections.

In addition to one or more modified nucleosides, the modified mRNAs for use in the compositions, vectors, constructs, methods, and kits described herein can comprise any additional modifications known to one of skill in the art and as described in US Patent Publications 2012-0046346-A1 and 20120251618A1, and PCT Publication WO 2012/019168. Such other components include, for example, a 5' cap (e.g., the Anti-Reverse Cap Analog (ARCA) cap, which contains a 5'-5'-triphosphate guanine-guanine linkage where one guanine contains an N7 methyl group as well as a 3'-O-methyl group; caps created using recombinant Vaccinia Virus Capping Enzyme and recombinant 2'-O-methyltransferase enzyme, which can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure); a poly(A) tail (e.g., a poly-A tail greater than 30 nucleotides in length, greater than 35 nucleotides in length, at least 40 nucleotides, at least 45 nucleotides, at least 55 nucleotides, at least 60 nucleotide, at least 70 nucleotides, at least 80 nucleotides, at least 90 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, or more); a Kozak sequence;

a 3' untranslated region (3' UTR); a 5' untranslated region (5' UTR); one or more intronic nucleotide sequences capable of being excised from the nucleic acid, or any combination thereof.

The modified mRNAs for use in the compositions, vectors, constructs, methods, and kits described herein can further comprise an internal ribosome entry site (IRES). An IRES can act as the sole ribosome binding site, or can serve as one of multiple ribosome binding sites of an mRNA. An mRNA containing more than one functional ribosome binding site can encode several peptides or polypeptides, such as the pDC-inducing factors described herein, that are translated independently by the ribosomes ("multicistronic mRNA"). When nucleic acids are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SW) or cricket paralysis viruses (CrPV).

In some embodiments of the compositions, vectors, constructs, methods, and kits described herein, the synthetic, modified RNA molecule comprises at least one modified nucleoside. In some embodiments of the compositions, vectors, methods, and kits described herein, the synthetic, modified RNA molecule comprises at least two modified nucleosides.

In some embodiments of the compositions, vectors, constructs, methods, and kits described herein, the modified nucleosides are selected from the group consisting of 5-methylcytosine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In some embodiments, the modified nucleosides are 5-methylcytosine (5mC), pseudouracil, or a combination thereof.

Modified mRNAs need not be uniformly modified along the entire length of the molecule. Different nucleotide modifications and/or backbone structures can exist at various positions in the nucleic acid. One of ordinary skill in the art will appreciate that the nucleotide analogs or other modification(s) can be located at any position(s) of a nucleic acid such that the function of the nucleic acid is not substantially decreased. A modification can also be a 5' or 3' terminal modification. The nucleic acids can contain at a minimum one and at maximum 100% modified nucleotides, or any intervening percentage, such as at least 50% modified nucleotides, at least 80% modified nucleotides, or at least 90% modified nucleotides.

In some embodiments of the present disclosure, the vector or construct is a replicating viral vector or particle, such as a Paramyxoviridae vector, Rhabdoviral vector, Alphaviral and/or Flaviviral particles, or a non-viral vector or particle, such as a naked Alphaviral or Flaviviral RNA replicon.

In some embodiments, it is preferred, but not absolutely necessary, that each occurrence of a given nucleoside in a molecule is modified (e.g., each cytosine is a modified cytosine e.g., 5-methylcytosine, each uracil is a modified uracil, e.g., pseudouracil, etc.). For example, the modified mRNAs can comprise a modified pyrimidine such as uracil or cytosine. In some embodiments, at least 25%, at least 50%, at least 80%, at least 90% or 100% of the uracil in the nucleic acid are replaced with a modified uracil. It is also contemplated that different occurrences of the same nucleo- side can be modified in a different way in a given synthetic, modified RNA molecule. The modified uracil can be replaced by a compound having a single unique structure, or can be replaced by a plurality of compounds having different structures (e.g., 2, 3, 4 or more unique structures). In some embodiments, at least 25%, at least 50%, at least 80%, at least 90% or 100% of the cytosine in the nucleic acid may be replaced with a modified cytosine. The modified cytosine can be replaced by a compound having a single unique structure, or can be replaced by a plurality of compounds having different structures (e.g., 2, 3, 4 or more unique structures) (e.g., some cytosines modified as 5mC, others modified as 2'-O-methylcytosine or other cytosine analog). Such multi-modified synthetic RNA molecules can be pro- duced by using a ribonucleoside blend or mixture compris- ing all the desired modified nucleosides, such that when the RNA molecules are being synthesized, only the desired modified nucleosides are incorporated into the resulting RNA molecule encoding the pDC-inducing factor.

In certain embodiments it is desirable to intracellularly degrade a modified nucleic acid introduced into the cell, for example if precise timing of protein production is desired. Thus, in some embodiments of the compositions, vectors, methods, and kits described herein, provided herein are modified nucleic acids comprising a degradation domain, which is capable of being acted on in a directed manner within a cell.

While it is understood that induced pDCs can be gener- ated by delivery of pDC-inducing factors in the form of nucleic acid (DNA or RNA) or amino acid sequences, in some embodiments of the compositions, vectors, methods, and kits described herein, induced pDCs can be induced using other methods, such as, for example, by treatment of cells with an agent, such as a small molecule or cocktail of small molecules, that induce expression of one or more of the pDC-inducing factors.

Detection of expression of pDC-inducing factors intro- duced into cells or induced in a cell population using the compositions, vectors, methods, and kits described herein, can be achieved by any of several techniques known to those of skill in the art including, for example, Western blot analysis, immunocytochemistry, and fluorescence-mediated detection.

In order to distinguish whether a given combination of pDC-inducing factors has generated induced pDCs, one or more DC activities or parameters can be measured, such as, in some embodiments, differential expression of surface antigens. The generation of induced DCs using the compo- sitions, vectors, methods, and kits described herein prefer- ably causes the appearance of the cell surface phenotype characteristic of endogenous pDCs, such as CD45 and MHC-II, for example.

DCs are most reliably distinguished from other immune cells by their functional behavior. Functional aspects of DC phenotypes, or DC activities, such as the ability of an induced pDC to secrete cytokines can be easily determined by one of skill in the art using routine methods known in the art. In some embodiments of the aspects described herein, functional assays to identify reprogramming factors can be used. For example, in some embodiments, cytokine secre- tion can be used to confirm immune-modulatory properties of induced pDCs generated using the compositions, vectors, methods, and kits described herein. In particular, ability to respond to intracellular DNA though TLR7 and TLR9 pathways and secrete type I interferons is particularly rel- evant to characterize pDC functionality.

As used herein, "cellular parameter," "DC parameter," or "cytokine secretion" refer to measureable components or qualities of endogenous or natural DCs, particularly com- ponents that can be accurately measured. A cellular param- eter can be any measurable parameter related to a phenotype, function, or behavior of a cell. Such cellular parameters include, changes in characteristics and markers of a DC or DC population, including but not limited to changes in viability, cell growth, expression of one or more or a combination of markers, such as cell surface determinants, such as receptors, proteins, including conformational or posttranslational modification thereof, lipids, carbohydrates, organic or inorganic molecules, nucleic acids, e.g. mRNA, DNA, global gene expression patterns, etc. Such cellular parameters can be measured using any of a variety of assays known to one of skill in the art. For example, viability and cell growth can be measured by assays such as Trypan blue exclusion, CFSE dilution, and 3H-thymidine incorporation. Expression of protein or polypeptide markers can be mea- sured, for example, using flow cytometric assays, Western blot techniques, or microscopy methods. Gene expression profiles can be assayed, for example, using RNA-sequencing methodologies and quantitative or semi-quantitative real- time PCR assays. A cellular parameter can also refer to a functional parameter or functional activity. While most cellular parameters will provide a quantitative readout, in some instances a semi-quantitative or qualitative result can be acceptable. Readouts can include a single determined value, or can include mean, median value or the variance, etc. Characteristically a range of parameter readout values can be obtained for each parameter from a multiplicity of the same assays. Variability is expected and a range of values for each of the set of test parameters will be obtained using standard statistical methods with a common statistical method used to provide single values.

In some embodiments of the compositions, vectors, meth- ods, and kits described herein, additional factors and agents can be used to enhance induced pDC reprogramming. For example, factors and agents that modify epigenetic path- ways can be used to facilitate reprogramming into induced pDCs.

Essentially any primary somatic cell type can be used for producing induced pDCs or reprogramming somatic cells to induced pDCs according to the presently described compo- sitions, vectors, methods, and kits. Such primary somatic cell types also include other stem cell types, including pluripotent stem cells, such as induced pluripotent stem cells (iPS cells); other multipotent stem cells; oligopotent stem cells; and unipotent stem cells. Some non-limiting examples of primary somatic cells useful in the various aspects and embodiments of the methods described herein include, but are not limited to, fibroblasts, epithelial, endothelial, neu- ronal, adipose, cardiac, skeletal muscle, hematopoietic or immune cells, hepatic, splenic, lung, circulating blood cells, gastrointestinal, renal, bone marrow, and pancreatic cells, as well as stem cells from which those cells are derived. The cell can be a primary cell isolated from any somatic tissue including, but not limited to, spleen, bone marrow, blood, brain, liver, lung, gut, stomach, intestine, fat, muscle, uterus, skin, spleen, endocrine organ, bone, etc. The term "somatic cell" further encompasses, in some embodiments, primary cells grown in culture, provided that the somatic cells are not immortalized. Where the cell is maintained under in vitro conditions, conventional tissue culture conditions and methods can be used, and are known to those of skill in the art. Isolation and culture methods for various primary somatic cells are well within the abilities of one skilled in the art.

In some embodiments of these aspects and all such aspects described herein, the somatic cell is a fibroblast cell.

In some embodiments of these aspects and all such aspects described herein, the somatic cell can be a hematopoietic lineage cell.

In some embodiments of these aspects and all such aspects described herein, the somatic cell can be a cancer cell or a tumor cell.

In some embodiments of the compositions, vectors, constructs, methods, and kits described herein, a somatic cell to be reprogrammed or made into an induced pDC cell is a cell of hematopoietic origin. As used herein, the terms "hematopoietic-derived cell," "hematopoietic-derived differentiated cell," "hematopoietic lineage cell," and "cell of hematopoietic origin" refer to cells derived or differentiated from a multipotent hematopoietic stem cell (HSC). Accordingly, hematopoietic lineage cells for use with the compositions, vectors, constructs, methods, and kits described herein include multipotent, oligopotent, and lineage-restricted hematopoietic progenitor cells, granulocytes (e.g., promyelocytes, neutrophils, eosinophils, basophils), erythrocytes (e.g., reticulocytes, erythrocytes), thrombocytes (e.g., megakaryoblasts, platelet-producing megakaryocytes, platelets), monocytes (e.g., monocytes, macrophages), dendritic cells, and lymphocytes (e.g., T-lymphocytes, which carry T-cell receptors (TCRs), B-lymphocytes or B cells, which express immunoglobulin and produce antibodies, NK cells, NKT cells, and innate lymphocytes). As used herein, the term "hematopoietic progenitor cells" refer to multipotent, oligopotent, and lineage-restricted hematopoietic cells capable of differentiating into two or more cell types of the hematopoietic system, including, but not limited to, granulocytes, monocytes, erythrocytes, megakaryocytes, and lymphocytes B-cells and T-cells. Hematopoietic progenitor cells encompass multi-potent progenitor cells (MPPs), common myeloid progenitor cells (CMPs), common lymphoid progenitor cells (CLPs), granulocyte-monocyte progenitor cells (GMPs), and pre-megakaryocyte-erythrocyte progenitor cell. Lineage-restricted hematopoietic progenitor cells include megakaryocyte-erythrocyte progenitor cells (MEP), ProB cells, PreB cells, PreProB cells, ProT cells, double-negative T cells, pro-NK cells, pre-granulocyte/macrophage cells, granulocyte/macrophage progenitor (GMP) cells, and pro-mast cells (ProMCs).

Cells of hematopoietic origin for use in the compositions, vectors, methods, and kits described herein can be obtained from any source known to comprise these cells, such as fetal tissues, umbilical cord blood, bone marrow, peripheral blood, mobilized peripheral blood, spleen, liver, thymus, lymph, etc. Cells obtained from these sources can be expanded ex vivo using any method acceptable to those skilled in the art prior to use in with the compositions, vectors, constructs, methods, and kits for making induced pDCs described herein. For example, cells can be sorted, fractionated, treated to remove specific cell types, or otherwise manipulated to obtain a population of cells for use in the methods described herein using any procedure acceptable to those skilled in the art. Mononuclear lymphocytes may be collected, for example, by repeated lymphocytophereses using a continuous flow cell separator as described in U.S. Pat. No. 4,690,915, or isolated using an affinity purification step of CLP method, such as flow-cytometry using a cytometer, magnetic separation, using antibody or protein coated beads, affinity chromatography, or solid-support affinity separation where cells are retained on a substrate according to their expression or lack of expression of a specific protein or type of protein, or batch purification using one or more antibodies against one or more surface antigens specifically expressed by the cell type of interest. Cells of hematopoietic origin can also be obtained from peripheral blood. Prior to harvest of the cells from peripheral blood, the subject can be treated with a cytokine, such as e.g., granulocyte-colony stimulating factor, to promote cell migration from the bone marrow to the blood compartment and/or promote activation and/or proliferation of the population of interest. Any method suitable for identifying surface proteins, for example, can be employed to isolate cells of hematopoietic origin from a heterogeneous population. In some embodiments, a clonal population of cells of hematopoietic origin, such as lymphocytes, is obtained. In some embodiments, the cells of hematopoietic origin are not a clonal population.

Further, in regard to the various aspects and embodiments of the compositions, vectors, constructs, methods, and kits described herein, a somatic cell can be obtained from any mammalian species, with non-limiting examples including a murine, bovine, simian, porcine, equine, ovine, or human cell. In some embodiments, the somatic cell is a human cell. In some embodiments, the cell is from a non-human organism, such as a non-human mammal.

In general, the methods for making induced pDCs described herein involve culturing or expanding somatic cells, such as cells of hematopoietic origin, in any culture medium that is available and well-known to one of ordinary skill in the art. Such media include, but is not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®, and serum-free medium for culture and expansion of DCs. Many media are also available as low-glucose formulations, with or without sodium. The medium used with the methods described herein can, in some embodiments, be supplemented with one or more immunostimulatory cytokine. Commonly used growth factors include, but are not limited to, G-CSF, GM-CSF, TNF-α, IL-4, IL-3, the Flt-3 ligand and the kit ligand. In addition, in preferred embodiments, the immunostimulatory cytokine is selected from the group consisting of the interleukins (e.g., IL-1α, IL-1β, IL-2, IL-3, IL-4, IL-6, IL-8, IL-9, IL-10, IL-12, IL-18, IL-19, IL-20), the interferons (e.g., IFN-α, IFN-β, IFN-γ), tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), the Flt-3 ligand and the kit ligand.

Cells in culture can be maintained either in suspension or attached to a solid support, such as extracellular matrix components or plating on feeder cells, for example. Cells being used in the methods described herein can require additional factors that encourage their attachment to a solid support, in some embodiments, such as type I and type II collagen, chondroitin sulfate, fibronectin, "superfibronectin" and fibronectin-like polymers, gelatin, poly-D and poly-L-lysine, thrombospondin and vitronectin. In some embodiments, the cells are suitable for growth in suspension cultures. Suspension-competent host cells are generally monodisperse or grow in loose aggregates without substantial aggregation. Suspension-competent host cells include cells that are suitable for suspension culture without adaptation or manipulation (e.g., cells of hematopoietic origin, such as lymphoid cells) and cells that have been made suspension-competent by modification or adaptation of attachment-dependent cells (e.g., epithelial cells, fibroblasts).

In some embodiments of these aspects and all such aspects described herein, the isolated induced pDC further comprise a pharmaceutically acceptable carrier for administration to a subject in need.

Also provided herein, in some aspects, are methods of treating a subject in need of treatment to induce antigen-specific immune responses to eliminate cancer cells or infectious agents using the pDC-inducing compositions and vectors, and methods of preparing induced pDCs described herein, or using the isolated induced pDCs and cell clones thereof produced using any of the combinations of pDC-inducing factors, pDC-inducing compositions and vectors, or methods of preparing induced pDCs described herein. In such methods of treatment, somatic cells, such as fibroblast cells or hematopoietic lineage cells, can first be isolated from the subject, and the isolated cells transduced or transfected, as described herein with a pDC-inducing composition comprising expression vectors or synthetic mRNAs, respectively. The isolated induced pDCs produced using any of the combinations of pDC-inducing factors, pDC-inducing compositions and vectors, or methods of preparing induced pDCs described herein, can then be administered to the subject, such as via systemic injection of the induced pDCs to the subject.

Also provided herein, in some aspects, are methods of treating a subject in need of treatment to induce antigen-specific immune responses to eliminate cancer cells or infectious agents using the pDC-inducing compositions and vectors and any of the combinations of pDC-inducing factors described herein. In such methods of treatment, cancer cells are transduced, as described herein with a pDC-inducing composition comprising expression vectors. Cancer cells can be first isolated from the subject, transduced with a pDC-inducing composition comprising expression vectors and then administered to the subject, such as via systemic injection. Alternatively, cancers cells can be transduced in situ or in vivo with pDC-inducing composition comprising viral expression vectors.

The reprogrammed induced pDCs generated using the compositions, vectors, constructs, methods, and kits described herein can, in some embodiments of the methods of treatment described herein, be used directly or administered to subjects in need of immunotherapies. Accordingly, various embodiments of the methods described herein involve administration of an effective amount of a induced pDC or a population of induced pDCs, generated using any of the compositions, vectors, methods, and kits described herein, to an individual or subject in need of a cellular therapy. The cell or population of cells being administered can be an autologous population, or be derived from one or more heterologous sources. Further, such induced pDCs can be administered in a manner that permits them to migrate to lymph node and activate effector T cells.

A variety of means for administering cells to subjects are known to those of skill in the art. Such methods can include systemic injection, for example, i.v. injection, or implantation of cells into a target site in a subject. Cells may be inserted into a delivery device which facilitates introduction by injection or implantation into the subject. Such delivery devices can include tubes, e.g., catheters, for injecting cells and fluids into the body of a recipient subject. In one preferred embodiment, the tubes additionally have a needle, e.g., through which the cells can be introduced into the subject at a desired location. The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells remain viable.

Accordingly, the cells produced by the methods described herein can be used to prepare cells to treat or alleviate several cancers and tumors including, but not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

In addition to the above, the methods of the invention can be used to prevent or eliminate infection by pathogens known to predispose to certain cancers. Pathogens of particular interest for use in the cancer vaccines provided herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, (1983).

In addition to the above, the methods of the invention can be used for viral infections. Exemplary viral pathogens include, but are not limited to, infectious virus that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-Ill; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses such as the SARS coronavirus); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bir-naviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; *P. oxyiridae* (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class I=interaally transmitted; class 2=parenterally transmitted (i.e. Hepatitis C); Norwalk and related viruses, and astro viruses).

In addition to the above, the methods of the invention can be used to target gram negative and gram positive bacteria in vertebrate animals. Such gram positive bacteria include, but are not limited to *Pasteurella* sp., Staphylococci sp., and *Streptococcus* sp. Gram negative bacteria include, but are not limited to, *Escherichia coli, Pseudomonas* sp., and *Salmonella* sp. Specific examples of infectious bacteria include but are not limited to: *Helicobacter pyloris, Borella burgdorferi, Legionella pneumophilia, Mycobacteria* sp. (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus (viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus infuenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelii*.

In addition to the above, the methods of the invention can be used to target pathogens that include, but are not limited to, infectious fungi and parasites that infect mammals, and more particularly humans. Examples of infectious fungi include, but are not limited to: *Cryptococcus neoformans, Histoplasma capsulatum, Coccidioides immitis, Blastomyces dermatitidis, Chlamydia trachomatis*, and *Candida albicans*.

In addition to the above, the methods of the invention can be used to target parasites such as intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense, Wuchereria bancrofti, Brugia malayi, Brugia timori, Ascaris lumbricoides, Onchocerca volvulus* and *Schistosoma mansoni*.

If modified induced pDCs can be used to induce a tolerogenic response including the suppression of a future or existing immune response, to one or more target antigens. Thus, induced pDCs are useful for treating or preventing an undesirable immune response including, for example, transplant rejection, graft versus host disease, allergies, parasitic diseases, inflammatory diseases and autoimmune diseases. Examples of transplant rejection, which can be treated or prevented in accordance with the present invention, include rejections associated with transplantation of bone marrow and of organs such as heart, liver, pancreas, kidney, lung, eye, skin etc. Examples of allergies include seasonal respiratory allergies; allergy to aeroallergens such as hay fever; allergy treatable by reducing serum IgE and eosinophilia; asthma; eczema; animal allergies, food allergies; latex allergies; dermatitis; or allergies treatable by allergic desensitization. Autoimmune diseases that can be treated or prevented by the present invention include, for example, psoriasis, systemic lupus erythematosus, myasthenia gravis, stiff-man syndrome, thyroiditis, Sydenham chorea, rheumatoid arthritis, diabetes and multiple sclerosis. Examples of inflammatory disease include Crohn's disease, chronic inflammatory eye diseases, chronic inflammatory lung diseases and chronic inflammatory liver diseases, autoimmune hemolytic anemia, idiopathic leucopoenia, ulcerative colitis, dermatomyosis, scleroderma, mixed connective tissue disease, irritable bowel syndrome, systemic lupus erythromatosus (SLE), multiple sclerosis, myasthenia gravis, Guillan-Barre syndrome (antiphospholipid syndrome), primary myxoedema, thyrotoxicosis, pernicious anemia, autoimmune atrophic gastritis, Addison's disease, insulin-dependent diabetes mellitus (IDDM), Goodpasture's syndrome, Behcet's syndrome, Sjogren's syndrome, rheumatoid arthritis, sympathetic ophthalmia, Hashimoto's disease/hypothyroiditis, celiac disease/dermatitis herpetiformis, and demyelinating disease primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock.

Pharmaceutically acceptable carriers and diluents include saline, aqueous buffer solutions, solvents and/or dispersion media. The use of such carriers and diluents is well known in the art. The solution is preferably sterile and fluid. Preferably, prior to the introduction of cells, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

It is preferred that the mode of cell administration is relatively non-invasive, for example by intravenous injection, pulmonary delivery through inhalation, topical, or intranasal administration. However, the route of cell administration will depend on the tissue to be treated and may include implantation. Methods for cell delivery are known to those of skill in the art and can be extrapolated by one skilled in the art of medicine for use with the methods and compositions described herein.

Also provided herein, in some aspects, are kits for making induced pDCs, the kits comprising any of the pDC-inducing compositions comprising one or more expression vector components described herein.

Also provided herein, in some aspects, are kits comprising one or more of the pDC-inducing factors described herein as components for the methods of making the induced pDCs described herein.

Accordingly, in some aspects, provided herein, are kits for preparing induced dendritic cells comprising the following components: (a) one or more expression vectors encoding at least one, two, three, four, five, six, seven, eight, or more pDC-inducing factors selected from: IRF8 (SEQ. ID. 1, SEQ. ID. 2), SPIB (SEQ. ID. 3, SEQ. ID. 4), ARID5A (SEQ. ID. 5, SEQ. ID. 6), BCL11A (SEQ. ID. 7, SEQ. ID. 8), CBFA2T3 (SEQ. ID. 9, SEQ. ID. 10), CREB3L2 (SEQ. ID. 11, SEQ. ID. 12), ETS1 (SEQ. ID. 13, SEQ. ID. 14), HDAC5 (SEQ. ID. 15, SEQ. ID. 16), HHEX (SEQ. ID. 17, SEQ. ID. 18), HOXA5 (SEQ. ID. 19, SEQ. ID. 20), ID3 (SEQ. ID. 21, SEQ. ID. 22), IKZF1 (SEQ. ID. 23, SEQ. ID. 24), IKZF2 (SEQ. ID. 25, SEQ. ID. 26), IKZF3 (SEQ. ID. 27, SEQ. ID. 28), IKZF5 (SEQ. ID. 29, SEQ. ID. 30), IRF7 (SEQ. ID. 31, SEQ. ID. 32), MEF2C (SEQ. ID. 33, SEQ. ID. 34), MYB (SEQ. ID. 35, SEQ. ID. 36), RUNX2 (SEQ. ID. 37, SEQ. ID. 38), STAT3 (SEQ. ID. 39, SEQ. ID. 40), TCF4 (SEQ. ID. 41, SEQ. ID. 42), TCF12 (SEQ. ID. 43, SEQ. ID. 44), STAT1 (SEQ. ID. 45, SEQ. ID. 46), TSC22D1 (SEQ. ID. 47, SEQ. ID. 48), and (b) packaging and instructions therefor.

The kits described herein, in some embodiments, can further provide the synthetic mRNAs or the one or more expression vectors encoding pDC-inducing factors in an admixture or as separate aliquots.

In some embodiments, the kits can further comprise an agent to enhance efficiency of reprogramming. In some embodiments, the kits can further comprise one or more antibodies or primer reagents to detect a cell-type specific marker to identify cells induced to the pDC state.

In some embodiments, the kits can further comprise a buffer. In some such embodiments, the buffer is RNase-free TE buffer at pH 7.0. In some embodiments, the kit further comprises a container with cell culture medium.

All kits described herein can further comprise a buffer, a cell culture medium, a transduction or transfection medium and/or a media supplement. In preferred embodiments, the buffers, cell culture mediums, transfection mediums, and/or media supplements are DNAse and RNase-free. In some embodiments, the synthetic, modified RNAs provided in the kits can be in a non-solution form of specific quantity or mass, e.g., 20 μg, such as a lyophilized powder form, such that the end-user adds a suitable amount of buffer or medium to bring the components to a desired concentration, e.g., 100 ng/μl.

All kits described herein can further comprise devices to facilitate single-administration or repeated or frequent infusions of the cells generated using the kits components described herein, such as a non-implantable delivery device, e.g., needle, syringe, pen device, or an implantable delivery device, e.g., a pump, a semi-permanent stent (e.g., intravenous, intraperitoneal, intracisternal or intracapsular), or a reservoir. In some such embodiments, the delivery device can include a mechanism to dispense a unit dose of a pharmaceutical composition comprising the induced pDCs. In some embodiments, the device releases the composition continuously, e.g., by diffusion. In some embodiments, the device can include a sensor that monitors a parameter within a subject. For example, the device can include pump, e.g., and, optionally, associated electronics.

In an embodiment, induced pDCs are made by the hand of man by, e.g., modifying the gene expression of at least one of the factors disclosed herein of a somatic cell, a pluripotent cell, a progenitor cell or a stem cell, or by exposing any one of these cell types to at least one protein or RNA that produces at least one protein as disclosed herein. The cells can further be made by exposing them to small molecules that turn on at least one of the factors disclosed herein. In some aspects at least two, three, four, five, six, seven, or eight factors are used to make the induced pDCs.

In an embodiment, expression data for Clec9a, Tlr7, Tlr9 and candidate TFs in DC subsets and other myeloid cells (monocytes, macrophages and microglia) was obtained from Immgen database (www.immaen.ora). Expression data was analyzed by cluster 3.0 (log-transformed data; centered genes; centered, clustered and normalized cell types) and displayed by Treeview. Alternatively, expression values were displayed using GraphPad Prism.

In an embodiment, mouse Embryonic Fibroblasts (MEFs) were isolated and purified in the following way: Clec9aCre/Cre animals (10) were crossed with Rosa26-stopflox-tdTomato reporter mice (The Jackson Laboratory) to generate double homozygous Clec9aCre/Cre RosatdTomato/tdTomato (Clec9A-tdTomato) mice. All animals were housed under controlled temperature (23±2° C.), subject to a fixed 12-h light/dark cycle, with free access to food and water.

In an embodiment, primary cultures of MEFs were isolated from E13.5 embryos of Clec9A-tdTomato or C57BL/6 mice (6, 10). Head, fetal liver and all internal organs were removed and the remaining tissue was mechanically dissociated. Dissected tissue was enzymatic digested using 0.12% trypsin/0.1 mM Ethylenediaminetetraacetic acid (EDTA) solution (3 mL per embryo), and incubation at 37° C. for 15 min. Additional 3 mL of same solution per embryo were added, followed by another 15 min incubation period. A single cell suspension was obtained and plated in 0.1% gelatin-coated 10-cm tissue culture dishes in growth media. Cells were grown for 2-3 days until confluence, dissociated with Tryple Express and frozen in Fetal Bovine Serum (FBS) 10% dimethyl sulfoxide (DMSO). Before plating for lentiviral transduction, MEFs were sorted to remove residual CD45+ and tdTomato+ cells that could represent cells with hematopoietic potential.

In an embodiment, HEK293T cells and MEFs were maintained in growth medium [Dulbecco's modified eagle medium (DMEM) supplemented with 10% (v/v) FBS, 2 mM L-Glutamine and antibiotics (10 μg/ml Penicillin and Streptomycin)]. All cells were maintained at 37° C. and 5% (v/v) CO2. All tissue culture reagents were from Thermo Fisher Scientific unless stated otherwise.

In an embodiment, viral transduction and reprogramming experiments were performed in the following way: Clec9A-tdTomato MEFs were seeded at a density of 40,000 cells per well on 0.1% gelatin coated 6-well plates. Cells were incubated overnight with a ratio of 1:1 FUW-TetO-TFs and FUW-M2rtTA lentiviral particles in growth media supplemented with 8 μg/mL polybrene. When testing combinations of TFs, equal MOIs of each individual viral particle were applied. Cells were transduced twice in consecutive days and after overnight incubation, media was replaced with fresh growth media. After the second transduction, growth media was supplemented with Doxycycline (1 μg/mL)—day 0. Media was changed every 2-3 days for the duration of the cultures. Emerging tdTomato+ cells were analyzed 5-8 days post-transduction.

In an embodiment, flow cytometry analysis was performed in the following way: Transduced Clec9A-tdTomato MEFs were dissociated with TrypLE Express, resuspended in 200 μL PBS 5% FBS and kept at 4° C. prior analysis in BD FACS LSR II (BD Biosciences). For the analysis of MHC-1l cell surface marker expression, dissociated cells were incubated with APC-conjugated rat anti-mouse I-A/I-E antibody (Biolegend) or APC-Cy7-conjugated anti-CD45 antibody (Biolegend) diluted in PBS 5% FBS at 4° C. for 30 minutes in the presence of rat serum (1/100, GeneTex) to block unspecific binding. Cells were washed with PBS 5% FBS, resuspended in PBS 5% FBS and analyzed in a BD FACS LSR II. Flow cytometry data were analyzed using FlowJo software (FLOWJO, LLC, version 7.6).

In an embodiment, fluorescence-activated cell sorting (FACS) was performed in the following way: To purify Clec9A-tdTomato MEFs, cells were incubated at 4° C. for 30 minutes with APC-Cy7-conjugated anti-CD45 antibody (Biolegend) diluted in PBS 5% FBS. Subsequently, MEFs were washed with PBS 5% FBS, resuspended in PBS 5% FBS and tdTomato– CD45– MEFs were purified in BD FACSAria III. When described tdTomato+ cells were purified using BD FACSAria III. FACS data was processed in FlowJo software.

In an embodiment, freshly isolated spleens from Clec9a-tdTomato mice were homogenized using the frosted ends of 2 sterile slides. Cells were harvested in PBS supplemented with 5% FBS and filtered through a 70 μm cell strainer (BD Biosciences). Red blood cells were lysed with BD Pharm Lyse (BD Biosciences) for 8 min at room temperature. Lysis was stopped by addition of 5 volumes of PBS 5% FBS. Splenocytes were washed once to obtain single cell suspensions, which were incubated at 4° C. for 30 minutes with a mixture of FITC-conjugated anti-CD11c antibody (Biolegend), APC-conjugated anti-Bst2 antibody (Biolegend), APC-Cy7-conjugated anti-B220 antibody (Biolegend) and BV605-conjugated anti-Siglec-H antibody (Biolegend) diluted in PBS 5% FBS in the presence of rat serum. Single staining and fluorescent minus one controls were included for proper compensation and gating. After 30 minutes at 4° C., cells were washed and resuspended with PBS 3% FBS and analyzed in BD FACSAria III (BDiosciences). Data resulting from this analysis were treated using FlowJo software. Splenic pDCs are identified as live single cells CD11c$^{low}$ Bst2$^+$ B220$^+$ Siglec-H$^+$.

In an embodiment, an inflammatory cytokine assay was performed in the following way: tdTomato+ cells were FACS sorted at day 9 and cultured with 1 μg/mL of R848 (Invivogen) and 0.5 μM CpG ODN 1668 (Invivogen) for TLR 7 and TLR9 overnight stimulation, respectively. Levels of the cytokines interferon-α (IFN-α), interferon-β (IFN-β), interleukin-10 (IL-10), interleukin-6 (IL-6), tumor necrosis factor-α (TNF-α), C—C Motif Chemokine Ligand 5 (CCL5) and C—X—C motif chemokine ligand 10 (CXCL10), were assessed at day 10. 50 μL of culture supernatants from a 96-well plate well were collected and analyzed by LEGENDplex™ Mouse Anti-Virus Response Panel (13-plex) with V Plate (Biolegend), according to manufacturer's instructions. Acquisition was performed with a BD FACS LSR II and data were analyzed using LEGENDplex™ Data Analysis, version 8.0 (Biolegend).

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a transcription factor" or "the transcription factor" also includes the plural forms "transcription factors" or "the transcription factors," and vice versa. In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skilled in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

The disclosure should not be seen in any way restricted to the embodiments described and a person with ordinary skill in the art will foresee many possibilities to modifications thereof.

The above described embodiments are combinable.

The following table provides an overview of the sequences included in the present disclosure.

TABLE 1

| SEQ. ID.s included in the present disclosure. | | | |
|---|---|---|---|
| SEQ. ID. | Sequence description (Polynucleotide) | SEQ. ID. | Sequence description (Polypeptide) |
| 1 | Human IRF8 | 49 | Human IRF8 |
| 2 | Mouse IRF8 | 50 | Mouse IRF8 |
| 3 | Human SPIB | 51 | Human SPIB |
| 4 | Mouse SPIB | 52 | Mouse SPIB |
| 5 | Human ARID5A | 53 | Human ARID5A |
| 6 | Mouse ARID5A | 54 | Mouse ARID5A |
| 7 | Human BCL11A | 55 | Human BCL11A |
| 8 | Mouse BCL11A | 56 | Mouse BCL11A |
| 9 | Human CBFA2T3 | 57 | Human CBFA2T3 |
| 10 | Mouse CBFA2T3 | 58 | Mouse CBFA2T3 |
| 11 | Human CREB3L2 | 59 | Human CREB3L2 |
| 12 | Mouse CREB3L2 | 60 | Mouse CREB3L2 |
| 13 | Human ETS1 | 61 | Human ETS1 |
| 14 | Mouse ETS1 | 62 | Mouse ETS1 |
| 15 | Human HDAC5 | 63 | Human HDAC5 |
| 16 | Mouse HDAC5 | 64 | Mouse HDAC5 |
| 17 | Human HHEX | 65 | Human HHEX |

TABLE 1-continued

TABLE 1-continued

SEQ. ID.s included in the present disclosure.

| SEQ. ID. | Sequence description (Polynucleotide) | SEQ. ID. | Sequence description (Polypeptide) |
|---|---|---|---|
| 18 | Mouse HHEX | 66 | Mouse HHEX |
| 19 | Human HOXA5 | 67 | Human HOXA5 |
| 20 | Mouse HOXA5 | 68 | Mouse HOXA5 |
| 21 | Human ID3 | 69 | Human ID3 |
| 22 | Mouse ID3 | 70 | Mouse ID3 |
| 23 | Human IKZF1 | 71 | Human IKZF1 |
| 24 | Mouse IKZF1 | 72 | Mouse IKZF1 |
| 25 | Human IKZF2 | 73 | Human IKZF2 |
| 26 | Mouse IKZF2 | 74 | Mouse IKZF2 |
| 27 | Human IKZF3 | 75 | Human IKZF3 |
| 28 | Mouse IKZF3 | 76 | Mouse IKZF3 |
| 29 | Human IKZF5 | 77 | Human IKZF5 |
| 30 | Mouse IKZF5 | 78 | Mouse IKZF5 |
| 31 | Human IRF7 | 79 | Human IRF7 |
| 32 | Mouse IRF7 | 80 | Mouse IRF7 |
| 33 | Human MEF2C | 81 | Human MEF2C |
| 34 | Mouse MEF2C | 82 | Mouse MEF2C |

SEQ. ID.s included in the present disclosure.

| SEQ. ID. | Sequence description (Polynucleotide) | SEQ. ID. | Sequence description (Polypeptide) |
|---|---|---|---|
| 35 | Human MYB | 83 | Human MYB |
| 36 | Mouse MYB | 84 | Mouse MYB |
| 37 | Human RUNX2 | 85 | Human RUNX2 |
| 38 | Mouse RUNX2 | 86 | Mouse RUNX2 |
| 39 | Human STAT3 | 87 | Human STAT3 |
| 40 | Mouse STAT3 | 88 | Mouse STAT3 |
| 41 | Human TCF4 | 89 | Human TCF4 |
| 42 | Mouse TCF4 | 90 | Mouse TCF4 |
| 43 | Human TCF12 | 91 | Human TCF12 |
| 44 | Mouse TCF12 | 92 | Mouse TCF12 |
| 45 | Human STAT1 | 93 | Human STAT1 |
| 46 | Mouse STAT1 | 94 | Mouse STAT1 |
| 47 | Human TSC22D1 | 95 | Human TSC22D1 |
| 48 | Mouse TSC22D1 | 96 | Mouse TSC22D1 |

The following claims further set out particular embodiments of the disclosure.

The invention claimed is:

1. A construct or a vector encoding a combination of at least three transcription factors, wherein the combination of transcription factors comprises IRF8, SPIB, and IKZF2, wherein said construct or vector is a viral vector, a plasmid, or an RNA vector.

2. The construct or vector according to claim 1, wherein the vector is a viral vector.

3. The construct or vector according to claim 2, wherein the viral vector is selected from the group consisting of: a retroviral, adenoviral, lentiviral, herpes viral, pox viral, paramyxoviral, rhabdoviral, alphaviral, flaviral and adeno-associated viral vector.

4. The construct or vector according to claim 1, wherein the construct or vector is synthetic mRNA, naked alphavirus RNA replicons or naked flavivirus RNA replicons.

5. The construct or vector according to claim 1, wherein the construct or vector further codes for one or more other transcription factors selected from the group consisting of: ARID5A, BCL11A, CBFA2T3, CREB3L2, ETS1, IKZF1, STAT1, TCF4, TCF12, and TSC22D1.

6. The construct or vector according to claim 5, wherein the transcription factors are selected from:

a. IRF8 comprising a sequence having at least 95% identity with SEQ. ID. NO. 1 or SEQ. ID. NO. 2, b. SPIB comprising a sequence having at least 95% identity with SEQ. ID. NO. 3 or SEQ. ID. NO. 4, c. ARID5A comprising a sequence having at least 95% identity with SEQ. ID. NO. 5 or SEQ. ID. NO. 6, d. BCL11A comprising a sequence having at least 95% identity with SEQ. ID. NO. 7 or SEQ. ID. NO. 8, e. CBFA2T3 comprising a sequence having at least 95% identity with SEQ. ID. NO. 9 or SEQ. ID. NO. 10, f. CREB3L2 comprising a sequence having at least 95% identity with SEQ. ID. NO. 11 or SEQ. ID. NO. 12, g. ETS1 comprising a sequence having at least 95% identity with SEQ. ID. NO. 13 or SEQ. ID. NO. 14, h. IKZF1 comprising a sequence having at least 95% identity with SEQ. ID. NO. 23 or SEQ. ID. NO. 24, i. IKZF2 comprising a sequence having at least 95% identity with SEQ ID NO. 25 or SEQ ID NO. 26, j. TCF4 comprising a sequence having at least 95% identity with SEQ. ID. NO. 41 or SEQ. ID. NO. 42, k. TCF12 comprising a sequence having at least 95% identity with SEQ. ID. NO. 43 or SEQ. ID. NO. 44, l. STAT1 comprising a sequence having at least 95% identity with SEQ. ID. NO. 45 or SEQ. ID. NO. 46, or m. TSC22D1 comprising a sequence having at least 95% identity with SEQ. ID. NO. 47 or SEQ. ID. NO. 48.

\* \* \* \* \*

SEQUENCE LISTING

<160> NUMBER OF SEQ ID NOS: 96

<210> SEQ ID NO 1
<211> LENGTH: 2669
<212> TYPE: DNA
<213> ORGANISM: Homo sapiens

<400> SEQUENCE: 1

```
gtgaggtcat ggaggccagc attgccttct catggcaggt gtcccggagt ccctgaatct      60
gatgtgtgac cggaatggtg gtcggcggct tcgacagtgg ctgatcgagc agattgacag     120
tagcatgtat ccaggactga tttgggagaa tgaggagaag agcatgttcc ggatcccttg     180
gaaacacgct ggcaagcaag attataatca ggaagtggat gcctccattt ttaaggcctg     240
ggcagttttt aaagggaagt ttaaagaagg ggacaaagct gaaccagcca cttggaagac     300
gaggttacgc tgtgctttga ataagagccc agattttgag gaagtgacgg accggtccca     360
actggacatt tccgagccat acaaagttta ccgaattgtt cctgaggaag agcaaaaatg     420
caaactaggc gtggcaactg ctggctgcgt gaatgaagtt acagagatgg agtgcggtcg     480
ctctgaaatc gacgagctga tcaaggagcc ttctgtggac gattacatgg ggatgatcaa     540
aaggagccct tccccgccgg aggcctgtcg gagtcagctc cttccagact ggtgggcgca     600
gcagcccagc acaggcgtgc cgctggtgac ggggtacacc acctacgacg cgcaccattc     660
agcattctcc cagatggtga tcagcttcta ctatgggggc aagctggtgg gccaggccac     720
caccacctgc cccgagggct gccgcctgtc cctgagccag cctgggctgc ccggcaccaa     780
gctgtatggg cccgagggcc tggagctggt gcgcttcccg ccggccgacg ccatccccag     840
cgagcgacag aggcaggtga gcggaagct gttcgggcac ctggagcgcg gggtgctgct     900
gcacagcagc cggcagggcg tgttcgtcaa gcggctgtgc cagggccgcg tgttctgcag     960
cggcaacgcc gtggtgtgca aaggcaggcc caacaagctg gagcgtgatg aggtggtcca    1020
ggtcttcgac accagccagt tcttccgaga gctgcagcag ttctataaca gccagggccg    1080
gcttcctgac ggcagggtgg tgctgtgctt tggggaagag tttccggata tggccccctt    1140
gcgctccaaa ctcattctcg tgcagattga gcagctgtat gtccggcaac tggcagaaga    1200
ggctgggaag agctgtggag ccggctctgt gatgcaggcc cccgaggagc cgccgccaga    1260
```

-continued

```
ccaggtcttc cggatgtttc cagatatttg tgcctcacac cagagatcat ttttcagaga   1320
aaaccaacag atcaccgtct aagtgcgtcg cttgggcgcc ccaccccgtc tgcgtcctgc   1380
atccatctcc ctgttacagt ggcccgcatc atgattaaag aatgtggatc cctctgtctg   1440
gggtgggatg ccttactttg cacttaattt aataagggca ttctcggagg agtagacgtt   1500
taatacgaag tggcggcata gccctgccga gatgtcggtg atggcctgga tgctgtaacc   1560
acaacctgtg gctaaaaatt ttattttcta tcctttaccc gtcattatca ttagttgcta   1620
tgattctttc tgcattttcg gttaactatc atttccaaag acttgtcatt cagtaatatt   1680
agcagatagc tgcttcgata aaggaatttg gagtttaaaa atcaacttgt gaaaacaagg   1740 ttgttttgt ctttatcgtt tgttagagtt atagatttat gatttcatag gcttgattct     1800
atgtgaaata tcttttact tttatgcatt ttaataagat ttaaaaatat ttagattaaa     1860
gcccccttta atgagtacaa gaaaaactct tggcttgtta gaagaaagta tattctttct   1920
agaatttggt gcaggaatat gtgttcatat ccaggcaaac gggtgtgttt ttatcttcag   1980
acaatgaaac cttctcctct ggggctttgt tgccaggaag attagaacta aatttatttt   2040
tttcatttct gtcatgaaat cattccagat acctcttttc ttctttccaa atggttttca   2100
catgtgtttg aaatatttgt acttcgaatt gtcggatttt ccatgtcctc ctttctcctt   2160
tgtgcccagc ctgagtcagc accaatcccg cattcagaac ctcccagtga aagggcagcc   2220
ttcattttga gaaggtggaa ggtgttaggg tttgggagac agctcatcca atctcccaag   2280
tctcatggtg gatttgtgac tgtgagagtt ccggtttaa aatctgaaaa gccagatatg     2340
cctgtttcct tttcccagca ccatgcctgt ggaggggaca gtcagaccca gaggtccttt   2400
acgtgtggat ggagttcaca ggcgaataga ggagaggacc aggggacgtg gcttgtccct   2460
tttgtccaac aaagcattat atttttaaga atggcagacc tgtttgctga agtgttcata   2520
agataacaat aggcttgaat ctccaattca aatgaatgtc aaagcacata tctttaatat   2580
gctgaatgaa tatttatttt tgtatccatt aaaacagtat attgatctct tttattcttt   2640
attaaaataa aatgctcttt tttaaagct                                       2669
```

<210> SEQ ID NO 2
<211> LENGTH: 3391
<212> TYPE: DNA
<213> ORGANISM: Mus musculus

<400> SEQUENCE: 2

```
ttccaagccc actggtggca gttagggctg ctgtgtggct aaaaccagcc ctggagagac     60
ctcatctccc tcctctcagg ctgctgccgt cttttcctggc cccactacca cctgcaagcg   120
gcctggagtt tctgaccctc aggcctcttt ccagcaatcc tgactttgtg ggacatgctg   180
gctctggatg tgactatgtt cttggggata tcttgacttc tcactgatga taacttcttt   240 ttttttttt tttccctacc ccaagaggtc attttagttg gaagactaga agtgctgtgt   300
tctggttttc agggtgggcg tctgtccaac tgctttgggg atttccaggc tgttctagta   360
aatgctggct gcaagtccct gtgcacaaat gccctctctc cccacgctgt aggaaaagca   420
gacccgagag tgtccaagtg tgccattagg tgtctgggga tggcgggcct ggatatggag   480
tccctgagct ggctttgtac tgtccctttg ttctcactga gggctgattg taagagggac   540
tccctgtgtt gttggaggag tcctctagga tacaggctct gattgcagga tgtgtgaccg   600
gaacggcggg cggcggctgc ggcagtggct gatcgaacag atcgcagca gcatgtaccc     660 ggggctgatc tggaaaatg atgagaagac catgttccgt atccctggaa agcatgccgg   720
```

-continued

```
caagcaggat tacaatcagg aggtggatgc ttccatcttc aaggcctggg cagtttttaa    780
agggaagttt aaagagggag acaaagctga accagccacg tggaagacga ggttacgctg    840
tgctctgaac aagagcccag attttgaaga agtgactgac cggtcccagc tggacatttc    900
tgagccatat aaagtttacc gaattgtccc cgaggaagaa caaaaatgca agctgggcgt    960
ggcacctgca ggctgcatga gcgaagttcc tgagatggag tgtggccgct cagagattga   1020
ggagctgatc aaggaacctt ctgtggatga gtacatgggt atgaccaaga ggagcccatc   1080
cccaccagag gcctgcagga gccagatcct ccctgactgg tgggtccagc agcccagtgc   1140
aggcctgcca ctggtgaccg gatatgccgc ctatgacaca caccattcag ctttctccca   1200
gatggtcatc agcttctact acgggggcaa gctggtgggc caggccacca ccacctgcct   1260
tgaaggctgc cgtctctccc tgagccagcc ggggctgcct aagttgtatg gccggatgg   1320 cctggaaccc gtgtgctttc cgacggccga caccatcccc agtgagcggc agaggcaggt   1380
gacccggaag ctgtttgggc acctggaacg tggcgtgcta ctgcacagca accgcaaggg   1440
cgtgttcgtg aagcggctgt gccagggccg cgtgttctgc agcggcaacg cggtggtgtg   1500
caagggcagg cccaacaagc tggagcggga cgaggtggtg caggtctttg acaccaacca   1560
gttcatccga gagctgcagc aattctacgc cacccagagc cgcctacctg acagcagggt   1620
ggtcctgtgc ttcggggagg agtttccgga cactgtgccc ttgcgctcca aactcattct   1680
ggtgcaggta gagcagctgt atgccaggca gctggtggag aagcgggca agagctgcgg   1740 tgctggctcc ctgatgccag ccctggagga gccccagccg gaccaggctt tccgcatgtt   1800
tccggatatc tgtacctcac accagagacc cttttttaga gaaaatcaac agatcaccgt   1860
ctaagcctca gtccgggcac cccacctcgc ctgagctcaa gcttcaagag tctgtgacta   1920
agagaattcc gaaaggatgt ggagccctct gactggggtg ggcgggtgtc ctccaagggg   1980
cctccggaag cccacagagg gatgcgctcc tgctcaggca ggtgtcagaa gcttgcaggg   2040
gctgtggccg caacctgtga ttaaagcatt cctttcctgc gtttccccct tcaccactaa   2100
tggctggcct ttctgtgtgc tgaggtcttt cgacagttca aatcatctgg tggcagcaga   2160
ctcgcctttg cccttctgcg gccgagggcg gagatttatg actttctctg cttggttgga   2220
gaagaagaat ctttactatt cagcttcttt tcttttttggc cagaactctg aaaaaaaaaa   2280
aaactctttt taagacaata tttgtattct cacaggctca gctgtcaatc acttgagacc   2340
ttccctgtaa agtggggcag attttaaata tgggtgtaga tactgcttgc agccttcgca   2400 ggaatttttgg ttgtggttca ttgattcaca cagactctgt gtcagctgac agggctgtgt   2460
ggggcatcaa aggaggacca ggcactgtgg agaagaccca ttcactggca tctcacccett   2520 ccttgtccag ctccataccc agtcctaaga cccagtgaaa agccacgtcc aaactgtgct   2580
ctgggctcat cagtgcccac ccacgtacca gggaaaggca cacccctac ccagtgggca   2640 cagagcggaa tgtcccccta ccgcaccatt tgcgccccca atctggctgt ccaacctagt   2700
ttgtaagtaa tctaaatcag tgactatagc cccgcctaag ggacacttcc cggaggaggg   2760
agccgctgaa aaggagttag tttgagggtc agtacacaac aggggcagaa agccaagcag   2820
atgtgggggc agggagagtc atcatctgct tttgtctgag agaaggagag cttctccgtt   2880
tgttcaactt tgtaacaagc tgggttacat gctccacgca gctagagaag cctaggtgct   2940
ctgcattccc tggggaactg caggaaagcc ttacctgctg actgttgctc tggggaaaag   3000
cctgagggtc cagagcagct acaagctaca ggccatacct tacaacctga aaagctaagg   3060
```

-continued

```
accacggtga ccttcccggc tactgtgtga aggtgctggg tggggcctgc tcaacagaca      3120
gggtcgacag agtgtgtgat acatgcaaac agaatccttg gagtgtgtga tacatgcaaa      3180
cagaatcctg ggccctgct tctcccctc agtcaaagca ggagtgtccc ttccgaagcc        3240
aggacaacct gttcacaagg ccccttgtca catgtcacct tccacctgcc tcaaggagtg      3300
ctagtgtcca aatatttatt tttgtattct cttaagaagt attgatttca tcctttatta      3360
aaaaaagttg ctctttcaca aaaaaaaaaa a                                     3391

<210> SEQ ID NO 3
<211> LENGTH: 3792
<212> TYPE: DNA
<213> ORGANISM: Homo sapiens

<400> SEQUENCE: 3
ggcaaacagc ccgcccggca ccaccatgct cgccctggag gctgcacagc tcgacgggcc        60
acacttcagc tgtctgtacc cagatggcgt cttctatgac ctggacagct gcaagcattc       120
cagctaccct gattcagagg gggctcctga ctccctgtgg gactggactg tggccccacc       180
tgtcccagcc accccctatg aagccttcga cccggcagca gccgctttta gccaccccca       240
ggctgcccag ctctgctacg aacccccac ctacagccct gcaggaacc tcgaactggc         300 ccccagcctg gaggccccgg ggcctggcct ccctgcatac cccacggaga acttcgctag        360
ccagaccctg gttcccccgg catatgcccc gtaccccagc cctgtgctat cagaggagga       420
agacttaccg ttggacagcc ctgccctgga ggtctcggac agcgagtcgg atgaggccct       480
cgtggctggc cccgagggga agggatccga ggcagggact cgcaagaagc tgcgcctgta       540
ccagttcctg ctggggctac tgacgcgcgg ggacatgcgt gagtgcgtgt ggtgggtgga       600
gccaggcgcc ggcgtcttcc agttctcctc caagcacaag gaactcctgg cgcgccgctg       660
gggccagcag aaggggaacc gcaagcgcat gacctaccag aagctggcgc gcgccctccg       720
aaactacgcc aagaccggcg agatccgcaa ggtcaagcgc aagctcacct accagttcga       780
cagcgcgctg ctgcctgcag tccgccgggc ctgagcacac ccgaggctcc cacctgcgga      840
gccgctgggg gacctcacgt cccagccagg atcccctgg aagaaaaagg gcgtccccac        900
actctaggtg ataggactta cgcatcccca ccttttgggg taaggggagt gctgccctgc       960
cataatcccc aagcccagcc cgggcctgtc tgggattccc cacttgtgcc tggggtcctc      1020
tgggatttct ttgtcatgta cagactccct gggatcctca tgttttgggt gacaggacct     1080
atggaccact atactcgggg aggcagggta gcagttcttc cagaatccca agagcttctc      1140
tgggattttc ttgtgatatc tgattcccca gtgaggcctg ggacgttttt aagatcgctg      1200
tgtgtctgta aaccctgaat ctcatctggg gtggggccc tgctggcaac cctgagccct       1260
gtccaaggtt ccctcttgtc agatctgaga tttcctagtt atgtctgggg ccctctggga      1320
gctgttatca tctcagatct cttcgcccat ctatggctgt gttgtcacat ctgtcccctc      1380 attttgaga tccccaatt ctctggaact attctgctgc ccctttttat gtgtctggag        1440
ttccccaatc acatctaggg ctcctccaag atccttttgt catgtctgaa atcactcttg      1500
agaggtctgg ggtggaggat ggggagtcag tgaaatgtgt catgtctggg ccctgtcagg      1560
gacacccttg ttatatctgg gatcctccaa tcacatctga gacctcctag gctctccatc      1620
tgatatgccc tttcagggac cccacaaaga ctgagttctc atgggatcc taccttcct        1680 agtgccactc cctatggcca tgctgaagac cactctggcc acgcgactga tttttgggtga     1740 tcatggcagc tccccaccca tgtcatttct aaccagaagt ctcaaggtcg tcacccccct      1800
```

-continued

```
gcccccaac cgaggccccg gtcgctggtg gtggtctctt tagtgcactg tagcacttgg      1860
tggtggaggt gtgagggatc cacattaaca gcaggccatc agctgggcaa tggctcacac      1920
ctgtaatccc agcactttgg gaggcgaggc aggggggaatg gcttgaaccc aggcattcaa      1980
gaccagcctg ggcaacataa tgagacctcg tctctacaaa acataacaaa aacaattagc      2040
cgagcgtggg ggtgaacacc tgtggtccca gctgctcagg aggctgaggt gggaggatct      2100
cttgagccca ggaagtagga ggctgtagtg agctgtaatc gtgccactgc actccagcct      2160
gggcgacaga gtgagacacc gtcttaaaaa caaaaacaag gccgggcacg gtggctcatg      2220
cctgttgtcc cagcactttg ggaggccgag gcaggcggat cacgaggtcg agagatcgag      2280
accatcctgg ccaacatggt gaaaccctgt ctctactaaa aatacagaaa ttagctgggc      2340
gtggtggcac gtgcctgtag tcccagctac tcgggaggct gaggcaagag aatcgcttga      2400
acgtgggagg cagaggttgc agtgagccta gattgtgcca ctgcactcca gcctggggga      2460
cagagcgaga ctccgtctga aaataaaaac aacaaaaaca gcagaccatt caaaatagggg      2520 agactttgca taatccagat ttctgccttc acttaaaact ttggacggtc tggagagagt      2580
cggccagttt tcggtggggg gtggggagct ggaacaggac agtagccttt cctaatgagg      2640
catttgttct ccaatctgcc ccagtcgctg ccatccctgg ctatctcacc ctagcagctt      2700
ctcaagcctg ttggctttag accactgtat aaacccagct ggaactgaag cctgggtgga      2760
ctatggagcc ctggttggga ccccaggga gtcaaaggct gcgggccaag aggccagagg      2820
tccttgagcc tgggtgggca ggtggatcta gggtgcatga cttgctgctt cccaacctta      2880
gtttgtccct tctgtgaaaa agggagagaa ggaggaggaa gatctcaaaa agactttcca      2940
gcccagtgcg gtggctcacg cctgtaatcc cagcactttg ggaggccgat gcaggtggat      3000
cacctgaggt aggagttcaa gaccagcctg accaacatag tgaagcccct tctctactaa      3060
aaatacaaaa ttagctgggc gtggtggcat gtgcctgtac tcccagctac ttgggaggct      3120
gaggcaggag aatcgcttga acctgggagg cggaggttgt agtgagctga gatcacacca      3180
ctgcacacca gcctgggcga caagagcgaa actccgtctc aaaaaaaaaa aactgttgca      3240
gccccgttga gcctttgaca ccgcctgaaa tccaccccac tcccaggagg aggaggagga      3300
aggaatgcca atgacctaga gacacgagaa gtccatgtgg aggcacacag cagctgatgg      3360
cagagcccag gctgggacct gcccttaaga gaatgagtgg gaaggggggag ggaggaaggg      3420 caggtaaaac gtcctcccca gggcccctg caacggggaa ggtacttttt acaaaagcta      3480
tcattgtcac cctaaatgtg gaataaaata agatgcatcg acgtagacaa acctcctggg      3540
accttttgtc agggactgca atcctgcccc tccactgagg ccgctggctc tcagagacac      3600
cgtgacatca cgggtgatga tgagaggagt tcaaagagaa aattatatgc tggcgcggtg      3660
gctctgtaat cccaacactt tgggggggcca aggcaggagg atcgcttgag tacaggagtt      3720
tgaaaccagc ctgggcaaga tagtgagatc cccttcccac ccgtctacaa aaaaaataaa      3780
aaattagcgg gg      3792
```

```
<210> SEQ ID NO 4
<211> LENGTH: 2786
<212> TYPE: DNA
<213> ORGANISM: Mus musculus

<400> SEQUENCE: 4
agcctgctct gaaccaccat gcttgctctg gaggctgcac agctggatgg cccacactta      60
```

-continued

```
agctgtttgt acccagaagg agtcttctac gacctggaca gctgcaagcc cttcagttac      120
ccagattcag atggggggcct tgactctaca tggggctgga cagaggcccc gcctgctcct      180
gccatcgctc cctatgaagc cttcgatcct gctactgctg cctttagcca ctcccaaact      240
gttcagctct gttatagcca tggtcctaac ccctccacct atagccccat ggggaccctc      300
gacccagccc ccagcttgga ggccccaggg cctggcctcc aggtgtaccc cccagaggac      360
ttcaccagcc agaccctggg ctccttggct tatgctccgt accccagccc tgtgctatca      420
gaggaagaag acattatgct ggacagcccc gccctggagg tctcggacag tgagtcagac      480
gaggccctct tggctggctc cgaggggagg ggatctgagg caggtgcacg caagaagctg      540
cgcctgtacc agttcttgct ggggttgctc ctacgcgggg acatgcgcga gtgcgtgtgg      600
tgggtggagc caggtgccgg cgtcttccag ttctcctcca agcacaagga gttgttggct      660
cgccgctggg gccagcagaa gggcaaccgc aagcgcatga cgtatcagaa gctggcccga      720
gcgctgcgca actatgccaa gacaggcgaa atccgcaagg tcaaacgcaa actcacctac      780
cagtttgaca gcgcgctgct gccagcctcc cggcatgtct gagcactccg ctaaggaccc      840
ctttctggcc cctaagtccc atggagcccc atatgagggc agtcagggtt ctcagctctc      900
cctagagcct ccccagagtt tcctgtgccg tgtataggat tccaatctag gatggtcgtg      960
tttgagggag cactggccat tctacacggt ttcagaatgg caggtttctc ggggggggggg     1020 gggatggggg agccctgatg tcgtctacgg ttccagaaac cgcagttctt gcgagtcctg     1080
tgagctcaca tgacatctca ccagcaggtg gcgctgtcta cagcccccc caaacccttg     1140 ttttgttggc cagataggtc ggtccctctg tactccccct gaagcccttg ttagatctga     1200
ggtctagtta tgtttggagc tctctgagaa ccctgtgcca cctgtgtgtg acttttctct     1260
gcgtccgttt atgactttg tttgtttgag acagggtctc attatgtagc tcaggctggc      1320
cccccaactt ttaacaatcg tcctgcctcg gcctcctgag tgctgggatg acaagggtgc      1380
accatcacac caggtttttt cctttttttga gagattttac tatgtaaccc gggctgggct     1440
attctcaagc tagtggcagt cctcttgcct caggctcctc ttgcctcagg cacccccttgg     1500 gaccctctgg gacctatgtc cgagatgaat ggctgggtaa ggtagggtgg gaggttcagt     1560
gaaccttata ggttgggccc ttccttctgg gatcccttga tcatatggga agttctctag     1620
gctctcagca gccctgcatt cacacactga ctgaggcgcg acctgtatgt tgtgtttgag     1680
ggggatgtgt ggcagaggta tggctgtggc aaggccggtg cctttttattc ttgagattga     1740 gtcttatgta gctcaggctg gtcttgaact cactctcact gtgtagctag ggaagacctt     1800
gagcccttgc ctcagccaga atgctcagat gtcaggcagc gcaccacgtg actgtttctt     1860
tccattgtct tgtctttttg ttgttgttgt tttcgagaca gggtttctct gtgtagccct     1920
ggccgttctg gaactcactc tgtagaccag gctggcctta aactcagaaa tccacctgcc     1980
tctgcctctc aaatgctggg attaaaggcg tgcaccacca cgcccttttt ccttttttctt     2040 aagtcaaggt ctatttgtgt agcccaggct ggcttcaagc tcatgacact cttcctgcct     2100
ctgcgtctgg aactatgaac ataccttact actctgtgct tacccacgcc atgggtagac     2160
agacttctag acttggtcaa ccccccaccca caaggcaggc aaattaagtc cctgcaggtg     2220 cttttctttgg aggaaagccc gctttcatag tgatctgtca agctagaaag cactcccgcc     2280
acccagatat ctaagtgtga atctttggac aactggtgac ttctggccag cttttctggg     2340
gccggcctct gtccaggtgt ctgcccagga ccctgctcag tgcctgtctg tctcacacca     2400
gtgacttcct cacacccgcc tgttcaggcc cagtctttttc cgttcaagtg ctacaggcca     2460
```

-continued

```
agtaggctca aactgtgggt ttgtcttggg catccacagc agaatcagaa cccagagctt      2520
tgaagcctga gtgaggggag gggggcactc aggcttccgt ctctctgaga aacagacgat      2580
gaagaggccc ttaaaactct ttgcaacccc atgagcctcc ccaatgagcc tgtgacacac      2640
cggaactcac ctctgtgggt ggccgggagg gggaacaggg tcatggaaga tccagatgtc      2700
catgtggtca aggctaaact gtactaaata aaattatttc tcatcaccac tatacatgca      2760
taataaataa agtgtacatc aaaatt                                           2786

<210> SEQ ID NO 5
<211> LENGTH: 2343
<212> TYPE: DNA
<213> ORGANISM: Homo sapiens

<400> SEQUENCE: 5
atctcagaga gcgcggggtc cggacagccg cgcgctgagg gtctcggggc gggcgccgcg       60
ggacctctcc gggccatggc agccctgtc aaagggaaca ggaagcagtc cacggagggt      120
gacgccctag acccacctgc atcccccaaa cctgctggca agcagaacgg aatccagaac      180
cccatctcgc tggaggactc ccccgaggca gcgcggggag gggaggagga gcaggagcgg      240
gaggaggagc aggccttcct ggtcagcctc tacaagttca tgaaggagcg acacacgccc      300
atcgagaggt gccccatct cggcttcaag cagattaacc tgtggaagat ctacaaagca      360
gtggagaagc tggggggccta tgagctgcag tccatggccc taggagagag aatcggctgg      420
ccgctgctgg agccgcagag cagctgccaa actgcagtcc ttcgagtccc tgcgagggcg      480
gccggagctg caaggacccc gccgccaggg ggcgcccgcc ggccgcgccc tcacgaggtg      540
cccttgcagg tgaccgggcg ccgcctctgg aagaacgtgt acgacgagct gggggggcagc      600 ccaggcagca ccagcgcggc cacgtgcacg cgccgccact acgagaggct ggtcctgcca      660
tacgtgcggc acctgaaggg ggaggatgac aagccgctgc ccacctccaa gcccaggaaa      720
cagtacaaga tggctaagga aacagggggg gatgatgggg ccaccgagag gccgaagaag      780
gccaaggagg agcggcgcat ggaccagatg atgccaggaa agaccaaagc agatgctgct      840
gacccagcac cacttcccag ccaggagccc cccaggaaca gcacagaaca gcagggcctg      900
gcctctgggt cttctgtgtc ctttgtgggt gccagcggct gtcctgaggc ctacaagcgg      960
ctcctatcca gcttctactg caaggggaca cacggcatca tgtcaccact ggccaaaaag     1020
aagctcctgg cccaggtgag caaggtggag gccttgcagt gccaggagga gggctgccgc     1080
catggggcag agccccaggc gtccccagct gttcacctcc cagagagtcc ccagagcccc     1140
aaagggctga ctgagaactc caggcaccgg ctgacccctc aggagggatt gcaggcccca     1200
ggtggcagcc tcagagagga ggcgcaggca ggccctgcc cggcagcccc catcttcaag     1260
ggctgcttct acacccaccc caccgaggtg ctgaagcctg tcagccagca ccccagggac     1320
ttcttctcta gacttaaaga tggggtgcta ttggggcctc ctggcaaaga ggggctgtca     1380
gtgaaagagc cccagctggt gtggggcgga gacgctaacc gcccttctgc gttccataaa     1440
ggtggctcca gaaagggcat cctctacccc aagcccaaag cctgctgggt gtcccccatg     1500
gccaaggtcc cagccgagag ccccacgctc ccgcccacct tccccagtag cccaggcctg     1560
ggcagcaagc gcagcctgga ggaagagggt gctgcccaca gtgggaagag actgcgggcc     1620
gtgtctccct tcttaagga ggcggatgcc aagaagtgtg tgggccaaacc tgcagggtcc     1680 ggcctggtct cctgccttct gggcccagcc ctggggcctg tgcccccaga ggcctacagg     1740
```

-continued

```
ggcaccatgc tgcactgccc gctgaacttc actggcaccc cgggcccctt gaagggccag    1800
gctgcactcc ccttcagccc cctggtcatc ccggccttcc cggcccactt cctggccacc    1860
gcaggcccct cgcccatggc cgctggcctg atgcacttcc ccccaacgtc cttcgacagt    1920
gccctccgcc acagactttg cccggcctca tctgcctggc acgcaccacc agtcacaacc    1980
tatgcagcgc cccacttctt ccacctcaac accaagctgt aggccagccc atggtgttgt    2040
gtacactgtg gagtcgacag gggcctacaa caggcaggta ctgctgccag ggggctctga    2100
actagtgcct gctacccagg acacccgggc catgcccctg gctgggcagc ctggcacaag    2160
tgaagaagaa ggcagtggga aaactgggtt tatctcaagg cagcagcctg agcccaggag    2220
cagaggaccc agttgttata aggcgctggg agaggatggg cagctcccac tgccccagag    2280
cggagctcga agcacccagg ttgcccacgg aaaatccaat aaaaagacac cagtgtgaat    2340
cca                                                                   2343
```

```
<210> SEQ ID NO 6
<211> LENGTH: 5699
<212> TYPE: DNA
<213> ORGANISM: Mus musculus

<400> SEQUENCE: 6
```

```
agtcgagcgg cgccggtagt cagtcgcgcc gagagcgctg ggacaggacg gctgtgcgtg      60
tagagggtct ctgcatagcg acgcgcgctc tcgctgggcc atggcagcac ctccggccaa     120
agggaacaca gagcagtcag aagaaggtga cctcccgcag cttcctgtat cccccaagcc     180
agatgatgag cagagcagga gccagagccc cacccagctc caggactccc ctgaggcagg     240
tggggagcag gaggaggaac aggccttcct ggtcagcctc tacaagttca tgaaggagcg     300
acacacgccc atcgagaggg tgccccatct tggcttcaag cagattaacc tgtggaagat     360
ctacaaggca gtggagaagc tgggggccta tgagctggtg acaggccgcc gcctctggaa     420
gaacgtgtat gatgaacttg gcggtagccc aggcagcacc agtgcggcca catgcacacg     480
ccgccactat gagaggctgg tcctcccata tgtgcggcat ctgaaggggg aggacgacaa     540
gccactgcct cctaccaagc ccaggaagca atacaagatg gccaaggagc tgaggggaga     600
cgatgggacc actgagaagc tgaagaaggc caaggactca gaggagaggc gggtggagca     660
gaccacgcca ggaaagacca atcagatgc cactggccag acacagcttc cctgccaggg     720
atcctcgagg gacagcacag aacagctggg cccagtatct ggaccctctc caccactcac     780
gggtgctagt agctgccctg aggcctacaa gcggctcttg tcaagctttt actgcaaagg     840
ggcgcatggc atcatgtcac cactggccaa aaagaaactc ctggcccagg tcagcaaggc     900
agaggccttg cagtgccaag aagagggctg tcgccatgga gcaaggagcc ccaacaagga     960
cattcaagac agtccccaga acctaagagg gccggctgag aactctgaac accagctaac    1020 ccccgggaa ggattgcagg cccctggtgg gagcaccagg atggaggccc aagtgggccc    1080
ctgccctaca gccccatgt tctcaggctg ttttcatgcg taccccaccg aggtgctgaa    1140
acctgtcagc cagcacccta gggacttctt ctccggcctt aaagacaggg tgctgttggg    1200
accacctggt aaagaagaag tccgacaac caaagagtcc catctggtgt gggggtggga    1260
tgccaaccac ccctctgcat tccataaagg cagcacaaga aaaagaagtt ctacccccaa    1320
acccaaagcc tgctgggtgt ctcccatggc caaggtccct actgagaggc ctggagcccc    1380
atcccctcat cccagtagcc caggtcttgg cagtaagcgc ggcttggaag aagagggatt    1440
cgctcatggt ggcaagaaac tgagggcagt gtctcccttt ctgaaggagg tggattccaa    1500
```

-continued

```
ggagactggg ggcaagcctg cagcccctgg cttggctgta tcctgtctac tgggcccaac    1560
cccgggcccc actcctccag aggcctacag gggcaccatg ctgcggtgtc ctctaaactt    1620
caccggtagc gcagaccctc tgaagggcca ggcctcactc cccttcagcc ccctggtcat    1680
ccctgctttc ccagcccacc ttctggctac aacaggctcc tcacctatgg ctgccagcct    1740
gatgcatttc cctcccacgc cctatgacgc tgtcctacgc aacagactgg gtccagcttc    1800
gtctgcctgg cacatgccac ccgtcacaac ctatgcggca cctcacttct tccacctcaa    1860
caccaaactg taggccagag cctatcctgc tatgctgtgg aggatttgat gggcagctgc    1920
cgccattatc tcaggcctga gccgactacc cagattccca ggccagtgag gctccccgag    1980
tctgtgtctc tctggtacag acagcaggga ggcagtgggg cttgtctgaa tgaagcagcc    2040
cgggcccaaa gccaggggac caagttgtgg taagatcatg aaagtacctg agctggtatt    2100
ttctctccac tgagaggccg gggagctagt tggcagctca aggcatccag gttggccatg    2160
aaagacccaa taaaaagaca ctggtgtgat tgcactcagc cctggggtgt acagcactgg    2220
atgtttgcaa ggggaggtga ggcaggagca agtgtgtagg tgtggtgacc aatgtgcgag    2280
caaagatgaa aggaggccac tctggcctgg ctgccatcac cccactggaa gggtggcagg    2340
gccagagcca aactcagcct ctggtgcaca gatgaacagc tgtgattcct ttcgctccag    2400
ctccagcctc ggggcacctg actgttgagg ttgccacggt gccaaagccc agagcacact    2460
ggtgacctgt gagacaagat ggaggggctg tgtcactgca accctctgag ctgagccaca    2520
cgcccccatc ccagaaggcc tcgggtcttt cagtgaacgg catcacttgc tctgagaggt    2580
tcttgctgtg ttgctcaggt tagtctcgga ctcccgacct aaagaattcc tgctgcggcc    2640
ttctcagtag ctggaactac tggtgtgaac ctgtgaagag gggatttgtg ggagctcaca    2700
taaaacccaa gtgaatctgt cctggtagtg ggcagacctg tgagcccagc tgcctagtgt    2760
tcccagtgag cgacctgtca cattcacacc tactttcctg ttctacatac tgggtgaagg    2820 gtagaggggga cccatctcta cctgtgaatc tgttgccaag tcacagtgat atttacctgt    2880
ggttgctcca ggtgcccaca cagaaatccc atggcttggc acccattcct accttggaca    2940
tggcttgctc tgccagtccc aaggagactg tcagtacagc ttcacactgt tcctggaaag    3000
gcagtgccac tgtggaccag agatgccagg atgccagtga gccaagtcaa cagatggtta    3060
ctgacctaca tcatgggaac tcaccctgtt cctgacctca ggccatgggt aggagggcaa    3120 gttttatgg cccccttagt tcacaggcgg aatggccaag gccagagaca gcaggtgtca    3180
ttgaggatgt ctggctctgg gaaacgggtg gccaggaaa gcagctgcct gtggaaaaga    3240
gctgggacac aggtgtcctc caagaccagg tagctagagg gtaagggtcc cactgatgca    3300
tcttgcaact ccccaccttc cttctggaga taccaggatg ccagcctgag tattcagatg    3360
acaagccctg agctcctggc tacccccactg cacccatgtg ctacctgtct gggagctttt    3420 acagcccgt gaggagggat tctaggctag caaatgccct ggctgttggg ctgtacactg    3480
tggggtcagg tcccaggata gacagagggt accttcgtgc gtgcgtggaa ggatcccctt    3540
catctacaaa gtaacactag tctcaacctg ctcaaaggtg gcgtatgaca gacagcctga    3600
taatggtagc ttgttccaag ctgcaggaac ggagccctct gcaggttcat ctggagaata    3660
cacagctggg agggtagggt gtgtggcttt ctgggttgta ctccactctg cttcagcaaa    3720
aactctagaa atgaatgcac atcaggcttc ctgggaaatc ttgggacttt gcacccatgc    3780
gctagcccca catgattctc cttccttctg tgaatgagag aactcagctc agaggtgact    3840
```

```
ccaaacactg tggtacacac accttcctat gttcacttgt gtccctaaca ggttcccccca    3900 gaggacccac aggccagcaa agctcttggc gtctgtgtcc agggcataac ttgtggtctg    3960
agcctacttc caaatcattc gtgacatttg agctaataat ggtgggagga ggcagaggcc    4020
actctggtat ttgtgctgac cccacccctg tccgtggtcc tggctcattt ccctggaaac    4080
agcttaagtg tgatgagttg ggcattcagt gggaaatacc tttgtttgcc ttgggtgtca    4140
aagcatgctg cccctgtaac tgtcttaggt ggcattggtt agcattacat gtgcatctcc    4200
cacacgaggc aagtatcacc accgccatag ttgtttggtt ggttggtttt cttggcttct    4260
ttttaagaca ggatttctct gtgtagccct ggctgacctg gaacttactc tgtagaccag    4320
gctggtctct aatagaggtc caccctctgc ctctacttgg attaaagata tgcaccacca    4380
tgcccagcaa ccacctcgcc cagcaaccat cagagtttta aaccgaatgg ctgggaattt    4440
tcctttgaag accttgcgaa tggctacagg aggtgatgga gaaacagcag caagtccccg    4500
agggagtggc gagagagtgg ggccaggagc caggggggct gttgggcagg acggaggaa    4560 gccagagatg acttaggctg catttagaac cttctagtcc aggaggcagt tgggctttta    4620
tgtgaaataa agaaagatgg aagagagtcc tggctcccag atttggttgt ttgctttatg    4680
gtgctaggga tggaaccctg gacatttttt atgctcagca agctctgatc acttgctgca    4740
tcccagccct ggactctggc aagtggtagg tgtggacact ggagactaga acagagtagg    4800
gaacgtatcc ttggagatgg cagagtcaac atctggacac aggtctggag atgctgcgga    4860
cacatctggc cagcgtgtct gtttatactg tgagcagagt gagtgtgggg gctgggcttg    4920
gagaagggaa gcgagctagg cagtgatcac agtagagcaa agccgtccaa gggcacagcc    4980
agggcacaag agctcgggtt tccacttgac cttagcagcg tgagtatcat tgcacctagg    5040
aggccggctg gacacaatct caaggcaagg gacaactaag caccactcca gtgggagccg    5100
aagtggctgc atgaagggca tcaacagaga accagggaat gaagtgggga tggggggagg    5160
gagttgggaa cagtgggtaa gatctctaga ctgcagatct tggtgtgctg tggggacttg    5220
atggggtggg tgcacatgag aggcttggct gaatcagcag ctattggttg ctggatgagc    5280
tagagcaaga aggggtcaac agagctcagg catgggggac tttgaaacaa gggcagcggg    5340
catgctgggt gggcacagcc gccagggtaa ggtgtgtagg cacaggaaag gaggtgatgg    5400
ggcctcagca aaaaacacag cacaggaggc aagaagcaaa ggttaccttc cacatgaagt    5460
tgctgggctg gccagagcct tagactggca gaatagacat tagagaaggc cagaggcaat    5520
gaaaaacttc atggctttaa aggaatttta aatcaagagc agaggctgcc tggcatgttt    5580
agatgtgttt gtttttctagt gtgctggatg gaacccagag ccttgggtat gctgggcaag    5640
tatccaacac tgagctatat catttggtgt tttttaaaaa aaagaattaa caatatttg     5699
```

<210> SEQ ID NO 7
<211> LENGTH: 6102
<212> TYPE: DNA
<213> ORGANISM: Homo sapiens

<400> SEQUENCE: 7

```
gtctctgtcc atccagactc ctgacgttca agttcgcagg gacgtcacgt ccgcacttga      60
acttgcagct cagggggggct tttgccattt ttttcatctc tctctctctc tctccctcta    120
tctctcttct ctctctctcc ctctttttttt tttttttttt tttttttttt ttgcttaaaa    180
aaaagccatg acggctctcc cacaattcat cttccctgcg ccatctttgt attatttcta    240
atttattttg gatgtcaaaa ggcactgatg aagatatttt ctctggagtc tccttctttc    300
```

```
taacccggct ctcccgatgt gaaccgagcc gtcgtccgcc cgccgccgcc gccgccgccg      360
ccgccgcccg ccccgcagcc caccatgtct cgccgcaagc aaggcaaacc ccagcactta      420
agcaaacggg aattctcgcc cgagcctctt gaagccattc ttacagatga tgaaccagac      480 cacgcccgt tgggagctcc agaaggggat catgacctcc tcacctgtgg gcagtgccag        540
atgaacttcc cattgggggga cattcttatt tttatcgagc acaaacggaa acaatgcaat      600
ggcagcctct gcttagaaaa agctgtggat aagccacctt cccttcacc aatcgagatg        660 aaaaaagcat ccaatcccgt ggaggttggc atccaggtca cgccagagga tgacgattgt      720
ttatcaacgt catctagagg aatttgccccc aaacaggaac acatagcaga taaacttctg     780
cactggaggg gcctctcctc ccctcgttct gcacatggag ctctaatccc cacgcctggg      840
atgagtgcag aatatgccccc gcagggtatt tgtaaagatg agcccagcag ctacacatgt     900
acaacttgca aacagccatt caccagtgca tggtttctct tgcaacacgc acagaacact      960
catggattaa gaatctactt agaaagcgaa cacggaagtc ccctgacccc gcgggttggt     1020
atcccttcag gactaggtgc agaatgtcct tcccagccac ctctccatgg gattcatatt     1080
gcagacaata accccttta cctgctaaga ataccaggat cagtatcgag agaggcttcc      1140
ggcctggcag aagggcgctt tccacccact ccccccctgt ttagtccacc accgagacat     1200
cacttggacc cccaccgcat agagcgcctg ggggcggaag agatggccct ggccacccat     1260
cacccgagtg cctttgacag ggtgctgcgg ttgaatccaa tggctatgga gcctcccgcc     1320
atggatttct ctaggagact tagagagctg gcagggaaca cgtctagccc accgctgtcc     1380
ccaggccggc ccagccctat gcaaaggtta ctgcaaccat tccagccagg tagcaagccg     1440
cccttcctgg cgacgccccc cctccctcct ctgcaatccg ccccctcctcc ctcccagccc    1500 ccggtcaagt ccaagtcatg cgagttctgc ggcaagacgt tcaaatttca gagcaacctg     1560
gtggtgcacc ggcgcagcca cacgggcgag aagccctaca agtgcaacct gtgcgaccac     1620
gcgtgcaccc aggccagcaa gctgaagcgc cacatgaaga cgcacatgca caatcgtcc      1680 cccatgacgg tcaagtccga cgacggtctc tccaccgcca gctccccgga acccggcacc     1740
agcgacttgg tgggcagcgc cagcagcgcg ctcaagtccg tggtggccaa gttcaagagc     1800
gagaacgacc ccaacctgat cccggagaac ggggacgagg aggaagagga ggacgacgag     1860
gaagaggaag aagaggagga agaggaggag gaggagctga cggagagcga gagggtggac     1920
tacggcttcg ggctgagcct ggaggcggcg cgccaccacg agaacagctc gcggggcgcg     1980
gtcgtgggcg tgggcgacga gagccgcgcc ctgcccgacg tcatgcaggg catggtgctc     2040
agctccatgc agcacttcag cgaggccttc caccaggtcc tgggcgagaa gcataagcgc     2100
ggccacctgg ccgaggccga gggccacagg gacacttgcg acgaagactc ggtggccggc     2160
gagtcggacc gcatagacga tggcactgtt aatggccgcg gctgctcccc gggcgagtcg     2220
gcctcggggg gcctgtccaa aaagctgctg ctgggcagcc ccagtcgct gagccccttc     2280 tctaagcgca tcaagctcga gaaggagttc gacctgcccc cggccgcgat gcccaacacg     2340
gagaacgtgt actcgcagtg gctcgccggc tacgcggcct ccaggcagct caaagatccc     2400
ttccttagct tcggagactc cagacaatcg ccttttgcct cctcgtcgga gcactcctcg     2460
gagaacggga gtttgcgctt ctccacaccg cccgggggagc tggacggagg gatctcgggg    2520
cgcagcggca cggggaagtgg agggagcacg ccccatatta gtggtccggg cccgggcagg   2580
cccagctcaa aagagggcag acgcagcgac acttgtgagt actgtgggaa agtcttcaag    2640
```

-continued

```
aactgtagca atctcactgt ccacaggaga agccacacgg gcgaaaggcc ttataaatgc    2700
gagctgtgca actatgcctg tgcccagagt agcaagctca ccaggcacat gaaaacgcat    2760
ggccaggtgg ggaaggacgt ttacaaatgt gaaatttgta agatgccttt tagcgtgtac    2820
agtaccctgg agaaacacat gaaaaaatgg cacagtgatc gagtgttgaa taatgatata    2880
aaaactgaat agaggtatat taatacccct ccctcactcc cacctgacac ccccttttttc    2940 accactcccc ttccccatcg ccctccagcc ccactccctg taggattttt ttctagtccc    3000
atgtgattta aacaaacaaa caaacaaaca gaagtaacga agctaagaat atgagagtgc    3060
ttgtcaccag cacacctgtt ttttttcttt ttcttttttct tttttctttt tccttttttt    3120
tttttttcct ttatgttctc accgtttgaa tgcatgatct gtatggggca atactattgc    3180
attttacgca aactttgagc ctttctcttg tgcaataatt tacatgttgt gtatgttttt    3240
ttttaaactt agacagcatg tatggtatgt tatggctatt ttaaattgtc cctaattcgt    3300
tgctgagcaa acatgttgct gtttccagtt ccgttctgag agaaaaagag agagagagag    3360
aaaaagacca tgctgcatac attctgtaat acatatcatg tacagtttta ttttataacg    3420
tgaggaggaa aaacagtctt tggattaacc ctctatagac agaatagata gcactgaaaa    3480
aaaatctcta tgagctaaat gtctgtctct aaagggttaa atgtatcaat tggaaaggaa    3540
gaaaaaaggc cttgaattga caaattaaca gaaaaacaga acaagtttat tctatcattt    3600
ggttttaaaa tatgagtgcc ttggatctat taaaaccaca tcgatggttc tttctacttg    3660
ttataaactt gtagcttaat tcagcattgg gtgaggtaat aaaccttagg aactagcata    3720
taattctata ttgtatttct cacaacaatg gctacctaaa aagatgaccc attatgtcct    3780
agttaatcat cattttttcct ttagtttaat tttataaaca aaactgatta taccagtata    3840
aaagctactt tgctcctggt gagagcttaa aagaaatggg ctgttttgcc caaagtttta    3900
ttttttttaa acaatgatta aattgaatgt gtaatgtgca aaagccctgg aacgcaatta    3960
aatacactag taaggagttc attttatgaa gatatttgct ttaataatgt cttttttaaaa    4020 atactggcac caaaagaaat agatccagat ctacttggtt gtcaagtgga caatcaaatg    4080
ataaacttta agaccttgta taccatattg aaaggaagag gctgacaata aggtttgaca    4140
gaggggaaca gaagaaaata atatgattta ttagcacaac gtggtactat ttgccattta    4200
aaactagaac aggtatataa gctaatattg atacaatgat gattaactat gaattcttaa    4260
gacttgcatt taaatgtgac attcttaaaa aaagaagaga aagaatttta agagtagcag    4320
tatatatgtc tgtgctccct aaaagttgta cttcatttct tttccataca ctgtgtgcta    4380
tttgtgttaa catggaagag gattcattgt tttttattttt atttttttaa tttttttcttt    4440 tttattaagc tagcatctgc cccagttggt gttcaaatag cacttgactc tgcctgtgat    4500
atctgtatct tttctctaat cagagataca gaggttgagt ataaaataaa cctgctcaga    4560
taggacaatt aagtgcactg tacaattttc ccagtttaca ggtctatact taagggaaaa    4620
gttgcaagaa tgctgaaaaa aaattgaaca caatctcatt gaggagcatt ttttaaaaac    4680
taaaaaaaaa aaaactttgc cagccattta cttgactatt gagcttactt acttggacgc    4740
aacattgcaa gcgctgtgaa tggaaacaga atacacttaa catagaaatg aatgattgct    4800
ttcgcttcta cagtgcaagg attttttttgt acaaaacttt tttaaatata aatgttaaga    4860
aaaatttttt ttaaaaaaca cttcattatg tttagggggg aactgcattt tagggttcca    4920
ttgtcttggt ggtgttacaa gacttgttat ccatttaaaa atggtagtgg aaattctatg    4980
ccttggatac acaccgctct tcaggttgta aaaaaaaaaa acatacattg gggaaaggtt    5040
```

-continued

```
taagattata tagtacttaa atataggaaa atgcacactc atgttgattc ctatgctaaa    5100
atacatttat ggtctttttt ctgtatttct agaatggtat ttgaattaaa tgttcatcta    5160
gtgttaggca ctatagtatt tatattgaag cttgtatttt taactgttgc ttgttctctt    5220
aaaaggtatc aatgtacctt ttttggtagt ggaaaaaaaa aagacaggct gccacagtat    5280 attttttaa tttggcagga taatatagtg caaattattt gtatgcttca aaaaaaaaaa    5340
aaagagagaa acaaaaaagt gtgacattac agatgagaag ccatataatg gcggtttggg    5400
ggagcctgct agaatgtcac atggatggct gtcataggg ttgtacatat ccttttttgt     5460 tccttttttcc tgctgccata ctgtatgcag tactgcaagc taataacgtt ggtttgttat    5520
gtagtgtgct ttttgtccct ttccttctat caccctacat tccagcatct taccttcata    5580
tgcagtaaaa gaaagaaaga aaaaaaagg aaaaaaaaaa aaaaaccaat gttttgcagt     5640
ttttttcatt gccaaaaact aaatggtgct ttatatttag attggaaaga atttcatatg    5700
caaagcatat taaagagaaa gcccgcttta gtcaatactc ttttgtaaat ggcaatgcag    5760
aatattttgt tattggcctt ttctattcct gtaatgaaag ctgtttgtcg taacttgaaa    5820
ttttatcttt tactatggga gtcactattt attattgctt atgtgccctg ttcaaaacag    5880
aggcacttaa tttgatcttt tatttttctt tgttttttatt ttttttttta tttagatgac    5940
caaaggtcat tacaacctgg cttttttattg tatttgtttc tggtctttgt taagttctat    6000
tggaaaaacc actgtctgtg tttttttggc agttgtctgc attaacctgt tcatacaccc    6060
attttgtccc tttattgaaa aaataaaaaa aattaaagta ca                       6102
```

<210> SEQ ID NO 8
<211> LENGTH: 6122
<212> TYPE: DNA
<213> ORGANISM: Mus musculus

<400> SEQUENCE: 8

```
gacgttcaag ttcgcaggga cgtcacgtcc gcacttgaac ttgcagctca ggggggcttt     60
tgccattttt ttcatctctc tctctccctc tatccctctt ctctcttcct ctctctcttt    120
tttttcctta aaaaaaaaaa agccatgacg gctctcccac aattcatctt ccctgcgcca    180
tctttgtatt atttctaatt tattttggat gtcaaaaggc actgatgaag atattttctc    240
tggagtctcc ttctttctaa cccggctctc ccgatgtgaa ccgagccgtc gtccgcacgc    300
cgccgccgcc gccgccgccc gccccgcagc ccaccatgtc tcgccgcaag caaggcaaac    360
cccagcactt aagcaaacgg gaattctcgc ccgaacctct tgaagccatt cttacagatg    420
atgaaccaga ccatggcccg ttgggagctc cagaagggga ccacgacctt ctcacctgtg    480
ggcagtgcca gatgaatttc ccactggggg acattcttat ttttatcgag cacaaacgga    540
aacaatgcaa tggcagcctc tgcttagaaa aaggtgtgga taagccgcct tccccttctc    600
ccatcgagat gaaaaaggca tccaatcctg tggaggttgg catccaggtc acgccagagg    660
atgacgattg tttatcaacg tcatctagag gaatttgccc caaacaggaa cacatagcag    720
ataaacttct gcactggagg ggcctgtcct ctcctcggtc tgcacacgga gctctaatcc    780
ccacgcccgg gatgagtgca gaatatgccc cgcagggtat ttgtaaagat gagcccagca    840
gctacacatg tacaacttgc aaacagccat tcaccagtgc atggtttctc ttgcaacacg    900
cacagaacac tcatggatta agaatctact tagaaagtga acacggaagt cccctgaccc    960
cgcgggttgg tatcccttca ggactaggtg cagaatgtcc ttcccagcca cctctccatg   1020
```

-continued

```
ggattcatat tgcagacaat aacccctta acctgctaag aataccagga tcagtatcga   1080
gagaggcttc cggcctggca gaagggcgct ttccacccac tcccccctg tttagtccac     1140 caccgagaca tcacttggac ccccaccgca tagagcgcct gggggcggaa gagatggccc     1200
tggccaccca tcacccgagt gcctttgaca gggtgctgcg gttgaatcca atggctatgg    1260
agcctcccgc catggatttc tctaggagac ttagagagct ggcagggaac acgtctagtc    1320
caccgctgtc cccaggccgg cccagtccta tgcaaaggtt actgcaacca ttccagccag    1380
gtagcaagcc acccttcctg gcgacgcccc ccctccctcc tctgcaatcc gcccctcctc     1440
cctcccaacc cccggtcaag tccaagtcat gcgagttctg cggcaagacg ttcaaatttc    1500
agagcaactt ggtggttcac cgacgcagcc atactggtga gaagccctat aagtgcaacc    1560
tgtgcgacca cgcgtgcaca caggccagca agctgaagcg tcacatgaag acacacatgc    1620
acaaatcgtc ccccatgaca gtcaagtccg acgatggcct ctccacagcc agctccccgg    1680
aacctggtac cagcgacctg gtgggcagcg ccagcagtgc gctcaagtca gtggtggcca     1740
agttcaagag tgagaacgac cccaacttga tcccagagaa cggggatgag gaggaagagg    1800
aggacgacga ggaagaagaa gaagaggagg aagaggagga ggaggagctg acggagagcg     1860
agagggtgga ctacggcttc gggctgagcc tggaggctgc acgccaccat gagaacagct    1920
ctcggggcgc agtggtgggc gtgggcgacg agggccgcgc cctgcccgat gtcatgcagg   1980
gcatggtgct cagctccatg cagcacttca gcgaggcctt ccaccaggtc ctgggcgaaa     2040
agcataagcg tagccacctg gccgaggccg agggccatag ggacacttgt gatgaagact    2100
cggtggccgt tgagtcagac cgcatagacg atggcactgt taatggtcgt ggctgctccc    2160
ccggcgaatc ggcttcgggg ggtctgtcca aaaagctgct gctgggtagc cccagctcgc    2220
tgagcccctt ctccaagcgc atcaagctgg agaaggagtt tgacctgccc ccggccgcga   2280
tgcctaacac ggagaacgtg tattcgcagt ggctcgctgg ctatgcggcc tccaggcagc    2340
tcaaagatcc cttccttact ttcggagact ccagacaatc gccttttgcc tcctcatcag   2400
agcactcctc ggagaacggg agcttgcgct tctccacacc gcccggggag ctggacggag    2460
ggatctcagg gcgcagcggc acaggaagtg gagggagcac gccccatatt agtggtccgg    2520
gcccgggcag gcccagctca aaagagggca gacgcagcga cacttgtgag tactgtggga    2580
aagtcttcaa gaactgtagc aatctcactg tccacaggag aagccacacg ggcgaaaggc    2640
cttataaatg cgagctgtgc aactatgcct gtgcccagag tagcaagctc accaggcaca    2700
tgaaaacgca tggccaggtg gggaaggacg tttacaaatg tgaaatttgt aagatgcctt    2760
ttagcgtgta cagtaccctg gagaaacaca tgaaaaaatg gcacagtgat cgagtgttga    2820
ataatgatat aaaaactgaa tagaggtata ttaataccct ccctcactcc cacttgatgc    2880 ccccccttcca cccccttcccc attgtcctc cagccctact ccctgtagga ttttctagt      2940 cccatgtgat caaacaaaca aacaaacaaa caacagaggg aatggaagct aagaatatga    3000
atgagtgctt gtcaccagca cacctggttt tttgttttgt ttttcctttt ttttttcttt    3060
ttcttcttct ttttttttaaa ttttaaattc tttatgttct caccgtttga atgcatgttt   3120
ggggcaatac tattgcattt tacgcaaact ttgagccttt ctcttgtgca ataatttaca    3180
tgttgtgtat gttttttcccc ccttaactta gacagcatgt atggtatgtt acggctattt   3240
taaattgtcc ctaattcatt atgagcaaac atgttgttgc tgtttccagt tccattctga    3300
gagtgtgagg gagggagggt agaaacaaac gcatgctgca tacataattc tgtaatacag     3360
atcatgtgca gctttatttt ataacacgag gagggaaacg gtgtctgggt tgactaaccc    3420
```

```
tctgcagaca gagcagatag cagtgaaaaa aaggtgctaa atgtctgtct ctaaagggtt    3480
acatgtatta attggagagg gaaaaaaggc cttgaattga caaattaaca gaagaacaag    3540
tttattctat catttggctt ttaaaatgag tgccttggat ctattcaaac catgttgatg    3600 gtttttttttc tgcttgttat aaacttgtag tttaatctag cattgggtga ggtaataaac    3660
tttaggacct agcatgtaat ctgtgttgt atttctcaca acaatggcta cctaaaaata    3720
tgacccatta tgtcctagtt aatcattgat ttttgccttt aactttgtga acaaaactga    3780
ttataccagt ataaaagcta ctttgctcct tgtgagagca taaaagaaat gggctgtttc    3840
gcctaaagtt ttattttatt ttatttttaa atggttatca aattgaatgt gaaatgtgca    3900
aaggccctgg aatgtgatga aatacattag caagaagttc atcttgtgac aatacttgtt    3960
taaaatgatg catttaatga aattctggcg ccaaaagaag tagatccggc tctagttggt    4020
tgttgagtgg acaataaaat gataaagccc tttagaggac atttgaaaga acaggctgat    4080
atgatgagag agagagagag agacagaaaa cggtagtgat tggttagcac gatgtagtac    4140
tgtttgccat ttgaaactag aacaggtgta taaggggcca gcgatacaat gatgattaac    4200
tctgaagctc taagacttgc atttaatgtg acagtcttca aaaagaagag gaagaccttt    4260
aagagcagca gtatctatgt ctgtgctccc tggaagttgt acttcatttc ttttccatac    4320
actgtgtgct atttgtgtta acattgaaga ggatttgttt ttattttgtt ttattctttc    4380
tttctttctt ttttcttcct tctttgtttt aagctagcat ctgccccagt tggtgttcaa    4440
atagcacttg actctgccta tgatacctgt atcttttctc taatcagaga tacagaggtt    4500
gagtataaaa taaacctgct cagataggac aattaagtgc actgtacagt tttcccagtt    4560
tacaggtctt tattaaggga aacgttgcaa gaatgctgaa aacaattgaa cacaatctca    4620
atgatgagca ttaaaaaata ataaaaaaaa acaagcaaac ctaaaaaaaa ctaagacaga    4680
cgttgccagc cattgacttg actattgagc ttcctcactt ggatgcaaca ttgcaagcgc    4740
tgtggatgga aacaacacac ttaacataga aacgaatgac tcctttgctt ctacagtgca    4800
aggatttttg tacaaaactt ttttaagtat aaatgttaag aaaagaattt ttaaaaagac    4860
acttcattat gtttagggg gaacagcatt ttagggttcc attgtcttgg tggtgttaca    4920
agacctgtta tccatttaaa aatggtagtg gaaattctat gccttggatc acacaccgct    4980
cttcaggttg taaaaaaaaa tgaaaacaaa acaaaacaaa aaaaaaacat acatgggaa    5040 aggtttaaga ttatatagta cttaaaaata ggaaaacgca cactcatgtt gattcctatg    5100 ctaaacaca gttatggtct tctttctgta tttctagaat ggtatttgaa ttaaatgttc    5160
atctagtgtt aggcactata gtatttatat tgaagcttgt attttttaact gttgcttgtt    5220 cactcaaaag gtatcaatgt acctttttgt tagtagaaaa aaaaagacag gctgccacag    5280
tatatttttt taatttggca ggataatata gtgcaaatta tttgtatgct gagagagaga    5340
gagagagaga gagagagaga gagagaggtg tgacattgta cagagaagcc atataatggc    5400
ggtttgggga gcctgctaga atgtcacatg gatggctgtc atagggggttg tacatatcct    5460 tttccccctt tcctgctgcc atgctgtacg cagcactgca agctaatagc gttggtttgt    5520
tatgtagtgt gctttggccc ctcctccccg ctcacccgac attccagcat cttaccttca    5580
tatgcagtaa aagaaagaaa gaaaaaaaaa aaggaaaaaa aaaacaacaa caatgttttg    5640
cagttttttt cattgccaaa aactaaatgg tgctttatat ttagattgga gagaatttct    5700
tatgcaaagc atattaaaga gaaagcccgc tttagtcaat acttttttgt aaatggcaat    5760
```

-continued

```
gcagaatatt ttgttattgg ccttttctat tcctgtaatg aaagctgttt gtcgtaactt      5820
gaaattttat cttttactat gggagtcact atttattatt gcttatatgc cctgttcaaa      5880
acagaggcac ttaatttgat cttttatttt tctctgtttt tattattatt ttttttaatt      5940
tggatgacca aaggtcattg caacctggct ttttactgta tttgtttctg gtctttgtta      6000
agttctattg gaaaaaccac tgtctgtgtt tttttggcag ttgtctgcat taacctgttc      6060
atacacccat tttgtccctt tattgaaaaa aaataaaaaa attaaagtac taaaaaaaaa      6120
aa                                                                      6122

<210> SEQ ID NO 9
<211> LENGTH: 4480
<212> TYPE: DNA
<213> ORGANISM: Homo sapiens

<400> SEQUENCE: 9
aaaccggaat ggcccgaggg aaggccgcgc agggcagggc cccagatggt tcctgtcagg        60
gaagtggcgg gcgcagctgc aggcctccgg ccccggcatt atcacgggga cacagctggc       120
tgcctcaccc gcaggctgca gggagacctt ccccagcctg cagccccagg cccgccccgc       180
gtcacatgag ccccagggct cccaccccct ccccagggca gaggacaccc agttggtggc       240
cgggagggcc tcggctttcc agggacagag gcccaactcc aggacgcccc agctggccca       300
gcccctcctc tttccctcaa ggctgcagga ggtcgggaaa ggcagtcctg gtagaggcct       360
gtcctgggct ccaggttggc ccctgagggt ggcctcctc atgccggctt caagactgag       420
ggacagggca gccagttcag cctcgggatc cacctgtggc tccatgtccc agacgcaccc      480
tgtgctggag agcggcctcc tggcatctgc cggctgctcc gcaccccggg gtcccaggaa       540
gggcggccca gccccagtgg acaggaaagc taaggcctca gcgatgccgg actccccagc       600
ggaggtgaag acgcagcccc ggtccacacc ccccagcatg ccgcccccac cgcctgccgc       660
atcccagggg gccacacgcc ccccctcctt cacgccacac acacatcgag aggacgggcc       720
tgcgacgctg ccccacggcc gttttcatgg ctgcttaaaa tggtctatgg tctgtctctt       780
gatgaacggc agcagccact caccaacagc catcaatggt gcaccgtgca cacccaacgg       840
cttcagcaat ggcccggcca cctcgtccac agcctccttg tccacacagc acctgccccc       900
agcctgcggg gcccggcagc tcagcaagct caagcgcttc ctcaccacac tgcagcagtt       960
tggcagcgac atctccccag agattgggga gcgcgtgcgc acactggtgc tgggcctggt      1020
gaactcgaca ttgacgatcg aggagtttca ttccaagctt caggaggcca ccaacttccc      1080
tctgcggccg tttgtcattc ccttcctgaa ggcaaacctg cccttgctgc agcgggagct      1140
cctgcactgt gcacgcctgg ccaagcagac gcccgcccag tacttggccc agcatgagca      1200
gctcctgctg gacgccagcg cctcctcccc catcgactcc tcagagctgc tactggaagt      1260
caacgagaac ggcaagagga ggacgcccga caggaccaaa gagaacgggt cagaccgcga      1320
cccgctgcac cccgagcacc tcagcaaacg gccatgcacc ctgaaccctg cccagcgcta      1380
cagccccagc aacgggccac cgcagcccac accgccgccg cactaccgcc tggaggacat      1440
agccatggcc caccacttcc gagatgccta ccgccaccca gaccccccggg agctacgaga      1500 gcgccatcgg ccgcttgtgg tgcctgggtc ccggcaggaa gaagtgatcg accacaagct      1560
cacagagcgt gagtgggcag aagagtggaa gcacctcaac aacctcctga actgcatcat      1620
ggacatggtg gagaagacgc ggcgctcgct cacggtgctg cgcaggtgcc aggaggccga      1680
ccgcgaggag ctcaaccact gggcgcggcg ctacagcgac gccgaggaca caaagaaggg      1740
```

```
ccccgctccc gccgcggccc ggccccgcag cagctccgcc ggtcccgaag ggcctcagct      1800
agacgtgcct cgcgagttcc tgccgaggac cctcaccggc tacgtgcctg aggacatctg      1860
gaggaaggct gaagaggccg tgaatgaggt gaagcggcag gccatgtcgg agctgcagaa      1920
agccgtgtcg gacgcggagc gcaaagcgca cgagctcatc accacggagc gtgccaagat      1980
ggagcgggcc ctggccgagg cgaagcggca ggcctccgag gacgccctga cggtcatcaa      2040
ccagcaggag gactccagcg agagctgctg gaactgcggg cggaaagcca gtgagacgtg      2100
cagcggctgc aacgcggcac gctactgcgg gtccttctgc cagcatcggg actgggagaa      2160
gcatcaccac gtgtgtggcc agagcctgca gggccccaca gccgtggtgg ccgacccggt      2220
gcctggaccg cccgaagccg cccacagcct gggcccctcc ctgcctgtgg gtgctgccag      2280
ccccagcgaa gccggctctg cggggccttc tcgccccggc tcccccagcc cacctggccc      2340
actggacacc gtgccccgct gacccccactg gcccctggcc tgccggacac agcaccgtgc      2400
caaccccacc cagctccagg cccaccggat gctgtgcctg gcctccgatg cctggcctgc      2460
cagacactgc gccccgcctg acctggggga gccgaccaat tagtcactgc tgctactgcc      2520
cctctccgaa agaagacaca gaaccaacaa aaccgcattc agtgcacctg cctcagctac      2580
ctaatgattc cgcgcggaga cctcctgaca acgtctcttc aagcatcctc agaagcctcg      2640
actgagcttt agacagcaga gcagatgccg caggcgcggc ggctctgccc acctctcttt      2700
tcctctctgt ctgtctctcc ccctctgtct tctctatcct ctctctctct atgactatca      2760
cacactttct cttcaatgaa aaaatcgaat tggtggctta tattttcagc aaagaatttt      2820
ggggggtttt gtgtgttggc aaaagagcta ctcagaaatg gacaagaaa acgggggggt      2880 tctccccctc ctgattaaaa agggagaaag aaaactgcga ttttatagct ggagatctga      2940
acccagctgt gcccctcccc caggggcgtg aggctgatca gcgaagacgg gaggaaagat      3000
ttcgatttct gactcaagat gcattttttgg tttcagattt tttttcctg taatgttaaa      3060 ctctttggct ttaagtaaaa atccaaaaag ttttttttaaa aaagcaaagg aagcatactt      3120
gtgaactacc ttgctagcta gccagccaag gataccggac acacctctgc tccaaaggaa      3180
atccaaaaaa gcaaacacaa gaaatcaaaa tccaaaattt gtttgtcact gccaaagtat      3240 tttttttcact gtttcacttg ctcttggggtt tgtttggatg tgggtctttt tctcttctgt      3300
tctgattttt tttgtggggtg tcgggatatt tgggtgcaga gggtttgtgc ccagttagaa      3360
gcgacttttg ttctcttctg cgtaggcgtt ggtgcgtccg ccgcgtgtgc gtggtccgtg      3420
tgccgttgct ccggcctgcg tctccatatg tgtaggaaag gacacgccgt ctgtcctcac      3480 gcccctgtg acttttcata tttccgtttt ccacttgtgg aaaaaaagtg ctaaagttt      3540 cttcccagag agagcataat tccgaaacaa aactgtgaca atcttttggg ttgattctcg      3600
actgcttttc gagcatgcgg agccagcagg cctccctgaa acactgcttc tcggccagcc      3660
cgtcctcctc tacctctctc ctctccgcgc cctccgacct ctctcggccc cctcaccccca      3720 gctccgacct ctctcagccc catcgcccca actccaacct ctcggcccca tcgccccacc      3780
gcagctactc cccttcttc caaacttttg cagaaaaaac aaaaaaacta caaacaaaag      3840
cagccctctg cctcctcccc agggaagacc ctgaccgtgt acatagccct ggtgctcctg      3900
cccagccacc cctcagatgc gttcgcctct ggccctgggg tgtgtctcgg tgacgttttc      3960
tatcagacgt gctccctccc atcctccagc cctgcccacc ctccctccac tcctctcaac      4020
tgcctcagcg atttcaagaa ggaaataaag ggataaagaa attcatgctt gcaccgagta      4080
```

```
caaggacaga cagcaggcac ggcccgcagc ctggcatctg tgcgtgtggc gtggcccgtg      4140
gcttggcatc tgtgtgcgtg gtgtggcccg tggcctggca tctgtgtgcg tggcgtggcc      4200
cgtggcctgg catctgtgtg tgtggcgtgg cccgtggcct ggcatctgtg cgcgtggcgt      4260
ggcccgtggc ctggcatctg tgtgcgtggc tatcaggagt ctaggaact cagtgcaata      4320 cgggagtgac ccagctactg aaccagccac gaacagcccg ccagaggcct gaagctgagc      4380
gtgtacgtta atgtgaatgt atatagtctt tgcagaggtc caaatgatat tcatgatggt      4440
aataaacgag atgtttgcca aataaaaaac agaaaccgca                            4480

<210> SEQ ID NO 10
<211> LENGTH: 7659
<212> TYPE: DNA
<213> ORGANISM: Mus musculus

<400> SEQUENCE: 10
agggccacaa cccagctctg ccggctgtag tgactagaaa ggcctggagc ctccaaggaa        60
cagaggcacg ggctccgaga cgccaaagct cctccagccc tcctgttctc tccagacccc       120
acgaaatcag aaaaggtgct tcagggtggg ctctggaggc cggccagctc cctccagccc       180
caggtaccat caatctccgg ctccatctgc agctccatgt cccaggcatc caccaccact       240
ctggagagtg gggcactcct ctcgggaccc cggggtcttc agaatggaag cccagctcac       300
aggaaggaga aggctgcagc aatgccagac tccccggctg aagtgaagac gcagcccgg        360 tccacacccc ccagcatgcc gcccccacct cccacctcat cccagggagc cacacgacca       420
ccctccttca cacctcacac acatggcgag gatggacctg cgacgtctct tccccatggc       480
cgtttccacg gctgcttaaa gtggtccatg gtctgtctct tgatgaacgg cagcagccac       540
tcacccacgg ccatccacgg tgccccatct acacccaatg gcttcagcaa cggcccagcc       600
acctcatcca cggcctcgct ctccacacag cacctgcccc cggcgtgcgg ggcacggcag       660
ctcagcaagc ttaagcgttt cctcaccacc ctacagcagt ttggcagtga catctcacct       720
gagatcgggg agcgcgtgcg cacactggtg ctgggcctgg tgaactcaac tctgacgatc       780
gaagagtttc atgccaagct ccaggaagcc accaactttc cactgaggcc gtttgttatc       840
ccttttctga aggctaatct tccactgctg cagcgtgagc tcctgcactg tgcccgcctg       900
gccaaacaga cacctgccca gtacctggcc cagcacgaac agctgctgct ggacgccagc       960
gccacctccc ctgtcgactc gtctgagctc ctgctggaag tcaacgagaa cggcaaaagg      1020
agaacacctg acaggaccaa agagaatgga tcagaccggg accctctgca ccccgaccac      1080
ctcagtaagc ggtcctgcac cctgagcccc gccagcgct gcagcccag caatgggctg      1140 ccccacccga cgccaccccc accccgcac tatcgcctgg aggacatggc catggccac       1200 catttccggg actcctaccg ccatcctgat ccccgagagc tacgggaacg ccaccggccc      1260
ctggccatac ctgggtctcg acaagaagaa gtgattgatc acaggctcac agaacgcgag      1320
tgggcagaag aatggaagca cctcaacagt cttctgaact gcatcatgga catggtggag      1380
aagacccggc gatccctcac cgtcctgcgc cggtgtcagg aggccgaccg tgaggaactc      1440
aaccactgga tccggtgcta cagtgactct gaggaggga agaagggccc tacccccatc      1500
tctgcccggt ccctcaacag ctgcagtggc cctgaggggt ctcagctaga tgttcaccgg      1560
gacttcacgc ccaggaccct gtctggctac atgcctgaag agatctggag gaaggctgaa      1620
gaagctgtga atgaggtgaa gcgccaggcc atgtcagaac tacagaaagc tgtgtctgat      1680
gcggagcgca aagcccatga actcatcacc acagagcgtg ccaagatgga acgagccctg      1740
```

-continued

```
gcggaggcca agcgacaggc ctcggaggat gccctgactg tcatcaacca gcaagaggac      1800
tccagcgaga gctgctggaa ctgcgggcgc aaggccagcg agacgtgcag tggctgtaac      1860
gccgcccgct actgcgggtc cttctgtcag cacaaagact gggagaaaca ccatcacgtg      1920
tgcggccaga gtctgcaggg ccccgcggct gcagtggctg acccactacc tggacagcct      1980
gacgccactg ccagccccag cgaagccggc tcggcagggc cctctcgtcc ctgctctccg      2040
gggccgccag gcccgctgga cgctgctgtg ccccgctgac ctccagatct gacacccagc      2100
ccatggacgc catgccctgc caacctcctg gccccaccgt ggcccaccag ttgcctggag      2160
ccattgctgc tactgcttct ctccaaaaga aaacacagat ccaacagaac tgcatccgtg      2220
cagccccagc tacctgacaa ggtctgccgg gacctctaca gcctctcgtc catcgcaagc      2280
accctcagaa agcatcgcag agcgtcagac agtggcacca gcaggagtgt ggccagctcc      2340
gccgctgtct gtccctctg tgtccgtctc tctgtgtccg tctgtctttc tgcgtctgcc       2400
tctctctgtg tgtctctccg tgtctttgtc tcctgccgtt tccctgactc tccggcgtct      2460
ctgtctttgt aaagtccaca tgatctctct gtcatcagag aaacctagtt ggtagctttt      2520
cttttccatg aagaactttt ggagattttg ttttgttttg ttggcaaaca agctacttag      2580
aaatggacaa agaagactgt ggggttctcc ccattcctca tgagtaaggg aagaaactgt      2640 gattttttcta tccagagttg ctgtatcgcc cagccagccc caggggcatc agcgagcaca      2700
cagcagagat aatgagagca actgcaattt ccaacttaag aagcagcttt tgtttcaggt      2760
tttactcctt taatgtcaaa ctctttggct ttaagtgaaa aaaaaaaaa ggaaaaaaaa       2820 atccaaaaag tttttttttt ttttaagcaa aagaaacaca cctgtaaact accttgccag      2880
ctagccagcc aaggatgcca gacacacctc gctccaaagg aagcccaaaa aagcaaactc      2940
aagaaattga aatccaaaat ttattttat cactgccaaa gtattttctt catggtctct       3000
ccgccctggg ttggtttgca tgtcagtctt tgatttgggt tttgattttg ttcaggggt       3060 gttgggatgc tgggatttgg tgggtggggc caagaagaaa cctttgttc ctttttgact       3120 agtaggcagc atccttgctg ggcagagcca tcggcagcaa ggccacgtga ccctcagcac      3180
cgcatccaga agccccagtc agcgtgagcc tgagcgttgt gtgccctagg gctccgtcca      3240
tgcgttccct acatgcaagg gaggcacctc cttccatcgg tccccacacc ttcctgggac      3300
ttctcataag tcatttccac ttgtgaaaaa aaaaaaagtg ctaaagtgct cttcccagag      3360
agagcacact tcctaaacga aactgtgaca atctttttgg ttgattcttg actgcttttg      3420
agagcataag gagacagcaa atcacgcttt ctcagttttc cctcctctac ctctctgctc      3480
ttccatccca ccctacctcc atctcggccc catcaccctg cccccagtgt cttgctgtgg      3540
ctaccctcat ttctttcaaa cttttacaga aaaaaaggaa aaagaaaaaa aaaaaacacg      3600
aaagccagca gccacccgca cctcacccgg aagactccag cccggctgta catatccctg      3660
tgttgtatcc ccaatgttgg tctccagtcc tgggggtgac ggtgatgctt gcccatctac      3720
actctagccc ctgcccaccc tgcccttcgc ccgctcgact ccctcaagga ttcaaggagg      3780
aaatgaagga agaaggctca tgcctgtacc aaacaaaaag agacagcaga ctcagtccag      3840
gtctgcacct ctgttgtggc tgcagcaagc cgcaggccta gcgtgcaata tgggggattg      3900
ctcctgaacc ctgggcccgg gggggccctg cccagagcaa ggtgtgcagc gtgtgttaat      3960
gtgaatgtac atagtctcca cagaggtccc aaaccgtggc atcagtaccg aggagatgtt      4020
tgccaaataa aaagaaatta agacaaacca cggaagtctg tgaggtttag gaaacgcttt      4080
```

-continued

```
ggaaggagtc tgagtcctat aggcttcttt ggtggctggt gtttcttcac agctgtatga    4140
ccattgttta acagaacgtt ctatggattc tgttgggtag cccggaatgg agcctgacag    4200
caacccttgc tcggaaggct ggggtagatc tcattccctg gaaggttccc gcggccgcag    4260
ccctccaagg ccgcagagat gtattcttgt gggtttcaga gaagccagga cacaaggcgg    4320
cctcctgcct gcccgccctt ctctagtgga ccagtcctcc tgagcgtctg cctgcaaaca    4380
ctgagtctgt gtgctggtag agcgagacct gcctcccgtc gcaaggagca tcactggatt    4440
ccattcccaa ctgtacccca tgcggtactt cttgtctctg ctactccact gcatgcagca    4500
accttggccc ttccagaagg gcaggccagt gaccactggt aggaaagagc tctgggtgat    4560
ggggtggtga gcaccatgtt gggggggggg gggaacaaag ctaagcccct caggttgtgc    4620
ttaagagctg tagtctctag aagtccgggc caggagtcct gaggtggcat tcctgatgac    4680
ctacgtccct ggtgtcagga cttcggagca cctgctccta tgtggtccag atattctgag    4740
gtaggtccca aagggtcacc agtttgcttt agttcaaata cctcctttct tacccttacc    4800
agccttaccc accttttagg aacagagggc ccaccacaga caacaaaatg ctgcccagcc    4860
aaattcatct ccatgagcca ggttacatat ttagggttta gcagagacac caccccccca    4920
tctatactct agccgttggg agcgacagcc cctcaaggcg gctgtcagat ggcattggac    4980
cacagtgagt ctcctgtgca tgggatttga ctagcaattg tagacatcga gggtgagatg    5040
ccatgtctgc taggcagagc tcaggagtca aggcaagtgc agaatcaggg tggcagggag    5100
atggggctgg aaagggttag gtgtcgcctg aggcaaggag gctggaggat aaggtggggt    5160
tgctaagccg ggcaccgagg ccctggctaa gctgtgagtt gtgctttgac cccagctacc    5220
cagagacctc acagcacaac cagacaacct cacagctttg aagggacagg gaccatgggt    5280
gttctttatt gggaggtata ccctgggtgg ccataaccgc agcctaccct tggtttcaac    5340
ctacagtctg cctgggggctc tccacagagc tgggggcggg gcatggtact ccatccccat    5400
ccctgctacc tttctctggt tcacacacca tggacccagg ccctgcctcc tgggaaccac    5460
agccaagcat gaaccaaacc ccctaggcga tgtggctctc acagagcctt gctcccccag    5520
agcctccaac tcagaatacc actttacttc ctgttctgtg gccaaagcta aaccaggaag    5580
gctgagtagg gagggcaggt agcaggcaga gctctccaac ccccaaggcc cagcccagat    5640
cccatctcat gaccttatgg cttcttggca caagtcctgt gtgtcccagc cctgcctcag    5700
acccagactg gcctttccgt gaggactacc caagagacta ctttccagct cagtcctaag    5760
ctctgctcag gagcggaggc cagtgtttct cctcccaggt gtggtcacag ctggatagga    5820
actggctgaa tgacaccaca gctcaggtcc cacccactgc ctgacaagtg agaggagcca    5880
gcccccaggg gagcacccag aaggattcag ttaacaggga catctgtcag aagacctgag    5940
agggttagct ggggatggag aaggccaaga atgggaggcg gggcctctgt gggcagtgtc    6000
accttaaggc cacagtgggc agggatcagg atgggaccca aagtttagtt tctccaaata    6060
aatcattagg ctgacaccaa agtatcatcc cggcacccat ctgtcctggc atccatctgt    6120
ccactcttgt actcctcagc ctaacggaca gatcaacgct ttcctgagct cctccttctg    6180
acacgtgcag ccatcttccc atgaacccgt ttgcctctga ccattcatca tcctctgcct    6240
cccttccagc caactacccc catctatcta tcttgaccca ttggcaaatc catctttcca    6300
cctgtccatt gctccatcca aactgtctct ccaccccacc atcccagcat actatacta    6360 cgcccttaca ccttccagcc ccatgcacac aaccatgttc cctatcatct ctctattcac    6420
tgtactcaga gttctgtcag ctccatcagt gtaccaaaga caccaggtcc tcctacgccc    6480
```

-continued

```
tctactctgc ttggcctaaa ctgtccaggg ctgctctagg aatatctacc catgaggcaa      6540
caggcgtctc ccacccctgg cactctgccc caccatggtg ttcagatacc tccagaaata      6600
tgagttctta ccgtaggcat cgtgggcagg ttggatacat tcttgtggca gctgtgacac      6660
atctggagct gcttggggag agaagggaac aagaattgtg ctgtggggtg ggtctgtacg      6720
cctgctcacg agctctggaa gcctgggtta ggcagccacg ttccctgaaa ttagggcaaa      6780
gtccttgttt ccaggagtct gtccagaaga gagcaagcca gggctggcct cccttgacac      6840
cggggtgctc ttagtcccct gtgcccctgg acttttgtgc accattccca tcttctctgt      6900
taggatcccg aggagctcag agttggacct gtccggtctg cccctcctca atccacggat      6960
ggaaaggagt atttgctggg tgtttgggac cattcacaag tcccctgggg aactccttgc      7020
tcatcctgaa gctcctacta tgtagggaag cttctgaaat gaggctgggc agagacccct      7080
gggtacccat catgctggca agaggaagag aagataggga gagaagcctg aggcgagctg      7140
ggctcagggg gactgtctat tcctggagac agctcacaga taaagcccag gacagtcaac      7200
caacaactcg cacaagtccc caaatcctag aaacctctgt cttgtgttct gttccttttc      7260
cttccgttca gctggccctt agggtaccaa gccagactgg gagacaggaa tgcagcatct      7320
gagtcaaagc atggcctgct cagcacatcc tcctgctccc aacccagaca agaggcccag      7380
gagccctcag ctcacaccat acctggggtg agcatagcat cacacagcct gcctggggag      7440
ccactgcttc tcccctaca ggagctggga ggagagtact ggatgttttg ttcatgaaaa      7500
gctgtgttcc atgccctaca catctatctg ggtgctgggt cccgccaccc acctctatct      7560
actgctgtcc tatatgtttg ccctgtgggc cacggatgtg gcgatcaggt taattacatc      7620
tgtgtaataa agtaagcatt tgctacgacg aaaaaaaaa                            7659
```

<210> SEQ ID NO 11
<211> LENGTH: 7441
<212> TYPE: DNA
<213> ORGANISM: Homo sapiens

<400> SEQUENCE: 11

```
agagccgagg agccctgggg tccctcaaag tttgtgtctg gagccgtagc ggcaagtggg        60
cttgcggcta agggattttc ctgggatgag agcgggtctt ctgccttcat tttggatgca       120
catcccgctt tagccccggc agcctttggt ccggctcgtg tccctgggga ttctcggatc       180
tccgaggaca ccggacggga gcgcttggcc atcctctctc cggcagagga gcagacgttt       240
gctttccaag tgcaaaacta cagacacgcg cgcgcacaca cgcaagcaca cgcggagaga       300
gaggaacctt gccggtccga ggcagctctg cgcgtcccct cctgcgctta gcatcctcgg       360
cccagcgcgg cccgcaccgc catggaggtg ctggagagcg gggagcaggg cgtgctgcag       420
tgggaccgca agctgagcga gctgtcagag cccgggacg gcgaggccct catgtaccac       480
acgcacttct cagaacttct ggatgagttt tcccagaacg tcttgggtca gctcctgaat       540
gatcctttcc tctcagagaa gagtgtgtca atggaggtgg aaccttcccc gacgtccccg       600
gcgcctctca tccaggctga gcacagctac tccctgtgcg aggagcctcg ggcccagtcg       660
cccttcaccc acattaccac cagtgacagc ttcaatgacg atgaggtgga aagtgagaaa       720
tggtacctgt ctacagactt cccttcaaca tccatcaaga cagagccagt tacagacgaa       780
ccacccccag gactcgttcc gtctgtcact ctgaccatca cagccatctc caccccgttg       840
gaaaaggagg aacctcctct ggaaatgaac actggggttg attcctcgtg ccagaccatt       900
```

```
attcctaaaa ttaagctgga gcctcatgaa gtggatcagt ttctaaactt ctctcctaaa    960
gaagccccag tggaccacct gcatttgccg cccaccccc cgagcagtca cggcagtgac    1020
tcagagggca gcctgagtcc caacccacgc ctgcacccct tcagcctgcc tcagacccac    1080 agccctcca gagctgcacc ccgggcccc tccgccctct ccagctcccc tctcctcacg    1140
gctcctcata aactgcaggg atcaggccct ctggtcctga cagaggagga gaagaggacc    1200
ctgatcgctg agggctatcc catccccacc aaattgcccc tgtcaaaatc agaggagaag    1260
gccctgaaga aaattcggag gaagatcaag aataagattt ctgctcagga aagtaggaga    1320
aagaagaaag aatacatgga cagcctggag aaaaaagtgg agtcttgttc aactgagaac    1380
ttggagcttc ggaagaaggt agaggttcta gagaacacta ataggactct ccttcagcaa    1440
ctccagaagc ttcagacttt ggtgatgggc aaggtttctc gaacctgcaa gttagctggc    1500
acgcagactg gcacctgcct catggttgtg gtgctgtgct ttgccgttgc attcggcagc    1560
ttctttcaag gctacgggcc ctatccttct gccaccaaga tggctctgcc cagccagcat    1620
tccctgcagg agccctacac agcctccgtg gtgagatcca gaaacctgct gatctacgag    1680
gaacattctc ccccagagga gtcatccagc ccgggctcgg ctggggagct ggggggctgg    1740
gatagaggtt cctccctgct cagggtgtca gggctggagt ccaggccgga tgtggatctt    1800
ccccatttca ttatctcgaa tgagaccagc ctggagaagt cagtgctttt ggagctgcag    1860
cagcacctgg tcagcgccaa actggagggg aatgaaacac taaaagttgt agaactcgac    1920
agaagagtga acaccacttt ctaaagaggc tgcctgcacc ccctcccttt cccttaactc    1980 tactttaca tccccaaacc acctttgtca tcagcttttc ctctttgcca ctggatcttc    2040
atggagacat gggcaagcat tagtggcttc agattggaga ccagcctggg acttccctgc    2100
agtgagagag catctcccc tggtccatgc ccctcctgtg cagaagggag cctgcatccc    2160
tcccttcctt tctcttactg ccataggaaa ttattttagg ggttggaggt gggacaagca    2220
ggcttgtttc caccaatagt gccaaaaaga tattgcctaa tgtgcacctg tgaggtgtaa    2280 cccccccgctt tggagacgag atggctcttg ttcagtcaag accccagact ctggccacaa    2340
aaatgccata atgcctgttg gtatttggca aagcactgac ccgtgtcctc cgttgctcgc    2400
actggggtct ctggtgtgaa cacccccgac agcagccctc cgcccactct gccccctggg    2460
agccctcgct ggatcgtctc gtctcctgca gcagcactgg caggcgaggg ctctcgttca    2520
tattctcagg ccgcaagtgc aatgcctgag gggatcaggc ttttctactc caggcaaacc    2580
tgccccatct tgtcgctttt aggacctccc acaacctggt tccccacaca tccatagttc    2640
tgcctcccca gcttctcctc cccagttgta aatagtattt attagcttgc cgaggcttcc    2700
tgctagcaac cacactgaag agatcgatgc ctcctttcaa gctagccaag ttttctgcga    2760
gccttcagag ctaggagggc accctaggct ctgggatccc gtgtctttcc agacaatgtt    2820
ttgtttcctt tcctttgttt tttctttaa ctggaataat taccattgaa aaagaagttc    2880
ctttgagcat gtatgtgtct gcctctagga tgagctcaga gcgagagatg acacaatgcc    2940
tcactcaggc cccgggctcc ctggccacaa gctttttcta tcctgttttc atgacagaga    3000
aggggaagcc ctgttctgac aacagacatt tcagacaacc ttgctggctt ccacacctg    3060 cctggccccc tcctccctcc acacttccac tttgtcctcc tcgtccccta cctcaacaaa    3120
gcagggtggg gtaggtgaca tttgtgtatc cacattctta cctttggtag tcaggtttgg    3180
ctactttgca gctcgcccaa agagatacaa cctaatcccc aacctacttt tagttttttt    3240 gtttttttt tatggttaaa agtaactttt gtagtttaaa aaaatctttc ctctttcata    3300
```

-continued

```
taaataagaa gtggaaattg ccttttttatt gtgtaatgta gaaaaccctc aagtgttttt    3360
tccgagcttg ggaaagattt tgtgtaggaa atgtgcatag agtttgtatt ttatttttat    3420
tagcagctga aatgcctttg gttttggctt ctctctctcc ctctctctct ctgtctctcc    3480
ttctctctct ccccccacca cccaccccca cacacgtcat ctgcattgtt attggagcct    3540
gtacttagag ggattaagcc cacaccctgg cttccattcc atatcaggta caggatttga    3600
tgttattaac atttgtcgtc atacctcata agtcggtccc tgccttgtct gtctaggccc    3660
atttggggct ccctgtgagt gattcccctc tctctgctat gctggagacg gttccagcct    3720
ggaaagcggc caagttcatc ttctcactgt gagtggaagc tggatcgggc ccccgtagtc    3780
ctggcagccc tgttgtctgg agggttcttg ttgtccctcc cattagccag ggcggagact    3840
gtctgagctg tgcaggagga gggttgctag taggttctgc ttctgcttct ctctgctcca    3900
ctgtctgcag cccagatcct gttgggcctg gctggtgtct ggtaaccatg ggcctccact    3960
gacccatccc tctcttttaa actgtcaggt cattatcagg cataggcagc ctatagggcc    4020
caaagaaggc aaaaagataa gatttactca agtagcattt gggcaatgag gaaggaaagg    4080
tttcaaattt aggggcagaa gtgagagaat gagccaaccc atgtacctgc tgcaactgaa    4140
ccagactggg tttcaaggc tcccagacgt agagtaggaa acgtgctctt ctaaatgagg    4200
agggagaaga taaaggaaac ttctagcccc tgtccttagt gctttgagga ttttattttc    4260
tcccttacta cgcttgcttg acgtcactct ctctcgacct ccaaacagca ggactctttc    4320
tctgggaaac catccttcca aaacggaatc tatgtagaca atgggacgtt aggcagagag    4380
ctcagatggc cctttttaagg gggctccaag aaccaacatc actgctcttt tagataaacc    4440
tctgccctcc actccttgct tgagtgggtt aaaggaacta acagttgtcc ctttaggagg    4500
acaaaatggg gtcaagagga cacagaagag ttgtatagca ccagattggt tccaaatagt    4560
taatggatgt gtgcacattt tctgttcagg gattaagacc agaatatcag tggatttgtt    4620
ttccccacca agtggcctct tagactagtc attaacttat gattagctct aaagatttca    4680
aatagtggca gacagtgtct tctgaatgta agttttgaga aatacgagtc tgtcagagcg    4740
gccataagcc ataaagagtc aatctcttaa ttatattttt catcatgtaa acaagtttcc    4800 catttcctt tcttagattg caccagtgaa ggagatgttt tgcaaagatt cagagaacta    4860 attttttcact ggataagacc tgagtaaccc agaccccccca ccgtggttct tttcacagcc    4920
ctcgactttg cacttaaaaa gggatattgt aaatgaaagg ctgcagtgcc agtttttaaga    4980 aagaatttct gtgaagtgtg aggactctgg agtctagctc acataaagag agtgttatat    5040
aaaaatccga cagctgaact aggttgctct ttttttggcag ggagtgggga tgagatttga    5100
caccaatatg ggcaaaatta gataaccttt tggttaatat aaatgatttt gatttggagg    5160
cctaatttgt agattgtgaa agcagctttt agtttaactt attcacagac cccttataat    5220
taccatgttt tttttttttct tcctaaatct cttggttcag cttgtgaatc ttacgtgccc    5280
gtaaagttgg gatgttgaat tggctcttct ttgttctggc agtgagtcaa gtgtccagca    5340
ttttttcata agtgttttttt aaaattgttc tccagcattt tatggctcct ccctcccatg    5400
tcctcagacc cagcaaaagc gtagaggcag aattagaggc ctctccaggc cagctcctct    5460
gcccacatgt catacaaggt gtgaatttga gcacagtcca gaaatggaga catcccaccc    5520
ccagttgaat aatggcccat tcatgccaac cttgccaaca cggagagggc agagatgcac    5580
tagaagacct tcatcctccc cttcctctgc cccaagtcac tacagttggt tctattgaag    5640
```

-continued

```
ccagtcttta agaaacctgg gttaaagaca ccagcacttc tgcttgctgg gctggctgga      5700
cctgtgaagc catgggcagg tagtgccctc ttgagagtca tttttatttgg ccaccttcag     5760 gtgagactat ccatagacac atgctaggat aggccccgct gggagggcag ttacaggaga      5820
gagtaggtgg tggtgacgtg agggctgtga aggatccaga gacaagactt agatgtttcg      5880
ttcattcact cactcattca gttactccta agactttttca gtttcataag gaagagtgtt     5940
gcctgaggcc ctagggaata ttggggaata gaagggattg aggaaacatt aataatagtt      6000
attcaaaaga cccaaatgct tatacttctc tctcccttct tctctctctg acacacacac      6060
acacacacac acacacac acacacacgt gcacattcct cccttacatg ctcatttgtg        6120
ccttaaatgt gccttatagg taaatccagg atgactgagg aatccctcgt cactgggaga      6180
ttttgtatat attctttttat tattagattg agttgggtgt ggggaaaaat ttttttctga     6240
aggctcaaaa gtggtttcct aaaagtgagc cactatcaga tttgcacatc aggagaaaag      6300
aaatagggtt acgtccatta ggaaaatccc agtttgcagg agtgcaatca catcaaaaaa      6360
acaaccagcc aggattaaag gtattataaa tcctcatagc ggaacatttc tcagggcaaa      6420
ggaacctggc tcatttgaag attaatgttc catgcctttg tggtcaaagg gtcagcactt      6480
aacacaggaa aaaactaggt gttgtttttgt tttgttattt tggacaacat aaaattcagg     6540 aatgtttttat ttagccttgg tttctagaag gaagggaaat aatatttctt gagcatttac     6600
tagggtgttg cgtgctgtgc taagtaaatt ttaagtcttt cagttttata gatacggaaa      6660
acaagggtga ctctttacca caggatgaat aaagaactaa gtaatatggg aaatgcagca      6720
atttctggac tagctgagcc gattccttcc tgtgagcaca ctgtaagctt tcaagttctc      6780
tgggcaggaa ttacagcacc tgtcccctgc aatggccctg ctgtgtgatg ctcatcgctt      6840
cccttcgtgc tggagcagtc ccccaggtgt ccatctccta tcttttttgtt ccaatcttct     6900 gtgagttcca gctagcaggc tttacatctg gggaaaggaa aaccaggggt tttagctctg      6960
ttctctgctc ccatccttcg ctcaccagct gagtgagaac atgaacttttt tgcaccatgt     7020 acccatggct tacactactt agaaaatcac cttttcagat aaaacagttt atgagttcat      7080
agagaacacc agcactcttt gacaaaactg tgagtgaccc tttttaaaca atgctgagca      7140
ggccctgagc tataatcaac ggtgagcttt aatgtctatg ctgacagtta ggttttgctc      7200
tcttttgtaa caggttacgt agaccagcag tgtttaaatc taaatacgtt gtgagtctgt      7260
tatctgtcct atcgcgtttt ttaaatgact ttttattctt tatcatagct aagtaaatac      7320
caaaaaaaaa aaaagctttt gtaggacact tgtacttagt ttgggaaaaa aaaataaatt      7380
gaaattgtta tgcttttgta tttccatttc ttgcaaataa atattttttc ttaaatagta      7440
a                                                                       7441
```

```
<210> SEQ ID NO 12
<211> LENGTH: 3318
<212> TYPE: DNA
<213> ORGANISM: Mus musculus

<400> SEQUENCE: 12
gggagtctca agtttgtct ggagccctag tggggagtgg gcttgttgcg cgaggactttt         60 cttgggatga gcgctgcctt tttgccttcc ttttggatgc acagcccgat ttaacccctg        120
caccttccgc ccgatcccag caggcttgtc ctccccgggg agtcacagat ttccgaggac        180
aagggtcgcg tagccttcgg cagggctctc ccgagttcct gctccagtgc ataagttcca        240
cgcgcgcaca cgccaagtac acggggagaa gcgtctcacc ggcccgcggc ggctctgcgc        300
```

```
ggtcccctcc tgcctcagca tcctcggccc tgcgcggcgc ccaccgccat ggaggtgctg      360
gagagcgggg agcagagcgt cctgcagtgg gaccgcaagc tgagcgagct gtcagagccc      420
ggagagactg aggccctcat gtaccacacg cacttctcgg agctcctaga cgagttttcc      480
cagaacgtcc tgggtcagct cctgagtgac cctttcctct cagagaagag cgagtcaatg      540
gaggtggagc catctccaac atcaccagcg cctctcatcc aggctgaaca cagctactct      600
ctgagcgagg agcccggac tcagtcacca tttacccatg cggctaccag cgacagcttc      660
aatgacgagg aggtggagag tgaaaaatgg tacctgtcta cagagtttcc ttcagctacc      720
atcaagacag agccaatcac agaggagcag cccccgggac ttgtcccttc tgtcactctg      780
accatcacag ccatttccac tccttttgaa aaagaagagt cccctctgga tatgaatgct      840
gggggggact cctcatgcca gacgcttatt cctaagatta agctggagcc gcacgaagtg      900
gatcagttct taaacttctc cccgaaagaa gcctccgtgg atcaactgca cttaccacca      960
acaccaccca gtagtcacag cagtgactct gagggcagct tgagccccaa cccacgcctg     1020
catcccttca gcctgtctca ggcccacagc cctgccagag ccatgccccg gggcccctct     1080
gccttgtcca catctcctct cctcacagct ccacataagc tgcagggatc gggccccctg     1140
gtcctgacag aagaggagaa gaggaccctg gttgccgagg gctatcccat tcccaccaag     1200
ctgcctctga caaatctgga ggagaaggcc ctgaagaaaa tccggagaaa gatcaagaat     1260
aagatttctg cccaagaaag caggagaaag aagaaagaat acatggacag cctggagaaa     1320
aaagtggagt cttgttcaac tgagaacttg gagcttcgga agaaggtgga ggtgctggag     1380
aacaccaata ggactctcct tcagcaactt cagaagcttc agactttggt gatggggaag     1440
gtctctcgaa cctgcaagtt agctggcaca cagactggca cctgcctcat ggtcgttgtg     1500
ctttgctttg ctgttgcatt tggaagcttc tttcaaggct atgggcctta tccttctgcc     1560
accaagatgg ctctgcccag ccagcatcct ctgtcagagc catacacagc ctccgtggtg     1620
agatccagga acctgctaat ctatgaggaa cacgctcccc tggaagagtc gtcgagccca     1680
gcctcagccg gggagctggg gggctgggac agaggctcct ctctgctcag ggcatcgtcg     1740
gggcttgagg ccctgccaga ggtggatctt ccccatttcc ttatctccaa tgagacgagc     1800
ttggagaagt cagtactgtt ggagcttcag cagcacctgg tcagcagcaa actggaaggg     1860
aacgaaacac tcaaggttgt agagctggag aggagagtga cgccaccttt ctgaggagag     1920
ctccaccctc ctcttctcct aactccatct gatcgtcctt tcagtttccc cttcaccact     1980
ggatctcgag gaggagatgg cctagtgtta cggctcgaga caggaggcca gcccaggggg     2040
ttctgcttat gtgtccccgt ggctctccac aaaagggagc tagcacctct ccatcccttt     2100
ctcttactgc cattggaaat tattttaggg ctgagatagg ggtggaacga gcaggcttgt     2160
ttccaccaat agtgccaaga agacactgcc tgattcttcc ccgggaggag tgactcctct     2220
gaagaagaca tgactcatgt tcagttgaga ccccagactc tagccacaca catgccacag     2280
acatgccagg gagtggcaaa gcactgactc ctgagctccc ttcctcacta ggactccagt     2340
gtgaccctgc actgagagga ccaaagcgtc attgcagtct tctctccacc ctgtaccccg     2400
gagtcctgat tggatgtctg cagaggcaga tggggctccc accatatttt caggccgcaa     2460
gtgcaattcc tgaaggcatc aggctcttct ctcccaggct ctcctgccca ctgtgttgtt     2520
tgtaggacac cccacacccc actcatacac agcctgcatc tccacaggac aatagctctg     2580
tctccctggc ctccctccc catttgtaaa tagtatttat tagcttgctc aagctcccag     2640
```

-continued

```
ctggccatag tgaaaagatt tcccctttca accagcaaag tcttctgttg gcctttggaa        2700
caggagagtc cccggaatct aggaccctag tctttgtact tgatgccttg tttccccct         2760 tttcttcttt aaaattgggg acctataaca tcatcgctgt tgcggaatcc acttaggcat        2820
gtgtcccctg atggatgaat acatgggaat ggtggatact gtcttctgac tcaggctcta        2880
ggctccatgg cttcctctct ctggtcctgc cacacagaag gaaagccctg tccaggataa        2940
tgagcgttgc tgacacccct gctagcttgt cctgcctacc tgcttacccc actccctcac        3000
cttcctcctt cccttctgcc ctccatccac ctgccttaac taattgggc tggagttggt         3060 cattttgta cacccacagt ggtacctttt acagtcaggt ttggatactt tgcagctcat         3120
ccaaagagac ataactaaac cctaaactct ttttttgttg ttgttgttgt tgttttttt          3180 ttttatgatt aaaaagtaaa aattgtagtt taaaaaatcc tttcctcttt catacaaata         3240
agaaatggaa attgctcgtt tattgtataa gatagaagat tcgtttaaag tgtttcccca        3300
ccccaccccc cagcttgt                                                       3318
```

<210> SEQ ID NO 13
<211> LENGTH: 5139
<212> TYPE: DNA
<213> ORGANISM: Homo sapiens

<400> SEQUENCE: 13

```
agttggaaag agaccacaga ctttgaggga agctcactca ggatctgctc tccggcaaag          60
tagtaagtga ggtgctgaga gcagaatgag ctactttgtg gattctgctg ggagcagccc         120
cgtcccttac tcagcgcctc gtcctgcagt ggtgaggcaa ggacctagca acacttatga         180
agatcctcga atgaactgtg gtttccagtc caattatcac cagcaaagac cttgctaccc         240
cttttgggat gagatggcaa ctcaggaagt tcctactggt cttgaacact gtgtctcaga         300
tatggaatgt gcagatgtcc cactattaac tccaagcagc aaagaaatga tgtctcaagc         360
attaaaagct actttcagtg gtttcactaa agaacagcaa cgactgggga tcccaaaaga         420
cccccggcag tggacagaaa cccatgttcg ggactgggtg atgtgggctg tgaatgaatt        480
cagcctgaaa ggtgtagact tccagaagtt ctgtatgaat ggagcagccc tctgcgccct         540
gggtaaagac tgcttttctcg agctggcccc agactttgtt ggggacatct tatgggaaca       600
tctagagatc ctgcagaaag aggatgtgaa accatatcaa gttaatggag tcaacccagc        660
ctatccagaa tcccgctata cctcggatta cttcattagc tatggtattg agcatgccca        720
gtgtgttcca ccatcggagt tctcagagcc cagcttcatc acagagtcct atcagacgct        780 ccatccatc agctcggaag agctcctctc cctcaagtat gagaatgact accctcggt          840 cattctccga gaccctctcc agacagacac cttgcagaat gactactttg ctatcaaaca        900
agaagtcgtc accccagaca acatgtgcat ggggaggacc agtcgtggta aactcggggg        960
ccaggactct tttgaaagca tagagagcta cgatagttgt gatcgcctca cccagtcctg       1020
gagcagccag tcatctttca acagcctgca gcgtgttccc tcctatgaca gcttcgactc      1080
agaggactat ccggctgccc tgcccaacca caagcccaag ggcaccttca aggactatgt       1140
gcgggaccgt gctgacctca ataaggacaa gcctgtcatt cctgctgctg ccctagctgg       1200
ctacacaggc agtggaccaa tccagctatg gcagtttctt ctggaattac tcactgataa      1260
atcctgtcag tcttttatca gctggacagg agatggctgg gaattcaaac tttctgaccc      1320
agatgaggtg gccaggagat ggggaaagag gaaaaacaaa cctaagatga attatgagaa      1380
actgagccgt ggcctacgct actattacga caaaaacatc atccacaaga cagcggggaa      1440
```

-continued

```
acgctacgtg taccgctttg tgtgtgacct gcagagcctg ctggggtaca cccctgagga    1500
gctgcacgcc atgctggacg tcaagccaga tgccgacgag tgatggcact gaaggggctg    1560
gggaaaccct gctgagacct tccaaggaca gccgtgttgg ttggactctg aattttgaat    1620
tgttattcta ttttttattt tccagaactc attttttacc ttcaggggtg ggagctaagt    1680
cagttgcagc tgtaatcaat tgtgcgcagt tgggaaagga aagccaggac ttgtggggtg    1740
ggtgggacca gaaattcttg agcaaatttt caggagaggg agaagggcct tctcagaagc    1800
ttgaaggctc tggcttaaca gagaaagaga ctaatgtgtc caatcatttt taaaaatcat    1860
ccatgaaaaa gtgtcttgag ttgtggaccc attagcaagt gacattgtca catcagaact    1920
catgaaactg atgtaaggca attaatttgc ttctgttttt aggtctggga gggcaaaaaa    1980 gaggtggggtg ggatgaaaca tgttttgggg ggggatgcac tgaaaatctg agaactattt    2040
acctatcact ctagtttttga agcaaagatg gacttcagtg gggaggggcc aaaaccgttg    2100
ttgtgttaaa atttatttta ttaaattttg tgccagtatt tttttttctta aaaatcgtct    2160 taagctctaa ggtggtctca gtattgcaat atcatgtaag tttgttttta tttgccggct    2220
gaggattctg tcacaatgaa agaaaactgt ttatatagac cccattggaa aagcaaaacg    2280
ctctcactga gatcagggat cccaaattca tgggacttat ataagaagga caattaatgc    2340
tgatttgggt acaggggaat tatgtgtgtg aatgtcatct acaattaaaa aaaattagca    2400 catccctta cttacttgtt atcagtggat tctcggggtt tggacttaat gttgagctaa    2460
gaagcattaa gtctttgaac tgaatgtatt ttgcatccct ggttttggac gacagtaaac    2520
gtaggagcac tgttgaagtc ctggaaggga gatcgaagga ggaagattga cttggttctt    2580
tcttagtcct atatctgtag catagatgac ttggaataaa agctgtatgc atgggcatta    2640
cccctcaggt cctaagaaat aagtcctgaa tgcatgtcgt tccaaactaa cactctgtaa    2700 ttttctttt atgtcttatt ttccaagagt cctccatttt ttgcacccccc tcaccgccaa    2760 ctctgttatt cagtagagag aagtgtacgg ctttctgatt ggtgagtgaa aaagtaactt    2820
gagacacgac ctaagttgaa gagtttagac ttgctgagtt ttagaagtga tggaaattaa    2880
gagagcattt caataaaatg tgacttggct gtctttggaa gagaagtgca aggctttcct    2940
ttgaagaatt taaattagtc cggtaggatg tcaggtgaga ctgtgtatgc aaaatgaatg    3000
gcacaggtga tgccagggcc tcttgcttgg gtctgatgtc ttggcacagg gtaagtgaag    3060
gttaattcca gaagagagga atgacttgaa ggcaaaggaa actaaggaag gaggttcagt    3120
gaggaaaata aggttgtcca tgagatttga atagattttt agttccccca aggtttaaat    3180
acaaacatag tcaagcaagg tagtcatctt tctgctggtt gtgaggggga atctgaaaat    3240 ggagtttttag aggaaaagtc aacatctaac tagtgaggaa aagtgcctaa tacaattaga    3300
atctccctca ctctatagtt gcccagttga aaggataagg aggaggggtg gctttatgg     3360 acttccatga gagaaggaaa gaaatatttc aggtaagctt ctcagggctg gccctttttg    3420
ggatttggat gagaaattgg aagtactaac tactttctag catatcttta agaaaattga    3480
ttgttattta ctcccagatc ctcttgcaga cccagaatta tcaggaacat agctctgtga    3540
ttcatgagtg tccccatact gatgaattgg agcatccata tggaaagcaa aggcagaatt    3600
atcccagctg tattattttg atcttttgga tgcaggtgcc ttaatgaagc tctcaaaata    3660
ttttaggagc tgctcaggga gtgttgggtg gaactgtttg gactacattg ttttctctta    3720
gattatgtga ttttttgttgg gcactggcaa aaggtgtgtg tgtgaatgtg tgcatgtgtg    3780
```

-continued

```
tgaatgttgt gtgtgtgtgt gtgtgtgtgt gtgtgtgtgt gtgtgtgtgt gtttgcagac    3840
atgcaaaact gcagctgaaa taatacctta gatttctagg taagtctttc cacatttcaa    3900
taatgggtaa gagtagaacc agggccgggt atcaattatt gcttgctgtt tgcaaccagg    3960
cataaaatca ctttctcaaa tcatccaccg ttcctattaa atttatgccg gaaactctcc    4020
ttctgtgagt ataactcctg cagttcctat agcagataag atataagaaa gtgcctccta    4080
gtgctcctcc gcccgcttgt ttgctaaaat tccctttctc tctaagtcca ccattttcaa    4140
gatttgtaga tagtgtatta gttaagacag ctttgtcgat ctggccagat gtttttttctc   4200 ctttgtccaa aggccagaga ccatcccagg aagagtggtg ggtggtttat acactggaaa    4260
tgttgcgttt atgctttta aaaacacacg ttaacttcag aggaaggatg ggcaaatctg     4320
gtctagctgg gtgaaaccct tattttccca gagatgcctt aacctttgtt ggttttggct    4380
ttagggttca gagtcacttt tgttcccttc tccattctgg agagggactt cccctacata    4440
gagccctgat ttttgtggct gtggggattg gaggtagcat tcaaagatca gatgtgcttt    4500
tcctcacttt ggagatgaac actctgggtt ttacagcatt aacctgccta accttcatgg    4560
tgagaaatac accatctctc ttctagtcat gctgtgcatg ccgcttactc tgttggggtc    4620
tatataaatt tgttgaactc ttacctacat tccaaagaag tttcaaggaa ccataaatat    4680
atgtatacat atacatatat aaaatatata tattaaaata aaattatcag gaatactgcc    4740
tcagttattg aactttttttt tttaagaata cttttttttt aagctgagaa gtatagggat   4800
gaaaaagatg ttatattgtg tttgactatt ttccaacttg tattttcata taatttatat    4860 ttttttaaaag ctgaaaattt agaagcaaga tgaaaaaaag gaaaagcagg tgcttttttaa  4920 aaatcagaac tgaggtagct tagagatgta gcgatgtaag tgtcgatgtt tttttaaaaa    4980
aaaatgcaaa aaaattctta tggcggagtt ttttgtttgt ttattttagt agctgatgct    5040
ggcacatcat tttgctggag agtttttttat atactgtagc ctgatttcat attgtatttt   5100
aaactgtgtg aaattaaaaa caaagaattt cattcataa                            5139
```

```
<210> SEQ ID NO 14
<211> LENGTH: 5065
<212> TYPE: DNA
<213> ORGANISM: Mus musculus

<400> SEQUENCE: 14
taaagcggag gcgagctgca ctgcgccagc gccggccagc cgtgcgagcg agcaagggag     60
cgagcgcccc ggacggagga gggagcgagc gcccgggaca gaggagcgag cgggcgggcg    120
aggcgcgggc gaggctggga cctaagcgcg ctctctgctc cgccaagtgc caacttcgcg    180
cggactggct gggcgcgcac cttcccgcgg ggcggtcagc gggaatttga gattttaggg    240
ttgcgctctg tccccttcca ctgggttcaa aaatccccat taaaaagcaa aacaacagtt     300
acagcaaact tactctcatc ccgccggccc cctcaactcc gggcaccatg aaggcggccg    360
tcgatctcaa gccgactctc accatcatca agacagaaaa agtggatctc gagcttttcc    420
cttccccgga catggaatgt gcagatgtcc cgctgttaac tccgagcagc aaagaaatga    480
tgtcccaagc cttgaaagct actttcagtg gtttcacaaa agaacagcag cgactgggaa    540
tccccaaaga cccccggcag tggacagaaa cccacgtccg ggactgggtg atgtgggctg    600
tgaatgagtt cagcctgaaa ggtgtggact ccagaagtt ctgtatgagt ggagcagcac    660
tgtgtgccct gggtaaagaa tgcttcctcg agctggctcc agactttgtt ggggatatcc    720
tgtgggagca tctagagatc ctgcagaaag aggatgtgaa accatatcag gttaatggag    780
```

```
ccaaccctac ctacccagaa tcctgttaca cctcggatta cttcatcagc tacggtatcg      840
agcatgctca gtgtgttcct ccctcagagt tctcagagcc cagcttcatc acagagtcct      900
atcagacgct gcatcctatc agctcggaag aactcctgtc cctcaagtat gagaacgact      960
acccttctgt cattctccag gaccctctcc agacagacac cttgcagaca gactactttg     1020
ccatcaagca agaggtgtta actccagaca acatgtgcct ggggagagcc agtcgtggta     1080
aactcggggg ccaggactct tttgagagcg tagagagcta cgatagttgt gaccgcctca     1140
cccagtcctg gagcagccag tcatccttca acagcctgca gcgggtcccc tcctatgaca     1200
gcttcgacta cgaggattat cccgctgccc tgcccaacca caagcccaag ggcaccttca     1260
aggactatgt gcgtgaccgt gctgacctca caaggacaa gcctgtcatt cctgctgctg      1320
ccctggctgg ctacacagga agtgggccga tccagctgtg gcagtttctt ctggaattac     1380
tcactgataa gtcttgtcag tcctttatca gctggacagg agatggctgg gaattcaagc     1440
tttctgaccc agatgaggtg gccaggagat ggggaaagag gaaaaacaaa cctaagatga     1500
attatgagaa actgagccgt ggccttcgct actattatga caaaaatatc atccacaaga     1560
cggcgggcaa gcgctacgta taccgctttg tgtgcgacct gcagagcctg ctgggataca     1620
cccctgaaga gctgcacgcc atgctggatg taaagccgga tgctgactag tcatggacag     1680
acgcgcagaa ggaaggggct gggggaaccc tgctgagacc tttcaaagag caaccctgtt     1740
ggttggactc ttcattttta attgttattc aatgtttat tttccagaac tcatttttca      1800
cattcagggg tgggagctga gggagcgccg ctgtattcca ttggccattg gtgggccgga     1860
aagaggaggt caggacctgc ggggtgggcg gggcaatagc tcctgagcag actttcagaa     1920
gggagaggtc ttctcagaag cctgttggac ctggcttgca gaggaaaaaa aaacttaagt     1980
gtccgttttt tttttttttt tttttaaatc aaagaaaaaa aaattcatct tgagttgtgg     2040
atctactagt gggaggaatg atcacattga gatgaaagag attgatgaaa gccagtcagt     2100
tttgtgggtg ggctgaaaac agtttcttca ggggattact aaactcaaga attattaacc     2160
tttctacttt ttgaaacaat gatggacttt gattgaaggg gtccaaaact gttttttatgt    2220 tgaagtttat tttattaaat tttgtgccag tattttttt tccttaaaaa aatatcgtct      2280
taagctctaa ggtggtctca gtattgcagt attgtgagtt tgttgttatt tgctggctga     2340
ggactcttgt cacagtgaaa gacaactgtt tatatagacc ccattggaaa aatcccagtt     2400
ctgtactgag atcagagacc ccaaactctt acagctaaag gaaacgaatg ctgatctggg     2460
gacaggggga ctgtgcgtgt gacttccacc tgcggtttgt aaaaactgtt ttcctttgat     2520
tcactgtcag gctttggact tagtgttagt tacggggcgt taagtctctg cactgaatgt     2580
attctgcagc tcttctatgg aatcgtcggc atcatagcac agttcaagtc ttggaaacga     2640
aatccaagga gcaggattaa cctgggtttt ggttaaaccg ctacccgaaa catggaagac     2700
tcagaataaa agccgtttgc atgggcatta ccccgagggt cttaaggcct caatgcatgc     2760
cattccaaac taacattctc agttctcctc tactttgtct tatgttcccc ccggcatccc     2820
tcattgctgc ccctccctca tcactgatca gtgaaagtgg agtgtaatgc atcctgacac     2880
gtgactgaaa gtgtagtttc agccatcaca acacaaatcc aagagtccag acttgctagg     2940
gctcggaggc cacggcagtg gagagggtat ttcagtagca tgtgactcgg cctcctttga    3000
agacttggtg ctcgtcaggt aggatttcag gtgagactgc ttgccgggaa gtggcaggga    3060
gcactggcac ttgacctgtt accacctcag cagagggcaa gcccaggtca actgcggtga    3120
```

```
gagggagacg gagaaaatac aagggaaggc gcttaggtaa ggaaaataag gtggcccgag      3180
acagttagat agatgtttag tttcctccaa gtttaaactc agacttaatt gaggcagcca      3240
tcatcctgcc tgatgggaga ggagacctga aaataagcca ttgtgggtta aaaaaaaaag      3300
taaggagaca tgcctgggat cattagaatc ccttccactg tatagctgcc tagttaagac      3360
agtgacagtg acatccctga gagaagagag gcaattggct gaggtgggcc tctccaggct      3420 caccccttcgg ggtttgtagc tccctggtat catcttccag gagagttgat ggctgactcc      3480
cacattccct tgaagactct gaattactaa gactataact cttgtccgtg ggtgttctgt      3540
actgactgag tggagcatcc ccacaaggaa gcaaaggcca aacattccag ctatatattt      3600
tgatcttaca aatgcaggtg ccttaatgaa gctctcaaaa tatttaggag ctgctcaggg      3660
agtgttaggt gggatcattt ggattatgct gtttttctctt atgttatgtg atctttgttg      3720
ggcactgaca gtgtgagtgt gtgtgtgtgt gtgtgtgtac atttgtataa agttgcagct      3780
gaaatagtac tgaattttct acttagagtc tgttcacatt tccataatgg tgaatgaaag      3840
agtacagccg gggctggtat tgttgtttgc tctttgcaac agggcttaaa aaaatcactt      3900
ccccaagtct tcacccttct ccatattggg ttcctgctgg gaatgcccct cctgagagcc      3960
taccacctgc agtcccctag cagagaagac ataagaaagt gtctcccaca ctcctcagcg      4020
tgctgacttg cctgccttga tgcccttttct ccctaggtcc accactttttc aggatttgta      4080 gatagtatat tagtcagaca gctttgttgt ccatctggcc agatgctttc ccccatctcc      4140
tccgaaggcc agagaccatc ccaggaagag tggcgggtgg tttatacact ggaaatgtag      4200
cagcattgct gcattgatgc tcttttaaaa cacgttcact tcacaggaag gatgaacaga      4260
tctgacctag ctgggcgact ccatcatttt cccagagaaa tgctttaacc tgtgtggctg      4320
gctttgggct cagaggcggg gctaaggatg ctccctgcgg agagctctga tggtgtggcc      4380
atggagacct tgtaagcatt caggatcaga gatgctcttc ctcactttgg agaccagcac      4440
tctgggtttt aaagcattaa ccttcatggt gaaatcacac cttctctctc ctagccatgc      4500
tgtgcatgcg gccttctctg ttggggtcta tataaacctg ttgaactctt acgtacattc      4560
caaagacgtt tcaaggaacc acaagtatat gtatacaaat acatatatga agtatatatg      4620
ttaaagtgaa tttatctcta tcaggaatac tgcctcagtt attgaatttt ttttaaggat      4680 acttttttttt ttaaagctga gaattattga ggtgaaaaag atgttatatt gtgtttgact      4740
ttttccaact tgtattttca tataatttat atttttttaaa tgctgaaaat ttaaaagcaa      4800
gatttaaaaa ggaaaagcag gtgctttttta aaaatcagaa ctgaggtagc ttagagatgt      4860
agcgatgtaa gtgtcttaaa tgtttttttgt ttttttttta aaaacaaatg caaaaaattc      4920
ttatggggga gttttttggtt tgtttcattt aagtagctga tgctggcaca tcattttgct      4980
ggaaaatttt ttatatactg taggctgatt tcatattgta ttttaaactg tgtgaaatta      5040
aagaaacaaa gaaattcatt cataa                                            5065
```

<210> SEQ ID NO 15
<211> LENGTH: 5322
<212> TYPE: DNA
<213> ORGANISM: Homo sapiens

<400> SEQUENCE: 15

```
gttgttgttg gtggcggcgg cgagcggagc cggaggagcc gccgcaaaga tggaggagcc       60
gtcgaggagg tgctgccgcc gctgccgccg ccgctgctgc cgccgccgcc cgcgaagccg      120
gagctcgagc cgcagcgggg atgccgttct gagtgcctga ctgcctcgcc ccgaaggatg      180
```

-continued

```
gcctcggatg ggcattagag gcacggcggc cccgggctcc cgtcccgtcc gtctgtctgt      240
tatcgtctgt ctctcttgac atcaccgcag ctccaccccc tcccgtccca gcccccaacg      300
ccagcttcct gcaggcccag agccggcatg aactctccca acgagtcggc agatgggatg      360
tcaggtcggg aaccatcctt ggaaatcctg ccgcggactt ctctgcacag catccctgtg      420
acagtggagg tgaagccggt gctgccaaga gccatgccca gttccatggg gggtgggggt      480
ggaggcagcc ccagccctgt ggagctacgg ggggctctgg tgggctctgt ggaccccaca      540
ctgcgggagc agcaactgca gcaggagctc ctggcgctca agcagcagca gcagctgcag      600
aagcagctcc tgttcgctga gttccagaaa cagcatgacc acctgacaag gcagcatgag      660
gtccagctgc agaagcacct caagcagcag caggagatgc tggcagccaa gcagcagcag      720
gagatgctgg cagccaagcg gcagcaggag ctggagcagc agcggcagcg ggagcagcag      780
cggcaggaag agctggagaa gcagcggctg gagcagcagc tgctcatcct gcggaacaag      840
gagaagagca aagagagtgc cattgccagc actgaggtaa agctgaggct ccaggaattc      900
ctcttgtcga agtcaaagga gcccacacca ggcggcctca accattccct cccacagcac      960
cccaaatgct ggggagccca ccatgcttct ttggaccaga gttcccctcc ccagagcggc     1020 cccctggga cgcctccctc ctacaaactg cctttgcctg ggccctacga cagtcgagac     1080
gacttccccc tccgcaaaac agcctctgaa cccaacttga aagtgcgttc aaggctaaaa     1140
cagaaggtgg ctgagcggag aagcagtccc ctcctgcgtc gcaaggatgg gactgttatt     1200 agcacctta agaagagagc tgttgagatc acaggtgccg ggcctggggc gtcgtccgtg     1260
tgtaacagcg cacccggctc cggccccagc tctcccaaca gctcccacag caccatcgct     1320
gagaatggct ttactggctc agtccccaac atccccactg agatgctccc tcagcaccga     1380
gccctccctc tggacagctc ccccaaccag ttcagcctct acacgtctcc ttctctgccc     1440
aacatctccc tagggctgca ggccacggtc actgtcacca actcacacct cactgcctcc     1500
ccgaagctgt cgacacagca ggaggccgag aggcaggccc tccagtccct gcggcagggt     1560
ggcacgctga ccggcaagtt catgagcaca tcctctattc ctggctgcct gctgggcgtg     1620
gcactggagg gcgacgggag cccccacggg catgcctccc tgctgcagca tgtgctgttg     1680
ctggagcagg cccggcagca gagcaccctc attgctgtgc cactccacgg gcagtcccca     1740
ctagtgacgg gtgaacgtgt ggccaccagc atgcggacgg taggcaagct cccgcggcat     1800
cggcccctga ccgcactca gtcctcaccg ctgccgcaga gtcccaggc cctgcagcag     1860 ctggtcatgc aacaacagca ccagcagttc ctggagaagc agaagcagca gcagctacag     1920
ctgggcaaga tcctcaccaa gacagggag ctgcccaggc agcccaccac ccaccctgag     1980 gagacagag aggagctgac ggagcagcag gaggtcttgc tgggggaggg agccctgacc     2040
atgccccggg agggctccac agagagtgag agcacacagg aagacctgga ggaggaggac     2100
gaggaagacg atggggagga ggaggaggat tgcatccagg ttaaggacga ggaggcgag     2160 agtggtgctg aggaggggcc cgacttggag gagcctggtg ctggatacaa aaaactgttc     2220
tcagatgccc agccgctgca gcctttgcag gtgtaccagg cgcccctcag cctggccact     2280
gtgccccacc aggccctggg ccgtacccag tcctcccctg ctgcccctgg gggcatgaag     2340 agcccccag accagcccgt caagcacctc ttcaccacag gtgtggtcta cgacacgttc     2400
atgctaaagc accagtgcat gtgcgggaac acacacgtgc accctgagca tgctggccgg     2460
atccagagca tctggtcccg gctgcaggag acaggcctgc ttagcaagtg cgagcggatc     2520
```

-continued

```
cgaggtcgca aagccacgct agatgagatc cagacagtgc actctgaata ccacaccctg    2580
ctctatggga ccagtcccct caaccggcag aagctagaca gcaagaagtt gctcggcccc    2640
atcagccaga agatgtatgc tgtgctgcct tgtgggggca tcggggtgga cagtgacacc    2700
gtgtggaatg agatgcactc ctccagtgct gtgcgcatgg cagtgggctg cctgctggag    2760
ctggccttca aggtggctgc aggagagctc aagaatggat ttgccatcat ccggccccca    2820
ggacaccacg ccgaggaatc cacagccatg ggattctgct tcttcaactc tgtagccatc    2880
accgcaaaac tcctacagca gaagttgaac gtgggcaagg tcctcatcgt ggactgggac    2940
attcaccatg gcaatggcac ccagcaggcg ttctacaatg accctctgt gctctacatc    3000 tctctgcatc gctatgacaa cgggaacttc tttccaggct ctggggctcc tgaagaggtt    3060
ggtggaggac caggcgtggg gtacaatgtg aacgtggcat ggacaggagg tgtggaccc    3120 cccattggag acgtggagta ccttacagcc ttcaggacag tggtgatgcc cattgcccac    3180
gagttctcac ctgatgtggt cctagtctcc gccgggtttg atgctgttga aggacatctg    3240
tctcctctgg gtggctactc tgtcaccgcc agatgttttg gccacttgac caggcagctg    3300
atgaccctgg cagggggccg ggtggtgctg gccctggagg gaggccatga cttgaccgcc    3360
atctgtgatg cctctgaggc ttgtgtctcg gctctgctca gtgtagagct gcagcccttg    3420
gatgaggcag tcttgcagca aaagcccaac atcaacgcag tggccacgct agagaaagtc    3480
atcgagatcc agagcaaaca ctggagctgt gtgcagaagt tcgccgctgg tctgggccgg    3540
tccctgcgag aggcccaagc aggtgagacc gaggaggccg agactgtgag cgccatggcc    3600
ttgctgtcgg tgggggccga gcaggcccag gctgcggcag cccgggaaca cagccccagg    3660
ccggcagagg agcccatgga gcaggagcct gccctgtgac gccccggccc ccatccctct    3720
gggcttcacc attgtgattt tgtttatttt ttctattaaa aacaaaaagt cacacattca    3780
acaaggtgtg ccgtgtgggt ctctcagcct tgcccctcct gctcctctac gctgcctcag    3840
gcccccagcc ctgtggcttc cacctcagct ctagaagcct gctccctctg cagggggtgg    3900
tggtgtcttc ccagccctgt cccatgtgtc cctccccca ttttcctgca ttctgtctgt    3960
ccttttcctc cttggagcct gggccagctc aaggtgggca cggggggccca gacagtactc    4020 tccagttctg gggcccccg agtgaggagg gaacgggaag tcggtgcctt ggtttcagct    4080
gatttggggg gaaatgcctt aatttcactc tcctcccttc tccagcctca ggggaggatc    4140
tggaggatcc actactgtct ttaagatgca gagtggaggg gaggtgggca cccaccctgc    4200
gattctccac cctttccct tctttcgtcc tcaccatctc tgcagacccc tctcctcctc    4260
cttcctcttg gtctcagcac tgatgggagg ctggtgccca agctgtggcc tgcagtctgt    4320
gaggagggct gtcttgcctc acactcctca cagcctactt ccccttcccc ggggctgaga    4380
gggtgaaagt gtgtggggaa ggagaggact ggtttcctgg gttctcaggg gccaggagga    4440
gtaacagaac caggtctgct ccccacctta ctcggatggc ctccctgccc ctctgctggc    4500
acagcctggg caagggagaa aggtggtccc tgcagagggg ctccaggctg gtgagagccc    4560
ccctgctgtc aggaccagat tttcccagcc atccagcatg ctgcggggag aaggggcaga    4620
ggctcacctc cctcctgggg ccttttgttt tggatcctgg ggatggtgag aatggaggtt    4680
ctagaagggg taaggccaga acccagggat ccaggagtcg gctctcagct ggagcttcca    4740
taccttctgg gctcccttg ctgaccacca gcccaaggga gctaagacca ggaggggggct    4800 gggcgctgtc ccttctcttt cccaggagcc ctgccagggg ctgtgggcct acaaggcttc    4860 cagggggatgc catccagcct gtaggaaacc aaagatggga agtggctcct aggggggctga    4920
```

-continued

```
ctcttccttc ctcctcctcc ccagtaccac atatacttc tctccttcta tctccagggc      4980
cccaccaatc tgtttacata tttattatcc tatgggggcc tgagcaggat tgagggagcc      5040
aggggagggg caggagtccc agcaccatcg gttcatagtg tgcttgtgtg tttgttttag      5100
atcctcctgg gggatgggga tggggccagg ctcagtgtac taggcctctc tgtgctgagc      5160
cccaggctcc cggcccctta cccactctct ccctgtggct ggtctggttc tcatgtaaac      5220
ccactccttg cttttgtctcc ctggatatgg atttcagtta agtattttgt aacccgttac      5280
actgtgtgtc cttgtgtaaa taaacttgtt tctggcagtg cc                         5322
```

<210> SEQ ID NO 16
<211> LENGTH: 4332
<212> TYPE: DNA
<213> ORGANISM: Mus musculus

<400> SEQUENCE: 16

```
ggtcacgtga cgagagtgac gtctccgaat gttgttgttg gtggcggcgg cgagcggagc        60
cggaggagcc gccgcaaaga tggaggagcc gtcgaggagg cgctgccgct gctgttgccg       120
ccgctgctgc cgccgccgcc cgcgaagccg gagctcgagc cgcagcgggg atgccgttct       180
gagtgcctga ctgcctcgcc ccgccccgaa ggatggcctt ggatgggcat tagaggcact       240
gcggccctgg gctcgggctc ctgtcccgtc cgtctgtctg ttatcgtctg tctctcttga       300
catcacagca gctccgcccc ctcccgtccc agcccccaac gtcagcttcc tgcaggccca       360
gagccggcat gaactctccc aacgagtcgg cttccttcca gagggattgg aggctcagga       420
ctggctggtg aggagaggca gtatcaaccc agagaggaag tagaagatga caaaaaaggg       480
ggaagagaga agatccaggc tggctgcttg gtgtccagtc cgttgtttgc ccccagcagt       540
ggccaaagct gaccccagat gcatgggtcc tctgcctgca cccttctcta gtccagccac       600
tggccaccca gactttggtc cacgctcctg gagcggagag caggcccttc agcctcatta       660
gcctccctgc gtctgctgcc tccggagcgc gcccaggccg gatgaggtgc ctccttgcct       720
cgtgggtccc agcggcagtg gcctgaggga gtccttgagc agccagctgg ccccgctgac       780 cacctttcc ctcaccggct tccgcctcgg gcggcccctc cctggcatgc tgctggtgcc       840
caaggcacag gggcttgtgg agatgctgca gaccatctat gagaccgagt cctgtttctc       900
agcagatggc atgtcaggcc gggaaccatc cttggaaatc ctgccacgga ctcctctgca       960
cagcatccct gtggcagtgg aggtgaagcc ggtgctgcca ggagccatgc ccagctccat      1020 gggggtgga ggtggaggta gccccagccc cgtggagctt cggggggctc tggcgggccc      1080
catggaccct gcgctacggg agcagcaact gcagcaggag ctcctggtcc tcaagcagca      1140
gcagcagctc cagaagcagc tcctgttcgc cgagttccag aagcagcacg accacttgac      1200
gcggcagcac gaggtccagc tgcagaagca cctcaagcag cagcaggaga tgctggcggc      1260
taagaggcag caggagctgg agcagcagcg gcagcgggag cagcagcggc aggaggagct      1320
ggagaaacag cggctggagc agcagctgct catcctgcgc aacaaggaga gagcaaaga      1380 gagtgccatc gccagcaccg aggtaaagct gaggctccag gaattcctgt tgtccaagtc      1440
aaaggagccc acgccaggcg gcctcaacca ttccctccca cagcacccca aatgctgggg      1500
agcccaccac gcttctttgg accagagttc ccctcccag agcggccctc ctgggacgcc      1560
tccctcctac aaattgcctt tgcttgggcc ctatgacagc cgtgatgact ttcccctccg      1620
taaaacggcc tcggaaccca acttaaaagt acgttcgagg ctaaaacaga aggtagccga      1680
```

-continued

```
gaggagaagc agtcccctcc tgcgtcgaaa ggatggcact gttattagta cttttaagaa    1740
gagagcagtt gagatcaccg gcacggggcc tggggtgtcg tccgtgtgta acagtgcgcc    1800
cggctctggc cccagctctc ccaacagttc ccacagcacc atcgctgaga acggctttac    1860
tggctcagtc cccaacatcc ccactgagat gatcccccag caccgggccc tccctctgga    1920
cagttcccca aaccagttca gcctctatac gtctccttct ctgcccaaca tctccctagg    1980
gctgcaggcc actgtcactg tcaccaactc gcacctcacc gcctccccga agctgtcaac    2040
acagcaggag gctgagaggc aggcccttca gtccctgcgg cagggcggca cactgaccgg    2100
caagttcatg agcacatcct ccatccctgg ctgcctgttg ggagtggcac tggagggtga    2160
cacaagcccc cacgggcacg cttccctgct gcagcacgtt ttgctcctgg agcaggcccg    2220
gcaacagagc acgctcatag cagtgccgct ccatgggcag tccccactgg tgacgggtga    2280
acgtgtggcc accagcatga ggacggtggg taagctcccg aggcaccgac ctctgagccg    2340
cactcagtcc tccccgctgc cgcagagtcc ccaggccctg cagcagctgg tcatgcagca    2400
gcagcaccag cagttcctgg agaagcagaa gcagcagcag atgcagctgg gcaagatcct    2460 taccaaaaact ggggagctgt caaggcagcc caccactcac ccggaggaga cagaagagga    2520
gctgacggag cagcaggagg ccttgctggg agagggggcc ctgaccattc cccgggaagg    2580
ctctacagaa agtgagagca cccaggaaga cctagaagag gaggaggagg aggaggagga    2640
ggaagaggag gactgcattc aggtcaagga tgaggatggc gagagtggtc ctgatgaagg    2700
ccctgactta gaagagtcca gtgctggtta caaaaagttg ttcgcagatg cccagcagtt    2760
acagcccctc caggtgtacc aggcacccct cagcctggcc actgtgcctc atcaggccct    2820
gggccgcacc cagtcctcac ctgctgctcc tgggagcatg aagagcccca cagaccaacc    2880
cactgtggtg aagcacctct tcaccacagg tgtggtctat gacacgttca tgctgaagca    2940
ccagtgtatg tgcggaaaca cacacgtgca cccagagcac gccggccgca tccagagcat    3000
ctggtcccgg ctgcaggaaa ctggtctgct cggcaagtgt gagcggatcc ggggtcgtaa    3060
agccacactg gatgaaatcc agaccgtgca ctctgagtac cacaccctgc tctatgggac    3120 cagcccctt aaccggcaga agctggacag caagaagctg cttggcccca tcagccagaa    3180
gatgtacgcc atgctgccct gtgggggcat tggggtggac agtgacacgg tgtggaatga    3240
gatgcactcc tcaagtgccg tgcgaatggc agtgggctgc ctggtggagc tggccttcaa    3300
ggtggctgca ggagagctca agaatggatt tgctatcatc cggcccccag gacaccatgc    3360
tgaggagtcc acagccatgg gattctgctt cttcaactcc gtagccatca cagctaaact    3420
cctgcagcag aagctgagcg tgggcaaggt cctcatcgtg gactgggata ttcaccatgg    3480
caacggcacc cagcaagcat ctacaacga tccctctgtg ctctacatct ccctgcatcg    3540
ctacgacaac gggaacttct ttccaggctc tggggctcct gaagaggttg gtggagggcc    3600
aggtgtgggg tacaacgtaa atgtggcgtg gacaggaggt gtggatcccc ccattggaga    3660
tgtggaatac ctgacagcct tcaggacagt ggtgatgccc attgcccagg agttctcacc    3720
tgacgtcgtc ctagtctccg ctgggtttga tgctgttgaa ggacatctgt ctccactggg    3780
tggctattct gtcaccgcca gatgttttgg ccacttgacc aggcagctca tgacactggc    3840
tgggggccgg gtggtgctgg ccctggaggg aggccatgac ttgaccgcca tctgtgatgc    3900
ctctgaggcc tgtgtctcgg ctctgctcag cgtggagctg cagcccttgg atgaagcagt    3960
cttgcagcaa aagcccagcg tcaatgcggt tgccacacta gagaaagtca tcgagatcca    4020
gagcaaacac tggagctgtg tacagaggtt tgccgctggt ctgggctgct cgctgcggga    4080
```

```
ggctcagaca ggtgagaaag aggaggccga gactgtgagc gccatggccc tgctttccgt    4140
gggggctgag caggcccagg ctgttgccac tcaagagcac agccccaggt aagccagcag    4200
aggagcccat ggagcaggag cctgccctgt gacaccctgg cccccatccc tctgggcttc    4260
atcattgtga ttttgtttat tttttctatt aaaaacaaaa agtcacacat tcaaaaaaaa    4320
aaaaaaaaaa aa                                                        4332

<210> SEQ ID NO 17
<211> LENGTH: 1724
<212> TYPE: DNA
<213> ORGANISM: Homo sapiens

<400> SEQUENCE: 17
agctctgcga ggggccggag cgcggcggag ccatgcagta cccgcacccc gggccggcgg      60
cgggcgccgt gggggtgccg ctgtacgcgc ccacgccgct gctgcaaccc gcacacccga     120 cgcccttta catcgaggac atcctgggcc gcgggcccgc cgcgcccacg cccgcccca      180 cgctgccgtc ccccaactcc tccttcacca gcctcgtgtc ccctaccgg accccggtgt     240 acgagcccac gccgatccat ccagccttct cgcaccactc cgccgccgcg ctggccgctg     300
cctacggacc cggcggcttc ggggccct c tgtaccccct cccgcggacg gtgaacgact     360
acacgcacgc cctgctccgc cacgaccccc tgggcaaacc tctactctgg agccccttct     420
tgcagaggcc tctgcataaa aggaaaggcg gccaggtgag attctccaac gaccagacca     480
tcgagctgga gaagaaattc gagacgcaga aatatctctc tccgcccgag aggaagcgtc     540
tggccaagat gctgcagctc agcgagagac aggtcaaaac ctggtttcag aatcgacgcg     600
ctaaatggag gagactaaaa caggagaacc ctcaaagcaa taaaaaagaa gaactggaaa     660
gtttggacag ttcctgtgat cagaggcaag atttgcccag tgaacagaat aaaggtgctt     720
ctttggatag ctctcaatgt tcgccctccc ctgcctccca ggaagacctt gaatcagaga     780
tttcagagga ttctgatcag gaagtggaca ttgagggcga taaaagctat tttaatgctg     840
gatgatgacc actggcattg gcatgttcag aaaactggat ttaggaataa tgttttgcta     900
cagaaaatct tcatagaaga actggaaggc tatataagaa agggaatcaa ttctctggta     960
ttctggaaac ctaaaaatat ttggtgcact gctcaattaa caaacctaca tggagacctt    1020
aattttgact taacaaatag tttatgtact gctcttaggt tgtttgata aagtgacatt    1080 atagtgatta aattcttccc cctttaaaaa aacagttagt ggttttcact atttataaaa    1140
aattaatttt gaactttttg ttaaatttt aagttatagc tttaaaggtt ttaataggac    1200
cttcttgaac gacttttctg taatctgttt atctcccact taatggaaag gcaaaggggt    1260
accccaaatc cagaggtgcc tacatttcag gcagccttgg agtatttaa aaggaaaaca    1320 ttctttactt ttatatgaca ttcttatact gctgtctcaa atccaaaaac atttcagagc    1380
tcttgtctca gagatgtgtg ttcttttgt cagagatatg gttgatgaga atcttaaatg    1440
cttgttttgc actatcactt agtacctgtt tgaccaaggt gttaaggga tagtacctcc    1500 caattcaagc agagaaactg acctgactaa agttaatcgc agatgaacta gaagtcacag    1560
gttaattaaa tgtaagtaga ttgtagatac tgtttttat caaacaatgt ttataatgtg    1620
tatatagaat tgttcactgt aaaaaaaatg gccaaaatgt gtttttttt taataagtaa    1680 cttgactata aaataaagcc gtccgtggga cgactgacct cgtt                    1724

<210> SEQ ID NO 18
```

<211> LENGTH: 1771
<212> TYPE: DNA
<213> ORGANISM: Mus musculus

<400> SEQUENCE: 18

```
agctctctgc gaggggctgc ggagcggcca tgcagttccc gcacccgggg cccgcggctg      60
cgcccgccgt gggagtcccg ctgtatgcgc ccacgccgct gctgcagccc gctcacccga     120
cgcccttcta catcgacgac atcttgggtc gcgggcccgc cgcccccacg cccactccca     180
cgctgccgtc ccccaactcc tccttcacca gcctcgtgtc ctcctaccgg accccggtgt     240
acgagcccac gccggtccac cccgccttct cgcaccaccc ggccgccgcg ctggccgccg     300
cctacggccc cagtggcttc ggaggccctc tgtacccgtt cccgcggacg gtgaacgact     360
acacgcacgc cctactccgc cacgacccc tgggcaagcc cttgctctgg agccccttcc      420
tccagcgacc tctgcacaaa aggaaaggcg gtcaagtgag gttctccaac gaccagaccg     480
tcgagctgga gaagaagttc gagactcaga aatacctctc cccacccgag agaaagcgtc     540
tggccaagat gttacagctc agtgagagac aggtcaaaac ctggtttcag aatcgccgag     600
ctaaatggag aagactgaaa caggagaatc ctcaaagcaa caaaaaggat gcgttggaca     660
gtttggacac ttcctgtgag cagggtcaag acttgcccag tgaacagaat aaaggtgcct     720
ctttggatcg ttcgcagtgt tcaccctccc cagcctctca ggaagacccc gactcggaga     780
tctcagagga ttccgaccag gaggtggaca tcgagggggg taaaggctac tttaatgctg     840
gatgacagtc atcggccatg tttagagacc ggactttaga ataatgtttt gctacagacc     900
aactggaaaa ttcggggggga gagagagaga gagaaagaga gagagagaga gagagagaga     960
gagagataac aattcttgta gagttttgaa aatgtttggt gcactggcta attaacaaac    1020
atgcattgcg ttgagacctt aactttggtt taacatacgg tatctatacc agttttttaag    1080 ttgttttgat aaagtgacta aatgtgacct catttttttaa aaagtgaatt tatttctatt    1140
tatgagaggt aatttgaact tttgtctaaa gcttaaatta tgactttaaa ggttttaagt    1200
tttaggaggc tgatcttgac tgactttcct aagtctgtag ctattccctc gactttagag    1260
gtgcacttag gtgggggcaa catttgggga atccatggaa cactttgaaa gggtataccc    1320 aactttttaca tggcatctta cattgctgcc ttaactccaa agccatttca gagcacttgg    1380
ctcccggtgt ctgttcttac aagcaagata gttgataaga ttctaaaaat cttgtttttgc    1440 tcagccagtg cctctgaccc tggtgttaag ggatgacgca gtccctacag gcagggaaac    1500
tgactcattt gagactgatc tcacacgaac tagaaatagc aggacaattc aatgtaagta    1560
gattgtagat agtgtgtttt atagaaactg tgtctataac atgtatatag cattacttct    1620
tgtaaaaact ctgccaaaat gatgtttgtt tgtttggttg gttttttgta atttaatgaa    1680
ttaactttca tatacattca tcatcagatg aacgaccctg tttgaattct cattctttgg    1740
ttaaaatacc taaacatgac acctaaagag c                                    1771
```

<210> SEQ ID NO 19
<211> LENGTH: 1670
<212> TYPE: DNA
<213> ORGANISM: Homo sapiens

<400> SEQUENCE: 19

```
ataaattgtg caagggtgct atagacgcac aaacgaccgc gagccacaaa tcaagcacac      60
atatcaaaaa acaaatgagc tcttattttg taaactcatt ttgcggtcgc tatccaaatg     120 gccccggacta ccagttgcat aattatggag atcatagttc cgtgagcgag caattcaggg     180
```

-continued

```
actcggcgag catgcactcc ggcaggtacg gctacggcta caatggcatg gatctcagcg      240
tcggccgctc gggctccggc cactttggct ccggagagcg cgcccgcagc tacgctgcca      300
gcgccagcgc ggcgcccgcc gagcccaggt acagccagcc ggccacgtcc acgcactctc      360
ctcagcccga tccgctgccc tgctccgccg tggccccctc gcccggcagc gacagccacc      420
acggcgggaa aaactcccta agcaactcca gcggcgcctc ggccgacgcc ggcagcaccc      480
acatcagcag cagagagggg gttggcacgg cgtccggagc cgaggaggac gccctgcca      540 gcagcgagca ggcgagtgcg cagagcgagc cgagcccggc gccgcccgcc caaccccaga      600
tctacccctg gatgcgcaag ctgcacataa gtcatgacaa cataggcggc ccggaaggca      660
aaagggcccg gacggcctac acgcgctacc agaccctgga gctggagaag gagttccact      720
tcaaccgtta cctgacccgc agaaggagga ttgaaatagc acatgctctt tgcctctccg      780
agagacaaat taaaatctgg ttccaaaacc ggagaatgaa gtggaaaaaa gataataagc      840
tgaaaagcat gagcatggcc gcggcaggag gggccttccg tccctgagta tctgagcgtt      900
taaagtactg agcagtatta gcggatcccg cgtagtgtca gtactaaggt gactttctga      960
aactcccttg tgttccttct gtgaagaagc cctgttctcg ttgccctaat tcatctttta     1020
atcatgagcc tgtttattgc cattatagcg cctgtataag tagatctgct ttctgttcat     1080
ctctttgtcc tgaatggctt tgtcttgaaa aaaatagat gttttaactt atttatatga     1140
agcaagctgt gttacttgaa gtaactataa caaaaaaga aaagagaaaa aaaaacacac     1200
aaaaagtccc ccttcaatct cgtttagtgc caatgttgtg tgttgcactc aagttgttta     1260
actgtgcatg tgcgtggaag tgttcctgtc tcaatagctc caagctgtta aagatatttt     1320
tattcaaact acctatattc cttgtgtaat taatgctgtt gtagaggtga cttgatgaga     1380
cacaacttgt tcgacgtgta gtgactagtg actctgtgat gaaaactgtg actccaagcg     1440
gtgtgtccct gcgtgccttt ataggaccct ttgcacgaac tctggaagtg gctcttataa     1500
gcgcagcttc agtgatgtat gttttttgtga acaaagttac aaatattgtc caagtctggc     1560
tgttttaagc aaactgtgat cagctttttt tttttttttt tttttttttgt atttgttttt     1620 aaggaaaaaa tactgactgg aacaaaaaat aaactttcta ttgtaagttc                1670
```

```
<210> SEQ ID NO 20
<211> LENGTH: 1877
<212> TYPE: DNA
<213> ORGANISM: Mus musculus

<400> SEQUENCE: 20
```

```
ctccacccaa ctcccccatt agtgcacgag tttacctcta gaggtcatca ggcaggattt       60
acgactggac aacaaaagca cgtgattcga agtcgtaccc catatttggg tgcctacgta      120
ggagggaacc gagtacatgt cccagtcatt tccataattc atcataaatt gtgcaagggt      180
gctatagacg cacaaacgac cgcgagccac aaatcaagca cacatatcaa aaaacaaatg      240
agctcttatt ttgtaaactc attttgcggt cgctatccaa atggcccgga ctaccagttg      300
cataattatg gagatcatag ttccgtgagc gaacaattca gggactcggc gagcatgcac      360
tccggcaggt acggctacgg ctacaatggc atggatctca gcgtcggccg ttcgggttcc      420
ggccactttg gctccggcga gcgcgcccgc agctacgcgg ctggggccag tgcggcgccc      480
gccgagccca ggtacagcca gccggccacg tccacgcact cgccaccgcc cgacccgctg      540
ccctgctcag cggtggcccc ctcgcccggc agcgacagcc accacggcgg gaaaaactcc      600
```

-continued

```
ctgggcaact ccagcggcgc ctcggccaac gccggcagca cccacatcag cagcagagag      660 gggggttggca cggcgtccgc agccgaggag gacgcccctg ccagcagcga gcaggcgggc      720
gcccagagcg agccgagccc ggcgccgccc gctcagcccc agatctaccc ctggatgcgc      780
aagctgcaca ttagtcacga caatataggt ggcccagaag gcaaaagggc ccggacggcc      840
tacactcgct accagaccct ggagctggag aaagaattcc acttcaaccg ctacctgacc      900
cgccgaagaa ggatcgaaat agctcatgcc ctttgcctct ccgagagaca aattaaaatc      960
tggttccaaa acaggaggat gaagtggaaa aaagataata agctgaaaag catgagtatg     1020
gccgcggcag gggggggcttt ccgcccctga gcatctgagc ggccaaagta ctgagcagta     1080
gtagccgggc agctctctgt agtgtcagta ctaaggtgac tttctgaaac tccccttgtg     1140
ttccttctgt gaagaagccc tgttctcgtt gccctaattc atctttttaat catgagcctg     1200 tttattgcca ttatagcgcc tgtataagta gatctgcttc tgttcatctc tttgtcctga     1260
atggctttgt cttgaaaaaa aaatagatgt tttaacttat ttatatgaag caagctgtgt     1320
tacttgaagt aactaaaaca aaaaaaaaaa aaaagaaaa gagaaaaaaa aactacacac     1380
acaaaaagcc cccccacctc gtttagtgcc aatgttgtgt gttgcacttg agttctttaa     1440
tgtgcatgta cgtggaagtg ttcctgtctc aatagctcca agctgttaaa gatattttta     1500
ttcaaactac ctatattcct tgtgtaatta atgctgttgt agaggtgact tgataagaca     1560
caaattaact tgttcaacgt gtagtggcta gtggctctgt gacgaaaact gtgactccaa     1620
gcggtgtgtc cctgcgtgcc tttgtaggac cctttgcacg aactctggaa gtggctctta     1680
taagcgcagc ttcagtgatg tatgtttttg tgaaaaagtt acaaatattg tccaagtctg     1740
gctgtttaag caaactgtga tcagcttttt ttttttttttg tatttgtttt taaggaaaaa     1800
aaacactgac tggaaacaaa acaaaataaa ctttctattg taagttctct tggtctgatt     1860
tatgccaaat agcaagc                                                    1877
```

```
<210> SEQ ID NO 21
<211> LENGTH: 950
<212> TYPE: DNA
<213> ORGANISM: Homo sapiens

<400> SEQUENCE: 21
gcgttgcagg tcactgtagc gggacttctt ttggttttct ttctctttgg ggcacctctg       60
gactcactcc ccagcatgaa ggcgctgagc ccggtgcgcg gctgctacga ggcggtgtgc       120
tgcctgtcgg aacgcagtct ggccatcgcc cggggccgag ggaagggccc ggcagctgag       180
gagccgctga gcttgctgga cgacatgaac cactgctact cccgcctgcg ggaactggta       240 cccgagtcc cgagaggcac tcagcttagc caggtggaaa tcctacagcg cgtcatcgac        300
tacattctcg acctgcaggt agtcctggcc gagccagccc ctggaccccc tgatggcccc       360
caccttccca tccagacagc cgagctcact ccggaacttg tcatctccaa cgacaaaagg       420
agcttttgcc actgactcgg ccgtgtcctg acacctccag aacgcaggtg ctggcgcccg       480
ttctgcctgg accccggga acctctcctg ccggaagccg gacggcaggg atgggcccca        540
acttcgccct gcccacttga cttcaccaaa tcccttcctg gagactaaac ctggtgctca       600
ggagcgaagg actgtgaact tgtggcctga agagccagag ctagctctgg ccaccagctg       660
ggcgacgtca ccctgctccc accccacccc caagttctaa ggtctcttca gagcgtggag       720
gtgtggaagg agtggctgct ctccaaacta tgccaaggcg cggcagagc tggtcttctg        780 gtctccttgg agaaaggttc tgttgccctg atttatgaac tctataatag agtatatagg       840
```

-continued

```
ttttgtacct tttttacagg aaggtgactt tctgtaacaa tgcgatgtat attaaacttt      900
ttataaaagt taacattttg cataataaac gatttttaaa cacttgtgta              950

<210> SEQ ID NO 22
<211> LENGTH: 964
<212> TYPE: DNA
<213> ORGANISM: Mus musculus

<400> SEQUENCE: 22
gcactgtttg ctgctttagg tgtctctttt cctccctctc tatctctact ctccaacatg       60
aaggcgctga gcccggtgcg cggctgctac gaggcggtgt gctgcctgtc ggaacgtagc      120
ctggccattg cgcgaggccg cggtaagagc ccgtcgaccg aggagcctct tagcctcttg      180
gacgacatga accactgcta ctcgcgcctg cgggaactgg tgccgggagt cccgcgaggc      240
actcagctta gccaggtgga aatcctgcag cgtgtcatag actacatcct cgaccttcag      300
gtggtcctgg cagagccggc gcctggaccc ccggacggtc cgcatctccc gatccagaca      360
gctgagctca ctccggaact tgtgatctcc aaggacaaga ggagcttttg ccactgaccc      420
ggtcgtcctg gcacctcccg aacgcaggtg ctggcgcccg ttccgcttgg gaccctggga      480
ctctgggacc ctctctccag ccggaagcct gagggcatgg atgagcttcg atcttaaccc      540
agccctcttc acttaccctg aactcaacgc ctcgaggctg gacctggagc ccgagagaag      600
gactgaactt gggtggcctg aagagctagc acacgctggt cagcagctgg gcaacgtcac      660
tctgtcccca ccctgactca agtctaaaag actggctttt ccgagaatgg ggtgtcgaga      720
gggtgtgggg ggatgcgagt ggctgccctg cgcactctgc caaggcagca taagagctgt      780
tcttctggtt tccttggaga aaagctctgc tgccctgatt atgaactcta aatagagta      840 tatagctttt gtaccttttt tacaggaagg tgactttctg taatcatgtg atgtatatta      900 aacttttat aaaagttaac attttgcata ataaaccatt tttgaacact ttgaaaaaaa      960
aaaa                                                                    964

<210> SEQ ID NO 23
<211> LENGTH: 6255
<212> TYPE: DNA
<213> ORGANISM: Homo sapiens

<400> SEQUENCE: 23
actctaacaa gtgactgcgc ggcccgcgcc cggggcggtg actgcggcaa gcccctggg        60 tccccgcgcg gcgcatccca gcctgggcgg gacgctcggc cgcggcgagg cgggcaagcc      120
tggcagggca gagggagccc cggctccgag gttgctcttc gcacccgagg atcagtcttg      180
gccccaaagc gcgacgcaca aatccacata acctgaggac catggatgct gatgaggtc       240 aagacatgtc ccaagtttca gggaaggaaa gccccctgt aagcgatact ccagatgagg       300
gcgatgagcc catgccgatc cccgaggacc tctccaccac ctcgggagga cagcaaagct      360
ccaagagtga cagagtcgtg gccagtaatg ttaaagtaga gactcagagt gatgaagaga      420 atggcgtgc ctgtgaaatg aatgggaag aatgtgcgga ggatttacga atgcttgatg       480
cctcgggaga gaaaatgaat ggctcccaca gggaccaagg cagctcggct ttgtcgggag      540
ttggaggcat cgacttcct aacggaaaac taaagtgtga tatctgtggg atcatttgca      600
tcgggcccaa tgtgctcatg gttcacaaaa gaagccacac tggagaacgg cccttccagt      660
gcaatcagtg cgggggcctca ttcacccaga agggcaacct gctccggcac atcaagctgc      720
```

-continued

```
attccgggga gaagcccttc aaatgccacc tctgcaacta cgcctgccgc cggagggacg      780
ccctcactgg ccacctgagg acgcactccg ttggtaaacc tcacaaatgt ggatattgtg      840
gccgaagcta taaacagcga agctctttag aggaacataa agagcgctgc cacaactact      900
tggaaagcat gggccttccg ggcacactgt acccagtcat taaagaagaa actaatcaca      960
gtgaaatggc agaagacctg tgcaagatag gatcagagag atctctcgtg ctggacagac     1020
tagcaagtaa cgtcgccaaa cgtaagagct ctatgcctca gaaatttctt ggggacaagg     1080
gcctgtccga cacgccctac gacagcagcg ccagctacga gaaggagaac gaaatgatga     1140
agtcccacgt gatggaccaa gccatcaaca acgccatcaa ctacctgggg gccgagtccc     1200
tgcgcccgct ggtgcagacg cccccgggcg gttccgaggt ggtcccggtc atcagcccga     1260
tgtaccagct gcacaagccg ctcgcggagg gcaccccgcg ctccaaccac tcggcccagg     1320
acagcgccgt ggagaacctg ctgctgctct ccaaggccaa gttggtgccc tcggagcgcg     1380
aggcgtcccc gagcaacagc tgccaagact ccacggacac cgagagcaac aacgaggagc     1440
agcgcagcgg tctcatctac ctgaccaacc acatcgcccc gcacgcgcgc aacgggctgt     1500
cgctcaagga ggagcaccgc gcctacgacc tgctgcgcgc cgcctccgag aactcgcagg     1560
acgcgctccg cgtggtcagc accagcgggg agcagatgaa ggtgtacaag tgcgaacact     1620
gccgggtgct cttcctggat cacgtcatgt acaccatcca catgggctgc cacggcttcc     1680
gtgatccttt tgagtgcaac atgtgcggct accacagcca ggaccggtac gagttctcgt     1740
cgcacataac gcgaggggag caccgcttcc acatgagcta aagccctccc gcgcccccac     1800
cccagacccc gagccacccc aggaaaagca caaggactgc cgccttctcg ctcccgccag     1860
cagcatagac tggactggac cagacaatgt tgtgtttgga tttgtaactg tttttgttt      1920 tttgtttgag ttggttgatt ggggtttgat ttgcttttga aaagattttt atttttagag     1980
gcagggctgc attgggagca tccagaactg ctaccttcct agatgtttcc ccagaccgct     2040
ggctgagatt ccctcacctg tcgcttccta gaatcccctt ctccaaacga ttagtctaaa     2100
ttttcagaga gaaatagata aaacacgcca cagcctggga aggagcgtgc tctaccctgt     2160
gctaagcacg gggttcgcgc accaggtgtc tttttccagt ccccagaagc agagagcaca     2220
gcccctgctg tgtgggtctg caggtgagca gacaggacag gtgtgccgcc acccaagtgc     2280
caagacacag cagggccaac aacctgtgcc caggccagct tcgagctaca tgcatctagg     2340
gcggagaggc tgcacttgtg agagaaaata ctatttcaag tcatattctg cgtaggaaaa     2400
tgaattggtt ggggaaagtc gtgtctgtca gactgccctg ggtggaggga gacgccgggc     2460
tagagccttt gggatcgtcc tggattcact ggctttgcgg aggctgctca gatggcctga     2520
gcctcccgag gcttgctgcc ccgtaggagg agactgtctt cccgtgggca tatctgggga     2580
gccctgttcc ccgcttttc actcccatac ctttaatggc ccccaaaatc tgtcactaca      2640
atttaaacac cagtcccgaa atttggatct tctttctttt tgaatctctc aaacggcaac     2700
attcctcaga aaccaaagct ttatttcaaa tctcttcctt ccctggctgg ttccatctag     2760
taccagaggc ctcttttcct gaagaaatcc aatcctagcc ctcattttaa ttatgtacat     2820
ctgtttgtag ccacaagcct gaatttctca gtgttggtaa gtttctttac ctaccctcac     2880
tatatattat tctcgtttta aaacccataa aggagtgatt tagaacagtc attaattttc     2940
aactcaatga aatatgtgaa gcccagcatc tctgttgcta acacacagag ctcacctgtt     3000
tgaaaccaag ctttcaaaca tgttgaagct ctttactgta aaggcaagcc agcatgtgtg     3060
tccacacata cataggatgg ctggctctgc acctgtagga tattggaatg cacagggcaa     3120
```

-continued

```
ttgagggact gagccagacc ttcggagagt aatgccacca gatcccctag gaaagaggag    3180
gcaaatggca ctgcaggtga gaaccccgcc catccgtgct atgacatgga ggcactgaag    3240
cccgaggaag gtgtgtggag attctaatcc caacaagcaa gggtctcctt caagattaat    3300
gctatcaatc attaaggtca ttactctcaa ccacctaggc aatgaagaat ataccatttc    3360
aaatatttac agtacttgtc ttcaccaaca ctgtcccaag gtgaaatgaa gcaacagaga    3420
ggaaattgta cataagtacc tcagcattta atccaaacag gggttcttag tctcagcact    3480
atgacatttt gggctgacta cttatttgtt aggcgggagc tctcctgtgc attgtaggat    3540
aattagcagt atccctggtg gctacccaat agacgccagt agcaccccga attgacaacc    3600
caaactctcc agacatcacc aactgtcccc tgcgaggaga aatcactcct gggggagaac    3660
cactgaccca aatgaattct aaaccaatca aatgtctggg aagccctcca agaaaaaaaa    3720
tagaaaagca cttgaagaat attcccaata ttcccggtca gcagtatcaa ggctgacttg    3780
tgttcatgtg gagtcattat aaattctata aatcaattat tccccttcgg tcttaaaaat    3840
atatttcctc ataaacattt gagttttgtt gaaaagatgg agtttacaaa gataccattc    3900
ttgagtcatg gatttctctg ctcacagaag ggtgtggcat ttggaaacgg gaataaacaa    3960
aattgctgca ccaatgcact gagtgaagga agagagacag aggatcaagg gctttagaca    4020
gcactccttc aatatgcaat cacagagaaa gatgcgcctt atccaagtta atatctctaa    4080
ggtgagagcc ttcttagagt cagtttgttg caaatttcac ctactctgtt cttttccatc    4140 catcccctg agtcagttgg ttgaaggag ttattttttc aagtggaatt caaacaaagc    4200
tcaaaccaga actgtaaata gtgattgcag gaattctttt ctaaactgct ttgccctttc    4260
ctctcactgc cttttatagc caatataaat gtctctttgc caccttttg ttgtggtttt    4320 atattgtaac accatttttc tttgaaacta ttgtatttaa agtaaggttt catattatgt    4380
cagcaagtaa ttaacttatg tttaaaaggt ggccatatca tgtaccaaaa gttgctgaag    4440
tttctcttct agctggtaaa gtaggagttt gcatgacttc acactttttt tgcgtagttt    4500
cttctgttgt atgatggcgt gagtgtgtgt cttgggtacc gctgtgtact actgtgtgcc    4560
tagattccat gcactctcgt tgtgtttgaa gtaaatattg gagaccggag ggtaacaggt    4620
tggcctgttg attacagcta gtaatcgctg tgtcttgttc cgccccctcc ctgacacccc    4680
agcttcccag gatgtggaaa gcctggatct cagctccttg ccccatatcc cttctgtaat    4740
ttgtacctaa agagtgtgat tatcctaatt caagagtcac taaaactcat cacattatca    4800
ttgcatatca gcaaagggta aagtcctagc accaattgct tcacatacca gcatgttcca    4860
tttccaattt agaattagcc acataataaa atcttagaat cttccttgag aaagagctgc    4920
ctgagatgta gttttgttat atggttcccc accgaccatt tttgtgcttt tttcttgttt    4980 tgtttttgttt tgactgcact gtgagttttg tagtgtcctc ttcttgccaa aacaaacgcg    5040
agatgaactg gacttatgta gacaaatcgt gatgccagtg tatccttcct ttcttcagtt    5100
ccagcaataa tgaatggtca actttttaa aatctagatc tctctcattc atttcaatgt    5160
atttttactt taagatgaac caaaattatt agacttattt aagatgtaca ggcatcagaa    5220
aaaagaagca cataatgctt ttggtgcgat ggcactcact gtgaacatgt gtaaccacat    5280
attaatatgc aatattgttt ccaatacttt ctaatacagt tttttataat gttgtgtgtg    5340
gtgattgttc aggtcgaatc tgttgtatcc agtacagctt taggtcttca gctgcccttc    5400
tggcgagtac atgcacagga ttgtaaatga gaaatgcagt catatttcca gtctgcctct    5460
```

```
atgatgatgt taaattattg ctgtttagct gtgaacaagg gatgtaccac tggaggaata      5520
gagtatcctt ttgtacacat tttgaaatgc ttcttctgta gtgatagaac aaataaatgc      5580
aacgaatact ctgtctgccc tatcccgtga agtccacact ggcgtaagag aaggcccagc      5640
agagcaggaa tctgcctaga ctttctccca atgagatccc aatatgagag ggagaagaga      5700
tgggcctcag gacagctgca ataccacttg ggaacacatg tggtgtcttg atgtggccag      5760
cgcagcagtt cagcacaacg tacctcccat ctacaacagt gctggacgtg ggaattctaa      5820
gtcccagtct tgagggtggg tggagatgga gggcaacaag agatacattt ccagttctcc      5880
actgcagcat gcttcagtca ttctgtgagt ggccgggccc agggccctca caatttcact      5940
accttgtctt ttacatagtc ataagaatta tcctcaacat agccttttga cgctgtaaat      6000
cttgagtatt catttaccct tttctgatct cctggaaaca gctgcctgcc tgcattgcac      6060
ttctcttccc gaggagtggg gtaaatttaa aagtcaagtt atagttttgga tgttagtata      6120 gaattttgaa attgggaatt aaaaatcagg actgggact gggagaccaa aaatttctga      6180
tcccatttct gatggatgtg tcacaccttt tctgtcaaaa taaaatgtct tggaggttat      6240
gactccttgg tgaaa                                                        6255

<210> SEQ ID NO 24
<211> LENGTH: 5451
<212> TYPE: DNA
<213> ORGANISM: Mus musculus

<400> SEQUENCE: 24
gtcagggtcc cgaagccgcg tgccgtgcgc gcaggccggg tgggctgtgg gacaagccga        60
gcgggaggcg agtcgcaagc gccaacccaa agtttgcacg gtgcggggcg aggggcgcgc       120
gctccgggct gccgcaggtg gcggcgcggt gagcccgggc caggtgcccc ggcagcgggg       180
cggcgctgtc gtgcgggaca gccgggctgc caggggctcg gagccgggtc ggagcccgcg       240 ggggcgggg agtgtggcga gaaatgggga acaatgcgag tgagcaactt gaggaagtca       300
ttgtgaaaga aagctgggaa ttgctccgca gccaacttag cagggcactc taacaagtgc       360
ctgcgcggcc gcgcccgggc cggggacagg ggcagcccgg cgcagtacag cccatcccgg       420
gacgctcggc cgcggctgcc ggagacccgg taggtcccgc ggggtgcagg agcccccaga       480
tccccggctg ctcttcgcgc cccaggatca ttcttggccc ccaaagcgcg cgcacacaat       540
ccacataacc tgaagacaat ggatgtcgat gagggtcaag acatgtccca agtttcagga       600
aaggagagcc ccccagtcag tgacactcca gatgaagggg atgagcccat gcctgtccct       660
gaggacctgt ccactacctc tggagcacag cagaactcca agagtgatcg aggcatggcc       720
agtaatgtta aagtagagac tcagagtgat gaagagaatg ggcgtgcctg tgaaatgaat       780
ggggaagaat gtgcagagga tttacgaatg cttgatgcct cgggagagaa aatgaatggc       840
tcccacaggg accaaggcag ctcggctttg tcaggagttg gaggcattcg acttcctaac       900
ggaaaactaa agtgtgatat ctgtgggatc gtttgcatcg gcccaatgt gctcatggtt       960 cacaaaagaa gtcatactgg tgaacggcct ttccagtgca accagtgtgg ggcctccttt      1020
acccagaaag gcaacctcct gcggcacatc aagctgcact cgggtgagaa gcccttcaaa      1080
tgccatcttt gcaactatgc ctgccgccgg agggacgccc tcaccggcca cctgaggacg      1140
cactccgttg gtaagcctca caatgtggga tattgtggcc ggagctataa acagcgaagc      1200
tctttagagg agcataaaga gcgatgccac aactacttgg aaagcatggg ccttccgggc      1260
atgtacccag tcattaagga agaaactaac cacaacgaga tggcagaaga cctgtgcaag      1320
```

-continued

```
ataggagcag agaggtccct tgtcctggac aggctggcaa gcaatgtcgc caaacgtaag    1380
agctctatgc ctcagaaatt tcttggagac aagtgcctgt cagacatgcc ctatgacagt    1440
gccaactatg agaaggagga tatgatgaca tcccacgtga tggaccaggc catcaacaat    1500
gccatcaact acctgggggc tgagtccctg cgcccattgg tgcagacacc ccccggtagc    1560
tccgaggtgg tgccagtcat cagctccatg taccagctgc acaagccccc ctcagatggc    1620
cccccacggt ccaaccattc agcacaggac gccgtggata acttgctgct gctgtccaag    1680
gccaagtctg tgtcatcgga gcgagaggcc tccccgagca acagctgcca agactccaca    1740
gatacagaga gcaacgcgga ggaacagcgc agcggcctta tctacctaac caaccacatc    1800
aacccgcatg cacgcaatgg gctggctctc aaggaggagc agcgcgccta cgaggtgctg    1860
agggcggcct cagagaactc gcaggatgcc ttccgtgtgg tcagcacgag tggcgagcag    1920
ctgaaggtgt acaagtgcga acactgccgc gtgctcttcc tggatcacgt catgtatacc    1980
attcacatgg gctgccatgg ctttcgggat ccctttgagt gtaacatgtg tggttatcac    2040
agccaggaca ggtacgagtt ctcatcccat atcacgcggg gggagcatcg ttaccacctg    2100
agctaaaccc agccaggccc cactgaagca caaagatagc tggttatgcc tccttcccgg    2160
cagctggacc cacagcggac aatgttggga gtggatttgc aggcagcatt tgttctttta    2220
tgttggttgt ttggcgtttg atttgcgttg gaagataagt ttttaatgtt agtgacagga    2280
ttgcattgca tcaggaacat tcacaacatc catccttcta gccagttttg ttcactggta    2340
gctgaggttt cccggatatg tggcttccta acactctccc cacccacccc accccccaaa    2400
acagagcctg aatcttcatg aagtgaataa aacaattatc caagaaggag taaggtggat    2460
cttgccctaa gcagagttta tgccacaaag attctccaaa tcccccaaga cagcacagcc    2520
actggggttg agccatctca gggagctctg caggtgagcc agaggaccag atataaggca    2580
gctggggagg agcagggaca tcagcctgtg cagagaccaa ggccaaaggt tgaactttga    2640
aagactatta agtcatatat tgtatggcaa tatggtgtct ggacaagttg tgcaatgtgc    2700 tgaaggggaag ggattggaga gccttgaaga ctcttcttca tttgcctgat caacccgacc    2760
tccagagggt ttgttgccca gtaagacgag ctcagtgctc ttgtgatcat ttttctctta    2820
tcgtttccat gccgttgatg gccctgaagc tcatcactgc attttagaac ccaatcctga    2880
aattgggacc ttttttttaa acttctgata ctgtaaaact tcttggaagc caaagctttc    2940
ttccaagccc catcctcagt tatcctggtt cctgttcttc cccgagctga tagtaccagg    3000
acctgttatt ccacaaaagc acaggcatcc gtcacttcaa ttcaatccct gttcagatta    3060
tagatatgga ctttgctatc ttgataaatg tcttctctat gttattttgt ctgaaaaacc    3120
tataaaacca ttattaagaa tgaccatttt tagatggaag aaatgagccc agcatctcag    3180
tggctaaaac acaaaatatc catgctttta aacaaaattg ttaaatattc cgaagctctc    3240
tagtataaac accaagtagc atgtgttttc acataaagaa gacaggggcc atgcaacctt    3300
tatcaagtgg aggtattaga atgttgtaat gtttggagac acagtgtgac cagtacaggt    3360
tcccagagag gaatgcccac catatcacag aaaggtagag gtgggatctg gtatagccag    3420
accaagacag ggatgtcacg ctgaagccaa gtcagttagc tgaagattct caacaggaag    3480
gcctctctta agagtcagta ataggggttgt taccatccac cacctcaaca aaacaaaaag    3540
cttataattg taaatgttta cagcactgtc ttcgcagaaa ctttctgagg tgattccaaa    3600
gaactagagg ggagatggtc tataacagct cttgaagtaa acgaggttct tagtctcagc    3660
```

-continued

```
tctcctgaca tatagggctt gatcattact ggtagggatt gttctgtgaa ttgcttacta      3720
ctacccctgg tctctcccca gtagatgcca ggaacattct agctgatacc taactgtctt      3780
cccaggtgtt cgagggagca aaccactgat ctaaactcta aacgctgaag tacgcaggtt      3840
ttctaaaaat gacaagccct tgaaaccttt cccagtaggc agcctcgagc tggacttgtg      3900
tctttggaat gctgatgaat tctatagatc agcattgcaa atacacttca aatacgtctg      3960
agttcaagtg cagggactga gttcaccaag gtgtgaaatg tgctcaaaaa gttcaaaagt      4020
gtgtgtttct ttgtttctaa aacattgtgg catctttttc atttgtttct aaaacttttt      4080
ttttagaaac aaatgaagca cttggaaagt gaaagtaaaa ttacaaatat aaggatttac      4140
actgaagaga gaaaaatttt aggaactata gctgtgaaaa gattttgttc aaaaggcagg      4200
ctagccttac ccaaattcat atatggcagg tgtcaacctc ccaagcttac agttagcagg      4260
cagcttttgc tcactcatcc ttagccatga gagccattaa gtgtggtcca agaaagatgg      4320
ctccaaaccc tacccccgac ccaccagtgg tattcagaga ttaaagcaga attgtaaata      4380
gtggcttcag gagctctttt ttagaatgct ttgcccctc ctctcactgc cttttttagc      4440
caatataaat gtcaatttgc acaccttttg ttgtggtttt atattgtaac agcatttttt      4500
tgaaactatt gtatttaaga taaggtttca tattatgtcc acaagtaatt aaattatgtt      4560
tgaaggtggc tatatgctgt atcagaagtt gatgatgttt ttctttagct ggtaaaggag      4620
ggttttgcat gacctcactg tttgttctgt ggtttgttct gttgtatgat gtgtgtcttg      4680
agttttgctg tgtgatgaag tgcgctgaga ttccagtgcc ctcaagttgt gttttaagta      4740
gctatcagag gcaagagggt tcctaagagc aggttgacct gttggcgaca gatggcaatc      4800
accatttctc attccttctt ctccctgtta ccccagcttc ctgtcccagg tcccttctgt      4860
gattcttacc ttagtgtgca tgtgtgtctg tcctggtgag agtcaggagc atcgatatgt      4920
tatcattgca ttatcaccaa gggcacgcac agcctagcac ctgttgcttc agataccgtc      4980
acactctgtt tccaatttag atacaaccac ataataaaat gttagagtct tcaatgggaa      5040
gcagaggtgc ttgttataaa gatgggggct tatgcttgtg tcacattttg tgttctttc      5100 ttcttttgtt tggtttaac ttaattgtga cccttgtaac atcatcttgc caaaaaaaaa      5160
aaaaaagttg aactggattt atgtagacat gtcaagacgt actatctatt tctttgtcag      5220
ttatagcaat aagagtggat aaactctaaa atccagatct cccacaatga acatccgtgt      5280
tctttctatg attttttcttt ctttatggtg agccacaatt aaacttgaga tgtacagcca      5340
cccaaaccca ggaagctcat gtgcatctgg tgctatggca ctcactgtga ataagtgtga      5400
ccagatatta atatgcaata ttgtttccaa tcctttctaa tacattttttt c      5451
```

<210> SEQ ID NO 25
<211> LENGTH: 9515
<212> TYPE: DNA
<213> ORGANISM: Homo sapiens

<400> SEQUENCE: 25

```
atttcttggt tttgtttatc agccgatctg tttgctggat ttgggcttgg aatgacccac        60
ctgtaaagtg cttttccttc ctcctcccct tgaactctgc aggggcttg gcttggaggg       120 ggcaagggag ggaaagagag aaggggaaa cacaaaaaac ttctttcttt ctccctccgt       180
ttatcttcag cccgacattg tcacctcctc tttgaggggt tagaagaagc tgagatctcc       240
cgacagagct ggaaatgcat tgcactttga ctatggaaac agaggctatt gatggctata       300
taacgtgtga caatgagctt tcacccgaaa gggagcactc caatatggca attgacctca       360
```

-continued

```
cctcaagcac acccaatgga cagcatgcct caccaagtca catgacaagc acaaattcag      420
taaagctaga aatgcagagt gatgaagagt gtgacaggaa acccctgagc cgtgaagatg      480
agatcagggg ccatgatgag ggtagcagcc tagaagaacc cctaattgag agcagcgagg      540
tggctgacaa caggaaagtc caggagcttc aaggcgaggg aggaatccgg cttccgaatg      600
gtaaactgaa atgtgacgtc tgtggcatgg tttgcattgg gcccaatgtg cttatggtac      660
ataaaaggag tcacactggt gaacgcccct tccactgtaa ccagtgtgga gcttctttta      720
ctcagaaggg caaccttctg agacacataa agttacactc tggagagaag ccgttcaaat      780
gtcctttctg tagctacgcc tgtagaagaa gggacgccct cacaggacac ctcaggaccc      840
attctgtggg taaacctcac aagtgcaact actgtggacg aagctacaag cagcgcagtt      900
cactggagga gcacaaggaa cgctgccaca actatctcca gaatgtcagc atggaggctg      960
ctgggcaggt catgagtcac catgtacctc ctatggaaga ttgtaaggaa caagagccta     1020
ttatggacaa caatatttct ctggtgcctt ttgagagacc tgctgtcata gagaagctca     1080
cggggaatat gggaaaacgt aaaagctcca ctccacaaaa gtttgtgggg gaaaagctca     1140
tgcgattcag ctaccagat attcactttg atatgaactt aacatatgag aaggaggctg     1200
agctgatgca gtctcatatg atggaccaag ccatcaacaa tgcaatcacc taccttggag     1260
ctgaggccct tcaccctctg atgcagcacc cgccaagcac aatcgctgaa gtggccccag     1320
ttataagctc agcttattct caggtctatc atccaaatag gatagaaaga cccattagca     1380
gggaaactgc tgatagtcat gaaaacaaca tggatggccc catctctctc atcagaccaa     1440
agagtcgacc ccaggaaaga gaggcctctc ccagcaatag ctgcctggat tccactgact     1500
cagaaagcag ccatgatgac caccagtcct accaaggaca ccctgcctta aatcccaaga     1560
ggaaacaaag cccagcttac atgaaggagg atgtcaaagc tttggatact accaaggctc     1620
ctaagggctc tctgaaggac atctacaagg tcttcaatgg agaaggagaa cagattaggg     1680
ccttcaagtg tgagcactgc cgagtccttt tcctagacca tgtcatgtac accattcaca     1740
tgggttgcca tggctaccgg gacccactgg aatgcaacat ctgtggctac agaagccagg     1800
accgttatga gtttttcatca cacattgttc gagggggagca cacattccac taggcctttt     1860
cattccaaag gggacccta tgaagtaaag aactgcacat gaagaaatac tgcacttaca     1920
atcccacctt tcctcaaatg ttgacatacc tttattttt tttaatatta ttactgttga     1980
taattcttat tttgtggagg cagtgtcatt tgctctgcct aattacgata aggaagaaac     2040
agaagagaga aggggcggga atattgtttc tttatcacct ggcttgttta ttttgtggga     2100
atttaagagc agtccatttc taccaaggca tatcatgctt tgaaaaatca cttgattcat     2160
aaagattcac ctaagagatt ctgatttgcc actgatattc agaattatga tggaagacag     2220
gaaagttcag agttttctgg gtaggacttt ggtggtttaa aaatggtata agtaacttta     2280
ttcttgaaag aagaatgtgt ttcaaactgt aaaccaattt tttgttcttc agagatcatg     2340
gaacacaaac acattgttat tttcagtgat aactcctaag aggagctgag ttgttgtggg     2400
ttctatgttt acttccccta tggaatttat aattcagtat gttttacact gtaccatata     2460
gcaaaacttt taaactacag gtagttaagg gccaccataca atacatctga ggtcctgtga     2520
tcttattttt ctaaacgtaa gcactgtttt tccatagttt tgatgactgg cattttatag     2580
acaccctggc agccttactt ttaacaccttt taaggaatag tatttttatg tagttttcag     2640
aataacatat ggtctaagag tggataaaag gcagtcaata atttctggga gggacttcta     2700
```

```
ctttcataaa tttgtttgag aggtttctt ttaaagttgt aatgtgatgg cagcatagta   2760
tatgtatttg tttctaaaag tatgcttacg attgtcactt tatcagcatt taatcagtgt   2820
taaccagtca gcagaaaaat ataattatgc taacagtagg gggagaaaac ccacttagaa   2880
atcccttttc tggtatttct cttttcacta gttttttttca agatgtgacc tcccggtgtt   2940
ctgtccatag ttcattcatc ctttactctt cgagtagaag gtcttaaaag tcttcctgtc   3000
ggctgtttct ttcaaaatct cctcagagca attgctaatt tggcctgaat ctggtaactt   3060
gaaccctgta aggttacaga actagggcta tttattttag catttcttca gtagtattta   3120
ctactcttgt tgcaaagaaa agggaatggg acttctttgt aacctgtacc ttggacaaca   3180
gataaaagaa acaaaaaaat aagaaagttt acttttaccc ttcttggagt ctagaatgtg   3240
acagaacccc caaaggaaag tcctgcacat ttttctgttt ccaaaacatt taattgtgta   3300
agtccttgtc agaaatgaat ctcaatccct tagtatagaa ttccccttac atggtatagg   3360
ttgccatatt tcatgtgcag attttaattt catttatgtg ggcgctctgt tttttctttg   3420
cagtccagcc acattagagg ggaggaaccg agtgatattt attcaagtca ttttaggggg   3480
acatacttgg aaggcagaac ttgctgcttc tgtttgggga ggacagacct gactgtgact   3540
ggattatctg ataaccattt gtgaatactg aaattctgtt aggcagtaac tgataactgc   3600
tctaaaggat cattaaatag gatgctgaaa ttatgtatct taatacagtg tggtatgaga   3660
attaccaagt caagagaatt gtggacataa gcaagtttgg ccccaatact gctcttaact   3720
cattttccag cttactattt gctatttaaa tggtaggcac cagctaagca cttctaagca   3780
ctaacacagc tagaactagg caaaaatggt tagaactcag ctctcttcta ctagtccctg   3840
tcataattat ttttgggaaa atgtccaaac tgcccccttt aaatctaagg gaatgcacca   3900
aaacagagat atatagaatg tcaaccattt cattttttttt tttctgcatg ccttggtaca   3960
tagtgaacat acaacctatt taaagataaa gcatgttttt gagactcgct cacccccccc   4020
cacccaacca ctcccaaata ataattggga tgccattttt tttcctttg gatgaggtaa   4080 ataattttaa ggttcacaat tttgtctttt actgcaattt aaggaaacat ttggatgtca   4140
gtcaatatgt tcataatttt ggctgtgtgc gaatttctgc tggcattatc tatgaatttt   4200
cttcctactt attttttttt cagtatatga acaatcatgt atctacctgc cccaggatga   4260
aactaaattt aggtggaccc taaaccttat gaagacagtg ctgaggcact ttccttttct   4320
gatttcatct tttttgggaat ctgtttttatt gaaggtagtt agtagttgag agtgcatttg   4380
ctacaagcat atacttgtat cttcctagct tcatgaggaa cagaaagagg tggatatggc   4440
tcagggtgtg gcaggacaa ttgaggacaa agtcaattca aatttgtggg tcagaaagaa   4500 ttttgtgga cgtagtgttt ttggagaaac tctggatggt tatatgtgca tgcctttttct   4560 tcaaaaggaa atacgcaagg ttgtagcatc taaaaataaa cataagagtc agacaccaaa   4620
taaatcaagt tttacataac agttgtatgc ccagtttgtt taggtgagat ttcacattac   4680
agaaagtatt tgaggagcat gaaaatgggt tatcttctgt attttccagt ttggcaaaag   4740
ttcagaattt catcacattg ctttgcccta attttgccca gaattttatc ttagcctctc   4800
tctgacagtg atgaatcatg ctcaaaagcc attctaattg gaccttttta agacagggaa   4860
agggatcagt aggcggattg gaagaaattt caagtcattg aaatattcca ttgagatttc   4920
ctaaagggac aaaattggga aaataagaaa ctacgactta gatttggcta cgtagtagaa   4980
agtatctccc ctacatacat acaggcaatt gtatgtatga atcataatggt atatgtgtgt   5040 gtatactaca cacacattct tttaaagaga attcatggaa aaaaaagcag ttggagtgat   5100
```

-continued

```
cagatgtatt gcaaaaacat acagagaatt taaatgacag ttaataccaa gaaattagtt      5160
gggtttactt tatcaggtcg taataggaat cactaaagaa gttactagtg tgtctttagg      5220
accagtggca actcttaaac taaaactttg ggtccttatt atctacttac agaacaaagt      5280
gaaacaaaca atgattaagc tgattggata tacattcaaa gatatttaat gtaaagtttt      5340
ttggaatacg aagaaaattc agaaaataaa tattatcaac agttacttat tggcaaatag      5400
agaaagacaa gaatagttta gtgagcccgg tattttgttt ttatagtttt tatctcagtt      5460
gtacaactca caaaaccatg aagtctttgg tattttataa atgtttaaca aaatttacat      5520
cagattaagg catttagatg aaaattatta tgttctcact atcttccaaa ttttatttca      5580
tcctatctcc aaaatgattt cttagggtac aaaaagagca gacggggctg taaaaataca      5640
agcaaaaaac tgtgtgcccc tagtttcagg cagaacttaa actgtcagag gtactagcta      5700
catgatttgt tttttaactt tggattgttc acgtccaaaa atggataaat tacatttgtg      5760
tttatcatca gttgcatttt atgtattatt ttaataaata ctatctgaat gaagactatt      5820
ctaaaccaga aaattcccca aatccaaaag aaaaaaaaag tgggaagagg tgaaattgaa      5880
gtttgtgtat atgaaagtta tcttagacat atttttaatt ctccagtttc tgcaaaataa      5940
ttaaaatata cagtaactgg tctcctaaat cctgaattta atgtattaaa tacttatgtt      6000
ctttatattg gtgccttttt aaaatgcatt gagagtgttg gttagctgtt gcagctgtac      6060
aacactttta atatgcattt ttaaaaatca cttaaaattg agtactatat aattcatctc      6120
tgcattttta gtgcaaatct ttagagcaat ttctaataga gaaattttca gctcagctgt      6180
taaaaggaaa aggaaacttt gaaactagac tttactacct ttttagtttc atagtatttc      6240
tgaatatgat tacaagatta tgcaggtaaa atatagagtg aaactttacc tgtgaattga      6300
attataattt gtgtttttgt tttgttttta aggaagaata agttctgtat caaacaagaa      6360
tttattagat aatttttttgg tcaataaaat acagtattca tttggatttt catctccaga      6420
ctagtattgt tctagtcttg gaatctgtat tttctaatct gttagaaaat agagattgaa      6480
aattgatgga ataatgtgaa aaagcaggta attaattctc cttgaacaaa gcaaaactga      6540
acagtcatat cacattgcta ttctccaaag cataatctca aatggtttca tatcatggtt      6600
gtgtattact tgcaatgggt gtgttaggat atgacagctt tttaaaaaaa tgagctgctg      6660
gttatacaaa gcaaatggca tatgaccaag aagctgtgat atgctagtgt ttcttttttat      6720 catagtgtat tactaggcca aataatgaca ccttgaatat ttttacattt attgcagaaa      6780
ccttaaactt tggaatttcc ataaggtttt tatgtaatat tctatttcta gcttttttagt      6840 tttatcttgc tgtactgtaa gtttgaggat attttttcacc tgcactctta ggaataagtt      6900
cataattctg tttatggggc tttcctccca taacactgca tttgtatatt ttctgtataa      6960
aatatgtgtt gtgtattaac ctttatccca tacagagagt ggtacatgaa tgactagttt      7020
tctaagatgt cctttttatt gtgaataaaa tataaaagtt aaaggccctc tgctaagtca      7080
cataaagtac agcatataag ttcatatagg tacaaataaa tgagtttgca gtgaattggg      7140
ccttcaaatt acctcaagtg acagatagta agaaaagctt cttgagcagg tggaggtcac      7200 tgaatccct actatgcact taccaagatt ttacttactt taatttactg gaaattgatt      7260
ttttaaaaaa tgactacact gtaacaaggg aagggatctg ggttttttttg ttgtttttatt      7320 cttgtttttt ttaagtagtt caaattctga aactgtgatt taaaaatttt ttacagtcaa      7380
gcattctgat tttgaacata actcccttcc ctttctgtgt aacaaaggtc tctctgttat      7440
```

-continued

```
ctcttaaatt ttgttacatc tccctcagcc tctttctttg tccgtctccc ttctgtcatt     7500
gtctatggat gtttacctct ctgttctcct aaaagtttga agattaggtc aactcttatt     7560
tctagttcat tggtaattta atcttaattt ttttttcgtg attttttgttg gttgtataat    7620 ctgctgacgt attttttatac tcaagtgtag ttttctatta aaaagaaaag tggttggatt    7680
aaaaatagta agctatgtaa ccctcatgtt actttcactt tcaaatattg ggtacctaaa     7740
acattacttc agagattatg taatcctatt atagtatgtt tgctttcctt tattgttgga     7800
ttttacattc tgatttggct ttcctccaaa aaatgtatat catgaaagac tagacagtta     7860
tttgcaagtg tttagaaagg tgttaaaaat gtaaagcaaa gagtcttaac tttctcctaa     7920
ttgggagaaa aatgctttaa cattactata ataatattcc aggtttggag ggggtctcca     7980
ggccccatat ttgctgttaa tagttggacc ttttagacca tgtgttattt gcaatcccag     8040
aatgattgct tctgctatta gttaaaaaga tactattctt ttctttctgt acaagtgcaa     8100
tactcccctt gaagtcttaa aaactatggt gattttttttt tcttttctga cctattcttc    8160
ctttagctaa tgacaaaaag aaactcataa aagtcatagt atgttaaagg acacaacaag     8220
caaagagaaa aacactccac aatcaaaaga ttacagaatg tggaaaccac tagtctgatc     8280
tcatggtatc tttatttaag ctaaatttcc atggaaatta gtaatctttt gcttgaaaaa     8340
tgtgtcctaa agttgaactt tttacagatt gaatcttctt agaccctcgc ccaatgctct     8400
aaattaagaa cctaatactt aatatttta ttttacttct cccctttag aaataaactt      8460 ttaaataaaa gcaaagcact tagctgagtt ttaaacactt acatatcacc tattggagaa     8520 attttttta aaaatatttg gagcagtcct gtttcatac aaatttaagt aagaggtatt       8580
tttcttatac atatttatat gtagtgtgct aattttcttt ttttataccct gtgtccctgt    8640 agtaaaactg ctgtaatata aatacatgtt ttgttaaaag ataacatttc tttggcattt     8700
cttttaaagg cagttactgc atttctgcat ttgtacagta tgtgtcttgg ccattttaga     8760
tattctttct ttaacaatac caaaggtaat tagactattt taaagactaa ttgcttgaca     8820
gtttctaggg tattttgtgt tttagaagca aaaaagaaa aaaaaatagg tcaaaccagt      8880
aaacctcatt tttttttcaaa ctaataattt ggggaaataa aaactattgt ttaaaaaaga    8940
aatatatata tatatatata aatatatatg taaagttaaa attccatacc ttgtatgtca     9000
ggtttgctaa gtgtaatgta gtttttttaa ggctcaaata ccatacctca gaaaatgagg     9060
tttactatgg aaatactgaa acagtctttg cagctgtgtg acaagtcact ctactacata     9120
ctgatttgga gacctccgct aaatagtttt atcactgcag actaaaatgt gggacttgta     9180
tcttctttgt ttttaatgca cacacataca tgttctgtgc atgtatgtgg ttactgtgta     9240
tatgtgtatg agtgttgtat atgcatgtgt gagtgtgtgt ctgtatgtgt gtacaactaa     9300
agaagctgca gaaactttgt aatactttgt gaaaaggatt atattataaa ggtttgtact     9360
gtctgagtgc acagctactg gaataaattt agggaatctc aggaacaagc atataatttg     9420
tccaagattt atttcttctc agaagtgtaa gtgcagtttt taattctgta tattatttaa     9480
tattttacca ataaaataaa cttctgacat aaaaa                                9515
```

<210> SEQ ID NO 26
<211> LENGTH: 9457
<212> TYPE: DNA
<213> ORGANISM: Mus musculus

<400> SEQUENCE: 26

```
tgtttgctgg attcggtctt ggaatgaccc acctgtaaag tgctttccct cctcctcggc      60
```

```
ttcaactctg cagggggctt tgcctggagg gggcagggag ggaagggggg ggggacacaa      120
aaaacttctt tctttctttc tttctttctc cgtttctctt cagcccgaca ttgtcacctc      180
ctccttgagg ggttagaaga agctgggagc tcccgacaga gctggaaatg gtgatgactg      240 tttttttaatc agaggacaat ttcttttcac tgcactttga ctatggaaac agacgcaatt     300
gatggctata aacatgtga caatgagctt tcacccgaag gggaacacgc caatatggcc        360
attgacctca cctcaagcac acccaatgga cagcacgcct cgccaagtca catgacaagc      420
acaaattctg taaagctgga aatgcagagt gatgaagagt gtgacaggca gccctgagc       480 cgtgaggatg agatcagggg ccacgatgag gggagcagcc tagaagaacc cctaattgag      540
agcagcgagg tggccgacaa caggaaagtc caggacttc aaggcgaggg aggaatccgg        600
cttccgaatg gtaaactgaa atgtgacgtc tgtggcatgg tttgcattgg gcccaatgtg      660
cttatggtac ataaaaggag tcacactggt gagcggccct tccactgtaa ccagtgcgga      720
gcttctttta cccagaaggg caaccttctg agacacataa agttacactc tggagagaag      780
cccttcaaat gtcctttctg tagctatgct tgtagaagaa gggacgctct cacaggacac      840
ctcaggaccc attctgtggg taaacctcac aagtgtaact actgtggccg aagctacaag      900
cagcgcagct cactggagga acacaaggaa cgctgtcaca actatctcca gaatgtcagc      960
atggaggctg ccgggcaggt catgagtcac catgtaccgc ctatggaaga ttgtaaggaa     1020
caagagccta tcatggacaa caatatttct ctggtgcctt ttgagagacc tgctgtcata    1080
gagaagctca cggcaaatat gggaaagcgc aaaagctcca ctcctcagaa gtttgtgggg    1140
gaaaagctta tgcgattcag ctacccagat attcattttg atatgaactt aacatatgag    1200
aaggaggctg agctgatgca gtctcatatg atggaccaag ccatcaacaa tgcaatcacc    1260
taccttggag ctgaggccct tcaccctctg atgcagcatg caccaagcac aatcgctgag    1320
gtggccccag ttataagctc agcttattct caggtctatc atccaaacag gatagaaaga    1380
cccattagca gggaaacatc tgatagtcac gaaaacaaca tggatggccc catctctctc    1440
atcagaccaa agagtcgacc ccaggaaaga gaggcctcgc ccagcaatag ctgcctcgat    1500
tctactgact cagaaagtag ccatgatgac cgccagtcct accaaggaaa ccctgcctta    1560
aatcccaaga ggaaacaaag cccagcttac atgaaggagg atgtcaaggc tttggatgct    1620
accaaggccc ccaagggctc tctgaaggac atctataagg ttttcaatgg agaaggagaa    1680
cagataaggg ccttcaagtg tgagcactgc cgagtccttt ttctagacca tgtcatgtac    1740
accattcaca tggggttgcca tggctaccgg gacccactgg aatgcaacat ctgtggctac    1800
agaagccagg accgctacga attttcatca cacattgttc gaggggagca cacattccac    1860
taggcctttt cattccaaag gggacccta tgaagaactg cacatgaaga aatactgcac     1920
ttacagtccc accttccctc ggatggcgac atgctgtctt ctggatgctg tcactgtcta    1980
taattcttat tttgtggaca aaatgtcatt tgctctgcct aactacaatg aggaagaaac    2040
aaaagaaaag ggatgggatg ttcaatgata acttggcttg tttatttcgt gagcatttaa    2100
agcagttcat tgcagccatg catccttgtt aaggcctatc ataatttagg agatcattca    2160
gttcatagag gttcatccaa gagattctga tctgccattc atattcagga ttgtgataga    2220
aggcaggaaa gttgagagtt ttctgggtag gatgcttggc aatttaaaat ggtctaagtc    2280
attttactct caaagaagtt tcaaaatgta aaccgatttt attttctgtt cgttagagat    2340
catggaacac aaaaacaatg ttattttcca taactactag gatgagttga attgttgtgg    2400
```

-continued

```
gttctgtgtt taccteccct acggaattta taattgagta tgttttacac tgtatcatat    2460
agcaaaaatt ttaaactaca ggtagtcaag ggccgctacg atacatctga ggtcctttga    2520
tcttattttt ctaaacttgg cgcactgttt ttccatagtt ttgatgactg gcattttata    2580
gacaccctgg cagccttact tttaacacct gtaacaaata gtattttta tgtagttttc     2640 agaataacat atggtctcaa gagtgggtaa gaggcagtca gtaatttcca ggaagaattc    2700
tgcttttcac aatttgagat tttttttaa gctgtaatat gatggcagct tagtatacat     2760
gtttgcttct aaaggtgtgt ttacgatcgt cactttatca gcattcaatc agtgttaaca    2820
agtcagcaga aaagtgtaat taggcgaaca gtaggggggaa ttcccactct aagaacccttt   2880 ttctggtatt tctcttcaag ctgtgaccac tcagtgttct gtccacagtc cattcctctt    2940
tgactcttgg aatagaaggt cttaaaaagc cttgctagca gttgcttctt ttaaaatctt    3000
ggagcaactg ttaattggac ctgaaagtgg taacttgaac cctggaaggt ctttattta    3060 ctagggctat ttattccact atttcttcag taataagagt tactaccttt gctggagaca    3120
aaagggaact tctttgttac ctgaataaca tagtgcaggt caaacaaaca agcaaaaagt    3180
tttctttcag ccttcccgga gttgagaatg tgaccatctt taggagaagg tcccgcactt    3240
taaaaataaa aacaaaaaat ccaactctag agttccttat cagaaatgaa tctcaacccc    3300
ttagtcaaga attttctgtc gtctcttaat ttgcacgtga gaaatacttc catatctcat    3360
gctcaggttt taatctgatc tttgtgagtt ctcaattgtt ttttttttt tttttctttt     3420 tcttttctga acttgacttg catttgtggg taggattgga gcacactgtt atcaaggcat    3480 tcggggggaat caacttggca gacataactt gctgcttgtg tttgaggaaa acaaacctga    3540
ccataactgg attatttgac agtcatttgt aaatgctgag aggtctgctg tgtggtaaca    3600
catcgctgct ccaacagtcc cttgagtgac atgcccaaac catgtcactg cactttgcct    3660
tgggaagtac cacgactgga gaagtaccca cggatgagca gtgtgctccg aactcgcttt    3720
gcaggtttct gtctgatcat ttaaggaact tcttagctct tccatagcca gagcgaggta    3780
gttctgactt gcctctttta ctaatcctta tcttagttct ttctggagaa atatccaact    3840
ggttccttaa catgtaagag aatgcaccaa accagagcta tatcaaatgc caattgttgg    3900
ttttgttttt tttttttttgg cggggggggg ggggggggtt gtatcccttg gtacatttta   3960
aaaacatagc ttcctcgggg atgaaacatc tcatcatgcc ttccctatcc ccacttaccc    4020
tacacactct ggaatcacag tgaaaggat atttatttct gaatgaggta aataagttta     4080
aggctcctga cttctttgtt ttaactgcaa cttgaggaag catctggatg tctgtcagtg    4140
tgtccctttc ggctctttgt gaacacctgc aggcatctgc tatctcttcc ttctctctgc    4200
tagcacctgc tctattaaca atcatgtacc tacctgccct gggatgacac tgaatttagg    4260
tgtactggaa gagttgtgtc cttcccctac gaaggtggta ccgatgtgct ctgcctttct    4320
gatcccattt tattggaaaa cctgatgtac tcaaaggcgt gaactataag ggtagattgg    4380
ctgtacatat gcacttagcc tttctttct ttttcagctg catggcacaa gatacagaaa      4440
aaaaagtaga tagctctgct gtgacaggga caaatgggga caagctgaat tcaagatttg    4500
tgggttacga taaactttgt ggacatagtg ctgtctgagg gaccctcaat gactgtattt    4560
gcctcttttt caccaaagag aataggagac atggtagcac ctaaaaatag gtatgaaggc    4620
cagataccaa ataaatcaaa tttacataac cgttacaaga ccagtttatt taggtgacat    4680
tttacagttg agagagaatt tgaggggcac gaaaatgggt tatcctctgt gttttccagt    4740
ttgtcaggaa tttatcagat ggctctgccc taattttgcc cagattttt tttttttatc      4800
```

-continued

```
accagttcct tctggagaaa catgctgcgt ctctatagta gtgattgatt gcttgttata    4860
aaggcttttt agaacagtga gagccgccag cccaatgagc ggtagaggga agtgtgaaac    4920
actgtcattc aaacattccg ttaataattc tctggataaa atgggggatgt gagggccaac    4980 cattaagatt tagaatgaag ttggctgcct ggctggcata catacaggtc agtgtttgaa    5040
tgcagtacag tttgcatgca catgcatatt gcacattctt ttaatgaaaa ttcacagaaa    5100
agaagcaatt agcattgcca gttgtattac aaaagcttag agttagaagt acagtacagt    5160
tactacgcca gcagttgggt ctaattcagc aggttgtatt aagaaagccc catgttgtca    5220
gtgtgtcttt aaggctaatg gcaatttaaa tcacaaatct ccattgtctg catccagaaa    5280
aacaaacaaa gcaaggcaaa aaacaatgaa acaatgaaaa gatattgagt tgactggaga    5340
atatttgaag aaatatagat tttttttgtg agaggaagaa gttgcaggaa gtaatttagc    5400
aaccttggct tgtgtttgtg cttctctgac ccagttgcac acctcacaag tttggtcttt    5460
ccaaaccttc atcttctctc ctaaatgaca agttagggta gaaagattca tggaagaggc    5520
tggagaggac aaggagagct gtctgcccct agattcagga ctgcgcctta cactgtccaa    5580
gtcacctgcc acatactgtc ttagccttga aattgtagat tggtggtgat cgtcagttgt    5640
acttcatgtt attttaataa ctactgtctg tataattatt ctacagcaaa agctcccca    5700 aatccaaaag gggaaaaaag tgagggatga attgaaactt tgtatatata aaagttattt    5760
tataaatgtt ttagtcttcc agtttctgca aaataattaa aatatacagt aactggtctc    5820
ttaaaccctg aacttaatgt attaaatact tataaaattt tatattggtg ccttttaaaa    5880
atgcattgag agtgttggtt agctctttag ctctaccaca cttttactgt gtatttttta    5940
agaaaaaaaa aaatcacata aaatctaagt actctctaat tcacctttgt gttcttagaa    6000
gaagaagaaa aaaactgcta aaagaatttc cagacttta gctgagctgg caaaagtgac    6060
aaaaaaaaaa aaaaaaaaaa caaactttga aaccagattt taatctttttt agcttgatga    6120 tatttctgga cattattcta tggtagaggc aaaatagaag gtagactcac atatcagcaa    6180
tgaattggat tatgctatat gttttgattt cttcttgagg aagaatatgt tttgcatcac    6240
acaggggttt ctttgtataa tttggagtca gtaattacag tattgctttg ctttgtttta    6300
aatacccgac tgatgttact ctagtcttgg gtcttctgtc tcttctgtct tctaacctgt    6360
ggttgttttg tgaaatggcg tgggaatgca gatcattgtc tcctcttgaa caagacaaag    6420
ctcagcacac tagtcccgtg actggtctcc aaaatgtcat ctcagatgtg tagtctgggg    6480
tcgtctgtca cttctaaggg gtgtcttcaa ctatgacagc ttttttaaaaa cgagctgctg    6540 gctgggtaaa gcagacatca tatgaccaag aagctgtgat acgctagtgt ttccttctgt    6600
catcgtgttg tactcttagg ccaaataatg acaccttgac tgtttttaca tttactacag    6660
aaacctaaac ttttggaatt ttcaaaggtt tttatgtaat gttctatttc acagcggttt    6720 cctttttctct tgctgtactg agtctgtgag tattttttttt ttcagatgca ctcttggaaa    6780
taagttctga attctgttta tggcgtttct ctcgcttgac actccgtgta tagatgttct    6840
gtataagttt gttatgaatc cacctttctc atgtatggac agtgagaagt acatgaacaa    6900
ctagtttcct aagatgactt ttatattatg aattaatatg aaatttacag gtcatgtgca    6960
ccttaagtgc agaatcaaaa cttcctatag gtccacataa gcagttctca gtgaaccggg    7020
ccttcagttt acctcaagtg acatgtagta aggaaagccc gggaacatgg aggtcactct    7080
ctgcagcaca gtgcacttag tagcatgttg ctgaatctca gttacagaaa atggatattt    7140
```

-continued

```
aaaggaacac actggaagga tgcaagggat tgagggactg ctgatatttt cgttgttgct    7200
gttgctttgt gcttttcaaa aagttgttca aattatggaa ctgtgatcta aaaacggttt    7260
gacagtggag caccagagag gatgtccacc actcacttgc ccttcggtac gactaagctc    7320
tgagtttgcg tcttcaactc taccttcctc tcccctcctc atccctactc tgtctgtggc    7380
cctcctctcg gtgtcatttc ctcttggtgg ctctcttgac actcctacta gttaggaggt    7440
caactctgaa cttctgactc attaaatctt aatttttgtc tcagtggttt tagttagctg    7500
tgtagtctgc tggcgtattt ttatacccac gtgtagtttt atattttaa agcgtggttg     7560 agttgacatg gtgcactccg tagtccttat tttgcttcac tctcaagtag gaggcaccta    7620
acgtgactcc agaaattctg taatcagagt atccgtctgg ctcctttgtg cttggatttt    7680
gatttgtttg gctttcttct aaatacaaa tcatacaaga gtagactttc cccccaccat     7740
agaggataaa aatgtaaagc aaagagtctt aactttctcc caaccggggg gcggggcgag    7800
tgctgtccca cttctgcagt gatgttccag gctcagaggg gtctccagac cccaggcttg    7860
cctgtcatcg ggtctcttcg accctgttat ttgcagcttt gggatggttt cttttgctat    7920
ggagtttaac agctcttctt ttttccataa aagtgcaata cccctcttga agtcttaaaa    7980
actatggtaa ttttcttctt ttctttctct gacatttgtc tcattagcca atgatgaaaa    8040
gaaatctttg gaaattctaa catgtcatag gacataggca aatatggaaa ccactctgct    8100
atgaaaagtt gaaaaaaaaa acgtattaac aaacgactcc tctgactttc tagaaacttc    8160
gtttagacta aattttcttt gaaatcatga atgaaagttt atcctgaggc tgaaatataa    8220
tttttctccc actcttgtct aatgctctta agttaaataa ctaatattta atgttttcat    8280
ttctctcatt ttggaaaata aatatcaaag cacttaggtc aggtttaaat caatattacc    8340
tgttggaaaa aaattttttt acatatttaa agcagacctg tttcaatgca gatggagaag    8400 tatctttttgt attattcata tttatatgta gtgtgttctt ttcttttttt aatacctgtg    8460
tttctgtagt aagactgctg taatgtaaat acacgtttta ttaaaaagta acatttcttt    8520
ggcatttctt ttgatggcac atactgtatt tttacagtat atgtcttggc tacttaactt    8580 tttttttcttt aataatacca aaggtaatta gactattttta aggactaatt gcttgacagt    8640
ttctagacta ctttgatttt tttagaagaa aaagaaaaa aggataaaaa aaagtcaaac     8700
cagtgaacct catttttttca aactaataat ttggggaaat aaaaactatt gtttaaaaag    8760
aaatatatat aaatatatat ataaatatct gtaaaattaa aatcccagac cttgtatgtc    8820
aggtttgctc agtgtaatgt agggtttttt tttgttttgt ttttgttttt gtttttaaag    8880
gctcaaatac ctcagaaaat ggggtttact atggaaatac tgcgacagtc tctgcagctg    8940
tgtgagctgt cattctgctg catactgatt gggagacctc cactaaacag tttttatcact    9000 gcagactaaa atgtgggact tgtattttct ttgttttttaa tgcacacacg tgcatgctct    9060
gtgcgtgtat gtgggtaccg tgtatatgtg tgtgagtgtt gtatatgcat gtgtgaatgt    9120
gtgtgtgtgt gcgtgcttgt gtgtgtgtgt gcgtgcttgt gtgtgtgtgt gtgtgtgtgt    9180
gtgtgtgtac aactgaagaa gctgcaaaaa ctttgtaata ctttgtgaaa gggttatatt    9240
ataaaggttt gtactgtctg agtgcacagc tactggaata aacttagcca atctcaggaa    9300
caagcatata atttgtccaa gatttatttc ttctcagaag tgtaagtgca gtttttaatt    9360
ctgtatatta tttaatattt taccaataaa ataaacttct gacagaaatt atttggtaca    9420
aaaaaaaaaa aaaaaaaaaa aaaaaaaaaa aaaaaaa                             9457
```

<210> SEQ ID NO 27
<211> LENGTH: 9788
<212> TYPE: DNA
<213> ORGANISM: Homo sapiens

<400> SEQUENCE: 27

```
aaccccgcgc accggcaggt cgccggctcc tgcccttttc agtctgcgcc gacgcggctg        60
ccggatcccg gggactcccc gcgccgggaa tctcccgcca gctgcgcgct gagtccaggc       120
gacggcagga gcacgtggag aggccgagta gccacagcgg cagctccagc ccggcccggc       180
agcgacatgg aagatataca aacaaatgcg gaactgaaaa gcactcagga gcagtctgtg       240
cccgcagaaa gtgcagcggt tttgaatgac tacagtttaa ccaaatctca tgaaatggaa       300
aatgtggaca gtggagaagg cccagccaat gaagatgaag acataggaga tgattcaatg       360
aaagtgaaag atgaatacag tgaaagagat gagaatgttt taaagtcaga acccatggga       420
aatgcagaag agcctgaaat cccttacagc tattcaagag aatataatga atatgaaaac       480
attaagttgg agagacatgt tgtctcattc gatagtagca ggccaaccag tggaaagatg       540
aactgcgatg tgtgtggatt atcctgcatc agcttcaatg tcttaatggt tcataagcga       600
agccatactg gtaacgccc attccagtgt aatcagtgtg gggcatcttt tactcagaaa       660
ggtaacctcc tccgccacat taaactgcac acaggggaaa aaccttttaa gtgtcacctc       720
tgcaactatg catgccaaag aagagatgcg ctcacggggc atcttaggac acattctgtg       780
gagaaaccct acaaatgtga gttttgtgga aggagttaca agcagagaag ttcccttgag       840
gagcacaagg agcgctgccg tacatttctt cagagcactg acccagggga cactgcaagt       900
gcggaggcaa gacacatcaa agcagagatg ggaagtgaaa gagctctcgt actggacaga       960
ttagcaagca atgtggcaaa acgaaaaagc tcaatgcctc agaaattcat tggtgagaag      1020
cgccactgct ttgatgtcaa ctataattca agttacatgt atgagaaaga gagtgagctc      1080
atacagaccc gcatgatgga ccaagccatc aataacgcca tcagctatct tggcgccgaa      1140
gccctgcgcc ccttggtcca gacaccgcct gctcccacct cggagatggt tccagttatc      1200
agcagcatgt atcccatagc cctcacccgg gctgagatgt caaacggtgc ccctcaagag      1260
ctggaaaaga aaagcatcca ccttccagag aagagcgtgc cttctgagag aggcctctct      1320
cccaacaata gtggccacga ctccacggac actgacagca accatgaaga acgccagaat      1380
cacatctatc agcaaaatca catggtcctg tctcgggccc gcaatgggat gccacttctg      1440
aaggaggttc cccgctctta cgaactcctc aagcccccgc ccatctgccc aagagactcc      1500
gtcaaagtga tcaacaagga aggggaggtg atggatgtgt atcggtgtga ccactgccgc      1560
gtcctcttcc tggactatgt gatgttcacg attcacatgg gctgccacgg cttccgtgac      1620
cctttcgagt gtaacatgtg tggatatcga agccatgatc ggtatgagtt ctcgtctcac      1680
atagccagag gagaacacag agccctgctg aagtgaatat ctggtctcag ggattgctcc      1740
tatgtattca gcatcgtttc taaaaaccaa tgacctcgcc taacagattg ctctcaaaac      1800
atactcagtt ccaaacttct tttcatacca tttttagctg tgttcacagg ggtagccagg      1860
gaaacactgt cttccttcag aaattattcg caggtctagc atattattac ttttgtgaaa      1920
cctttgtttt cccatcaggg acttgaattt tatggaattt aaaagccaaa aaggtatttg      1980
gtcattatct tctacagcag tggaatgagt ggtcccggag atgtgctata tgaaacattc      2040
tttctgagat atatcaacca cacgtggaaa agcctttcag tcatacatgc aaatccacaa      2100
agaggaagag ctgaccagct gaccttgctg ggaagcctca cccttctgcc cttcacaggc      2160
```

-continued

```
tgaagggtta agatctaatc tccctaatct aaatgacagt ctaagagtaa gtaaaagaac    2220
agccataaaa taagtatctg ttacgagtaa ctgaagaccc cattctccaa gcatcagatc    2280
catttcctat cacaacattt ttaaaaaatg tcatctgatg gcacttctgc ttctgtcctt    2340
taccttccca tctccagtga aaagctgagc tgctttgggc taaaccagtt gtctatagaa    2400
gaaaatctat gccagaagaa ctcatggttt taaatataga ccatcatcga aactccagaa    2460
atttatccac tgtggatgat gacatcgctt tcctttggtc aaggttggca gagcaagggt    2520
ataaaggggg aaattgtttg gcagcaccaa cagaaaacaa acaaacaaaa aacagctacc    2580
taaaacttct tgaaagagtt catggagaat tggtgataca gacccaaagc aaatttgcca    2640
atgatatttt ccacaaaaaa agtccaaaaa gtatggctca gcctcccct ccccacagga    2700 gaggaattgg agatagatgg catgtgtgtt tagatcggag ttgagctccg gaatggggtg    2760
aggagggaca cctctattga gaggttctcc ttgatcaggc aggcttcggc ccttttttttc   2820 ccatttaaat ggaactgctg tattccatga aaattcctga aagtctgatc acggttctgc    2880
agatgtataa gtcatccttg tcactcataa tatgtacata ctatcaggag gagtgctgtt    2940
atcatggtaa aattagcact ggaataggag gtcacaaaat gctggctaat tagctatgtg    3000
actttgagaa atcgtttaac tttttttttt tttttttttt tgagacagga tctcactctg    3060
ttgcccaggc tggagtgcag tggtgcaatc atggctcagt gcagcctcga cctccccagg    3120
ctcaggtgat cctcccacct cagcctcttg agtactggga caacaagtgc acaccaccat    3180
gtctggctac attttgttct ttttgtagag atagggtct cactatgttg cccatgctgg    3240
tcttgaactc ctgggctcaa gcaatcagcc cgcctcagcc tcctaaagtg ctgggattac    3300
aggtgtgagc caccacaccc agccttattt aactcttaaa actcagtttc cggccaggct    3360
cggtggctca cacctgtaat cccaacactt tgggaagccg aggcaggcgc atcatttgag    3420
gtcaggagtt cgagaccagc ctgacccaca tggtgaaacc ctgtctctac taaaaataca    3480
aaaattagct gggcagtagt ggcacatgcc tgtaatccca gctactccgg aggctgaggc    3540
agaaaaatcg cttaagcctg ggaggttgag gttgcggtga gtggagatca cactactgca    3600
ctccagtctg ggcgacagag tgagaccctg tctcaaacaa aacaaaacaa aaacaaacaa    3660
acaaaaacaa aaaaaactca gtttcctcat ccataaaata ggaattagat ttcaatgttc    3720
tcttaggtcc cttctagctt taattcatat gtgattatgc agtaaccaca aggtattttt    3780
taaacctcct aatgtatgga tattaagcag aagagtattt atatgaatac atgtttcaca    3840
ttcctttggt atgaaaatgg tgtgttaagt ttttccttta accactgagt tgtgaatgtg    3900
aagaaggtgg tggagaggaa caaaaaacag aaaggtattt tgatcttgcc acaaagcata    3960
cacacaaatt ggcacatgca gctgtttgcc aaagccttct ttttttttt acttttaag    4020 aaattatgtt agggaaaata aattctgctt ccagggacaa cttcatggag cctatttaca    4080
aattaagagt cagcttaatt tgtaacattt ctaccagagc caagaatccc aaattcctgg    4140
tagattagtg ttttatttct aaggggctta tgcattcggc tccaactcaa ctcgtctatg    4200
tgctgccagt aattaaaatg ttccacctca gactgcacaa atggcttatc cttctttgtg    4260
gcatggcgtc tgtctcagga aaaaaggttt tatgaaattc catggcaaca gtcccaacat    4320
gtttgagact tcagctaaag gaatggatgt attttggtgt gtagtcttca gtatatcact    4380
gtatttccgt aatactagac tccaagctat gccagattgc ttattcccctt tgtgaaagag    4440 gagttgctca ttacgttctt gaaatatcgc acatcctgtt ggttcttcaa gggacaagag    4500
aaagagaatt tggaagcagg gattagtaga agagaaaacg agggaaagga agcctttcca    4560
```

-continued

```
ccagattagt gttcaagtct ttgcagagga gaccaacttt ttttgttttc ttttgttttg   4620
agacagtctc tcgctctgtt gcccaggctg gagtgcagtg gcgcgatctc ggctcacggc   4680
aacctccgcc tcccgggttc aagcaattct cctgcctcag cctcccaagt agctgggatt   4740
acaggtgctc accaccaagc ccggctaatt tttgtatttt tagtagagac aaggtttcac   4800
catgttggcc aggccagtct caaactcctg acctcaggtg atctgcccgc cttggcctcc   4860
cacagtgctg ggattacagg catgagctac cgcacccagc ctgagaccac cttttgcatc   4920
tcaagattgt gaaaccaagg cccattccac cagcctgggg actcttttta tagatatgat   4980
cctccttttt cctgtgacta atgaatttgc tgcatgattt ctattcttct gaggttagtt   5040
ttctgagtaa ggtgaccact cacaaaggca ctttctttgt ggcattctga gcctagattg   5100
gggcccatca attccagaaa aaatttatgt gtggaaactc tgcatcctta agtcttgaag   5160
ttgaaccaga tatgcagtgg ttaccatcac acagataaac gctgccttct gtacataccc   5220
cttatgctgt actaattaac aaaccccttg ccagggctgg ggaggtgagg gtgaaggaga   5280
atcttagcag aagggcagag tcaggacttg catctgccac tgctgggcac tgaagccctg   5340
gagcagcttc agatagtacc tgtactttct catgcagact ccctctgaac aagagccttg   5400
taggcccctc tccttcattt cccaccagcc tcttatcagg cgggctttcc accatacacc   5460
caggaggcca cggtctgagg aacaaccaaa cccatgcaaa gggccgggcg cgatagctca   5520
cgcctgtaat gccagcactt tgggaggctg gggcaggcag atcacctgag gttgggagtt   5580
cgagacctgc ctgaccaaca tggagaaacc cccatctcta ctaaaaatac aaaattagcc   5640
gggcgtgatg gcacatgcct gtaatcccag ctactcagga ggctgaggca ggagaatcgc   5700
ttgaacccgg gaggcggagg ttgcggtgag ccgagatggc accactgcac tccagcctcg   5760
gcaacaagag cgaaactctg tctaaaacaa aaacaaacaa acaaacaaaa aaacccaggc   5820
aaagtttcct tgcagccaag gtgacagaac tgggctgagg gtggaaaaga aacagaacca   5880
gtgctccagg tgtttttttaa ttttttaatt tattttttatt tttttttgtat atgtatatat   5940 atgtatgtat attttagagg accagggtct cactatgttg cctaggccag actcaaactc   6000
ctgtgctcaa gcaatcctgc ctcagcctcc caagtagctg ggattacagg catgcacaaa   6060
caatgcccag ctctccaaat gttttctgtc actacctgaa gtgttgcatc ggtacttcct   6120
acggaaagaa aactaaatag aagtgtctct cccgtgagcc cccaccacta ccaccagaaa   6180
aaaaaaagag agaaaatgaa ctcatcagtc tttagtttcc tcaagttatt ctcccaaaaa   6240
gacattcgcc ttggcacaga taagccagct aatcttatgc tttatgaccc actgtgagct   6300
gttcctgaca cagcttctga ctttgtcagt gacaaaattt ctcacctttt aaatgcagtg   6360
cttaacattt tgttaggccc atactcaaaa tcggccagat ataaaatgac ctcagatttt   6420
gatctcctag gctcaaacaa tcctcctacc tcagcctccc aagtagctgg gactataggc   6480
acaccaccat gcacagctaa ttttttttgt attttctgc agagatggcg tttcgccata   6540
ctgcccaggc tagtctcaaa atcctgggct caagcaatct gcccacctca gcctcccaaa   6600
gtgctggaac tacaggcaag agccactgcg cccagccaca acctcagatt tctttggcaa   6660
acagaaatgt ttaaaaacac aaaattttgc tcaggtgaaa cactgtgtta ctatcaaatc   6720
tcacatccac ataaagtttt tcttttcggc tttgtttcgt gaggaacaga cagaacaaag   6780
tttttccagg tagcatctgt atcactatta ttctcctatt tcctgtacca cccccacctc   6840
cccaagccct actgaatgtg aggtttagaa tgttttaagg agggtcaggt gcggtggctc   6900
```

-continued

```
acgcctgtaa tcccagcact ttgggaggcc aaggcgggcg gatcacctga gtttgggagt    6960
tcgagaccag cctgaccaac atggagaaac cctgtctcta ctaaaaatac aaaattagcc    7020
aggcgtggtg gcacatgcct gtaatcccag ctacttagga ggctgaggca ggagaatcgc    7080
ttgaacccag gaggaggagg ttgtggtgag ccgagatcgt gccattgcac tccagcctgg    7140
gtgacagagt gagactccat ctcgaaaaaa aaaatacaaa aattagctgg gtgtggtggt    7200
gcacacctgt aatcccagct actcgggagg ctgacgcagg agaattgctt gaacctggga    7260
ggtggaggtt gcagtgagcc gagatcgcgc cattgcaatc cagcctggac aacagagtga    7320
gactccatct caaaaaaaaa aaaaaaaaga atgttttaag gaaaaaaata gtactgttac    7380
atataatccc aggtgataag accacaatgg aaatgtttaa gtcctcactt taaagagtac    7440
cccactgaga gaggtatgt tggactctag cagagatttg gaaactctgg gacactcaag    7500
atgtgaaaga gcctggctat ctgaggactc aaagagtcag catcgggact tgtgagctca    7560
agaagagaaa agggagtggt gaaactttgt cctaaaagtt agcaccagga acagaagaaa    7620
aaaacccgat atatagtgat acctcatctt ttagagaatg ggaagctatt tttgtgttca    7680
cacagaaagt atagttcaaa aaacctctat atccagagtt cagacaagga gaatgatttg    7740
agatataagt gccgatgaag gaggtcaatt ttgatctgaa accagcagct ggacctgggc    7800
cacctcagga aaaggactct gttctccaag gcagcacgac tgaatggttc tgagaataag    7860
ccagggttca ggactcctga ccctttagga ccatggactc agaagagcct gaaggacaat    7920
tgtgggcttt aaacttctga gagcttgtaa agtaacacaa gactgtgcct ctcccttgcc    7980
ccagctgtag atagtctttg ccccaccatt gttatgaaga tacacagggt tttgcagttt    8040
gaataaattg gatacaagtt tcctcttttt ttttttcttt ttgagacaaa gtctcgctct    8100
gtttccccag gctgagtgca gtggcacaat caaggcttac ttgccgcctc aacctcctgg    8160
gctcaagcaa cgagccatcc tcccgtctta gcctcccaac tagctgagac tacaggcgtg    8220
ggtcaccaca cccagctaat ttttgtactt tttgtagaga cagggtctca ccatgttgcc    8280
caggctggtc ctgaactcct gggctcaagt aatctgccca cctcagcctc ccaaagtgtt    8340
ggggttacag gcgtgaggca ccgcggctgg cctgagtttc ttcttaatac tgtatcacaa    8400
ttgtgggctg tcttatgtgt tgatatcgat tgagctattt gaaataggaa tgttaatggg    8460
tgtattaaat ttttgtaagg atataacaat atctaccttc caaggatgtt gtgaggtttt    8520
ccatgatttt gtatatgagc taatgttacc tttgaggggt ggtgtgcatt atgttggatg    8580
attgtaaatt ttcagtggaa aatgtaccgt gtcctaaatt taaagacatg aaaaatatcc    8640
caagatcata ctagatcata atagcaattc ctttacaaat gaattatgga ggtaactgat    8700
ctctaacagt ttccttcatg ttgtttttaat gcacaagggc agaggatctg ctgacccttg    8760
gaaccagcgt gagctaacca cgtgctatag acacttcatg gtgtcgcacc cagggaagtc    8820
aaagcgcttt gctccctcac tgtctgtgag tcctcagcca ttagtacccc acccccgct    8880 gctccaaaac ttgagttatt tcaaatgttt ctcactgttc atctctccac tgaccccact    8940
ccagaaagcc tggagagagt cccaagatgc cacccacctt ccccaatccc tcgccacaga    9000
tctgtgtcta tctcacactc tgtaagtgcc gctttgcttc ttcctctctt gaaaagactg    9060
agaacacaca ttttaacatg ttaggaaaat ggggcagcct aaaaaatgac tgatcccacc    9120
gccagtgact catgtatact ccaggctagc agacaaggcc cttttttggtg ggcctgcttc    9180 tgtgggttca cagaaaccaa attactgtgg gttgcaaaga attagcaggt catttacaaa    9240
gcagacatcc cttcacccag actgtggttt tgcatgctca ggttctcagt ctatgagctt    9300
```

-continued

```
tggtgcagga tcattttggc tactggaaaa accatagctt attttaaatt tctggttgcc    9360
aaagccacca cacgtgtggt ctgtggatga ccattgtctg cagaatgacg aggaaggaac    9420
agaatgtggt ttggggctca gggtggcctt cccactggga gggaaggcgg gagggagccc    9480
ttgccctggg ttttgacaca gcctgtgctc acagcctctc ctctcatctg catttctcag    9540
aaatgccctc cctgcccagt ggtgactttc cctcgtcact cctatggagt tctacctgga    9600
gcccagccat gtgtgtgaact gtgaagttta ctcctctgta aagatggttt aaagaaagtc    9660
agcttctgaa atgtaacaat gctaacccttt gctggaaccc tgtaagaaat agccctgctg    9720 atagtttttct aggtttatca tgtttgattt ttacactgaa aaataaaaaa atcctggtat    9780
gtttgaaa                                                            9788
```

<210> SEQ ID NO 28
<211> LENGTH: 4098
<212> TYPE: DNA
<213> ORGANISM: Mus musculus

<400> SEQUENCE: 28

```
ttccacgcga tcagggttcc tcaggcttga cattcaaaag tgggtgcgga acccgcggca      60
ctcggagcgt gctttaaagc ggccgccagc cagcgccgct ctaacctcgc gccccggctg     120
ccggcggctc ccgccctgca tctgcgccga cgcgaccgag cgatcccggg gcctccctgc     180
gcccggaatc tcccgccagc cgcgcgggtc cccacggcag cagcacgtgg agcggccgcg     240
gagcctgagc gacagctgca gcccgcgcgg cccgcggcga catggaagat atacaaccga     300
ctgtggagct gaaaagcacg gaggagcagc ctctgcccac agagagccca gacgctctga     360
atgactacag cttgcccaaa cctcatgaga tagaaaacgt ggacagtaga gaagccccag     420
ccaatgaaga cgaagatgca ggagaagatt cgatgaaagt gaaagatgaa tacagcgaca     480
gagatgagaa cattatgaag ccggagccca tgggagatgc agaagagagt gaaatgcctt     540
acagctatgc aagagaatac agcgactatg aaagcattaa gctggagaga cacgtgccct     600
atgacaacag cagaccaacc ggtgggaaga tgaactgcga cgtgtgcggg ttatcctgca     660
ttagcttcaa cgtcttgatg gttcataagc gaagccatac cggcgaacgc ccgttccagt     720
gtaatcagtg cgggggcatct tttactcaga aaggtaacct cctccgtcat attaaactgc     780 acacgggggga aaaacctttt aagtgtcacc tctgcaacta cgcatgccaa aggagagatg     840
cgctcacggg acaccttagg acacattctg tggagaagcc gtacaagtgt gagttctgcg     900
gaagaagcta caagcagaga agctccctgg aggagcacaa ggaacgctgc cgagcttttc     960
ttcagaaccc tgacctgggg gacgctgcaa gtgtggaggc aagacacatc aaagccgaga    1020
tgggaagtga gagagctctc gtcctggaca gattagcaag caatgtggct aagcgaaaaa    1080
gctcgatgcc tcagaaattc atcggtgaga agcggcactg cttcgatgcc aactacaatc    1140
ccggctacat gtacgagaag gagaacgaga tgatgcagac ccggatgatg gaccaagcca    1200
tcaataacgc catcagctat ctaggggctg aagcccttcg ccccttagtc cagactccgc    1260
ctgctcccac ctctgagatg gtcccagtca tcagcagtgt gtaccccata gcacttactc    1320
gggccgatat gcccaatggg gccccgcagg agatggaaaa gaaacggatc ctcctgccag    1380
agaagatctt gccttctgaa cgaggtctgt cccccaataa cagtgcccag gactccacag    1440
acaccgacag caaccacgag gatcgccaac atctctacca gcaaagccac gtggtcctcc    1500
cccaggcccg caatgggatg cctcttctga aggaggtccc tcgctctttt gaactcctca    1560
```

-continued

```
agccccctcc catctgcctg agggactcca tcaaagtgat caacaaagaa ggggaggtga    1620
tggatgtgtt tcgatgtgac cactgccacg tcctcttcct agattatgtg atgttcacca    1680
tccacatggg gtgccatggt ttccgtgatc cctttgagtg taacatgtgt ggctatcgaa    1740
gccacgatcg ctatgagttc tcctctcaca tcgccagagg agagcacaga gccatgttga    1800
agtgagcatc tgtcctcaat gcgagggtca acattgtttt ttaaagctga tggtagcctt    1860
atccagtaga ctgaactcaa acccacagtc ccacccagtt ctgttagctc tcaatcatgt    1920
ccacatgaac agtcagggaa ataactgtct tcattcagaa actgtttgca gagctatcat    1980
gttactctgt gaaacctccc ttcccatcag ttgagtttga tgggatttaa aagccaaaga    2040
agtatctggt tcattatctt ttgtagcaat agacagccat ctactggagc tcccggccaa    2100
ttggaacagt cctccgtggg ccgcaggagt cattcactgg aatacagcag ccatatgtgg    2160
aaaagccctt tgatcctatg cccagatcca cacagcggaa gagccgccca gctgcccttg    2220
ctcttgggca ccaacacaag gcagaagcct tagcgtgtag tccccctccc ttcacgttct    2280
aacagcaagg aagaggtggc cgtacagtaa ggacctgctg atagtaatgg aagaccctat    2340
tcttggagca tcaacccact tcctatcaaa caaaactgaa gccacctgag caaggaccct    2400
tctcctttac ctacggtcac aagggtgaac ctcagatgat ttggcctgag ccagaccctg    2460
atcctcctgc ctccgtctgg aggaaaattc tactccagaa gaactgatgc gtttaaatat    2520
tgggtatcat tgaaaccgca gagtcatgca ccgagggggtg gtatttgtct cctttgattg    2580
ggattggtag agcaagtggt ggggacatag tttaagggta cagtgcctgc caggtacaac    2640
caccacacca gggggcaaag agggaagaaa gaaaatggag ggaagagagg ttggctgagt    2700
agagcgtgta aggttgactg gttggcaacc cttgtcacct tggtggagta ctggctgaaa    2760
ccccaaagaa catttgaaaa gtgattttttg gcaaaggagc caaaatgtgc tgcttagttc    2820
cccaccacct cccacccac aggcgtgaga tcagggacag aaccacagat gttctctcag    2880
gacggtgtga catcacactc tcctgggtta gaaatgcatg gttttttatta tattactcta    2940 ttttcaaaac agggtctcct ggtgccccgg caagcctcaa actcattgct ggctgaagct    3000
gcccagcact ctgagcctcc tgcctcagcc tacagagtgc tgggttgaga gggttatcag    3060
caccgtggtg ttgggcttct gctgtcctaa agaggagctg ccacatccca ctgagagtct    3120
gggaaggctg atcttgttct gtagatagac caggtagtca cctttgtcac acaggcacca    3180
agacatcaag attcttggaa aaatgctcca taaacaagca ctggaatcga ggccaccaac    3240
cgtgcttgcc aagctcatat ttgcaactaa ttggttaact ctaaaagaca aatgccctca    3300
accataaaat aagagtagca tccaaaccct cttgatggtc acttctggct ttgatacatg    3360
attattcaat agccacaggt tttttgcttt tgttttttgtt tttttaactt cttgatgtgt    3420
gggcattaag cagacaagtc tgcgtgtgag aatgtgtttc atatgtcttt gatgtgaaaa    3480
tatagttgtg ttaagttttt ccttcagcta ctgagtcatg accatgaagg aggcgatgag    3540
gggggactaa ggacaggaag ggttttgatc atgcagtcgt gtatacacga gctggcatct    3600
gcagcagccg tgtacacacg agctggcatc tacagcttct tgccggagcc ctttttcttcc    3660 tttcctttta aaagaacttg tgttaggaa aaataagttc tgcttacagg gacggcttca    3720
tggagcctat ttacaaatta agagcttagc ttttatgaac atttctgcca gagccaggaa    3780
tcccaaattc ccggtatgtt agcatttttcc ttctaagggg cttatggatt cggctcttac    3840
tcattcatgt atacgatgcc agtaattaaa acattcctcc tcaaacacac aaatagctta    3900
gcctgccttg tagcatggtg tctgtctcag ggtaaggggg gtgggttatg agattccgtg    3960
```

```
gcaacaattc tgtggcaaca atcccgtgtc agcttaaggg ctaggtgtct tcagcacatc    4020
tctgcatctc agcagaatcg gatgtgagct gcaccacatt gttcatgccc actgtgaaag    4080
aggacctgcc tagtctag                                                   4098

<210> SEQ ID NO 29
<211> LENGTH: 4553
<212> TYPE: DNA
<213> ORGANISM: Homo sapiens

<400> SEQUENCE: 29
agcaggctgc cggctcggac ggcggcgacg cggcaggaca gggcggataa gaaggagcgg     60
ccggagactg gagctgggtt cgtggcgggc cggctgatcc ggacggagac tcaacctctg    120
tatggctttt caattttagt tgaaattctc tctccatggc cttttggagt cccttgctgt    180
atctccgaag taaatttcaa ttactctaca tttcatcaat gttggagtgg caagaaaaag    240
gaggaacaga tttgggggtga aaagttttgt tttctaggtc taacaaactg taaatgttaa    300
aaaagcaaag atgggtgaaa aaaaaccaga gcctttggac ttcgtgaaag attttcagga    360
atacctgact cagcagaccc atcacgtgaa catgatttct ggatcagtta gtggggacaa    420
agaagcagag gctcttcagg gagctggaac agatggtgat caaaatggac ttgatcaccc    480
atctgttgaa gtttccttgg atgaaaactc aggaatgtta gtagacgggt ttgaaaggac    540
ctttgatggg aagcttaagt gtcggtactg caactatgcc agcaaaggaa cagcccggct    600
tattgaacac atcagaatcc acacaggtga aaaacctcat cgatgtcatc tttgtccatt    660
tgcatctgct tatgagcgtc atctggaagc ccatatgcgt tctcatactg gagaaaaacc    720
atacaaatgt gaattatgtt ccttccgctg cagtgatcga agtaacttgt cccatcatcg    780
aaggcgcaag cataaaatgg taccaattaa aggtactagg tcttccttaa gcagcaagaa    840
aatgtggggg gttttacaga agaaaacaag caatctgggc tatagcagaa gagcactaat    900
caacttaagt ccaccttcca tggtggttca gaaaccagac taccttaacg attttaccca    960
cgaaatccca aatatccaga ctgactccta tgaaagtatg gcaaaaacca caccaactgg    1020
tggccttcca agggacccccc aagaactcat ggttgataac cctttgaatc agctctcgac    1080
tctagcaggg cagttgtcca gtctgccacc cgaaaaccaa aaccctgcat ccctgatgt    1140 agttccctgc cctgatgaaa agcctttcat gattcagcag ccctctaccc aagcagtagt    1200
ttctgccgta tcagcaagta ttcctcagag ctcctctccc acaagcccag aacctcggcc    1260
atcccatagt caaaggaact atagtccagt ggcaggtcca agcagtgagc caagtgccca    1320
cacgagcact cccagcatag gaaacagcca gccaagcacc ccagccccag ccctgccggt    1380
ccaggaccct cagcttctgc accactgcca gcactgtgat atgtactttg cagacaacat    1440
cctttacact attcatatgg gatgtcatgg gtatgaaaat cctttttcagt gtaatatatg    1500 tggatgcaaa tgtaaaaaca agtatgattt tgcctgtcat tttgcaagag ggcaacataa    1560
ccaacattga ttgaaaatag tcatatttta cttagttttg ctgttttgt ggtttggttt    1620 ttttttgtttt ttgtttttggt catccctaat aaagtgtctg ctaattcaag gcttatacat    1680
tatatttata gaatataaat ttgtcagtgg aataaaattt cccctttttt tcataaaaat    1740
ctggtcaggg tcatttatat attagaacag ttagacacat tggtgtctct ttttttccttt    1800 cctttcgaca ttggagaatt gggagtgcagt cataatctta caagatgttc atttgaattt    1860
ctcacattta tggtccataa aaacttcaag gcttatccat actttttgatg tttcaatatg    1920
```

```
cattgaactg gatgttattt ctgccatatt tcaaaatggt agaataaatt acagaattta    1980
ttactactca tttcagtgtt tagtacagaa attgccttaa aaattgctat taattgaaat    2040
atcatttagt tcacattcct taagttgaat cggtagtttc atttcaactg ataatagtaa    2100
agctatttca gtttagtaaa aattttcttt tttccacaag aggaaatgta aaacagttaa    2160
gacttgaaat tgaaaattct tttaatattt aaaataactt gtttattcaa tgtctaaaca    2220
catgtcagtt ttccactgga tttttatttt cacaggtaaa tacactagag tgctagatgc    2280 cttttttcccc tgtcagtttg actttcattt aaatccttca ttctgatatc attactgtta    2340
ggtgaggtgg ataactataa tgagaatctc ttattcttcc tattcctttg atgaccaaag    2400
agataaagtg aagtcatcct tattattaaa atgcagcctc caaacaaatt tctcaagatt    2460
ccttttcctt ccttctatcc attttctgcc cataatttcc aagaaaaggt gggtatggaa    2520
acacatgaga gaatgtgata gtgaagtcat atttacaaaa ctgagaacat gtccaaaatg    2580
gattcttgtc tcctcttcag aattagccat ttaaaatatt ttctgtgact tcaaattgta    2640
attcttattt gcagttttac cagtcttcat gtacagtgac gaaactgtgt agaaactaaa    2700
tcatcgcttt agtaagaaag gataaaaagg tgtggaagtg aatataaaat gcatctaaac    2760
atgacattta atttgtttat aaaaataaga cttactaaat atagagtaat tcattttgaa    2820
taggaggcta ttgttttttat attgtgtaat aactcacgta ctctgaagag agcttggtca    2880
aacaataaaa tacattgtta ctaacttggt ttcttttctg tgtactttgc aaaaattcta    2940
tttttaattt tgttcatatg ttgaatgtgc ccctaattgg catcttaaag agaatagtaa    3000
gcatctatta accaaaaaag aactctaata gtaaaggaaa gggaaatatt ggtggtatgt    3060
acccacaaaa cccccaagtg ccaagttaat ggaatctctg ctttcccttt cagatgctag    3120
aaagccactg taatgagttc ttgcagttta gcatccagtc taagctactg cattgtttaa    3180
agagcagcat caaggacact ttctccaaac tggaactctc ttctttgtca aatcttgtac    3240
tttaaaattc tacaattctg ttacattgtt gtttaaatca cagactgctc agatccattt    3300
tactgcagta gtttccaagt gtgtaacttg gctttagtat ttatcagttg ccagaaagaa    3360
acaggttgtc atttggaagt ttttgtggtt attttttccc atttttattc ttcagataaa    3420
agcagtaccc caaaatagaa aatgaaaatt ttcatgaaac aaagagaact cccttgttaa    3480
aaccagctta ttaactctgt attctgtcaa atgcattttt ttctaacaac tgaccatgga    3540
tgttgtgaag gtgcatttta atttaaacat ggaaaagatt tttttcataa ttacatacta    3600
gaatgtaaaa ttataatttt gccatgactt aaagagcaca gttgatatcc caaaggtttt    3660
gatgctaaga agctacagtt attctaaatg cactaaaatg tttgaggcaa atctacctta    3720
gaggcttttt tggtatggta tttttttaaaa tatttagatt ttatttaaat ttcctgtgag    3780
ttattctgta tttgaaaaga tgttcgtgtc ttcccctctg tattgaatgt ttcactcatt    3840 ttattttttaa tcaaatattt tatagaaatg agttgttggg aagagtttaa catgcactat    3900
ttatagtact ttgccgttaa caggcaatgt tctgaaacta aatttatttt tgttcagtga    3960
acataagttt agattttttaa agttggtaga taatttatct ccactaatat ttttttaaga    4020
aactgtgaag agattaactg ggaataattt tatttcagat tttactaatg tagtatgtag    4080
ctacaacttc ttgaacttca agttaaggct agacatttac tttgaaaaaa ttccactggg    4140
tgtttccagg gctatttcat tttagaaata agtgtttgcc attcttctgc aaaaactgga    4200 caagggaat actacaaaaa atactcagag ataaaatcct catttcaagt tctacaaaat    4260
atttatcaaa tgaatgttaa ttttttttta attccctgct aaagacgttt tcattagtct    4320
```

-continued

```
tagagggtat atgctttcta gaacttgttt ttgttaacat gtgctttgat gtaaagaaca    4380
tattttgtat gcaaaacata acttgcatta tggttgtaca atacactata ttgtttaggg    4440
attccggaaa gcagtttaat gcagaaataa ctatatctag tatgcagttc atattgtgaa    4500
tgaagctttg cttttgtaat aaataaataa gactttctaa tgacaaaaaa aaa           4553
```

```
<210> SEQ ID NO 30
<211> LENGTH: 4440
<212> TYPE: DNA
<213> ORGANISM: Mus musculus

<400> SEQUENCE: 30
```

```
cagctgcgac gctgacgaac gctgaggcgg tggcggtggc ggcgacggca gtgaaaaggg      60
ctgtggggat tcctcggtgc ggttgtcagg agatataaca gactttcaac ttaaagaaag     120
aaagaaaaaa aaaagcacca agatgggtga aaagaaacca gagcctttgg actttgtaaa     180
agatttccag gaatacctga cccagcgaga gcatcatgtg aacatgattt cgggatcagt     240
tagtggggac aaagaagcag agactcttca gggagctgga acagatggcg atcagaatgg     300
ccttgatcac ccgtctgttg aagtttccct ggatgaaaac tcaggaatgt tagtagacgg     360
gtttgagagg accttcgatg ggaagctcaa gtgtcggtac tgcaactatg ccagcaaagg     420
aacggccagg ctcattgagc acatcaggat ccacacaggc gagaagcctc acaggtgtca     480
cttatgtcca tttgcatctg cttacgagcg ccacctggaa gcccatatgc gctctcacac     540
tggggaaaaa ccatacaaat gtgaattgtg ctccttccgc tgcagtgacc gaagtaacct     600
gtcccaccat cgaaggcgca aacataaaat ggtaccaatt aaaggtacca ggtcttcctt     660
aagcagcaag aaaatgtggg gggtttaca aaagaaaaca agcaatctgg ggtatagcag      720
aagagcacta atcaacttaa gtccaccttc catggtggtc cagaaaccag actaccttaa     780
tgattttaca cacgaaatcc caaatattca gactgactcc tatgaagcta tggctaaaac     840
tacaccaact ggtggcctgc caagggaccc ccaagaactc atggttgaca ccctttgaa      900 tcagctctct actttagcag gacagttgtc cagcttgcca ccagaaaacc aaaaccctgc     960
ctctcctgat gtagatgcct gccctgatga aaagcctttc atgattcagc aaccctctgc    1020
ccaagcagtt gtctctgctg tgtcagcaag tattcctcag agctcctccc ccacaagtcc    1080
ggaaccgcgg ccatcgcata gtcagaggaa ctacagtcca gtggcagggc ccagcagtga    1140
accaagtgcc cacaccagta ctcccagcat aggaaacagc cagccaagca ctccagctcc    1200
aaccctgccg gtgcaggatc ctcagcttct acaccactgc cagcactgtg acgtgtactt    1260
tgcagacaac gtcctttaca ctgtccacat ggggtgccat gggtatgaca gcccctttca    1320
gtgtaacgta tgtgggtgca aatgtaaaga caagtacgat tttgcctgtc attttgcaag    1380
agggcaacac aaccagcact gaacacaatc aacattgttc tcacttggtt tggccttttg    1440
ggagtttgta gtttggtttt tagtttgatc atccctaata aggtatatgc taatttaaaa    1500
tttatacatt ctagtctata aaatagaagt ttgatagtga aaaagggttt tgttaacttt    1560
tcataaaagt ctggtcaggg ttatttatgc attagatagt tagatgcatt gctgtctttt    1620
tcatttacac ctatgagagt taaagtacag ttgtaatcag tttcctacac ttgtccataa    1680
ggattcccag ggttatctgt actcctgatg cttcaggata tacattacag ctaatgttct    1740
ttctgccata tgtcaaaatg gcacacttct cataaaatct tttataacat ttcagtgttt    1800
atagacaaac tgcctttaag tttgctccta attaaaatac tattttcatt cacataactt    1860
```

-continued

```
aagttgaatt agtttcatta caaccaaaac cagtagttat ttcagtgtaa taaatatttc    1920
tcttcaagga gaagcataaa acagttcttt caaatttaaa ttataaaatg aaaatcttgg    1980
aagttgaaat ttggggctaa attgaaaatt gtgtttggta tttgagatat ctgttcattt    2040
aatgtgtaaa catgttagtt tttagctttt catttatata tgtatttata tattttgagt    2100
attattttaa agccacaggt aaatatacta gagtgctaga tgcctttttt caatctgatc    2160
tttcatgtaa attctgcatt cacctgttac tggtgtcagg taagattgac agccacactg    2220
attattttat tcttcccagt ctttgatgac caaagaggaa gtgagcgcat catcccactg    2280
agatgcttcc agagcctccg aggctccttt cctgccctct gtgcataatt gcccgtaatg    2340
tccacgaagg gttggtctag aaacccagag acgtaataag tgaggaaaca gctacaaacc    2400
cagagcatgc ccagacagag cctccttgcc tctccagagc agagcaggcc atggaaagtc    2460
ctccctgtga gtctttatgg acagagacgg tgggatcgtc accacagtgg gaaaggataa    2520
atagagttat tatgaagcac atttaaatgt gtcatttaac ttacttagaa ttagagtggt    2580
tcattttata taggaagcca ttattttgt attgtgtaat aagtagctta ctctgaagag    2640
agcctggcaa aacaataaaa cattgtcact tactattggt ttctgtgtac cttgcaaatt    2700
tttcattttt atttggttaa tagcttgaaa atattctcaa ttggcttctt aaagaaatac    2760
cctgtcaagc atttattaac caaaaaatag cctcttacag taaataagag ggaactatga    2820
gagtgtctac ccgtgaagcc ccaagtgccc tggtaatgga cctgctctcc ctccctgtgc    2880
tggaaagcca ttccgagggt gcctgtgcgt acacagccag tcttggctcc tcccaactgc    2940
actgttaaag cgcagccccg aagacacttt ctagtgattt tggtctgttg cttaaatcat    3000
ttactagatt agttttaggg caacactttc caaatacata acttgactgt tgtgcttatc    3060
agctgccaga aagaaacagg ttattgttgg gaaaccttgc tgtttttaaa gtttgattca    3120
attaaaagca atacttccaa atagacagtg aaaacttccc aaaagaggaa gaagcccagt    3180
gtactgccgc acatctgtag tcccagctgc ttgaagcaga ggcgggaaga gtgctagagc    3240
ccaggaggtc cctgccaggc cgggcaacac tgcaagacac agtctcaaag gccaagcagc    3300
cgaaagggct ctcctcacag ccagctttat cacctctacg ttctgggcca aacagtgaca    3360
tgggcatttt ggttttccta acaactaacg atgaatgttc tgaaggtaca tttcatttta    3420
aatacgaaaa aaacttttca taattacaga caagaaggaa aaacccccga ttttccaata    3480
atataaagag cacagttggt cttccaaagg tgtccatgtg tgaagctaca agtacttcga    3540
aatgcactaa aattttgaag caaatctacc ttaggaactt ttttgaaatt gtactttaa    3600 aggtttaggc ttttgcttaa atattctgag ttaaattctg tactaggaaa gatgttggat    3660
tctttcctta aatactaaat aagttcctca tcttattttt aatcaaatgt tttatagaaa    3720
tgagttgaga aaagttgacc atgcactatt tatagtactt tgccataaca ggcaatgttc    3780
taaaactaaa tttattttg tttagtgaac atgagtttag attttaaag ttggtaattt    3840 atctccacta atattttttt aaagaaactg tgaagagatt aacagaataa ttttatttca    3900
gattttacta atgtagtgtg tagctacaac ttgacattca agtgaagact agacttctgt    3960
tttgaaattt ttccatcagg tagtttcagt ggtttcattt tagaaatgtg tttgcagatg    4020
tttgacaaag ggaatattac taaaaaagaa aagcaaaaaa aaaaaaaact tatcaaatga    4080
agaattgtta gaaaaattta aattcccgtc taaagacatt tttgttagtc ttaggggta    4140 ggtatttgct ttctagaact tgttttttgtt gatagtattt gctttctaga acttgttttt    4200
gttgatagct ggatgtatgg aacctgtttt ctatgcgagg tgcaagtctt gcactacagt    4260
```

-continued

```
tgtaagatat attatattgt ttagggatca agaaagcaat ctatgctgaa gtaactatag    4320
tatgtagttc ctattgtgaa taatgctttg cttttgtaat gtattaataa aaagtaacac    4380
tttctaatga aaaaaaaaaa aaaaaaaaaa aaaaaaaaaa aaaaaaaaaa aaaaaaaaaa    4440

<210> SEQ ID NO 31
<211> LENGTH: 2008
<212> TYPE: DNA
<213> ORGANISM: Homo sapiens

<400> SEQUENCE: 31
gagacgaaac ttcccgtccc ggcggctctg gcacccaggg tccggcctgc gccttcccgc      60
caggcctgga cactggttca acacctgtga cttcatgtgt gcgcgccggc cacacctgca     120
gtcacacctg tagccccctc tgccaagaga tccataccga ggcagcgtcg gtggctacaa     180
gccctcagtc cacacctgtg gacacctgtg acacctggcc acacgacctg tggccgcggc     240
ctggcgtctg ctgcgacagg agcccttacc tcccctgtta taacacctga ccgccaccta     300
actgcccctg cagaaggagc aatggccttg gctcctgaga ggtaagagcc cggcccaccc     360
tctccagatg ccagtccccg agcgccctgc agccggccct gactctccgc ggccgggcac     420
ccgcagggca gccccacgcg tgctgttcgg agagtggctc cttggagaga tcagcagcgg     480
ctgctatgag gggctgcagt ggctggacga ggcccgcacc tgtttccgcg tgccctggaa     540
gcacttcgcg cgcaaggacc tgagcgaggc cgacgcgcgc atcttcaagg cctgggctgt     600
ggcccgcggc aggtggccgc ctagcagcag gggaggtggc ccgccccccg aggctgagac     660
tgcggagcgc gccggctgga aaaccaactt ccgctgcgca ctgcgcagca cgcgtcgctt     720
cgtgatgctg cgggataact cggggggaccc ggccgacccg cacaaggtgt acgcgctcag     780
ccgggagctg tgctggcgag aaggcccagg cacggaccag actgaggcag aggccccgc     840 agctgtccca ccaccacagg gtgggccccc agggccattc ctggcacaca cacatgctgg     900
actccaagcc ccaggccccc tccctgcccc agctggtgac aaggggggacc tcctgctcca     960 ggcagtgcaa cagagctgcc tggcagacca tctgctgaca gcgtcatggg gggcagatcc    1020
agtcccaacc aaggctcctg gagagggaca agaagggctt cccctgactg gggcctgtgc    1080
tggaggccca gggctccctg ctggggagct gtacgggtgg gcagtagaga cgaccccag    1140 cccccgggccc cagcccgcgg cactaacgac aggcgaggcc gcggccccag agtccccgca    1200
ccaggcagag ccgtacctgt caccctcccc aagcgcctgc accgcggtgc aagagcccag    1260
cccaggggcg ctggacgtga ccatcatgta caagggccgc acggtgctgc agaaggtggt    1320
gggacacccg agctgcacgt tcctatacgg cccccccagac ccagctgtcc gggccacaga    1380
cccccagcag gtagcattcc ccagccctgc cgagctcccg gaccagaagc agctgcgcta    1440
cacggaggaa ctgctgcggc acgtggcccc tgggttgcac ctggagcttc gggggccaca    1500
gctgtgggcc cggcgcatgg gcaagtgcaa ggtgtactgg gaggtgggcg acccccagg    1560 ctccgccagc ccctccaccc cagcctgcct gctgcctcgg aactgtgaca cccccatctt    1620
cgacttcaga gtcttcttcc aagagctggt ggaattccgg gcacggcagc gccgtggctc    1680
cccacgctat accatctacc tgggcttcgg gcaggacctg tcagctggga ggcccaagga    1740
gaagagcctg gtcctggtga agctggaacc ctggctgtgc cgagtgcacc tagagggcac    1800
gcagcgtgag ggtgtgtctt ccctggatag cagcagcctc agcctctgcc tgtccagcgc    1860
caacagcctc tatgacgaca tcgagtgctt ccttatggag ctggagcagc ccgcctagaa    1920
```

```
cccagtctaa tgagaactcc agaaagctgg agcagcccac ctagagctgg ccgcggccgc     1980
ccagtctaat aaaaagaact ccagaaca                                       2008

<210> SEQ ID NO 32
<211> LENGTH: 1876
<212> TYPE: DNA
<213> ORGANISM: Mus musculus

<400> SEQUENCE: 32
tgagataaaa cccgtcccgg cggctccggt accagggtcc agcctgtgac agcccatcca       60
ggctcggacg ctggattaac acctgtgaca tcacgtgtgc gctcccgcta catctgtagt      120
cacatctaca gccaccttgg cagaggaatc tacactgagt tctgaaccta ggtgaccaca      180
agttctcaaa cctcatctgt gaccctcaac accctaatac ctgggtcaca cttgtgaaac      240
tgaaattcct acctgttacc aacacttgta acgtttaaaa cacatttgtg aaacttggtc      300
acactatctg tggctacaac ctaaaaccat agaggcaccc aagggccctt atttgcaata      360
gctgactgct ccagtgacta caaggcatca cagagtagta gcatctactt tgattctccc      420
agactgcctg tgtagacgga gcaatggctg aagtgagggg ggtccagcga gtgctgtttg      480
gagactggct attggggggag gtcagcagcg gccagtacga ggggctgcag tggctgaacg      540
aggctcgcac agtcttccgc gtaccctgga agcatttcgg tcgtagggat ctggatgaag      600
aagatgcaca gatcttcaag gcctgggctg tggcccgagg gaggtggcca cctagtggag      660
ttaacctgcc acccccagag gctgaggctg ctgagcgaag agagcgaaga ggctggaaga      720
ccaacttccg ctgtgcactc cacagcacag ggcgttttat cttgcgccaa gacaattcag      780
gggatccagt tgatccgcat aaggtgtacg aacttagccg ggagcttgga tctactgtgg      840
gcccagccac ggaaaatagg gaagaagtga gcctcagcaa tgctctgccc acacagggtg      900
tgtccccagg atcatttctg gcaagagaaa atgctgggct ccaaacccca agccctctgc      960
tttctagtga tgccgggggac ctcttgcttc aggttctgca gtacagccac atactggaat     1020
ccgagtctgg ggcagacccc gtcccaccac aggctcctgg ccaggagcaa gaccgtgttt     1080
acgaggaacc ctatgcagca tggcaggtgg aagctgtccc cagtcccagg cctcaacagc     1140
cagctctcac cgagcgcagc cttgggttcc tggatgtgac catcatgtac aagggccgca     1200
cagtgctaca ggcagtggtg gggcacccca gatgcgtgtt cctgtacagc cccatggccc     1260
cagcagtaag aacttcagag ccccagccgg tgatctttcc cagtcctgct gagctcccag     1320
atcagaagca gctgcactac acagagacgc ttctccagca tgtgtctccc ggccttcagc     1380
tggagcttcg aggaccgtca ctgtgggccc tgcgtatggg caagtgcaag gtgtactggg     1440
aggtaggcag ccctatgggc actaccggcc cctccacccc accccagctg ctggagcgca     1500
accgccacac ccccatcttc gacttcagca ctttcttccg agaactggag gagtttcggg     1560
ctcggaggcg gcaagggtca ccacactaca ccatctacct gggttttggg caagacttgt     1620
cagcagggag gcccaaggag aagaccctga tcctggtgaa gctggagcca tgggtatgca     1680
aggcatacct ggagggcgtg cagcgtgagg gtgtgtcctc cctggacagc agcagtctcg     1740
gcttgtgctt gtctagcacc aacagtctct acgaagacat cgaacacttc ctcatggacc     1800
tgggtcagtg gccttgactc agaatcccaa ctcccaataa atagttcaaa atcagtggaa     1860
aaaaaaaaaa aaaaaa                                                    1876

<210> SEQ ID NO 33
<211> LENGTH: 7281
```

```
<212> TYPE: DNA
<213> ORGANISM: Homo sapiens

<400> SEQUENCE: 33
gcagtcacag acacttgagc acacgcgtac acccagacat cttcgggctg ctattggatt      60
gactttgaag gttctgtgtg ggtcgccgtg gctgcatgtt tgaatcaggt ggagaagcac     120
ttcaacgctg gacgaagtaa agattattgt tgttattttt tttttctctc tctctctctc     180
ttaagaaagg aaaatatccc aaggactaat ctgatcgggt cttccttcat caggaacgaa     240
tgcaggaatt tgggaactga gctgtgcaag tgctgaagaa ggagatttgt ttggaggaaa     300
caggaaagag aaagaaaagg aaggaaaaaa tacataattt cagggacgag agagagaaga     360
aaaacgggga ctatggggag aaaaaagatt cagattacga ggattatgga tgaacgtaac     420
agacaggtga catttacaaa gaggaaattt gggttgatga agaaggctta tgagctgagc     480
gtgctgtgtg actgtgagat tgcgctgatc atcttcaaca gcaccaacaa gctgttccag     540
tatgccagca ccgacatgga caaagtgctt ctcaagtaca cggagtacaa cgagccgcat     600
gagagccgga caaactcaga catcgtggag acgttgagaa agaagggcct taatggctgt     660
gacagcccag accccgatgc ggacgattcc gtaggtcaca gccctgagtc tgaggacaag     720
tacaggaaaa ttaacgaaga tattgatcta atgatcagca ggcaaagatt gtgtgctgtt     780
ccacctccca acttcgagat gccagtctcc atcccagtgt ccagccacaa cagtttggtg     840
tacagcaacc ctgtcagctc actgggaaac cccaacctat tgccactggc tcacccttct     900
ctgcagagga atagtatgtc tcctggtgta acacatcgac ctccaagtgc aggtaacaca     960
ggtggtctga tgggtggaga cctcacgtct ggtgcaggca ccagtgcagg gaacgggtat    1020
ggcaatcccc gaaactcacc aggtctgctg gtctccacctg gtaacttgaa caagaatatg    1080
caagcaaaat ctcctccccc aatgaattta ggaatgaata accgtaaacc agatctccga    1140
gttcttattc caccaggcag caagaatacg atgccatcag tgtctgagga tgtcgacctg    1200
cttttgaatc aaaggataaa taactcccag tcggctcagt cattggctac cccagtggtt    1260
tccgtagcaa ctcctacttt accaggacaa ggaatgggag gatatccatc agccatttca    1320
acaacatatg gtaccgagta ctctctgagt agtgcagacc tgtcatctct gtctgggttt    1380
aacaccgcca gcgctcttca ccttggttca gtaactggct ggcaacagca acacctacat    1440
aacatgccac catctgccct cagtcagttg ggagcttgca ctagcactca tttatctcag    1500
agttcaaatc tctccctgcc ttctactcaa agcctcaaca tcaagtcaga acctgtttct    1560
cctcctagag accgtaccac cacccccttcg agatacccac aacacacgcg ccacgaggcg    1620
gggagatctc ctgttgacag cttgagcagc tgtagcagtt cgtacgacgg gagcgaccga    1680
gaggatcacc ggaacgaatt ccactccccc attggactca ccagaccttc gccggacgaa    1740
agggaaagtc cctcagtcaa gcgcatgcga ctttctgaag gatgggcaac atgatcagat    1800
tattacttac tagtttttttt tttttttcttg cagtgtgtgt gtgtgctata ccttaatggg    1860
gaaggggggt cgatatgcat tatatgtgcc gtgtgtggaa aaaaaaaag tcaggtactc    1920 tgttttgtaa aagtactttt aaattgcctc agtgatacag tataaagata aacagaaatg    1980
ctgagataag cttagcactt gagttgtaca acagaacact tgtacaaaat agattttaag    2040
gctaacttct tttcactgtt gtgctccttt gcaaatgta tgttacaata gatagtgtca    2100
tgttgcaggt tcaacgttat ttacatgtaa atagacaaaa ggaaacattt gccaaaagcg    2160
gcagatcttt actgaaagag agagcagctg ttatgcaaca tatagaaaaa tgtatagatg    2220
```

```
cttggacaga cccggtaatg ggtggccatt ggtaaatgtt aggaacacac caggtcacct     2280
gacatcccaa gaatgctcac aaacctgcag gcatatcatt ggcgtatggc actcattaaa     2340
aaggatcaga gaccattaaa agaggaccat acctattaaa aaaaaatgtg gagttggagg     2400
gctaacatat ttaattaaat aaataaataa atctgggtct gcatctctta ttaaataaaa     2460
atataaaaat atgtacatta cattttgctt attttcatat aaaaggtaag acagagtttg     2520
caaagcattt gtggcttttt gtagtttact taagccaaaa tgtgtttttt tccccttgat     2580
agcttcgcta atattttaaa cagtcctgta aaaaaccaaa aaggactttt tgtatagaaa     2640
gcactaccct aagccatgaa gaactccatg ctttgctaac caagataact gttttctctt     2700
tgtagaagtt ttgttttga aatgtgtatt tctaattata taaaatatta agaatctttt     2760
aaaaaaatct gtgaaattaa catgcttgtg tatagctttc taatatatat aatattatgg     2820
taatagcaga agttttgtta tcttaatagc gggagggggg tatatttgtg cagttgcaca     2880
tttgagtaac tattttcttt ctgttttctt ttactctgct tacattttat aagtttaagg     2940
tcagctgtca aaaggataac ctgtggggtt agaacatatc acattgcaac accctaaatt     3000
gtttttaata cattagcaat ctattgggtc aactgacatc cattgtatat actagtttct     3060
ttcatgctat ttttattttg tttttttgcat ttttatcaaa tgcagggccc ctttctgatc     3120
tcaccatttc accatgcatc ttggaattca gtaagtgcat atcctaactt gcccatattc     3180
taaatcatct ggttggtttt cagcctagaa tttgatacgc tttttagaaa tatgcccaga     3240
atagaaaagc tatgttgggg cacatgtcct gcaaatatgg ccctagaaac aagtgatatg     3300
gaatttactt ggtgaataag ttataaaattc ccacagaaga aaaatgtgaa agactgggtg     3360
ctagacaaga aggaagcagg taaagggata gttgctttgt catccgtttt taattatttt     3420
aactgaccct tgacaatctt gtcagcaata taggactgtt gaacaatccc ggtgtgtcag     3480
gacccccaaa tgtcacttct gcataaagca tgtatgtcat ctatttttc ttcaataaag     3540 agatttaata gccatttcaa gaaatcccat aaagaacctc tctatgtccc ttttttttaat     3600 ttaaaaaaaa tgactcttgt ctaatattcg tctataaggg attaattttc agaccctta      3660 ataagtgagt gccataagaa agtcaatata tattgtttaa aagatatttc agtctaggaa     3720
agattttcct tctcttggaa tgtgaagatc tgtcgattca tctccaatca tatgcattga     3780
catacacagc aaagaagata taggcagtaa tatcaacact gctatatcat gtgtaggaca     3840
tttcttatcc atttttttctc ttttacttgc atagttgcta tgtgtttctc attgtaaaag     3900
gctgccgctg ggtggcagaa gccaagagac cttattaact aggctatatt tttcttaact     3960
tgatctgaaa tccacaatta gaccacaatg cacctttggt tgtatccata aaggatgcta     4020
gcctgccttg tactaatgtt ttatatatta aaaaaaaaaa atctatcaac catttcatat     4080
atatcccact actcaaggta tccatggaac atgaaagaat aacatttatg cagaggaaaa     4140
acaaaaacat ccctgaaaat atacacactc atacacacac acgcacaggg gaataaaata     4200
agaaaatcat tttcctcacc atagacttga tcccatcctt acaacccatc cttctaactt     4260
gatgtgtata aaatatgcaa acatttcaca aatgttcttt gtcatttcaa aatactttag     4320
tatatcaata tcagtagata ccagtgggtg ggaaagggtc attacatgaa aatatgaaga     4380
aatagccata ttagttttttt aacctgcaat ttgcctcagc aacaaagaaa aagtgaattt     4440
ttaatgctga agataaagta agctaaagta ccagcagaag ccttggctat ttatagcagt     4500
tctgacaata gttttataag aacatgaaga gaacagaatc acttgaaaat ggatgccagt     4560
catctcttgt tcccactact gaattcttat aaagtggtgg caagataggg aagggataat     4620
```

```
ctgagaattt ttaaaagatg atttaatgag aagaagcaca attttgattt tgatgagtca    4680
ctttctgtaa acaatcttgg tctatcttta cccttatacc ttatctgtaa tttaccattt    4740
attgtatttg caaagctagt atggttttta atcacagtaa atcctttgta ttccagactt    4800
tagggcagag ccctgaggga gtattatttt acataacccg tcctagagta acattttagg    4860
caacattctt cattgcaagt aaaagatcca taagtggcat tttacacggc tgcgagtatt    4920
gttatatcta atcctatttt aaaagatttt tggtaatatg aagcttgaat actggtaaca    4980
gtgatgcaat atacgcaagc tgcacaacct gtatattgta tgcattgctg cgtggaggct    5040
gtttatttca acctttttaa aaattgtgtt ttttagtaaa atggcttatt ttttcccaaa    5100
ggtggaattt agcattttgt aatgatgaat ataaaaatac ctgtcatccc cagatcattt    5160
aaaagttaac taaagtgaga atgaaaaaac aaaattccaa gacacttttt aaaagaatgt    5220
ctgccctcac acactttttat ggatttgttt ttcttacata cccatctttt aacttagaga    5280
tagcattttt tgccctcttt attttgttgt ttgtttctcc agagagtaaa cgctttgtag    5340
ttcttctttt aaaaaacatt tttttttaaag aagaagaagc cacttgaacc ctcaataaag    5400
gctgttgcct aagcatggca tacttcatct gttctcattt gtgccatctg ccgtgatgtc    5460 gtcacttttta tggcgttaat ttcctgccac tacagatctt ttgaagattg ctggaatact    5520
ggtgtctgtt agaatgcttc agactacaga tgtaattaaa ggcttttctt aatatgtttt    5580
aaccaaagat gtggagcaat ccaagccaca tatcttctac atcaaatttt tccattttgg    5640
ttattttcat aatctggtat tgcatttttgc cttccctgtt catacctcaa attgattcat    5700
acctcagttt aattcagaga ggtcagttaa gtgacggatt ctgttgtggt ttgaatgcag    5760
taccagtgtt ctcttcgagc aaagtagacc tgggtcactg taggcatagg acttggattg    5820
cttcagatgg tttgctgtat cattttttctt ctttttcttt tcctggggac ttgtttccat    5880
taaatgagag taattaaaat cgcttgtaaa tgagggcata caagcatttg caacaaatat    5940
tcaaatagag gctcacagcg gcataagctg gactttgtcg ccactagatg acaagatgtt    6000
ataactaagt taaaccacat ctgtgtatct caagggactt aattcagctg tctgtagtga    6060
ataaaagtgg gaaattttca aaagtttctc ctgctggaaa taaggtataa tttgtatttt    6120
gcagacaatt cagtaaagtt actggctttc ttagtgatgc agtgtccgtg gtgcattttt    6180
ttaaattaat gttttgctgt ttaaatttat tcaattttat tgtgtttttt aaaaagcagc    6240
ttatgccaca agcacaaatg agctttctca gttttcaact caaaatatta tatgaaaaga    6300
tggatatgtg tgtctgtgtg ggagggggtgt gaattggatg acggttctta gggtattaca    6360
gaattcagcc agtggtggaa gtctaaggtt cttattgaat ggttcaactt ctttatcaaa    6420
gaagttccat gaagatcttt gataacctgt ttaaatgtac agaatttttc aaaagccact    6480
gtgaaaagca gtaccataag ttatttttta actaaaatct gtagaaagtg tttccaaaag    6540
agttcctttt ttcttcttcg aagtaatttc taaaagttga aaacataggc ttataaatct    6600
gaataaatta gtgaattcat acattttaga gactatcaaa tatatccatt attaacattc    6660
aataataatc tctaaagggg aatgtcctta aaaagattga tagaaagatt aatttaaaaa    6720
ctgaaaagga aaacaagaca ccaccagtta gccagctgga gaacttggac ttttgcatta    6780
gtagtgatat ctgctccaaa aagaatgcag ttcgaggaaa tgttgcatgt ggcttcaaaa    6840
tagcagtgct ttctgctttg ttctcttgta ttcattttca gcaaacatgt attaagcaat    6900
tattatatgt aactcatgtg gtgattccag gatgaatgaa gttgtagccc tttctcttag    6960
```

-continued

```
gaaacttata aactaatagg agataaaagg cattctcagg gaagtctaca aagtgctatg     7020
agggagccac tttggccatc ctggggcaga gcagaccaga ggctcagagc atggacactt     7080
cctcatccac ccagcagaag cctttcactt gattttgaag gtgggcagga ttgagaaagg     7140
cccagaaggg gatgagttca aagctgtttg tgggcatgtg acccctgcag tcacatatgg     7200
ccctagcttg tgtttcgttt agtgttctgc tatcattatc ctgataatat cctgataata     7260
aaattatcct taataatttt a                                              7281

<210> SEQ ID NO 34
<211> LENGTH: 6451
<212> TYPE: DNA
<213> ORGANISM: Mus musculus

<400> SEQUENCE: 34
gagcagttct gtgttctttt gccagcactg acaaaggtct ggttgtcaat gataccttta       60
cagctaaatt tactccagag tgacatgaac aggtgcaccc tggcctgcca gacacttgtg      120
cagagggatc acgcatctca ccgcttgacg atcaaggggg caaagcttcg gtgttcatag      180
aaaaggagag gaggcgagcg cagcccaaac tgggggtttt ctcttcaaag ccagctggtc      240
tggctttatt ctacaggaat ttttttacct gtcagagttt ggacaacaaa gccctcagca      300
ggtgctgacg ggaacaactt cctggagaag cagaaaggca ctggtgccaa caaaagcatt      360
gaaaactgtg aagtaacctc tggagagatg aagtgaagcg tggaaggcca atggctgtgg      420
cagtgaagaa gtgcagaggg aacgaatgca gggatttggg aactgagctg tgcgcgtgct      480
gaagaaggaa acgtgtttga aggaaacagg aaagagaaag aaaaggaagg aaaaaataca      540
taatttcagg gacgagagag agaagaaaca cggggactat ggggagaaaa aagattcaga      600
ttacgaggat aatggatgag cgtaacagac aggtgacttt tacgaagagg aaatttggat      660
tgatgaagaa ggcttatgag ctgagcgtgc tgtgcgactg tgagattgca ctgatcatct      720
tcaacagcac caacaagctg ttccagtacg ccagcactga catggataag gtgttgctca      780
agtacaccga gtacaacgag ccgcacgaga gccggacaaa ctcagacatt gtggagacat      840
tgagaaagaa gggcctcaat ggctgtgaca gcccagatcc cgatgcagac gattcagtag      900
gtcacagccc tgagtctgag gacaagtaca ggaaaattaa cgaagatatt gatctaatga      960
tcagcaggca aagattgtgt gctgttccac ctcccagctt tgagatgcca gttaccatcc     1020
cagtgtccag ccataacagt ttggtgtaca gcaatcctgt cagcacactg ggaaaccca      1080 atcttctgcc actggcccac ccgtctctgc agaggaatag tatgtctcct ggtgtaacac     1140
atagacctcc aagtgcaggt aacacaggcg gtctgatggg cggagatctg acatccggtg     1200
caggcaccag cgcagggaat ggatacggca accccggaa ctcaccaggc ctgctggtct     1260
cacctggtaa cctgaacaag aatatacaag ccaaatctcc tcccctatg aatctaggaa     1320 tgaataatcg taagccagat ctccgcgttc ttatcccacc tggcagcaag aacacgatgc     1380
catcagtgtc tgaggatgtg gatctgctgt tgaatcaaag gataaataac tcccagtcgg     1440
ctcagtcatt ggctaccccg gtggtttccg tagcaactcc tactttacca ggacaaggaa     1500
tgggaggata tccatcagcc atttcaacaa catatggtac tgagtactct ctgagtagcg     1560
cagatctgtc atctctgtct ggcttcaaca ctgccagtgc gctccacctc ggctctgtaa     1620
ctggctggca gcagcagcac ctacataaca tgccgccatc tgccctcagt cagttgggag     1680
cttgcactag cactcatta tctcagagtt caaatctctc cctgcttct actcaaagcc     1740 tcagcatcaa gtcagaacct gtttctcctc ctagagaccg taccaccacc ccttcgagat     1800
```

```
acccacaaca caccacgcgc cacgaggcgg ggaggtctcc tgttgacagc ttgagcagct   1860
gtagcagttc ctacgatggg agcgaccgag aggatcaccg gaacgaattc cactccccca   1920
ttggactcac cagaccttcg ccggacgaaa gggaaagtcc ttcagtcaag cgcatgcgac   1980
tctctgaagg atgggcaaca tgatcacatt attacttaat agttttttt tttcttgcag    2040 tgtgtgtgtg tgctatacct taatggggaa ggggggtcg atatgcatta tatgtgccgt    2100
gtgtggaaaa aaaaaaaaaa gtcaggtact ctgttttgta aaagtacttt taaattgcct    2160
cagtgataca gtataaagat aaacagaaat gctgagatac gcttagcact tgagttgtac   2220
aacagaacac ttgtacaaaa tagattttaa ggctaacttc ttttcactgt tgtgacccctt   2280 tgcaaaatgt atgttacaat agatagtgtc atgttgcagg ttcaacgtta tttacatgta    2340
aatagacaaa aggaaacatt tgccaaaagc ggcagatctt tactgaaaga gagagcagct   2400
gttatgcaac atatagaaaa atgtatagag gtttggacag acccggcaag tggtgactac   2460
cggtaattgt aggaacacgc ctgtcaccta acatccaagc acgctcacaa acctgcaggc   2520
atatcattgg cgtatggcac tcattcaaaa ggatcagaaa ccattcagag aggaccatac   2580
ctaccttaaa agaaaagaga agaaaggaaa ggaaaggaaa gggaaaaaaa agtgtggcgt    2640
ttgagagcta acatatttaa ttaaataaat aaatctgggt ctgcatctct tattaaataa   2700
aaatataaaa atatgtacat tacattttgc ttattttcat ataaaaggta agaaagagtt   2760
tgcaaagcat ttgtggcttt ttgtagttta cttaagccaa aatgtgtttt tccctcaata   2820
gcttcgctaa tattttaaac agtcctgtaa aaacccacca aggacttttt gtatagaaag   2880
cactacccta agccatgagg atctccatgc tttgctaacc aagataactg ttttctcttt    2940
gtagaagttt tgtttttgaa atgtgtattt ctaattatat aaaatattaa gaatctttta   3000
aaaatctgtg aaattaacat gcttgtgtat agctttctaa tatatataat attatggtaa   3060
tggcagaagt tttgtttttct taatagcggg aggggggtat atttgtgcag ttgcacattt   3120
gagtaactat tttctttctg atttcttttta ctctgcatac attttataag ttcaaggtca   3180
gctgtcaaaa ggataagctg tggggttaga acatattaca ttgcaacatc ctaaattgtt   3240
tttaaaacgt cagcaaacta ttgggtcaac tgacatccat tgtatatact aattggtttc   3300
tttcaaacta tttttttttt tggtttggtt ttgaattgtt ggtttctttt cattttatca   3360
aaagcagggc cccttttcaga tctctcttca tttcaccata catcttggaa ttctgtaagt   3420
ttgtatccta acttgcccat attctaaatt tacatagttt attttcagcc ttgagttgga   3480 tgtttttttag aaatatgccc agagtaagaa gctgtgttgg agcctaagtc ctgcaagctg   3540
ggtcctgggg gcgaccgacc tgctttactt gatggataag ttacagagtt ctggaggaga   3600
acaaggtgaa agcctgggtg ctggagagga aggaaacagt taaagggtag ttacttggta   3660
tccaccttca tgattttaac tgacccataa caatgttgtc agcagtatag gactgttgaa   3720
cagcctggtg tgtcaggacc cccaaatgtc acttctgcct aaagcatgta tgtcacctat   3780
ttttttcttc aataaagaaa tttaacagcc atttcaagaa atcccacttt aaaaaaaaaa   3840
aaaaacaaac ctttctctat gtccccccc cttttttta attttcaaga taatttaact   3900
cttgtctaat attcttgtgt aagggattaa ttttcagacc cctttaaaag tgagtgccat   3960
aaagagtcaa tatatagtgt tgaagtggta tttcaggcta ggaattattc ccttctcttg   4020
gaatgtgaag atctgtcgat tcatcctgtc attaatcctg acatacagaa caaagaatgc   4080
agtaacatta gccctgccag gtcacgtgta ggacgtgctt atccagtttt ttcccccttt   4140
```

-continued

```
acctgcatag ttgctacata catgtttctc actgtaaaag gctgccgctg ggtggcagaa    4200
gccaaaagac cttattaacg aggctatatt tttcttaact tgatctgcaa tccagaatta    4260
gaccacaatg caccttttggt ggtatccata taggatgcta gcctgccttg tagtaatgtt    4320
ttatatgtta aaaacaaaat aaagacatca accatttcac atatattcta ctactaaagg    4380
tatcaatgga acatgaagac gagtatttag gcagaagcaa aacaggaaac catccttaca    4440
aacatgctta cctgcacatc tgtttgcatg gtcatgtgta cattcaaaca tgcacataaa    4500
gtgaacaaga aagtcagcca ttatttcacg ccagacttga ttccatcctg agaattcatg    4560
tttataatta aatgtgtgtt aaatatgcaa gcatatcaca aatgttcctt gtcctttcaa    4620
agtgcatttg ttcatcaaga tcaatagaat cttaccagtg ggtaggaaag gatcatataa    4680
aatatgaaga aatagccata ttaaattttt tgctgtcatt tgcctccgca acaaagcgag    4740
tgtaagtgtc taatgctgaa gctagagtga actcatgtgc cagcagaggc ctcctctctt    4800
tatagcaatt ctgacaatag gtttgtttgt ttgtttgttt gtttttacaa actcaagaaa    4860
aacagactca cttgaaaaaa tggatgccag tcacctggtt cccactactg tcgtagcaga    4920
tagcgaaggg acaatctgag acttgtagag atgatttaat gagaagcaca attttttattg   4980 tgaccagtca cgttctatca ccaggcactg tcttgtcttt gcccttgcct tttctgtaac    5040
tcaccattta ttgtatttac aaatctagta agggtttga tcacaccaag ttctttgtat     5100
tgagaagtct agggcagagc tctgggggat tgttatttta cattacctgg cctagagtag    5160
catattagac aacagtcatc attgcaagta ggaggaccgt aaatggcatt ttacatgact    5220
gcaagtattg ttataccgaa tcctatttta aaagagtttt agtaacggtg agctgagaaa    5280
ttctggtcat ggtgagcagc aggcgcaagc catgcagcct gtggactgtg cgcattgata    5340
tgtggaggct gttgatttca acctttttta aacttgtgtt ttttagtaaa attgcttatt    5400
tttttcccaa aggtggaatt taatgttttg tagtgatgaa tatgaaaatg cctgtcatct    5460
ttagatcatt gaaaggttaa ctaacatgag aatttcagag caaattccaa tactctttta    5520
aaaagcgtgt ctgccctctc ttacttctat gtatttgttt atcgacacac tcaccctttc    5580
tgagatagca ttttgctccc ttgatccccc ccttttttttg tcccttcgaa gagtaaatgc   5640
tttgtatttc tttctttaaa aaatttactt taaagaagaa gccacttgaa ccttcaataa    5700
aggctgttgc ctaaacatgg cgtacttcat ctgttcccgc ctctgccatc tgctacggtg    5760
tcgtcagttg tatggcatta atttcctgcc actagagata ttttgaagat tgcttgaatg    5820
ctggtgtctg ttagaatgct tctgactaca gatgtaatta aaggcttttc ttactatgtt    5880
ttaaccaaag atgtggagca atccaagccg catatctact gcattaaatt tgtccatttg    5940
gttattcata atcgggtatt gcattttgcc ttccctgtcc atacctcaaa ttgattgata    6000
cctcagttta attcagagag gttcgctaag tgttggattc tagttgtggt ttgaatgcag    6060
cagtgtactc ttgaagtaag caggcaaggg tcactgcagg catgaagctt ggattgcttc    6120
agatggtttg ccgtatcgtt tttcttcctt ttccttttct ggggacttgt ttccattcaa    6180
tgacaattaa aatagcttgt aaatgagggc atacaagcat ttgcaacaag tattcaaata    6240
gaggctcaca gcggcataag ctggactttg tcgccactag atgacaagat ggtataccta    6300
agctaaccac acgtgtgtat ctcaagggac ttaaattcag ctgtctgtag tgaattcaag    6360
tgggaaattt tcaaaagttt ctcctgctgg aaataaggta taatttgtat tttgcagaca    6420
attcagtaaa gttactggct ttcttagtga t                                   6451
```

<210> SEQ ID NO 35
<211> LENGTH: 3684
<212> TYPE: DNA
<213> ORGANISM: Homo sapiens

<400> SEQUENCE: 35
acactttaat atcaacctgt ttcctcctcc tccttctcct cctcctccgt gacctcctcc      60
tcctctttct cctgagaaac ttcgccccag cggtgcggag cgccgctgcg cagccgggga     120
gggacgcagg caggcggcgg gcagcgggag gcggcagccc ggtgcggtcc ccgcggctct     180
cggcggagcc ccgcgcccgc cgcgccatgg cccgaagacc ccggcacagc atatatagca     240
gtgacgagga tgatgaggac tttgagatgt gtgaccatga ctatgatggg ctgcttccca     300
agtctggaaa gcgtcacttg gggaaaacaa ggtggacccg ggaagaggat gaaaaactga     360
agaagctggt ggaacagaat ggaacagatg actggaaagt tattgccaat tatctcccga     420
atcgaacaga tgtgcagtgc cagcaccgat ggcagaaagt actaaaccct gagctcatca     480
agggtccttg gaccaaagaa gaagatcaga gagtgataga gcttgtacag aaatacggtc     540
cgaaacgttg gtctgttatt gccaagcact aaaggggag aattggaaaa caatgtaggg     600
agaggtggca taaccacttg aatccagaag ttaagaaaac ctcctggaca gaagaggaag     660
acagaattat ttaccaggca cacaagagac tggggaacag atgggcagaa atcgcaaagc     720
tactgcctgg acgaactgat aatgctatca agaaccactg gaattctaca atgcgtcgga     780
aggtcgaaca ggaaggttat ctgcaggagt cttcaaaagc cagccagcca gcagtggcca     840
caagcttcca gaagaacagt catttgatgg gtttttgctca ggctccgcct acagctcaac     900
tccctgccac tggccagccc actgttaaca acgactattc ctattaccac atttctgaag     960
cacaaaatgt ctccagtcat gttccatacc ctgtagcgtt acatgtaaat atagtcaatg    1020
tccctcagcc agctgccgca gccattcaga gacactataa tgatgaagac cctgagaagg    1080
aaaagcgaat aaaggaatta gaattgctcc taatgtcaac cgagaatgag ctaaaaggac    1140
agcaggtgct accaacacag aaccacacat gcagctaccc cgggtggcac agcaccacca    1200
ttgccgacca caccagacct catggagaca gtgcacctgt ttcctgtttg ggagaacacc    1260
actccactcc atctctgcca gcggatcctg gctccctacc tgaagaaagc gcctcgccag    1320
caaggtgcat gatcgtccac cagggcacca ttctggataa tgttaagaac ctcttagaat    1380
ttgcagaaac actccaattt atagattctg attcttcatc atggtgtgat ctcagcagtt    1440
ttgaattctt tgaagaagca gatttttcac ctagccaaca tcacacaggc aaagccctac    1500
agcttcagca aagagagggc aatgggacta aacctgcagg agaacctagc ccaagggtga    1560
acaaacgtat gttgagtgag agttcacttg acccacccaa ggtcttacct cctgcaaggc    1620
acagcacaat tccactggtc atccttcgaa aaaaacgggg ccaggccagc cccttagcca    1680
ctggagactg tagctccttc atatttgctg acgtcagcag ttcaactccc aagcgttccc    1740
ctgtcaaaag cctacccttc tctccctcgc agttcttaaa cacttccagt aaccatgaaa    1800
actcagactt ggaaatgcct tctttaactt ccaccccccct cattggtcac aaattgactg    1860
ttacaacacc atttcataga gaccagactg tgaaaactca aaaggaaaat actgttttta    1920
gaaccccagc tatcaaaagg tcaatcttag aaagctctcc aagaactcct acaccattca    1980
aacatgcact tgcagctcaa gaaattaaat acggtcccct gaagatgcta cctcagacac    2040
cctctcatct agtagaagat ctgcaggatg tgatcaaaca ggaatctgat gaatctggaa    2100
ttgttgctga gtttcaagaa aatggaccac ccttactgaa gaaaatcaaa caagaggtgg    2160

-continued

```
aatctccaac tgataaatca ggaaacttct tctgctcaca ccactgggaa ggggacagtc      2220
tgaataccca actgttcacg cagacctcgc ctgtggcaga tgcaccgaat attcttacaa      2280
gctccgtttt aatggcacca gcatcagaag atgaagacaa tgttctcaaa gcatttacag      2340
tacctaaaaa caggtccctg gcgagcccct tgcagccttg tagcagtacc tgggaacctg      2400
catcctgtgg aaagatggag gagcagatga catcttccag tcaagctcgt aaatacgtga      2460
atgcattctc agcccggacg ctggtcatgt gagacatttc cagaaaagca ttatggtttt      2520
cagaacactt caagttgact tgggatatat cattcctcaa catgaaactt ttcatgaatg      2580
ggagaagaac ctatttttgt tgtggtacaa cagttgagag cagcaccaag tgcatttagt      2640
tgaatgaagt cttcttggat ttcacccaac taaaaggatt tttaaaaata aataacagtc      2700
ttacctaaat tattaggtaa tgaattgtag ccagttgtta atatcttaat gcagattttt      2760
ttaaaaaaaa cataaaatga tttatctgta ttttaaagga tccaacagat cagtattttt      2820
tcctgtgatg ggttttttga aatttgacac attaaaaggt actccagtat ttcacttttc      2880
tcgatcacta aacatatgca tatattttta aaaatcagta aaagcattac tctaagtgta      2940
gacttaatac catgtgacat ttaatccaga ttgtaaatgc tcatttatgg ttaatgacat      3000
tgaaggtaca tttattgtac caaaccattt tatgagtttt ctgttagctt gctttaaaaa      3060
ttattactgt aagaaatagt tttataaaaa attatatttt tattcagtaa tttaattttg      3120
taaatgccaa atgaaaaacg tttttttgctg ctatggtctt agcctgtaga catgctgcta      3180
gtatcagagg ggcagtagag cttggacaga aagaaaagaa acttggtgtt aggtaattga      3240
ctatgcacta gtatttcaga cttttttaatt ttatatatat atacatttt tttccttctg      3300 caatacattt gaaaacttgt ttgggagact ctgcattttt tattgtggtt tttttgttat      3360
tgttggttta tacaagcatg cgttgcactt ctttttttggg agatgtgtgt tgttgatgtt      3420
ctatgttttg ttttgagtgt agcctgactg ttttataatt tgggagttct gcatttgatc      3480 cgcatccct gtggtttcta agtgtatggt ctcagaactg ttgcatggat cctgtgtttg      3540
caactgggga gacagaaact gtggttgata gccagtcact gccttaagaa catttgatgc      3600
aagatggcca gcactgaact tttgagatat gacggtgtac ttactgcctt gtagcaaaat      3660
aaagatgtgc ccttatttta ccta                                            3684
```

```
<210> SEQ ID NO 36
<211> LENGTH: 3777
<212> TYPE: DNA
<213> ORGANISM: Mus musculus

<400> SEQUENCE: 36
gggagtgtcc aaacctcttt gtttgatggc atctgtttac agagttacac tttaatatca        60
acctgtttcc tcctcctcct tctcctcctt ctcctcctcc tcctcggtga cctccttctc       120 ctccccttc tccggagaaa cttcgccccg gcggtgcgga gcgccgctgc gcagccgggg        180
gaggacgcag gcaaggcgga gggcagcggg aggcggcaac cggtgcggtc cccggggctc        240
ttggcggagc cccggcccgc ctcgccatgg cccggagacc ccgacacagc atctacagta        300
gcgatgaaga tgatgaagac attgagatgt gtgaccatga ctacgatggg ctgctgccca        360
aatctggaaa gcgtcacttg gggaaaacta ggtggacaag ggaagaggat gagaagctga        420
agaagctggt ggaacagaac ggaacagacg actggaaagt cattgccaat tatctgccca        480
accggacaga tgtgcagtgc caacaccggt ggcagaaagt gctgaaccct gaactcatca        540
aaggtccctg gaccaaagaa gaagatcaga gagtcataga gcttgtccag aaatatggtc        600
```

-continued

```
cgaagcgttg gtctgttatt gccaagcact taaaagggag aattggaaag cagtgtcggg    660
agaggtggca caaccatttg aatccagaag ttaagaaaac ctcctggaca gaagaggagg    720
acagaatcat ttaccaggca cacaagcgtc tggggaacag atgggcagag atcgcaaagc    780
tgctgcccgg acggactgat aatgctatca agaaccactg gaattccacc atgcgtcgca    840
aggtggaaca ggaaggctac ctgcaggagc cttccaaagc cagccagacg ccagtggcca    900
cgagcttcca gaagaacaat catttgatgg ggtttgggca tgcctcacct ccatctcagc    960
tctctccaag tggccagtcc tccgtcaaca gcgaatatcc ctattaccac atcgccgaag    1020
cacaaaacat ctccagtcac gttccctatc ctgtcgcatt gcatgttaat atagtcaacg    1080
tccctcagcc ggctgcggca gccatccaga gacactataa cgacgaagac cctgagaagg    1140
aaaagcgaat aaaggagctg gagttgctcc tgatgtcaac agagaacgag ctgaagggac    1200
agcaggcatt accaacacag aaccacactt gcagctaccc cgggtggcac agcacctcca    1260
ttgtggacca gaccagacct catggggata gtgcacctgt ttcctgtttg ggagaacacc    1320
atgccacccc atctctgcct gcagatcccg gctccctacc tgaagaaagt gcctcaccag    1380
caaggtgcat gatcgtccac cagggcacca ttctggacaa tgttaagaac ctcttagaat    1440
ttgcagaaac actccagttt atagattctg attcttcgtg gtgtgatctc agcagttttg    1500
aattctctga agaagcggca gcttttttcac ctagccagca gcccacaggc aaagccttcc    1560
agcttcagca aagagagggc catgggacta gatctgcagg agagcctagc ctgagggtga    1620
ccaggcgagt gctgagcgag gcatccctcg gcccagactc accccaagcg aggcacagca    1680
aggttccgct ggtcgtccta cgaaaaaggc ggggccaggc cagcccccta gccgctggag    1740
agcctagccc ctccctcttt gctgacgtca tcagctcaac tctcaagcgt tcccctgtca    1800
aaagcctacc cttctctccc tcgcagttct tgaacacttc cagcaaccat gaaagctcgg    1860
gcttagatgc acctacctta ccctccactc ctctcattgg tcacaaactg acaccatgtc    1920
gagaccagac tgtgaaaacc cagaaggaaa attccatctt tagaactcca gctatcaaaa    1980
ggtcaatcct cgaaagctct cctcgaactc ccacaccatt caaacatgcc cttgcagctc    2040
aagaaattaa atacggtccc ctgaagatgc tacctcagac cccctcccat gcagtggagg    2100
acctacaaga tgtgattaag caggaatcgg atgaatctgg aattgtggct gagtttcaag    2160
agagtggacc accgttactg aaaaaaatca agcaggaggt ggagtcgcca actgagaaat    2220
cgggaaactt cttctgctca aaccactggg cagagaacag cctgagcacc cagctgttct    2280
cgcaggcgtc tcctgtggca gatgccccaa atattcttac aagctctgtt ttaatgacac    2340
ctgtatcaga agatgaagac aatgtcctca aagcctttac cgtacctaag aacaggcccc    2400
tggtgggtcc cttgcagcca tgcagtggtg cctgggagcc agcatcctgt gggaagacag    2460
aggaccagat gacggcctcc ggtccggctc ggaaatacgt gaacgcgttc tcagctcgaa    2520
ctctggtcat gtgagacatt tccagaaaag cattatggtt ttcagaacac ttaaaagttg    2580
actttcgaca catggctcct cagcgtggag cgctccatgg ctgagagaag agcctgattt    2640
tgttgtggta caacagttga gagcagcacc aagtgcattt ttagttgctt gagatctcac    2700
ttgatttcac acaactaaaa aggatttttt tttttaaaaa taataataat gaataacagt    2760
cttacctaaa ttattaggta atgaattgtg accatttgtt aatatcataa tcagattttt    2820
taaaaaaaat aaaatgattt atttgtattt tagaggatac aacagatcag tatttttgac    2880
tgtggtgaat ttaaaaaaaa aatttacaca aagaaatatc ccagtattcc atgtatctca    2940
```

```
gtcactaaac atacacagag agatttttaa aaaccaggag aagcattatt ttgaatgtta        3000
gctaaatccc aagtaatact taatgcaacc ctctaggagc tcatttgtgg ctaataatct        3060
tggaaatatc tttattatac taaaccattt catgaggaga attttgttgt cagcttgctt        3120
gaaaagttat tactgtatga aatagtttta ttgaaaaaat tatattttta ttcagtaatt        3180
taattttgta aatgccaaat ggagaaatgt gttcgctgct atggttttag cctgtagtca        3240
tgctgctagc tagtgtcagg gggcaataga gcttagatgg aaaaaagaga aagagactcg        3300
gtgttagata acggactatg cactagtatt ccagactttt ttatttttat atatatgtac        3360
cttttccttt tgtaattgga aaacttattt gggagaattt tgcatttgtt gtacattttt        3420
gttttttagg atttttttttt tttgttgtta ttgtcgattt ataaaagcat tgcacttctt        3480
tttctttttt tgggagattt gtgttgttta tgtcatatgt tttgtttttga gttcagcctg        3540 aatgttcatc cgtttgggcg tttttctgac ttggaagaac attctctgta ggtttctaag        3600
tgtacagagc cggaactgcc tcgtggttcc tgggcttcag ggaagacaaa tatggaagtc        3660
aacagccagt ttctgccttg agagcatttg caagaatgct ggccttgaat tctgaaatga        3720
cagtgtatct actgccttgt agcaaaataa agctatcctc ttattttaca tacttcc         3777
```

<210> SEQ ID NO 37
<211> LENGTH: 5540
<212> TYPE: DNA
<213> ORGANISM: Homo sapiens

<400> SEQUENCE: 37

```
attcgcctca caaacaacca cagaaccaca agtgcggtgc aaactttctc caggaggaca         60
gcaagaagtc tctggttttt aaatggttaa tctccgcagg tcactaccag ccaccgagac        120
caacagagtc atttaaggct gcaagcagta tttacaacag agggtacaag ttctatctga        180
aaaaaaaagg agggactatg gcatcaaaca gcctcttcag cacagtgaca ccatgtcagc        240
aaaacttctt ttgggatccg agcaccagcc ggcgcttcag ccccccctcc agcagcctgc        300
agcccggcaa aatgagcgac gtgagcccgg tggtggctgc gcaacagcag cagcaacagc        360
agcagcagca acagcagcag cagcagcagc aacagcagca gcagcagcag gaggcggcgg        420
cggcggctgc ggcggcggcg gcggctgcgg cggcggcagc tgcagtgccc cggttgcggc        480
cgccccacga caaccgcacc atggtggaga tcatcgccga ccacccggcc gaactcgtcc        540
gcaccgacag ccccaacttc ctgtgctcgg tgctgccctc gcactggcgc tgcaacaaga        600
ccctgcccgt ggccttcaag gtggtagccc tcggagaggt accagatggg actgtggtta        660
ctgtcatggc gggtaacgat gaaaattatt ctgctgagct ccggaatgcc tctgctgtta        720
tgaaaaacca agtagcaagg ttcaacgatc tgagatttgt gggccggagt ggacgaggca        780
agagtttcac cttgaccata accgtcttca caaatcctcc ccaagtagct acctatcaca        840
gagcaattaa agttacagta gatggacctc gggaacccag aaggcacaga cagaagcttg        900
atgactctaa acctagtttg ttctctgacc gcctcagtga tttagggcgc attcctcatc        960
ccagtatgag agtaggtgtc ccgcctcaga acccacggcc ctccctgaac tctgcaccaa       1020
gtccttttaa tccacaagga cagagtcaga ttacagaccc caggcaggca cagtcttccc       1080
cgccgtggtc ctatgaccag tcttacccct cctacctgag ccagatgacg tccccgtcca       1140
tccactctac caccccgctg tcttccacac ggggcactgg gcttcctgcc atcaccgatg       1200
tgcctaggcg catttcagat gatgacactg ccacctctga cttctgcctc tggccttcca       1260
ctctcagtaa gaagagccag gcaggtgctt cagaactggg ccctttttca gaccccaggc       1320
```

```
agttcccaag catttcatcc ctcactgaga gccgcttctc caacccacga atgcactatc      1380
cagccacctt tacttacacc ccgccagtca cctcaggcat gtccctcggt atgtccgcca      1440
ccactcacta ccacacctac ctgccaccac cctaccccgg ctcttcccaa agccagagtg      1500
gacccttcca gaccagcagc actccatatc tctactatgg cacttcgtca ggatcctatc      1560
agtttcccat ggtgccgggg ggagaccggt ctccttccag aatgcttccg ccatgcacca      1620
ccacctcgaa tggcagcacg ctattaaatc caaatttgcc taaccagaat gatggtgttg      1680
acgctgatgg aagccacagc agttccccaa ctgtttttgaa ttctagtggc agaatggatg      1740
aatctgtttg gcgaccatat tgaaattcct cagcagtggc ccagtggtat ctgggggcca      1800
catcccacac gtatcaatat atacatatat agagagagtg catatatatg tatatcgatt      1860
agctatctac aaagtgccta ttttttagaa gatttttcat tcactcactc agtcatgatc      1920
ttgcagccat aagagggtag atattgagaa gcagaaggct caagagagac aattgcaatc      1980
gagcttcaga ttgtttacta tttaagatgt acttttacaa aggaacaaag aagggaaaag      2040
gtatttttgt ttttgttgtt tggtctgtta tcatcaataa cctgttcata tgccaattca      2100
gagaggtgga ctccaggttc aggagggaga agagcaaagc cgcttcctct ctgtgctttg      2160
aaacttcaca ccctcacggt ggcagctgtg tatggaccag tgccctccgc agacagctca      2220
caaaaccagt tgaggtgcac taaagggaca tgaggtagaa tggatgcttc catcacagta      2280
ccatcattca gaataactct tccaatttct gctttcagac atgctgcagg tcctcatctg      2340
aactgttggg ttcgtttttt ttttttttttt tcctgctcca agaaagtgac ttcaaaaata      2400
actgatcagg atagattatt ttattttact ttttaacact ccttctcccc tttttcccact      2460 gaaccaaaaa gaaatcccat ccctaaaacc tgccttctcc ttttatgcaa aactgaaaat      2520
ggcaatacat tattatagcc ataatggtat agatagtgat tgcgtttggc tatgtgttgt      2580
tttctttttt tttaaattat gaatatgtgt aaaatctgag gtaacttgct aacgtgaatg      2640
gtcatataac tttaaagata tatttataat tatttaatga catttggacc cttgaaacat      2700
ttcttagtgt attgatatgt tgacttcggt ctctaaaagt gctctttatt aaataacaaa      2760
tttcttcagt ggtctagagc catatctgaa atattgctaa gcaatttcag ttcatccagg      2820
cacaatgtga ttttaaaaaa tacttccatc tccaaatatt ttagatatag attgtttttg      2880
tgatgtatga aggaaatgtt atgtttagtt cttttcagatc tttgaatgcc tctaacacag      2940
ctttgccttc taaagcggta attagggatt taaaaaacaa cctttagccc tttatcagca      3000
tgaaatgctg gagtgatgtg gttttctaat ttctttgggg taattatgac tcttgtcata      3060
ttaaaaagac aagcacaagt aaatcattga actacagaaa aatgttctgt ggtttcatag      3120
ttaagcaaaa ctctaaatcg ccaggcttca tagcaaagac atagtcagct aaaagccgca      3180
catgtggata gagggttcaa ttatgagaca cctagtacag gagagcaaaa ttgcaccaga      3240
gattcttaac caaccagcct taccaaacaa cacaacaggg gaaccccaat ctgccttacc      3300
caaggcccca ctggcagctt tccacagaat ttgcatttag aggagcagaa tgacatcact      3360
gtcctttggg agtaggtcct ctgaaaaggc agcaggttcc agcaggtagc tgagctgaga      3420
ggacatatgg cccacgggga cctacagaca gcctttgaca tttgtatttc ttacaatgga      3480
gggccaagga gggcaagggg ctgtggagtt tggtgtctac tagtgtgtat gaatttgagc      3540
tagagtcctt ctgtggcatg cactttgacc actcctggca gtcacatggc agatttccaa      3600
gtgcaaatcc ttaatccaaa caaggatcat ctaatgacac caccaggcca atccctgctc      3660
```

```
tcctccccga aaagtcaggg tcccttcatt ggaatcctcc acccacccaa gcagaattta      3720
gcagagattt gccttcaaac cctaacggcc cccttgttct ctggtccttc tcaaacccac      3780 cttttgtaggc cacccagcat tgcaggacag cgtgtggggc agctggacct gtgcttcctg     3840
cctgggagtc tcccttggaa ttcatcctga ctccttctaa taaaaatgga tgggaaagca     3900
aaacactttg ccttctaaag gccgtatacc aagtatgctt agataaataa gccacttttc     3960
tattacttaa gtaagaagga agtagtaatt gatactattt attgtttgtg tgtggtagct     4020
tgaagcacac cactgtccat ttatttgtaa gtgtaaaata tgtgtgtttg tttcagcagc     4080
acttaaaaaa gccagtgtct ggttacacat ttcaatttta attaattgac ataaaaatgc     4140
taccgccagt gccagctgca tcctatttaa ttaaaaaggt actatatttg tacattattt     4200
tttaatgtta aaagggcttt tttaagtttta cagtacacat accgagtgac tttagggatg     4260
cttttgtgtt gaaatgttac tatagtggct gcaggcagca acccagaaac actttagaag     4320
ctttttttcc ttgggaaaaa ttcaagcact tcttccctcc accctcactc caaccacccc     4380
aatgggggta attcacattt cttagaacaa attctgccct tttttggtct agggattaaa     4440
attttgtttt tctttctttc tttttttttt tttttcactg aacccttaat ttgcactggg     4500
tcatgtgttt gatttgtgat ttcaagacca aagcaaagtc ttactactac tgtggaacca     4560
tgtactagtt cctgggaatt aaaatagcgt ggttctcttt gtagcacaaa cattgctgga     4620
atttgcagtc ttttcaatgc agccacattt ttatccattt cagttgtctc acaaattta     4680 acccatatca gagttccaga acaggtacca cagctttggt tttagattag tggaataaca     4740
ttcagcccag aactgagaaa ctcaacagat taactatcgt ttgctcttta gacggtctca     4800
ctgcctctca cttgccagag ccctttcaaa atgagcagag aagtccacac cattagggac     4860
catctgtgat aaattcagaa gggaggagat gtgtgtacac ctttaaggat tccctcaatt     4920
ccgaggaaag ggactggccc agaatccagg ttaatacatg gaaacacgaa gcattagcaa     4980
aagtaataat tatacctatg gtatttgaaa gaacaataat aaaagacact tcttccaaac     5040
cttgaatttg ttgtttttag aaaacgaatg catttaaaaa tattttctat gtgagaattt     5100
tttagatgtg tgtttacttc atgtttacaa ataactgttt gctttttaat gcagtacttt     5160
gaaatatatc agccaaaacc ataacttaca ataatttctt aggtattctg aataaaattc     5220
catttctttt ggatatgctt taccattctt aggtttctgt ggaacaaaaa tatttgtagc     5280
attttgtgta aatacaagct ttcattttta ttttttccaa ttgctattgc ccaagaattg     5340
ctttccatgc acatattgta aaaattccgc tttgtgccac aggtcatgat tgtggatgag     5400
tttactctta acttcaaagg gactatttgt attgtatgtt gcaactgtaa attgaattat     5460
ttggcatttt tctcatgatt gtaatattaa tttgaagttt gaatttaatt ttcaataaaa     5520 tggcttttt ggttttgtta                                                  5540
```

```
<210> SEQ ID NO 38
<211> LENGTH: 5740
<212> TYPE: DNA
<213> ORGANISM: Mus musculus

<400> SEQUENCE: 38
atgcttcatt cgcctcacaa acaaccacag aaccacaagt gcggtgcaaa ctttctccag       60
gaagactgca agaaggctct ggcgtttaaa tggttaatct ctgcaggtca ctaccagcca      120
ccgagaccaa ccgagtcagt gagtgctcta accacagtcc atgcaggaat atttaaggct      180
gcaagcagta tttacaacag agggcacaag ttctatctgg aaaaaaaagg agggactatg      240
```

-continued

```
gcgtcaaaca gcctcttcag cgcagtgaca ccgtgtcagc aaagcttctt ttgggatccg      300
agcaccagcc ggcgcttcag ccccccctcc agcagcctgc agcccggcaa gatgagcgac      360
gtgagcccgg tggtggctgc gcagcagcag caacagcagc agcagcagca gcaacagcag      420
cagcaacaac agcaacagca acaacagcag cagcagcagc agcagcagga ggcggccgca      480
gcagcagcgg cggcagcggc ggcggcagca gcggcggcgg ccgcagtgcc ccgattgagg      540
ccgccgcacg acaaccgcac catggtggag atcatcgcgg accacccggc cgaactggtc      600
cgcaccgaca gtcccaactt cctgtgctcc gtgctgccct cgcactggcg gtgcaacaag      660
accctgcccg tggccttcaa ggttgtagcc ctcggagagg taccagatgg gactgtggtt      720
accgtcatgg ccgggaatga tgagaactac tccgccgagc tccgaaatgc ctccgctgtt      780
atgaaaaacc aagtagccag gttcaacgat ctgagatttg tgggccggag cggacgaggc      840
aagagtttca ccttgaccat aacagtcttc acaaatcctc cccagtggc cacttaccac        900 agagctatta aagtgacagt ggacggtccc cgggaaccaa gaaggcacag acagaagctt      960
gatgactcta aacctagttt gttctctgat cgcctcagtg atttagggcg cattcctcat     1020
cccagtatga gagtaggtgt cccgcctcag aacccacggc cctccctgaa ctctgcacca     1080 agtccttta atccacaagg acagagtcag attacagatc ccaggcaggc acagtcttcc      1140
ccaccgtggt cctatgacca gtcttacccc tcctatctga gccagatgac atccccatcc     1200
atccactcca ccacgccgct gtcttccaca cggggcaccg ggctacctgc catcactgac     1260
gtgcccaggc gtatttcaga tgatgacact gccacctctg acttctgcct ctggccttcc     1320
tctctcagta agaagagcca ggcaggtgct tcagaactgg gccttttttc agaccccagg     1380
cagttcccaa gcatttcatc cctcactgag agccgcttct ccaacccacg aatgcactac     1440
ccagccacct ttacctacac cccgccagtc acgtcaggca tgtccctcgg catgtccgcc     1500
accactcact accacacgta cctgccacca ccctaccccg gctcttccca aagccagagt     1560
ggacccttcc agaccagcag cactccatat ctctactatg gtacttcgtc agcatcctat     1620
cagttcccaa tggtacccgg gggagaccgg tctccttcca ggatggtccc accatgcacc     1680
accacctcga atggcagcac gctattaaat ccaaatttgc ctaaccagaa tgatggtgtt     1740
gacgctgacg gaagccacag cagttcccca actgttttga attctagcgg cagaatggat     1800
gagtctgttt ggcggccata ttgaaattcg tcaaccatgg cccagtggca tggggggccac     1860 atcccgcatg tgttaatata tacatatata aagagagtgc ctatatatgt atattgatta     1920
gctaactaga agatttctca ttcaatccct agtcatgatc ttgcaaccct aagagggtgg     1980
gggcagtcat aactgggttt catattgttt actatttaag atgtcccctt taccaaggaa     2040
caaaccgtca aaggtgttgt ctggtctgtt ttcataagtg acctgttccc acgccggttc     2100
agagaggtgg actctgggtc tgggaggaag gagagacact tcctctctgt gctttgaaac     2160
cacagcctct gctgtgtggc agccggtaca ctctgcagac ccgcttacag agtcagatgt     2220
ggtgcactca gaaagggaca agaggcagag tggctgcttc tgtccgctgc cgtccactct     2280
gccgtccacc tgttccaaag ttttccttca gacttgctgc aggtactcat ttgaactttt     2340
gagttcactt ttttttttc ctattctaag aaagtgactt caaaaatact gatcaggaca     2400
gataatttta ttttaccttt tatattttct cacttccccc atttaaccaa aaagaaatcc     2460 cgttcccct cccccgttcc ttctgcttct ccctttatgc aaactgaaaa tggcaatgcc      2520
ttattattat agccataatg gtatagtgtt tgagttggct gtgtgttatg tgttttttc      2580
```

```
tttttttttc tttttttaaat tatgaatatg tgtaaaatct gaagtaactt gctaacgtga    2640
atggtcatat aactttaaag atatatttat aattatttaa tgacatttgg acatttggaa    2700
catttcttag tgtaatgata tgttgacttc ggtctctaaa agtgtgcttc ttcttcaata    2760
ccaagtttct tcagtgggct agagccatat cggaaatatt gctaagcaat ctcaattcct    2820
tcaggcataa tgtgattttt ttttttttttt gaagataact cccatctcca aatagtttag    2880
atgtagtttg ttttcacgat gtatgaagga gatgctctgt ttctttcttt caggcatttg    2940
attgcctctg acacagcttt gccttttaaa gcaataatta gggattaaaa taacaaaaac    3000
aaaacaaaag ccacctatag cccttttaaca cttaacgtgg cccctttact agcatgaaat    3060
gctggagaca tgtggtttcc taatttctcc attttggggg tggtgggagg ggggagggtg    3120
gccattatga ctcttatcat attaaaaagc caagcacaag tgattggttg aactgcagaa    3180
aagtgttctg tggtctctga gttgagcaaa actctaaatt gcaggcttcg tggttgaggg    3240
cctagtcagc tgaaagccac gcgtgtggta aaggctcagg catggcttgg agaacctagg    3300
aacacattag gagcctgcac ctaccagcct caccatacag ccattcaggg gaacccaaaa    3360
agtgccttac ccaaggaggg ccccccagcag ctttccagga agtcgaatga agtcgctgtc    3420
ctcggggaac tggtcagctg aagtagcaac cggtagctga tgtcagtaga caacagaacc    3480 tgtgggggacc tccaggaaac ctttgacatt ggaggctttc attaggcagg gccaacaaga    3540
gcagggaagg ccatgtaccc attggtatct gccattgtgt gtgagtttga gatccagccc    3600
tccttggagg atgtactgtg atcattcctg gtaccttagg gccaatccct aagtgtggct    3660
tcctaatcca ggccagggat cattcagtga taccaccagg ccaatcccag cattcctcct    3720
gcacaaagtg tttgtgtgtg gggggataga ttggggtggg gccaccttca tttgaatcct    3780
gagtcattct aagagttctg caagcttttg ccttcagcac cctataccc ctcgctctct    3840 gttccttctc aggttgacct ttgtcccaat gcgggacagt ccagaggcag atgggggacct    3900 atgtgtgcct ccaacctgcg ttttcctcag aattcatcct gactccctct gacacagatt    3960
gagggggggg ggaagaaacc caacccgcac caaagcaaaa cactttgcct tctaaaggct    4020
gtgcaccaag tagacgcaga tggtcagccc acctttgtgt ttccttaaga tggaaattgt    4080
aactgatgct atttattgtt tgtgtgtggt agcttgaagc acaccacggt ccatgtgttt    4140
gtctgatacc tatttcagca gcatttacaa aagccagtgt ctggttacac ttttcagttt    4200
tcattaatca acatgaaaat gttaccattg gtgccagctg caccctattt aatttttttta    4260 agggcactat atttgtacat ttcgttttta atgttaaagg gcttcttaaa gtttacagta    4320
cagttatcaa gggaatagag gggatgcatt agtgcctaaa tgttattcta gtggctgcag    4380
gcagcaaccc agaagcagtt ttgaaaacag gttgtttccc tctgtcctcc cttatttggg    4440
aaaattcaag tgctttcttc acctttcagg cacctcacgg tgactcccgt tacttagagc    4500
agtctgtcgt cgtcttcttc ttcttcctct tcctcttcct cttcctcttc ctcttcctct    4560
tcctcttcct cttcctcttc ctcttcttct tcttcttctt cttcttcttc ttcttcttct    4620
tcctcctagg gtttaaaatc ccccttcctc ttcccttatc tcttaaactc ttcatttgca    4680
ctgggtcaca cgtatgattt gtggttttaa gaccaaagca atgtcttatt actcttctgg    4740
agccgtttat gtgtactaac caacccttcc ctccacttcc ctgggtttag atgcacacgg    4800
ttctcaaagg agcacaaaca tggccagatt cacagtggga cccacacagc catgttaaaa    4860
aaaaaaacaa aaaaaaacct cttcacttgt ctgagaattt taacctgggc cccaattgct    4920
aacgggcacc atggcttggg tttcaggtta gggaacgttg cccagtgagt aacagaaaga    4980
```

-continued

```
cttaactgat ttaattagtt tgccctcatc cttcactcca agaccctaag aaaccgatca    5040
gagaaacatc tccacaccat tagaggttga gaagggagga gccatgtggg ggttccctcc    5100
gctcggagga aaggcactga ctgacctagt tagagtggta gcagaagcac ccatggtatc    5160
tgagagagca ataaacaata aaagatgatc ctcccaagct tagaatttgt tgttcttaaa    5220
gaagacgatg catctaaaac aaagaatttt tttttctatg tgggaacttt cttcgttgtc    5280
tgtttacttc atgtttacaa ataattgttt gctttttaat gcagtacttt aaaaaatata    5340
tcagccaaaa ccataactta cagtaatttt tttaggtatt ctgaataaaa ttccatgtct    5400
tttgatatgt ctactgttct taggtttctg tggaacaaca acaacaacaa caacaaaatt    5460
gtagcatttt gtgtaaatac agctttcgtt cttatttttt attttctga ttgctattgc      5520 ccaagatttg ctttctatgc acgtattgta caaattgtgc tttgtgccac aggtcatgat    5580
cgtggatgag tttactctga acttcaaagg gactatttgt attgtatgtt gcaactgtaa    5640
attgaattat ttggcatttc cccctctcat gattgtaata ttaatttgaa gtttgaattt    5700
aattttcaat aaaaaggctt ttttttttcct tttggttttg                          5740
```

```
<210> SEQ ID NO 39
<211> LENGTH: 4978
<212> TYPE: DNA
<213> ORGANISM: Homo sapiens

<400> SEQUENCE: 39
ggtttccgga gctgcggcgg cgcagactgg gaggggagc cggggggttcc gacgtcgcag        60 ccgagggaac aagccccaac cggatcctgg acaggcaccc cggcttggcg ctgtctctcc       120
ccctcggctc ggagaggccc ttcggcctga gggagcctcg ccgcccgtcc ccggcacacg       180
cgcagccccg gcctctcggc ctctgccgga gaaacagttg ggaccctga ttttagcagg        240 atggcccaat ggaatcagct acagcagctt gacacacggt acctggagca gctccatcag       300
ctctacagtg acagcttccc aatggagctg cggcagtttc tggccccttg gattgagagt       360
caagattggg catatgcggc cagcaaagaa tcacatgcca ctttggtgtt tcataatctc       420
ctgggagaga ttgaccagca gtatagccgc ttcctgcaag agtcgaatgt tctctatcag       480
cacaatctac gaagaatcaa gcagtttctt cagagcaggt atcttgagaa gccaatggag       540
attgcccgga ttgtggcccg gtgcctgtgg gaagaatcac gccttctaca gactgcagcc       600
actgcggccc agcaagggggg ccaggccaac cacccacag cagccgtggt gacggagaag        660
cagcagatgc tggagcagca ccttcaggat gtccggaaga gagtgcagga tctagaacag       720
aaaatgaaag tggtagagaa tctccaggat gactttgatt tcaactataa aaccctcaag       780
agtcaaggag acatgcaaga tctgaatgga acaaccagt cagtgaccag gcagaagatg        840
cagcagctgg aacagatgct cactgcgctg gaccagatgc ggagaagcat cgtgagtgag       900 ctggcgggc ttttgtcagc gatggagtac gtgcagaaaa ctctcacgga cgaggagctg        960
gctgactgga agaggcggca acagattgcc tgcattggag gcccgcccaa catctgccta      1020
gatcggctag aaaactggat aacgtcatta gcagaatctc aacttcagac ccgtcaacaa      1080
attaagaaac tggaggagtt gcagcaaaaa gtttcctaca aggggaccc cattgtacag       1140 caccggccga tgctggagga gagaatcgtg gagctgttta gaaacttaat gaaaagtgcc      1200
tttgtggtgg agcggcagcc ctgcatgccc atgcatcctg accggcccct cgtcatcaag      1260
accggcgtcc agttcactac taaagtcagg ttgctggtca aattccctga gttgaattat      1320
```

-continued

```
cagcttaaaa ttaaagtgtg cattgacaaa gactctgggg acgttgcagc tctcagagga   1380
tcccggaaat ttaacattct gggcacaaac acaaaagtga tgaacatgga agaatccaac   1440
aacggcagcc tctctgcaga attcaaacac ttgaccctga gggagcagag atgtgggaat   1500
gggggccgag ccaattgtga tgcttccctg attgtgactg aggagctgca cctgatcacc   1560
tttgagaccg aggtgtatca ccaaggcctc aagattgacc tagagaccca ctccttgcca   1620
gttgtggtga tctccaacat ctgtcagatg ccaaatgcct gggcgtccat cctgtggtac   1680
aacatgctga ccaacaatcc caagaatgta aacttttta ccaagccccc aattggaacc   1740
tgggatcaag tggccgaggt cctgagctgg cagttctcct ccaccaccaa gcgaggactg   1800
agcatcgagc agctgactac actggcagag aaactcttgg gacctggtgt gaattattca   1860
gggtgtcaga tcacatgggc taaattttgc aaagaaaaca tggctggcaa gggcttctcc   1920
ttctgggtct ggctggacaa tatcattgac cttgtgaaaa agtacatcct ggccctttgg   1980
aacgaagggt acatcatggg ctttatcagt aaggagcggg agcgggccat cttgagcact   2040
aagcctccag gcaccttcct gctaagattc agtgaaagca gcaaagaagg aggcgtcact   2100
ttcacttggg tggagaagga catcagcggt aagacccaga tccagtccgt ggaaccatac   2160
acaaagcagc agctgaacaa catgtcattt gctgaaatca tcatgggcta taagatcatg   2220
gatgctacca atatcctggt gtctccactg gtctatctct atcctgacat tcccaaggag   2280
gaggcattcg gaaagtattg tcggccagag agccaggagc atcctgaagc tgacccaggt   2340
agcgctgccc catacctgaa gaccaagttt atctgtgtga caccaacgac ctgcagcaat   2400
accattgacc tgccgatgtc cccccgcact ttagattcat tgatgcagtt tggaaataat   2460
ggtgaaggtg ctgaaccctc agcaggaggg cagtttgagt ccctcacctt tgacatggag   2520
ttgacctcgg agtgcgctac ctcccccatg tgaggagctg agaacggaag ctgcagaaag   2580
atacgactga ggcgcctacc tgcattctgc caccctcac acagccaaac cccagatcat   2640
ctgaaactac taactttgtg gttccagatt tttttaatc tcctacttct gctatctttg   2700
agcaatctgg gcactttaa aaatagagaa atgagtgaat gtgggtgatc tgcttttatc   2760
taaatgcaaa taaggatgtg ttctctgaga cccatgatca ggggatgtgg cggggggtgg   2820
ctagagggag aaaaaggaaa tgtcttgtgt tgttttgttc ccctgccctc ctttctcagc   2880 agcttttgt tattgttgtt gttgttctta gacaagtgcc tcctggtgcc tgcggcatcc   2940
ttctgcctgt ttctgtaagc aaatgccaca ggccacctat agctacatac tcctggcatt   3000
gcacttttta accttgctga catccaaata gaagatagga ctatctaagc cctaggtttc   3060
tttttaaatt aagaaataat aacaattaaa gggcaaaaaa cactgtatca gcatagcctt   3120
tctgtattta agaaacttaa gcagccgggc atggtggctc acgcctgtaa tcccagcact   3180
ttgggaggcc gaggcggatc ataaggtcag gagatcaaga ccatcctggc taacacggtg   3240 aaacccgtc tctactaaaa gtacaaaaaa ttagctgggt gtggtggtgg gcgcctgtag   3300
tcccagctac tcgggaggct gaggcaggag aatcgcttga acctgagagg cggaggttgc   3360
agtgagccaa aattgcacca ctgcacactg cactccatcc tgggcgacag tctgagactc   3420
tgtctcaaaa aaaaaaaaa aaaaagaaa cttcagttaa cagcctcctt ggtgctttaa   3480
gcattcagct tccttcaggc tggtaattta tataatccct gaaacgggct tcaggtcaaa   3540
cccttaagac atctgaagct gcaacctggc ctttggtgtt gaaataggaa ggtttaagga   3600
gaatctaagc attttagact ttttttata aatagactta ttttcctttg taatgtattg   3660 gcctttagt gagtaaggct gggcagaggg tgcttacaac cttgactccc tttctccctg   3720
```

-continued

```
gacttgatct gctgtttcag aggctaggtt gtttctgtgg gtgccttatc agggctggga      3780
tacttctgat tctggcttcc ttcctgcccc accctcccga ccccagtccc cctgatcctg      3840
ctagaggcat gtctccttgc gtgtctaaag gtccctcatc ctgtttgttt taggaatcct      3900
ggtctcagga cctcatggaa gaagaggggg agagagttac aggttggaca tgatgcacac      3960
tatgggnccc cagcgacgtg tctggttgag ctcagggaat atggttctta gccagtttct      4020
tggtgatatc cagtggcact tgtaatggcg tcttcattca gttcatgcag ggcaaaggct      4080
tactgataaa cttgagtctg ccctcgtatg agggtgtata cctggcctcc ctctgaggct      4140
ggtgactcct ccctgctggg gccccacagg tgaggcagaa cagctagagg gcctccccgc      4200
ctgcccgcct tggctggcta gctcgcctct cctgtgcgta tgggaacacc tagcacgtgc      4260
tggatgggct gcctctgact cagaggcatg gccggatttg gcaactcaaa accaccttgc      4320
ctcagctgat cagagtttct gtggaattct gtttgttaaa tcaaattagc tggtctctga      4380
attaaggggg agacgacctt ctctaagatg aacaggttc gccccagtcc tcctgcctgg      4440
agacagttga tgtgtcatgc agagctctta cttctccagc aacactcttc agtacataat      4500
aagcttaact gataaacaga atatttagaa aggtgagact tgggcttacc attgggttta      4560
aatcataggg acctagggcg agggttcagg gcttctctgg agcagatatt gtcaagttca      4620
tggccttagg tagcatgtat ctggtcttaa ctctgattgt agcaaaagtt ctgagaggag      4680
ctgagccctg ttgtggccca ttaaagaaca gggtcctcag gccctgcccg cttcctgtcc      4740
actgccccct ccccatcccc agcccagccg agggaatccc gtgggttgct tacctaccta      4800
taaggtggtt tataagctgc tgtcctggcc actgcattca aattccaatg tgtacttcat      4860
agtgtaaaaa tttatattat tgtgaggttt tttgtctttt tttttttttt ttttttttgg      4920
tatattgctg tatctacttt aacttccaga aataaacgtt atataggaac cgtaaaaa       4978
```

<210> SEQ ID NO 40
<211> LENGTH: 4520
<212> TYPE: DNA
<213> ORGANISM: Mus musculus

<400> SEQUENCE: 40

```
aattatgcat ggaggcgtgt cttggccagt ggcggctggg tggggattgg ctggaggggc        60
tgtaattcag cggtttccgg agctgcagtg tagacaggga gggggaacct ggggttccga       120
cgtcgcggcg gagggaacga gccctaaccg gatcgctgag gtacaacccc gctcggtgtc       180
gcctgaccgc gtcggctagg agaggccagg cggccctcgg gagcccagca gctcgcgcct       240
ggagtcagcg caggccggcc agtcgggcct cagccccgga gacagtcgag acccctgact       300
gcagcaggat ggctcagtgg aaccagctgc agcagctgga cacacgctac ctggagcagc       360
tgcaccagct gtacagcgac agcttcccca tggagctgcg gcagttcctg gcaccttgga       420
ttgagagtca agactgggca tatgcagcca gcaaagagtc acatgccacg ttggtgtttc       480
ataatctctt gggtgaaatt gaccagcaat atagccgatt cctgcaagag tccaatgtcc       540
tctatcagca caaccttcga agaatcaagc agtttctgca gagcaggtat cttgagaagc       600
caatggaaat tgcccggatc gtggcccgat gcctgtggga gagtctcgc ctcctccaga       660 cggcagccac ggcagcccag caagggggcc aggccaacca cccaacagcc gccgtagtga       720
cagagaagca gcagatgttg gagcagcatc ttcaggatgt ccggaagcga gtgcaggatc       780
tagaacagaa aatgaaggtg gtggagaacc tccaggacga ctttgatttc aactacaaaa       840
```

-continued

```
ccctcaagag ccaaggagac atgcaggatc tgaatggaaa caaccagtct gtgaccagac    900
agaagatgca gcagctggaa cagatgctca cagccctgga ccagatgcgg agaagcattg    960
tgagtgagct ggcggggctc ttgtcagcaa tggagtacgt gcagaagaca ctgactgatg   1020
aagagctggc tgactggaag aggcggcagc agatcgcgtg catcggaggc cctcccaaca   1080
tctgcctgga ccgtctggaa aactggataa cttcattagc agaatctcaa cttcagaccc   1140
gccaacaaat taagaaactg gaggagctgc agcagaaagt gtcctacaag ggcgacccta   1200
tcgtgcagca ccggcccatg ctggaggaga ggatcgtgga gctgttcaga aacttaatga   1260
agagtgcctt cgtggtggag cggcagccct gcatgcccat gcacccggac cggcccttag   1320
tcatcaagac tggtgtccag tttaccacga aagtcaggtt gctggtcaaa tttcctgagt   1380
tgaattatca gcttaaaatt aaagtgtgca ttgataaaga ctctggggat gttgctgccc   1440
tcagagggtc tcggaaattt aacattctgg gcacgaacac aaaagtgatg aacatggagg   1500
agtctaacaa cggcagcctg tctgcagagt tcaagcacct gacccttagg gagcagagat   1560
gtgggaatgg aggccgtgcc aattgtgatg cctccttgat cgtgactgag gagctgcacc   1620
tgatcacctt cgagactgag gtgtaccacc aaggcctcaa gattgaccta gagacccact   1680
ccttgccagt tgtggtgatc tccaacatct gtcagatgcc aaatgcttgg gcatcaatcc   1740
tgtggtataa catgctgacc aataacccca agaacgtgaa cttcttcact aagccgccaa   1800
ttggaacctg ggaccaagtg gccgaggtgc tcagctggca gttctcgtcc accaccaagc   1860
gggggctgag catcgagcag ctgacaacgc tggctgagaa gctcctaggg cctggtgtga   1920
actactcagg gtgtcagatc acatgggcta aattctgcaa agaaaacatg gctggcaagg   1980
gcttctcctt ctgggtctgg ctagacaata tcatcgacct tgtgaaaaag tatatcttgg   2040 cccttttggaa tgaagggtac atcatggggtt tcatcagcaa ggagcgggag cgggccatcc   2100
taagcacaaa gcccccgggc accttcctac tgcgcttcag cgagagcagc aaagaaggag   2160
gggtcacttt cacttgggtg gaaaaggaca tcagtggcaa gacccagatc cagtctgtag   2220
agccatacac caagcagcag ctgaacaaca tgtcatttgc tgaaatcatc atgggctata   2280
agatcatgga tgcgaccaac atcctggtgt ctccacttgt ctacctctac cccgacattc   2340
ccaaggagga ggcatttgga aagtactgta ggcccgagag ccaggagcac cccgaagccg   2400
acccaggtag tgctgccccg tacctgaaga ccaagttcat ctgtgtgaca ccaacgacct   2460
gcagcaatac cattgacctg ccgatgtccc cccgcacttt agattcattg atgcagtttg   2520
gaaataacgg tgaaggtgct gagccctcag caggagggca gtttgagtcg ctcacgtttg   2580
acatggatct gacctcggag tgtgctacct cccccatgtg aggagctgaa accagaagct   2640
gcagagacgt gacttgagac acctgccccg tgctccaccc ctaagcagcc gaacccccata   2700 tcgtctgaaa ctcctaactt tgtggttcca gattttttt tttaatttcc tacttctgct   2760
atctttgggc aatctgggca ctttttaaaa tagagaaatg agtgagtgtg ggtgataaac   2820
tgttatgtaa agaggagagc acctctgagt ctggggatgg ggctgagagc agaagggagc   2880 aagggggaaca cctcctgtcc tgcccgcctg ccctcctttt tcagcagctc ggggttggtt   2940
gttagacaag tgcctcctgg tgcccatggc atcctgttgc cccactctgt gagctgatac   3000
cccaggctgg gaactcctgg ctctgcactt tcaaccttgc taatatccac atagaagcta   3060
ggactaagcc cagaggttcc tctttaaatt aaaaaaaaaa aaaataagaa ttaaagggca   3120
aaacacactg acacagcata gcctttccat atcaaggaat actcagttaa cagcctctcc   3180
agcgctgtct tcaggctgat catctatata aaccctggaa tggttgcaga tcaaatctgt   3240
```

-continued

```
aaaagagatc cgagagctgt ggcttggcct ctggttcaaa cacaaaggct agagagaacc      3300
tagatatccc tgggtttttgt ttacccagta tgcttgtcgg ttggaggtgt gaggtaggcc      3360
aagggcactg gaaagccttt gtcatcaccc tactccctcc ccaacccaga ctccagaccc      3420
tgtttcaggg tcagcctgcc ctgtgggtgc cttactgggc ctaggtcaa cctgccttcc       3480 tttcccactt gaccttgctg gtagtatgtc cccttcccat gtccaaaggc cctctgtcct      3540
gcttctattg ggaatccctg cctcaggacc ttgtgtcgag agggattgcc ttacaggttt      3600
gaacctgcct cagactacag gccctcagca aagctcaggg agtatggtcc ttattctatg      3660
cgcttggttc ccagggatat ctgtaaccac agggcaaaag ctgacatata ctccaggtct      3720
gccctcatat gagtggtgta ttcttggcct cccctgagac tggcaactgt ctgctcccca      3780
ttgggtctcc caggtgaggt ggaacacagt tcctgcacct actgtggcct ccatgtcgct      3840
tgcttgcttc gctcactcag cttactggaa cactgagtgt tcaaggcaag cctttcctga      3900
cagaggcatg gctagattca gtgactcaaa gccacctcat tcagctgatc agtgtctgtg      3960
gaattgtttc cttccagtta accagtgtct gaattaaggg cagtgaggac attgtctcca      4020
agacgaactg cttgccttga ccaccccagc cttctgcttc gagacagtta ctgctctccc      4080
accccatcaa tgttctttag ttatacaata agctgaactt ataaactgaa agggtattta      4140
ggaaggcaag gcttgggcat ttttatggct ttcaatcctg gggacccagg aacaaggtga      4200
gggcttctct ggggctggtg ttgtacctca ggggctctgg gaagtctgtg tgcctgggtt      4260
aaccacccat agtgagcccc tggaactgcc cactttccct ctccttggcc ccacttggcc      4320
ccagcctcac ccagcctgca gactgcttag cctttcagtg cagtggcttg tgttctggcc      4380
actgcactca gattccaatg taaactttct agtgtaaaaa tttatattat tgtgggttgt      4440
tttttgttgt tgtttgtttt tgtatattgc tgtaactact ttaacttcca gaaataaaga      4500
ttatatagga actgtctggc                                                   4520
```

<210> SEQ ID NO 41
<211> LENGTH: 8232
<212> TYPE: DNA
<213> ORGANISM: Homo sapiens

<400> SEQUENCE: 41

```
gatgtctaca gtatcacctt tcttgtagat tggcacttat gcggccaaag gaacaacacc       60 atgtttttcta aaaggctgga gaaaatacca caggtgcctc tcctctttcc cttcatcttc      120
atcattttga caaattactc aaagatggag ggtgcagttg aaagccagcc atcatttttt       180
aaaacttctc aggacattgt aacatgcact tgggttgaga actgctactc gagcttctcc       240
aggaggccct tggagcaaat gttttgtaaa caccaatcta agaacattat ctcttggacg       300
ggcatggtgg ctcacacctg taatcccagc actttgggag gccaaggttt gtgtgatttt       360
gctaaaatgc atcaccaaca gcgaatggct gccttaggga cggacaaaga gctgagtgat       420
ttactggatt tcagtgcgat gttttcacct cctgtgagca gtgggaaaaa tggaccaact       480
tctttggcaa gtggacattt tactggctca aatgtagaag acagaagtag ctcagggtcc      540
tgggggaatg gaggacatcc aagcccgtcc aggaactatg gagatgggac tccctatgac      600
cacatgacca gcagggacct tgggtcacat gacaatctct ctccaccttt tgtcaattcc      660
agaatacaaa gtaaaacaga aaggggctca tactcatctt atgggagaga atcaaactta      720
cagggttgcc accagcagag tctccttgga ggtgacatgg atatgggcaa cccaggaacc      780
```

-continued

```
ctttcgccca ccaaacctgg ttcccagtac tatcagtatt ctagcaataa tccccgaagg      840
aggcctcttc acagtagtgc catggaggta cagacaaaga aagttcgaaa agttcctcca      900
ggtttgccat cttcagtcta tgctccatca gcaagcactg ccgactacaa tagggactcg      960
ccaggctatc cttcctccaa accagcaacc agcactttcc ctagctcctt cttcatgcaa     1020
gatggccatc acagcagtga cccttggagc tcctccagtg ggatgaatca gcctggctat     1080
gcaggaatgt tgggcaactc ttctcatatt ccacagtcca gcagctactg tagcctgcat     1140
ccacatgaac gtttgagcta tccatcacac tcctcagcag acatcaattc cagtcttcct     1200
ccgatgtcca ctttccatcg tagtggtaca aaccattaca gcacctcttc ctgtacgcct     1260
cctgccaacg ggacagacag tataatggca aatagaggaa gcggggcagc cggcagctcc     1320
cagactggag atgctctggg gaaagcactt gcttcgatct attctccaga tcacactaac     1380
aacagctttt catcaaaccc ttcaactcct gttggctctc ctccatctct ctcagcaggc     1440
acagctgttt ggtctagaaa tggaggacag gcctcatcgt ctcctaatta tgaaggaccc     1500
ttacactctt tgcaaagccg aattgaagat cgtttagaaa gactggatga tgctattcat     1560
gttctccgga accatgcagt gggcccatcc acagctatgc ctggtggtca tggggacatg     1620
catggaatca ttggaccttc tcataatgga gccatgggtg gtctgggctc agggtatgga     1680
accggccttc tttcagccaa cagacattca ctcatggtgg ggacccatcg tgaagatggc     1740
gtggccctga gaggcagcca ttctcttctg ccaaaccagg ttccggttcc acagcttcct     1800
gtccagtctg cgacttcccc tgacctgaac ccaccccagg acccttacag aggcatgcca     1860
ccaggactac aggggcagag tgtctcctct ggcagctctg agatcaaatc cgatgacgag     1920
ggtgatgaga acctgcaaga cacgaaatct tcggaggaca agaaattaga tgacgacaag     1980
aaggatatca aatcaattac taggtcaaga tctagcaata atgacgatga ggacctgaca     2040
ccagagcaga aggcagagcg tgagaaggag cggaggatgg ccaacaatgc ccgagagcgt     2100
ctgcgggtcc gtgacatcaa cgaggctttc aaagagctcg gccgcatggt gcagctccac     2160
ctcaagagtg acaagcccca gaccaagctc ctgatcctcc accaggcggt ggccgtcatc     2220
ctcagtctgg agcagcaagt ccgagaaagg aatctgaatc cgaaagctgc gtgtctgaaa     2280
agaagggagg aagagaaggt gtcctcagag cctccccctc tctccttggc cggcccacac     2340
cctggaatgg gagacgcatc gaatcacatg ggacagatgt aaaagggtcc aagttgccac     2400
attgcttcat taaaacaaga gaccacttcc ttaacagctg tattatctta aacccacata     2460
aacacttctc cttaacccccc attttttgtaa tataagacaa gtctgagtag ttatgaatcg     2520
cagacgcaag aggtttcagc attcccaatt atcaaaaaac agaaaaacaa aaaaagaaa      2580 gaaaaaagtg caacttgagg gacgactttc tttaacatat cattcagaat gtgcaaagca     2640
gtatgtacag gctgagacac agcccagaga ctgaacggca atctttccac actgtggaac     2700
aatgcatttg tgcctaaact tctttttggaa aaaaaaaata taattaattt gtaagtctga     2760
aaaaaaaata tttaatttaa aaaaaattgt aaacttgcaa taatgaaaaa gtgtacttct     2820
gaagaaaact acatgaacgt ttttgttggt attcaagtca gctagtgttt ataattactg     2880
gatattgaat taggggaagc tcggctgccc tagtaacaaa accagcaaac gtcctgatga     2940
caacgaagtg atgacattag ccattcctta gggtaggagg aacagatgga tcttatagac     3000
ctatgacaaa tatatatata aatatatata taaatatata ttaaaaattt agtgactatg     3060
gtaagctttt gttcatttgt ttcagacttt tttctcctgt aaaaaaatag tactgattaa     3120
cttttttaaa agaaagattt tactgtaaat atggatttt tttttttggg tcttatttct     3180
```

```
gtcccttttcc ctggtttgtt atcgtaacct gtagtgccaa ctctgcttcc agaggggtag       3240
tgcaggatga aatgctgacc ctgatgttgc ttctcattca taaataagta gaaagttgtt       3300
tctccagtct tttgggaaca caggacttaa aagtcacatc atgtgtagat attacaagca       3360
gcattaccaa gacatggcaa aaagagtttg tctgaattgt aatgttgcgt ttgtgaacct       3420
attctgggat tttcagaggt acaaggttag aatgctacaa tgttaccact gtgccttcca       3480
atgtttatat catcggaaac ataacataat caaagtggct gtgatttaac aaaatgatta       3540
aagtgttacc tacctgtgta gccgaagtag tgtgcagtga ggcgtttctg aatacatggt       3600
cagatttttg gaaaaaaaca aaaacaaaaa aaacaagtaa agttcaaaaa ccgtcaaatg       3660
agaaaattgc aagtagtgtg acagagctga ttgattttgt tgctttcttg attttttttt       3720
tcaaaatggg tttactaaaa tgtagatgac ttaactgcct cctccttcgt ctgaaaaatg       3780
ccaatattca atcatcatgc agcattataa caagccttat aagtcctaaa gcattaagtt       3840
gcactttttt gaggaggggt agtgcagtat ttctctggcc agtatgaatg aagtttatac       3900
ttaccatatt tgatagaaac atagatcaag ctatggcaca gcgactcatc agatagctag       3960
ctttgacgtc tgggcacaat tgaaccaact tccatcgtga atctttataa tgattgactt       4020
tggtgtatag tgcagtaaac aaatagtgct cctagttaag tatttgtcag catccttttg       4080
tctctaactt gtttctattt ttacagccac acaattcttg gcatgtatta agaaaaaaaa       4140
aaatccctgt tcaagtagtt tttccaccta tcagcactga gtaaatgcca taaatccatt       4200
gaaatggtct aaatgttcca tctgttctcc tgttttgcca gttatatagt aatgaaatac       4260
atttgtaaat tttatgcaac aaatggcaaa cgtatcatta ttttgaaatt gtgtatgtaa       4320
aagttatatt tttacatgta gactcttgtt attatgtgtt ttaatacatt gtatcagttt       4380 ttgtttttttt ttaaaaactg tggtttaaaa agaagtctca tttaaatgaa atagctacaa       4440
gaatcagaat tttatgttca tttctgaaaa tgtaagaaca aataagatag ttaccacgtg       4500
gtcatctttt acaaacccat aaacattttg attagctgtg tgtgtgttga aaaactgtaa       4560
atatgttcag tagcgataaa actaaaataa ctttgatttg ttgataagtt cctaaaatgt       4620
ggaggtggat taaaacctta ggagaatagc agaaatcaaa cttcatgaaa agttattttg       4680
gggctttcct gtgaaatgta tgaacaaaga ggctcagaga aggacatgga agacaataat       4740
gtatactctc tcctcctccc tgaataatga aaaccatgtg tatttgttcc ctccgtatgt       4800
taaagatttc cttttagtgg tacattctgc actcattttg tatagtctac caaggcgggt       4860
atccctagga acaatattat ataggaagca ggtatactct gatcacattc aggataagtg       4920
tacagaagaa aatacggtgt ttactcttta gggaactgga aacactccct gcattgatgt       4980
acattttaag aatggcactt ttgatacatg ttatcataaa ggtgcttaat agagctgaat       5040
taaagttttt caaatctgta aacaaagcaa aaaagtaaat tgtagtcatt tgattatttt       5100
ttaaattggt gctttatatt ttgttctcac tcagagtaaa agctgcaatt tattgttcac       5160
cagctttgat gtattcatta ctcagtaatg caatacctct attgttgaat tcccttttgga      5220 aataagtgaa aattctaacg gccactgaaa gctgctcgct aggttttgct tggtggagaa       5280
acataatctg cacctatcca tattaattgg gttgtatccc cattaaaaaa gaaaaaaagg       5340
gaatgtggcc tttttagtgt gtttttttatt gttgttgttt tgtaattatc aaacccaggt       5400
aagatattgg tatcctgcac tggattttca aatgaagttc agcagaagac agttaagatt       5460
aaagtactat acaaaaattt caaaagggtc catactacgc tatctgtatg acgacactta       5520
```

-continued

```
ggctggggat ctctttcaga aactcggact ttaaaagcaa cttggagcag ttgatccacc    5580
tccacattca agtaatttat gaatatgcag aataggggatc tgttcatcta gaaattttta   5640
ccatttgtct tctgtgtagc tgcaaggaac actaatgttt atacaactgt cagtccaccc   5700
agtggtgcaa ctggttctga ttcagtcttc cgattccttt ttattttca cttttttccta   5760 tttctgaatt tttttttta tttgtgatct tgattttgat gaggggttgg ggagtgggga    5820
gggagtcgaa ccaagacttg gagttaagag gattttcatc ttttgcatcc aacaggcaga   5880
atatgatctg tgtccaaaag tgaacttgag tcaggaatga atcaatttca gcataaacaa    5940
gcacaaaaat ttagtctgct ggctgactgg aagcaaaaaa gtcaagatgg aatatgatga   6000
attccaacac aatggggcac caaggccttt aggcctctct ttttattttg ctttggtttt    6060
gtttgttttt ctttagagac atgctctttc tcatgggact tgaagtggac tcatctttgt   6120
gcagtgctgg ttttgccata ctcatttcaa gtattataga catatgtaat ggtgaaaata   6180
tatgaactgt ggcctttttc attcttgtta cttgtgatgc aattaagtga agataagaaa   6240
aaaaaaaaaa aagcagagat ttaccatgta tcagtgcctg gcttttttgtt ataaagcttt   6300 gtttgtctag tgctctttttg ctataaaata gactgtagta caccctagta ggaaaaaaaa   6360
aaaactaaat ttaaaaataa aaaatatatt tggcttattt ttcgcaggag caatccttt     6420 ataccatgaa tattacaaaa aaattgtcag attctgaata tttcttcttt gtagattttt    6480
ggaatcatta tgagtaaaag tttgttactt tattttacta tttaaaagat gttatttttac   6540 catgtgttac caagatgaaa ctgtatgggt agctttttttg tttgtttttt gttttgtttt   6600 tgttttttgtt tttgttttta gttgtaggtc gcagcgggga aatttttttgc gactgtacac  6660 atagctgcag cattaaaaac ttaaaaaaat tgttaaaaaa aaaaaaaggg aaaacatttc    6720
aaaaaaaaaa aaaagataa acagttacac cttgtttttca atgtgtggct gagtgcctcg    6780
attttttcat gttttttggtg tatttctgat ttgtagaagt gtccaaacag gttgtgtgct   6840
ggagttcctt caagacaaaa acaaacccag cttggtcaag gccattacct gtttcccatc     6900
tgtagttatt cgatgaagtc atgtacatga ccgttctgta gcaataaatg tgccattttt    6960
ataaactgtt tctgacactt gtttcatttc attttgcatt gtccatatag ctatgattct    7020
cttctgtaag taaaacgcat ctatatttca ttttccaagt gttggaggta ttgacagctt    7080
aacaaacaaa acatacaaaa aaaatcacaa aaacaaattg aaaagcaaag cacatgattg     7140
atcaaggaag agatgcccett aatgaaaatg gaacgggatg catgcaaaac aaaaagaaaa    7200
ctgtctagag gattaactaa ttgaaggaat ataattaatg tgtgtgtaac actgaagcta    7260
tgcatttgaa gagctctgaa ctgcaccagt gttttcggtt gtgctgcagg ttgctaagtc    7320
aagtcagcct taacctttttg caccagttgg tcggctgttt ggcagaacat tctcagatct   7380
tttcagtcaa aaatctaaga tgatttattt tgtatcactt tgttaaaagc tgaatattgt    7440
taactacagt taatattaac actgtattta tactttctca aactacatcc gccccaccac     7500
ttctggttgc ctctgttgac tattaatcca gatgtaaaca accagatgtt tttttctaac    7560
ttgtacaaac tgacgtgtgt caactatcat ggaaggaaaa aaatgtacag attaaaatta    7620
ttcagtgtta tgtactgtaa gttaatattt ttgtagaatg gacatcaatc tactttgcaa    7680
aatttggagg ctatttcaac attgcactgt agaaatgtaa agtaatgtat gcaatgtaaa    7740
ggaaagcccg cggtagctga gcgcttcata acagaatgtt ctaatcaagt acgtggtatt    7800
tggggatgtc tccaatattg ctcttgtatt cttttctaatt gggtttagtg actagttgaa   7860
ggaaaatgtt ataacgccat ttggttcaca tgtgaagtgc cctccatagc caaatgttgg    7920
```

```
gatttttttt ttttttcgttt ttggttggac tgtttgcaga tatttaaatt ttatgaaatt    7980
tccaaagatt ttggttgata accccctttt accttctaaa tgatttgaga tgttcttatg    8040
ttcttactgt gtgttttaaa tatatataaa agagccacaa gcatttagtc ttttagtatt    8100
atatttgatc atataactac tactgaaaag gggtgggggg gaatgtgcct gtgcacccct    8160
acagtatctt gtgtagtgtc tattaacatt gttctctttt agaggaccac attaaaaggt    8220
acattaatct ta                                                        8232

<210> SEQ ID NO 42
<211> LENGTH: 7462
<212> TYPE: DNA
<213> ORGANISM: Mus musculus

<400> SEQUENCE: 42
ggagcagccg cggccgcagc gccttctctt tataagccgc agtgcccgga tgtgaatgga      60
ttacaatgta tctttcaggg aaacctatta ttatcaatgt gactcctcgg gggagtcaat     120
gatggtgttg gggaggagga tgatgatgag acgcctctaa acttggaaca agtttaggac     180
tttgaaagag aagagaaaaa aaaatacaac caacaagacc gaagaacaat tataactatc     240
cagtgttgat tattttttata aacaatacga aaaagttgtc ggatttttttt ttttaatgat   300 tacttttttgg ggggaggga ttttgttaca gtttgatgat ggaaaatgca aaaaccgagc      360
caggtgcata atcttgtaat ctgtggctaa ccctggaaca ggactgactt ctatttaaaa     420
tactcttttg ggggaacact catgtgagac actaagttct tgcagaagat ttttgtctct     480 cttttttaaag tctctttcct tggaatattg tgagcatatt tgtggccatt gaaggtttgt    540
gtgattttgc taaaatgcat caccaacagc gaatggctgc cttagggacg gacaaagagc      600
tgagtgattt actggatttc agtgcgatgt tttcgcctcc tgtaagcagt gggaaaaatg     660
gaccaacttc tttggcgagt ggacatttca ctggctcaaa tgtagaagac agaagtagct     720
cagggtcctg gggaactgga ggccatccaa gcccgtccag gaactatgga gatgggactc     780
cctatgacca catgactagc agggatcttg ggtcacatga caatctctct ccacctttttg    840 tcaattccag aatacaaagt aaaacagaaa ggggctcata ctcatcttat gggagagaaa     900
acgttcaggg ttgccaccag cagagtctcc tcggagggga catggatatg ggcaatccag     960
gaaccctttc gcccaccaaa cctggctccc agtactatca gtattcaagc aataatgccc    1020
gccggaggcc tcttcacagt agtgccatgg aggtacagac aaagaaagtc cgaaaagttc    1080
ctccgggttt gccgtcttca gtctacgctc cttcagccag cactgccgac tacaacaggg    1140
actcgccagg ctatccttcc tccaagccag cagccagcac tttccctagc tccttcttca    1200
tgcaagatgg ccatcacagc agcgaccctt ggagctcctc cagcgggatg aatcagcccg    1260
gctacggagg gatgctgggc aattcttctc atatcccaca gtccagcagc tactgtagcc    1320
tgcatccaca tgaacgtttg agctatccat cccactcctc ggcagacatc aactccagtc    1380
ttcctccgat gtccacgttc catcgtagtg gcacaaacca ttacagcacc tcttcctgca    1440 cacccctgc caacggaaca gacagtataa tggcaaacag aggaactggg gcagcaggca    1500
gctcgcagac tggagacgct ctagggaaag ccctagcttc gatctattct cctgaccaca    1560
cgaacaacag cttttcctcc aatccttcaa ctcctgtggg ctcccctcct tcactctcag    1620
caggcacagc tgtttggtct agaaatggag gacaggcctc gtcatctccc aattatgaag    1680
gacccttgca ctcactgcaa agccgaatcg aagaccgttt ggaaagactg gacgatgcga    1740
```

-continued

```
ttcatgttct ccggaaccac gcagtgggcc cgtccacagc tgtgcctggt ggccatgggg    1800
acatgcatgg gatcatggga ccctcccaca acggagcgat gggtagcctg ggctcagggt    1860
acggaactag tcttctctca gccaacagac actcgctcat ggttggggcc caccgtgaag    1920
atggcgtggc tctgagaggc agccattctc tcctgccaaa ccaggttccg gtcccacaac    1980
ttccggtcca gtctgcaact tcccctgact tgaacccacc ccaagaccct tacagaggga    2040
tgccaccagg cctccagggc cagagcgtgt cttctggtag ctctgagatc aaatccgacg    2100
acgagggcga tgagaacctg caagacacaa aatcttctga ggacaagaaa ttagatgacg    2160
acaagaagga tatcaaatca attactaggt caagatctag caataacgat gatgaggacc    2220
tgaccccaga gcagaaggct gagcgcgaga aggaacggag gatggccaat aatgcccgtg    2280
agcgcctgag ggtccgagat atcaacgagg ctttcaagga gcttggccgt atggtgcagc    2340
tccacctgaa gagcgacaag ccccagacca agctcctgat tctccaccag gccgtggctg    2400
tcatcctcag cctggagcag caagttcgag aaaggaatct gaacccgaaa gctgcctgtc    2460
tgaaaagaag ggaggaagag aaggtgtcct cagagcctcc cccactctcc ttggctggcc    2520
cacaccctgg gatgggagac gcagcgaatc acatgggaca gatgtgaaaa ggtccaagtt    2580
gctaccttgc ttcattaaac aagagaccac ttccttaaca gctgtattac cctaaaccca    2640
cataaacact gctccttaac cccgtttttt tttgtaatat aagacaagtc tgagtagtta    2700
tgaatcgcag acgcaagagg tttcagcatt cccaattatc aaaaaacaga aaacaaaca    2760 aaaaaatgaa tgaaagaaag aaagaaagaa aaaaatgcaa cttgagggac gacttctta    2820 acatatcact ctgaatgtgc gaagcggtat gtacaggctg agacacagcc cagagactga    2880
atggcaatcc tcccacactg tggagcaatg catttgtgcc taaacttctt ttggaaaaaa    2940
aaaatataat taatttgtaa gtctgaaaaa aatatttaat ttaaaaaaaa attgtaaact    3000
tgcaataatg aaaaagtgta cttctgaaga aaacgacatg aacgttttg ttggtattca    3060 cgtcagctag tgtttctaat taccggatat tgaatagggg aagcccggct gccctcgtaa    3120
caaaaccagc aaacgtcctg atggcaacga agtgatgaca ttagccattc cttagggtag    3180
gagggacaga tggatgttat agacctatga caaatatata tataaatata tatataaata    3240
tatattaaaa atttagtgac tatggtaagc ttttgttgat ttgtttcaga cttttttctc    3300
ctgtaaaaaa atagtactga ttaactttt taaaagaaag attttactgt aaatatggat    3360 ttttttttt gtctgatttt tgtcccttcc cccggtttgt tatcgtaacc tgtagtgcca    3420
actctgcttc cggaggggca gtgcaggacg aaatgctgac cctgaagttg cttctcattc    3480
acaaatagta aaaagttgtt tctccagtct tttgggaaca caggacttaa aagtcacatc    3540
atgtgtagga attacatgca gcattgcccg ggcgaggcaa aaagcgtttg tctggcttgt    3600
ggcgctgccc ttgttaccct cccctgggat tttcagaggt acacggttag aatgctacaa    3660
tgttaccact gtgccttcca atgtttatat catcggaaac ataacataat caaagtggct    3720
gtgatttaac aaaaaaaacg attcaagtgt tacctacctg tgtagccgaa gtagtgtgca    3780
gtgaccgaga cgtttctgaa tacatggtca gattttttt ggaaaaaata caaaaattaa    3840
aaaaaaaaaa aaaaagaaa aaaagaaaaa aaaactaaaa aagaaagtca agttcaaaaa    3900
ccgtcaaatg agaaaattgc aaggagtgtg acagagctga ttgattttg ttgctttctt    3960 gattttttt tcaaaatggg tttactaaaa agtagatgac ttacctgcct cctccttcgt    4020
ctgaaaaaaa aaaaaaatgc caaccaatca tgcagcatta taacaagcct tataagccct    4080
aaagcattaa gttgcacttt tgtgaggagg ggtaacgcag tattctctct ggccagtatg    4140
```

-continued

```
agtgaagttt atacttaaca tttgatagaa acatagatca aactacggca cagcaactca      4200
tcagatagct agcgttgact ctgggcacaa ttgaaccaat tcccatcgta agtctttcca      4260
acaatggact ttggtgtgta gtgcagtgaa cacataggac tcctacgtaa gcatttgtca      4320
gcatcctttt gtctctaact cggttctgtt ttgacagcca cacaatcttg gcatgtatta      4380
aggaaaaaaa aaatccctgt tgaagtagtt tttccaccta tcagcactga gtaaatgcca      4440
taactccgcg gaaatggtct aaatacccca tttgttgtcc tgaactacca gttacatagt      4500
gacgaaacac atctgtaaat tttatgcaac caatggcaaa cctatcatta ttttgaaact      4560
gtgtatgtaa aagttatatt tttacatgta gactcttgtt attatgtgtt ttaatacatt      4620
gtatcagttt tttgtttttt tttaaactgt gtggttttaa aaagtcattt aaatgaaata      4680
gtgagctaca agaatctgaa atttatgttc atttctgaaa atgtaagaac aaataagata      4740
gttaccacgt ggtcaccttt tacaaaccca tgaacatttt gattagctgt gtgcatgtgt      4800
gtgcgtgtgt gctcttgcgc gtgtgtgtgt gtgtgtgtgt gtgtgtatgt gtgtgtgttg      4860
aaaattgtaa atatgttcag tagcgataaa actaaaatgc tttgatttgt tgagaagttc      4920
ctaaaatgtg gaggtggatt gaaaatgtag gggaatagca ggaatcaaat ctcataaaaa      4980
gttcttcggg gactttgctg tgatgcggtg gcacaaaggt gctccaagaa gggcaaagaa      5040
gaaagacagt aacttcccct cctccctgaa cgatggaaaa catgtgtacg tggtctctca      5100
ccatgttaaa gatttttttt ccgtgataca ttctgcactc attttgtata gtctgccaag      5160
gcgggtatcc ctaggaacaa tattattata taggaaacag gtatcgtccg atcacattca      5220
ggagaagcgt atagaaaaga atatggtgtt tactctttag ggaactggaa atcctccccg      5280
cattgatgga tatcttcaga gtggcacttt tgatacatgt tatcataaag gtgcttacta      5340
aagcagaatc aaagtttttc aactctgtaa acaaagcaaa aaattaaatt tttaaattaa      5400
atcatttgag attttttttt tcaattggtg cttttatatt ttgttctcac tcggacagag      5460
aaaaagctgc aatttcatgt tctcaccagc tttgatgtat tcattacttg gtaatgtaat      5520
atggctattg tcaaattcct tttggaaata agcaaaagac tccccaaagg ccagcagcag      5580
ctgctggcta ctttctgctt ggtgcggaaa cctgatctga ccctctttgt agtaatcagg      5640
tgtatctcca gttttaaaaa gaaggagaaa ggaaatgtgg ccgtttttaac gtgttggttt      5700 tgttttgttt tgttttgttt tgttttcctt gttgttattt tgtaattatc aaacccaggt      5760
aagatattgg tattcctgca ctggattttt gaaagaaact tagcagaagt caggattaaa      5820
atactacaca aacatttcat aagtgttcat cctatactag acatacacga aggcggtgag      5880
gcttaggtgc aggatcggtt taagagactt tgaaagcaac ttggaacagt tgatccacct      5940
ccacattaaa gtaaattatg aatatgcaga attagggatc tgtccatctt ggagttgtta      6000
ctctttttgt cttctgtatg gcagtgatga acactaatgc tttgacagct ttcagcccac      6060
ccagtggtcc aactgattcc aattcagtct tccgattcct ggttttgttt tgtctttcca      6120
cttttttttt cctatcttga ttttattgtt attgttattg ttattattat tattattatt      6180
attattaata ttcatgatgt ttgtttttgat gagggattgg gaagtgggag ggagtcgaac      6240
tgagactagg ggctgagagg atttttttttt ttccatcttt gcatccaaca ggcagaatat      6300
ggtctgtgtc caaaacggaa cttaagtcag gaaggaaacc attcagcata aacaagcaca      6360
acatgtagtc tgccggctga ctggaagcat aaataaataa ataaataaca catacggagg      6420
tgaagatgga atgtgctgga ttccaagaca atggggcacc aaggcctgag ggcctcctct      6480
```

-continued

```
tgactttgct ttggttatgt ttgttttctt tagagatgtc ttttctcatg ggacttgaag      6540
tgactcatct ctgtgcagta ctggtttcgc catatgctca tttcaagtat tatagacata      6600
tgtaatggtg aaatatatga actgtggcct tttctcattct tgttacttgt gatgcaatta     6660
agtgaagata agaaaaaaaa aaagcagaga tttaccatgt atcagtgcct ggctttttgt      6720
tataaagctt cgtctgtcta gtgctctttt tgctataaaa aatagactgt agtacaccct      6780
agtaggaaaa aaaactaaa tttaaaaata aaaaaatata tttggcttat ttttcgcagg       6840
agtaatcctt ttataccatg gatattacaa aaaaaaatgt cagattctga gtatttcttc      6900
tttgtagatt tttggaatca ttatgagtaa aagtttgtta ctttattttg ctatttaaaa      6960
gatgttattt taccatgtgt tactgaaagg aaactgtatg gtagagcttc tgtttgtttt      7020
tgttttcagg tttttttttgt ttgtttgttt ttagttgtag gtcgcagtat gaactttttt     7080
tttgtttctc gttatgtttt gttttgtttt tgcgactgta cacatagctg cagcattaaa      7140
aacttttaaa aaattgttta aaaaaaaaga aaaaaaggga aaacgtttta aaaaaaaaga      7200
taaacagtta caccttgttt tcaatgtgtg gctgagtgcc tcaatttttt catgtttttg      7260
gtgtatttct gatttgtaga agtgtccaaa caggttgtgt gccggacttc cttcaagagg      7320
cccacagccc agcttggtct agacctgttc ccatctgtag ttactcgatg aagtcatgta      7380
catgaccgtt ctgtagcaat aaatgtgcca tttttataaa ctgtctctga cacttttttc      7440
atttcacctc tcgtgcacat ag                                               7462
```

```
<210> SEQ ID NO 43
<211> LENGTH: 6104
<212> TYPE: DNA
<213> ORGANISM: Homo sapiens

<400> SEQUENCE: 43
gagccgagcg cggtggtgag gccgcctcag cgaaaaaaat gtccgcctga agagacccac       60
aagttctatt cgggggggacc gacagcccgc cccgggagga aggggcggcc aggcccgaaa      120
gccgcctccc cctcccagac ccgagagctc gtgcggggca aagtgaaccg agccgctggg       180
cggtgcaagg ggaagcccaa gcccgttctc ccggccaaag tgaactttaa tcggggtggt       240
tggatgcgga gacgggggcgg cagaagtggc cgaagatgaa tccccagcaa caacgcatgg      300
ccgctatagg gaccgacaag gagctgagcg acctactgga cttcagtgcg atgttttccc       360
cacctgttaa tagtgggaaa actagaccaa ctacactggg aagcagtcaa ttcagtggat       420
caggtattga tgaaagagga ggtacaacat cttgggggaac aagtggtcaa ccaagtcctt       480
cctatgattc atctagaggt tttacagaca gccctcatta cagtgatcac ttgaatgaca       540
gtcgattagg agcccatgaa ggcttgtccc caacacettt catgaactca aatctgatgg       600
gaaaaacatc agagagaggc tcatttttccc tgtacagcag agatactgga ttaccaggct       660
gtcaatctag tctcctgaga caagatctgg ggcttgggag cccagcacag ctatcttctt        720
caggaaaacc tgggacagca tactattcat tctctgctac aagttccagg aggagaccac       780
tccatgactc tgcagcgctt gatcccttgc aagcaaaaaa agtcagaaag gtgcctcctg       840
gtttgccttc ttctgtatat gcaccatccc caaattcaga tgatttcaac cgtgaatctc       900
ctagttatcc atctcctaag ccaccaacca gtatgttcgc tagcactttc tttatgcaag       960
atgggaccca caattcttct gacctttgga gttcatcaaa tgggatgagc cagcctggtt       1020
ttggtggaat tctggggacc tccacttccc acatgtctca atccagtagt tatggcaacc      1080
ttcattcaca tgaccgcttg agttatcctc cacactcagt ttcaccaaca gacataaaca      1140
```

-continued

```
cgagtcttcc accaatgtcc agctttcatc gcggcagtac cagcagttca ccttacgttg    1200
ctgcctcaca cactcctccc atcaatggat cagacagcat tctaggaacc agagggaatg    1260
ctgctggaag ctcacagaca ggtgatgcac ttggaaaggc tttggcatct atttattctc    1320
ctgaccatac cagcagtagt tttccgtcaa atccatcaac accagttgga tcaccttcac    1380
ctctcacagg taccagtcag tggccaagac ctggagggca agcaccttca tccccaagct    1440
atgaaaactc actccactcc ctgaaaaatc gagttgagca gcaacttcac gagcatttgc    1500
aagatgcaat gtccttctta aaggatgtct gtgagcagtc tcgaatggag gatcgtttag    1560
acagactgga tgatgcaatc catgtgctgc ggaaccatgc tgtgggacct tccaccagtt    1620
tgcctgctgg tcacagtgat atacatagtt tattgggacc atcccataat gcaccaattg    1680
gaagcctcaa ttcaaactat ggaggatcaa gccttgttgc aagcagtcga tcagcttcaa    1740
tggttggaac tcatcgggaa gactctgtca gtctcaatgg caatcattca gtcctgtcta    1800
gtacagtcac tacttcaagc acagacctga accataaaac acaagaaaat tatagaggtg    1860
gcttgcaaag tcagtctgga actgttgtta caacagaaat caagactgaa aacaaagaaa    1920
aggatgaaaa ccttcatgaa cctccttcat cagatgacat gaagtcagat gatgaatcct    1980
cccaaaaaga tatcaaggtt tcatctagag gcagaacaag cagtactaat gaagatgagg    2040
atttgaaccc tgaacagaag atagaaaggg agaaggagag gcggatggct aacaatgcca    2100
gagaacgctt acgcgtgcgg gatattaatg aagcattcaa agagcttggc cgaatgtgtc    2160
agcttcactt gaagagtgaa aaaccccaaa caaaactcct tattcttcat caagccgtgg    2220
cagtcatcct tagtctagaa cagcaagtca gagagaggaa ccttaacccc aaagcagcct    2280
gccttaagag aagggaagaa gaaaaagttt ctgccgtatc ggcagagccg ccaaccacac    2340
tgccaggaac ccatcctggg cttagtgaaa ctaccaaccc tatgggtcat atgtaaacat    2400
cagccagttc cagagttatc agtaggctag atagaaggtg acctctcctc ataaggactt    2460
ggacaactca gattatctga agacacaaac ctgacaggag ggagaagaaa aaacaaaaca    2520
cttgaaccaa gaaactcaaa tgtaatccta cgatcaaagc aactggtcaa cacttccatc    2580
agaagtgaag ataggaagct catcagatag aacatcagcc catgagatgt ttgcaacaaa    2640
tcttttgttg caagcagtgt gtcgcttctg cacaatcaga gactgtctcg atctctccac    2700
tcaccgtgga agttgccttg tgcctaaact gaattgacaa atgcattgta actacaaatt    2760
ttatttattg ttatgaaact gtaaggtcta catataaagg gaaaaagtta atgtggaaag    2820
ctgatctaca ctcagctgat gccagcatac attaaagcgg ttcacgtgca gagaacaaag    2880
cagtgacaac cattggccct tagcattccc ggcataccta ttagtgtctt aaaaaggaag    2940
ggaaaagtct tttgttgccc tctcctatcc tcttgccata tgaatagcgt tttccatgaa    3000
ataggaaaat attacttggt atagcatttc tcttgctctc attttttgat ttattttat    3060 tttctctttg tgggtgttat atttgatctc taaatctgaa cagttatgg tcacagtcca     3120 gcctcctccg tgcagccctg tgtgctttgc acatttacct tacagtggta agcagagacc    3180
atctgtgacc atagcctagc tagcatttta aaagggaaa ttttgttctc taggttttcc     3240
cccaaataaa cattgcttta tttctaataa taaccaagac ttttcaagct tctagatctc    3300
ataggaaagc ttgtaatagc aaaattgtaa attacaaggg aagaatctac tttttagaaa    3360
tcgctttgtt ttccaagcag taagtactac atacagtact tgtaaagtgt tagctgtaag    3420
taagcacaaa atacatttaa aatacaaaga cgattttttc aggctgtgat tatggtgaac    3480
```

-continued

```
ataacaaaac ccagtagtca ccaaggcagg tagtgtgata aatgaacaca ccactctgag   3540
gctaattacc taatggaata caagagcaat ggtcacccgt atttccttat cctagccttt   3600
atttctctgt catttggatg gctggtcaat ggggaagaat tgagtgggtg atttaatcaa   3660
ctgcaaacca tctgcccctg tcccaaaatg atgagccaga ttagcattaa accagtactt   3720
gtcagtccat cttaatactg ttcattaagg cactctctgt ctctaatcct taggagttgt   3780
tttaaaagac ataatcactt tgaacttcca tgaaacctgt cttccaccac aacaaccctg   3840
ggagagaaaa acatgctaaa ggaggtatct tggcttaata attccttata gccaatatca   3900
acagtggcaa tcagcacaca gaggaaagga cccaaatcac tatgtagctt aaagatttct   3960
gttaatttga aagaacaaaa acaagacaga acttctggta ctctaatcag gatgattcct   4020
aacaagtcag tcatttgtga acttagtgga cttttttggtt actttaattt gcatatattc   4080
tccagttaca tcggactcta tctgtggcct tgttcttcat ttcagtgtta atcagctaaa   4140
cagaagttgt tgcttatgat gtgtgagtga acatatgcca ctgcctggcc tttttttctt   4200
cagagcttgt tgtctttttc gctatattag actttgcagt atgcccagaa gctttccttc   4260
ataaaataga aagaaaaaaa catttggctt attttttcact gtagctagtc ttttatacaa   4320
taatcttgta agaaaatttc ttgaattcta aatattactc tttctagatt tttgaaatca   4380
aaaagttttc agtaaaaagt ttcttacttt attttattat attaggtagt aaaaaatgta   4440
gggttattta ccataacctg ttcattaata tcagaaattt acaatagcat tttaagacca   4500
tagtaggatt ctagcatacc gtgtagtacc tatggagtat tgtaagagct aattgttgga   4560
gatgaattgc ttctcatctt gttctccagt ttccattgtt ggtttattgc agatttgtat   4620
cctgtgtcaa attcaaggta ttattgataa accttttcaa ccagcagcaa gaagttcaaa   4680 ttttttttctg tcactgtaac agaaaacaca atatgtatat aacatttatg tagcaataaa   4740
tgtgccatct ttttttttaac acagtaaaat agtgagtttt ttacatttct ctttctcaaa   4800
taataatgta ttttgtttta ttttctccat ctcattcgtc ccagaaacac tcacactgct   4860
tttcctaact gcattaccga cattatctgg gaaacccttc aggacagaat caggcttgtg   4920
gagctaagtt ggcaatctgg tctagagctt ctctagcttg tgcttttctc ctcttgccct   4980
cactactgac ggtggccttt taacctttttc ctaaagattg accaaacagc aactagtagt   5040
tatagaaaat ctactcattt gtagatacag agaaaaatga agaagatgga aaaagactca   5100
aaagaggctt tttaagttat tcttcaaagc acttttcaca tttccccata cccttttctca   5160 caaaaaaagt gtcataatta agtaatggta ttgtttactg tttaaaagtt aaaagatcaa   5220
aaatttgctt ttatcccagt ttttaaccac aaaaaaaagc gtagggatta tccatgagga   5280
cttcatgcca agcaagaacc tcaaacaaac tagacaaact ttttttttttga cagtgaatga   5340 cttttttgtag gacctgtgcg tgcgaaaccc atggcaattg tcacatcctc ttggtatgct   5400
ggcagattgc ttctcttggt gaattatgaa atccactgtt cacattgggt gcctaacaga   5460
acattttgct tcttgtggga tttagtgaaa actattaaac ttgttaagtt gattttatac   5520
aaaacgataa ataaaaagct ctaagaagaa aatgtataat cttagagctg aaataaaata   5580
tagagaccat ctagtaaatg acctcattaa tatatctgtg aaaactgaga ctcagattgt   5640
atgtctctaa gaacacataa ttagtaacag atcaagacac ttaaaacttt ccctacaaaa   5700
cctccctgcc ttgactttct ctttctcttt gcagatttct aggccgcttc tgctcagtgt   5760
cttcattttc ttccatattt gttttatttc attttttcttt tctatagttc atgttttctt   5820
tttccttgga aactcaaaat ttaaacacac gtcgtgtgtg tgtgtgtgtg tgtgtctgtg   5880
```

```
tgtgtgtgac ttaaagaatc ttaagctttg gcattaaata gtcctcgatt caaatctaag      5940
ctcaacatct gattaacttc attttcctat ctgaaaaatg gagataacat tagaattgtg      6000
taagtattga atgaaacaat gtatggaaag ctcttatggt tcttgtcacc taagaagtac      6060
ttaataaatg ataaatattt ttaaataaat aatattataa ccaa                       6104

<210> SEQ ID NO 44
<211> LENGTH: 4707
<212> TYPE: DNA
<213> ORGANISM: Mus musculus

<400> SEQUENCE: 44
ggaaaaaaaa aaaaatgtcc gcctgaggag acccacaagt tctatcgggg ggacagccag        60
cccgcccggg gagccacggg cggctaagcc cgagagccgc ccgagtcgcg ccgactcaag       120
cactcgcggg ggcccgaggc aacgcagccg ccggcggcgc gtggggaggg ggaaagcctg       180
agcccgcgct cccggccaaa gtgaacttta atcgggaagg ttggatgcgg agcccgggcg       240
gcaggacctg ctagaagtgg ctgaagatga atccccagca gcagcgcatg gccgcgatag       300
ggaccgacaa ggagctgagc gacctgctgg acttcagtgc gatgttttct ccacctgtta       360
atagtgggaa aacgagacca acaacactgg gaagtagtca gttcagcggg tcaggtatgg       420
atgagcgtgg aggaacaaca tcttggggaa caagtggtca accaagcccc tcctatgatt       480
catctagagg ttttacagac agccctcatt acagtgatca cttgaatgac agtcgattag       540
gaacccacga aggcttgtcc ccaacacctt tcatgaactc aaatctgata gggaaaacat       600
cagagagagg ctcattttcc ctgtacagca gagactctgg actctcaggc tgtcagtcta       660
gtctcctgag acaagatcta ggacttggga gcccggcaca gctgtcttct tcaggaaagc       720
ctggaacacc atactactca ttctctgcca caagttcgag aagaagaccg ctccatgatt       780
ctgtagccct agatccttta caagcgaaga aagtaagaaa ggtgcctcct ggcctacctt       840
cttctgtata tgcaccatcc ccaaattctg acgatttcaa ccgtgaatct cctagttacc       900
catctcccaa gccaccaacc agtatgttcg ctagcacttt ctttatgcaa gatgggaccc       960
acagttcttc tgacctttgg agttcatcga atgggatgag ccagcctggt tttggtggaa      1020
ttctggggac ctccacatcc cacatgtctc agtccagtag ttatggcagc cttcattcac      1080
atgaccgctt gagttatcct ccacactcag tgtcaccaac agacataaac acaagtcttc      1140
cgccaatgtc cagcttccac cgtggtagta ccagcagctc accatatgtt gccgcctcac      1200
atactcctcc catcaatgga tcagatagca tcctaggaac cagagggaat gctgctggaa      1260
gctcacagac gggtgatgca cttgggaagg ccttggcatc tatttattcc cctgaccaca      1320
caagcagtag ttttccatca aaccatcaa caccagtggg atctccttca cctctcacag      1380
gtaccagtca gtggcccaga ctggagggc aagctccttc atctccaagc tatgaaaact      1440
cacttcactc cctgaaaaat cgagttgagc agcaacttca cgagcatttg caagatgcaa      1500
tgtccttctt aaaggatgtc tgtgagcagt ctcgaatgga agaccgctta gacaggctgg      1560
atgatgctat ccatgtgcta cgaaaccatg cagttggacc ttctaccagt ctgcctacta      1620
gccacagtga catacacagt ttgctgggac catcccataa tgcatcaatt ggaaacctca      1680
attcaaacta tggaggatcc agccttgtta caaatagtcg atcagcttcg atggtcggaa      1740
cacatcggga gattcagtc agtctcaatg gcaatcattc ggtcctgtct agtactgttg      1800
ctgcctcaaa cacagaactg aaccataaaa caccagaaaa tttcagaggt ggtgtacaaa      1860
```

-continued

```
atcagtctgg aagtgttgtt ccaacagaaa tcaagactga aaacaaagaa aaagatgaaa      1920
accttcatga acctccttca tcagatgaca tgaaatcaga tgatgagtcc tcccagaaag      1980
acatcaaggt ctcatctagg ggcagaacaa gcagtaccaa tgaagacgag gatctgaatc      2040
cagaacagaa aatcgaaagg gagaaggaaa ggcggatggc taacaatgcc agagagcgcc      2100
tgcgcgtgcg ggatattaac gaggcgttca aggagcttgg ccgaatgtgt cagcttcatt      2160
tgaagagtga aaaacctcag acaaaacttc tcattcttca tcaggccgtg gcagtcatcc      2220
ttagtctaga acagcaagtg agagagagga acctcaaccc caaagcagcc tgccttaaga      2280
gaagagaaga agaaaaagtc tctgctgcgt cagcagagcc gcccaacacg ttgccaggag      2340
cccatcctgg gcttagtgag tctaccaacc ctatgggtca tctgtaaaca tcagccagtt      2400
ccagagtcat cagtaggcta aatagaaggt gacctctcct cataagattt ggacaactca      2460
gattatctga agacacaaac ctggcaggag ggagaagaaa aagcaaaaca cttgaaacca      2520
gaaactcata tgtaatcctg tgatcaaagc aactggtcag cacttcatca gacgtgagca      2580
taggaagctc agcagagacc gtcggccgtg aggtgtttgc agcatatcac tctgctgtaa      2640
tcagtgtgtc gcttctgcac aatcagagac tgtctcatct ctccactcaa cgtggaagtt      2700
gccttgtgcc taaactgaat tgacaaatgc attgtaacta caaattttat ttattgttat      2760
ggaactgtga ggtctacata taaagggaaa agttcatgtg ggaagctgat gtacactcag      2820
ctgatgccag cattgttaaa gctgttcaca gagcagtggc aaccattggc ccttagcatt      2880
cccggcatac ctgttagtgt cttaaaaagg aagggagtcc tttgttgccc tctccgacct      2940
tcgccatatg aatagtgatt tccatgaaat aggaaaaata ttacttcgta tagcatttct      3000
ctcttgtttt tttcactcat ttttatttcc tctttgtggg tgttatattt gatctgagtc      3060
tgcatagttt atggtcacag tccagaaccc tccttgcagt cctgtatgct ttgttcatgt      3120
ccttgaagtg ataagcagac accatctgtg accatagcct agctaatatt ttgaaagggg      3180
aagttttgtc ccctggattt gcccccaaat aaacattgct ttatttctaa taatcactaa      3240
gacttttcag gcttctaggt ttcatagtaa agctataata gcaagaagtg taacttacaa      3300
gggagagttt acttttttagg aattgctttg ttttccgagc agtaagtact acacaatata      3360
gtacttgtaa agtgttagct gataagtaag cacagaatgc attcagtaca atacaaagat      3420
gacttttcct ggtgagtctc cgggacaggc agtgtgatga atgcactcaa ccgctctgag      3480
gctaattacc tatggaatcc aagagcaatg gtcacggttc cttaccctag ctttacttct      3540
gtcctttgag ttggctggtc cgtggggggt ggggcaggag ggtgacttaa tcacctgcaa      3600
accacctgcc cccaccccaa gaagagccag attagcaccg agctgtacct gtcagtctgt      3660
cttagcatta tgcattaagg caccctctgt ctctaatccc ttacagttgt tttttaagaca     3720 cagtaatcac tttaaacttc catgaaatct gtcttccacc acagcaccct gggagagaaa      3780
aacatgctaa gcgtgatggt cttggctaag taactcctta aagccaatag cagtggcagt      3840
ctgcacagaa gaaaaatccc aagtcgttct gtaacttaga gacaccggag aattttgaaa      3900
gaacaaaaac catgaagaca gcacttcaga tcctccatca ggactctggt gaacacgtca      3960
gtctttggcg aacttagtgg acttaatttg tatatgttct ccagttagat cagactctat      4020
ctgtggcctt gttcttcatt tcagtgttaa tcagctaaaa cagcagttgt tgctatgatg      4080
tgtgagtgaa cataagccac tgcctggcct tttttcttca gagcttgtcg tcttttttcgc     4140 tatattagac tttgcagtat gcccagaagc tttccttcat aaaatagaaa gaaaaaaaca      4200
tttggcttat ttttcactgt agctagtctt ttatacaata atcttgtaag aaaatttctt      4260
```

-continued

```
gaattctaaa tattactctt tctagatttt tgaaatcaaa agttttcagt aaaaagtttc    4320
ttactttatt ttattatatt aggtagttaa agaaaatgta gggttattta ccataacctg    4380
ttcattaata tcagaaattt acaatagcat tttaagagca tagtaggttc tagcatacca    4440
tgtagttcct atggagtatt gtgagagcga attgttggag atgagctgct tttcatcttg    4500
ttctccagtt tccattgttg gtttattgca gatttgtatt ctgtgtcaaa ttcaaggtat    4560
tattgataaa ccttttcaac cagcagcaag aagttcaaat ttcttttttc tgtcgctgta    4620
acagaaaaca cagtatgtat ataacattta tgtagcaata aatgtgccat cctttttttt    4680
aacatagtaa actagtgagt tttttac                                        4707
```

```
<210> SEQ ID NO 45
<211> LENGTH: 4116
<212> TYPE: DNA
<213> ORGANISM: Homo sapiens

<400> SEQUENCE: 45
gtttcgcttt cctgcgcaga gtctgcggag gggctcggct gcaccggggg gatcgcgcct      60
ggcagacccc agaccgagca gaggcgaccc agcgcgctcg ggagaggctg caccgccgcg     120
cccccgccta gcccttccgg atcctgcgcg cagaaaagtt tcatttgctg tatgccatcc     180
tcgagagctg tctaggttaa cgttcgcact ctgtgtatat aacctcgaca gtcttggcac     240
ctaacgtgct gtgcgtagct gctcctttgg ttgaatcccc aggcccttgt tggggcacaa     300
ggtggcagga tgtctcagtg gtacgaactt cagcagcttg actcaaaatt cctggagcag     360
gttcaccagc tttatgatga cagtttttccc atggaaatca gacagtacct ggcacagtgg     420
ttagaaaagc aagactggga gcacgctgcc aatgatgttt catttgccac catccgtttt     480
catgacctcc tgtcacagct ggatgatcaa tatagtcgct tttctttgga gaataacttc     540
ttgctacagc ataacataag gaaaagcaag cgtaatcttc aggataattt tcaggaagac     600
ccaatccaga tgtctatgat catttacagc tgtctgaagg aagaaaggaa aattctggaa     660
aacgcccaga gatttaatca ggctcagtcg gggaatattc agagcacagt gatgttagac     720
aaacagaaag agcttgacag taaagtcaga aatgtgaagg acaaggttat gtgtatagag     780
catgaaatca gagcctgga agatttacaa gatgaatatg acttcaaatg caaaaccttg     840
cagaacagag aacacgagac caatggtgtg gcaaagagtg atcagaaaca agaacagctg     900
ttactcaaga gatgtgtattt aatgcttgac aataagagaa aggaagtagt tcacaaaata     960
atagagttgc tgaatgtcac tgaacttacc cagaatgccc tgattaatga tgaactagtg    1020
gagtggaagc ggagacagca gagcgcctgt attggggggc cgcccaatgc ttgcttggat    1080
cagctgcaga actggttcac tatagttgcg gagagtctgc agcaagttcg gcagcagctt    1140
aaaaagttgg aggaattgga acagaaatac acctacgaac atgaccctat cacaaaaaac    1200
aaacaagtgt tatgggaccg caccttcagt ctttttccagc agctcattca gagctcgttt    1260
gtggtggaaa gacagccctg catgccaacg caccctcaga ggccgctggt cttgaagaca    1320
ggggtccagt tcactgtgaa gttgagactt ttggtgaaat tgcaagagct gaattataat    1380
ttgaaagtca agtcttatt tgataaagat gtgaatgaga gaaatacagt aaaaggattt    1440
aggaagttca acattttggg cacgcacaca aaagtgatga acatggagga gtccaccaat    1500
ggcagtctgg cggctgaatt tcggcacctg caattgaaag aacagaaaaa tgctggcacc    1560
agaacgaatg agggtcctct catcgttact gaagagcttc actcccttag ttttgaaacc    1620
```

-continued

```
caattgtgcc agcctggttt ggtaattgac ctcgagacga cctctctgcc cgttgtggtg     1680
atctccaacg tcagccagct cccgagcggt tgggcctcca tcctttggta caacatgctg     1740
gtggcggaac ccaggaatct gtccttcttc ctgactccac catgtgcacg atgggctcag     1800
ctttcagaag tgctgagttg gcagttttct tctgtcacca aaagaggtct caatgtggac     1860
cagctgaaca tgttgggaga gaagcttctt ggtcctaacg ccagccccga tggtctcatt     1920
ccgtggacga ggttttgtaa ggaaaatata aatgataaaa attttccctt ctggctttgg     1980
attgaaagca tcctagaact cattaaaaaa cacctgctcc ctctctggaa tgatgggtgc     2040
atcatgggct tcatcagcaa ggagcgagag cgtgccctgt tgaaggacca gcagccgggg     2100
accttcctgc tgcggttcag tgagagctcc cgggaagggg ccatcacatt cacatgggtg     2160
gagcggtccc agaacggagg cgaacctgac ttccatgcgg ttgaacccta cacgaagaaa     2220
gaactttctg ctgttacttt ccctgacatc attcgcaatt acaaagtcat ggctgctgag     2280
aatattcctg agaatcccct gaagtatctg tatccaaata ttgacaaaga ccatgccttt     2340
ggaaagtatt actccaggcc aaaggaagca ccagagccaa tggaacttga tggccctaaa     2400
ggaactggat atatcaagac tgagttgatt tctgtgtctg aagttcaccc ttctagactt     2460
cagaccacag acaacctgct ccccatgtct cctgaggagt ttgacgaggt gtctcggata     2520
gtgggctctg tagaattcga cagtatgatg aacacagtat agagcatgaa tttttttcat     2580
cttctctggc gacagttttc cttctcatct gtgattccct cctgctactc tgttccttca     2640
catcctgtgt ttctagggaa atgaaagaaa ggccagcaaa ttcgctgcaa cctgttgata     2700
gcaagtgaat ttttctctaa ctcagaaaca tcagttactc tgaagggcat catgcatctt     2760
actgaaggta aaattgaaag gcattctctg aagagtgggt ttcacaagtg aaaaacatcc     2820
agatacaccc aaagtatcag gacgagaatg aggggtcctt tgggaaaggag aagttaagca     2880 acatctagca aatgttatgc ataaagtcag tgcccaactg ttataggttg ttggataaat     2940
cagtggttat ttagggaact gcttgacgta ggaacggtaa atttctgtgg gagaattctt     3000
acatgttttc tttgctttaa gtgtaactgg cagtttttcca ttggtttacc tgtgaaatag     3060
ttcaaagcca agtttatata caattatatc agtcctcttt caaaggtagc catcatggat     3120
ctggtagggg gaaaatgtgt attttattac atctttcaca ttggctattt aaagacaaag     3180
acaaattctg tttcttgaga agagaatatt agctttactg tttgttatgg cttaatgaca     3240
ctagctaata tcaatagaag gatgtacatt tccaaattca caagttgtgt ttgatatcca     3300
aagctgaata cattctgctt tcatcttggt cacatacaat tatttttaca gttctcccaa     3360
gggagttagg ctattcacaa ccactcattc aaaagttgaa attaaccata gatgtagata     3420
aactcagaaa tttaattcat gtttcttaaa tgggctactt tgtcctttt gttattaggg     3480 tggtatttag tctattagcc acaaaattgg gaaaggagta gaaaaagcag taactgacaa     3540
cttgaataat acaccagaga taatatgaga atcagatcat ttcaaaactc atttcctatg     3600
taactgcatt gagaactgca tatgtttcgc tgatatatgt gttttttcaca tttgcgaatg     3660 gttccattct ctctcctgta cttttttccag acactttttt gagtggatga tgtttcgtga     3720
agtatactgt attttttacct tttttccttcc ttatcactga cacaaaaagt agattaagag     3780
atgggtttga caaggttctt ccctttttaca tactgctgtc tatgtggctg tatcttgttt     3840
ttccactact gctaccacaa ctatattatc atgcaaatgc tgtattcttc tttggtggag     3900
ataaagattt cttgagtttt gttttaaaat taaagctaaa gtatctgtat tgcattaaat     3960
ataatatgca cacagtgctt tccgtggcac tgcatacaat ctgaggcctc ctctctcagt     4020
```

-continued

```
ttttatatag atggcgagaa cctaagtttc agttgatttt acaattgaaa tgactaaaaa    4080
acaaagaaga caacattaaa acaatattgt ttctaa                              4116

<210> SEQ ID NO 46
<211> LENGTH: 5150
<212> TYPE: DNA
<213> ORGANISM: Mus musculus

<400> SEQUENCE: 46
aggtgcggat ccgggtgcgg gtgcgggtgg aagtggggcg ccctctcctc ggacctgggg      60
tctgctgccc acaggtgacc tgtcatcccg cagagagaac gccaggagcc ggatcgcttg     120
cccaactctt ggcgctgctt ggctctctta tcctgccgtt ctcacttcta ggtcgtttca     180
gctctgctcc ataccctgag ccggcgccac gccgccgcgc atgcaactgg catataactt     240
gctgtgtgtg gtgattgctt gtgttgaatc ccgaacctgc acccggagac agcccaagga     300
tgtcacagtg gttcgagctt cagcagctgg actccaagtt cctggagcag gtccaccagc     360
tgtacgatga cagtttcccc atggaaatca gacagtacct ggcccagtgg ctggaaaagc     420
aagactggga gcacgctgcc tatgatgtct cgtttgcgac catccgcttc catgacctcc     480
tctcacagct ggacgaccag tacagccgct tttctctgga gaataatttc ttgttgcagc     540
acaacatacg gaaaagcaag cgtaatctcc aggataactt ccaagaagat cccgtacaga     600
tgtccatgat catctacaac tgtctgaagg aagaaaggaa gattttggaa aatgcccaaa     660
gatttaatca ggcccaggag ggaaatattc agaacactgt gatgttagat aaacagaagg     720
agctggacag taaagtcaga aatgtgaagg atcaagtcat gtgcatagag caggaaatca     780
agaccctaga agaattacaa gatgaatatg actttaaatg caaaacctct cagaacagag     840
aaggtgaagc caatggtgtg gcgaagagcg accaaaaaca ggaacagctg ctgctccaca     900
agatgttttt aatgcttgac aataagagaa aggagataat tcacaaaatc agagagttgc     960
tgaattccat cgagctcact cagaacactc tgattaatga cgagctcgtg gagtggaagc    1020
gaaggcagca gagcgcctgc atcgggggac cgcccaacgc ctgcctggat cagctgcaaa    1080
gctggttcac cattgttgca gagaccctgc agcagatccg tcagcagctt aaaaagctgg    1140
aggagttgga acagaaattc acctatgagc ccgaccctat tacaaaaaac aagcaggtgt    1200
tgtcagatcg aaccttcctc ctcttccagc agctcattca gagctccttc gtggtagaac    1260
gacagccgtg catgcccact cacccgcaga ggcccctggt cttgaagact ggggtacagt    1320
tcactgtcaa gctgagactg ttggtgaaat gcaagagct gaactataac ttgaaagtga    1380
aagtctcatt tgacaaagat gtgaacgaga aaaacacagt aaaggatttt cggaagttca    1440
acatcttggg tacgcacaca aaagtgatga acatggaaga atccaccaac ggaagtctgg    1500
cagctgagtt ccgacacctg caactgaagg aacagaaaaa cgctgggaac agaactaatg    1560
aggggcctct cattgtcacc gaagaacttc actctcttag ctttgaaacc cagttgtgcc    1620
agccaggctt ggtgattgac ctggaggtct ttgttccctt tcagaccacc tctcttcctg    1680
tcgtggtgat ctccaacgtc agccagctcc ccagtggctg ggcgtctatc ctgtggtaca    1740
acatgctggt gacagagccc aggaatctct ccttcttcct gaacccccg tgcgcgtggt    1800 ggtcccagct ctcagaggtg ttgagttggc agtttttcatc agtcaccaag agaggtctga    1860
acgcagacca gctgagcatg ctgggagaga agctgctggg ccctaatgct ggccctgatg    1920
gtcttattcc atggacaagg ttttgtaagg aaaatattaa tgataaaaat ttctccttct    1980
```

-continued

```
ggccttggat tgacaccatc ctagagctca ttaagaagca cctgctgtgc ctctggaatg      2040
atgggtgcat tatgggcttc atcagcaagg agcgagaacg cgctctgctc aaggaccagc      2100
agccagggac gttcctgctt agattcagtg agagctcccg ggaaggggcc atcacattca      2160
catgggtgga acggtcccag aacggaggtg aacctgactt ccatgccgtg gagccctaca      2220
cgaaaaaaga actttcagct gttactttcc cagatattat tcgcaactac aaagtcatgg      2280
ctgccgagaa cataccagag aatcccctga agtatctgta ccccaatatt gacaaagacc      2340
acgcctttgg gaagtattat tccagaccaa aggaagcacc agaaccgatg gagcttgacg      2400
accctaagcg aactggatac atcaagactg agttgatttc tgtgtctgaa gtccaccctt      2460
ctagacttca gaccacagac aacctgcttc ccatgtctcc agaggagttt gatgagatgt      2520
cccggatagt gggccccgaa tttgacagta tgatgagcac agtataaaca cgaatttctc      2580
tctggcgaca ttttttttccc atctgtgatt ccttcctgct actgttcctt catatgcagt      2640
atttctaggg aaatgcaaga aagaaagagc atcacatttg ctgagcactg ctggtagaaa      2700
gtggatattt ctctaattag aaacctgtta ctctgaagga cttcatgcat cttactgaag      2760
gtgaaatgga aagtcactta acacaaaatg gattttgtaa acaaagacca agagatccac      2820
ccaagcacca ggactagagt gcgagtattt ggggcaaggt gaggagaacg gtcactttag      2880
taatggtctg taatcagtgc ccaagtgctg cacatcactg gaaagagaca tacttatggg      2940
ggaggggcct tcttgatgga ggaatgtttc tgtcccggga gacattggca cttcccctct      3000
cctggatggc cggaagtctt ccactgtttt acatatggca cagttcaaag tcaactttag      3060
atccaatgct ctatcaaact atagtgggca tccttcatgt gagtgggaag aaaacaaccg      3120
tgctccttac tgcagcttct gccaaggcat ggttgctctc ctcagggact agctttgttg      3180
gtggcaatgg ctacacaaaa ctaaacacca acagaagtaa gaccatttc atgagtactc       3240 catcaagtta aagggttttt gttgtctttt tggtcatgga ttgaataaaa ttgtctttgc       3300
acatccatta aggggggccag ctttcttaaa gcaatttttc ttttttttta actaaaatta     3360
gatataggtg aactcatgtt ttttagtggg ctgaacttat cggtttttagc tggttgtctt     3420 aattagccat aaacttggag aaagcagtga cttcttgaat ccttagccaa atatgagtat      3480
cagataattt tattatttttt ttttcgagac agggtttctc tgtgtagccc tggctattct      3540
ggaactcact ctgtagatca ggctggcctg gaactcagaa atccgcctgt ctctgcctcc      3600
cgagtgctgg gattaaaggt gtgcaccacc aatgcctggt gagataactt taaagaactc      3660
cctataaatg catgagaacc actgttactg atgaatgtgg ttttttgaca actacattca      3720
caaatggcct gtcttgtgtt ttgtcaccgt tttgagggat gatgtttttgt ggcacgtgtg     3780 tgatcacagc ctgatggttc tggtcgtggg ttggttcttc tgggccagct ttcacagact      3840
gctgcgcagc tgcacctaca gtgctgcccc ataatactgt ttcactttgg tgaagatcag      3900
cccaccttac accccgagtg caggtgtgaa ccacggtaag tgtgcacagt ccttagggaa      3960
aacagggacg cagaggcctg cctcctctct tttccatgcc aaaatgaaat gaccaagaaa      4020
caaaacattt aaaaagttgt ttctaaatgc tgagacctaa ccattgctta tatactgttg      4080
tctgttgaaa cagtttgtta caatttcatt ctgttgaact aggtgagact ttaagaaatg      4140
ttgaaattat gttaatttcc tattattatt taatataaag atatttaaaa tgtctagtgt      4200
tatgagttgg tttaatatat atctcatgta tgtatcagtc ctattttaag cgcttttttaa     4260 aaaagacttg tttaggtata tattttatgt atatgggtgt tttatctgaa tgtatggaca      4320
ccagaagaga gcactgggtc ccatgagact acagtcaaat gggatcacag tcagatgcaa      4380
```

```
ttttgagctg ccatgtgggt gctgggattt gaactcaggg cctctggaag aacagccagt      4440
gcttttaact gctgaaccat ctcttgggac gcctatgggt cctattttaa aggaagaccg      4500
atatttccca agtgtcaccc ttgcttactc tactgcagac acaggaacta tggcagttta      4560
aggtaggtca gcgggcaggc ccagcggtga ggcctctctg aggtagaggc ctggggatca      4620
ggcgtttagt cattcaaggc cggcagggct ccatgggatc acatccaagt cagggcaaga      4680
catccactta cactttcagg tagctgcctg ttagacgtca ccaagcatgt cctagcttaa      4740
gtatgacgag gatggcattt tctaagtaca gagcatatat gtagcacttg ggataagctg      4800
atctagggac ttcctgaggc ggcagagctt aaagtggact ccattgactg cttggagact      4860
actgtggaat gaaggcatgt ctcagtaaac agaacaaacc tgtggcatct gtctgcctca      4920
gggaggcatc agacaaagct ggaaaggatt tagaaaattc ttttacctac tctgggagct      4980
gggaggctgt ccttcatccc gagggcatta tttatctgaa ggcatctttt gtttaagatt      5040
cattcatttg ttcctcaaat atgttcagtg cctgccttgc accaggcact attctagatg      5100
cgttgaaggc actaataaaa gaaatgcctc acagtaaaaa aaaaaaaaaa                  5150
```

```
<210> SEQ ID NO 47
<211> LENGTH: 5961
<212> TYPE: DNA
<213> ORGANISM: Homo sapiens

<400> SEQUENCE: 47
aaagtgaatg gcgaaggact gaagggatcc ccccttcggg tccccggccg ccctgttcac        60
cctcgttcat cctcctttcc gaagctcgct ctcgaaggca ggagcgaccg gcgcctttgg       120
ctgaggagga ggagaaggag gaatcgcgcc aggcggagcg tcaggtcccg ttttcctctc       180
cggcgtctcc aatacaaaga ttacggtgca gaaggaaatt gcactcgtct cctccgcgcc       240
cccggtaccc aacacaatgc accagccgcc tgagtccacc gccgcggccg ccgccgctgc       300
agacattagc gctaggaaga tggcgcaccc ggcaatgttc cctcgaaggg gcagcggtag       360
tggcagcgcc tctgctctca atgcagcagg taccggcgtc ggtagtaatg ccacatcttc       420
cgaggatttt ccgcctccgt cgctgcttca gccgccgccc cctgcagcat cttctacgtc       480
gggaccacag cctccgcctc cacaaagcct gaacctcctt tcgcaggctc agctgcaggc       540
acagcctctt gcgccaggcg gaactcaaat gaaaaagaaa agtggcttcc agataactag       600
cgttactcct gctcagatct ccgctagtat cagctctaac aacagtatag cagaggacac       660
tgagagctat gatgatctgg atgaatctca cacggaagat ctctcttctt cggagatcct       720
tgatgtgtca ctttccaggg ctactgactt aggggagccc gaacgcagct cctcagaaga       780
gaccctaaat aacttccagg aagccgagac acctggggca gtctctccca accagcccca       840
ccttcctcag cctcatttgc ctcaccttcc acaacagaat gttgtgatca tgggaatgc        900 tcatccacac cacctccatc accaccatca gattcatcat gggcaccacc tccaacatgg       960
tcaccaccat ccatctcatg ttgctgtggc cagtgcatcc attactggtg ggccaccctc      1020
aagcccagta tctagaaaac tctctacaac tggaagctct gacagtatca caccagttgc      1080
accaacttct gctgtatcat ccagtggttc acctgcatct gtaatgacta atatgcgtgc      1140
tccaagtact acaggtggaa taggtataaa ttctgttact ggcactagta cagtaaataa      1200
tgttaacatt actgctgtgg gtagtttaa tcctaatgtg acaagcagca tgcttggtaa       1260
tgttaatata agtacaagca atattcctag tgctgctggt gtgagtgttg ggcctggagt      1320
```

```
taccagtggt gttaatgtga atatcttgag tggcatgggc aatggtacta tttcttcctc    1380
tgctgctgtt agcagtgttc ctaatgcagc tgcagggatg actgggggat cggtttcaag    1440
tcagcagcaa caaccaacag ttaacacttc gaggttcaga gttgtgaagt tagattctag    1500
ttctgagccc tttaaaaaag gtagatggac ttgcactgag ttctatgaaa aagaaaatgc    1560
tgtacctgct acagaaggtg tgctgataaa taaagtggtg gagactgtaa agcaaaatcc    1620
gatagaagtg acttctgaaa gggagagcac tagtgggagt tcagtgagca gtagtgtcag    1680
cacactgagt cactatacag agagtgtggg aagtggagag atgggagccc ctactgtggt    1740
ggtgcagcag cagcagcagc aacaacaaca acaacagcaa caaccagctc tccaaggtgt    1800
gaccctccaa cagatggatt ttggtagcac tggtccacag agtattccag cagttagtat    1860
accacagagt atttctcagt cacagatctc acaagtacaa ttacagtctc aagaactgag    1920
ctatcagcaa aagcaaggtc ttcagccagt acctctgcaa gccactatga gtgctgcaac    1980
tggtatccag ccatcgcctg taaatgtggt tggtgtaact tcagctttag gtcagcagcc    2040
ttccatttcc agtttggctc aaccccagct accatattct caggcggctc ctccagtgca    2100
aactcccctt ccaggggcac caccacccca acagttacag tatggacaac agcaaccaat    2160
ggtttctaca cagatggccc caggccatgt caaatcagtg actcaaaatc ctgcttcaga    2220
gtatgtacaa cagcagccaa ttcttcaaac agcaatgtcc tccggacagc ccagttctgc    2280
aggagtagga gcaggaacaa cagtgattcc tgtggctcag ccacagggta ccagctgcc    2340 agtgcagccc acagcagtcc cagcacaacc tgcaggggca tctgtccagc ctgttggcca    2400
ggctccggca gcagtgtctg ctgtacctac tggcagtcag attgcaaata ttggtcagca    2460
agcaaacata cctactgcag tgcagcagcc ctctacccag gttccacctt cagttattca    2520
gcagggtgct cctccatctt cgcaagtggt tccacctgct caaactggga ttattcatca    2580
gggagttcaa actagtgctc caagccttcc tcaacaattg gttattgcat cccaaagttc    2640
cttgttaact gtgcctcccc agccacaagg agtagaacca gtagctcaag gaattgtttc    2700
acagcagttg cctgcagtta gttctttgcc ctctgctagt agtatttctg ttacaagtca    2760
ggttagttca actggtcctt ctggaatgcc ttctgcccca acaaacttgg ttccaccaca    2820
aaatatagca caaacccctg ctacccaaaa tggtaatttg gttcaaagtg ttagtcaacc    2880
tcccttgata gcaactaata caaatttgcc tttggcacaa cagataccac taagttctac    2940
ccagttctcc gcacaatcat tagctcaggc aattggaagc caaattgaag atgccaggcg    3000
tgcagcggag ccctccttag ttggcttacc tcagactatc agtggtgaca gtgggggaat    3060
gtcagcagtt tcagatggga gtagcagcag cctagcagcc tctgcttctc ttttcccgtt    3120
gaaggtgcta ccgctgacga cacccctggt ggatggcgag gatgagagct cctctggtgc    3180
aagtgtggta gctattgaca acaaaatcga gcaagctatg gatctagtga aaagccattt    3240
gatgtatgcg gtcagagaag aagtggaggt cctcaaagag caaatcaaag aactaataga    3300
gaaaaattcc cagctggagc aggagaacaa tctgctgaag acactggcca gtcctgagca    3360
gcttgcccag tttcaggccc agctgcagac tggctccccc cctgccacca cccagccaca    3420
gggcaccaca cagccccccg cccagccagc atcgcagggc tcaggaccaa ccgcatagct    3480
gcctatgccc ccgcagaact ggctgctgcg tgtgaactga acagacggag aagatgtgct    3540
agggagaatc tgcctccaca gtcacccatt tcattgctcg ctgcgaaaga gacgtgagac    3600
tgacatatgc cattatctct tttccagtat taaacactca tatgcttatg gcttggagaa    3660
atttcttagt tgggtgaatt aaaggttaat ccgagaatta gcatggatat accgggacct    3720
```

```
catgcagctt ggcagatatc tgagaaatgg tttaattcat gctcaggagc tgtgtgcctt    3780
tccatccctt ccggctccct acccctcact tccaagggtt ctctctcctg cttgcgctta    3840
gtgtcctaca tggggttgtg aagcgatgga gctcctcact ggactcgcct ctctcctctc    3900
ctccccccag gaggaacttg aaaggagggt aaaaagacta aaatgagggg gaacagagtt    3960
cactgtacaa atttgacaac tgtcaccaaa attcataaaa aacaatagta ctgtgcctct    4020
ttcttctcaa acaatggatg acacaaaact atgagagtga caaaatggtg acaggtagct    4080
gggacctagg ctatcttacc atgaaggttg ttttgcttat tgtatatttg tgtatgtagt    4140
gtaactattt tgtacaatag aggactgtaa ctactattta ggttgtacag attgaaattt    4200
agttgtttca ttggctgtct gaggaggtgt ggactttat atatagatct acataaaaac     4260
tgctacatga caaaaaccac acctaaagaa attttaagaa tttggcacag ttactcactt     4320
tgtgtaatct gaaatctagc tgctgaatac gctgaagtaa atccttgttc actgaagtct    4380
ttcaattgag ctggttgaat actttgaaaa atgctcagtt ctaactaatg aaatggattt    4440
cccagtaggg gtttctgcat atcacctgta tagtagttat atgcatatgt ttctgtgcat    4500
gttctctaca caattgtaag gtgtcactgt atttaactgt tgcacttgtc aactttcaat    4560
aaagcatata aatgttgata aacaagtgtt tttcatatga ccctgttaac ataatggcag    4620
tcatttccac aactgtttcc aggtaaagtt aacaatttga ctagtaaaat cctgaagggc    4680
agtggaatga ttggaaaagt aggggcgtga tttgactgca tgaagtaaaa ggaaattgac    4740
acattgagtt gttcagcagg taagagaaga gacagtggag gagtccagct caattctaac    4800
tactgtgtga cttggacagg ttgcttcact cctggacgga tgtaggggtt tgaaagagat    4860
gatctcttac attccccttt ggctttaaaa ttctaggagt ccttgaaaat cttaattttt    4920
tactgaactg agaggaagaa ggagccttat tctgtgtata attggaataa gcagatctag    4980
gatcaaaaga cggaagttgg agaagctgat ttccactta agaaccctgt caccctgggt     5040
tgggatgttt ctcctagtgt aggatgagtt tctagctcct gggataattc gttttgtcta    5100
agcaaaagat gatttgaggt gggaccagat gagcaaggat gtccttgcag ttgattctgc    5160
atgactataa aacaggccaa aattaaaacc acgaaggaat cctgaggcag attggcccct    5220
ggcacctgag gagtgagcct gagggatccc actctgcagt aggagtaacg tgagcgagca    5280
agtgaatggg gtgggtttac cggctctgta atctatcaac ctagggcctc agcagtggcc    5340
ccctgcccag taggaattgg accaatccca agttctaagg cttgtcttaa gtccttgcag    5400
aacaaggaca aactttctga atcattcatt tctctcatct agagctggtg ggagattgag    5460
aggtgaatgg gacatccaag atccctaaaa agaattgttc gatagcgtgc atgtgttata    5520
aagtggtgac acgggcatcc tgttgaaatg atggatggct cactgccata ggctgatagc    5580
agttgtcata aagatatttt gggggaattt gaaaaggacg taaagaaaaa tctttcatat    5640
tggcttgttg gttatataac ttcaaattta ataaaggaat acttacgtag taattacatt    5700
tccttgaaaa aactatagtg aatagaaatc cctagccatt tcattttta tgtttttaat     5760 gaagatcttt aaaataccat aggtggtaat cgtggaaaat ttgaaaaatc tcatgtcagt    5820
gtattaagat ggtggagaag tttttttctc cattatttaa tggaactttg ggtcttttta    5880
ttaaaaatgt gagactcatg aaattttggc agctgaatat ttgtgaaata agaatgaatt    5940
attaaaagat gtctttccat a                                              5961
```

<210> SEQ ID NO 48

```
<211> LENGTH: 4601
<212> TYPE: DNA
<213> ORGANISM: Mus musculus

<400> SEQUENCE: 48
ctggaggggg aagtgaatgg cgaaggactg aaggggtccc ccttcggttc cccagccacc       60
tggttcaccc ggttcatcct cccttcccga agttagccct cgaaggcacg agcagccggc      120
gccttcggca gaggaggagg aggaggaggg atcgcgtcgg gcggagcttc aggtcctgtt      180
cgtctctccg gcttctccat acaaagatta cggtgcagaa ggaaattgca cttgcctcct      240 ccgcccccg gtacccagca caatgcacca gccgccggag tccaccgccg cggcggccgc      300
tgctgcagac attagtgcta ggaagatggc gcacccggca atgttccctc gaaggggcag      360
cggtggtggc agcgcctctg ctctcaatgc agcaggtacg ggcgtcagtg gtgctgctcc      420
atcttctgaa gattttcctc ctccttcgct gctccagccg ccgcctcctg ctgcatcttc      480
cacgcaggga ccccagcctc cgcctccaca aagcctgaac ctcctctcgc aggctcagct      540
gcagggacag cctcttgcgc caggcggaac tcagatgaaa aagaaaagtg gcttccagat      600
aactagcgtt actccggctc agatctctgc cagcatcagc tccaacaaca gcatcgcgga      660
ggacaccgag agctacgacg atctggatga gtcgcacacg gaagatctct cctcttccga      720
gatcctcgac gtctcccttt ccagggccac tgacttaggt gagcctgaac gaagctcctc      780
agaggagact ctgaataact tccaggaagc tgagacacct ggggcagtct ctcctaacca      840
gccccacctt cctcagcctc atttgcctca ccttccacaa cagaacgttg tgatcaatgg      900
gaatgcccat ccccaccacc tccatcatca ccatcaccct catcatgggc accaccttca      960
ccatgggcac catcattcat cacatgctgc tgtggccggt ccatccattc ccggagggcc     1020
accctcgagc ccagtgtcca ggaaactctc tacaactgga agttctgatg gtggtgtgcc     1080
agtcgcacct cctcctgcag taccatcgag tggcttacca gcatcagtga tgacgaacat     1140
ccgtactcca agtactacag gaagcctagg tataaattcg gttactgca cgagcgctac      1200 gaataatgtt aacattgctg ctgtgggtag tttcagtccc agtgtgacga acagcgtgca     1260
tggtaatgct aatataaata caagcaatat ccctaatgct gctagcataa gtggtgggcc     1320
tggagttacc agtgttgtta attcgagtat cttgagtggc atgggcaatg gtaccgtttc     1380
ttcctctcct gttgctaaca gtgtccttaa tgcagctgca ggtatcactg tgggagtggt     1440
ttccagtcag cagcagcagc agcagcagca gcaaccaaca gttaacacat cgaggttcag     1500
ggttgtgaag ttagactcta cttctgaacc ctttaaaaaa ggtcgatgga cttgcacaga     1560
attctatgag aaggaaaacg ctgtgccagc tacagaaggc gtggccgtca ataaagtggt     1620
ggagacggtg aagcaaaccc ccacggaagc atcgtcctcg gagagggaga gcactagtgg     1680
gagttctgtg agcagtagtg tgagcacact gagtcactac acggagagtg tgggaagtgg     1740
agagatgatg ggagccccgg ctgtggtggc gccgcagcag ccgccgctac caccagcgcc     1800
tccaggtctt caaggtgtgg ctctccaaca gctagagttc agtagccctg ctccacagag     1860
tattgcggcg gttagtatgc cacagagtat ttctcagtca cagatgtcac aagtacagtt     1920
acagcctcaa gagttgagct ttcagcagaa gcagactctt cagcctgtcc ctctgcaagc     1980
caccatgagt gccgcaactg gtatccagcc ttcccctgtc agcgtggtcg gcatcacggc     2040
ggctgtaggt cagcagcctt ctgtttccag cctggctcaa ccgcagctgc catattctca     2100
gacagctcct cccgtgcaaa ctcctcttcc aggggcacca ccccagcagt acaatatgg      2160 gcagcagcaa ccaatggttc ctgcgcagat agccccaggc catggccagc cagtgactca     2220
```

-continued

```
aaatccaact tcagagtatg tgcagcagca gcagcagcca atatttcaag cagcattgtc    2280
ctctgggcag tccagttcca cgggcacggg ggcaggaata tcagtgattc ctgtggctca    2340
ggcacagggg atccagctgc cagggcagcc cacagcagta caaacacaac ctgcaggggc    2400
ggctgggcag cccattggcc aggctcaaac agcagtgtcc actgtaccaa ctggcggtca    2460
gattgcaagt atcggtcaac aggcaaacat acccactgca gtacagcagc cctctaccca    2520
agttacacct tcagttattc agcaaggtgc tcctccatct tcacaagtag tcctacctgc    2580
tccaaccggg atcattcatc agggagttca aacccgtgct tcaagccttc cacaacaatt    2640
ggtcattgca ccccagagta ccttggtaac tgtgcctccc cagccacagg gagtagaaac    2700
cgtggcccaa ggggttgttt cccagcagtt gcccacaggc agtcctctgc cctctgctag    2760
cactatttct gttacaaatc aggttagttc agccgctcct tctggaatgc cttctgtccc    2820
aacaaactta gttccaccac agaatatagc acaacccca gccacccaaa atggcagttt    2880
ggttcaaagt gttagtcaat ctcccttgat agccactaac ataaatttgc ctttggcaca    2940
acagatacca ctaagttcta ctcagttctc tacacaatca ttagctcagg ccattggaag    3000
ccaaatggaa gatgccaggc gcccagcgga gccctcctta ggcggcttac ctcagactat    3060
gagtggtgac agtggggaa tgtcagcagt ttcagatggg agtagcagca gcctagcagc    3120
ccctgcttct ctcttcccgt tgaaggtgct accgctgaca acacccctgg tggatggcga    3180
ggacgagagc tctggtgcaa gtgtggtagc tatcgacaac aaaatagagc aagctatgga    3240
tctggtgaaa agccatttga tgtatgcggt gagggaggaa gtggaagttc tgaaggagca    3300
gatcaaagaa ctaatagaga aaaactccca gctggagcag gagaacaatc tgctgaagac    3360
gctggccagt ccggagcagc tcgcccagtt tcaggcccag ctgcagactg gctcccctcc    3420
ggccaccacg cagccacagg ggaccacaca gccccctgca cagccagcat cccagggctc    3480
aggatcaacc gcatagcctc ctaggcccca acagaactgg ctgctgctgc tgctgtctga    3540
actgaacaga ccgaagagat gtgctagaga gaagccgcct ccacagtcac ccatttcatt    3600
gctgtctacg aaagagacgt gagactcaca cgctgttctc gctttctccc cagtattaag    3660
cactcataag cttttggctt gaagaaatgt actagttgag tgaattaaag gttaatcaga    3720
gagtgagcag ggatgtgccc tgtgcaacgt ggcagatgtc tgaggaatgg tttaattgac    3780
cccgaggagc tctgtgcctt ttcaaccctc cccagccgcc caccctgctt ctgagagctc    3840
gggcggctcg ccttcgtggg gctcgcctgc gtggggttcg gaaagtgggc tgctcctgga    3900
ttctgcgctc tcttctcctt cccttcaaag aactcggaga ggccagaaac aagactgcaa    3960
tggggggcgg ggggagggat gatgcagtcc ttatacaaaa ccgacaactg tcaccaaagc    4020
ttataaaaca cgatagtact gtccctcttt tctgaaccat cagaagacac aaaactgtta    4080
gtgacacaac ggtgacaggt agctgggacc taggctatct tattatgaag gttgttttgc    4140
ttgttgtata tttgtgtatg tagtgtaacg aatttgtacc atagaggact gtccgtaact    4200
actgtttagc ttctacacat tgaaatgtag atgtttcatt ggctgtctga aaaggtgtgg    4260
cttgtccttc ctagagagat ctacttaaaa actgctttgt gacaaaaacc acacctgaag    4320 aaatttttaag aatttggccc agttagtcac tctgtgtaat cccggaatct agctgctgaa    4380
gtcttgcgaa gtaaactccc cgtgaccgat gtcagttaag ctggtgatac ctggagaagt    4440
ggtcagttgc taaggaagtg gatttcccag tagggggttc tgcacctcac ctgtatagtc    4500
gttctgcgca tgtcccccac acagtcccca ctgtatttac ctgttctact tgtcaccttt    4560
```
caataaagca tatcaaatgt tgatacaaaa aaaaaaaaaa a                                        4601

<210> SEQ ID NO 49
<211> LENGTH: 436
<212> TYPE: PRT
<213> ORGANISM: Homo sapiens

<400> SEQUENCE: 49

Met Ala Gly Val Pro Glu Ser Leu Asn Leu Met Cys Asp Arg Asn Gly
1               5                   10                  15

Gly Arg Arg Leu Arg Gln Trp Leu Ile Glu Gln Ile Asp Ser Ser Met
                20                  25                  30

Tyr Pro Gly Leu Ile Trp Glu Asn Glu Glu Lys Ser Met Phe Arg Ile
            35                  40                  45

Pro Trp Lys His Ala Gly Lys Gln Asp Tyr Asn Gln Glu Val Asp Ala
        50                  55                  60

Ser Ile Phe Lys Ala Trp Ala Val Phe Lys Gly Lys Phe Lys Glu Gly
65                  70                  75                  80

Asp Lys Ala Glu Pro Ala Thr Trp Lys Thr Arg Leu Arg Cys Ala Leu
                85                  90                  95

Asn Lys Ser Pro Asp Phe Glu Glu Val Thr Asp Arg Ser Gln Leu Asp
            100                 105                 110

Ile Ser Glu Pro Tyr Lys Val Tyr Arg Ile Val Pro Glu Glu Glu Gln
            115                 120                 125

Lys Cys Lys Leu Gly Val Ala Thr Ala Gly Cys Val Asn Glu Val Thr
        130                 135                 140

Glu Met Glu Cys Gly Arg Ser Glu Ile Asp Glu Leu Ile Lys Glu Pro
145                 150                 155                 160

Ser Val Asp Asp Tyr Met Gly Met Ile Lys Arg Ser Pro Ser Pro Pro
                165                 170                 175

Glu Ala Cys Arg Ser Gln Leu Leu Pro Asp Trp Trp Ala Gln Gln Pro
                180                 185                 190

Ser Thr Gly Val Pro Leu Val Thr Gly Tyr Thr Thr Tyr Asp Ala His
            195                 200                 205

His Ser Ala Phe Ser Gln Met Val Ile Ser Phe Tyr Tyr Gly Gly Lys
        210                 215                 220

Leu Val Gly Gln Ala Thr Thr Thr Cys Pro Glu Gly Cys Arg Leu Ser
225                 230                 235                 240

Leu Ser Gln Pro Gly Leu Pro Gly Thr Lys Leu Tyr Gly Pro Glu Gly
                245                 250                 255

Leu Glu Leu Val Arg Phe Pro Pro Ala Asp Ala Ile Pro Ser Glu Arg
                260                 265                 270

Gln Arg Gln Val Thr Arg Lys Leu Phe Gly His Leu Glu Arg Gly Val
            275                 280                 285

Leu Leu His Ser Ser Arg Gln Gly Val Phe Val Lys Arg Leu Cys Gln
        290                 295                 300

Gly Arg Val Phe Cys Ser Gly Asn Ala Val Val Cys Lys Gly Arg Pro
305                 310                 315                 320

Asn Lys Leu Glu Arg Asp Glu Val Val Gln Val Phe Asp Thr Ser Gln
                325                 330                 335

Phe Phe Arg Glu Leu Gln Gln Phe Tyr Asn Ser Gln Gly Arg Leu Pro
                340                 345                 350

Asp Gly Arg Val Val Leu Cys Phe Gly Glu Glu Phe Pro Asp Met Ala
            355                 360                 365

-continued

```
Pro Leu Arg Ser Lys Leu Ile Leu Val Gln Ile Glu Gln Leu Tyr Val
    370             375             380

Arg Gln Leu Ala Glu Glu Ala Gly Lys Ser Cys Gly Ala Gly Ser Val
385             390             395             400

Met Gln Ala Pro Glu Glu Pro Pro Asp Gln Val Phe Arg Met Phe
            405             410             415

Pro Asp Ile Cys Ala Ser His Gln Arg Ser Phe Phe Arg Glu Asn Gln
            420             425             430

Gln Ile Thr Val
        435
```

```
<210> SEQ ID NO 50
<211> LENGTH: 424
<212> TYPE: PRT
<213> ORGANISM: Mus musculus

<400> SEQUENCE: 50

Met Cys Asp Arg Asn Gly Gly Arg Arg Leu Arg Gln Trp Leu Ile Glu
1               5               10              15

Gln Ile Asp Ser Ser Met Tyr Pro Gly Leu Ile Trp Glu Asn Asp Glu
            20              25              30

Lys Thr Met Phe Arg Ile Pro Trp Lys His Ala Gly Lys Gln Asp Tyr
        35              40              45

Asn Gln Glu Val Asp Ala Ser Ile Phe Lys Ala Trp Ala Val Phe Lys
    50              55              60

Gly Lys Phe Lys Glu Gly Asp Lys Ala Glu Pro Ala Thr Trp Lys Thr
65              70              75              80

Arg Leu Arg Cys Ala Leu Asn Lys Ser Pro Asp Phe Glu Glu Val Thr
            85              90              95

Asp Arg Ser Gln Leu Asp Ile Ser Glu Pro Tyr Lys Val Tyr Arg Ile
            100             105             110

Val Pro Glu Glu Glu Gln Lys Cys Lys Leu Gly Val Ala Pro Ala Gly
        115             120             125

Cys Met Ser Glu Val Pro Glu Met Glu Cys Gly Arg Ser Glu Ile Glu
    130             135             140

Glu Leu Ile Lys Glu Pro Ser Val Asp Glu Tyr Met Gly Met Thr Lys
145             150             155             160

Arg Ser Pro Ser Pro Glu Ala Cys Arg Ser Gln Ile Leu Pro Asp
            165             170             175

Trp Trp Val Gln Gln Pro Ser Ala Gly Leu Pro Leu Val Thr Gly Tyr
            180             185             190

Ala Ala Tyr Asp Thr His His Ser Ala Phe Ser Gln Met Val Ile Ser
        195             200             205

Phe Tyr Tyr Gly Gly Lys Leu Val Gly Gln Ala Thr Thr Thr Cys Leu
    210             215             220

Glu Gly Cys Arg Leu Ser Leu Ser Gln Pro Gly Leu Pro Lys Leu Tyr
225             230             235             240

Gly Pro Asp Gly Leu Glu Pro Val Cys Phe Pro Thr Ala Asp Thr Ile
            245             250             255

Pro Ser Glu Arg Gln Arg Gln Val Thr Arg Lys Leu Phe Gly His Leu
            260             265             270

Glu Arg Gly Val Leu Leu His Ser Asn Arg Lys Gly Val Phe Val Lys
        275             280             285

Arg Leu Cys Gln Gly Arg Val Phe Cys Ser Gly Asn Ala Val Val Cys
    290             295             300
```

```
Lys Gly Arg Pro Asn Lys Leu Glu Arg Asp Glu Val Val Gln Val Phe
305                 310                 315                 320

Asp Thr Asn Gln Phe Ile Arg Glu Leu Gln Gln Phe Tyr Ala Thr Gln
                325                 330                 335

Ser Arg Leu Pro Asp Ser Arg Val Val Leu Cys Phe Gly Glu Glu Phe
            340                 345                 350

Pro Asp Thr Val Pro Leu Arg Ser Lys Leu Ile Leu Val Gln Val Glu
            355                 360                 365

Gln Leu Tyr Ala Arg Gln Leu Val Glu Glu Ala Gly Lys Ser Cys Gly
        370                 375                 380

Ala Gly Ser Leu Met Pro Ala Leu Glu Glu Pro Gln Pro Asp Gln Ala
385                 390                 395                 400

Phe Arg Met Phe Pro Asp Ile Cys Thr Ser His Gln Arg Pro Phe Phe
                405                 410                 415

Arg Glu Asn Gln Gln Ile Thr Val
                420
```

```
<210> SEQ ID NO 51
<211> LENGTH: 262
<212> TYPE: PRT
<213> ORGANISM: Homo sapiens

<400> SEQUENCE: 51
```

```
Met Leu Ala Leu Glu Ala Ala Gln Leu Asp Gly Pro His Phe Ser Cys
1                   5                   10                  15

Leu Tyr Pro Asp Gly Val Phe Tyr Asp Leu Asp Ser Cys Lys His Ser
                20                  25                  30

Ser Tyr Pro Asp Ser Glu Gly Ala Pro Asp Ser Leu Trp Asp Trp Thr
            35                  40                  45

Val Ala Pro Pro Val Pro Ala Thr Pro Tyr Glu Ala Phe Asp Pro Ala
        50                  55                  60

Ala Ala Ala Phe Ser His Pro Gln Ala Ala Gln Leu Cys Tyr Glu Pro
65                  70                  75                  80

Pro Thr Tyr Ser Pro Ala Gly Asn Leu Glu Leu Ala Pro Ser Leu Glu
                85                  90                  95

Ala Pro Gly Pro Gly Leu Pro Ala Tyr Pro Thr Glu Asn Phe Ala Ser
            100                 105                 110

Gln Thr Leu Val Pro Pro Ala Tyr Ala Pro Tyr Pro Ser Pro Val Leu
        115                 120                 125

Ser Glu Glu Glu Asp Leu Pro Leu Asp Ser Pro Ala Leu Glu Val Ser
        130                 135                 140

Asp Ser Glu Ser Asp Glu Ala Leu Val Ala Gly Pro Glu Gly Lys Gly
145                 150                 155                 160

Ser Glu Ala Gly Thr Arg Lys Lys Leu Arg Leu Tyr Gln Phe Leu Leu
                165                 170                 175

Gly Leu Leu Thr Arg Gly Asp Met Arg Glu Cys Val Trp Trp Val Glu
            180                 185                 190

Pro Gly Ala Gly Val Phe Gln Phe Ser Ser Lys His Lys Glu Leu Leu
            195                 200                 205

Ala Arg Arg Trp Gly Gln Gln Lys Gly Asn Arg Lys Arg Met Thr Tyr
        210                 215                 220

Gln Lys Leu Ala Arg Ala Leu Arg Asn Tyr Ala Lys Thr Gly Glu Ile
225                 230                 235                 240

Arg Lys Val Lys Arg Lys Leu Thr Tyr Gln Phe Asp Ser Ala Leu Leu
```

-continued

```
                245                 250                 255

Pro Ala Val Arg Arg Ala
            260

<210> SEQ ID NO 52
<211> LENGTH: 267
<212> TYPE: PRT
<213> ORGANISM: Mus musculus

<400> SEQUENCE: 52

Met Leu Ala Leu Glu Ala Ala Gln Leu Asp Gly Pro His Leu Ser Cys
1               5                   10                  15

Leu Tyr Pro Glu Gly Val Phe Tyr Asp Leu Asp Ser Cys Lys Pro Phe
            20                  25                  30

Ser Tyr Pro Asp Ser Asp Gly Gly Leu Asp Ser Thr Trp Gly Trp Thr
        35                  40                  45

Glu Ala Pro Pro Ala Pro Ala Ile Ala Pro Tyr Glu Ala Phe Asp Pro
        50                  55                  60

Ala Thr Ala Ala Phe Ser His Ser Gln Thr Val Gln Leu Cys Tyr Ser
65                  70                  75                  80

His Gly Pro Asn Pro Ser Thr Tyr Ser Pro Met Gly Thr Leu Asp Pro
                85                  90                  95

Ala Pro Ser Leu Glu Ala Pro Gly Pro Gly Leu Gln Val Tyr Pro Pro
            100                 105                 110

Glu Asp Phe Thr Ser Gln Thr Leu Gly Ser Leu Ala Tyr Ala Pro Tyr
            115                 120                 125

Pro Ser Pro Val Leu Ser Glu Glu Glu Asp Ile Met Leu Asp Ser Pro
        130                 135                 140

Ala Leu Glu Val Ser Asp Ser Glu Ser Asp Glu Ala Leu Leu Ala Gly
145                 150                 155                 160

Ser Glu Gly Arg Gly Ser Glu Ala Gly Ala Arg Lys Lys Leu Arg Leu
                165                 170                 175

Tyr Gln Phe Leu Leu Gly Leu Leu Leu Arg Gly Asp Met Arg Glu Cys
            180                 185                 190

Val Trp Trp Val Glu Pro Gly Ala Gly Val Phe Gln Phe Ser Ser Lys
            195                 200                 205

His Lys Glu Leu Leu Ala Arg Arg Trp Gly Gln Gln Lys Gly Asn Arg
        210                 215                 220

Lys Arg Met Thr Tyr Gln Lys Leu Ala Arg Ala Leu Arg Asn Tyr Ala
225                 230                 235                 240

Lys Thr Gly Glu Ile Arg Lys Val Lys Arg Lys Leu Thr Tyr Gln Phe
                245                 250                 255

Asp Ser Ala Leu Leu Pro Ala Ser Arg His Val
            260                 265

<210> SEQ ID NO 53
<211> LENGTH: 648
<212> TYPE: PRT
<213> ORGANISM: Homo sapiens

<400> SEQUENCE: 53

Met Ala Ala Pro Val Lys Gly Asn Arg Lys Gln Ser Thr Glu Gly Asp
1               5                   10                  15

Ala Leu Asp Pro Pro Ala Ser Pro Lys Pro Ala Gly Lys Gln Asn Gly
            20                  25                  30

Ile Gln Asn Pro Ile Ser Leu Glu Asp Ser Pro Glu Ala Gly Gly Glu
```

-continued

```
              35                    40                    45

Arg Glu Glu Glu Gln Glu Arg Glu Glu Gln Ala Phe Leu Val Ser
     50                    55                    60

Leu Tyr Lys Phe Met Lys Glu Arg His Thr Pro Ile Glu Arg Val Pro
65                    70                    75                    80

His Leu Gly Phe Lys Gln Ile Asn Leu Trp Lys Ile Tyr Lys Ala Val
                   85                    90                    95

Glu Lys Leu Gly Ala Tyr Glu Leu Gln Ser Met Ala Leu Gly Glu Arg
                  100                   105                   110

Ile Gly Trp Pro Leu Leu Glu Pro Gln Ser Ser Cys Gln Thr Ala Val
                  115                   120                   125

Leu Arg Val Pro Ala Arg Ala Ala Gly Ala Ala Arg Thr Pro Pro Pro
         130                   135                   140

Gly Gly Ala Arg Arg Pro Arg Pro His Glu Val Pro Leu Gln Val Thr
145                   150                   155                   160

Gly Arg Arg Leu Trp Lys Asn Val Tyr Asp Glu Leu Gly Gly Ser Pro
                  165                   170                   175

Gly Ser Thr Ser Ala Ala Thr Cys Thr Arg Arg His Tyr Glu Arg Leu
                  180                   185                   190

Val Leu Pro Tyr Val Arg His Leu Lys Gly Glu Asp Asp Lys Pro Leu
                  195                   200                   205

Pro Thr Ser Lys Pro Arg Lys Gln Tyr Lys Met Ala Lys Glu Asn Arg
         210                   215                   220

Gly Asp Asp Gly Ala Thr Glu Arg Pro Lys Lys Ala Lys Glu Glu Arg
225                   230                   235                   240

Arg Met Asp Gln Met Met Pro Gly Lys Thr Lys Ala Asp Ala Ala Asp
                  245                   250                   255

Pro Ala Pro Leu Pro Ser Gln Glu Pro Pro Arg Asn Ser Thr Glu Gln
                  260                   265                   270

Gln Gly Leu Ala Ser Gly Ser Ser Val Ser Phe Val Gly Ala Ser Gly
                  275                   280                   285

Cys Pro Glu Ala Tyr Lys Arg Leu Leu Ser Ser Phe Tyr Cys Lys Gly
         290                   295                   300

Thr His Gly Ile Met Ser Pro Leu Ala Lys Lys Lys Leu Leu Ala Gln
305                   310                   315                   320

Val Ser Lys Val Glu Ala Leu Gln Cys Gln Glu Glu Gly Cys Arg His
                  325                   330                   335

Gly Ala Glu Pro Gln Ala Ser Pro Ala Val His Leu Pro Glu Ser Pro
                  340                   345                   350

Gln Ser Pro Lys Gly Leu Thr Glu Asn Ser Arg His Arg Leu Thr Pro
                  355                   360                   365

Gln Glu Gly Leu Gln Ala Pro Gly Gly Ser Leu Arg Glu Glu Ala Gln
         370                   375                   380

Ala Gly Pro Cys Pro Ala Ala Pro Ile Phe Lys Gly Cys Phe Tyr Thr
385                   390                   395                   400

His Pro Thr Glu Val Leu Lys Pro Val Ser Gln His Pro Arg Asp Phe
                  405                   410                   415

Phe Ser Arg Leu Lys Asp Gly Val Leu Leu Gly Pro Pro Gly Lys Glu
                  420                   425                   430

Gly Leu Ser Val Lys Glu Pro Gln Leu Val Trp Gly Gly Asp Ala Asn
                  435                   440                   445

Arg Pro Ser Ala Phe His Lys Gly Gly Ser Arg Lys Gly Ile Leu Tyr
         450                   455                   460
```

```
Pro Lys Pro Lys Ala Cys Trp Val Ser Pro Met Ala Lys Val Pro Ala
465                 470             475             480

Glu Ser Pro Thr Leu Pro Pro Thr Phe Pro Ser Ser Pro Gly Leu Gly
                485             490             495

Ser Lys Arg Ser Leu Glu Glu Glu Gly Ala Ala His Ser Gly Lys Arg
            500             505             510

Leu Arg Ala Val Ser Pro Phe Leu Lys Glu Ala Asp Ala Lys Lys Cys
        515             520             525

Gly Ala Lys Pro Ala Gly Ser Gly Leu Val Ser Cys Leu Leu Gly Pro
    530             535             540

Ala Leu Gly Pro Val Pro Pro Glu Ala Tyr Arg Gly Thr Met Leu His
545             550             555             560

Cys Pro Leu Asn Phe Thr Gly Thr Pro Gly Pro Leu Lys Gly Gln Ala
                565             570             575

Ala Leu Pro Phe Ser Pro Leu Val Ile Pro Ala Phe Pro Ala His Phe
                580             585             590

Leu Ala Thr Ala Gly Pro Ser Pro Met Ala Ala Gly Leu Met His Phe
            595             600             605

Pro Pro Thr Ser Phe Asp Ser Ala Leu Arg His Arg Leu Cys Pro Ala
            610             615             620

Ser Ser Ala Trp His Ala Pro Pro Val Thr Thr Tyr Ala Ala Pro His
625             630             635             640

Phe Phe His Leu Asn Thr Lys Leu
                645

<210> SEQ ID NO 54
<211> LENGTH: 590
<212> TYPE: PRT
<213> ORGANISM: Mus musculus

<400> SEQUENCE: 54

Met Ala Ala Pro Pro Ala Lys Gly Asn Thr Glu Gln Ser Glu Glu Gly
1               5               10              15

Asp Leu Pro Gln Leu Pro Val Ser Pro Lys Pro Asp Asp Glu Gln Ser
            20              25              30

Arg Ser Gln Ser Pro Thr Gln Leu Gln Asp Ser Pro Glu Ala Gly Gly
        35              40              45

Glu Gln Glu Glu Glu Gln Ala Phe Leu Val Ser Leu Tyr Lys Phe Met
    50              55              60

Lys Glu Arg His Thr Pro Ile Glu Arg Val Pro His Leu Gly Phe Lys
65              70              75              80

Gln Ile Asn Leu Trp Lys Ile Tyr Lys Ala Val Glu Lys Leu Gly Ala
                85              90              95

Tyr Glu Leu Val Thr Gly Arg Arg Leu Trp Lys Asn Val Tyr Asp Glu
            100             105             110

Leu Gly Gly Ser Pro Gly Ser Thr Ser Ala Ala Thr Cys Thr Arg Arg
            115             120             125

His Tyr Glu Arg Leu Val Leu Pro Tyr Val Arg His Leu Lys Gly Glu
        130             135             140

Asp Asp Lys Pro Leu Pro Pro Thr Lys Pro Arg Lys Gln Tyr Lys Met
145             150             155             160

Ala Lys Glu Leu Arg Gly Asp Asp Gly Thr Thr Glu Lys Leu Lys Lys
            165             170             175

Ala Lys Asp Ser Glu Glu Arg Arg Val Glu Gln Thr Thr Pro Gly Lys
```

-continued

```
                  180              185              190

Thr Lys Ser Asp Ala Thr Gly Gln Thr Gln Leu Pro Cys Gln Gly Ser
            195              200              205

Ser Arg Asp Ser Thr Glu Gln Leu Gly Pro Val Ser Gly Pro Ser Pro
        210              215              220

Pro Leu Thr Gly Ala Ser Ser Cys Pro Glu Ala Tyr Lys Arg Leu Leu
225              230              235              240

Ser Ser Phe Tyr Cys Lys Gly Ala His Gly Ile Met Ser Pro Leu Ala
            245              250              255

Lys Lys Lys Leu Leu Ala Gln Val Ser Lys Ala Glu Ala Leu Gln Cys
            260              265              270

Gln Glu Glu Gly Cys Arg His Gly Ala Arg Ser Pro Asn Lys Asp Ile
        275              280              285

Gln Asp Ser Pro Gln Asn Leu Arg Gly Pro Ala Glu Asn Ser Glu His
        290              295              300

Gln Leu Thr Pro Arg Glu Gly Leu Gln Ala Pro Gly Gly Ser Thr Arg
305              310              315              320

Met Glu Ala Gln Val Gly Pro Cys Pro Thr Ala Pro Met Phe Ser Gly
            325              330              335

Cys Phe His Ala Tyr Pro Thr Glu Val Leu Lys Pro Val Ser Gln His
            340              345              350

Pro Arg Asp Phe Phe Ser Gly Leu Lys Asp Arg Val Leu Leu Gly Pro
            355              360              365

Pro Gly Lys Glu Glu Gly Pro Thr Thr Lys Glu Ser His Leu Val Trp
        370              375              380

Gly Gly Asp Ala Asn His Pro Ser Ala Phe His Lys Gly Ser Thr Arg
385              390              395              400

Lys Arg Ser Phe Tyr Pro Lys Pro Lys Ala Cys Trp Val Ser Pro Met
            405              410              415

Ala Lys Val Pro Thr Glu Arg Pro Gly Ala Pro Ser Pro His Pro Ser
            420              425              430

Ser Pro Gly Leu Gly Ser Lys Arg Gly Leu Glu Glu Glu Gly Phe Ala
            435              440              445

His Gly Gly Lys Lys Leu Arg Ala Val Ser Pro Phe Leu Lys Glu Val
        450              455              460

Asp Ser Lys Glu Thr Gly Gly Lys Pro Ala Ala Pro Gly Leu Ala Val
465              470              475              480

Ser Cys Leu Leu Gly Pro Thr Pro Gly Pro Thr Pro Glu Ala Tyr
            485              490              495

Arg Gly Thr Met Leu Arg Cys Pro Leu Asn Phe Thr Gly Ser Ala Asp
            500              505              510

Pro Leu Lys Gly Gln Ala Ser Leu Pro Phe Ser Pro Leu Val Ile Pro
            515              520              525

Ala Phe Pro Ala His Leu Leu Ala Thr Thr Gly Ser Ser Pro Met Ala
        530              535              540

Ala Ser Leu Met His Phe Pro Pro Thr Pro Tyr Asp Ala Val Leu Arg
545              550              555              560

Asn Arg Leu Gly Pro Ala Ser Ser Ala Trp His Met Pro Pro Val Thr
            565              570              575

Thr Tyr Ala Ala Pro His Phe Phe His Leu Asn Thr Lys Leu
            580              585              590
```

<210> SEQ ID NO 55

```
<211> LENGTH: 835
<212> TYPE: PRT
<213> ORGANISM: Homo sapiens

<400> SEQUENCE: 55

Met Ser Arg Arg Lys Gln Gly Lys Pro Gln His Leu Ser Lys Arg Glu
1               5                   10                  15

Phe Ser Pro Glu Pro Leu Glu Ala Ile Leu Thr Asp Asp Glu Pro Asp
                20                  25                  30

His Gly Pro Leu Gly Ala Pro Glu Gly Asp His Asp Leu Leu Thr Cys
            35                  40                  45

Gly Gln Cys Gln Met Asn Phe Pro Leu Gly Asp Ile Leu Ile Phe Ile
        50                  55                  60

Glu His Lys Arg Lys Gln Cys Asn Gly Ser Leu Cys Leu Glu Lys Ala
65                  70                  75                  80

Val Asp Lys Pro Pro Ser Pro Ser Pro Ile Glu Met Lys Lys Ala Ser
                85                  90                  95

Asn Pro Val Glu Val Gly Ile Gln Val Thr Pro Glu Asp Asp Asp Cys
                100                 105                 110

Leu Ser Thr Ser Ser Arg Gly Ile Cys Pro Lys Gln Glu His Ile Ala
            115                 120                 125

Asp Lys Leu Leu His Trp Arg Gly Leu Ser Ser Pro Arg Ser Ala His
        130                 135                 140

Gly Ala Leu Ile Pro Thr Pro Gly Met Ser Ala Glu Tyr Ala Pro Gln
145                 150                 155                 160

Gly Ile Cys Lys Asp Glu Pro Ser Ser Tyr Thr Cys Thr Thr Cys Lys
                165                 170                 175

Gln Pro Phe Thr Ser Ala Trp Phe Leu Leu Gln His Ala Gln Asn Thr
                180                 185                 190

His Gly Leu Arg Ile Tyr Leu Glu Ser Glu His Gly Ser Pro Leu Thr
            195                 200                 205

Pro Arg Val Gly Ile Pro Ser Gly Leu Gly Ala Glu Cys Pro Ser Gln
        210                 215                 220

Pro Pro Leu His Gly Ile His Ile Ala Asp Asn Asn Pro Phe Asn Leu
225                 230                 235                 240

Leu Arg Ile Pro Gly Ser Val Ser Arg Glu Ala Ser Gly Leu Ala Glu
                245                 250                 255

Gly Arg Phe Pro Pro Thr Pro Pro Leu Phe Ser Pro Pro Arg His
                260                 265                 270

His Leu Asp Pro His Arg Ile Glu Arg Leu Gly Ala Glu Glu Met Ala
            275                 280                 285

Leu Ala Thr His His Pro Ser Ala Phe Asp Arg Val Leu Arg Leu Asn
        290                 295                 300

Pro Met Ala Met Glu Pro Pro Ala Met Asp Phe Ser Arg Arg Leu Arg
305                 310                 315                 320

Glu Leu Ala Gly Asn Thr Ser Ser Pro Pro Leu Ser Pro Gly Arg Pro
                325                 330                 335

Ser Pro Met Gln Arg Leu Leu Gln Pro Phe Gln Pro Gly Ser Lys Pro
                340                 345                 350

Pro Phe Leu Ala Thr Pro Pro Leu Pro Pro Leu Gln Ser Ala Pro Pro
            355                 360                 365

Pro Ser Gln Pro Pro Val Lys Ser Lys Ser Cys Glu Phe Cys Gly Lys
        370                 375                 380

Thr Phe Lys Phe Gln Ser Asn Leu Val Val His Arg Arg Ser His Thr
```

```
385               390               395               400

Gly Glu Lys Pro Tyr Lys Cys Asn Leu Cys Asp His Ala Cys Thr Gln
            405               410               415

Ala Ser Lys Leu Lys Arg His Met Lys Thr His Met His Lys Ser Ser
            420               425               430

Pro Met Thr Val Lys Ser Asp Asp Gly Leu Ser Thr Ala Ser Ser Pro
            435               440               445

Glu Pro Gly Thr Ser Asp Leu Val Gly Ser Ala Ser Ser Ala Leu Lys
        450               455               460

Ser Val Val Ala Lys Phe Lys Ser Glu Asn Asp Pro Asn Leu Ile Pro
465               470               475               480

Glu Asn Gly Asp Glu Glu Glu Glu Asp Asp Glu Glu Glu Glu Glu
                485               490               495

Glu Glu Glu Glu Glu Glu Glu Glu Leu Thr Glu Ser Glu Arg Val Asp
            500               505               510

Tyr Gly Phe Gly Leu Ser Leu Glu Ala Ala Arg His His Glu Asn Ser
            515               520               525

Ser Arg Gly Ala Val Val Gly Val Gly Asp Glu Ser Arg Ala Leu Pro
        530               535               540

Asp Val Met Gln Gly Met Val Leu Ser Ser Met Gln His Phe Ser Glu
545               550               555               560

Ala Phe His Gln Val Leu Gly Glu Lys His Lys Arg Gly His Leu Ala
            565               570               575

Glu Ala Glu Gly His Arg Asp Thr Cys Asp Glu Asp Ser Val Ala Gly
            580               585               590

Glu Ser Asp Arg Ile Asp Asp Gly Thr Val Asn Gly Arg Gly Cys Ser
            595               600               605

Pro Gly Glu Ser Ala Ser Gly Gly Leu Ser Lys Lys Leu Leu Leu Gly
        610               615               620

Ser Pro Ser Ser Leu Ser Pro Phe Ser Lys Arg Ile Lys Leu Glu Lys
625               630               635               640

Glu Phe Asp Leu Pro Pro Ala Ala Met Pro Asn Thr Glu Asn Val Tyr
            645               650               655

Ser Gln Trp Leu Ala Gly Tyr Ala Ala Ser Arg Gln Leu Lys Asp Pro
            660               665               670

Phe Leu Ser Phe Gly Asp Ser Arg Gln Ser Pro Phe Ala Ser Ser Ser
            675               680               685

Glu His Ser Ser Glu Asn Gly Ser Leu Arg Phe Ser Thr Pro Pro Gly
        690               695               700

Glu Leu Asp Gly Gly Ile Ser Gly Arg Ser Gly Thr Gly Ser Gly Gly
705               710               715               720

Ser Thr Pro His Ile Ser Gly Pro Gly Pro Gly Arg Pro Ser Ser Lys
            725               730               735

Glu Gly Arg Arg Ser Asp Thr Cys Glu Tyr Cys Gly Lys Val Phe Lys
            740               745               750

Asn Cys Ser Asn Leu Thr Val His Arg Arg Ser His Thr Gly Glu Arg
            755               760               765

Pro Tyr Lys Cys Glu Leu Cys Asn Tyr Ala Cys Ala Gln Ser Ser Lys
        770               775               780

Leu Thr Arg His Met Lys Thr His Gly Gln Val Gly Lys Asp Val Tyr
785               790               795               800

Lys Cys Glu Ile Cys Lys Met Pro Phe Ser Val Tyr Ser Thr Leu Glu
            805               810               815
```

-continued

```
Lys His Met Lys Lys Trp His Ser Asp Arg Val Leu Asn Asn Asp Ile
            820                 825                 830

Lys Thr Glu
        835

<210> SEQ ID NO 56
<211> LENGTH: 773
<212> TYPE: PRT
<213> ORGANISM: Mus musculus

<400> SEQUENCE: 56

Met Ser Arg Arg Lys Gln Gly Lys Pro Gln His Leu Ser Lys Arg Glu
1               5                   10                  15

Phe Ser Pro Glu Pro Leu Glu Ala Ile Leu Thr Asp Asp Glu Pro Asp
            20                  25                  30

His Gly Pro Leu Gly Ala Pro Glu Gly Asp His Asp Leu Leu Thr Cys
        35                  40                  45

Gly Gln Cys Gln Met Asn Phe Pro Leu Gly Asp Ile Leu Ile Phe Ile
    50                  55                  60

Glu His Lys Arg Lys Gln Cys Asn Gly Ser Leu Cys Leu Glu Lys Gly
65                  70                  75                  80

Val Asp Lys Pro Pro Ser Pro Ser Pro Ile Glu Met Lys Lys Ala Ser
            85                  90                  95

Asn Pro Val Glu Val Gly Ile Gln Val Thr Pro Glu Asp Asp Asp Cys
            100                 105                 110

Leu Ser Thr Ser Ser Arg Gly Ile Cys Pro Lys Gln Glu His Ile Ala
        115                 120                 125

Asp Lys Leu Leu His Trp Arg Gly Leu Ser Ser Pro Arg Ser Ala His
    130                 135                 140

Gly Ala Leu Ile Pro Thr Pro Gly Met Ser Ala Glu Tyr Ala Pro Gln
145                 150                 155                 160

Gly Ile Cys Lys Asp Glu Pro Ser Ser Tyr Thr Cys Thr Thr Cys Lys
                165                 170                 175

Gln Pro Phe Thr Ser Ala Trp Phe Leu Leu Gln His Ala Gln Asn Thr
            180                 185                 190

His Gly Leu Arg Ile Tyr Leu Glu Ser Glu His Gly Ser Pro Leu Thr
        195                 200                 205

Pro Arg Val Gly Ile Pro Ser Gly Leu Gly Ala Glu Cys Pro Ser Gln
    210                 215                 220

Pro Pro Leu His Gly Ile His Ile Ala Asp Asn Asn Pro Phe Asn Leu
225                 230                 235                 240

Leu Arg Ile Pro Gly Ser Val Ser Arg Glu Ala Ser Gly Leu Ala Glu
                245                 250                 255

Gly Arg Phe Pro Pro Thr Pro Pro Leu Phe Ser Pro Pro Pro Arg His
            260                 265                 270

His Leu Asp Pro His Arg Ile Glu Arg Leu Gly Ala Glu Glu Met Ala
        275                 280                 285

Leu Ala Thr His His Pro Ser Ala Phe Asp Arg Val Leu Arg Leu Asn
    290                 295                 300

Pro Met Ala Met Glu Pro Pro Ala Met Asp Phe Ser Arg Arg Leu Arg
305                 310                 315                 320

Glu Leu Ala Gly Asn Thr Ser Ser Pro Pro Leu Ser Pro Gly Arg Pro
                325                 330                 335

Ser Pro Met Gln Arg Leu Leu Gln Pro Phe Gln Pro Gly Ser Lys Pro
```

-continued

```
                340             345             350

Pro Phe Leu Ala Thr Pro Pro Leu Pro Pro Leu Gln Ser Ala Pro Pro
        355             360             365

Pro Ser Gln Pro Pro Val Lys Ser Lys Ser Cys Glu Phe Cys Gly Lys
        370             375             380

Thr Phe Lys Phe Gln Ser Asn Leu Val Val His Arg Arg Ser His Thr
385             390             395             400

Gly Glu Lys Pro Tyr Lys Cys Asn Leu Cys Asp His Ala Cys Thr Gln
                405             410             415

Ala Ser Lys Leu Lys Arg His Met Lys Thr His Met His Lys Ser Ser
            420             425             430

Pro Met Thr Val Lys Ser Asp Asp Gly Leu Ser Thr Ala Ser Ser Pro
            435             440             445

Glu Pro Gly Thr Ser Asp Leu Val Gly Ser Ala Ser Ser Ala Leu Lys
        450             455             460

Ser Val Val Ala Lys Phe Lys Ser Glu Asn Asp Pro Asn Leu Ile Pro
465             470             475             480

Glu Asn Gly Asp Glu Glu Glu Glu Asp Asp Glu Glu Glu Glu Glu Glu
            485             490             495

Glu Glu Glu Glu Glu Glu Glu Leu Thr Glu Ser Glu Arg Val Asp
            500             505             510

Tyr Gly Phe Gly Leu Ser Leu Glu Ala Ala Arg His His Glu Asn Ser
        515             520             525

Ser Arg Gly Ala Val Val Gly Val Gly Asp Glu Gly Arg Ala Leu Pro
        530             535             540

Asp Val Met Gln Gly Met Val Leu Ser Ser Met Gln His Phe Ser Glu
545             550             555             560

Ala Phe His Gln Val Leu Gly Glu Lys His Lys Arg Ser His Leu Ala
            565             570             575

Glu Ala Glu Gly His Arg Asp Thr Cys Asp Glu Asp Ser Val Ala Gly
        580             585             590

Glu Ser Asp Arg Ile Asp Asp Gly Thr Val Asn Gly Arg Gly Cys Ser
        595             600             605

Pro Gly Glu Ser Ala Ser Gly Gly Leu Ser Lys Lys Leu Leu Leu Gly
        610             615             620

Ser Pro Ser Ser Leu Ser Pro Phe Ser Lys Arg Ile Lys Leu Glu Lys
625             630             635             640

Glu Phe Asp Leu Pro Pro Ala Ala Met Pro Asn Thr Glu Asn Val Tyr
            645             650             655

Ser Gln Trp Leu Ala Gly Tyr Ala Ala Ser Arg Gln Leu Lys Asp Pro
            660             665             670

Phe Leu Thr Phe Gly Asp Ser Arg Gln Ser Pro Phe Ala Ser Ser Ser
            675             680             685

Glu His Ser Ser Glu Asn Gly Ser Leu Arg Phe Ser Thr Pro Pro Gly
        690             695             700

Glu Leu Asp Gly Gly Ile Ser Gly Arg Ser Gly Thr Gly Ser Gly Gly
705             710             715             720

Ser Thr Pro His Ile Ser Gly Pro Gly Pro Gly Arg Pro Ser Ser Lys
            725             730             735

Glu Gly Arg Arg Ser Asp Thr Cys Pro Ser His Thr Pro Val Arg Arg
            740             745             750

Ser Thr Pro Arg Ala Gln Asp Val Trp Gln Phe Ser Asp Gly Ser Ser
            755             760             765
```

```
Arg Thr Leu Lys Phe
    770

<210> SEQ ID NO 57
<211> LENGTH: 653
<212> TYPE: PRT
<213> ORGANISM: Homo sapiens

<400> SEQUENCE: 57

Met Pro Ala Ser Arg Leu Arg Asp Arg Ala Ala Ser Ser Ala Ser Gly
1               5                   10                  15

Ser Thr Cys Gly Ser Met Ser Gln Thr His Pro Val Leu Glu Ser Gly
            20                  25                  30

Leu Leu Ala Ser Ala Gly Cys Ser Ala Pro Arg Gly Pro Arg Lys Gly
        35                  40                  45

Gly Pro Ala Pro Val Asp Arg Lys Ala Lys Ala Ser Ala Met Pro Asp
    50                  55                  60

Ser Pro Ala Glu Val Lys Thr Gln Pro Arg Ser Thr Pro Pro Ser Met
65                  70                  75                  80

Pro Pro Pro Pro Ala Ala Ser Gln Gly Ala Thr Arg Pro Pro Ser
                85                  90                  95

Phe Thr Pro His Thr His Arg Glu Asp Gly Pro Ala Thr Leu Pro His
                100                 105                 110

Gly Arg Phe His Gly Cys Leu Lys Trp Ser Met Val Cys Leu Leu Met
                115                 120                 125

Asn Gly Ser Ser His Ser Pro Thr Ala Ile Asn Gly Ala Pro Cys Thr
    130                 135                 140

Pro Asn Gly Phe Ser Asn Gly Pro Ala Thr Ser Ser Thr Ala Ser Leu
145                 150                 155                 160

Ser Thr Gln His Leu Pro Pro Ala Cys Gly Ala Arg Gln Leu Ser Lys
                165                 170                 175

Leu Lys Arg Phe Leu Thr Thr Leu Gln Gln Phe Gly Ser Asp Ile Ser
                180                 185                 190

Pro Glu Ile Gly Glu Arg Val Arg Thr Leu Val Leu Gly Leu Val Asn
                195                 200                 205

Ser Thr Leu Thr Ile Glu Glu Phe His Ser Lys Leu Gln Glu Ala Thr
    210                 215                 220

Asn Phe Pro Leu Arg Pro Phe Val Ile Pro Phe Leu Lys Ala Asn Leu
225                 230                 235                 240

Pro Leu Leu Gln Arg Glu Leu Leu His Cys Ala Arg Leu Ala Lys Gln
                245                 250                 255

Thr Pro Ala Gln Tyr Leu Ala Gln His Glu Gln Leu Leu Leu Asp Ala
                260                 265                 270

Ser Ala Ser Ser Pro Ile Asp Ser Ser Glu Leu Leu Leu Glu Val Asn
    275                 280                 285

Glu Asn Gly Lys Arg Arg Thr Pro Asp Arg Thr Lys Glu Asn Gly Ser
    290                 295                 300

Asp Arg Asp Pro Leu His Pro Glu His Leu Ser Lys Arg Pro Cys Thr
305                 310                 315                 320

Leu Asn Pro Ala Gln Arg Tyr Ser Pro Ser Asn Gly Pro Pro Gln Pro
                325                 330                 335

Thr Pro Pro Pro His Tyr Arg Leu Glu Asp Ile Ala Met Ala His His
                340                 345                 350

Phe Arg Asp Ala Tyr Arg His Pro Asp Pro Arg Glu Leu Arg Glu Arg
```

```
            355                   360                   365

His Arg Pro Leu Val Val Pro Gly Ser Arg Gln Glu Glu Val Ile Asp
    370                   375                   380

His Lys Leu Thr Glu Arg Glu Trp Ala Glu Glu Trp Lys His Leu Asn
385                   390                   395                   400

Asn Leu Leu Asn Cys Ile Met Asp Met Val Glu Lys Thr Arg Arg Ser
                    405                   410                   415

Leu Thr Val Leu Arg Arg Cys Gln Glu Ala Asp Arg Glu Glu Leu Asn
                420                   425                   430

His Trp Ala Arg Arg Tyr Ser Asp Ala Glu Asp Thr Lys Lys Gly Pro
                435                   440                   445

Ala Pro Ala Ala Ala Arg Pro Arg Ser Ser Ser Ala Gly Pro Glu Gly
            450                   455                   460

Pro Gln Leu Asp Val Pro Arg Glu Phe Leu Pro Arg Thr Leu Thr Gly
465                   470                   475                   480

Tyr Val Pro Glu Asp Ile Trp Arg Lys Ala Glu Glu Ala Val Asn Glu
                485                   490                   495

Val Lys Arg Gln Ala Met Ser Glu Leu Gln Lys Ala Val Ser Asp Ala
                500                   505                   510

Glu Arg Lys Ala His Glu Leu Ile Thr Thr Glu Arg Ala Lys Met Glu
                515                   520                   525

Arg Ala Leu Ala Glu Ala Lys Arg Gln Ala Ser Glu Asp Ala Leu Thr
            530                   535                   540

Val Ile Asn Gln Gln Glu Asp Ser Ser Glu Ser Cys Trp Asn Cys Gly
545                   550                   555                   560

Arg Lys Ala Ser Glu Thr Cys Ser Gly Cys Asn Ala Ala Arg Tyr Cys
                565                   570                   575

Gly Ser Phe Cys Gln His Arg Asp Trp Glu Lys His His His Val Cys
                580                   585                   590

Gly Gln Ser Leu Gln Gly Pro Thr Ala Val Val Ala Asp Pro Val Pro
                595                   600                   605

Gly Pro Pro Glu Ala Ala His Ser Leu Gly Pro Ser Leu Pro Val Gly
            610                   615                   620

Ala Ala Ser Pro Ser Glu Ala Gly Ser Ala Gly Pro Ser Arg Pro Gly
625                   630                   635                   640

Ser Pro Ser Pro Pro Gly Pro Leu Asp Thr Val Pro Arg
                645                   650
```

```
<210> SEQ ID NO 58
<211> LENGTH: 620
<212> TYPE: PRT
<213> ORGANISM: Mus musculus

<400> SEQUENCE: 58

Met Ser Gln Ala Ser Thr Thr Thr Leu Glu Ser Gly Ala Leu Leu Ser
1               5                   10                  15

Gly Pro Arg Gly Leu Gln Asn Gly Ser Pro Ala His Arg Lys Glu Lys
                20                  25                  30

Ala Ala Ala Met Pro Asp Ser Pro Ala Glu Val Lys Thr Gln Pro Arg
            35                  40                  45

Ser Thr Pro Pro Ser Met Pro Pro Pro Pro Thr Ser Ser Gln Gly
        50                  55                  60

Ala Thr Arg Pro Pro Ser Phe Thr Pro His Thr His Gly Glu Asp Gly
65                  70                  75                  80
```

-continued

```
Pro Ala Thr Ser Leu Pro His Gly Arg Phe His Gly Cys Leu Lys Trp
            85          90                  95

Ser Met Val Cys Leu Leu Met Asn Gly Ser Ser His Ser Pro Thr Ala
            100             105             110

Ile His Gly Ala Pro Ser Thr Pro Asn Gly Phe Ser Asn Gly Pro Ala
            115             120             125

Thr Ser Ser Thr Ala Ser Leu Ser Thr Gln His Leu Pro Pro Ala Cys
    130             135             140

Gly Ala Arg Gln Leu Ser Lys Leu Lys Arg Phe Leu Thr Thr Leu Gln
145             150             155             160

Gln Phe Gly Ser Asp Ile Ser Pro Glu Ile Gly Glu Arg Val Arg Thr
            165             170             175

Leu Val Leu Gly Leu Val Asn Ser Thr Leu Thr Ile Glu Glu Phe His
            180             185             190

Ala Lys Leu Gln Glu Ala Thr Asn Phe Pro Leu Arg Pro Phe Val Ile
            195             200             205

Pro Phe Leu Lys Ala Asn Leu Pro Leu Leu Gln Arg Glu Leu Leu His
    210             215             220

Cys Ala Arg Leu Ala Lys Gln Thr Pro Ala Gln Tyr Leu Ala Gln His
225             230             235             240

Glu Gln Leu Leu Leu Asp Ala Ser Ala Thr Ser Pro Val Asp Ser Ser
            245             250             255

Glu Leu Leu Leu Glu Val Asn Glu Asn Gly Lys Arg Arg Thr Pro Asp
            260             265             270

Arg Thr Lys Glu Asn Gly Ser Asp Arg Asp Pro Leu His Pro Asp His
            275             280             285

Leu Ser Lys Arg Ser Cys Thr Leu Ser Pro Ala Gln Arg Cys Ser Pro
    290             295             300

Ser Asn Gly Leu Pro His Pro Thr Pro Pro Pro Pro His Tyr Arg
305             310             315             320

Leu Glu Asp Met Ala Met Ala His His Phe Arg Asp Ser Tyr Arg His
            325             330             335

Pro Asp Pro Arg Glu Leu Arg Glu Arg His Arg Pro Leu Ala Ile Pro
            340             345             350

Gly Ser Arg Gln Glu Glu Val Ile Asp His Arg Leu Thr Glu Arg Glu
            355             360             365

Trp Ala Glu Glu Trp Lys His Leu Asn Ser Leu Leu Asn Cys Ile Met
    370             375             380

Asp Met Val Glu Lys Thr Arg Arg Ser Leu Thr Val Leu Arg Arg Cys
385             390             395             400

Gln Glu Ala Asp Arg Glu Glu Leu Asn His Trp Ile Arg Cys Tyr Ser
            405             410             415

Asp Ser Glu Glu Gly Lys Lys Gly Pro Thr Pro Ile Ser Ala Arg Ser
            420             425             430

Leu Asn Ser Cys Ser Gly Pro Glu Gly Ser Gln Leu Asp Val His Arg
            435             440             445

Asp Phe Thr Pro Arg Thr Leu Ser Gly Tyr Met Pro Glu Glu Ile Trp
    450             455             460

Arg Lys Ala Glu Glu Ala Val Asn Glu Val Lys Arg Gln Ala Met Ser
465             470             475             480

Glu Leu Gln Lys Ala Val Ser Asp Ala Glu Arg Lys Ala His Glu Leu
            485             490             495

Ile Thr Thr Glu Arg Ala Lys Met Glu Arg Ala Leu Ala Glu Ala Lys
```

-continued

```
                500                 505                 510

Arg Gln Ala Ser Glu Asp Ala Leu Thr Val Ile Asn Gln Gln Glu Asp
        515                 520                 525

Ser Ser Glu Ser Cys Trp Asn Cys Gly Arg Lys Ala Ser Glu Thr Cys
        530                 535                 540

Ser Gly Cys Asn Ala Ala Arg Tyr Cys Gly Ser Phe Cys Gln His Lys
545                 550                 555                 560

Asp Trp Glu Lys His His His Val Cys Gly Gln Ser Leu Gln Gly Pro
                565                 570                 575

Ala Ala Ala Val Ala Asp Pro Leu Pro Gly Gln Pro Asp Ala Thr Ala
                580                 585                 590

Ser Pro Ser Glu Ala Gly Ser Ala Gly Pro Ser Arg Pro Cys Ser Pro
        595                 600                 605

Gly Pro Pro Gly Pro Leu Asp Ala Ala Val Pro Arg
        610                 615                 620

<210> SEQ ID NO 59
<211> LENGTH: 520
<212> TYPE: PRT
<213> ORGANISM: Homo sapiens

<400> SEQUENCE: 59

Met Glu Val Leu Glu Ser Gly Glu Gln Gly Val Leu Gln Trp Asp Arg
1               5                   10                  15

Lys Leu Ser Glu Leu Ser Glu Pro Gly Asp Gly Glu Ala Leu Met Tyr
            20                  25                  30

His Thr His Phe Ser Glu Leu Leu Asp Glu Phe Ser Gln Asn Val Leu
        35                  40                  45

Gly Gln Leu Leu Asn Asp Pro Phe Leu Ser Glu Lys Ser Val Ser Met
    50                  55                  60

Glu Val Glu Pro Ser Pro Thr Ser Pro Ala Pro Leu Ile Gln Ala Glu
65                  70                  75                  80

His Ser Tyr Ser Leu Cys Glu Glu Pro Arg Ala Gln Ser Pro Phe Thr
                85                  90                  95

His Ile Thr Thr Ser Asp Ser Phe Asn Asp Asp Glu Val Glu Ser Glu
            100                 105                 110

Lys Trp Tyr Leu Ser Thr Asp Phe Pro Ser Thr Ser Ile Lys Thr Glu
        115                 120                 125

Pro Val Thr Asp Glu Pro Pro Pro Gly Leu Val Pro Ser Val Thr Leu
    130                 135                 140

Thr Ile Thr Ala Ile Ser Thr Pro Leu Glu Lys Glu Glu Pro Pro Leu
145                 150                 155                 160

Glu Met Asn Thr Gly Val Asp Ser Ser Cys Gln Thr Ile Ile Pro Lys
            165                 170                 175

Ile Lys Leu Glu Pro His Glu Val Asp Gln Phe Leu Asn Phe Ser Pro
            180                 185                 190

Lys Glu Ala Pro Val Asp His Leu His Leu Pro Pro Thr Pro Pro Ser
        195                 200                 205

Ser His Gly Ser Asp Ser Glu Gly Ser Leu Ser Pro Asn Pro Arg Leu
    210                 215                 220

His Pro Phe Ser Leu Pro Gln Thr His Ser Pro Ser Arg Ala Ala Pro
225                 230                 235                 240

Arg Ala Pro Ser Ala Leu Ser Ser Ser Pro Leu Leu Thr Ala Pro His
                245                 250                 255
```

```
Lys Leu Gln Gly Ser Gly Pro Leu Val Leu Thr Glu Glu Glu Lys Arg
        260             265             270

Thr Leu Ile Ala Glu Gly Tyr Pro Ile Pro Thr Lys Leu Pro Leu Ser
        275             280             285

Lys Ser Glu Glu Lys Ala Leu Lys Lys Ile Arg Arg Lys Ile Lys Asn
        290             295             300

Lys Ile Ser Ala Gln Glu Ser Arg Arg Lys Lys Lys Glu Tyr Met Asp
305             310             315             320

Ser Leu Glu Lys Lys Val Glu Ser Cys Ser Thr Glu Asn Leu Glu Leu
                325             330             335

Arg Lys Lys Val Glu Val Leu Glu Asn Thr Asn Arg Thr Leu Leu Gln
        340             345             350

Gln Leu Gln Lys Leu Gln Thr Leu Val Met Gly Lys Val Ser Arg Thr
        355             360             365

Cys Lys Leu Ala Gly Thr Gln Thr Gly Thr Cys Leu Met Val Val Val
        370             375             380

Leu Cys Phe Ala Val Ala Phe Gly Ser Phe Phe Gln Gly Tyr Gly Pro
385             390             395             400

Tyr Pro Ser Ala Thr Lys Met Ala Leu Pro Ser Gln His Ser Leu Gln
                405             410             415

Glu Pro Tyr Thr Ala Ser Val Val Arg Ser Arg Asn Leu Leu Ile Tyr
                420             425             430

Glu Glu His Ser Pro Pro Glu Glu Ser Ser Ser Pro Gly Ser Ala Gly
            435             440             445

Glu Leu Gly Gly Trp Asp Arg Gly Ser Ser Leu Leu Arg Val Ser Gly
        450             455             460

Leu Glu Ser Arg Pro Asp Val Asp Leu Pro His Phe Ile Ile Ser Asn
465             470             475             480

Glu Thr Ser Leu Glu Lys Ser Val Leu Leu Glu Leu Gln Gln His Leu
                485             490             495

Val Ser Ala Lys Leu Glu Gly Asn Glu Thr Leu Lys Val Val Glu Leu
            500             505             510

Asp Arg Arg Val Asn Thr Thr Phe
        515             520
```

```
<210> SEQ ID NO 60
<211> LENGTH: 521
<212> TYPE: PRT
<213> ORGANISM: Mus musculus

<400> SEQUENCE: 60
```

```
Met Glu Val Leu Glu Ser Gly Glu Gln Ser Val Leu Gln Trp Asp Arg
1               5               10              15

Lys Leu Ser Glu Leu Ser Glu Pro Gly Glu Thr Glu Ala Leu Met Tyr
            20              25              30

His Thr His Phe Ser Glu Leu Leu Asp Glu Phe Ser Gln Asn Val Leu
        35              40              45

Gly Gln Leu Leu Ser Asp Pro Phe Leu Ser Glu Lys Ser Glu Ser Met
        50              55              60

Glu Val Glu Pro Ser Pro Thr Ser Pro Ala Pro Leu Ile Gln Ala Glu
65              70              75              80

His Ser Tyr Ser Leu Ser Glu Glu Pro Arg Thr Gln Ser Pro Phe Thr
                85              90              95

His Ala Ala Thr Ser Asp Ser Phe Asn Asp Glu Glu Val Glu Ser Glu
            100             105             110
```

-continued

```
Lys Trp Tyr Leu Ser Thr Glu Phe Pro Ser Ala Thr Ile Lys Thr Glu
        115                 120                 125

Pro Ile Thr Glu Glu Gln Pro Pro Gly Leu Val Pro Ser Val Thr Leu
        130                 135                 140

Thr Ile Thr Ala Ile Ser Thr Pro Phe Glu Lys Glu Glu Ser Pro Leu
145                 150                 155                 160

Asp Met Asn Ala Gly Gly Asp Ser Ser Cys Gln Thr Leu Ile Pro Lys
                165                 170                 175

Ile Lys Leu Glu Pro His Glu Val Asp Gln Phe Leu Asn Phe Ser Pro
                180                 185                 190

Lys Glu Ala Ser Val Asp Gln Leu His Leu Pro Pro Thr Pro Pro Ser
                195                 200                 205

Ser His Ser Ser Asp Ser Glu Gly Ser Leu Ser Pro Asn Pro Arg Leu
        210                 215                 220

His Pro Phe Ser Leu Ser Gln Ala His Ser Pro Ala Arg Ala Met Pro
225                 230                 235                 240

Arg Gly Pro Ser Ala Leu Ser Thr Ser Pro Leu Leu Thr Ala Pro His
                245                 250                 255

Lys Leu Gln Gly Ser Gly Pro Leu Val Leu Thr Glu Glu Glu Lys Arg
                260                 265                 270

Thr Leu Val Ala Glu Gly Tyr Pro Ile Pro Thr Lys Leu Pro Leu Thr
                275                 280                 285

Lys Ser Glu Glu Lys Ala Leu Lys Lys Ile Arg Arg Lys Ile Lys Asn
        290                 295                 300

Lys Ile Ser Ala Gln Glu Ser Arg Arg Lys Lys Lys Glu Tyr Met Asp
305                 310                 315                 320

Ser Leu Glu Lys Lys Val Glu Ser Cys Ser Thr Glu Asn Leu Glu Leu
                325                 330                 335

Arg Lys Lys Val Glu Val Leu Glu Asn Thr Asn Arg Thr Leu Leu Gln
                340                 345                 350

Gln Leu Gln Lys Leu Gln Thr Leu Val Met Gly Lys Val Ser Arg Thr
        355                 360                 365

Cys Lys Leu Ala Gly Thr Gln Thr Gly Thr Cys Leu Met Val Val Val
        370                 375                 380

Leu Cys Phe Ala Val Ala Phe Gly Ser Phe Phe Gln Gly Tyr Gly Pro
385                 390                 395                 400

Tyr Pro Ser Ala Thr Lys Met Ala Leu Pro Ser Gln His Pro Leu Ser
                405                 410                 415

Glu Pro Tyr Thr Ala Ser Val Val Arg Ser Arg Asn Leu Leu Ile Tyr
                420                 425                 430

Glu Glu His Ala Pro Leu Glu Glu Ser Ser Ser Pro Ala Ser Ala Gly
        435                 440                 445

Glu Leu Gly Gly Trp Asp Arg Gly Ser Ser Leu Leu Arg Ala Ser Ser
        450                 455                 460

Gly Leu Glu Ala Leu Pro Glu Val Asp Leu Pro His Phe Leu Ile Ser
465                 470                 475                 480

Asn Glu Thr Ser Leu Glu Lys Ser Val Leu Leu Glu Leu Gln Gln His
                485                 490                 495

Leu Val Ser Ser Lys Leu Glu Gly Asn Glu Thr Leu Lys Val Val Glu
        500                 505                 510

Leu Glu Arg Arg Val Asn Ala Thr Phe
        515                 520
```

<210> SEQ ID NO 61
<211> LENGTH: 485
<212> TYPE: PRT
<213> ORGANISM: Homo sapiens

<400> SEQUENCE: 61

```
Met Ser Tyr Phe Val Asp Ser Ala Gly Ser Ser Pro Val Pro Tyr Ser
1               5                   10                  15

Ala Pro Arg Pro Ala Val Val Arg Gln Gly Pro Ser Asn Thr Tyr Glu
            20                  25                  30

Asp Pro Arg Met Asn Cys Gly Phe Gln Ser Asn Tyr His Gln Gln Arg
        35                  40                  45

Pro Cys Tyr Pro Phe Trp Asp Glu Met Ala Thr Gln Glu Val Pro Thr
    50                  55                  60

Gly Leu Glu His Cys Val Ser Asp Met Glu Cys Ala Asp Val Pro Leu
65                  70                  75                  80

Leu Thr Pro Ser Ser Lys Glu Met Met Ser Gln Ala Leu Lys Ala Thr
                85                  90                  95

Phe Ser Gly Phe Thr Lys Glu Gln Gln Arg Leu Gly Ile Pro Lys Asp
                100                 105                 110

Pro Arg Gln Trp Thr Glu Thr His Val Arg Asp Trp Val Met Trp Ala
            115                 120                 125

Val Asn Glu Phe Ser Leu Lys Gly Val Asp Phe Gln Lys Phe Cys Met
    130                 135                 140

Asn Gly Ala Ala Leu Cys Ala Leu Gly Lys Asp Cys Phe Leu Glu Leu
145                 150                 155                 160

Ala Pro Asp Phe Val Gly Asp Ile Leu Trp Glu His Leu Glu Ile Leu
                165                 170                 175

Gln Lys Glu Asp Val Lys Pro Tyr Gln Val Asn Gly Val Asn Pro Ala
            180                 185                 190

Tyr Pro Glu Ser Arg Tyr Thr Ser Asp Tyr Phe Ile Ser Tyr Gly Ile
            195                 200                 205

Glu His Ala Gln Cys Val Pro Pro Ser Glu Phe Ser Glu Pro Ser Phe
    210                 215                 220

Ile Thr Glu Ser Tyr Gln Thr Leu His Pro Ile Ser Ser Glu Glu Leu
225                 230                 235                 240

Leu Ser Leu Lys Tyr Glu Asn Asp Tyr Pro Ser Val Ile Leu Arg Asp
                245                 250                 255

Pro Leu Gln Thr Asp Thr Leu Gln Asn Asp Tyr Phe Ala Ile Lys Gln
            260                 265                 270

Glu Val Val Thr Pro Asp Asn Met Cys Met Gly Arg Thr Ser Arg Gly
            275                 280                 285

Lys Leu Gly Gly Gln Asp Ser Phe Glu Ser Ile Glu Ser Tyr Asp Ser
    290                 295                 300

Cys Asp Arg Leu Thr Gln Ser Trp Ser Ser Gln Ser Ser Phe Asn Ser
305                 310                 315                 320

Leu Gln Arg Val Pro Ser Tyr Asp Ser Phe Asp Ser Glu Asp Tyr Pro
                325                 330                 335

Ala Ala Leu Pro Asn His Lys Pro Lys Gly Thr Phe Lys Asp Tyr Val
            340                 345                 350

Arg Asp Arg Ala Asp Leu Asn Lys Asp Lys Pro Val Ile Pro Ala Ala
            355                 360                 365

Ala Leu Ala Gly Tyr Thr Gly Ser Gly Pro Ile Gln Leu Trp Gln Phe
    370                 375                 380
```

```
Leu Leu Glu Leu Leu Thr Asp Lys Ser Cys Gln Ser Phe Ile Ser Trp
385                 390                 395                 400

Thr Gly Asp Gly Trp Glu Phe Lys Leu Ser Asp Pro Asp Glu Val Ala
                405                 410                 415

Arg Arg Trp Gly Lys Arg Lys Asn Lys Pro Lys Met Asn Tyr Glu Lys
                420                 425                 430

Leu Ser Arg Gly Leu Arg Tyr Tyr Tyr Asp Lys Asn Ile Ile His Lys
            435                 440                 445

Thr Ala Gly Lys Arg Tyr Val Tyr Arg Phe Val Cys Asp Leu Gln Ser
        450                 455                 460

Leu Leu Gly Tyr Thr Pro Glu Glu Leu His Ala Met Leu Asp Val Lys
465                 470                 475                 480

Pro Asp Ala Asp Glu
                485
```

```
<210> SEQ ID NO 62
<211> LENGTH: 440
<212> TYPE: PRT
<213> ORGANISM: Mus musculus

<400> SEQUENCE: 62

Met Lys Ala Ala Val Asp Leu Lys Pro Thr Leu Thr Ile Ile Lys Thr
1               5                   10                  15

Glu Lys Val Asp Leu Glu Leu Phe Pro Ser Pro Asp Met Glu Cys Ala
                20                  25                  30

Asp Val Pro Leu Leu Thr Pro Ser Ser Lys Glu Met Met Ser Gln Ala
            35                  40                  45

Leu Lys Ala Thr Phe Ser Gly Phe Thr Lys Glu Gln Gln Arg Leu Gly
        50                  55                  60

Ile Pro Lys Asp Pro Arg Gln Trp Thr Glu Thr His Val Arg Asp Trp
65                  70                  75                  80

Val Met Trp Ala Val Asn Glu Phe Ser Leu Lys Gly Val Asp Phe Gln
                85                  90                  95

Lys Phe Cys Met Ser Gly Ala Ala Leu Cys Ala Leu Gly Lys Glu Cys
                100                 105                 110

Phe Leu Glu Leu Ala Pro Asp Phe Val Gly Asp Ile Leu Trp Glu His
            115                 120                 125

Leu Glu Ile Leu Gln Lys Glu Asp Val Lys Pro Tyr Gln Val Asn Gly
        130                 135                 140

Ala Asn Pro Thr Tyr Pro Glu Ser Cys Tyr Thr Ser Asp Tyr Phe Ile
145                 150                 155                 160

Ser Tyr Gly Ile Glu His Ala Gln Cys Val Pro Pro Ser Glu Phe Ser
                165                 170                 175

Glu Pro Ser Phe Ile Thr Glu Ser Tyr Gln Thr Leu His Pro Ile Ser
            180                 185                 190

Ser Glu Glu Leu Leu Ser Leu Lys Tyr Glu Asn Asp Tyr Pro Ser Val
        195                 200                 205

Ile Leu Gln Asp Pro Leu Gln Thr Asp Thr Leu Gln Thr Asp Tyr Phe
        210                 215                 220

Ala Ile Lys Gln Glu Val Leu Thr Pro Asp Asn Met Cys Leu Gly Arg
225                 230                 235                 240

Ala Ser Arg Gly Lys Leu Gly Gly Gln Asp Ser Phe Glu Ser Val Glu
                245                 250                 255

Ser Tyr Asp Ser Cys Asp Arg Leu Thr Gln Ser Trp Ser Ser Gln Ser
```

-continued

```
                260               265                  270

Ser Phe Asn Ser Leu Gln Arg Val Pro Ser Tyr Asp Ser Phe Asp Tyr
        275               280               285

Glu Asp Tyr Pro Ala Ala Leu Pro Asn His Lys Pro Lys Gly Thr Phe
        290               295               300

Lys Asp Tyr Val Arg Asp Arg Ala Asp Leu Asn Lys Asp Lys Pro Val
305               310               315               320

Ile Pro Ala Ala Ala Leu Ala Gly Tyr Thr Gly Ser Gly Pro Ile Gln
                325               330               335

Leu Trp Gln Phe Leu Leu Glu Leu Leu Thr Asp Lys Ser Cys Gln Ser
                340               345               350

Phe Ile Ser Trp Thr Gly Asp Gly Trp Glu Phe Lys Leu Ser Asp Pro
                355               360               365

Asp Glu Val Ala Arg Arg Trp Gly Lys Arg Lys Asn Lys Pro Lys Met
        370               375               380

Asn Tyr Glu Lys Leu Ser Arg Gly Leu Arg Tyr Tyr Tyr Asp Lys Asn
385               390               395               400

Ile Ile His Lys Thr Ala Gly Lys Arg Tyr Val Tyr Arg Phe Val Cys
                405               410               415

Asp Leu Gln Ser Leu Leu Gly Tyr Thr Pro Glu Glu Leu His Ala Met
                420               425               430

Leu Asp Val Lys Pro Asp Ala Asp
        435               440

<210> SEQ ID NO 63
<211> LENGTH: 1123
<212> TYPE: PRT
<213> ORGANISM: Homo sapiens

<400> SEQUENCE: 63

Met Asn Ser Pro Asn Glu Ser Ala Asp Gly Met Ser Gly Arg Glu Pro
1               5                   10                  15

Ser Leu Glu Ile Leu Pro Arg Thr Ser Leu His Ser Ile Pro Val Thr
                20                  25                  30

Val Glu Val Lys Pro Val Leu Pro Arg Ala Met Pro Ser Ser Met Gly
        35                  40                  45

Gly Gly Gly Gly Gly Ser Pro Ser Pro Val Glu Leu Arg Gly Ala Leu
        50                  55                  60

Val Gly Ser Val Asp Pro Thr Leu Arg Glu Gln Gln Leu Gln Gln Glu
65                  70                  75                  80

Leu Leu Ala Leu Lys Gln Gln Gln Leu Gln Lys Gln Leu Leu Phe
                85                  90                  95

Ala Glu Phe Gln Lys Gln His Asp His Leu Thr Arg Gln His Glu Val
                100                 105                 110

Gln Leu Gln Lys His Leu Lys Gln Gln Gln Glu Met Leu Ala Ala Lys
        115                 120                 125

Gln Gln Gln Glu Met Leu Ala Ala Lys Arg Gln Gln Glu Leu Glu Gln
        130                 135                 140

Gln Arg Gln Arg Glu Gln Gln Arg Gln Glu Glu Leu Glu Lys Gln Arg
145                 150                 155                 160

Leu Glu Gln Gln Leu Leu Ile Leu Arg Asn Lys Glu Lys Ser Lys Glu
                165                 170                 175

Ser Ala Ile Ala Ser Thr Glu Val Lys Leu Arg Leu Gln Glu Phe Leu
                180                 185                 190
```

285 286

```
Leu Ser Lys Ser Lys Glu Pro Thr Pro Gly Gly Leu Asn His Ser Leu
        195                 200             205

Pro Gln His Pro Lys Cys Trp Gly Ala His His Ala Ser Leu Asp Gln
        210                 215             220

Ser Ser Pro Pro Gln Ser Gly Pro Pro Gly Thr Pro Pro Ser Tyr Lys
225                 230             235                 240

Leu Pro Leu Pro Gly Pro Tyr Asp Ser Arg Asp Asp Phe Pro Leu Arg
                245             250             255

Lys Thr Ala Ser Glu Pro Asn Leu Lys Val Arg Ser Arg Leu Lys Gln
                260             265             270

Lys Val Ala Glu Arg Arg Ser Ser Pro Leu Leu Arg Arg Lys Asp Gly
        275                 280             285

Thr Val Ile Ser Thr Phe Lys Lys Arg Ala Val Glu Ile Thr Gly Ala
        290                 295             300

Gly Pro Gly Ala Ser Ser Val Cys Asn Ser Ala Pro Gly Ser Gly Pro
305                 310             315                 320

Ser Ser Pro Asn Ser Ser His Ser Thr Ile Ala Glu Asn Gly Phe Thr
                325             330             335

Gly Ser Val Pro Asn Ile Pro Thr Glu Met Leu Pro Gln His Arg Ala
                340             345             350

Leu Pro Leu Asp Ser Ser Pro Asn Gln Phe Ser Leu Tyr Thr Ser Pro
                355             360             365

Ser Leu Pro Asn Ile Ser Leu Gly Leu Gln Ala Thr Val Thr Val Thr
        370                 375             380

Asn Ser His Leu Thr Ala Ser Pro Lys Leu Ser Thr Gln Gln Glu Ala
385                 390             395                 400

Glu Arg Gln Ala Leu Gln Ser Leu Arg Gln Gly Gly Thr Leu Thr Gly
                405             410             415

Lys Phe Met Ser Thr Ser Ser Ile Pro Gly Cys Leu Leu Gly Val Ala
                420             425             430

Leu Glu Gly Asp Gly Ser Pro His Gly His Ala Ser Leu Leu Gln His
        435                 440             445

Val Leu Leu Leu Glu Gln Ala Arg Gln Gln Ser Thr Leu Ile Ala Val
        450                 455             460

Pro Leu His Gly Gln Ser Pro Leu Val Thr Gly Glu Arg Val Ala Thr
465                 470             475                 480

Ser Met Arg Thr Val Gly Lys Leu Pro Arg His Arg Pro Leu Ser Arg
                485             490             495

Thr Gln Ser Ser Pro Leu Pro Gln Ser Pro Gln Ala Leu Gln Gln Leu
                500             505             510

Val Met Gln Gln Gln His Gln Gln Phe Leu Glu Lys Gln Lys Gln Gln
        515                 520             525

Gln Leu Gln Leu Gly Lys Ile Leu Thr Lys Thr Gly Glu Leu Pro Arg
        530                 535             540

Gln Pro Thr Thr His Pro Glu Glu Thr Glu Glu Leu Thr Glu Gln
545                 550             555                 560

Gln Glu Val Leu Leu Gly Glu Gly Ala Leu Thr Met Pro Arg Glu Gly
                565             570             575

Ser Thr Glu Ser Glu Ser Thr Gln Glu Asp Leu Glu Glu Glu Asp Glu
                580             585             590

Glu Asp Asp Gly Glu Glu Glu Glu Asp Cys Ile Gln Val Lys Asp Glu
        595                 600             605

Glu Gly Glu Ser Gly Ala Glu Glu Gly Pro Asp Leu Glu Glu Pro Gly
```

-continued

```
        610              615              620

Ala Gly Tyr Lys Lys Leu Phe Ser Asp Ala Gln Pro Leu Gln Pro Leu
625              630              635              640

Gln Val Tyr Gln Ala Pro Leu Ser Leu Ala Thr Val Pro His Gln Ala
        645              650              655

Leu Gly Arg Thr Gln Ser Ser Pro Ala Ala Pro Gly Gly Met Lys Ser
        660              665              670

Pro Pro Asp Gln Pro Val Lys His Leu Phe Thr Thr Gly Val Val Tyr
        675              680              685

Asp Thr Phe Met Leu Lys His Gln Cys Met Cys Gly Asn Thr His Val
        690              695              700

His Pro Glu His Ala Gly Arg Ile Gln Ser Ile Trp Ser Arg Leu Gln
705              710              715              720

Glu Thr Gly Leu Leu Ser Lys Cys Glu Arg Ile Arg Gly Arg Lys Ala
        725              730              735

Thr Leu Asp Glu Ile Gln Thr Val His Ser Glu Tyr His Thr Leu Leu
        740              745              750

Tyr Gly Thr Ser Pro Leu Asn Arg Gln Lys Leu Asp Ser Lys Lys Leu
        755              760              765

Leu Gly Pro Ile Ser Gln Lys Met Tyr Ala Val Leu Pro Cys Gly Gly
        770              775              780

Ile Gly Val Asp Ser Asp Thr Val Trp Asn Glu Met His Ser Ser Ser
785              790              795              800

Ala Val Arg Met Ala Val Gly Cys Leu Leu Glu Leu Ala Phe Lys Val
        805              810              815

Ala Ala Gly Glu Leu Lys Asn Gly Phe Ala Ile Ile Arg Pro Pro Gly
        820              825              830

His His Ala Glu Glu Ser Thr Ala Met Gly Phe Cys Phe Phe Asn Ser
        835              840              845

Val Ala Ile Thr Ala Lys Leu Leu Gln Gln Lys Leu Asn Val Gly Lys
        850              855              860

Val Leu Ile Val Asp Trp Asp Ile His His Gly Asn Gly Thr Gln Gln
865              870              875              880

Ala Phe Tyr Asn Asp Pro Ser Val Leu Tyr Ile Ser Leu His Arg Tyr
        885              890              895

Asp Asn Gly Asn Phe Phe Pro Gly Ser Gly Ala Pro Glu Glu Val Gly
        900              905              910

Gly Gly Pro Gly Val Gly Tyr Asn Val Asn Val Ala Trp Thr Gly Gly
        915              920              925

Val Asp Pro Pro Ile Gly Asp Val Glu Tyr Leu Thr Ala Phe Arg Thr
        930              935              940

Val Val Met Pro Ile Ala His Glu Phe Ser Pro Asp Val Val Leu Val
945              950              955              960

Ser Ala Gly Phe Asp Ala Val Glu Gly His Leu Ser Pro Leu Gly Gly
        965              970              975

Tyr Ser Val Thr Ala Arg Cys Phe Gly His Leu Thr Arg Gln Leu Met
        980              985              990

Thr Leu Ala Gly Gly Arg Val Val  Leu Ala Leu Glu Gly  Gly His Asp
        995              1000              1005

Leu Thr  Ala Ile Cys Asp Ala  Ser Glu Ala Cys Val  Ser Ala Leu
        1010              1015              1020

Leu Ser  Val Glu Leu Gln Pro  Leu Asp Glu Ala Val  Leu Gln Gln
        1025              1030              1035
```

-continued

```
Lys Pro Asn Ile Asn Ala Val Ala Thr Leu Glu Lys Val Ile Glu
    1040            1045            1050

Ile Gln Ser Lys His Trp Ser Cys Val Gln Lys Phe Ala Ala Gly
    1055            1060            1065

Leu Gly Arg Ser Leu Arg Glu Ala Gln Ala Gly Glu Thr Glu Glu
    1070            1075            1080

Ala Glu Thr Val Ser Ala Met Ala Leu Leu Ser Val Gly Ala Glu
    1085            1090            1095

Gln Ala Gln Ala Ala Ala Ala Arg Glu His Ser Pro Arg Pro Ala
    1100            1105            1110

Glu Glu Pro Met Glu Gln Glu Pro Ala Leu
    1115            1120

<210> SEQ ID NO 64
<211> LENGTH: 1121
<212> TYPE: PRT
<213> ORGANISM: Mus musculus

<400> SEQUENCE: 64

Met Leu Leu Val Pro Lys Ala Gln Gly Leu Val Glu Met Leu Gln Thr
1           5               10              15

Ile Tyr Glu Thr Glu Ser Cys Phe Ser Ala Asp Gly Met Ser Gly Arg
            20              25              30

Glu Pro Ser Leu Glu Ile Leu Pro Arg Thr Pro Leu His Ser Ile Pro
            35              40              45

Val Ala Val Glu Val Lys Pro Val Leu Pro Gly Ala Met Pro Ser Ser
        50              55              60

Met Gly Gly Gly Gly Gly Ser Pro Ser Pro Val Glu Leu Arg Gly
65              70              75              80

Ala Leu Ala Gly Pro Met Asp Pro Ala Leu Arg Glu Gln Gln Leu Gln
                85              90              95

Gln Glu Leu Leu Val Leu Lys Gln Gln Gln Gln Leu Gln Lys Gln Leu
            100             105             110

Leu Phe Ala Glu Phe Gln Lys Gln His Asp His Leu Thr Arg Gln His
            115             120             125

Glu Val Gln Leu Gln Lys His Leu Lys Gln Gln Gln Glu Met Leu Ala
    130             135             140

Ala Lys Arg Gln Gln Glu Leu Glu Gln Gln Arg Gln Arg Glu Gln Gln
145             150             155             160

Arg Gln Glu Glu Leu Glu Lys Gln Arg Leu Glu Gln Gln Leu Leu Ile
            165             170             175

Leu Arg Asn Lys Glu Lys Ser Lys Glu Ser Ala Ile Ala Ser Thr Glu
            180             185             190

Val Lys Leu Arg Leu Gln Glu Phe Leu Leu Ser Lys Ser Lys Glu Pro
            195             200             205

Thr Pro Gly Gly Leu Asn His Ser Leu Pro Gln His Pro Lys Cys Trp
    210             215             220

Gly Ala His His Ala Ser Leu Asp Gln Ser Ser Pro Pro Gln Ser Gly
225             230             235             240

Pro Pro Gly Thr Pro Pro Ser Tyr Lys Leu Pro Leu Leu Gly Pro Tyr
                245             250             255

Asp Ser Arg Asp Asp Phe Pro Leu Arg Lys Thr Ala Ser Glu Pro Asn
                260             265             270

Leu Lys Val Arg Ser Arg Leu Lys Gln Lys Val Ala Glu Arg Arg Ser
```

-continued

```
                275                 280                 285

Ser Pro Leu Leu Arg Arg Lys Asp Gly Thr Val Ile Ser Thr Phe Lys
    290                 295                 300

Lys Arg Ala Val Glu Ile Thr Gly Thr Gly Pro Gly Val Ser Ser Val
305                 310                 315                 320

Cys Asn Ser Ala Pro Gly Ser Gly Pro Ser Ser Pro Asn Ser Ser His
                325                 330                 335

Ser Thr Ile Ala Glu Asn Gly Phe Thr Gly Ser Val Pro Asn Ile Pro
            340                 345                 350

Thr Glu Met Ile Pro Gln His Arg Ala Leu Pro Leu Asp Ser Ser Pro
            355                 360                 365

Asn Gln Phe Ser Leu Tyr Thr Ser Pro Ser Leu Pro Asn Ile Ser Leu
    370                 375                 380

Gly Leu Gln Ala Thr Val Thr Val Thr Asn Ser His Leu Thr Ala Ser
385                 390                 395                 400

Pro Lys Leu Ser Thr Gln Gln Glu Ala Glu Arg Gln Ala Leu Gln Ser
                405                 410                 415

Leu Arg Gln Gly Gly Thr Leu Thr Gly Lys Phe Met Ser Thr Ser Ser
            420                 425                 430

Ile Pro Gly Cys Leu Leu Gly Val Ala Leu Glu Gly Asp Thr Ser Pro
            435                 440                 445

His Gly His Ala Ser Leu Leu Gln His Val Leu Leu Leu Glu Gln Ala
    450                 455                 460

Arg Gln Gln Ser Thr Leu Ile Ala Val Pro Leu His Gly Gln Ser Pro
465                 470                 475                 480

Leu Val Thr Gly Glu Arg Val Ala Thr Ser Met Arg Thr Val Gly Lys
                485                 490                 495

Leu Pro Arg His Arg Pro Leu Ser Arg Thr Gln Ser Ser Pro Leu Pro
            500                 505                 510

Gln Ser Pro Gln Ala Leu Gln Gln Leu Val Met Gln Gln Gln His Gln
            515                 520                 525

Gln Phe Leu Glu Lys Gln Lys Gln Gln Gln Met Gln Leu Gly Lys Ile
    530                 535                 540

Leu Thr Lys Thr Gly Glu Leu Ser Arg Gln Pro Thr Thr His Pro Glu
545                 550                 555                 560

Glu Thr Glu Glu Glu Leu Thr Glu Gln Gln Glu Ala Leu Leu Gly Glu
                565                 570                 575

Gly Ala Leu Thr Ile Pro Arg Glu Gly Ser Thr Glu Ser Glu Ser Thr
            580                 585                 590

Gln Glu Asp Leu Glu Glu Glu Glu Glu Glu Glu Glu Glu Glu Glu Glu
            595                 600                 605

Asp Cys Ile Gln Val Lys Asp Glu Asp Gly Glu Ser Gly Pro Asp Glu
    610                 615                 620

Gly Pro Asp Leu Glu Glu Ser Ser Ala Gly Tyr Lys Lys Leu Phe Ala
625                 630                 635                 640

Asp Ala Gln Gln Leu Gln Pro Leu Gln Val Tyr Gln Ala Pro Leu Ser
                645                 650                 655

Leu Ala Thr Val Pro His Gln Ala Leu Gly Arg Thr Gln Ser Ser Pro
            660                 665                 670

Ala Ala Pro Gly Ser Met Lys Ser Pro Thr Asp Gln Pro Thr Val Val
            675                 680                 685

Lys His Leu Phe Thr Thr Gly Val Val Tyr Asp Thr Phe Met Leu Lys
    690                 695                 700
```

-continued

```
His Gln Cys Met Cys Gly Asn Thr His Val His Pro Glu His Ala Gly
705                 710                 715                 720

Arg Ile Gln Ser Ile Trp Ser Arg Leu Gln Glu Thr Gly Leu Leu Gly
                    725                 730                 735

Lys Cys Glu Arg Ile Arg Gly Arg Lys Ala Thr Leu Asp Glu Ile Gln
                740                 745                 750

Thr Val His Ser Glu Tyr His Thr Leu Leu Tyr Gly Thr Ser Pro Leu
                755                 760                 765

Asn Arg Gln Lys Leu Asp Ser Lys Lys Leu Leu Gly Pro Ile Ser Gln
            770                 775                 780

Lys Met Tyr Ala Met Leu Pro Cys Gly Gly Ile Gly Val Asp Ser Asp
785                 790                 795                 800

Thr Val Trp Asn Glu Met His Ser Ser Ser Ala Val Arg Met Ala Val
                    805                 810                 815

Gly Cys Leu Val Glu Leu Ala Phe Lys Val Ala Ala Gly Glu Leu Lys
                820                 825                 830

Asn Gly Phe Ala Ile Ile Arg Pro Pro Gly His His Ala Glu Glu Ser
                835                 840                 845

Thr Ala Met Gly Phe Cys Phe Phe Asn Ser Val Ala Ile Thr Ala Lys
            850                 855                 860

Leu Leu Gln Gln Lys Leu Ser Val Gly Lys Val Leu Ile Val Asp Trp
865                 870                 875                 880

Asp Ile His His Gly Asn Gly Thr Gln Gln Ala Phe Tyr Asn Asp Pro
                    885                 890                 895

Ser Val Leu Tyr Ile Ser Leu His Arg Tyr Asp Asn Gly Asn Phe Phe
                900                 905                 910

Pro Gly Ser Gly Ala Pro Glu Glu Val Gly Gly Gly Pro Gly Val Gly
                915                 920                 925

Tyr Asn Val Asn Val Ala Trp Thr Gly Gly Val Asp Pro Pro Ile Gly
            930                 935                 940

Asp Val Glu Tyr Leu Thr Ala Phe Arg Thr Val Val Met Pro Ile Ala
945                 950                 955                 960

Gln Glu Phe Ser Pro Asp Val Val Leu Val Ser Ala Gly Phe Asp Ala
                965                 970                 975

Val Glu Gly His Leu Ser Pro Leu Gly Gly Tyr Ser Val Thr Ala Arg
                980                 985                 990

Cys Phe Gly His Leu Thr Arg Gln  Leu Met Thr Leu Ala  Gly Gly Arg
            995                 1000                1005

Val Val  Leu Ala Leu Glu Gly  Gly His Asp Leu Thr  Ala Ile Cys
    1010                1015                1020

Asp Ala  Ser Glu Ala Cys Val  Ser Ala Leu Leu Ser  Val Glu Leu
    1025                1030                1035

Gln Pro  Leu Asp Glu Ala Val  Leu Gln Gln Lys Pro  Ser Val Asn
    1040                1045                1050

Ala Val  Ala Thr Leu Glu Lys  Val Ile Glu Ile Gln  Ser Lys His
    1055                1060                1065

Trp Ser  Cys Val Gln Arg Phe  Ala Ala Gly Leu Gly  Cys Ser Leu
    1070                1075                1080

Arg Glu  Ala Gln Thr Gly Glu  Lys Glu Glu Ala Glu  Thr Val Ser
    1085                1090                1095

Ala Met  Ala Leu Leu Ser Val  Gly Ala Glu Gln Ala  Gln Ala Val
    1100                1105                1110
```

-continued

```
Ala Thr  Gln Glu His Ser Pro  Arg
    1115                 1120

<210> SEQ ID NO 65
<211> LENGTH: 270
<212> TYPE: PRT
<213> ORGANISM: Homo sapiens

<400> SEQUENCE: 65

Met Gln Tyr Pro His Pro Gly Pro Ala Ala Gly Ala Val Gly Val Pro
1               5                   10                  15

Leu Tyr Ala Pro Thr Pro Leu Leu Gln Pro Ala His Pro Thr Pro Phe
            20                  25                  30

Tyr Ile Glu Asp Ile Leu Gly Arg Gly Pro Ala Ala Pro Thr Pro Ala
        35                  40                  45

Pro Thr Leu Pro Ser Pro Asn Ser Ser Phe Thr Ser Leu Val Ser Pro
    50                  55                  60

Tyr Arg Thr Pro Val Tyr Glu Pro Thr Pro Ile His Pro Ala Phe Ser
65                  70                  75                  80

His His Ser Ala Ala Ala Leu Ala Ala Ala Tyr Gly Pro Gly Gly Phe
            85                  90                  95

Gly Gly Pro Leu Tyr Pro Phe Pro Arg Thr Val Asn Asp Tyr Thr His
            100                 105                 110

Ala Leu Leu Arg His Asp Pro Leu Gly Lys Pro Leu Leu Trp Ser Pro
            115                 120                 125

Phe Leu Gln Arg Pro Leu His Lys Arg Lys Gly Gly Gln Val Arg Phe
    130                 135                 140

Ser Asn Asp Gln Thr Ile Glu Leu Glu Lys Lys Phe Glu Thr Gln Lys
145                 150                 155                 160

Tyr Leu Ser Pro Pro Glu Arg Lys Arg Leu Ala Lys Met Leu Gln Leu
                165                 170                 175

Ser Glu Arg Gln Val Lys Thr Trp Phe Gln Asn Arg Arg Ala Lys Trp
            180                 185                 190

Arg Arg Leu Lys Gln Glu Asn Pro Gln Ser Asn Lys Lys Glu Glu Leu
            195                 200                 205

Glu Ser Leu Asp Ser Ser Cys Asp Gln Arg Gln Asp Leu Pro Ser Glu
    210                 215                 220

Gln Asn Lys Gly Ala Ser Leu Asp Ser Ser Gln Cys Ser Pro Ser Pro
225                 230                 235                 240

Ala Ser Gln Glu Asp Leu Glu Ser Glu Ile Ser Glu Asp Ser Asp Gln
            245                 250                 255

Glu Val Asp Ile Glu Gly Asp Lys Ser Tyr Phe Asn Ala Gly
            260                 265                 270

<210> SEQ ID NO 66
<211> LENGTH: 271
<212> TYPE: PRT
<213> ORGANISM: Mus musculus

<400> SEQUENCE: 66

Met Gln Phe Pro His Pro Gly Pro Ala Ala Ala Pro Ala Val Gly Val
1               5                   10                  15

Pro Leu Tyr Ala Pro Thr Pro Leu Leu Gln Pro Ala His Pro Thr Pro
            20                  25                  30

Phe Tyr Ile Asp Asp Ile Leu Gly Arg Gly Pro Ala Ala Pro Thr Pro
            35                  40                  45
```

```
Thr Pro Thr Leu Pro Ser Pro Asn Ser Ser Phe Thr Ser Leu Val Ser
    50              55                  60

Ser Tyr Arg Thr Pro Val Tyr Glu Pro Thr Pro Val His Pro Ala Phe
65              70                  75                  80

Ser His His Pro Ala Ala Ala Leu Ala Ala Ala Tyr Gly Pro Ser Gly
            85                  90                  95

Phe Gly Gly Pro Leu Tyr Pro Phe Pro Arg Thr Val Asn Asp Tyr Thr
            100                 105                 110

His Ala Leu Leu Arg His Asp Pro Leu Gly Lys Pro Leu Leu Trp Ser
            115                 120                 125

Pro Phe Leu Gln Arg Pro Leu His Lys Arg Lys Gly Gly Gln Val Arg
    130                 135                 140

Phe Ser Asn Asp Gln Thr Val Glu Leu Glu Lys Lys Phe Glu Thr Gln
145                 150                 155                 160

Lys Tyr Leu Ser Pro Pro Glu Arg Lys Arg Leu Ala Lys Met Leu Gln
                165                 170                 175

Leu Ser Glu Arg Gln Val Lys Thr Trp Phe Gln Asn Arg Arg Ala Lys
            180                 185                 190

Trp Arg Arg Leu Lys Gln Glu Asn Pro Gln Ser Asn Lys Lys Asp Ala
    195                 200                 205

Leu Asp Ser Leu Asp Thr Ser Cys Glu Gln Gly Gln Asp Leu Pro Ser
    210                 215                 220

Glu Gln Asn Lys Gly Ala Ser Leu Asp Arg Ser Gln Cys Ser Pro Ser
225                 230                 235                 240

Pro Ala Ser Gln Glu Asp Pro Asp Ser Glu Ile Ser Glu Asp Ser Asp
            245                 250                 255

Gln Glu Val Asp Ile Glu Gly Asp Lys Gly Tyr Phe Asn Ala Gly
            260                 265                 270

<210> SEQ ID NO 67
<211> LENGTH: 270
<212> TYPE: PRT
<213> ORGANISM: Homo sapiens

<400> SEQUENCE: 67

Met Ser Ser Tyr Phe Val Asn Ser Phe Cys Gly Arg Tyr Pro Asn Gly
1               5                   10                  15

Pro Asp Tyr Gln Leu His Asn Tyr Gly Asp His Ser Ser Val Ser Glu
            20                  25                  30

Gln Phe Arg Asp Ser Ala Ser Met His Ser Gly Arg Tyr Gly Tyr Gly
            35                  40                  45

Tyr Asn Gly Met Asp Leu Ser Val Gly Arg Ser Gly Ser Gly His Phe
    50                  55                  60

Gly Ser Gly Glu Arg Ala Arg Ser Tyr Ala Ala Ser Ala Ser Ala Ala
65              70                  75                  80

Pro Ala Glu Pro Arg Tyr Ser Gln Pro Ala Thr Ser Thr His Ser Pro
            85                  90                  95

Gln Pro Asp Pro Leu Pro Cys Ser Ala Val Ala Pro Ser Pro Gly Ser
            100                 105                 110

Asp Ser His His Gly Gly Lys Asn Ser Leu Ser Asn Ser Ser Gly Ala
            115                 120                 125

Ser Ala Asp Ala Gly Ser Thr His Ile Ser Ser Arg Glu Gly Val Gly
    130                 135                 140

Thr Ala Ser Gly Ala Glu Glu Asp Ala Pro Ala Ser Ser Glu Gln Ala
145                 150                 155                 160
```

```
Ser Ala Gln Ser Glu Pro Ser Pro Ala Pro Pro Ala Gln Pro Gln Ile
                165                 170                 175

Tyr Pro Trp Met Arg Lys Leu His Ile Ser His Asp Asn Ile Gly Gly
            180                 185                 190

Pro Glu Gly Lys Arg Ala Arg Thr Ala Tyr Thr Arg Tyr Gln Thr Leu
            195                 200                 205

Glu Leu Glu Lys Glu Phe His Phe Asn Arg Tyr Leu Thr Arg Arg Arg
        210                 215                 220

Arg Ile Glu Ile Ala His Ala Leu Cys Leu Ser Glu Arg Gln Ile Lys
225                 230                 235                 240

Ile Trp Phe Gln Asn Arg Arg Met Lys Trp Lys Lys Asp Asn Lys Leu
                245                 250                 255

Lys Ser Met Ser Met Ala Ala Ala Gly Gly Ala Phe Arg Pro
                260                 265                 270
```

```
<210> SEQ ID NO 68
<211> LENGTH: 270
<212> TYPE: PRT
<213> ORGANISM: Mus musculus

<400> SEQUENCE: 68
```

```
Met Ser Ser Tyr Phe Val Asn Ser Phe Cys Gly Arg Tyr Pro Asn Gly
1               5                   10                  15

Pro Asp Tyr Gln Leu His Asn Tyr Gly Asp His Ser Ser Val Ser Glu
            20                  25                  30

Gln Phe Arg Asp Ser Ala Ser Met His Ser Gly Arg Tyr Gly Tyr Gly
            35                  40                  45

Tyr Asn Gly Met Asp Leu Ser Val Gly Arg Ser Gly Ser Gly His Phe
        50                  55                  60

Gly Ser Gly Glu Arg Ala Arg Ser Tyr Ala Ala Gly Ala Ser Ala Ala
65                  70                  75                  80

Pro Ala Glu Pro Arg Tyr Ser Gln Pro Ala Thr Ser Thr His Ser Pro
            85                  90                  95

Pro Pro Asp Pro Leu Pro Cys Ser Ala Val Ala Pro Ser Pro Gly Ser
            100                 105                 110

Asp Ser His His Gly Gly Lys Asn Ser Leu Gly Asn Ser Ser Gly Ala
        115                 120                 125

Ser Ala Asn Ala Gly Ser Thr His Ile Ser Ser Arg Glu Gly Val Gly
        130                 135                 140

Thr Ala Ser Ala Ala Glu Glu Asp Ala Pro Ala Ser Ser Glu Gln Ala
145                 150                 155                 160

Gly Ala Gln Ser Glu Pro Ser Pro Ala Pro Pro Ala Gln Pro Gln Ile
                165                 170                 175

Tyr Pro Trp Met Arg Lys Leu His Ile Ser His Asp Asn Ile Gly Gly
            180                 185                 190

Pro Glu Gly Lys Arg Ala Arg Thr Ala Tyr Thr Arg Tyr Gln Thr Leu
            195                 200                 205

Glu Leu Glu Lys Glu Phe His Phe Asn Arg Tyr Leu Thr Arg Arg Arg
        210                 215                 220

Arg Ile Glu Ile Ala His Ala Leu Cys Leu Ser Glu Arg Gln Ile Lys
225                 230                 235                 240

Ile Trp Phe Gln Asn Arg Arg Met Lys Trp Lys Lys Asp Asn Lys Leu
                245                 250                 255

Lys Ser Met Ser Met Ala Ala Ala Gly Gly Ala Phe Arg Pro
```

-continued

```
              260              265              270
```

<210> SEQ ID NO 69
<211> LENGTH: 119
<212> TYPE: PRT
<213> ORGANISM: Homo sapiens

<400> SEQUENCE: 69

```
Met Lys Ala Leu Ser Pro Val Arg Gly Cys Tyr Glu Ala Val Cys Cys
1               5                   10                  15

Leu Ser Glu Arg Ser Leu Ala Ile Ala Arg Gly Arg Gly Lys Gly Pro
            20                  25                  30

Ala Ala Glu Glu Pro Leu Ser Leu Leu Asp Asp Met Asn His Cys Tyr
            35                  40                  45

Ser Arg Leu Arg Glu Leu Val Pro Gly Val Pro Arg Gly Thr Gln Leu
    50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Thr Pro Glu Leu Val Ile Ser Asn
            100                 105                 110

Asp Lys Arg Ser Phe Cys His
        115
```

<210> SEQ ID NO 70
<211> LENGTH: 119
<212> TYPE: PRT
<213> ORGANISM: Mus musculus

<400> SEQUENCE: 70

```
Met Lys Ala Leu Ser Pro Val Arg Gly Cys Tyr Glu Ala Val Cys Cys
1               5                   10                  15

Leu Ser Glu Arg Ser Leu Ala Ile Ala Arg Gly Arg Gly Lys Ser Pro
            20                  25                  30

Ser Thr Glu Glu Pro Leu Ser Leu Leu Asp Asp Met Asn His Cys Tyr
            35                  40                  45

Ser Arg Leu Arg Glu Leu Val Pro Gly Val Pro Arg Gly Thr Gln Leu
    50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Thr Pro Glu Leu Val Ile Ser Lys
            100                 105                 110

Asp Lys Arg Ser Phe Cys His
        115
```

<210> SEQ ID NO 71
<211> LENGTH: 519
<212> TYPE: PRT
<213> ORGANISM: Homo sapiens

<400> SEQUENCE: 71

```
Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30
```

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
            85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
            165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
            195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
            245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
            325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
            405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

```
Leu Arg Val Val Ser Thr Ser Gly Glu Gln Met Lys Val Tyr Lys Cys
    450             455                 460

Glu His Cys Arg Val Leu Phe Leu Asp His Val Met Tyr Thr Ile His
465             470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
                500                 505                 510

Glu His Arg Phe His Met Ser
        515

<210> SEQ ID NO 72
<211> LENGTH: 515
<212> TYPE: PRT
<213> ORGANISM: Mus musculus

<400> SEQUENCE: 72

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
                100                 105                 110

Pro Asn Gly Lys Leu Lys Cys Asp Ile Cys Gly Ile Val Cys Ile Gly
                115                 120                 125

Pro Asn Val Leu Met Val His Lys Arg Ser His Thr Gly Glu Arg Pro
        130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
                180                 185                 190

Arg Thr His Ser Val Gly Lys Pro His Lys Cys Gly Tyr Cys Gly Arg
                195                 200                 205

Ser Tyr Lys Gln Arg Ser Ser Leu Glu Glu His Lys Glu Arg Cys His
        210                 215                 220

Asn Tyr Leu Glu Ser Met Gly Leu Pro Gly Met Tyr Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
                260                 265                 270

Arg Lys Ser Ser Met Pro Gln Lys Phe Leu Gly Asp Lys Cys Leu Ser
        275                 280                 285

Asp Met Pro Tyr Asp Ser Ala Asn Tyr Glu Lys Glu Asp Met Met Thr
        290                 295                 300
```

-continued

```
Ser His Val Met Asp Gln Ala Ile Asn Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
            340                 345                 350

Asp Gly Pro Pro Arg Ser Asn His Ser Ala Gln Asp Ala Val Asp Asn
            355                 360                 365

Leu Leu Leu Leu Ser Lys Ala Lys Ser Val Ser Ser Glu Arg Glu Ala
        370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Glu Gln Arg Ala Tyr Glu
            420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
        450                 455                 460

Val Leu Phe Leu Asp His Val Met Tyr Thr Ile His Met Gly Cys His
465                 470                 475                 480

Gly Phe Arg Asp Pro Phe Glu Cys Asn Met Cys Gly Tyr His Ser Gln
                485                 490                 495

Asp Arg Tyr Glu Phe Ser Ser His Ile Thr Arg Gly Glu His Arg Tyr
            500                 505                 510

His Leu Ser
        515

<210> SEQ ID NO 73
<211> LENGTH: 526
<212> TYPE: PRT
<213> ORGANISM: Homo sapiens

<400> SEQUENCE: 73

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
        50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
            115                 120                 125

Val His Lys Arg Ser His Thr Gly Glu Arg Pro Phe His Cys Asn Gln
        130                 135                 140

Cys Gly Ala Ser Phe Thr Gln Lys Gly Asn Leu Leu Arg His Ile Lys
```

-continued

```
145             150             155             160

Leu His Ser Gly Glu Lys Pro Phe Lys Cys Pro Phe Cys Ser Tyr Ala
            165             170             175

Cys Arg Arg Arg Asp Ala Leu Thr Gly His Leu Arg Thr His Ser Val
            180             185             190

Gly Lys Pro His Lys Cys Asn Tyr Cys Gly Arg Ser Tyr Lys Gln Arg
            195             200             205

Ser Ser Leu Glu Glu His Lys Glu Arg Cys His Asn Tyr Leu Gln Asn
    210             215             220

Val Ser Met Glu Ala Ala Gly Gln Val Met Ser His His Val Pro Pro
225             230             235             240

Met Glu Asp Cys Lys Glu Gln Glu Pro Ile Met Asp Asn Asn Ile Ser
            245             250             255

Leu Val Pro Phe Glu Arg Pro Ala Val Ile Glu Lys Leu Thr Gly Asn
            260             265             270

Met Gly Lys Arg Lys Ser Ser Thr Pro Gln Lys Phe Val Gly Glu Lys
            275             280             285

Leu Met Arg Phe Ser Tyr Pro Asp Ile His Phe Asp Met Asn Leu Thr
    290             295             300

Tyr Glu Lys Glu Ala Glu Leu Met Gln Ser His Met Met Asp Gln Ala
305             310             315             320

Ile Asn Asn Ala Ile Thr Tyr Leu Gly Ala Glu Ala Leu His Pro Leu
            325             330             335

Met Gln His Pro Pro Ser Thr Ile Ala Glu Val Ala Pro Val Ile Ser
            340             345             350

Ser Ala Tyr Ser Gln Val Tyr His Pro Asn Arg Ile Glu Arg Pro Ile
            355             360             365

Ser Arg Glu Thr Ala Asp Ser His Glu Asn Asn Met Asp Gly Pro Ile
    370             375             380

Ser Leu Ile Arg Pro Lys Ser Arg Pro Gln Glu Arg Glu Ala Ser Pro
385             390             395             400

Ser Asn Ser Cys Leu Asp Ser Thr Asp Ser Glu Ser Ser His Asp Asp
            405             410             415

His Gln Ser Tyr Gln Gly His Pro Ala Leu Asn Pro Lys Arg Lys Gln
            420             425             430

Ser Pro Ala Tyr Met Lys Glu Asp Val Lys Ala Leu Asp Thr Thr Lys
            435             440             445

Ala Pro Lys Gly Ser Leu Lys Asp Ile Tyr Lys Val Phe Asn Gly Glu
    450             455             460

Gly Glu Gln Ile Arg Ala Phe Lys Cys Glu His Cys Arg Val Leu Phe
465             470             475             480

Leu Asp His Val Met Tyr Thr Ile His Met Gly Cys His Gly Tyr Arg
            485             490             495

Asp Pro Leu Glu Cys Asn Ile Cys Gly Tyr Arg Ser Gln Asp Arg Tyr
            500             505             510

Glu Phe Ser Ser His Ile Val Arg Gly Glu His Thr Phe His
            515             520             525
```

<210> SEQ ID NO 74
<211> LENGTH: 526
<212> TYPE: PRT
<213> ORGANISM: Mus musculus

<400> SEQUENCE: 74

```
Met Glu Thr Asp Ala Ile Asp Gly Tyr Ile Thr Cys Asp Asn Glu Leu
1               5                   10                  15

Ser Pro Glu Gly Glu His Ala Asn Met Ala Ile Asp Leu Thr Ser Ser
            20                  25                  30

Thr Pro Asn Gly Gln His Ala Ser Pro Ser His Met Thr Ser Thr Asn
            35                  40                  45

Ser Val Lys Leu Glu Met Gln Ser Asp Glu Glu Cys Asp Arg Gln Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Asp Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
            115                 120                 125

Val His Lys Arg Ser His Thr Gly Glu Arg Pro Phe His Cys Asn Gln
    130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
            165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg
            195                 200                 205

Ser Ser Leu Glu Glu His Lys Glu Arg Cys His Asn Tyr Leu Gln Asn
    210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
            245                 250                 255

Leu Val Pro Phe Glu Arg Pro Ala Val Ile Glu Lys Leu Thr Ala Asn
            260                 265                 270

Met Gly Lys Arg Lys Ser Ser Thr Pro Gln Lys Phe Val Gly Glu Lys
            275                 280                 285

Leu Met Arg Phe Ser Tyr Pro Asp Ile His Phe Asp Met Asn Leu Thr
    290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
            325                 330                 335

Met Gln His Ala Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
            355                 360                 365

Ser Arg Glu Thr Ser Asp Ser His Glu Asn Asn Met Asp Gly Pro Ile
    370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
            405                 410                 415

Arg Gln Ser Tyr Gln Gly Asn Pro Ala Leu Asn Pro Lys Arg Lys Gln
```

-continued

```
                420             425             430
Ser Pro Ala Tyr Met Lys Glu Asp Val Lys Ala Leu Asp Ala Thr Lys
        435             440             445

Ala Pro Lys Gly Ser Leu Lys Asp Ile Tyr Lys Val Phe Asn Gly Glu
        450             455             460

Gly Glu Gln Ile Arg Ala Phe Lys Cys Glu His Cys Arg Val Leu Phe
465             470             475             480

Leu Asp His Val Met Tyr Thr Ile His Met Gly Cys His Gly Tyr Arg
                485             490             495

Asp Pro Leu Glu Cys Asn Ile Cys Gly Tyr Arg Ser Gln Asp Arg Tyr
            500             505             510

Glu Phe Ser Ser His Ile Val Arg Gly Glu His Thr Phe His
            515             520             525
```

```
<210> SEQ ID NO 75
<211> LENGTH: 509
<212> TYPE: PRT
<213> ORGANISM: Homo sapiens

<400> SEQUENCE: 75

Met Glu Asp Ile Gln Thr Asn Ala Glu Leu Lys Ser Thr Gln Glu Gln
1               5               10              15

Ser Val Pro Ala Glu Ser Ala Ala Val Leu Asn Asp Tyr Ser Leu Thr
                20              25              30

Lys Ser His Glu Met Glu Asn Val Asp Ser Gly Glu Gly Pro Ala Asn
            35              40              45

Glu Asp Glu Asp Ile Gly Asp Asp Ser Met Lys Val Lys Asp Glu Tyr
        50              55              60

Ser Glu Arg Asp Glu Asn Val Leu Lys Ser Glu Pro Met Gly Asn Ala
65              70              75              80

Glu Glu Pro Glu Ile Pro Tyr Ser Tyr Ser Arg Glu Tyr Asn Glu Tyr
                85              90              95

Glu Asn Ile Lys Leu Glu Arg His Val Val Ser Phe Asp Ser Ser Arg
            100             105             110

Pro Thr Ser Gly Lys Met Asn Cys Asp Val Cys Gly Leu Ser Cys Ile
        115             120             125

Ser Phe Asn Val Leu Met Val His Lys Arg Ser His Thr Gly Glu Arg
        130             135             140

Pro Phe Gln Cys Asn Gln Cys Gly Ala Ser Phe Thr Gln Lys Gly Asn
145             150             155             160

Leu Leu Arg His Ile Lys Leu His Thr Gly Glu Lys Pro Phe Lys Cys
                165             170             175

His Leu Cys Asn Tyr Ala Cys Gln Arg Arg Asp Ala Leu Thr Gly His
            180             185             190

Leu Arg Thr His Ser Val Glu Lys Pro Tyr Lys Cys Glu Phe Cys Gly
        195             200             205

Arg Ser Tyr Lys Gln Arg Ser Ser Leu Glu Glu His Lys Glu Arg Cys
        210             215             220

Arg Thr Phe Leu Gln Ser Thr Asp Pro Gly Asp Thr Ala Ser Ala Glu
225             230             235             240

Ala Arg His Ile Lys Ala Glu Met Gly Ser Glu Arg Ala Leu Val Leu
                245             250             255

Asp Arg Leu Ala Ser Asn Val Ala Lys Arg Lys Ser Ser Met Pro Gln
            260             265             270
```

-continued

```
Lys Phe Ile Gly Glu Lys Arg His Cys Phe Asp Val Asn Tyr Asn Ser
        275                 280                 285

Ser Tyr Met Tyr Glu Lys Glu Ser Glu Leu Ile Gln Thr Arg Met Met
    290                 295                 300

Asp Gln Ala Ile Asn Asn Ala Ile Ser Tyr Leu Gly Ala Glu Ala Leu
305                 310                 315                 320

Arg Pro Leu Val Gln Thr Pro Pro Ala Pro Thr Ser Glu Met Val Pro
                325                 330                 335

Val Ile Ser Ser Met Tyr Pro Ile Ala Leu Thr Arg Ala Glu Met Ser
            340                 345                 350

Asn Gly Ala Pro Gln Glu Leu Glu Lys Lys Ser Ile His Leu Pro Glu
            355                 360                 365

Lys Ser Val Pro Ser Glu Arg Gly Leu Ser Pro Asn Asn Ser Gly His
        370                 375                 380

Asp Ser Thr Asp Thr Asp Ser Asn His Glu Glu Arg Gln Asn His Ile
385                 390                 395                 400

Tyr Gln Gln Asn His Met Val Leu Ser Arg Ala Arg Asn Gly Met Pro
                405                 410                 415

Leu Leu Lys Glu Val Pro Arg Ser Tyr Glu Leu Leu Lys Pro Pro Pro
            420                 425                 430

Ile Cys Pro Arg Asp Ser Val Lys Val Ile Asn Lys Glu Gly Glu Val
            435                 440                 445

Met Asp Val Tyr Arg Cys Asp His Cys Arg Val Leu Phe Leu Asp Tyr
    450                 455                 460

Val Met Phe Thr Ile His Met Gly Cys His Gly Phe Arg Asp Pro Phe
465                 470                 475                 480

Glu Cys Asn Met Cys Gly Tyr Arg Ser His Asp Arg Tyr Glu Phe Ser
                485                 490                 495

Ser His Ile Ala Arg Gly Glu His Arg Ala Leu Leu Lys
            500                 505
```

```
<210> SEQ ID NO 76
<211> LENGTH: 507
<212> TYPE: PRT
<213> ORGANISM: Mus musculus

<400> SEQUENCE: 76
```

```
Met Glu Asp Ile Gln Pro Thr Val Glu Leu Lys Ser Thr Glu Glu Gln
1               5                   10                  15

Pro Leu Pro Thr Glu Ser Pro Asp Ala Leu Asn Asp Tyr Ser Leu Pro
            20                  25                  30

Lys Pro His Glu Ile Glu Asn Val Asp Ser Arg Glu Ala Pro Ala Asn
        35                  40                  45

Glu Asp Glu Asp Ala Gly Glu Asp Ser Met Lys Val Lys Asp Glu Tyr
    50                  55                  60

Ser Asp Arg Asp Glu Asn Ile Met Lys Pro Glu Pro Met Gly Asp Ala
65                  70                  75                  80

Glu Glu Ser Glu Met Pro Tyr Ser Tyr Ala Arg Glu Tyr Ser Asp Tyr
                85                  90                  95

Glu Ser Ile Lys Leu Glu Arg His Val Pro Tyr Asp Asn Ser Arg Pro
            100                 105                 110

Thr Gly Gly Lys Met Asn Cys Asp Val Cys Gly Leu Ser Cys Ile Ser
            115                 120                 125

Phe Asn Val Leu Met Val His Lys Arg Ser His Thr Gly Glu Arg Pro
    130                 135                 140
```

```
Phe Gln Cys Asn Gln Cys Gly Ala Ser Phe Thr Gln Lys Gly Asn Leu
145                 150                 155                 160

Leu Arg His Ile Lys Leu His Thr Gly Glu Lys Pro Phe Lys Cys His
                165                 170                 175

Leu Cys Asn Tyr Ala Cys Gln Arg Arg Asp Ala Leu Thr Gly His Leu
            180                 185                 190

Arg Thr His Ser Val Glu Lys Pro Tyr Lys Cys Glu Phe Cys Gly Arg
            195                 200                 205

Ser Tyr Lys Gln Arg Ser Ser Leu Glu Glu His Lys Glu Arg Cys Arg
        210                 215                 220

Ala Phe Leu Gln Asn Pro Asp Leu Gly Asp Ala Ala Ser Val Glu Ala
225                 230                 235                 240

Arg His Ile Lys Ala Glu Met Gly Ser Glu Arg Ala Leu Val Leu Asp
                245                 250                 255

Arg Leu Ala Ser Asn Val Ala Lys Arg Lys Ser Ser Met Pro Gln Lys
            260                 265                 270

Phe Ile Gly Glu Lys Arg His Cys Phe Asp Ala Asn Tyr Asn Pro Gly
            275                 280                 285

Tyr Met Tyr Glu Lys Glu Asn Glu Met Met Gln Thr Arg Met Met Asp
        290                 295                 300

Gln Ala Ile Asn Asn Ala Ile Ser Tyr Leu Gly Ala Glu Ala Leu Arg
305                 310                 315                 320

Pro Leu Val Gln Thr Pro Pro Ala Pro Thr Ser Glu Met Val Pro Val
                325                 330                 335

Ile Ser Ser Val Tyr Pro Ile Ala Leu Thr Arg Ala Asp Met Pro Asn
            340                 345                 350

Gly Ala Pro Gln Glu Met Glu Lys Lys Arg Ile Leu Leu Pro Glu Lys
            355                 360                 365

Ile Leu Pro Ser Glu Arg Gly Leu Ser Pro Asn Asn Ser Ala Gln Asp
        370                 375                 380

Ser Thr Asp Thr Asp Ser Asn His Glu Asp Arg Gln His Leu Tyr Gln
385                 390                 395                 400

Gln Ser His Val Val Leu Pro Gln Ala Arg Asn Gly Met Pro Leu Leu
                405                 410                 415

Lys Glu Val Pro Arg Ser Phe Glu Leu Leu Lys Pro Pro Pro Ile Cys
            420                 425                 430

Leu Arg Asp Ser Ile Lys Val Ile Asn Lys Glu Gly Glu Val Met Asp
            435                 440                 445

Val Phe Arg Cys Asp His Cys His Val Leu Phe Leu Asp Tyr Val Met
        450                 455                 460

Phe Thr Ile His Met Gly Cys His Gly Phe Arg Asp Pro Phe Glu Cys
465                 470                 475                 480

Asn Met Cys Gly Tyr Arg Ser His Asp Arg Tyr Glu Phe Ser Ser His
            485                 490                 495

Ile Ala Arg Gly Glu His Arg Ala Met Leu Lys
        500                 505
```

<210> SEQ ID NO 77
<211> LENGTH: 419
<212> TYPE: PRT
<213> ORGANISM: Homo sapiens

<400> SEQUENCE: 77

Met Gly Glu Lys Lys Pro Glu Pro Leu Asp Phe Val Lys Asp Phe Gln

-continued

```
1                 5                 10                15
Glu Tyr Leu Thr Gln Gln Thr His His Val Asn Met Ile Ser Gly Ser
            20                25                30

Val Ser Gly Asp Lys Glu Ala Glu Ala Leu Gln Gly Ala Gly Thr Asp
            35                40                45

Gly Asp Gln Asn Gly Leu Asp His Pro Ser Val Glu Val Ser Leu Asp
    50                55                60

Glu Asn Ser Gly Met Leu Val Asp Gly Phe Glu Arg Thr Phe Asp Gly
65              70                75                80

Lys Leu Lys Cys Arg Tyr Cys Asn Tyr Ala Ser Lys Gly Thr Ala Arg
            85                90                95

Leu Ile Glu His Ile Arg Ile His Thr Gly Glu Lys Pro His Arg Cys
            100               105               110

His Leu Cys Pro Phe Ala Ser Ala Tyr Glu Arg His Leu Glu Ala His
            115               120               125

Met Arg Ser His Thr Gly Glu Lys Pro Tyr Lys Cys Glu Leu Cys Ser
    130               135               140

Phe Arg Cys Ser Asp Arg Ser Asn Leu Ser His His Arg Arg Arg Lys
145               150               155               160

His Lys Met Val Pro Ile Lys Gly Thr Arg Ser Ser Leu Ser Ser Lys
            165               170               175

Lys Met Trp Gly Val Leu Gln Lys Lys Thr Ser Asn Leu Gly Tyr Ser
            180               185               190

Arg Arg Ala Leu Ile Asn Leu Ser Pro Pro Ser Met Val Val Gln Lys
            195               200               205

Pro Asp Tyr Leu Asn Asp Phe Thr His Glu Ile Pro Asn Ile Gln Thr
    210               215               220

Asp Ser Tyr Glu Ser Met Ala Lys Thr Thr Pro Thr Gly Gly Leu Pro
225               230               235               240

Arg Asp Pro Gln Glu Leu Met Val Asp Asn Pro Leu Asn Gln Leu Ser
            245               250               255

Thr Leu Ala Gly Gln Leu Ser Ser Leu Pro Pro Glu Asn Gln Asn Pro
            260               265               270

Ala Ser Pro Asp Val Val Pro Cys Pro Asp Glu Lys Pro Phe Met Ile
            275               280               285

Gln Gln Pro Ser Thr Gln Ala Val Val Ser Ala Val Ser Ala Ser Ile
    290               295               300

Pro Gln Ser Ser Ser Pro Thr Ser Pro Glu Pro Arg Pro Ser His Ser
305               310               315               320

Gln Arg Asn Tyr Ser Pro Val Ala Gly Pro Ser Ser Glu Pro Ser Ala
            325               330               335

His Thr Ser Thr Pro Ser Ile Gly Asn Ser Gln Pro Ser Thr Pro Ala
            340               345               350

Pro Ala Leu Pro Val Gln Asp Pro Gln Leu Leu His His Cys Gln His
            355               360               365

Cys Asp Met Tyr Phe Ala Asp Asn Ile Leu Tyr Thr Ile His Met Gly
    370               375               380

Cys His Gly Tyr Glu Asn Pro Phe Gln Cys Asn Ile Cys Gly Cys Lys
385               390               395               400

Cys Lys Asn Lys Tyr Asp Phe Ala Cys His Phe Ala Arg Gly Gln His
            405               410               415

Asn Gln His
```

-continued

```
<210> SEQ ID NO 78
<211> LENGTH: 419
<212> TYPE: PRT
<213> ORGANISM: Mus musculus

<400> SEQUENCE: 78

Met Gly Glu Lys Lys Pro Glu Pro Leu Asp Phe Val Lys Asp Phe Gln
1               5                   10                  15

Glu Tyr Leu Thr Gln Gln Thr His His Val Asn Met Ile Ser Gly Ser
                20                  25                  30

Val Ser Gly Asp Lys Glu Ala Glu Thr Leu Gln Gly Ala Gly Thr Asp
            35                  40                  45

Gly Asp Gln Asn Gly Leu Asp His Pro Ser Val Glu Val Ser Leu Asp
        50                  55                  60

Glu Asn Ser Gly Met Leu Val Asp Gly Phe Glu Arg Thr Phe Asp Gly
65                  70                  75                  80

Lys Leu Lys Cys Arg Tyr Cys Asn Tyr Ala Ser Lys Gly Thr Ala Arg
                85                  90                  95

Leu Ile Glu His Ile Arg Ile His Thr Gly Glu Lys Pro His Arg Cys
            100                 105                 110

His Leu Cys Pro Phe Ala Ser Ala Tyr Glu Arg His Leu Glu Ala His
        115                 120                 125

Met Arg Ser His Thr Gly Glu Lys Pro Tyr Lys Cys Glu Leu Cys Ser
    130                 135                 140

Phe Arg Cys Ser Asp Arg Ser Asn Leu Ser His His Arg Arg Arg Lys
145                 150                 155                 160

His Lys Met Val Pro Ile Lys Gly Thr Arg Ser Ser Leu Ser Ser Lys
                165                 170                 175

Lys Met Trp Gly Val Leu Gln Lys Lys Thr Ser Asn Leu Gly Tyr Ser
            180                 185                 190

Arg Arg Ala Leu Ile Asn Leu Ser Pro Pro Ser Met Val Val Gln Lys
        195                 200                 205

Pro Asp Tyr Leu Asn Asp Phe Thr His Glu Ile Pro Asn Ile Gln Thr
    210                 215                 220

Asp Ser Tyr Glu Ala Met Ala Lys Thr Thr Pro Thr Gly Gly Leu Pro
225                 230                 235                 240

Arg Asp Pro Gln Glu Leu Met Val Asp Asn Pro Leu Asn Gln Leu Ser
                245                 250                 255

Thr Leu Ala Gly Gln Leu Ser Ser Leu Pro Pro Glu Asn Gln Asn Pro
            260                 265                 270

Ala Ser Pro Asp Val Asp Ala Cys Pro Asp Glu Lys Pro Phe Met Ile
        275                 280                 285

Gln Gln Pro Ser Ala Gln Ala Val Val Ser Ala Val Ser Ala Ser Ile
    290                 295                 300

Pro Gln Ser Ser Ser Pro Thr Ser Pro Glu Pro Arg Pro Ser His Ser
305                 310                 315                 320

Gln Arg Asn Tyr Ser Pro Val Ala Gly Pro Ser Ser Glu Pro Ser Ala
                325                 330                 335

His Thr Ser Thr Pro Ser Ile Gly Asn Ser Gln Pro Ser Thr Pro Ala
            340                 345                 350

Pro Thr Leu Pro Val Gln Asp Pro Gln Leu Leu His His Cys Gln His
        355                 360                 365

Cys Asp Val Tyr Phe Ala Asp Asn Val Leu Tyr Thr Val His Met Gly
        370                 375                 380
```

```
Cys His Gly Tyr Asp Ser Pro Phe Gln Cys Asn Val Cys Gly Cys Lys
385                 390                 395                 400

Cys Lys Asp Lys Tyr Asp Phe Ala Cys His Phe Ala Arg Gly Gln His
                405                 410                 415

Asn Gln His

<210> SEQ ID NO 79
<211> LENGTH: 516
<212> TYPE: PRT
<213> ORGANISM: Homo sapiens

<400> SEQUENCE: 79

Met Pro Val Pro Glu Arg Pro Ala Ala Gly Pro Asp Ser Pro Arg Pro
1               5                   10                  15

Gly Thr Arg Arg Ala Ala Pro Arg Val Leu Phe Gly Glu Trp Leu Leu
                20                  25                  30

Gly Glu Ile Ser Ser Gly Cys Tyr Glu Gly Leu Gln Trp Leu Asp Glu
            35                  40                  45

Ala Arg Thr Cys Phe Arg Val Pro Trp Lys His Phe Ala Arg Lys Asp
        50                  55                  60

Leu Ser Glu Ala Asp Ala Arg Ile Phe Lys Ala Trp Ala Val Ala Arg
65                  70                  75                  80

Gly Arg Trp Pro Pro Ser Ser Arg Gly Gly Gly Pro Pro Glu Ala
                85                  90                  95

Glu Thr Ala Glu Arg Ala Gly Trp Lys Thr Asn Phe Arg Cys Ala Leu
                100                 105                 110

Arg Ser Thr Arg Arg Phe Val Met Leu Arg Asp Asn Ser Gly Asp Pro
        115                 120                 125

Ala Asp Pro His Lys Val Tyr Ala Leu Ser Arg Glu Leu Cys Trp Arg
        130                 135                 140

Glu Gly Pro Gly Thr Asp Gln Thr Glu Ala Glu Ala Pro Ala Ala Val
145                 150                 155                 160

Pro Pro Pro Gln Gly Gly Pro Pro Gly Pro Phe Leu Ala His Thr His
                165                 170                 175

Ala Gly Leu Gln Ala Pro Gly Pro Leu Pro Ala Pro Ala Gly Asp Lys
                180                 185                 190

Gly Asp Leu Leu Leu Gln Ala Val Gln Gln Ser Cys Leu Ala Asp His
                195                 200                 205

Leu Leu Thr Ala Ser Trp Gly Ala Asp Pro Val Pro Thr Lys Ala Pro
        210                 215                 220

Gly Glu Gly Gln Glu Gly Leu Pro Leu Thr Gly Ala Cys Ala Gly Gly
225                 230                 235                 240

Pro Gly Leu Pro Ala Gly Glu Leu Tyr Gly Trp Ala Val Glu Thr Thr
                245                 250                 255

Pro Ser Pro Gly Pro Gln Pro Ala Ala Leu Thr Thr Gly Glu Ala Ala
                260                 265                 270

Ala Pro Glu Ser Pro His Gln Ala Glu Pro Tyr Leu Ser Pro Ser Pro
        275                 280                 285

Ser Ala Cys Thr Ala Val Gln Glu Pro Ser Pro Gly Ala Leu Asp Val
        290                 295                 300

Thr Ile Met Tyr Lys Gly Arg Thr Val Leu Gln Lys Val Val Gly His
305                 310                 315                 320

Pro Ser Cys Thr Phe Leu Tyr Gly Pro Pro Asp Pro Ala Val Arg Ala
                325                 330                 335
```

-continued

```
Thr Asp Pro Gln Gln Val Ala Phe Pro Ser Pro Ala Glu Leu Pro Asp
            340                 345             350

Gln Lys Gln Leu Arg Tyr Thr Glu Glu Leu Leu Arg His Val Ala Pro
            355                 360             365

Gly Leu His Leu Glu Leu Arg Gly Pro Gln Leu Trp Ala Arg Arg Met
        370                 375             380

Gly Lys Cys Lys Val Tyr Trp Glu Val Gly Gly Pro Pro Gly Ser Ala
385                 390                 395                 400

Ser Pro Ser Thr Pro Ala Cys Leu Leu Pro Arg Asn Cys Asp Thr Pro
                405                 410             415

Ile Phe Asp Phe Arg Val Phe Phe Gln Glu Leu Val Glu Phe Arg Ala
            420                 425             430

Arg Gln Arg Arg Gly Ser Pro Arg Tyr Thr Ile Tyr Leu Gly Phe Gly
            435                 440             445

Gln Asp Leu Ser Ala Gly Arg Pro Lys Glu Lys Ser Leu Val Leu Val
        450                 455             460

Lys Leu Glu Pro Trp Leu Cys Arg Val His Leu Glu Gly Thr Gln Arg
465                 470                 475                 480

Glu Gly Val Ser Ser Leu Asp Ser Ser Ser Leu Ser Leu Cys Leu Ser
                485                 490             495

Ser Ala Asn Ser Leu Tyr Asp Asp Ile Glu Cys Phe Leu Met Glu Leu
                500                 505             510

Glu Gln Pro Ala
        515
```

```
<210> SEQ ID NO 80
<211> LENGTH: 457
<212> TYPE: PRT
<213> ORGANISM: Mus musculus

<400> SEQUENCE: 80
```

```
Met Ala Glu Val Arg Gly Val Gln Arg Val Leu Phe Gly Asp Trp Leu
1               5                   10                  15

Leu Gly Glu Val Ser Ser Gly Gln Tyr Glu Gly Leu Gln Trp Leu Asn
            20                  25                  30

Glu Ala Arg Thr Val Phe Arg Val Pro Trp Lys His Phe Gly Arg Arg
        35                  40                  45

Asp Leu Asp Glu Glu Asp Ala Gln Ile Phe Lys Ala Trp Ala Val Ala
        50                  55                  60

Arg Gly Arg Trp Pro Pro Ser Gly Val Asn Leu Pro Pro Pro Glu Ala
65                  70                  75                  80

Glu Ala Ala Glu Arg Arg Glu Arg Arg Gly Trp Lys Thr Asn Phe Arg
                85                  90                  95

Cys Ala Leu His Ser Thr Gly Arg Phe Ile Leu Arg Gln Asp Asn Ser
            100                 105                 110

Gly Asp Pro Val Asp Pro His Lys Val Tyr Glu Leu Ser Arg Glu Leu
        115                 120                 125

Gly Ser Thr Val Gly Pro Ala Thr Glu Asn Arg Glu Glu Val Ser Leu
        130                 135                 140

Ser Asn Ala Leu Pro Thr Gln Gly Val Ser Pro Gly Ser Phe Leu Ala
145                 150                 155                 160

Arg Glu Asn Ala Gly Leu Gln Thr Pro Ser Pro Leu Leu Ser Ser Asp
                165                 170                 175

Ala Gly Asp Leu Leu Leu Gln Val Leu Gln Tyr Ser His Ile Leu Glu
```

-continued

```
                180                185                190

Ser Glu Ser Gly Ala Asp Pro Val Pro Pro Gln Ala Pro Gly Gln Glu
            195                200                205

Gln Asp Arg Val Tyr Glu Glu Pro Tyr Ala Ala Trp Gln Val Glu Ala
        210                215                220

Val Pro Ser Pro Arg Pro Gln Gln Pro Ala Leu Thr Glu Arg Ser Leu
225                230                235                240

Gly Phe Leu Asp Val Thr Ile Met Tyr Lys Gly Arg Thr Val Leu Gln
            245                250                255

Ala Val Val Gly His Pro Arg Cys Val Phe Leu Tyr Ser Pro Met Ala
            260                265                270

Pro Ala Val Arg Thr Ser Glu Pro Gln Pro Val Ile Phe Pro Ser Pro
        275                280                285

Ala Glu Leu Pro Asp Gln Lys Gln Leu His Tyr Thr Glu Thr Leu Leu
        290                295                300

Gln His Val Ser Pro Gly Leu Gln Leu Glu Leu Arg Gly Pro Ser Leu
305                310                315                320

Trp Ala Leu Arg Met Gly Lys Cys Lys Val Tyr Trp Glu Val Gly Ser
            325                330                335

Pro Met Gly Thr Thr Gly Pro Ser Thr Pro Pro Gln Leu Leu Glu Arg
            340                345                350

Asn Arg His Thr Pro Ile Phe Asp Phe Ser Thr Phe Phe Arg Glu Leu
            355                360                365

Glu Glu Phe Arg Ala Arg Arg Arg Gln Gly Ser Pro His Tyr Thr Ile
        370                375                380

Tyr Leu Gly Phe Gly Gln Asp Leu Ser Ala Gly Arg Pro Lys Glu Lys
385                390                395                400

Thr Leu Ile Leu Val Lys Leu Glu Pro Trp Val Cys Lys Ala Tyr Leu
            405                410                415

Glu Gly Val Gln Arg Glu Gly Val Ser Ser Leu Asp Ser Ser Ser Leu
            420                425                430

Gly Leu Cys Leu Ser Ser Thr Asn Ser Leu Tyr Glu Asp Ile Glu His
        435                440                445

Phe Leu Met Asp Leu Gly Gln Trp Pro
    450                455

<210> SEQ ID NO 81
<211> LENGTH: 473
<212> TYPE: PRT
<213> ORGANISM: Homo sapiens

<400> SEQUENCE: 81

Met Gly Arg Lys Lys Ile Gln Ile Thr Arg Ile Met Asp Glu Arg Asn
1                5                10                15

Arg Gln Val Thr Phe Thr Lys Arg Lys Phe Gly Leu Met Lys Lys Ala
            20                25                30

Tyr Glu Leu Ser Val Leu Cys Asp Cys Glu Ile Ala Leu Ile Ile Phe
            35                40                45

Asn Ser Thr Asn Lys Leu Phe Gln Tyr Ala Ser Thr Asp Met Asp Lys
        50                55                60

Val Leu Leu Lys Tyr Thr Glu Tyr Asn Glu Pro His Glu Ser Arg Thr
65                70                75                80

Asn Ser Asp Ile Val Glu Thr Leu Arg Lys Lys Gly Leu Asn Gly Cys
            85                90                95
```

-continued

```
Asp Ser Pro Asp Pro Asp Ala Asp Asp Ser Val Gly His Ser Pro Glu
        100             105             110

Ser Glu Asp Lys Tyr Arg Lys Ile Asn Glu Asp Ile Asp Leu Met Ile
        115             120             125

Ser Arg Gln Arg Leu Cys Ala Val Pro Pro Pro Asn Phe Glu Met Pro
    130             135             140

Val Ser Ile Pro Val Ser Ser His Asn Ser Leu Val Tyr Ser Asn Pro
145             150             155             160

Val Ser Ser Leu Gly Asn Pro Asn Leu Leu Pro Leu Ala His Pro Ser
            165             170             175

Leu Gln Arg Asn Ser Met Ser Pro Gly Val Thr His Arg Pro Pro Ser
        180             185             190

Ala Gly Asn Thr Gly Gly Leu Met Gly Gly Asp Leu Thr Ser Gly Ala
        195             200             205

Gly Thr Ser Ala Gly Asn Gly Tyr Gly Asn Pro Arg Asn Ser Pro Gly
    210             215             220

Leu Leu Val Ser Pro Gly Asn Leu Asn Lys Asn Met Gln Ala Lys Ser
225             230             235             240

Pro Pro Pro Met Asn Leu Gly Met Asn Asn Arg Lys Pro Asp Leu Arg
            245             250             255

Val Leu Ile Pro Pro Gly Ser Lys Asn Thr Met Pro Ser Val Ser Glu
            260             265             270

Asp Val Asp Leu Leu Leu Asn Gln Arg Ile Asn Asn Ser Gln Ser Ala
        275             280             285

Gln Ser Leu Ala Thr Pro Val Val Ser Val Ala Thr Pro Thr Leu Pro
    290             295             300

Gly Gln Gly Met Gly Gly Tyr Pro Ser Ala Ile Ser Thr Thr Tyr Gly
305             310             315             320

Thr Glu Tyr Ser Leu Ser Ser Ala Asp Leu Ser Ser Leu Ser Gly Phe
            325             330             335

Asn Thr Ala Ser Ala Leu His Leu Gly Ser Val Thr Gly Trp Gln Gln
        340             345             350

Gln His Leu His Asn Met Pro Pro Ser Ala Leu Ser Gln Leu Gly Ala
        355             360             365

Cys Thr Ser Thr His Leu Ser Gln Ser Ser Asn Leu Ser Leu Pro Ser
    370             375             380

Thr Gln Ser Leu Asn Ile Lys Ser Glu Pro Val Ser Pro Pro Arg Asp
385             390             395             400

Arg Thr Thr Thr Pro Ser Arg Tyr Pro Gln His Thr Arg His Glu Ala
            405             410             415

Gly Arg Ser Pro Val Asp Ser Leu Ser Ser Cys Ser Ser Ser Tyr Asp
            420             425             430

Gly Ser Asp Arg Glu Asp His Arg Asn Glu Phe His Ser Pro Ile Gly
        435             440             445

Leu Thr Arg Pro Ser Pro Asp Glu Arg Glu Ser Pro Ser Val Lys Arg
        450             455             460

Met Arg Leu Ser Glu Gly Trp Ala Thr
465             470
```

<210> SEQ ID NO 82
<211> LENGTH: 466
<212> TYPE: PRT
<213> ORGANISM: Mus musculus

<400> SEQUENCE: 82

```
Met Gly Arg Lys Lys Ile Gln Ile Thr Arg Ile Met Asp Glu Arg Asn
1               5               10              15

Arg Gln Val Thr Phe Thr Lys Arg Lys Phe Gly Leu Met Lys Lys Ala
            20              25              30

Tyr Glu Leu Ser Val Leu Cys Asp Cys Glu Ile Ala Leu Ile Ile Phe
        35              40              45

Asn Ser Thr Asn Lys Leu Phe Gln Tyr Ala Ser Thr Asp Met Asp Lys
    50              55              60

Val Leu Leu Lys Tyr Thr Glu Tyr Asn Glu Pro His Glu Ser Arg Thr
65              70              75              80

Asn Ser Asp Ile Val Glu Thr Leu Arg Lys Lys Gly Leu Asn Gly Cys
            85              90              95

Asp Ser Pro Asp Pro Asp Ala Asp Asp Ser Val Gly His Ser Pro Glu
            100             105             110

Ser Glu Asp Lys Tyr Arg Lys Ile Asn Glu Asp Ile Asp Leu Met Ile
        115             120             125

Ser Arg Gln Arg Leu Cys Ala Val Pro Pro Pro Ser Phe Glu Met Pro
    130             135             140

Val Thr Ile Pro Val Ser Ser His Asn Ser Leu Val Tyr Ser Asn Pro
145             150             155             160

Val Ser Thr Leu Gly Asn Pro Asn Leu Leu Pro Leu Ala His Pro Ser
            165             170             175

Leu Gln Arg Asn Ser Met Ser Pro Gly Val Thr His Arg Pro Pro Ser
            180             185             190

Ala Gly Asn Thr Gly Gly Leu Met Gly Gly Asp Leu Thr Ser Gly Ala
            195             200             205

Gly Thr Ser Ala Gly Asn Gly Tyr Gly Asn Pro Arg Asn Ser Pro Gly
    210             215             220

Leu Leu Val Ser Pro Gly Asn Leu Asn Lys Asn Ile Gln Ala Lys Ser
225             230             235             240

Pro Pro Pro Met Asn Leu Gly Met Asn Asn Arg Lys Pro Asp Leu Arg
            245             250             255

Val Leu Ile Pro Pro Gly Ser Lys Asn Thr Met Pro Ser Val Asn Gln
            260             265             270

Arg Ile Asn Asn Ser Gln Ser Ala Gln Ser Leu Ala Thr Pro Val Val
    275             280             285

Ser Val Ala Thr Pro Thr Leu Pro Gly Gln Gly Met Gly Gly Tyr Pro
    290             295             300

Ser Ala Ile Ser Thr Thr Tyr Gly Thr Glu Tyr Ser Leu Ser Ser Ala
305             310             315             320

Asp Leu Ser Ser Leu Ser Gly Phe Asn Thr Ala Ser Ala Leu His Leu
            325             330             335

Gly Ser Val Thr Gly Trp Gln Gln Gln His Leu His Asn Met Pro Pro
            340             345             350

Ser Ala Leu Ser Gln Leu Gly Ala Cys Thr Ser Thr His Leu Ser Gln
        355             360             365

Ser Ser Asn Leu Ser Leu Pro Ser Thr Gln Ser Leu Ser Ile Lys Ser
    370             375             380

Glu Pro Val Ser Pro Pro Arg Asp Arg Thr Thr Thr Pro Ser Arg Tyr
385             390             395             400

Pro Gln His Thr Thr Arg His Glu Ala Gly Arg Ser Pro Val Asp Ser
            405             410             415
```

```
Leu Ser Ser Cys Ser Ser Ser Tyr Asp Gly Ser Asp Arg Glu Asp His
            420                 425                 430

Arg Asn Glu Phe His Ser Pro Ile Gly Leu Thr Arg Pro Ser Pro Asp
            435                 440                 445

Glu Arg Glu Ser Pro Ser Val Lys Arg Met Arg Leu Ser Glu Gly Trp
    450                 455                 460

Ala Thr
465

<210> SEQ ID NO 83
<211> LENGTH: 761
<212> TYPE: PRT
<213> ORGANISM: Homo sapiens

<400> SEQUENCE: 83

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
            115                 120                 125

Gln Cys Arg Glu Arg Trp His Asn His Leu Asn Pro Glu Val Lys Lys
        130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
        210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ala Ile Gln Arg His Tyr Asn Asp Glu Asp
            275                 280                 285

Pro Glu Lys Glu Lys Arg Ile Lys Glu Leu Glu Leu Leu Leu Met Ser
        290                 295                 300

Thr Glu Asn Glu Leu Lys Gly Gln Gln Val Leu Pro Thr Gln Asn His
305                 310                 315                 320
```

-continued

```
Thr Cys Ser Tyr Pro Gly Trp His Ser Thr Thr Ile Ala Asp His Thr
            325             330             335

Arg Pro His Gly Asp Ser Ala Pro Val Ser Cys Leu Gly Glu His His
            340             345             350

Ser Thr Pro Ser Leu Pro Ala Asp Pro Gly Ser Leu Pro Glu Glu Ser
            355             360             365

Ala Ser Pro Ala Arg Cys Met Ile Val His Gln Gly Thr Ile Leu Asp
    370             375             380

Asn Val Lys Asn Leu Leu Glu Phe Ala Glu Thr Leu Gln Phe Ile Asp
385             390             395             400

Ser Asp Ser Ser Ser Trp Cys Asp Leu Ser Ser Phe Glu Phe Phe Glu
            405             410             415

Glu Ala Asp Phe Ser Pro Ser Gln His His Thr Gly Lys Ala Leu Gln
            420             425             430

Leu Gln Gln Arg Glu Gly Asn Gly Thr Lys Pro Ala Gly Glu Pro Ser
            435             440             445

Pro Arg Val Asn Lys Arg Met Leu Ser Glu Ser Ser Leu Asp Pro Pro
    450             455             460

Lys Val Leu Pro Pro Ala Arg His Ser Thr Ile Pro Leu Val Ile Leu
465             470             475             480

Arg Lys Lys Arg Gly Gln Ala Ser Pro Leu Ala Thr Gly Asp Cys Ser
            485             490             495

Ser Phe Ile Phe Ala Asp Val Ser Ser Ser Thr Pro Lys Arg Ser Pro
            500             505             510

Val Lys Ser Leu Pro Phe Ser Pro Ser Gln Phe Leu Asn Thr Ser Ser
            515             520             525

Asn His Glu Asn Ser Asp Leu Glu Met Pro Ser Leu Thr Ser Thr Pro
    530             535             540

Leu Ile Gly His Lys Leu Thr Val Thr Thr Pro Phe His Arg Asp Gln
545             550             555             560

Thr Val Lys Thr Gln Lys Glu Asn Thr Val Phe Arg Thr Pro Ala Ile
            565             570             575

Lys Arg Ser Ile Leu Glu Ser Ser Pro Arg Thr Pro Thr Pro Phe Lys
            580             585             590

His Ala Leu Ala Ala Gln Glu Ile Lys Tyr Gly Pro Leu Lys Met Leu
            595             600             605

Pro Gln Thr Pro Ser His Leu Val Glu Asp Leu Gln Asp Val Ile Lys
    610             615             620

Gln Glu Ser Asp Glu Ser Gly Ile Val Ala Glu Phe Gln Glu Asn Gly
625             630             635             640

Pro Pro Leu Leu Lys Lys Ile Lys Gln Glu Val Glu Ser Pro Thr Asp
            645             650             655

Lys Ser Gly Asn Phe Phe Cys Ser His His Trp Glu Gly Asp Ser Leu
            660             665             670

Asn Thr Gln Leu Phe Thr Gln Thr Ser Pro Val Ala Asp Ala Pro Asn
    675             680             685

Ile Leu Thr Ser Ser Val Leu Met Ala Pro Ala Ser Glu Asp Glu Asp
    690             695             700

Asn Val Leu Lys Ala Phe Thr Val Pro Lys Asn Arg Ser Leu Ala Ser
705             710             715             720

Pro Leu Gln Pro Cys Ser Ser Thr Trp Glu Pro Ala Ser Cys Gly Lys
            725             730             735
```

-continued

```
Met Glu Glu Gln Met Thr Ser Ser Ser Gln Ala Arg Lys Tyr Val Asn
            740                 745                 750

Ala Phe Ser Ala Arg Thr Leu Val Met
        755                 760

<210> SEQ ID NO 84
<211> LENGTH: 755
<212> TYPE: PRT
<213> ORGANISM: Mus musculus

<400> SEQUENCE: 84

Met Ala Arg Arg Pro Arg His Ser Ile Tyr Ser Ser Asp Glu Asp Asp
1               5                   10                  15

Glu Asp Ile Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
            115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Pro Ser Lys Ala Ser Gln Thr
            195                 200                 205

Pro Val Ala Thr Ser Phe Gln Lys Asn Asn His Leu Met Gly Phe Gly
    210                 215                 220

His Ala Ser Pro Pro Ser Gln Leu Ser Pro Ser Gly Gln Ser Ser Val
225                 230                 235                 240

Asn Ser Glu Tyr Pro Tyr Tyr His Ile Ala Glu Ala Gln Asn Ile Ser
                245                 250                 255

Ser His Val Pro Tyr Pro Val Ala Leu His Val Asn Ile Val Asn Val
            260                 265                 270

Pro Gln Pro Ala Ala Ala Ala Ile Gln Arg His Tyr Asn Asp Glu Asp
            275                 280                 285

Pro Glu Lys Glu Lys Arg Ile Lys Glu Leu Glu Leu Leu Leu Met Ser
    290                 295                 300

Thr Glu Asn Glu Leu Lys Gly Gln Gln Ala Leu Pro Thr Gln Asn His
305                 310                 315                 320

Thr Cys Ser Tyr Pro Gly Trp His Ser Thr Ser Ile Val Asp Gln Thr
                325                 330                 335

Arg Pro His Gly Asp Ser Ala Pro Val Ser Cys Leu Gly Glu His His
            340                 345                 350
```

```
Ala Thr Pro Ser Leu Pro Ala Asp Pro Gly Ser Leu Pro Glu Glu Ser
        355             360             365

Ala Ser Pro Ala Arg Cys Met Ile Val His Gln Gly Thr Ile Leu Asp
    370             375             380

Asn Val Lys Asn Leu Leu Glu Phe Ala Glu Thr Leu Gln Phe Ile Asp
385             390             395             400

Ser Asp Ser Ser Trp Cys Asp Leu Ser Ser Phe Glu Phe Ser Glu Glu
                405             410             415

Ala Ala Ala Phe Ser Pro Ser Gln Gln Pro Thr Gly Lys Ala Phe Gln
            420             425             430

Leu Gln Gln Arg Glu Gly His Gly Thr Arg Ser Ala Gly Glu Pro Ser
        435             440             445

Leu Arg Val Thr Arg Arg Val Leu Ser Glu Ala Ser Leu Gly Pro Asp
    450             455             460

Ser Pro Gln Ala Arg His Ser Lys Val Pro Leu Val Val Leu Arg Lys
465             470             475             480

Arg Arg Gly Gln Ala Ser Pro Leu Ala Ala Gly Glu Pro Ser Pro Ser
                485             490             495

Leu Phe Ala Asp Val Ile Ser Ser Thr Leu Lys Arg Ser Pro Val Lys
            500             505             510

Ser Leu Pro Phe Ser Pro Ser Gln Phe Leu Asn Thr Ser Ser Asn His
        515             520             525

Glu Ser Ser Gly Leu Asp Ala Pro Thr Leu Pro Ser Thr Pro Leu Ile
        530             535             540

Gly His Lys Leu Thr Pro Cys Arg Asp Gln Thr Val Lys Thr Gln Lys
545             550             555             560

Glu Asn Ser Ile Phe Arg Thr Pro Ala Ile Lys Arg Ser Ile Leu Glu
                565             570             575

Ser Ser Pro Arg Thr Pro Thr Pro Phe Lys His Ala Leu Ala Ala Gln
            580             585             590

Glu Ile Lys Tyr Gly Pro Leu Lys Met Leu Pro Gln Thr Pro Ser His
        595             600             605

Ala Val Glu Asp Leu Gln Asp Val Ile Lys Gln Glu Ser Asp Glu Ser
    610             615             620

Gly Ile Val Ala Glu Phe Gln Glu Ser Gly Pro Pro Leu Leu Lys Lys
625             630             635             640

Ile Lys Gln Glu Val Glu Ser Pro Thr Glu Lys Ser Gly Asn Phe Phe
            645             650             655

Cys Ser Asn His Trp Ala Glu Asn Ser Leu Ser Thr Gln Leu Phe Ser
            660             665             670

Gln Ala Ser Pro Val Ala Asp Ala Pro Asn Ile Leu Thr Ser Ser Val
            675             680             685

Leu Met Thr Pro Val Ser Glu Asp Glu Asp Asn Val Leu Lys Ala Phe
        690             695             700

Thr Val Pro Lys Asn Arg Pro Leu Val Gly Pro Leu Gln Pro Cys Ser
705             710             715             720

Gly Ala Trp Glu Pro Ala Ser Cys Gly Lys Thr Glu Asp Gln Met Thr
                725             730             735

Ala Ser Gly Pro Ala Arg Lys Tyr Val Asn Ala Phe Ser Ala Arg Thr
            740             745             750

Leu Val Met
        755
```

<210> SEQ ID NO 85
<211> LENGTH: 521
<212> TYPE: PRT
<213> ORGANISM: Homo sapiens

<400> SEQUENCE: 85

Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Glu Ala Ala Ala Ala Ala Ala Ala Ala
65                  70                  75                  80

Ala Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
            100                 105                 110

Leu Val Arg Thr Asp Ser Pro Asn Phe Leu Cys Ser Val Leu Pro Ser
            115                 120                 125

His Trp Arg Cys Asn Lys Thr Leu Pro Val Ala Phe Lys Val Val Ala
        130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
            195                 200                 205

Gln Val Ala Thr Tyr His Arg Ala Ile Lys Val Thr Val Asp Gly Pro
        210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
            260                 265                 270

Ala Pro Ser Pro Phe Asn Pro Gln Gly Gln Ser Gln Ile Thr Asp Pro
            275                 280                 285

Arg Gln Ala Gln Ser Ser Pro Pro Trp Ser Tyr Asp Gln Ser Tyr Pro
        290                 295                 300

Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                325                 330                 335

Arg Arg Ile Ser Asp Asp Asp Thr Ala Thr Ser Asp Phe Cys Leu Trp
            340                 345                 350

Pro Ser Thr Leu Ser Lys Lys Ser Gln Ala Gly Ala Ser Glu Leu Gly
        355                 360                 365

Pro Phe Ser Asp Pro Arg Gln Phe Pro Ser Ile Ser Ser Leu Thr Glu
        370                 375                 380

-continued

```
Ser Arg Phe Ser Asn Pro Arg Met His Tyr Pro Ala Thr Phe Thr Tyr
385                 390                 395                 400

Thr Pro Pro Val Thr Ser Gly Met Ser Leu Gly Met Ser Ala Thr Thr
                405                 410                 415

His Tyr His Thr Tyr Leu Pro Pro Pro Tyr Pro Gly Ser Ser Gln Ser
            420                 425                 430

Gln Ser Gly Pro Phe Gln Thr Ser Ser Thr Pro Tyr Leu Tyr Tyr Gly
            435                 440                 445

Thr Ser Ser Gly Ser Tyr Gln Phe Pro Met Val Pro Gly Gly Asp Arg
        450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
            515                 520

<210> SEQ ID NO 86
<211> LENGTH: 528
<212> TYPE: PRT
<213> ORGANISM: Mus musculus

<400> SEQUENCE: 86

Met Ala Ser Asn Ser Leu Phe Ser Ala Val Thr Pro Cys Gln Gln Ser
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
            35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Glu Ala Ala
65                  70                  75                  80

Ala Ala Ala Ala Ala Ala Ala Ala Ala Ala Ala Ala Ala Ala Ala Ala
                85                  90                  95

Val Pro Arg Leu Arg Pro Pro His Asp Asn Arg Thr Met Val Glu Ile
            100                 105                 110

Ile Ala Asp His Pro Ala Glu Leu Val Arg Thr Asp Ser Pro Asn Phe
            115                 120                 125

Leu Cys Ser Val Leu Pro Ser His Trp Arg Cys Asn Lys Thr Leu Pro
    130                 135                 140

Val Ala Phe Lys Val Val Ala Leu Gly Glu Val Pro Asp Gly Thr Val
145                 150                 155                 160

Val Thr Val Met Ala Gly Asn Asp Glu Asn Tyr Ser Ala Glu Leu Arg
                165                 170                 175

Asn Ala Ser Ala Val Met Lys Asn Gln Val Ala Arg Phe Asn Asp Leu
            180                 185                 190

Arg Phe Val Gly Arg Ser Gly Arg Gly Lys Ser Phe Thr Leu Thr Ile
            195                 200                 205

Thr Val Phe Thr Asn Pro Pro Gln Val Ala Thr Tyr His Arg Ala Ile
    210                 215                 220

Lys Val Thr Val Asp Gly Pro Arg Glu Pro Arg Arg His Arg Gln Lys
```

-continued

```
225                 230                 235                 240

Leu Asp Asp Ser Lys Pro Ser Leu Phe Ser Asp Arg Leu Ser Asp Leu
                245                 250                 255

Gly Arg Ile Pro His Pro Ser Met Arg Val Gly Val Pro Pro Gln Asn
                260                 265                 270

Pro Arg Pro Ser Leu Asn Ser Ala Pro Ser Pro Phe Asn Pro Gln Gly
                275                 280                 285

Gln Ser Gln Ile Thr Asp Pro Arg Gln Ala Gln Ser Ser Pro Pro Trp
                290                 295                 300

Ser Tyr Asp Gln Ser Tyr Pro Ser Tyr Leu Ser Gln Met Thr Ser Pro
305                 310                 315                 320

Ser Ile His Ser Thr Thr Pro Leu Ser Ser Thr Arg Gly Thr Gly Leu
                325                 330                 335

Pro Ala Ile Thr Asp Val Pro Arg Arg Ile Ser Asp Asp Asp Thr Ala
                340                 345                 350

Thr Ser Asp Phe Cys Leu Trp Pro Ser Ser Leu Ser Lys Lys Ser Gln
                355                 360                 365

Ala Gly Ala Ser Glu Leu Gly Pro Phe Ser Asp Pro Arg Gln Phe Pro
                370                 375                 380

Ser Ile Ser Ser Leu Thr Glu Ser Arg Phe Ser Asn Pro Arg Met His
385                 390                 395                 400

Tyr Pro Ala Thr Phe Thr Tyr Thr Pro Pro Val Thr Ser Gly Met Ser
                405                 410                 415

Leu Gly Met Ser Ala Thr Thr His Tyr His Thr Tyr Leu Pro Pro Pro
                420                 425                 430

Tyr Pro Gly Ser Ser Gln Ser Gln Ser Gly Pro Phe Gln Thr Ser Ser
                435                 440                 445

Thr Pro Tyr Leu Tyr Tyr Gly Thr Ser Ser Ala Ser Tyr Gln Phe Pro
                450                 455                 460

Met Val Pro Gly Gly Asp Arg Ser Pro Ser Arg Met Val Pro Pro Cys
465                 470                 475                 480

Thr Thr Thr Ser Asn Gly Ser Thr Leu Leu Asn Pro Asn Leu Pro Asn
                485                 490                 495

Gln Asn Asp Gly Val Asp Ala Asp Gly Ser His Ser Ser Ser Pro Thr
                500                 505                 510

Val Leu Asn Ser Ser Gly Arg Met Asp Glu Ser Val Trp Arg Pro Tyr
                515                 520                 525

<210> SEQ ID NO 87
<211> LENGTH: 770
<212> TYPE: PRT
<213> ORGANISM: Homo sapiens

<400> SEQUENCE: 87

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
                35                  40                  45

Lys Glu Ser His Ala Thr Leu Val Phe His Asn Leu Leu Gly Glu Ile
                50                  55                  60

Asp Gln Gln Tyr Ser Arg Phe Leu Gln Glu Ser Asn Val Leu Tyr Gln
65                  70                  75                  80
```

-continued

```
His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
            405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
            485                 490                 495

Pro Ile Gly Thr Trp Asp Gln Val Ala Glu Val Leu Ser Trp Gln Phe
```

```
            500             505             510
Ser Ser Thr Thr Lys Arg Gly Leu Ser Ile Glu Gln Leu Thr Thr Leu
        515             520             525

Ala Glu Lys Leu Leu Gly Pro Gly Val Asn Tyr Ser Gly Cys Gln Ile
    530             535             540

Thr Trp Ala Lys Phe Cys Lys Glu Asn Met Ala Gly Lys Gly Phe Ser
545             550             555             560

Phe Trp Val Trp Leu Asp Asn Ile Ile Asp Leu Val Lys Lys Tyr Ile
            565             570             575

Leu Ala Leu Trp Asn Glu Gly Tyr Ile Met Gly Phe Ile Ser Lys Glu
        580             585             590

Arg Glu Arg Ala Ile Leu Ser Thr Lys Pro Pro Gly Thr Phe Leu Leu
        595             600             605

Arg Phe Ser Glu Ser Ser Lys Glu Gly Gly Val Thr Phe Thr Trp Val
    610             615             620

Glu Lys Asp Ile Ser Gly Lys Thr Gln Ile Gln Ser Val Glu Pro Tyr
625             630             635             640

Thr Lys Gln Gln Leu Asn Asn Met Ser Phe Ala Glu Ile Ile Met Gly
            645             650             655

Tyr Lys Ile Met Asp Ala Thr Asn Ile Leu Val Ser Pro Leu Val Tyr
            660             665             670

Leu Tyr Pro Asp Ile Pro Lys Glu Glu Ala Phe Gly Lys Tyr Cys Arg
        675             680             685

Pro Glu Ser Gln Glu His Pro Glu Ala Asp Pro Gly Ser Ala Ala Pro
    690             695             700

Tyr Leu Lys Thr Lys Phe Ile Cys Val Thr Pro Thr Thr Cys Ser Asn
705             710             715             720

Thr Ile Asp Leu Pro Met Ser Pro Arg Thr Leu Asp Ser Leu Met Gln
            725             730             735

Phe Gly Asn Asn Gly Glu Gly Ala Glu Pro Ser Ala Gly Gly Gln Phe
            740             745             750

Glu Ser Leu Thr Phe Asp Met Glu Leu Thr Ser Glu Cys Ala Thr Ser
        755             760             765

Pro Met
    770

<210> SEQ ID NO 88
<211> LENGTH: 770
<212> TYPE: PRT
<213> ORGANISM: Mus musculus

<400> SEQUENCE: 88

Met Ala Gln Trp Asn Gln Leu Gln Gln Leu Asp Thr Arg Tyr Leu Glu
1               5               10              15

Gln Leu His Gln Leu Tyr Ser Asp Ser Phe Pro Met Glu Leu Arg Gln
            20              25              30

Phe Leu Ala Pro Trp Ile Glu Ser Gln Asp Trp Ala Tyr Ala Ala Ser
        35              40              45

Lys Glu Ser His Ala Thr Leu Val Phe His Asn Leu Leu Gly Glu Ile
    50              55              60

Asp Gln Gln Tyr Ser Arg Phe Leu Gln Glu Ser Asn Val Leu Tyr Gln
65              70              75              80

His Asn Leu Arg Arg Ile Lys Gln Phe Leu Gln Ser Arg Tyr Leu Glu
            85              90              95
```

-continued

```
Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
            130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
            195                 200                 205

Ala Leu Asp Gln Met Arg Arg Ser Ile Val Ser Glu Leu Ala Gly Leu
            210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
            290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
            370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
            450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
```

-continued

```
              515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
                675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Asp Leu Thr Ser Glu Cys Ala Thr Ser
                755                 760                 765

Pro Met
    770
```

```
<210> SEQ ID NO 89
<211> LENGTH: 773
<212> TYPE: PRT
<213> ORGANISM: Homo sapiens

<400> SEQUENCE: 89

Met Phe Ser Lys Arg Leu Glu Lys Ile Pro Gln Val Pro Leu Leu Phe
1               5                   10                  15

Pro Phe Ile Phe Ile Ile Leu Thr Asn Tyr Ser Lys Met Glu Gly Ala
                20                  25                  30

Val Glu Ser Gln Pro Ser Phe Phe Lys Thr Ser Gln Asp Ile Val Thr
                35                  40                  45

Cys Thr Trp Val Glu Asn Cys Tyr Ser Ser Phe Ser Arg Arg Pro Leu
    50                  55                  60

Glu Gln Met Phe Cys Lys His Gln Ser Lys Asn Ile Ile Ser Trp Thr
65                  70                  75                  80

Gly Met Val Ala His Thr Cys Asn Pro Ser Thr Leu Gly Gly Gln Gly
                85                  90                  95

Leu Cys Asp Phe Ala Lys Met His His Gln Gln Arg Met Ala Ala Leu
                100                 105                 110
```

-continued

```
Gly Thr Asp Lys Glu Leu Ser Asp Leu Leu Asp Phe Ser Ala Met Phe
        115                 120                 125

Ser Pro Pro Val Ser Ser Gly Lys Asn Gly Pro Thr Ser Leu Ala Ser
        130                 135                 140

Gly His Phe Thr Gly Ser Asn Val Glu Asp Arg Ser Ser Ser Gly Ser
145                 150                 155                 160

Trp Gly Asn Gly Gly His Pro Ser Pro Ser Arg Asn Tyr Gly Asp Gly
                165                 170                 175

Thr Pro Tyr Asp His Met Thr Ser Arg Asp Leu Gly Ser His Asp Asn
            180                 185                 190

Leu Ser Pro Pro Phe Val Asn Ser Arg Ile Gln Ser Lys Thr Glu Arg
            195                 200                 205

Gly Ser Tyr Ser Ser Tyr Gly Arg Glu Ser Asn Leu Gln Gly Cys His
        210                 215                 220

Gln Gln Ser Leu Leu Gly Gly Asp Met Asp Met Gly Asn Pro Gly Thr
225                 230                 235                 240

Leu Ser Pro Thr Lys Pro Gly Ser Gln Tyr Tyr Gln Tyr Ser Ser Asn
                245                 250                 255

Asn Pro Arg Arg Arg Pro Leu His Ser Ser Ala Met Glu Val Gln Thr
                260                 265                 270

Lys Lys Val Arg Lys Val Pro Pro Gly Leu Pro Ser Ser Val Tyr Ala
            275                 280                 285

Pro Ser Ala Ser Thr Ala Asp Tyr Asn Arg Asp Ser Pro Gly Tyr Pro
        290                 295                 300

Ser Ser Lys Pro Ala Thr Ser Thr Phe Pro Ser Ser Phe Phe Met Gln
305                 310                 315                 320

Asp Gly His His Ser Ser Asp Pro Trp Ser Ser Ser Ser Gly Met Asn
                325                 330                 335

Gln Pro Gly Tyr Ala Gly Met Leu Gly Asn Ser Ser His Ile Pro Gln
                340                 345                 350

Ser Ser Ser Tyr Cys Ser Leu His Pro His Glu Arg Leu Ser Tyr Pro
        355                 360                 365

Ser His Ser Ser Ala Asp Ile Asn Ser Ser Leu Pro Pro Met Ser Thr
        370                 375                 380

Phe His Arg Ser Gly Thr Asn His Tyr Ser Thr Ser Ser Cys Thr Pro
385                 390                 395                 400

Pro Ala Asn Gly Thr Asp Ser Ile Met Ala Asn Arg Gly Ser Gly Ala
                405                 410                 415

Ala Gly Ser Ser Gln Thr Gly Asp Ala Leu Gly Lys Ala Leu Ala Ser
            420                 425                 430

Ile Tyr Ser Pro Asp His Thr Asn Asn Ser Phe Ser Ser Asn Pro Ser
            435                 440                 445

Thr Pro Val Gly Ser Pro Pro Ser Leu Ser Ala Gly Thr Ala Val Trp
        450                 455                 460

Ser Arg Asn Gly Gly Gln Ala Ser Ser Ser Pro Asn Tyr Glu Gly Pro
465                 470                 475                 480

Leu His Ser Leu Gln Ser Arg Ile Glu Asp Arg Leu Glu Arg Leu Asp
                485                 490                 495

Asp Ala Ile His Val Leu Arg Asn His Ala Val Gly Pro Ser Thr Ala
            500                 505                 510

Met Pro Gly Gly His Gly Asp Met His Gly Ile Ile Gly Pro Ser His
        515                 520                 525

Asn Gly Ala Met Gly Gly Leu Gly Ser Gly Tyr Gly Thr Gly Leu Leu
```

-continued

```
            530                     535                     540

Ser Ala Asn Arg His Ser Leu Met Val Gly Thr His Arg Glu Asp Gly
545                     550                     555                     560

Val Ala Leu Arg Gly Ser His Ser Leu Leu Pro Asn Gln Val Pro Val
                        565                     570                     575

Pro Gln Leu Pro Val Gln Ser Ala Thr Ser Pro Asp Leu Asn Pro Pro
                        580                     585                     590

Gln Asp Pro Tyr Arg Gly Met Pro Pro Gly Leu Gln Gly Gln Ser Val
                595                     600                     605

Ser Ser Gly Ser Ser Glu Ile Lys Ser Asp Asp Glu Gly Asp Glu Asn
                610                     615                     620

Leu Gln Asp Thr Lys Ser Ser Glu Asp Lys Lys Leu Asp Asp Asp Lys
625                     630                     635                     640

Lys Asp Ile Lys Ser Ile Thr Arg Ser Arg Ser Ser Asn Asn Asp Asp
                        645                     650                     655

Glu Asp Leu Thr Pro Glu Gln Lys Ala Glu Arg Glu Lys Glu Arg Arg
                660                     665                     670

Met Ala Asn Asn Ala Arg Glu Arg Leu Arg Val Arg Asp Ile Asn Glu
                675                     680                     685

Ala Phe Lys Glu Leu Gly Arg Met Val Gln Leu His Leu Lys Ser Asp
                690                     695                     700

Lys Pro Gln Thr Lys Leu Leu Ile Leu His Gln Ala Val Ala Val Ile
705                     710                     715                     720

Leu Ser Leu Glu Gln Gln Val Arg Glu Arg Asn Leu Asn Pro Lys Ala
                        725                     730                     735

Ala Cys Leu Lys Arg Arg Glu Glu Glu Lys Val Ser Ser Glu Pro Pro
                        740                     745                     750

Pro Leu Ser Leu Ala Gly Pro His Pro Gly Met Gly Asp Ala Ser Asn
                        755                     760                     765

His Met Gly Gln Met
        770

<210> SEQ ID NO 90
<211> LENGTH: 670
<212> TYPE: PRT
<213> ORGANISM: Mus musculus

<400> SEQUENCE: 90

Met His His Gln Gln Arg Met Ala Ala Leu Gly Thr Asp Lys Glu Leu
1                       5                       10                      15

Ser Asp Leu Leu Asp Phe Ser Ala Met Phe Ser Pro Pro Val Ser Ser
                20                      25                      30

Gly Lys Asn Gly Pro Thr Ser Leu Ala Ser Gly His Phe Thr Gly Ser
                35                      40                      45

Asn Val Glu Asp Arg Ser Ser Ser Gly Ser Trp Gly Thr Gly Gly His
        50                      55                      60

Pro Ser Pro Ser Arg Asn Tyr Gly Asp Gly Thr Pro Tyr Asp His Met
65                      70                      75                      80

Thr Ser Arg Asp Leu Gly Ser His Asp Asn Leu Ser Pro Pro Phe Val
                        85                      90                      95

Asn Ser Arg Ile Gln Ser Lys Thr Glu Arg Gly Ser Tyr Ser Ser Tyr
                100                     105                     110

Gly Arg Glu Asn Val Gln Gly Cys His Gln Gln Ser Leu Leu Gly Gly
                115                     120                     125
```

```
Asp Met Asp Met Gly Asn Pro Gly Thr Leu Ser Pro Thr Lys Pro Gly
    130             135             140

Ser Gln Tyr Tyr Gln Tyr Ser Ser Asn Asn Ala Arg Arg Arg Pro Leu
145             150             155             160

His Ser Ser Ala Met Glu Val Gln Thr Lys Lys Val Arg Lys Val Pro
            165             170             175

Pro Gly Leu Pro Ser Ser Val Tyr Ala Pro Ser Ala Ser Thr Ala Asp
            180             185             190

Tyr Asn Arg Asp Ser Pro Gly Tyr Pro Ser Ser Lys Pro Ala Ala Ser
            195             200             205

Thr Phe Pro Ser Ser Phe Phe Met Gln Asp Gly His His Ser Ser Asp
    210             215             220

Pro Trp Ser Ser Ser Ser Gly Met Asn Gln Pro Gly Tyr Gly Gly Met
225             230             235             240

Leu Gly Asn Ser Ser His Ile Pro Gln Ser Ser Ser Tyr Cys Ser Leu
            245             250             255

His Pro His Glu Arg Leu Ser Tyr Pro Ser His Ser Ser Ala Asp Ile
            260             265             270

Asn Ser Ser Leu Pro Pro Met Ser Thr Phe His Arg Ser Gly Thr Asn
            275             280             285

His Tyr Ser Thr Ser Ser Cys Thr Pro Pro Ala Asn Gly Thr Asp Ser
    290             295             300

Ile Met Ala Asn Arg Gly Thr Gly Ala Ala Gly Ser Ser Gln Thr Gly
305             310             315             320

Asp Ala Leu Gly Lys Ala Leu Ala Ser Ile Tyr Ser Pro Asp His Thr
            325             330             335

Asn Asn Ser Phe Ser Ser Asn Pro Ser Thr Pro Val Gly Ser Pro Pro
            340             345             350

Ser Leu Ser Ala Gly Thr Ala Val Trp Ser Arg Asn Gly Gly Gln Ala
            355             360             365

Ser Ser Ser Pro Asn Tyr Glu Gly Pro Leu His Ser Leu Gln Ser Arg
    370             375             380

Ile Glu Asp Arg Leu Glu Arg Leu Asp Asp Ala Ile His Val Leu Arg
385             390             395             400

Asn His Ala Val Gly Pro Ser Thr Ala Val Pro Gly Gly His Gly Asp
            405             410             415

Met His Gly Ile Met Gly Pro Ser His Asn Gly Ala Met Gly Ser Leu
            420             425             430

Gly Ser Gly Tyr Gly Thr Ser Leu Leu Ser Ala Asn Arg His Ser Leu
            435             440             445

Met Val Gly Ala His Arg Glu Asp Gly Val Ala Leu Arg Gly Ser His
    450             455             460

Ser Leu Leu Pro Asn Gln Val Pro Val Pro Gln Leu Pro Val Gln Ser
465             470             475             480

Ala Thr Ser Pro Asp Leu Asn Pro Pro Gln Asp Pro Tyr Arg Gly Met
            485             490             495

Pro Pro Gly Leu Gln Gly Gln Ser Val Ser Ser Gly Ser Ser Glu Ile
            500             505             510

Lys Ser Asp Asp Glu Gly Asp Glu Asn Leu Gln Asp Thr Lys Ser Ser
            515             520             525

Glu Asp Lys Lys Leu Asp Asp Asp Lys Lys Asp Ile Lys Ser Ile Thr
    530             535             540

Arg Ser Arg Ser Ser Asn Asn Asp Asp Glu Asp Leu Thr Pro Glu Gln
```

-continued

```
545              550              555              560

Lys Ala Glu Arg Glu Lys Glu Arg Arg Met Ala Asn Asn Ala Arg Glu
                565              570              575

Arg Leu Arg Val Arg Asp Ile Asn Glu Ala Phe Lys Glu Leu Gly Arg
                580              585              590

Met Val Gln Leu His Leu Lys Ser Asp Lys Pro Gln Thr Lys Leu Leu
                595              600              605

Ile Leu His Gln Ala Val Ala Val Ile Leu Ser Leu Glu Gln Gln Val
                610              615              620

Arg Glu Arg Asn Leu Asn Pro Lys Ala Ala Cys Leu Lys Arg Arg Glu
625              630              635              640

Glu Glu Lys Val Ser Ser Glu Pro Pro Leu Ser Leu Ala Gly Pro
                645              650              655

His Pro Gly Met Gly Asp Ala Ala Asn His Met Gly Gln Met
                660              665              670

<210> SEQ ID NO 91
<211> LENGTH: 706
<212> TYPE: PRT
<213> ORGANISM: Homo sapiens

<400> SEQUENCE: 91

Met Asn Pro Gln Gln Gln Arg Met Ala Ala Ile Gly Thr Asp Lys Glu
1               5               10              15

Leu Ser Asp Leu Leu Asp Phe Ser Ala Met Phe Ser Pro Pro Val Asn
                20              25              30

Ser Gly Lys Thr Arg Pro Thr Thr Leu Gly Ser Ser Gln Phe Ser Gly
                35              40              45

Ser Gly Ile Asp Glu Arg Gly Gly Thr Thr Ser Trp Gly Thr Ser Gly
                50              55              60

Gln Pro Ser Pro Ser Tyr Asp Ser Ser Arg Gly Phe Thr Asp Ser Pro
65              70              75              80

His Tyr Ser Asp His Leu Asn Asp Ser Arg Leu Gly Ala His Glu Gly
                85              90              95

Leu Ser Pro Thr Pro Phe Met Asn Ser Asn Leu Met Gly Lys Thr Ser
                100             105             110

Glu Arg Gly Ser Phe Ser Leu Tyr Ser Arg Asp Thr Gly Leu Pro Gly
                115             120             125

Cys Gln Ser Ser Leu Leu Arg Gln Asp Leu Gly Leu Gly Ser Pro Ala
                130             135             140

Gln Leu Ser Ser Ser Gly Lys Pro Gly Thr Ala Tyr Tyr Ser Phe Ser
145             150             155             160

Ala Thr Ser Ser Arg Arg Arg Pro Leu His Asp Ser Ala Ala Leu Asp
                165             170             175

Pro Leu Gln Ala Lys Lys Val Arg Lys Val Pro Pro Gly Leu Pro Ser
                180             185             190

Ser Val Tyr Ala Pro Ser Pro Asn Ser Asp Asp Phe Asn Arg Glu Ser
                195             200             205

Pro Ser Tyr Pro Ser Pro Lys Pro Pro Thr Ser Met Phe Ala Ser Thr
                210             215             220

Phe Phe Met Gln Asp Gly Thr His Asn Ser Ser Asp Leu Trp Ser Ser
225             230             235             240

Ser Asn Gly Met Ser Gln Pro Gly Phe Gly Gly Ile Leu Gly Thr Ser
                245             250             255
```

```
Thr Ser His Met Ser Gln Ser Ser Ser Tyr Gly Asn Leu His Ser His
         260             265             270

Asp Arg Leu Ser Tyr Pro Pro His Ser Val Ser Pro Thr Asp Ile Asn
         275             280             285

Thr Ser Leu Pro Pro Met Ser Ser Phe His Arg Gly Ser Thr Ser Ser
     290             295             300

Ser Pro Tyr Val Ala Ala Ser His Thr Pro Pro Ile Asn Gly Ser Asp
305             310             315             320

Ser Ile Leu Gly Thr Arg Gly Asn Ala Ala Gly Ser Ser Gln Thr Gly
             325             330             335

Asp Ala Leu Gly Lys Ala Leu Ala Ser Ile Tyr Ser Pro Asp His Thr
         340             345             350

Ser Ser Ser Phe Pro Ser Asn Pro Ser Thr Pro Val Gly Ser Pro Ser
         355             360             365

Pro Leu Thr Gly Thr Ser Gln Trp Pro Arg Pro Gly Gly Gln Ala Pro
     370             375             380

Ser Ser Pro Ser Tyr Glu Asn Ser Leu His Ser Leu Lys Asn Arg Val
385             390             395             400

Glu Gln Gln Leu His Glu His Leu Gln Asp Ala Met Ser Phe Leu Lys
             405             410             415

Asp Val Cys Glu Gln Ser Arg Met Glu Asp Arg Leu Asp Arg Leu Asp
         420             425             430

Asp Ala Ile His Val Leu Arg Asn His Ala Val Gly Pro Ser Thr Ser
         435             440             445

Leu Pro Ala Gly His Ser Asp Ile His Ser Leu Leu Gly Pro Ser His
     450             455             460

Asn Ala Pro Ile Gly Ser Leu Asn Ser Asn Tyr Gly Gly Ser Ser Leu
465             470             475             480

Val Ala Ser Ser Arg Ser Ala Ser Met Val Gly Thr His Arg Glu Asp
             485             490             495

Ser Val Ser Leu Asn Gly Asn His Ser Val Leu Ser Ser Thr Val Thr
         500             505             510

Thr Ser Ser Thr Asp Leu Asn His Lys Thr Gln Glu Asn Tyr Arg Gly
         515             520             525

Gly Leu Gln Ser Gln Ser Gly Thr Val Val Thr Thr Glu Ile Lys Thr
     530             535             540

Glu Asn Lys Glu Lys Asp Glu Asn Leu His Glu Pro Pro Ser Ser Asp
545             550             555             560

Asp Met Lys Ser Asp Asp Glu Ser Ser Gln Lys Asp Ile Lys Val Ser
             565             570             575

Ser Arg Gly Arg Thr Ser Ser Thr Asn Glu Asp Glu Asp Leu Asn Pro
         580             585             590

Glu Gln Lys Ile Glu Arg Glu Lys Glu Arg Arg Met Ala Asn Asn Ala
         595             600             605

Arg Glu Arg Leu Arg Val Arg Asp Ile Asn Glu Ala Phe Lys Glu Leu
     610             615             620

Gly Arg Met Cys Gln Leu His Leu Lys Ser Glu Lys Pro Gln Thr Lys
625             630             635             640

Leu Leu Ile Leu His Gln Ala Val Ala Val Ile Leu Ser Leu Glu Gln
             645             650             655

Gln Val Arg Glu Arg Asn Leu Asn Pro Lys Ala Ala Cys Leu Lys Arg
         660             665             670

Arg Glu Glu Glu Lys Val Ser Ala Val Ser Ala Glu Pro Pro Thr Thr
```

```
                675                  680                  685

Leu Pro Gly Thr His Pro Gly Leu Ser Glu Thr Thr Asn Pro Met Gly
    690                  695                  700

His Met
705

<210> SEQ ID NO 92
<211> LENGTH: 706
<212> TYPE: PRT
<213> ORGANISM: Mus musculus

<400> SEQUENCE: 92

Met Asn Pro Gln Gln Gln Arg Met Ala Ala Ile Gly Thr Asp Lys Glu
1               5                   10                  15

Leu Ser Asp Leu Leu Asp Phe Ser Ala Met Phe Ser Pro Pro Val Asn
                20                  25                  30

Ser Gly Lys Thr Arg Pro Thr Thr Leu Gly Ser Ser Gln Phe Ser Gly
            35                  40                  45

Ser Gly Met Asp Glu Arg Gly Gly Thr Thr Ser Trp Gly Thr Ser Gly
        50                  55                  60

Gln Pro Ser Pro Ser Tyr Asp Ser Ser Arg Gly Phe Thr Asp Ser Pro
65                  70                  75                  80

His Tyr Ser Asp His Leu Asn Asp Ser Arg Leu Gly Thr His Glu Gly
                85                  90                  95

Leu Ser Pro Thr Pro Phe Met Asn Ser Asn Leu Ile Gly Lys Thr Ser
            100                 105                 110

Glu Arg Gly Ser Phe Ser Leu Tyr Ser Arg Asp Ser Gly Leu Ser Gly
            115                 120                 125

Cys Gln Ser Ser Leu Leu Arg Gln Asp Leu Gly Leu Gly Ser Pro Ala
    130                 135                 140

Gln Leu Ser Ser Ser Gly Lys Pro Gly Thr Pro Tyr Tyr Ser Phe Ser
145                 150                 155                 160

Ala Thr Ser Ser Arg Arg Arg Pro Leu His Asp Ser Val Ala Leu Asp
                165                 170                 175

Pro Leu Gln Ala Lys Lys Val Arg Lys Val Pro Pro Gly Leu Pro Ser
            180                 185                 190

Ser Val Tyr Ala Pro Ser Pro Asn Ser Asp Asp Phe Asn Arg Glu Ser
            195                 200                 205

Pro Ser Tyr Pro Ser Pro Lys Pro Pro Thr Ser Met Phe Ala Ser Thr
    210                 215                 220

Phe Phe Met Gln Asp Gly Thr His Ser Ser Ser Asp Leu Trp Ser Ser
225                 230                 235                 240

Ser Asn Gly Met Ser Gln Pro Gly Phe Gly Gly Ile Leu Gly Thr Ser
                245                 250                 255

Thr Ser His Met Ser Gln Ser Ser Ser Tyr Gly Ser Leu His Ser His
            260                 265                 270

Asp Arg Leu Ser Tyr Pro Pro His Ser Val Ser Pro Thr Asp Ile Asn
            275                 280                 285

Thr Ser Leu Pro Pro Met Ser Ser Phe His Arg Gly Ser Thr Ser Ser
    290                 295                 300

Ser Pro Tyr Val Ala Ala Ser His Thr Pro Pro Ile Asn Gly Ser Asp
305                 310                 315                 320

Ser Ile Leu Gly Thr Arg Gly Asn Ala Ala Gly Ser Ser Gln Thr Gly
                325                 330                 335
```

-continued

```
Asp Ala Leu Gly Lys Ala Leu Ala Ser Ile Tyr Ser Pro Asp His Thr
            340                 345                 350

Ser Ser Ser Phe Pro Ser Asn Pro Ser Thr Pro Val Gly Ser Pro Ser
            355                 360                 365

Pro Leu Thr Gly Thr Ser Gln Trp Pro Arg Ala Gly Gly Gln Ala Pro
    370                 375                 380

Ser Ser Pro Ser Tyr Glu Asn Ser Leu His Ser Leu Lys Asn Arg Val
385                 390                 395                 400

Glu Gln Gln Leu His Glu His Leu Gln Asp Ala Met Ser Phe Leu Lys
                405                 410                 415

Asp Val Cys Glu Gln Ser Arg Met Glu Asp Arg Leu Asp Arg Leu Asp
            420                 425                 430

Asp Ala Ile His Val Leu Arg Asn His Ala Val Gly Pro Ser Thr Ser
            435                 440                 445

Leu Pro Thr Ser His Ser Asp Ile His Ser Leu Leu Gly Pro Ser His
    450                 455                 460

Asn Ala Ser Ile Gly Asn Leu Asn Ser Asn Tyr Gly Gly Ser Ser Leu
465                 470                 475                 480

Val Thr Asn Ser Arg Ser Ala Ser Met Val Gly Thr His Arg Glu Asp
            485                 490                 495

Ser Val Ser Leu Asn Gly Asn His Ser Val Leu Ser Ser Thr Val Ala
            500                 505                 510

Ala Ser Asn Thr Glu Leu Asn His Lys Thr Pro Glu Asn Phe Arg Gly
            515                 520                 525

Gly Val Gln Asn Gln Ser Gly Ser Val Val Pro Thr Glu Ile Lys Thr
    530                 535                 540

Glu Asn Lys Glu Lys Asp Glu Asn Leu His Glu Pro Pro Ser Ser Asp
545                 550                 555                 560

Asp Met Lys Ser Asp Asp Glu Ser Ser Gln Lys Asp Ile Lys Val Ser
            565                 570                 575

Ser Arg Gly Arg Thr Ser Ser Thr Asn Glu Asp Glu Asp Leu Asn Pro
            580                 585                 590

Glu Gln Lys Ile Glu Arg Glu Lys Glu Arg Arg Met Ala Asn Asn Ala
            595                 600                 605

Arg Glu Arg Leu Arg Val Arg Asp Ile Asn Glu Ala Phe Lys Glu Leu
    610                 615                 620

Gly Arg Met Cys Gln Leu His Leu Lys Ser Glu Lys Pro Gln Thr Lys
625                 630                 635                 640

Leu Leu Ile Leu His Gln Ala Val Ala Val Ile Leu Ser Leu Glu Gln
                645                 650                 655

Gln Val Arg Glu Arg Asn Leu Asn Pro Lys Ala Ala Cys Leu Lys Arg
            660                 665                 670

Arg Glu Glu Glu Lys Val Ser Ala Ala Ser Ala Glu Pro Pro Asn Thr
            675                 680                 685

Leu Pro Gly Ala His Pro Gly Leu Ser Glu Ser Thr Asn Pro Met Gly
    690                 695                 700

His Leu
705
```

```
<210> SEQ ID NO 93
<211> LENGTH: 750
<212> TYPE: PRT
<213> ORGANISM: Homo sapiens

<400> SEQUENCE: 93
```

-continued

```
Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
                20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
        50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
            165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
            245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
            325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
            405                 410                 415
```

-continued

```
Thr Arg Thr Asn Glu Gly Pro Leu Ile Val Thr Glu Glu Leu His Ser
            420             425             430

Leu Ser Phe Glu Thr Gln Leu Cys Gln Pro Gly Leu Val Ile Asp Leu
            435             440             445

Glu Thr Thr Ser Leu Pro Val Val Val Ile Ser Asn Val Ser Gln Leu
        450             455             460

Pro Ser Gly Trp Ala Ser Ile Leu Trp Tyr Asn Met Leu Val Ala Glu
465             470             475             480

Pro Arg Asn Leu Ser Phe Phe Leu Thr Pro Pro Cys Ala Arg Trp Ala
                485             490             495

Gln Leu Ser Glu Val Leu Ser Trp Gln Phe Ser Ser Val Thr Lys Arg
            500             505             510

Gly Leu Asn Val Asp Gln Leu Asn Met Leu Gly Glu Lys Leu Leu Gly
            515             520             525

Pro Asn Ala Ser Pro Asp Gly Leu Ile Pro Trp Thr Arg Phe Cys Lys
            530             535             540

Glu Asn Ile Asn Asp Lys Asn Phe Pro Phe Trp Leu Trp Ile Glu Ser
545             550             555             560

Ile Leu Glu Leu Ile Lys Lys His Leu Leu Pro Leu Trp Asn Asp Gly
            565             570             575

Cys Ile Met Gly Phe Ile Ser Lys Glu Arg Glu Arg Ala Leu Leu Lys
            580             585             590

Asp Gln Gln Pro Gly Thr Phe Leu Leu Arg Phe Ser Glu Ser Ser Arg
            595             600             605

Glu Gly Ala Ile Thr Phe Thr Trp Val Glu Arg Ser Gln Asn Gly Gly
            610             615             620

Glu Pro Asp Phe His Ala Val Glu Pro Tyr Thr Lys Lys Glu Leu Ser
625             630             635             640

Ala Val Thr Phe Pro Asp Ile Ile Arg Asn Tyr Lys Val Met Ala Ala
            645             650             655

Glu Asn Ile Pro Glu Asn Pro Leu Lys Tyr Leu Tyr Pro Asn Ile Asp
            660             665             670

Lys Asp His Ala Phe Gly Lys Tyr Tyr Ser Arg Pro Lys Glu Ala Pro
            675             680             685

Glu Pro Met Glu Leu Asp Gly Pro Lys Gly Thr Gly Tyr Ile Lys Thr
            690             695             700

Glu Leu Ile Ser Val Ser Glu Val His Pro Ser Arg Leu Gln Thr Thr
705             710             715             720

Asp Asn Leu Leu Pro Met Ser Pro Glu Glu Phe Asp Glu Val Ser Arg
            725             730             735

Ile Val Gly Ser Val Glu Phe Asp Ser Met Met Asn Thr Val
            740             745             750
```

```
<210> SEQ ID NO 94
<211> LENGTH: 755
<212> TYPE: PRT
<213> ORGANISM: Mus musculus

<400> SEQUENCE: 94

Met Ser Gln Trp Phe Glu Leu Gln Gln Leu Asp Ser Lys Phe Leu Glu
1               5               10              15

Gln Val His Gln Leu Tyr Asp Asp Ser Phe Pro Met Glu Ile Arg Gln
            20              25              30

Tyr Leu Ala Gln Trp Leu Glu Lys Gln Asp Trp Glu His Ala Ala Tyr
            35              40              45
```

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Val Gln Met Ser Met Ile Ile Tyr Asn Cys Leu Lys Glu Glu
            100                 105                 110

Arg Lys Ile Leu Glu Asn Ala Gln Arg Phe Asn Gln Ala Gln Glu Gly
        115                 120                 125

Asn Ile Gln Asn Thr Val Met Leu Asp Lys Gln Lys Glu Leu Asp Ser
    130                 135                 140

Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
            165                 170                 175

Ser Gln Asn Arg Glu Gly Glu Ala Asn Gly Val Ala Lys Ser Asp Gln
            180                 185                 190

Lys Gln Glu Gln Leu Leu Leu His Lys Met Phe Leu Met Leu Asp Asn
        195                 200                 205

Lys Arg Lys Glu Ile Ile His Lys Ile Arg Glu Leu Leu Asn Ser Ile
    210                 215                 220

Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
            245                 250                 255

Asp Gln Leu Gln Ser Trp Phe Thr Ile Val Ala Glu Thr Leu Gln Gln
            260                 265                 270

Ile Arg Gln Gln Leu Lys Lys Leu Glu Glu Leu Glu Gln Lys Phe Thr
        275                 280                 285

Tyr Glu Pro Asp Pro Ile Thr Lys Asn Lys Gln Val Leu Ser Asp Arg
    290                 295                 300

Thr Phe Leu Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
            325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Ser Phe Asp Lys Asp Val
        355                 360                 365

Asn Glu Lys Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
            405                 410                 415

Asn Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Val Phe Val Pro Phe Gln Thr Thr Ser Leu Pro Val Val Val Ile
    450                 455                 460

-continued

```
Ser Asn Val Ser Gln Leu Pro Ser Gly Trp Ala Ser Ile Leu Trp Tyr
465                 470                 475                 480

Asn Met Leu Val Thr Glu Pro Arg Asn Leu Ser Phe Phe Leu Asn Pro
                485                 490                 495

Pro Cys Ala Trp Trp Ser Gln Leu Ser Glu Val Leu Ser Trp Gln Phe
                500                 505                 510

Ser Ser Val Thr Lys Arg Gly Leu Asn Ala Asp Gln Leu Ser Met Leu
                515                 520                 525

Gly Glu Lys Leu Leu Gly Pro Asn Ala Gly Pro Asp Gly Leu Ile Pro
        530                 535                 540

Trp Thr Arg Phe Cys Lys Glu Asn Ile Asn Asp Lys Asn Phe Ser Phe
545                 550                 555                 560

Trp Pro Trp Ile Asp Thr Ile Leu Glu Leu Ile Lys Lys His Leu Leu
                565                 570                 575

Cys Leu Trp Asn Asp Gly Cys Ile Met Gly Phe Ile Ser Lys Glu Arg
                580                 585                 590

Glu Arg Ala Leu Leu Lys Asp Gln Gln Pro Gly Thr Phe Leu Leu Arg
        595                 600                 605

Phe Ser Glu Ser Ser Arg Glu Gly Ala Ile Thr Phe Thr Trp Val Glu
        610                 615                 620

Arg Ser Gln Asn Gly Gly Glu Pro Asp Phe His Ala Val Glu Pro Tyr
625                 630                 635                 640

Thr Lys Lys Glu Leu Ser Ala Val Thr Phe Pro Asp Ile Ile Arg Asn
                645                 650                 655

Tyr Lys Val Met Ala Ala Glu Asn Ile Pro Glu Asn Pro Leu Lys Tyr
                660                 665                 670

Leu Tyr Pro Asn Ile Asp Lys Asp His Ala Phe Gly Lys Tyr Tyr Ser
        675                 680                 685

Arg Pro Lys Glu Ala Pro Glu Pro Met Glu Leu Asp Asp Pro Lys Arg
        690                 695                 700

Thr Gly Tyr Ile Lys Thr Glu Leu Ile Ser Val Ser Glu Val His Pro
705                 710                 715                 720

Ser Arg Leu Gln Thr Thr Asp Asn Leu Leu Pro Met Ser Pro Glu Glu
                725                 730                 735

Phe Asp Glu Met Ser Arg Ile Val Gly Pro Glu Phe Asp Ser Met Met
                740                 745                 750

Ser Thr Val
        755
```

<210> SEQ ID NO 95
<211> LENGTH: 1073
<212> TYPE: PRT
<213> ORGANISM: Homo sapiens

<400> SEQUENCE: 95

```
Met His Gln Pro Pro Glu Ser Thr Ala Ala Ala Ala Ala Ala Ala Asp
1               5                   10                  15

Ile Ser Ala Arg Lys Met Ala His Pro Ala Met Phe Pro Arg Arg Gly
                20                  25                  30

Ser Gly Ser Gly Ser Ala Ser Ala Leu Asn Ala Ala Gly Thr Gly Val
        35                  40                  45

Gly Ser Asn Ala Thr Ser Ser Glu Asp Phe Pro Pro Pro Ser Leu Leu
        50                  55                  60

Gln Pro Pro Pro Ala Ala Ser Ser Thr Ser Gly Pro Gln Pro Pro
65                  70                  75                  80
```

-continued

```
Pro Pro Gln Ser Leu Asn Leu Leu Ser Gln Ala Gln Leu Gln Ala Gln
            85                  90                  95

Pro Leu Ala Pro Gly Gly Thr Gln Met Lys Lys Ser Gly Phe Gln
            100                 105                 110

Ile Thr Ser Val Thr Pro Ala Gln Ile Ser Ala Ser Ile Ser Ser Asn
            115                 120                 125

Asn Ser Ile Ala Glu Asp Thr Glu Ser Tyr Asp Asp Leu Asp Glu Ser
    130                 135                 140

His Thr Glu Asp Leu Ser Ser Ser Glu Ile Leu Asp Val Ser Leu Ser
145                 150                 155                 160

Arg Ala Thr Asp Leu Gly Glu Pro Glu Arg Ser Ser Ser Glu Glu Thr
            165                 170                 175

Leu Asn Asn Phe Gln Glu Ala Glu Thr Pro Gly Ala Val Ser Pro Asn
            180                 185                 190

Gln Pro His Leu Pro Gln Pro His Leu Pro His Leu Pro Gln Gln Asn
            195                 200                 205

Val Val Ile Asn Gly Asn Ala His Pro His His Leu His His His His
    210                 215                 220

Gln Ile His His Gly His His Leu Gln His Gly His His His Pro Ser
225                 230                 235                 240

His Val Ala Val Ala Ser Ala Ser Ile Thr Gly Gly Pro Pro Ser Ser
            245                 250                 255

Pro Val Ser Arg Lys Leu Ser Thr Thr Gly Ser Ser Asp Ser Ile Thr
            260                 265                 270

Pro Val Ala Pro Thr Ser Ala Val Ser Ser Ser Gly Ser Pro Ala Ser
            275                 280                 285

Val Met Thr Asn Met Arg Ala Pro Ser Thr Thr Gly Gly Ile Gly Ile
    290                 295                 300

Asn Ser Val Thr Gly Thr Ser Thr Val Asn Asn Val Asn Ile Thr Ala
305                 310                 315                 320

Val Gly Ser Phe Asn Pro Asn Val Thr Ser Ser Met Leu Gly Asn Val
            325                 330                 335

Asn Ile Ser Thr Ser Asn Ile Pro Ser Ala Ala Gly Val Ser Val Gly
            340                 345                 350

Pro Gly Val Thr Ser Gly Val Asn Val Asn Ile Leu Ser Gly Met Gly
            355                 360                 365

Asn Gly Thr Ile Ser Ser Ser Ala Ala Val Ser Ser Val Pro Asn Ala
    370                 375                 380

Ala Ala Gly Met Thr Gly Gly Ser Val Ser Ser Gln Gln Gln Gln Pro
385                 390                 395                 400

Thr Val Asn Thr Ser Arg Phe Arg Val Val Lys Leu Asp Ser Ser Ser
            405                 410                 415

Glu Pro Phe Lys Lys Gly Arg Trp Thr Cys Thr Glu Phe Tyr Glu Lys
            420                 425                 430

Glu Asn Ala Val Pro Ala Thr Glu Gly Val Leu Ile Asn Lys Val Val
    435                 440                 445

Glu Thr Val Lys Gln Asn Pro Ile Glu Val Thr Ser Glu Arg Glu Ser
    450                 455                 460

Thr Ser Gly Ser Ser Val Ser Ser Ser Val Ser Thr Leu Ser His Tyr
465                 470                 475                 480

Thr Glu Ser Val Gly Ser Gly Glu Met Gly Ala Pro Thr Val Val Val
            485                 490                 495
```

Gln Gln Gln Gln Gln Gln Gln Gln Gln Gln Gln Gln Gln Pro Ala Leu
            500                 505                 510

Gln Gly Val Thr Leu Gln Gln Met Asp Phe Gly Ser Thr Gly Pro Gln
            515                 520                 525

Ser Ile Pro Ala Val Ser Ile Pro Gln Ser Ile Ser Gln Ser Gln Ile
            530                 535                 540

Ser Gln Val Gln Leu Gln Ser Gln Glu Leu Ser Tyr Gln Gln Lys Gln
545                 550                 555                 560

Gly Leu Gln Pro Val Pro Leu Gln Ala Thr Met Ser Ala Ala Thr Gly
                565                 570                 575

Ile Gln Pro Ser Pro Val Asn Val Val Gly Val Thr Ser Ala Leu Gly
                580                 585                 590

Gln Gln Pro Ser Ile Ser Ser Leu Ala Gln Pro Gln Leu Pro Tyr Ser
                595                 600                 605

Gln Ala Ala Pro Pro Val Gln Thr Pro Leu Pro Gly Ala Pro Pro Pro
            610                 615                 620

Gln Gln Leu Gln Tyr Gly Gln Gln Gln Pro Met Val Ser Thr Gln Met
625                 630                 635                 640

Ala Pro Gly His Val Lys Ser Val Thr Gln Asn Pro Ala Ser Glu Tyr
                645                 650                 655

Val Gln Gln Gln Pro Ile Leu Gln Thr Ala Met Ser Ser Gly Gln Pro
                660                 665                 670

Ser Ser Ala Gly Val Gly Ala Gly Thr Thr Val Ile Pro Val Ala Gln
            675                 680                 685

Pro Gln Gly Ile Gln Leu Pro Val Gln Pro Thr Ala Val Pro Ala Gln
            690                 695                 700

Pro Ala Gly Ala Ser Val Gln Pro Val Gly Gln Ala Pro Ala Ala Val
705                 710                 715                 720

Ser Ala Val Pro Thr Gly Ser Gln Ile Ala Asn Ile Gly Gln Gln Ala
                725                 730                 735

Asn Ile Pro Thr Ala Val Gln Gln Pro Ser Thr Gln Val Pro Pro Ser
            740                 745                 750

Val Ile Gln Gln Gly Ala Pro Pro Ser Ser Gln Val Val Pro Pro Ala
            755                 760                 765

Gln Thr Gly Ile Ile His Gln Gly Val Gln Thr Ser Ala Pro Ser Leu
            770                 775                 780

Pro Gln Gln Leu Val Ile Ala Ser Gln Ser Ser Leu Leu Thr Val Pro
785                 790                 795                 800

Pro Gln Pro Gln Gly Val Glu Pro Val Ala Gln Gly Ile Val Ser Gln
                805                 810                 815

Gln Leu Pro Ala Val Ser Ser Leu Pro Ser Ala Ser Ser Ile Ser Val
            820                 825                 830

Thr Ser Gln Val Ser Ser Thr Gly Pro Ser Gly Met Pro Ser Ala Pro
            835                 840                 845

Thr Asn Leu Val Pro Pro Gln Asn Ile Ala Gln Thr Pro Ala Thr Gln
            850                 855                 860

Asn Gly Asn Leu Val Gln Ser Val Ser Gln Pro Pro Leu Ile Ala Thr
865                 870                 875                 880

Asn Thr Asn Leu Pro Leu Ala Gln Gln Ile Pro Leu Ser Ser Thr Gln
                885                 890                 895

Phe Ser Ala Gln Ser Leu Ala Gln Ala Ile Gly Ser Gln Ile Glu Asp
            900                 905                 910

Ala Arg Arg Ala Ala Glu Pro Ser Leu Val Gly Leu Pro Gln Thr Ile

-continued

```
            915              920              925

Ser Gly Asp Ser Gly Gly Met Ser Ala Val Ser Asp Gly Ser Ser Ser
    930              935              940

Ser Leu Ala Ala Ser Ala Ser Leu Phe Pro Leu Lys Val Leu Pro Leu
945              950              955              960

Thr Thr Pro Leu Val Asp Gly Glu Asp Glu Ser Ser Ser Gly Ala Ser
                965              970              975

Val Val Ala Ile Asp Asn Lys Ile Glu Gln Ala Met Asp Leu Val Lys
            980              985              990

Ser His Leu Met Tyr Ala Val Arg  Glu Glu Val Glu Val  Leu Lys Glu
        995              1000             1005

Gln Ile  Lys Glu Leu Ile Glu  Lys Asn Ser Gln Leu  Glu Gln Glu
    1010             1015             1020

Asn Asn  Leu Leu Lys Thr Leu  Ala Ser Pro Glu Gln  Leu Ala Gln
    1025             1030             1035

Phe Gln  Ala Gln Leu Gln Thr  Gly Ser Pro Pro Ala  Thr Thr Gln
    1040             1045             1050

Pro Gln  Gly Thr Thr Gln Pro  Pro Ala Gln Pro Ala  Ser Gln Gly
    1055             1060             1065

Ser Gly  Pro Thr Ala
    1070

<210> SEQ ID NO 96
<211> LENGTH: 1077
<212> TYPE: PRT
<213> ORGANISM: Mus musculus

<400> SEQUENCE: 96

Met His Gln Pro Pro Glu Ser Thr Ala Ala Ala Ala Ala Ala Ala Asp
1               5               10              15

Ile Ser Ala Arg Lys Met Ala His Pro Ala Met Phe Pro Arg Arg Gly
            20              25              30

Ser Gly Gly Gly Ser Ala Ser Ala Leu Asn Ala Ala Gly Thr Gly Val
        35              40              45

Ser Gly Ala Ala Pro Ser Ser Glu Asp Phe Pro Pro Ser Leu Leu
    50              55              60

Gln Pro Pro Pro Pro Ala Ala Ser Ser Thr Gln Gly Pro Gln Pro Pro
65              70              75              80

Pro Pro Gln Ser Leu Asn Leu Leu Ser Gln Ala Gln Leu Gln Gly Gln
            85              90              95

Pro Leu Ala Pro Gly Gly Thr Gln Met Lys Lys Lys Ser Gly Phe Gln
            100             105             110

Ile Thr Ser Val Thr Pro Ala Gln Ile Ser Ala Ser Ile Ser Ser Asn
        115             120             125

Asn Ser Ile Ala Glu Asp Thr Glu Ser Tyr Asp Asp Leu Asp Glu Ser
    130             135             140

His Thr Glu Asp Leu Ser Ser Ser Glu Ile Leu Asp Val Ser Leu Ser
145             150             155             160

Arg Ala Thr Asp Leu Gly Glu Pro Glu Arg Ser Ser Ser Glu Glu Thr
            165             170             175

Leu Asn Asn Phe Gln Glu Ala Glu Thr Pro Gly Ala Val Ser Pro Asn
            180             185             190

Gln Pro His Leu Pro Gln Pro His Leu Pro His Leu Pro Gln Gln Asn
        195             200             205
```

-continued

```
Val Val Ile Asn Gly Asn Ala His Pro His His Leu His His His
    210             215             220

His Pro His His Gly His His Leu His His Gly His His His Ser Ser
225             230             235             240

His Ala Ala Val Ala Gly Pro Ser Ile Pro Gly Gly Pro Pro Ser Ser
            245             250             255

Pro Val Ser Arg Lys Leu Ser Thr Thr Gly Ser Ser Asp Gly Gly Val
            260             265             270

Pro Val Ala Pro Pro Ala Val Pro Ser Ser Gly Leu Pro Ala Ser
            275             280             285

Val Met Thr Asn Ile Arg Thr Pro Ser Thr Thr Gly Ser Leu Gly Ile
    290             295             300

Asn Ser Val Thr Gly Thr Ser Ala Thr Asn Asn Val Asn Ile Ala Ala
305             310             315             320

Val Gly Ser Phe Ser Pro Ser Val Thr Asn Ser Val His Gly Asn Ala
            325             330             335

Asn Ile Asn Thr Ser Asn Ile Pro Asn Ala Ala Ser Ile Ser Gly Gly
            340             345             350

Pro Gly Val Thr Ser Val Val Asn Ser Ser Ile Leu Ser Gly Met Gly
            355             360             365

Asn Gly Thr Val Ser Ser Ser Pro Val Ala Asn Ser Val Leu Asn Ala
    370             375             380

Ala Ala Gly Ile Thr Val Gly Val Val Ser Ser Gln Gln Gln Gln Gln
385             390             395             400

Gln Gln Gln Gln Pro Thr Val Asn Thr Ser Arg Phe Arg Val Val Lys
            405             410             415

Leu Asp Ser Thr Ser Glu Pro Phe Lys Lys Gly Arg Trp Thr Cys Thr
            420             425             430

Glu Phe Tyr Glu Lys Glu Asn Ala Val Pro Ala Thr Glu Gly Val Ala
            435             440             445

Val Asn Lys Val Val Glu Thr Val Lys Gln Thr Pro Thr Glu Ala Ser
    450             455             460

Ser Ser Glu Arg Glu Ser Thr Ser Gly Ser Ser Val Ser Ser Ser Val
465             470             475             480

Ser Thr Leu Ser His Tyr Thr Glu Ser Val Gly Ser Gly Glu Met Met
            485             490             495

Gly Ala Pro Ala Val Val Ala Pro Gln Gln Pro Pro Leu Pro Pro Ala
            500             505             510

Pro Pro Gly Leu Gln Gly Val Ala Leu Gln Gln Leu Glu Phe Ser Ser
            515             520             525

Pro Ala Pro Gln Ser Ile Ala Ala Val Ser Met Pro Gln Ser Ile Ser
    530             535             540

Gln Ser Gln Met Ser Gln Val Gln Leu Gln Pro Gln Glu Leu Ser Phe
545             550             555             560

Gln Gln Lys Gln Thr Leu Gln Pro Val Pro Leu Gln Ala Thr Met Ser
            565             570             575

Ala Ala Thr Gly Ile Gln Pro Ser Pro Val Ser Val Val Gly Ile Thr
            580             585             590

Ala Ala Val Gly Gln Gln Pro Ser Val Ser Ser Leu Ala Gln Pro Gln
            595             600             605

Leu Pro Tyr Ser Gln Thr Ala Pro Pro Val Gln Thr Pro Leu Pro Gly
    610             615             620

Ala Pro Pro Gln Gln Leu Gln Tyr Gly Gln Gln Gln Pro Met Val Pro
```

-continued

```
625                 630                 635                 640

Ala Gln Ile Ala Pro Gly His Gly Gln Pro Val Thr Gln Asn Pro Thr
            645             650                 655

Ser Glu Tyr Val Gln Gln Gln Gln Pro Ile Phe Gln Ala Ala Leu
            660             665             670

Ser Ser Gly Gln Ser Ser Ser Thr Gly Thr Gly Ala Gly Ile Ser Val
            675             680             685

Ile Pro Val Ala Gln Ala Gln Gly Ile Gln Leu Pro Gly Gln Pro Thr
            690             695             700

Ala Val Gln Thr Gln Pro Ala Gly Ala Ala Gly Gln Pro Ile Gly Gln
705             710             715             720

Ala Gln Thr Ala Val Ser Thr Val Pro Thr Gly Gly Gln Ile Ala Ser
            725             730             735

Ile Gly Gln Gln Ala Asn Ile Pro Thr Ala Val Gln Gln Pro Ser Thr
            740             745             750

Gln Val Thr Pro Ser Val Ile Gln Gln Gly Ala Pro Pro Ser Ser Gln
            755             760             765

Val Val Leu Pro Ala Pro Thr Gly Ile Ile His Gln Gly Val Gln Thr
            770             775             780

Arg Ala Ser Ser Leu Pro Gln Gln Leu Val Ile Ala Pro Gln Ser Thr
785             790             795             800

Leu Val Thr Val Pro Pro Gln Pro Gln Gly Val Glu Thr Val Ala Gln
            805             810             815

Gly Val Val Ser Gln Gln Leu Pro Thr Gly Ser Pro Leu Pro Ser Ala
            820             825             830

Ser Thr Ile Ser Val Thr Asn Gln Val Ser Ser Ala Ala Pro Ser Gly
            835             840             845

Met Pro Ser Val Pro Thr Asn Leu Val Pro Pro Gln Asn Ile Ala Gln
            850             855             860

Pro Pro Ala Thr Gln Asn Gly Ser Leu Val Gln Ser Val Ser Gln Ser
865             870             875             880

Pro Leu Ile Ala Thr Asn Ile Asn Leu Pro Leu Ala Gln Gln Ile Pro
            885             890             895

Leu Ser Ser Thr Gln Phe Ser Thr Gln Ser Leu Ala Gln Ala Ile Gly
            900             905             910

Ser Gln Met Glu Asp Ala Arg Arg Pro Ala Glu Pro Ser Leu Gly Gly
            915             920             925

Leu Pro Gln Thr Met Ser Gly Asp Ser Gly Gly Met Ser Ala Val Ser
            930             935             940

Asp Gly Ser Ser Ser Ser Leu Ala Ala Pro Ala Ser Leu Phe Pro Leu
945             950             955             960

Lys Val Leu Pro Leu Thr Thr Pro Leu Val Asp Gly Glu Asp Glu Ser
            965             970             975

Ser Gly Ala Ser Val Val Ala Ile Asp Asn Lys Ile Glu Gln Ala Met
            980             985             990

Asp Leu Val Lys Ser His Leu Met  Tyr Ala Val Arg Glu  Glu Val Glu
        995             1000             1005

Val Leu  Lys Glu Gln Ile Lys  Glu Leu Ile Glu Lys  Asn Ser Gln
    1010             1015             1020

Leu Glu  Gln Glu Asn Asn Leu  Leu Lys Thr Leu Ala  Ser Pro Glu
    1025             1030             1035

Gln Leu  Ala Gln Phe Gln Ala  Gln Leu Gln Thr Gly  Ser Pro Pro
    1040             1045             1050
```

-continued

```
Ala Thr  Thr Gln Pro Gln Gly  Thr Thr Gln Pro Pro  Ala Gln Pro
    1055              1060              1065

Ala Ser  Gln Gly Ser Gly Ser  Thr Ala
    1070              1075
```